United States Patent
Rao et al.

(10) Patent No.: US 7,456,288 B2
(45) Date of Patent: Nov. 25, 2008

(54) HETEROCYCLIC COMPOUNDS AND METHODS OF MAKING AND USING THEREOF

(75) Inventors: Yeleswarapu Koteswar Rao, Andhra Pradesh (IN); Manojit Pal, Andhra Pradesh (IN); Vedula Manohar Sharma, Andhra Pradesh (IN); Akella Venkateswarlu, Andhra Pradesh (IN); Ram Pillarisetti, Norcross, GA (US); Srinivas Padakanti, Hyderabad (IN); Kalleda Srinivasa Rao, Hyderabad (IN)

(73) Assignee: Reddy US Therapeutics, Inc., Norcross, GA (US)

( * ) Notice: Subject to any disclaimer, the term of this patent is extended or adjusted under 35 U.S.C. 154(b) by 588 days.

(21) Appl. No.: 10/976,284

(22) Filed: Oct. 28, 2004

(65) Prior Publication Data

US 2005/0119269 A1    Jun. 2, 2005

Related U.S. Application Data

(60) Provisional application No. 60/610,163, filed on Sep. 15, 2004.

(30) Foreign Application Priority Data

Oct. 28, 2003 (IN) .......................... 861/CHE/2003

(51) Int. Cl.
  *C07D 215/04* (2006.01)
(52) U.S. Cl. ....................................... 546/158; 546/157
(58) Field of Classification Search ................. 546/158, 546/157
  See application file for complete search history.

(56) References Cited

U.S. PATENT DOCUMENTS

| | | | |
|---|---|---|---|
| 3,773,919 | A | 11/1973 | Boswell et al. |
| 4,485,045 | A | 11/1984 | Regen |
| 4,544,545 | A | 10/1985 | Ryan et al. |
| 4,668,218 | A | 5/1987 | Virtanen |
| 4,859,581 | A | 8/1989 | Nicolson et al. |
| 5,013,556 | A | 5/1991 | Woodle et al. |
| 5,445,934 | A | 8/1995 | Fodor et al. |
| 5,458,135 | A | 10/1995 | Patton et al. |
| 5,514,670 | A | 5/1996 | Friedman et al. |
| 5,770,222 | A | 6/1998 | Unger et al. |
| 5,770,637 | A | 6/1998 | Vanderlaan et al. |
| 5,814,599 | A | 9/1998 | Mitragotri et al. |
| 5,837,832 | A | 11/1998 | Chee et al. |
| 5,849,695 | A | 12/1998 | Cohen et al. |
| 5,874,219 | A | 2/1999 | Rava et al. |
| 6,028,088 | A | 2/2000 | Pershadsingh et al. |
| 6,156,501 | A | 12/2000 | McGall et al. |
| 6,197,599 | B1 | 3/2001 | Chin et al. |
| 6,218,122 | B1 | 4/2001 | Friend et al. |
| 6,239,209 | B1 | 5/2001 | Yang et al. |
| 6,263,287 | B1 | 7/2001 | Zheng et al. |
| 6,273,913 | B1 | 8/2001 | Wright et al. |
| 2001/0014461 | A1 | 8/2001 | Hutchens et al. |
| 2001/0034023 | A1 | 10/2001 | Stanton et al. |
| 2001/0039016 | A1 | 11/2001 | Waldman et al. |
| 2002/0051730 | A1 | 5/2002 | Bodnar et al. |
| 2002/0086282 | A1 | 7/2002 | Pillarisetti et al. |

FOREIGN PATENT DOCUMENTS

| | | |
|---|---|---|
| EP | 0237507 A1 | 9/1987 |
| WO | WO 94/06498 A1 | 3/1994 |
| WO | WO 94/08552 A2 | 4/1994 |
| WO | WO 94/16970 A1 | 8/1994 |
| WO | WO 97/25086 A2 | 7/1997 |
| WO | WO 97/38731 A1 | 10/1997 |
| WO | WO 98/35888 A1 | 8/1998 |
| WO | WO 93/21232 A1 | 10/1999 |
| WO | WO 00/67776 A1 | 11/2000 |
| WO | WO 01/77668 A2 | 10/2001 |
| WO | WO 01/94946 A2 | 12/2001 |
| WO | WO 02/23197 A2 | 3/2002 |
| WO | WO 02/26139 A1 | 4/2002 |
| WO | WO 02/26271 A1 | 4/2002 |
| WO | 02/47687 | * 6/2002 |

OTHER PUBLICATIONS

Brownlee, M., et al. Nonensymatic Glycosylation and the Pathogensis of Diabetic Complications, Annals of Internal Medicine, Oct. 1984, 527-537, 101 (4), The American College of Physicians, Philadelphia, Pennsylvania, U.S.A.

Yang, C. et al., Advanced Glycation End Products Up-Regulate Gene Expression Found in Diabetic Glomerular Disease, Proceedings of the National Academy of Sciences of the United States of America, Sep. 1994, 9436-9440, vol. 91 (20), The National Academy of Sciences, Washington, D.C., U.S.A.

(Continued)

*Primary Examiner*—D. Margaret Seaman
(74) *Attorney, Agent, or Firm*—MacCord Mason PLLC

(57) ABSTRACT

Compounds of formula (I), and methods and/or compositions comprising compounds that are effective in modulating inflammatory responses, such as those resulting from AGE and glycated protein accumulation are provided. Methods and/or compositions comprising compounds that are effective in modulating smooth muscle cell proliferation and the diseases or conditions related thereto are also provided.

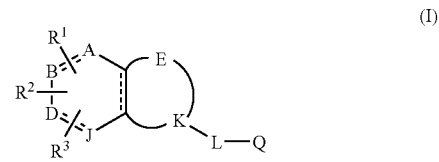

(I)

8 Claims, No Drawings

OTHER PUBLICATIONS

Tanji, N. et al., Expression of Advanced Glycation End Products and Their Cellular Receptor RAGE in Diabetic Nephropathy and Nondiabetic Renal Disease, Journal of the American Society of Nephrology, 2000, 1656-1666, vol. 11, No. 9, The American Society of Nephrology, Washington, D.C., U.S.A.

Schmidt, A.. et al., Activation of Receptor for Advanced Glycation End Products: A Mechanism for Chronic Vascular Dysfunction in Diabetic Vasculopathy and Atherosclerosis, Circulation Research, Mar. 1999, 489-497, vol. 84 (5), American Heart Association, U.S.A.

Yano, M. et al., Immunohistochemical Localization of Glycated Protein in Diabetic Rat Kidney, Diabetes Research Clinical Practice, 1990, 215-219, vol. 8 (3), Elsevier Science Publishers B.V.

Cohen, M. et al., Role of Amadori-Modified Nonenzymatically Glycated Proteins in the Pathogenesis of Diabetic Nephropathy, Journal of the American Society of Nephrology, 1996, 183-190, vol. 7, No. 2, The American Society of Nephrology, Washington, D.C., U.S.A.

Brownlee, M. et al., Aminoguanidine Prevents Diabetes-Induced Arterial Wall Protein Cross-Linking, Science, 1986, 1629-1632, vol. 232, The American Association for the Advancement of Science, Washington, D.C.

Li, Y. et al., Prevention of Cardiovascular and Renal Pathology of Aging by the Advanced Glycation Inhibitor Aminoguanidine, Proceedings of the National Academy of Sciences of the United States of America, Apr. 1996, 3902-3907, 93, The National Academy of Sciences, Washington D.C., U.S.A.

Piercy, V. et al., Potential Benefit of Inhibitors of Advanced Glycation End Products in the Progression of Type II Diabetes: A Study with Aminoguanidine in C57/BLKsJ Diabetic Mice, Metabolism, Dec. 1998, 1477-1480, vol. 47 (12), W. B. Saunders Company.

Yamamoto, Y. et al., Roles of the Age-Rage System in Vascular Injury in Diabetes, Annals of the New York Academy of Sciences, 2000, 163-172, 902 (1), The New York Academy of Sciences, U.S.A.

Wautier, J. et al., Receptor-Mediated Endothelial Cell Dysfunction in Diabetic Vasculopathy. Soluble Receptor for Advanced Glycation End Products Blocks Hyperpermeability In Diabetic Rats, Journal of Clinical Investigation, Jan. 1996, 238-243, vol. 97 (1), The American Society for Clinical Investigation, Ann Arbor, Michigan, U.S.A.

Schmidt, A.. et al., Advanced Glycation End Products Interacting with Their Endothelial Receptor Induce Expression of Vascular Cell Adhesion Molecule-1 (VCAM-1) in Cultured Human Endothelial Cells and in Mice. A Potential Mechanism for the Accelerated Vasculopathy of Diabetes, Journal of Clinical Investigation, 1995, 1395-1403, vol. 96 (3), The American Society for Clinical Investigation, Ann Arbor, Michigan, U.S.A.

Park, L. et al., Suppression of Accelerated Diabetic Atherosclerosis by the Soluble Receptor for Advanced Glycation Endproducts, Nature Medicine, Sep. 1998, 1025-1031, vol. 4 (9), Nature Publishing Group, New York, New York, U.S.A.

Taguchi, A. et al., Blockage of RAGE-Amphoterin Signalling Suppresses Tumour Growth and Metastases, Nature, 2000, 354-360, vol. 405, Nature Publishing Group, New York, New York, U.S.A.

Hofmann, M. et al., RAGE Mediates A Novel Proinflammatory Axis: A Central Cell Surface Receptor for s100/Calgranulin Polypeptides, Cell, Jun. 1999, 889-901, vol. 97 (7), Cell Press, U.S.A.

Yan, S. et al., Amyloid-β Peptide-Receptor for Advanced Glycation End Product End Product Interaction Elicits Neuronal Expression of Macrophage-Colony Stimulating Factor: A Proinflammatory Pathway in Alzheimer Disease, Proceedings of the National Academy of Sciences of the United States of America, May 1997, 5296-5301, vol. 94 (10), The National Academy of Sciences, Washington D.C., U.S.A.

Lander, H. et al., Activation of the Receptor for Advanced Glycation End Products Triggers a p21 (ras)-dependent Mitogen-Activated Protein Kinase Pathway Regulated by Oxidant Stress, Journal of Biological Chemistry, Jul. 1997, 17810-17814, vol. 272 (28), The American Society for Biochemistry and Molecular Biology.

Thornalley, P., Cell Activation by Glycated Proteins, AGE Receptors, Receptor Recognition Factors and Functional Classification of AGEs, Cellular Molecular Biology, 1998, 1013-1023, vol. 44 (7), France.

Orford, J. et al., The Comparative Pathobiology of Atherosclerosis and Restenosis, American Journal of Cardiology, Aug. 2000, 6H-11H, vol. 86, (4) (2), Excerpta Medica, Inc.

Bult, H., Restenosis: A Challenge for Pharmacology, Trends in Pharmocological Science, Jul. 2000, 274-279, vol. 21 (7), Elsevier Science Ltd., United Kingdom.

Schwartz, S., Smooth Muscle Migration in Atherosclerosis and Restenosis, Journal of Clinical Investigation, Jun. 1997, 2814-2816, vol. 99 (12), The American Society for Clinical Investigation, Ann Arbor, Michigan, U.S.A.

Peyrottes, S. et al, Oligodeoxynucleoside Phosphoramidates (P-NH$_2$): Synthesis and Thermal Stability of Duplexes with DNA and RNA Targets, Nucleic Acids Research, May. 1996, 1841-1848, vol. 24 (10), Oxford University Press, United Kingdom.

Chaturvedi, S. et al., Stabilization of Triple-Stranded Oligonucleotide Complexes: Use of Probes Containing Alternating Phosphodiester and Stereo-Uniform Cationic Phosphoramidate Linkages, Nucleic Acids Research, Jun. 1996, 2318-2323, vol. 24 (12), Oxford University Press, United Kingdom.

Beaucage, S. et al., Deoxynucleoside Phosphoramidites—A New Class of Key Intermediates for Deoxypolynucleotide Synthesis, Tetrahedron Letters, 1981, 1859-1862, vol. 22 (20), Pergamon Press Ltd.

Matteucci, M. D. et al., Synthesis of Deoxyoligonucleotides on A Polymer Support, Journal of the American Chemical Society, Jun. 1981, 3185-3191, vol. 103 (11), American Chemical Society, Washigton D.C., U.S.A.

Hradil, P. et al.., Preparation of 1,2-Disubstituted-3-Hydroxy-4(1*H*)-Quinolinones and the Influence of Substitution on the Course of Cyclization, Journal of Heterocyclic Chemistry, 1999, 141-144, vol. 36 (1).

Walpole, C. et al., Similarities and Differences in the Structure-Activity Relationships of Capsaicin and Resiniferatoxin Analogues, Journal of Medicinal Chemistry, Jul. 1996, 2939-2952, vol. 39 (15), American Chemical Society, Washigton D.C., U.S.A.

Buess, C. et al., Preparation and Mass Spectra of 2,5-Diaryl-1,4-Dithiins, Journal of Heterocyclic Chemistry, 1972, 887-889, vol. 9.

Hasem, M. et al., Oxidation of Dibromocyclopropanocycloalkanes to Ketones, Indian Journal of Chemistry, Section B—Organic Chemistry Including Medicinal Chemistry, Jan. 1990, 75-77, vol. 29B (1), Publications and Information Directorate, CSIR, New Delhi, India.

Radchenko, O., Synthesis of Polycarpine, A Cytotoxic Sulfur-Containing Alkaloid from the Ascidian *Polycarpa Aurata*, and Related Compounds, Tetrahedron Letters, May 1997, 3581-3584, vol. 38 (20), Elsevier Science Ltd.

Wilman, D., Prodrugs in Cancer Chemotherapy, Biochemical Society Transactions, 1986, 375-382, vol. 14, The Biochemical Society, United Kingdom.

Stella, V. et al., Prodrugs: A Chemical Approach to Targeted Drug Delivery, Directed Drug Delivery A Multidisciplinary Problem, 1985, 247-267, Humana Press, Clifton, New Jersey.

Massey, R., Catalytic Antibodies Catching On, Nature, Jul. 1987, 457-458, vol. 328, Nature Publishing Group, New York, New York, U.S.A.

Brem, H. et al., Interstitial Chemotherapy with Drug Polymer Implants for the Treatment of Recurrent Gliomas, Journal of Neurosurgery, 1991, 441-446, vol. 74, American Association of Neurological Surgeons, Charlottesville, Virginia.

Eppstein, D. et al., Biological Activity of Liposome-Encapsulated Murine Interferon Gamma is Mediated by a Cell Membrane Receptor, Proceedings of the National Academy of Sciences of the United States of America, Jun. 1985, 3688-3692, vol. 82 (11), The National Academy of Sciences, Washington D.C., U.S.A.

Hwang, K.. et al., Hepatic Uptake and Degradation of Unilamellar Sphingomyelin-Cholesterol Liposomes: A Kinetic Study, Proceedings of the National Academy of Sciences of the United States of America, Jul. 1980, 4030-4034, vol. 77 (7), The National Academy of Sciences, Washington D.C., U.S.A.

Dupont, H., et al., *Escherichia Coli* Diarrhea, Bacterial Infections of Humans: Epidemiology and Control, 1991, 239-254, 2$^{nd}$ Ed., Plenum Medical Book Co., New York, New York.

Wood, et al., Staphylococcal Enterotoxins and the Immune System, FEMS Microbiology Immunology, Jun. 1991, 121-133, vol. 76 (3), Elsevier Science Publishers B.V.

Marrack, P. et al., The Staphylococcal Enterotoxics and Their Relataives, Science, May 1990, 705-177, vol. 248, The American Association for the Advancement of Science, Washington, D.C.

Hinman, L. et al., Preparation and Characterization of Monoclonal Antibody Conjugates of the Calicheamicins: A Novel and Potent Family of Antitumor Antibiotics, Cancer Research, Jul. 1993, 3336-3342, vol. 53 (14), The American Association of Cancer Research, Philadelphia, Pennsylvania.

Lode, H. et al., Targeted Therapy with A Novel Enediyene Antibiotic Calicheamicin Theta[1], Effectively Suppresses Growth and Dissermination of Liver Metastases in a Syngeneic Model of Murine Neuroblastoma, Cancer Research, Jul. 1998, 2925-2928, vol. 58(14), The American Association of Cancer Research, Philadelphia, Pennsylvania.

Rosenberg, R. et al., Heparan Sulfate Proteoglycans of the Cardiovascular System—Specific Structures Emerge But How Is Synthesis Regulated?, Journal for Clinical Investigation, May 1997, 2062-2070, vol. 99 (9), The American Society of Clinical Investigation, Inc., Ann Arbor, Michigan.

Wight, T., The Extracellular Matrix and Atherosclerosis, Current Opinions in Lipidology, Oct. 1995, 326-334, vol. 6 (5), Lippincott Williams and Wilkins.

Vlodavsky, I. et al., Expression of Heparanase by Platelets and Circulating Cells of the Immune System: Possible Involvement in Diapedesis and Extravasation, Invasion Metastasis, 1992, 113-127, vol. 12, S. Karger Medical and Scientific Publishers.

Nakajima, M. et al., Tumor Metastasis-Associated Heparanase (Heparan Sulfate Endoglycosidase) Activity in Human Melanoma Cells, Jun. 1986, Cancer Letters, 277-283, vol. 31, Elsevier Scientific Publishers Ireland Ltd.

Nakajima, M. et al., Heparanases and Tumor Metastasis, Journal of Cellular Biochemistry, Jan. 1988, 157-167, vol. 36 (1), Alan R. Liss, Inc., New York, New York.

Ricoveri, W. et al., Heparan Sulfate Endoglycosidase and Metastatic Potential in Murine Fibrosarcoma and Melanoma, Cancer Research, Aug. 1986, 3855-3861, vol. 46 (8), The American Association for Cancer Research, Philadelphia, Pennsylvania.

Gallagher, J. et al., Heparan Sulphate-Degrading Endoglycosidase in Liver Plasma Membranes, Biochemical Journal, 1988, 719-726, vol. 250, The Biochemical Society, United Kingdom.

Dempsey, L.. et al., Heparanase Expression in Invasive Trophoblasts and Acute Vascular Damage, Glycobiology, 2000, 467-475, vol. 10 (5), Oxford Univerisity Press, United Kingdom.

Goshen, R. et al., Purification and Characterization of Placental Heparanase and Its Expression by Cultured Cytotrophoblasts, Molecular Human Reproduction, 1996, 679-684, vol. 2 (9), Oxford University Press, United Kingdom.

Parish, C. et al., Treatment of Central Nervous System Inflammation with Inhibitors of Basement Membrane Degradation, Immunology and Cell Biology, Feb. 1998, 104-113, vol. 76 (1), Blackwell Science.

Gilat, D. et al., Molecular Behavior Adapts to Context: Heparanase Functions as an Extracellular Matrix-Degrading Enzyme or as A T Cell Adhesion Molecule, Depending on the Local pH, Journal of Experimental Science, May 1995, 1929-1934, vol. 181 (5), Rockefellar University Press, New York, New York.

Graham, L. et al., Comparison of the Heparanase Enzymes from Melanoma Cells, Mouse Macrophages, and Human Platelets, Biochemistry and Molecular Biology International, May 1996, 563-571, vol. 39 (3), Academic Press, Australia.

Pillarisetti, S. et al., Lysolecithin-Induced Alteration of Subendothelial Heparan Sulfate Proteoglycans Increases Monocyte Binding to Matrix, The Journal of Biological Chemistry, Dec. 1995, 29760-29765, vol. 270 (5), The American Society for Biochemistry and Molecular Biology, Inc., Bethesda, Maryland.

Nakajima, M. et al., Heparan Sulfate Degradation: Relation to Tumor Invasive and Metastatic Properties of Mouse B16 Melanoma Sublines, Science, 1983, 611-613, vol. 220, The American Association for the Advancement of Science, Washington, D.C.

Nakajima, M. et al., Basement Membrane Degradative Enzymes as Possible Markers of Tumor Metastasis, Progress in Clinical Biology Research, 1986, 113-122, vol. 212.

Freeman, C. et al., A Rapid Quantitative Assay for the Detection of Mammalian Heparanase Activity, Biochemical Journal, Jul. 1997, 229-237, vol. 325, The Biochemical Society, United Kingdom.

Vlodavsky, I. et al., Mammalian Heparanase: Gene Cloning, Expression and Function in Tumor Progression and Metastasis, Nature Medicine, Jul. 1999, 793-802, vol. 5 (7), Nature Publishing Group, New York, New York.

Hulett M. et al., Cloning of Mammalian Heparanase, an Important Enzyme in Tumore Invasion and Metastasis, Nature Medicine, Jul. 1999, 803-809, vol. 5 97), Nature Publishing Group, New York, New York.

Khan, M. et al., A Rapid Colorimetric Assay for Heparinase Activity, Analytical Biochemistry, 1991, 373-376, vol. 196 (2), Academic Press, Inc., U.S.A.

Birrell, A. et al., Functional and Structural Abnormalities in the Nerves of Type I Diabetic Baboons: Aminoguanidine Treatment Does Not Improve Nerve Function, Diabetologica, 2000, 110-116, vol. 43, Springer-Verlag, Heidelberg.

Wada, R. et al., Only Limited Effects of Aminoguanidine Treatment on Peripheral Nerve Function, $(Na^+,K^+)$-ATPase Activity and Thrombomodulin Expression in Streptozotocin-Induced Diabetic Rats, Diabetologica, 1999, 743-747, vol. 42, Springer-Verlag, Heidelberg.

Soulis, T. et al., Effects of Aminoguanidine in Preventing Experimental Diabetic Nephropathy are Related to the Duration of Treatment, Kidney International, Aug. 1996, 627-634, vol. 50 (2), Blackwell Science, Inc.

Cooper, M. et al., The Cross-Link Breaker, N-Phenacylthiazolium Bromide Prevents Vascular Advanced Glycation End-Product Accumulation, Diabetologica, 2000, 660-664, vol. 43 (5), Springer-Verlag, Heidelberg.

Oturai, P. et al., Effects of Advanced Glycation End-Product Inhibition and Cross-Link Breakage in Diabetic Rats, Metabolism, Aug. 2000, 996-1000, vol. 49 (8), W. B. Saunders Company.

Laight, D. et al., Endothelial Cell Dysfunction and the Pathogenesis of Diabetic Macroangiopathy, Diabetes/Metabolism Research and Reviews, 1999, 274-282, vol. 15 (4), Wiley-Interscience.

Stehouwer. C. et al., Endothelial Dysfunction and Pathogenesis of Diabetic Angiopathy, Cardiovascular Research, 1997, 55-68, vol. 34 (1), Elsevier Science B.V.

Libby, P., Changing Concept of Atherogenisis, Journal of Internal Medicine, 2000, 349-358, vol. 247 (3), Blackwell Publishing, Stockholm, Sweden.

Van Lente, F., Markers of Inflammation as Predictors in Cardiovascular Disease, Clinica Chimica Acta, 2000, 31-52, vol. 293 (1-2), Elsevier Science B.V.

Horii, Y. et al., Role of Interleukin-6 in the Progression of Mesangial Proliferative Glomerulonephritis, Kidney International Supplement, Jan. 1993, S71-S75, vol. 39, Blackwell Scientific Publications.

Huber, S. et al., Interleukin-6 Exacerbates Early Atherosclerosis in Mice, Arteriosclerosis, Thrombosis, and Vascular Biology, 1999, 2364-2367, vol. 19, American Heart Association, Inc., U.S.A.

Shikano, M. et al., Usefulness of a Highly Sensitive Urinary and Serum IL-6 Assay in Patients with Diabetic Nephropathy, Nephron, 2000, 81-85, vol. 85 (1), Karger Medical and Scientific Publishers, Basel, Switzerland.

Pickup, J. et al., Plasma Interleukin-6, Tumour Necrosis Factor Alpha and Blood Cytokine Production in Type 2 Diabetes, Life Sciences, 2000, 291-300, vol. 67 (3), Elsevier Science, Inc., U.S.A.

Kado, S. et al., Circulating Levels of Interleukin-6, Its Soluble Receptor and Interleukin-6/Interleukin-6 Receptor Complexes in Patients with Type 2 Diabetes Mellitus, Acta Diabetologica, 1999, 67-72, vol. 36 (1-2), Springer-Verlag Italia Srl.

Eitner, F. et al., Role of Interleukin-6 in Mediating Mesangial Cell Proliferation and Matrix Production in Vivo, Kidney International, 1997, 69-78, vol. 51 (1), Blackwell Science, Inc.

Banba, N.et al., Possible Relationship of Monocyte Chemoattractant Protein-1 with Diabetic Nephropathy, Kidney International, Aug. 2000, 684-690, vol. 58 (2), Blackwell Science, Inc.

Haab, B. et al., Two-color, Rolling Circle Amplification on Antibody Microarrays for Sensitive, Multiplexed Serum-Protein Measurements, Genome Biology, 2001, 1-12, vol. 2 (2), BioMed Central Ltd.

Brown, M. et al., Knowledge-Based Analysis of Microarray Gene Expression Data by Using Support Vector Machines, Proceedings of the National Academy of Sciences of the United States of America, Jan. 2000, 262-267, vol. 97 (1), The National Academy of Sciences, Washington, D.C.

Getz, G. et al., Coupled Two-Way Clustering Analysis of Gene Microarray Data, Proceedings of the National Academy of Sciences of the United States of America, Oct. 2000, 12079-12084, vol. 97 (22), The National Academy of Sciences, Washington, D.C.

Harrington, C. et al., Monitoring Gene Expression Using DNA Microarrays, Current Opinions in Microbiology, Jun. 2000, 285-291, vol. 3 (3), Elsevier Science Ltd.

Holter, N. et al., Fundamental Patterns Underlying Gene Expression Profiles: Simplicity from Complexity, Proceedings of the National Academy of Sciences of the United States of America, Jul. 2000, 8409-8414, vol. 97 (15), The National Academy of Sciences, Washington, D.C.

MacBeath, G. et al., Printing Proteins as Microarrays for High-Throughput Function Determination, Science, Sep. 2000, 1760-1763, vol. 289 (5485), The American Association for the Advancement of Science, Washington, D.C.

Duggan, D. et al., Expression Profiling Using cDNA Microarrays, Nature Genetics, Jan. 1999, 10-14, vol. 21, Nature Publishing Group, New York, New York.

Lipshutz, R. et al., High Density Synthetic Oligonucleotide Array, Nature Genetics, 1999, 20-24, vol. 21, Nature Publishing Group, New York, New York.

Eisen, M. et al., Cluster Analysis and Display of Genome-Wide Expression Patterns, Proceedings of the National Academy of Sciences of the United States of America, Dec. 1998, 14863-14868, vol. 95 (25), The National Academy of Sciences, Washington, D.C.

Ermolaeva, O. et al., Data Management and Analysis for Gene Expression Arrays, Nature Genetics, Sep. 1998, 19-23, vol. 20 (1), Nature Publishing Group, Inc., New York, New York.

Hacia, J. et al., Two Color Hybridization Analysis Using High Density Oligonucleotide Arrays and Engery Transfer Dyes, Nucleic Acids Research, Aug. 1998, 3865-3866, vol. 26, Oxford University Press, United Kingdom.

Lockhart, D. et al., Genomics and DNA Chips, Nucleic Acids Symposium, Feb. 1998, 11-12, No. 38, Oxford University Press, United Kingdom.

Schena, M. et al., Microarrays: Biotechnology's Discovery Platforms for Functional Genomics, Trends in Biotechonology, Jul. 1998, 301-306, vol. 16 (7), Elsevier Science, Ltd.

Shalon, D. et al., Gene Expression Micro-Arrays: A New Tool for Genomic Research, Pathology and Biology, Feb. 1998, 107-109, vol. 46 (2), *Société d'Edition de l'Association d'Enseignement Médical des Hoôpitaux de Paris*, France.

Welford, S. et al., Detection of Differentially Expressed Genes in Primary Tumor Tissues Using Representational Differences Analysis Coupled to Microarray Hybridization, Nucleic Acids Research, Jun. 1998, 3059-3065, vol. 36, Oxford University Press, United Kingdom.

Blanchard, A. et al., High Density Oligonucleotide Arrays, Biosensors and Bioelectronics, 1996, 687-690, vol. 11, Elsevier Science Ltd.

Lockhart, D. et al., Expression Monitoring by Hybridization to High-Density Oligonucleotide Arrays, Nature Biotechnology, Dec. 1996, 1675-1680, vol. 14 (13), Nature Publishing Group, New York, New York.

Schena, M. et al., Parallel Human Genome Analysis: Microarray-Based Expression Monitoring of 1000 Genes, Proceedings of the National Academy of Sciences of the United of America, Oct. 1996, 10614-10619, vol. 93 (20), The National Academy of Sciences, Washington, D.C.

Tamayo, P. et al., Interpreting Patterns of Gene Expression with Self-Organizing Maps: Methods and Application to Hematopoietic Differentiation, Proceedings of the National Academy of Sciences of the United States of America, Oct. Mar. 1999, 2907-2912, vol. 96 (6), The National Academy of Sciences, Washington, D.C.

Schena, M. et al., Quantitative Monitoring of Gene Expression Patterns with A Complementary DNA Microarray, Science, Oct. 1995, 467-470, vol. 270, The American Association for the Advancement of Science, Washington, D.C.

Rival, Y. et al., Synthesis and Antibacterial Activity of Some Imidazo [1,2-α]pyrimidine Derivatives, Chemical and Pharmaceutical Bulletin, 1992, 1170-1176, vol. 40 (5), The Pharmaceutical Society of Japan, Tokyo, Japan.

* cited by examiner

HETEROCYCLIC COMPOUNDS AND METHODS OF MAKING AND USING THEREOF

CROSS-REFERENCE TO RELATED APPLICATION

This application claims the benefit of U.S. Provisional Patent Application Ser. No. 60/610,163, filed Sep. 15, 2004, which incorporated by reference in its entirety, and India Provisional Patent Application No. 861/CHE/2003, which is incorporated by reference herein in its entirety.

FIELD OF THE INVENTION

The present invention relates to compounds, pharmaceutical compositions, and methods of making and use thereof.

BACKGROUND OF THE INVENTION

Glycated proteins and advanced glycation end products (AGE) contribute to cellular damage, for example, diabetic tissue injury. This can occur by at least by two major mechanisms: modulation of cellular functions through interactions with specific cell surface receptors, and alteration of the extracellular matrix leading to the formation of protein cross-links. Studies suggest that glycated protein and AGE interactions with cells promote inflammatory processes and oxidative cellular injury. AGE increases lipoprotein oxidisability and atherogenicity. Further, AGE binding to matrix proteins induces synthesis of IL-1, TNFa, VCAM-1, Heme oxygenase, insulin like growth factor, IL-6 and activates NF-?B. Diseases for which glycated protein and AGE accumulation is a suspected etiological factor include, but are not limited to, vascular complications of diabetes, microangiopathies, renal insufficiency, and Alzheimer's disease.

The exact mechanism by which high plasma glucose causes microvascular damage, as seen in diabetes, are not completely understood. One potential mechanism by which hyperglycemia can be linked to microangiopathies is through the process of non-enzymatic glycation of critical proteins. Non-enzymatic glycation of critical proteins is discussed in Nonenzymatic glycosylation and the pathogenesis of diabetic complications, Ann. Intern. Med., 1984(101)527-537; Advanced glycation end products up-regulate gene expression found in diabetic glomerular disease, Proc. Natl. Acad. Sci. USA., 1994 (91)9436-40; Expression of advanced glycation end products and their cellular receptor RAGE in diabetic nephropathy and nondiabetic renal disease, J. Am. Soc. Nephrol., 2000 (11)1656-66; and Activation of receptor for advanced glycation end products: a mechanism for chronic vascular dysfunction in diabetic vasculopathy and atherosclerosis., Circ. Res., 1999 (84)489-97).

Non-enzymatic glycation, i.e., the linking of proteins with glucose, leads to the formation of glycated proteins. The first step in this glycation pathway involves the non-enzymatic condensation of glucose with free amino groups in the protein, primarily the epsilon-amino groups of lysine residues, forming the Amadori adducts. These early glycation products can undergo further reactions such as rearrangements, dehydration, and condensations to form irreversible advanced glycation end products (AGE). These are a highly reactive group of molecules whose interaction with specific receptors on the cell-surface that may lead to pathogenic outcomes. Accumulation of glycated proteins have been demonstrated in the basement membrane of patients with diabetes and are thought to be involved in the development of diabetic nephropathy and retinopathy. See Immunohistochemical localization of glycated protein in diabetic rat kidney., Diabetes Res. Clin. Pract., 1990(8)215-9; and Role of Amadori-modified nonenzymatically glycated serum proteins in the pathogenesis of diabetic nephropathy., J. Am. Soc. Nephrol., 1996(7)183-90. See Inhibitors of AGE formation, such as aminoguanidine, have been shown to block the formation of AGE and prevent development of diabetes complications, including diabetic retinopathy (Aminoguanidine prevents diabetes-induced arterial wall protein cross-linking, Science, 1986(232)1629-1632; Prevention of cardiovascular and renal pathology of aging by the advanced glycation inhibitor aminoguanidine, Proc. Natl. Acad. Sci. USA., 1996(93)3902-7; and Potential benefit of inhibitors of advanced glycation end products in the progression of type II diabetes: a study with aminoguanidine in C57/BLKsJ diabetic mice., Metabolism, 1998(47)1477-80.

One characterized AGE receptor is RAGE, receptor for AGE. See Activation of receptor for advanced glycation end products: a mechanism for chronic vascular dysfunction in diabetic vasculopathy and atherosclerosis, Circ. Res. 1999 (84)489-97; and Roles of the AGE-RAGE system in vascular injury in diabetes., Ann. NY Acad. Sci. 2000 (902)163-70; discussion 170-2. Several in vitro and in vivo studies demonstrate that blocking RAGE either by antibodies or by adding a soluble form of the receptor inhibits diabetic vasculopathy including diabetic atherosclerosis. See Receptor-mediated endothelial cell dysfunction in diabetic vasculopathy. Soluble receptor for advanced glycation end products blocks hyperpermeability in diabetic rats., J. Clin. Invest., 1996(97)238-43; Advanced glycation end products interacting with their endothelial receptor induce expression of vascular cell adhesion molecule-1 (VCAM-1) in cultured human endothelial cells and in mice. A potential mechanism for the accelerated vasculopathy of diabetes., J. Clin. Invest., 1995(96)1395-403; and Suppression of accelerated diabetic atherosclerosis by the soluble receptor for advanced glycation endproducts, Nat. Med. 1998(4)1025-31. Other than AGE, RAGE appears to mediate the binding of several other ligands that are involved in normal physiology as well as pathology. See Blockade of RAGE-amphoterin signalling suppresses tumour growth and metastases, Nature, 2000(405)354-60; RAGE mediates a novel proinflammatory axis: a central cell surface receptor for S100/calgranulin polypeptides, Cell, 1999(97)889-901; and Amyloid-beta peptide-receptor for advanced glycation end product interaction elicits neuronal expression of macrophage-colony stimulating factor: a proinflammatory pathway in Alzheimer disease, Proc. Natl. Acad. Sci., USA., 1997(94)5296-301. Thus, merely blocking RAGE might have other unintended consequences. Moreover, since blocking RAGE could lead to accumulation of AGE in circulation, the long-term effects of blocking RAGE are unknown and may be more harmful than the pathology sought to be treated.

One useful method to block AGE effects would be to develop inhibitors that block AGE induced signaling. See Activation of the receptor for advanced glycation end products triggers a p21 (ras)-dependent mitogen-activated protein kinase pathway regulated by oxidant stress, J. Biol. Chem., 1997(272)17810-4; and Cell activation by glycated proteins; AGE receptors, receptor recognition factors and functional classification of AGEs., Cell. Mol. Biol.(Noisy-le-grand), 1998(44)1013-23. However, the sequence of these signaling events leading to inflammation is not clear. Accordingly, what is needed are compounds that can block AGE-induced activities, particularly AGE-induced inflammation, or more particularly, AGE-induced signaling events.

Other chronic conditions for which adequate and effective therapies do not exist are treatments of antiproliferative disorders. Smooth muscle cell (SMC) hyperplasia is an important factor in the development of atherosclerosis and also is responsible for the significant number of failure rates following vascular procedures such as angioplasty and coronary artery bypass surgery. See, The comparative pathobiology of atherosclerosis and restenosis. Am. J. Cardiol. 86:6H-11H (2000); and Restenosis: a challenge for pharmacology. Trends Pharmacol Sci. 21:274-9. In the normal vessel, SMC are quiescent, but they proliferate when damage to the endothelium occurs. Naturally occurring growth modulators, many of which are derived from the endothelium, tightly control SMC proliferation in vivo.

Abnormal vascular smooth muscles cell (VSMC) proliferation may contribute to the pathogenesis of vascular occlusive lesions, including atherosclerosis, vessel re-narrowing after successful angioplasty (restenosis), and graft atherosclerosis after coronary transplantation. VSMC is discussed in The comparative pathobiology of atherosclerosis and restenosis. Am. J. Cardiol. 86:6H-11H; and Smooth muscle migration in atherosclerosis and restenosis. J Clin Invest. 100:S87-9. Many humans and animals have limited lifespans and lifestyles because of such conditions. Currently there are no known effective pharmacological treatments available that control these occlusive pathologies, particularly restenosis.

Percutaneous coronary artery intervention (PTCA) procedures are the most common in-patient hospital procedure in the United States. According to the American Heart Association, about one-third of the patients that undergo balloon angioplasty have restenosis of the widened segment within approximately six months. It may be necessary to perform another angioplasty or coronary artery bypass surgery on restenosed arteries. A key feature of restenosis is an injury response that results in activation of an inflammatory cascade and remodeling of the cells both inside and outside the carotid artery wall. This includes excessive growth of connective tissue and smooth muscle into the lumen of the artery known as neointimal hyperplasia. Currently there are no effective pharmacological treatments available that control the pathogenesis of vascular occlusive lesions, such as, but not limited to, arteriosclerosis, atherosclerosis, restenosis, and graft atherosclerosis after coronary transplantation. Identification of effective therapeutics with minimal side effects will restore quality of life without requiring additional surgical procedures such as coronary artery bypass surgery.

Smooth muscle cell (SMC) hyperplasia is a major event in the development of atherosclerosis and also may contribute to failure rates following vascular procedures such as angioplasty and coronary artery bypass surgery. In the normal vessel, SMC are quiescent, but they proliferate when damage to the endothelium occurs. Naturally occurring growth modulators, many of which are derived from the endothelium, tightly control SMC proliferation in vivo. Accordingly, there is a need for methods and compositions for the alteration of gene expression in arterial wall cells to inhibit thrombosis and SMC proliferation. In particular, what is needed are methods and compositions that inhibit SMC proliferation and related intimal hyperplasia.

U.S. Pat. No. 6,028,088 is directed to specific thiazolidinedione compounds, which are described as antiproliferative, anti-inflammatory and antiinfective agents. According to the disclosure, these specific compounds are used in the treatment of certain endocrine diseases, malignant, and non-malignant proliferative diseases, and cardiovascular disorders.

Thus, there is a need for treatments of vascular occlusive pathologic conditions, and particularly, restenosis. Since occurrence is frequent, the currently available treatments are costly and the conditions are refractory to many pharmacological therapies. The mechanisms involved in the control of vascular conditions related to SMC function are not clear and no conventional preventive therapy against SMC activation is available. Accordingly, methods and compositions for treatment and prevention of vascular occlusive conditions are needed. In particular, methods and compositions to prevent and treat restenosis following treatments of vascular tissues are needed. The present invention is directed to overcoming these and other deficiencies in the art.

SUMMARY OF THE INVENTION

The present invention is related to compounds of formula (I), and to methods and/or compositions comprising compounds that are effective in modulating inflammatory responses, such as those resulting from AGE and glycated protein accumulation. The present invention also is directed to methods and/or compositions comprising compounds that are effective in modulating smooth muscle cell proliferation and the diseases or conditions related thereto.

The present invention provides compounds and compositions that inhibit inflammatory responses, particularly those resulting from AGE and glycated protein accumulation. Further, the present invention provides compounds and compositions that inhibit smooth muscle cell proliferation, which may be mediated by pro-inflammatory cytokines like IL-6, IL-1, TNF-a, MCP-1, or by inducing the expression of perlecan, a heparin sulfate proteoglycan (HSPG).

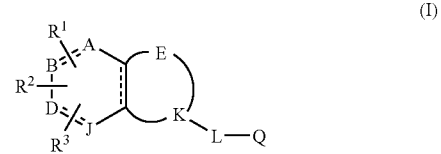

(I)

The present invention provides novel compounds of formula (I), their pharmaceutically acceptable salts, and pharmaceutical compositions containing one or more of such compounds, optionally in combination with other active ingredients.

The present invention also provides a process for preparing compounds of the formula (I) as defined above, their salts, and pharmaceutically acceptable compositions thereof.

The present invention also provides novel compounds of formula (II), their pharmaceutically acceptable salts, and pharmaceutical compositions containing one or more of such compounds, optionally in combination with other active ingredients.

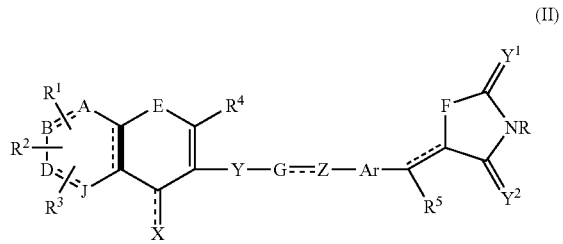

(II)

The present invention also provides a process for preparing compounds of the formula (II) as defined above, their salts, and pharmaceutically acceptable compositions thereof.

The present invention also provides novel compounds of formula (III), including but not limited to, their pharmaceutically acceptable salts and pharmaceutical compositions containing them, or their mixtures, or in combination with other active ingredients.

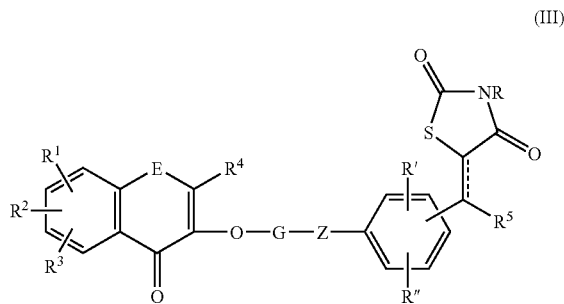

(III)

The present invention also provides a process for preparing compounds of the formula (III) as defined above, their salts, and pharmaceutically acceptable compositions thereof.

The present invention also provides novel compounds of formula (IV), their pharmaceutically acceptable salts, and pharmaceutical compositions containing one or more of such compounds, optionally in combination with other active ingredients.

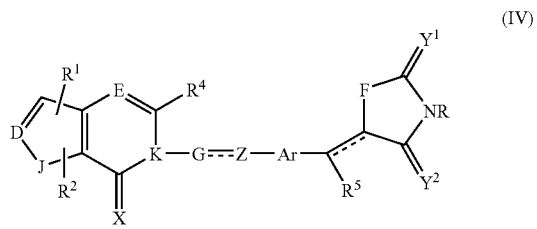

(IV)

The present invention also provides a process for preparing compounds of the formula (IV) as defined above, their salts, and pharmaceutically acceptable compositions thereof.

The present invention provides novel compounds of formula (V), their pharmaceutically acceptable salts, and pharmaceutical compositions containing one or more of such compounds, optionally in combination with other active ingredients.

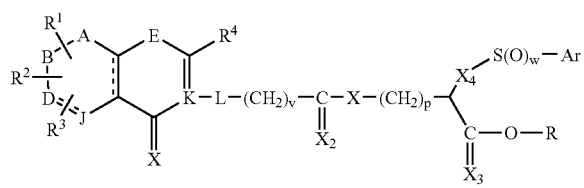

The present invention also provides a process for preparing compounds of the formula (V) as defined above, their pharmaceutically acceptable salts, and their pharmaceutically acceptable compositions.

According to one aspect of the present invention, a method of using a compound of formula (I) comprises treatment and/or prophylaxis of inflammatory conditions, such as those mediated by AGE or glycated protein accumulation. Such inflammatory conditions include diabetic vascular complications, including diabetic retinopathy, microangiopathies, renal insufficiency and Alzheimer's disease.

According to another aspect of the present invention, a method of inhibiting smooth muscle cell proliferation comprises administering an effective amount of a compound contemplated hereby. The present invention also provides methods for inhibiting an inflammatory response, including inflammatory responses in endothelial cells, comprising administering an effective amount of a compound contemplated hereby. The present invention also provides methods for inhibiting thrombosis comprising administering an effective amount of a compound contemplated hereby.

The present invention also provides a method for treating or preventing organ transplant vasculopathy in a subject comprising the step of administering a therapeutically effective amount of a compound contemplated hereby. The transplanted organ may include, but is not limited to, liver, kidney, heart, lung, pancreas, pancreatic islets, and skin. Such a method may further comprise the step of administering a therapeutically effective amount of an immunosuppressive agent. The immunosuppressive agent may include, but is not limited to, CellCept, Gengraf, Micrhogam, Neoral, Orthoclone OKT3, Prograf, Rapamune, Sandimmune, Thymoglobulin, and Zenapax.

The present invention also provides a method for treating or preventing restenosis in a subject comprising administering a therapeutically effective amount of a compound contemplated hereby. The present invention also provides a method for treating or preventing atherosclerosis in a subject comprising administering a therapeutically effective amount of a compound contemplated hereby.

The present invention also provides a method for treating disease mediated by inflammation in a subject comprising the step of administering a therapeutically effective amount of a compound contemplated hereby. More specifically, the disease mediated by inflammation may be an autoimmune disease. In this regard, the autoimmune disease may be alopecia areata, ankylosing spondylitis, antiphospholipid syndrome, autoimmune Addison's disease, autoimmune hemolytic anemia, autoimmune hepatitis, Behcet's disease, bullous pemphigoid, cardiomyopathy, celiac sprue-dermatitis, chronic fatigue immune dysfunction syndrome (CFIDS), chronic inflammatory demyelinating polyneuropathy, Churg-Strauss syndrome, cicatricial pemphigoid, CREST syndrome, cold agglutinin disease, Crohn's disease, discoid lupus, essential mixed cryoglobulinemia, fibromyalgia-fibromyositis, Graves' disease, Guillain-Barré, Hashimoto's thyroiditis, idiopathic pulmonary fibrosis, idiopathic thrombocytopenia purpura (ITP), IgA nephropathy, insulin dependent diabetes, juvenile arthritis, lichen planus, méni ère's disease, mixed connective tissue disease, multiple sclerosis, myasthenia gravis, pemphigus vulgaris, pernicious anemia, polyarteritis nodosa, polychondritis, polyglandular syndromes, polymyalgia rheumatica, polymyositis and dermatomyositis, primary agammaglobulinemia, primary biliary cirrhosis, psoriasis, Raynaud's phenomenon, Reiter's syndrome, rheumatic fever, rheumatoid arthritis, sarcoidosis, scleroderma, Sjögren's syndrome, stiff-man syndrome, systemic lupus erythematosus, Takayasu arteritis, temporal arteritis/giant cell arteritis, ulcerative colitis, uveitis, vasculitis, vitiligo, and Wegener's granulomatosis.

The present invention further provides a method for treating or preventing cancer in a subject comprising administering a therapeutically effective amount of a compound contemplated hereby. Moreover, the present invention provides a method for treating or preventing metastases in a subject comprising administering a therapeutically effective amount of a compound contemplated hereby to the subject.

Still another aspect of the present invention provides the methods, by using compound of formula (I), which also comprises treatment and/or prophylaxis of proliferative conditions, particularly for inhibition of proliferation of smooth muscle cells, comprising administration of compositions comprising compounds of formula (I). In accordance with the present invention, uses of such compositions comprise prevention and treatment of vascular occlusive conditions including atherosclerosis and restenosis.

Still another aspect of the present invention provides the methods for the treatment and/or prophylaxis of diseases mediated by inflammatory conditions and cellular proliferative conditions, by using the compound of formula (I).

Still yet another aspect of the present invention provides treatment and/or prophylaxis of a disease or disorder mediated by cell adhesion molecules like VCAM-1, where the diseases are inflammatory disorders selected from rheumatoid arthritis, osteoarthrites, asthama, dermatitis, psoriasis, organ transplantation or allograft rejection, autoimmune diabetes or multiple sclerosis; a cardiovascular disease selected from athresclerosis, restenosis, coronary artery disease, angina, small artery disease, diabetes mellitus, diabetic nepropathy or diabetic retinopathy and one of the cell adhesion molecules is VCAM-1.

Still another aspect of the present invention provides treatment and/or prophylaxis of of a disease by delivering the compound(s) of formula (I) at the site of the disease by using a compound(s) of formula (I) coated stents.

The present invention further provides pharmaceutical compositions containing compounds of the general formula (I), their salts, or any mixture thereof in combination with a suitable carrier, solvent, diluent, or medium typically employed in preparing such compositions.

Still further, the present invention provides various compounds and compositions that each may be administered by a route that is oral, parenteral, subcutaneous, intramuscular, intravenous, intrarticular, intrabronchial, intraabdominal, intracapsular, intracartilaginous, intracavitary, intracelial, intracelebellar, intracerebroventricular, intracolic, intracervical, intragastric, intrahepatic, intramyocardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, bolus, vaginal, rectal, buccal, sublingual, intranasal, or transdermal.

The compositions of the present invention also may include formulations of the compounds disclosed, which may be suitable for oral, rectal, ophthalmic, (including intravitreal or intracameral) nasal, topical (including buccal and sublingual), vaginal or parenteral (including subcutaneous, intramuscular, intravenous, intradermal, intratracheal, and epidural) administration. The formulations may conveniently be presented in unit dosage form and may be prepared by conventional pharmaceutical techniques. Such techniques include the step of bringing into association the active ingredient and the pharmaceutical carrier(s) or excipient(s). In general, the formulations are prepared by uniformly and intimately bringing into associate the active ingredient with liquid carriers or finely divided solid carriers or both, and then, if necessary, shaping the product.

Still yet another aspect of the present invention provides novel intermediates, a process for their preparation and use of the intermediates in processes for preparation of compound of formula (I), their salts, and pharmaceutically acceptable compositions thereof.

DEFINITIONS

It is to be understood that this invention is not limited to the particular methodology, protocols, cell lines, constructs, and reagents described herein and as such may vary. It is also to be understood that the terminology used herein is for the purpose of describing particular aspects only, and is not intended to limit the scope of the present invention which will be limited only by the appended claims.

As used herein and in the appended claims, the singular forms a "an", and "the" include plural reference unless the context clearly indicates otherwise. Thus, for example, reference to a "compound" is a reference to one or more such compounds and includes equivalents thereof known to those skilled in the art, and so forth.

Unless defined otherwise, all technical and scientific terms used herein have the same meaning as commonly understood to one of ordinary skill in the art at the time this invention was made.

All publications and patents mentioned herein are incorporated herein by reference for the purpose of describing and disclosing, for example, the constructs and methodologies that are described in the publications, which might be used in connection with the presently described invention. The publications discussed above and throughout the text are provided solely for their disclosure prior to the filing date of the present application. Nothing herein is to be construed as an admission that the inventors are not entitled to antedate such disclosure by virtue of prior invention.

As used herein, the term "compound" includes both the singular and the plural, and includes any single entity or combined entities that have activity that can be measured in the assays of the present invention and combinations, fragments, analogs or derivatives of such entities.

The term "glycated protein", as used herein, includes proteins linked to glucose, either enzymatically or non-enzymatically, primarily by condensation of free epsilon-amino groups in the protein with glucose, forming Amadori adducts. Furthermore, glycated protein, as used herein, includes not only proteins containing these initial glycation products, but also glycation products resulting from further reactions such as rearrangements, dehydration, and condensations that form irreversible advanced glycation end products (AGE). It should be understood that any agent that causes the cells or components of the assay to respond in a measurable manner is contemplated by the present invention. Enhanced formation and accumulation of glycated proteins and AGE are thought to play a major role in the pathogenesis of diabetic complications, and atherosclerosis, leading to the development of a range of diabetic complications including nephropathy, retinopathy and neuropathy. There is ample in vivo evidence that suggests that diabetes-related complications can be reduced by (1) preventing glycation of proteins, (2) by breaking the cross-links in glycated proteins (The cross-link breaker, N-phenacylthiazolium bromide prevents vascular advanced glycation end-product accumulation, Diabetologia, 2000(43)660-4) (or (3) by blocking glycated protein interaction with receptors. Despite the importance of AGE in the pathogenesis of diabetic microangiopathies, there are no currently available medications known to block AGE formation.

The term "phenylamine" refers to a primary or secondary benzeneamine, more commonly known as aniline. The amino group on the aniline may be optionally substituted with hydrogen, alkyl ($C_1$-$C_{12}$, straight chain or branched), cycloalkyl ($C_3$-$C_{10}$), or optionally substituted aryl groups. The phenyl ring of this aniline derivative may be optionally substituted with one or more functional groups, or a combination of functional groups such as alkyl, alkenyl, alkynyl, phenyl, benzyl, halo, cyano, nitro, hydroxy, thioxy, alkoxy, aryloxy, haloalkyloxy, alkylthio, arylthio, amino, alkyl amino, aryl amino, acyl, carboxyl, amido, sulfonamido, sulfonyl, sulfate, sulfonic acid, morpholino, piperazinyl, pyridyl, thienyl, furanyl, pyrroyl, pyrazoyl, phosphate, phosphonic acid, or phosphonate. If applicable, these groups can be represented in protected or unprotected forms used in standard organic synthesis.

The term "naphthylamine" refers to a primary or secondary a- or β-naphthylamine. The ring substructure in the naphthylamine may be optionally substituted with one or a combination of functional groups such as alkyl, alkenyl, alkynyl, phenyl, benzyl, halo, cyano, nitro, hydroxy, thioxy, alkoxy, aryloxy, haloalkyloxy, alkylthio, arylthio, amino, alkyl amino, aryl amino, acyl, carboxyl, amido, sulfonamido, sulfonyl, sulfate, sulfonic acid, morpholino, thiomorpholino, piperazinyl, pyridyl, thienyl, furanyl, pyrroyl, pyrazoyl, phosphate, phosphonic acid, or phosphonate. These groups can be represented in protected or unprotected forms used in standard organic synthesis.

The term "naphthylalkyl amine" refers to a primary or secondary a- and β-naphthylalkyl amine (for example, 2-a-naphthylethyl amine). The term "benzalkyl amine" refers to a primary or secondary benzylalkyl amine (for example, phenylethyl amine). These aryl alkyl substructures or compounds can be optically active or optically inactive. The aryl (ring) substructures of the naphthylalkyl and benzalkyl amines can be optionally subsituted with one or a combination of functional groups, such as alkyl, alkenyl, alkynyl, phenyl, benzyl, halo, cyano, nitro, hydroxy, thioxy, alkoxy, aryloxy, haloalkyloxy, alkylthio, arylthio, amino, alkyl amino, aryl amino, acyl, carbolyl, amido, sulfonamido, sulfonyl, sulfate, sulfonic acid, morpholino, piperazinyl, pyridyl, thienyl, furanyl, pyrroyl, pyrazoyl, phosphate, phosphonic acid, or phosphonate. If applicable these groups can be represented in protected or unprotected forms used in standard organic synthesis.

The term "quinolinyl amine" refers to primary or secondary quinolyl amines. These amines can be in optically active or inactive forms. The aryl (ring) substructure of the quinolyl amine may be optionally substituted with one a combination of functional groups such as alkyl, alkenyl, alkynyl, phenyl, benzyl, halo, cyano, nitro, hydroxy, thioxy, alkoxy, aryloxy, haloalkyloxy, alkylthio, arylthio, amino, alkyl amino, aryl amino, acyl, carboxyl, amido, sulfonamido, sulfonyl, sulfate, sulfonic acid, morpholino, thiomorpholino, piperazinyl, pyridyl, thienyl, furanyl, pyrroyl, pyrazoyl, phosphate, phosphonic acid, or phosphonate. These groups can be represented in protected or unprotected forms used in standard organic synthesis.

The term "heteroaryl amines" refers to pyrroles, pyrazoles, imidazoles, and indoles. The aryl (ring) substructure of the heteroaryl amine may be optionally substituted with one or a combination of functional groups such as alkyl, alkenyl, alkynyl, phenyl, benzyl, halo, cyano, nitro, hydroxy, thioxy, alkoxy, aryloxy, haloalkyloxy, alkylthio, arylthio, amino, alkyl amino, aryl amino, acyl, carboxyl, amido, sulfonamido, sulfonyl, sulfate, sulfonic acid, morpholino, thiomorpholino, piperazinyl, phosphate, phosphonic acid, or phosphonate. These groups can be represented in protected or unprotected forms used in standard organic synthesis.

The term "polynucleotide" refers generally to polymeric forms of nucleotides of any length, either ribonucleotides or deoxynucleotides. Thus, this term includes, but is not limited to, single-stranded, double-stranded, or multi-stranded DNA or RNA. Polynucleotides may further comprise genomic DNA, cDNA, or DNA-RNA hybrids. Moreover, the polynucleotides of the present invention may be synthetically produced.

Polynucleotides may comprise chemically modified, biochemically modified, or derivatized nucleotides. For example, a polynucleotide may comprise, in part, modified nucleotides such as methylated nucleotides or nucleotide analogs. Polynucleotides also may comprise sugars, caps, nucleotide branches, and linking groups such as fluororibose and thioate. In addition, the sequence of nucleotides may be interrupted by non-nucleotide components. Furthermore, a polynucleotide may be modified after polymerization to facilitate its attachment to other polynucleotides, proteins, metal ions, labeling components, or a solid support.

The backbone of the polynucleotide may comprise modified or optionally substituted sugar and/or phosphate groups. Alternatively, the backbone of the polynucleotide may comprise a polymer of synthetic subunits such as phosphoramidites and thus may be an oligodeoxynucleoside phosphoramidate or a mixed phosphoramidate-phosphodiester oligomer. See Peyrottes et al., NUCL. ACIDS RES. (1996) 24:1841-1848, and Chaturvedi et al., NUCL. ACIDS RES. (1996) 24:2318-2323.

The term "homology", as used herein, refers to a degree of complementarity. There may be partial homology or complete homology (i.e., identity). A partially complementary sequence is one that at least partially inhibits an identical sequence from hybridizing to a target polynucleotide; it is referred to using the functional term "substantially homologous". The inhibition of hybridization of the completely complementary sequence to the target sequence may be examined using a hybridization assay (Southern or Northern blot, solution hybridization) under conditions of low stringency. A substantially homologous sequence or probe will compete for and inhibit the binding (i.e., the hybridization) of a completely homologous sequence or probe to the target sequence under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target sequence which lacks even a partial degree of complementarity (for example, less than about 30% identity); in the absence of non-specific binding, the probe will not hybridize to the second non-complementary target sequence.

The term "gene" refers to a polynucleotide sequence that comprises coding sequences necessary for the production of a polypeptide or precursor, and also may include expression control sequences. The polypeptide can be encoded by a full length coding sequence or by any portion of the coding sequence. The gene may be derived in whole or in part from any source known to those of ordinary skill in the art including a plant, a fungus, an animal, a bacterial genome or episome, eukaryotic, nuclear or plasmid DNA, cDNA, viral DNA, or chemically synthesized DNA. A gene may constitute an uninterrupted coding sequence or it may include one or more introns, bound by the appropriate splice junctions. Moreover, a gene may contain one or more modifications in either the coding or the untranslated regions that could affect certain properties of the polynucleotide or polypeptide, such as the biological activity or the chemical structure of the expression product, the rate of expression, or the manner of expression control. Such modifications include, but are not limited to, mutations, insertions, deletions, and substitutions of one or more nucleotides. In this regard, such modified genes may be referred to as "variants" of the "native" gene (discussed below).

"Gene expression" refers to the process by which a polynucleotide sequence undergoes successful transcription and translation such that detectable levels of the nucleotide sequence are expressed.

The term "gene expression profile" refers to a group of genes representing a particular cell or tissue type (for example, neuron, coronary artery endothelium, or disease tissue) in any activation state. In one aspect, a gene expression profile is generated from cells exposed to a compound of the present invention. This profile may be compared to a gene expression profile generated from the same type of cell prior to treatment with a compound of the present invention. Furthermore, a series of gene expression profiles may be generated from cells treated with a compound of the present invention, specifically, at different doses or a time-course to assess the effects of the compound. A gene expression profile also is known as a gene expression signature.

The term "differential expression" refers to both quantitative as well as qualitative differences in the temporal and tissue expression patterns of a gene. For example, a differentially expressed gene may have its expression activated or completely inactivated in normal versus disease conditions. Such a qualitatively regulated gene may exhibit an expression pattern within a given tissue or cell type that is detectable in either control or disease conditions, but is not detectable in both. "Differentially expressed polynucleotide", as used herein, refers to a polynucleotide sequence that uniquely identifies a differentially expressed gene so that detection of the differentially expressed polynucleotide in a sample is correlated with the presence of a differentially expressed gene in a sample.

Similarly, a differentially expressed protein may have its expression activated or completely inactivated in normal versus disease conditions. Such a qualitatively regulated protein may exhibit an expression pattern within a given tissue or cell type that is detectable in either control or disease conditions, but is not detectable in both. A "differentially expressed protein", as used herein, refers to an amino acid sequence that uniquely identifies a differentially expressed protein so that detection of the differentially expressed protein in a sample is correlated with the presence of a differentially expressed protein in a sample.

"Cell type" as used herein, refers to a cell from a given source (for example, tissue or organ), a cell in a given state of differentiation, or a cell associated with a given pathology or genetic makeup.

The term "polypeptide" refers to a polymeric form of amino acids of any length, which may include translated, untranslated, chemically modified, biochemically modified and derivatized amino acids. A polypeptide may be naturally occurring, recombinant, or synthetic, or any combination of these.

Moreover, the term "polypeptide" as used herein, refers to proteins, polypeptides, and peptides of any size, structure, or function. For example, a polypeptide may comprise a string of amino acids held together by peptide bonds. A polypeptide may alternatively comprise a long chain of amino acids held together by peptide bonds. Moreover, a polypeptide also may comprise a fragment of a naturally occurring protein or peptide. A polypeptide may be a single molecule or may be a multi-molecular complex. In addition, such polypeptides may have modified peptide backbones as well.

The term "polypeptide" further comprises immunologically tagged proteins and fusion proteins, including, but not limited to, fusion proteins with a heterologous amino acid sequence, fusion proteins with heterologous and homologous leader sequences, and fusion proteins with or without N-terminal methionine residues.

The term "protein expression" refers to the process by which a polynucleotide sequence undergoes successful transcription and translation such that detectable levels of the amino acid sequence or protein are expressed.

The term "protein expression profile" refers to a group of proteins representing a particular cell or tissue type (for example, neuron, coronary artery endothelium, or disease tissue). In one aspect, a protein expression profile is generated from cells exposed to a compound of the present invention. This profile may be compared to a protein expression profile generated from the same type of cell prior to treatment with a compound of the present invention. Furthermore, a series of protein expression profiles may be generated from cells treated with a compound of the present invention, specifically, at different doses or a time-course to assess the effects of the compound. A protein expression profile also is known as a "protein expression signature".

As used herein, a "biomolecule" includes polynucleotides and polypeptides. Moreover, a "biomolecular sequence", as used herein, is a term that refers to all or a portion of a polynucleotide sequence. A biomolecular sequence also may refer to all or a portion of a polypeptide sequence.

A "host cell" as used herein, refers to a microorganism, a prokaryotic cell, a eukaryotic cell or cell line cultured as a unicellular entity that may be, or has been, used as a recipient for a recombinant vector or other transfer of polynucleotides, and includes the progeny of the original cell that has been transfected. It is understood that the progeny of a single cell may not necessarily be completely identical in morphology or in genomic or total DNA complement as the original parent due to natural, accidental, or deliberate mutation.

In the context of biomolecule, for example, Perlecan, the term "functional equivalent" refers to a protein or polynucleotide molecule that possesses functional or structural characteristics that are substantially similar to all or part of the native Perlecan protein or native Perlecan-encoding polynucleotides. A functional equivalent of a native Perlecan protein may contain modifications depending on the necessity of such modifications for a specific structure or the performance of a specific function. The term "functional equivalent" is intended to include the "fragments", "mutants", "derivatives", "alleles", "hybrids", "variants", "analogs", or "chemical derivatives", of native Perlecan.

In the context of immunoglobulins, the term "functional equivalent" refers to immunoglobulin molecules that exhibit immunological binding properties that are substantially similar to the parent immunoglobulin. As used herein, the term "immunological binding properties" refers to non-covalent interactions of the type which occur between an immunoglobulin molecule and an antigen for which the immunoglobulin is specific. Indeed, a functional equivalent of a monoclonal antibody immunoglobulin, for example, may inhibit the binding of the parent monoclonal antibody to its antigen. A functional equivalent may comprise $F(ab')_2$ fragments, F(ab) molecules, Fv fragments, single chain fragment variable displayed on phage (scFv), single domain antibodies, chimeric antibodies, or the like so long as the immunoglobulin exhibits the characteristics of the parent immunoglobulin.

As used herein, the term "isolated" refers to a polynucleotide, a polypeptide, an antibody, or a host cell that is in an environment different from that in which the polynucleotide, the polypeptide, the antibody, or the host cell naturally occurs. An isolated polynucleotide, polypeptide, antibody, or host cell is generally substantially purified.

As used herein, the term "substantially purified" refers to a compound that is removed from its natural environment and is at least about 60% free, at least about 65% free, at least about 70% free, at least about 75% free, at least about 80% free, at least about 83% free, at least about 85% free, at least about 88% free, at least about 90% free, at least about 91% free, at least about 92% free, at least about 93% free, at least about 94% free, at least about 95% free, at least about 96% free, at least about 97% free, at least about 98% free, at least about 99% free, at least about 99.9% free, or at least about 99.99% free from other components with which it is naturally associated. For example, a composition containing A is "substantially free of" B when at least about 85% by weight of the total A+B in the composition is A. Alternatively, A comprises at least about 90% by weight of the total of A+B in the composition, further still, at least about 95% or even 99% by weight.

"Diagnosis" as used herein, generally includes a determination of a subject's susceptibility to a disease or disorder, a determination as to whether a subject is presently affected by a disease or disorder, a prognosis of a subject affected by a disease or disorder (for example, identification of pre-metastatic or metastatic cancerous states, stages of cancer, or responsiveness of cancer to therapy), and therametrics (for example, monitoring a subject's condition to provide information as to the effect or efficacy of therapy).

The term "biological sample" encompasses a variety of sample types obtained from an organism which may be used in a diagnostic, monitoring, or other assay. The term encompasses blood and other liquid samples of biological origin, solid tissue samples such as a biopsy specimen, or tissue cultures or cells derived therefrom and the progeny thereof. The term specifically encompasses a clinical sample, and further includes cells in cell culture, cell supernatants, cell lysates, serum, plasma, urine, amniotic fluid, biological fluids, and tissue samples. The term also encompasses samples that have been manipulated in any way after procurement such as treatment with reagents, solubilization, or enrichment for certain components.

The terms "individual", "subject", "host", and "patient" refer to any mammalian subject for whom diagnosis, treatment, or therapy is desired. The individual, subject, host, or patient is optionally a human. Other subjects may include, but are not limited to, cattle, horses, dogs, cats, guinea pigs, rabbits, rats, primates, and mice.

The terms "treatment", "treating", "treat", are used herein to refer generally to obtaining a desired pharmacological and/or physiologic effect. The effect may be prophylactic in that it may completely or partially prevent a disease or symptom thereof and/or may be therapeutic in that it may partially or completely stabilize or cure a disease and/or adverse effect attributable to the disease. "Treatment" as used herein covers any treatment of a disease in a mammal, particularly a human, and includes: (a) preventing the disease or symptom from occurring in a subject which may be predisposed to the disease or symptom, but has not yet been diagnosed as having it; (b) inhibiting the disease symptom, i.e., arresting its development; or (c) relieving the disease symptom, i.e., causing regression of the disease or symptom.

The expression "therapeutically effective amount" refers to an amount of, for example, a compound contemplated hereby, that is effective for preventing, ameliorating, treating, or delaying the onset of a disease or condition.

A "prophylactically effective amount" refers to an amount of, for example, a compound contemplated hereby that is effective for preventing a disease or condition.

A "liposome" is a small vesicle composed of various types of lipids, phospholipids and/or surfactant, which is useful for delivery of a drug to a mammal. The compounds of the present invention may be delivered by a liposome. The components of the liposome are commonly arranged in a bilayer formation, similar to the lipid arrangement of biological membranes.

"Hybridization", broadly defined, refers to any process by which a polynucleotide sequence binds to a complementary sequence through base pairing. Hybridization conditions can be defined by, for example, the concentrations of salt or formamide in the prehybridization and hybridization solutions, or by the hybridization temperature, and are well known in the art. Hybridization can occur under various conditions stringency. Hybridization also may refer to the binding of a protein-capture agent to a target protein under certain conditions, such as normal physiological conditions.

As understood herein, the term "activation" refers to any alteration of a signaling pathway or biological response including, for example, increases above basal levels, restoration to basal levels from an inhibited state, and stimulation of the pathway above basal levels.

The term "biological activity" refers to the biological behavior and effects of a protein or peptide. The biological activity of a protein may be affected at the cellular level and the molecular level. For example, the biological activity of a protein may be affected by changes at the molecular level. For example, an antisense oligonucleotide may prevent translation of a particular mRNA, thereby inhibiting the biological activity of the protein encoded by the mRNA. In addition, an antibody may bind to a particular protein and inhibit that protein's biological activity.

The term "oligonucleotide" as used herein refers to a polynucleotide sequence comprising, for example, from about 10 nucleotides (nt) to about 1000 nt. Oligonucleotides for use in the present invention are, for example, from about 15 nt to about 150 nt, or from about 150 nt to about 1000 nt in length. The oligonucleotide may be a naturally occurring oligonucleotide or a synthetic oligonucleotide. Oligonucleotides may be prepared by the phosphoramidite method (Beaucage and Carruthers, TETRAHEDRON LETT. (1981) 22:1859-1862), or by the triester method (Matteucci et al., J. AM. CHEM. SOC. (1981) 103:3185), or by other chemical methods known in the art.

The term "microarray" refers generally to the type of genes or proteins represented on a microarray by oligonucleotides (polynucleotide sequences) or protein-binding agents, and where the type of genes or proteins represented on the microarray is dependent on the intended purpose of the microarray (for example, to monitor expression of human genes or proteins). The oligonucleotides or protein-binding agents on a given microarray may correspond to the same type, category, or group of genes or proteins. Genes or proteins may be considered to be of the same type if they share some common characteristics such as species of origin (for example, human, mouse, rat); disease state (for example, cancer); function (for example, protein kinases, tumor suppressors); same biological process (for example, apoptosis, signal transduction, cell cycle regulation, proliferation, differentiation). For example, one microarray type may be a "cancer microarray" in which each of the microarray oligonucleotides or protein-binding agents correspond to a gene or protein associated with a cancer. An "epithelial microarray" may be a microarray of oligonucleotides or protein-binding agents corresponding to unique epithelial genes or proteins. Similarly, a "cell cycle microarray" may be an microarray type in which the oligonucleotides or protein-binding agents correspond to unique genes or proteins associated with the cell cycle.

The term "detectable" refers to a polynucleotide expression pattern which is detectable via the standard techniques of polymerase chain reaction (PCR), reverse transcriptase-(RT) PCR, differential display, and Northern analyses, which are well known to those of skill in the art. Similarly, polypeptide expression patterns may be "detected" via standard techniques including immunoassays such as Western blots.

A "target gene" refers to a polynucleotide, often derived from a biological sample, to which an oligonucleotide probe is designed specifically to hybridize. It is either the presence or absence of the target polynucleotide that is to be detected, or the amount of the target polynucleotide that is to be quantified. The target polynucleotide has a sequence that is complementary to the polynucleotide sequence of the corresponding probe directed to the target. The target polynucleotide also may refer to the specific subsequence of a larger polynucleotide to which the probe is directed or to the overall sequence (for example, gene or mRNA) whose expression levels it is desired to detect.

A "target protein" refers to a polypeptide, often derived from a biological sample, to which a protein-capture agent specifically hybridizes or binds. It is either the presence or absence of the target protein that is to be detected, or the amount of the target protein that is to be quantified. The target protein has a structure that is recognized by the corresponding protein-capture agent directed to the target. The target protein or amino acid also may refer to the specific substructure of a larger protein to which the protein-capture agent is directed or to the overall structure (for example, gene or mRNA) whose expression levels it is desired to detect.

The term "complementary" refers to the topological compatibility or matching together of the interacting surfaces of a probe molecule and its target. The target and its probe can be described as complementary, and furthermore, the contact surface characteristics are complementary to each other. Hybridization or base pairing between nucleotides or nucleic acids, such as, for example, between the two strands of a double-stranded DNA molecule or between an oligonucleotide probe and a target are complementary.

The term "background" refers to non-specific binding or other interactions between, for example, polynucleotides, polypeptides, small molecules and polypeptides, or small molecules and polynucleotides. "Background" also may refer to the non-specific binding or other interactions in the context of assays including immunoassays.

In the context of microarrays, the term "background" refers to hybridization signals resulting from non-specific binding, or other interactions, between the labeled target polynucleotides and components of the oligonucleotide microarray (for example, the oligonucleotide probes, control probes, the microarray support) or between target proteins and the protein-binding agents of a protein microarray. Background signals also may be produced by intrinsic fluorescence of the microarray components themselves. A single background signal may be calculated for the entire microarray, or a different background signal may be calculated for each target polynucleotide or target protein. The background may be calculated as the average hybridization signal intensity, or where a different background signal is calculated for each target gene or target protein. Alternatively, background may be calculated as the average hybridization signal intensity produced by hybridization to probes that are not complementary to any sequence found in the sample (for example, probes directed to polynucleotides of the opposite sense or to genes not found in the sample such as bacterial genes where the sample is mammalian polynucleotides). The background also can be calculated as the average signal intensity produced by regions of the microarray which lack any probes or protein-binding agents at all.

A "small molecule" refers to a compound or molecular complex, either synthetic, naturally derived, or partially synthetic, composed of carbon, hydrogen, oxygen, and nitrogen, that also may contain other elements, and that may have a molecular weight of less than about 15,000, less than about 14,000, less than about 13,000, less than about 12,000, less than about 11,000, less than about 10,000, less than about 9,000, less than about 8,000, less than about 7,000, less than about 6,000, less than about 5,000, less than about 4,000, less than about 3,000, less than about 2,000, less than about 1,000, less than about 900, less than about 800, less than about 700, less than about 600, less than about 500, less than about 400, less than about 300, less than about 200, or less than about 100.

The term "fusion protein" refers to a protein composed of two or more polypeptides that, although typically not joined in their native state, are joined by their respective amino and carboxyl termini through a peptide linkage to form a single continuous polypeptide. It is understood that the two or more polypeptide components can either be directly joined or indirectly joined through a peptide linker/spacer.

The term "normal physiological conditions" means conditions that are typical inside a living organism or a cell. Although some organs or organisms provide extreme conditions, the intra-organismal and intra-cellular environment normally varies around pH 7 (i.e., from pH 6.5 to pH 7.5), contains water as the predominant solvent, and exists at a temperature above 0° C. and below 50° C. The concentration of various salts depends on the organ, organism, cell, or cellular compartment used as a reference.

The term "cluster" refers to a group of clones or biomolecular sequences related to one another by sequence homology. In one example, clusters are formed based upon a specified degree of homology and/or overlap (for example, stringency). "Clustering" may be performed with the sequence data. For instance, a biomolecular sequence thought to be associated with a particular molecular or biological activity in one tissue might be compared against another library or database of sequences. This type of search is useful to look for homologous, and presumably functionally related, sequences in other tissues or samples, and may be used to streamline the methods of the present invention in that clustering may be used within one or more of the databases to cluster biomolecular sequences prior to performing a method of the invention. The sequences showing sufficient homology with the representative sequence are considered part of a "cluster". Such "sufficient" homology may vary within the needs of one skilled in the art.

As used herein, the term "internal database" refers to a database maintained within a local computer network. It contains, for example, biomolecular sequences associated with a project. It also may contain information associated with sequences including, but not limited to, a library in which a given sequence is found and descriptive information about a likely gene associated with the sequence. The internal database is optionally maintained as a private database behind a firewall within an enterprise network. However, the present invention contemplates an internal database that is available to the public. The internal database may include sequence data generated by the same enterprise that maintains the database, and also may include sequence data obtained from external sources.

The term "external database", as understood herein, refers to a database located outside all internal databases. Typically, an enterprise network differing from the enterprise network maintaining the internal database will maintain an external database. The external database may be used, for example, to provide some descriptive information on biomolecular sequences stored in the internal database. For example, the external database may be GenBank and associated databases maintained by the National Center for Biotechnology Information (NCBI), which is part of the National Library of Medicine.

DETAILED DESCRIPTION OF THE INVENTION

The present invention is directed to compounds of general formula (I), its analogs, tautomeric forms, regioisomers, stereoisomers, polymorphs, pharmaceutically acceptable salts and pharmaceutically acceptable solvates thereof. Further, the present invention is directed to pharmaceutical compositions comprising compounds of general formula (I), its analogs, tautomeric forms, regioisomers, stereoisomers, polymorphs, pharmaceutically acceptable salts and pharmaceutically acceptable solvates thereof, either individually or in any combination thereof. Still further, the present invention is directed to methods of use of compounds of general formula (I), its analogs, tautomeric forms, regioisomers, stereoisomers, polymorphs, pharmaceutically acceptable salts and pharmaceutically acceptable solvates thereof, either individually or in any combination thereof. Even further, the present invention is directed to methods of making compounds of general formula (I), its analogs, tautomeric forms, regioisomers, stereoisomers, polymorphs, pharmaceutically acceptable salts and pharmaceutically acceptable solvates thereof.

Compounds of General Formula (I)

The present invention is related to compounds of formula (I), and to methods and/or compositions comprising compounds that are effective in modulating inflammatory responses, such as those resulting from AGE and glycated protein accumulation. The present invention also is directed to methods and/or compositions comprising compounds that are effective in modulating smooth muscle cell proliferation and the diseases or conditions related thereto.

According to one aspect of the present invention, various compounds of general formula (I)

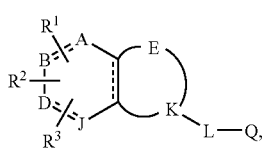

(I)

its tautomeric forms, its stereoisomers, its polymorphs, its pharmaceutically acceptable salts, and its pharmaceutically acceptable solvates are provided. According to this aspect,

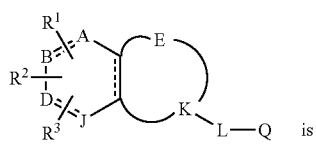 is

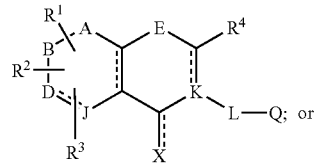

(Ia)

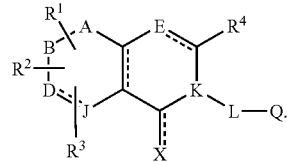

(Ib)

In this and other aspects, L is —Y—G=Z—Ar—,

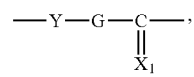

or —(CH$_2$)$_t$—, and Q is

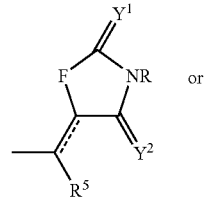

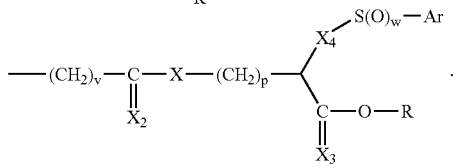

$R^1$, $R^2$, and $R^3$ independently are hydrogen, a hydroxy group, a halogen, a nitro group, a carboxy group, a carbamoyl group, an optionally substituted amino group, an alkyl group, a cycloalkyl group, an alkoxy group, a cycloalkoxy group, an alkenyl group, a cycloalkenyl group, an alkoxyalkyl group, an alkenyloxy group, a cycloalkenyloxy group, an acyl group, an acyloxy group, an aryl group, an aryloxy group, an aroyl group, an aroyloxy group, an aralkyl group, an aralkoxy group, a heterocyclyl group, a heteroaryl group, a heteroaralkyl group, a heteroaryloxy group, a heteroaralkoxy group, an alkoxycarbonyl group, an aryloxycarbonyl group, a heteroarylcarbonyl group, an alkylsulfonyl group, an arylsulfonyl group, a heteroarylsulfonyl group, an aralkylsulfinyl group, an alkylsulfinyl group, an arylsulfinyl group, a heteroarylsulfinyl group, an aralkylsulfinyl group, an alkylthio group, an arylthio group, a heteroarylthio group, an aralkylthio group, an aryloxyalkyl group, carboxylic acid or a derivative thereof, or sulfonic acid or a derivative thereof, wherein any two of $R^1$, $R^2$, and $R^3$ in combination optionally form a 5-member or 6-member saturated cyclic ring having from 1 to 3 heteroatoms, wherein the heteroatoms are O, S, or N. The cyclic ring formed by any two of $R^1$, $R^2$, or $R^3$ may be oxlanyl, 1,3-dioalanyl, or 1,4-dioxalanyl.

R⁴ is hydrogen, a hydroxy group, a halogen, a nitro group, a carboxy group, a carbamoyl group, an optionally substituted amino group, an alkyl group, a cycloalkyl group, an alkoxy group, a cycloalkoxy group, an alkenyl group, a cycloalkenyl group, an alkoxyalkyl group, an alkenyloxy group, a cycloalkenyloxy group, an acyl group, an acyloxy group, an aryl group, an aryloxy group, an aroyl group, an aroyloxy group, an aralkyl group, an aralkenyl group, an aralkynyl group, an aralkoxy group, a heterocyclyl group, a heterocyclenyl group, a heteroaryl group, a heteroaralkyl group, a heteroaryloxy group, a heteroaralkoxy group, an alkoxycarbonyl group, an aryloxycarbonyl group, an aralkoxycarbonyl group, a heteroarylcarbonyl group, an alkylsulfonyl group, an arylsulfonyl group, a heteroarylsulfonyl group, an alkylsulfinyl group, an arylsulfinyl group, an aralkylsulfinyl group, a heteroarylsulfinyl group, an aralkylsulfinyl group, an alkylthio group, an arylthio group, a heteroarylthio group, an aralkylthio group, an aryloxyalkyl group, an aralkoxyalkyl group, a fused heteroarylcycloalkyl group, a fused heteroarylcycloalkenyl group, a fused heteroarylheterocyclenyl group, carboxylic acid or a derivative thereof, or sulfonic acid or a derivative thereof.

Any of R¹, R², R³, and R⁴ independently optionally are substituted with hydrogen, a halogen, a nitro group, an amino group, a mono- or di-substituted amino group, a hydroxy group, an alkoxy group, a carboxy group, a cyano group, an oxo(O=) group, a thio(S=) group, an alkyl group, a cycloalkyl group, an alkoxy group, a haloalkoxy group, a cycloalkyl group, an aryl group, a benzyloxy group, an acyl group, an acyloxy group, an aroyl group, an alkoxycarbonyl group, an aryloxycarbonyl group, a heteroaryl group, a heterocyclyl group, an aralkyl group, an alkylsulfonyl group, an alkylsulfinyl group, an arylsulfonyl group, an arylsulfinyl group, an alkylthio group, an arylthio group, a heteroarylthio group, an aralkylthio group, or a heterocyclyl sulfonyl group, which is optionally substituted with a halogen, a hydroxyl group, a nitro group, an amino group, an alkyloxy group, or any combination thereof, and wherein the heterocycle group is optionally a substituted morpholinyl group, a thiomorpholinyl group, or a piperzinyl group, wherein the substituent on the heterocyclyl group is a halogen, a nitro group, an amino group, an alkyl group, an alkoxy group, or an aryl group.

According to this and other aspects, A, B, D, and J independently are O, S, N, >CH, or (—CH₂—)$_n$; '—' is an optional chemical bond; E is O, S, or —NR; K is N, C, or CH; Y and Z independently are O, —NR, (—CH₂—)$_u$, or S(=O)$_u$; G is —(CH₂)$_s$—, —(CH₂)$_s$—CH=CH—(CH₂)$_s$—, or —(CH₂)$_s$—C=C—(CH₂)$_s$—; X, X₁, X₂, X₃, and X₄ independently are O, S, or —NR; F is O, S, or —NR; Y¹ and Y² independently are O or S; n, w, u independently are an integer from 0-2; p, t, m, s, v independently are an integer from 0-5, and 'Ar' is a substituted or unsubstituted phenyl or a substituted or unsubstituted naphthyl group.

R and R⁵ independently are hydrogen, potassium, sodium, a hydroxy group, a halogen, a nitro group, an optionally substituted amino group, an alkyl group, an alkoxy group, an alkenyl group, an alkoxyalkyl group, a cycloalkenyloxy group, an acyl group, an aryl group, an aralkyl group, a heterocyclyl group, or a heteroaryl group.

The groups provided above are as follows:

'Halogen' is fluorine, chlorine, bromine, or iodine;

'Alkyl' group is a linear or branched (C₁-C₁₀)alkyl group. Exemplary alkyl groups include methyl, ethyl, n-propyl, iso-propyl, n-butyl, iso-butyl, t-butyl, n-pentyl, iso-pentyl, hexyl, heptyl, octyl.

'Cycloalkyl' group is a (C₃-C₇)cycloalkyl group which may be mon or polycyclic. Exemplary cycloalkyl groups include cyclopropyl, cyclobutyl, cyclopentyl, cyclohexyl.

'Alkoxy' is (C₁-C₁₀)alkyl-O—, wherein the (C₁-C₁₀)alkyl group is as defined above. Exemplary alkyl groups include methoxy, ethoxy, propoxy, butoxy, iso-propoxy.

'Cycloalkoxy' is a (C₃-C₆)cycloalkoxy group. Exemplary cycloalkoxy groups include cyclopropoxy, cyclobutoxy, cyclopentoxy, cyclohexoxy.

'Alkenyl' is a (C₂-C₆)alkenyl group. Exemplary alkenyl groups include ethenyl, propenyl, butenyl, pentenyl, hexenyl.

'Cycloalkenyl' is (C₃-C₇)cycloalkenyl group. Exemplary cycloalkenyl groups include cyclopropenyl, cyclobutenyl, cyclopentenyl, cyclohexenyl.

'Alkoxyalkyl' is a (C₁-C₆)alkoxy(C₁-C₁₀)alkyl group, where alkoxy and alkyl groups are as defined above. Exemplary alkoxyalkyl groups include methoxymethyl, methoxyethyl, methoxypropyl, ethoxymethyl, ethoxyethyl.

'Alkenyloxy' is (C₂-C₆)alkenyl-O—, where the (C₂-C₆) alkenyl group is as defined above. Exemplary alkenyl groups include ethenyloxy, propenyloxy, butenyloxy, pentenyloxy, hexenyloxy.

'Cycloalkenyloxy' is a (C₃-C₇)cycloalkenyl-O—, where the (C₃-C₇)cycloalkenyl group is as defined above. Exemplary cycloalkenyloxy groups include cycloethenyloxy, cyclopropenyloxy, cyclobutenyloxy, cyclopentenyloxy.

'Acyl' is H—CO— or (C₁-C₁₀)alkyl-CO—, where (C₁-C₁₀)alkyl group is as defined above. Exemplary acyl groups include acetyl, propionyl.

'Acyloxy' is (C₁-C₆)acyl-O—, where acyl group is as defined above. Exemplary acyloxy groups include acetyloxy, propionyloxy.

'Aryl' is monocylic or polycyclic ring system of about 5 to 14 carbon atoms. Exemplary groups include phenyl, naphthyl.

'Aryloxy' is an aryl-O— group, where the aryl group is as defined above. Exemplary aryloxy groups include phenoxy, naphthyloxy.

'Aroyl' is the aryl-CO— group, wherein the aryl group is as defined above. Exemplary aroyl groups include benzoyl, 1-naphthoyl.

'Aroyloxy' is the aroyl-O— group, wherein the aroyl group is as defined above. Exemplary aroyloxy groups include benzoyloxy, 1-naphthoyloxy.

'Aralkyl' is the aryl-(C₁-C₁₀)alkyl group, wherein aryl and (C₁-C₁₀)alkyl groups are as defined above. Exemplary aralkyl groups include benzyl, 2-phenylethyl.

'Aralkenyl' is aryl-(C₂-C₆)alkenyl group, wherein aryl and (C₂-C₆)alkenyl groups are as defined above.

'Aralkynyl' is aryl-(C₂-C₆)alkynyl group, wherein the aryl and group is as defined above.

'Aralkoxy' is aralkyl-O— group, wherein the aralkyl group as defined above. Exemplary aralkoxy groups include benzyloxy, 2-phenethyloxy.

'Heterocyclyl' is a non-aromatic saturated monocyclic or polycyclic ring system of about 5 to about 10 carbon atoms, having at least one hetero atom selected from O, S or N. Exemplary heterocyclyl groups include aziridinyl, pyrrolidinyl, piperidinyl, piperazinyl, morpholinyl, thiomorpholinyl, thiazolidinyl, 1,3-dioxolanyl, 1,4-dioxanyl.

'Heterocyclenyl' is a non-aromatic monocyclic or polycyclic hydrocarbon ring system of about 5 to 10 carbon atoms, having at least one hetero atom selected from O, S or N and one double bond. Exemplary heterocyclenyl groups include 1,2,3,4-tetrahydropyrimidine, 1,2-dihydropyridyl, 1,4-dihydropyridyl, 1,2,3,6-tetrahydropyridine, 1,4,5,6-tetrahydropyrimidine, 2-pyrrolinyl, 3-pyrrolinyl, 2-imidazolinyl, 2-pyrazolinyl.

'Heteroaryl' is an aromatic monocyclic or polycyclic ring system of about 5 to about 10 carbon atoms, having at least one heteroatom selected from O, S or N. Exemplary heteroaryl groups include as pyrazinyl, isothiazolyl, oxazolyl, pyrazolyl, pyrrolyl, pyridazinyl, thienopyrimidyl, furyl, indolyl, isoindolyl, 1,3-benzodioxole, 1,3-benzoxathiole, quinazolinyl, pyridyl, thiophenyl.

'Heteroaralkyl' is a heteroaryl-($C_1$-$C_{10}$)alkyl group, wherein the heteroaryl and ($C_1$-$C_{10}$)alkyl groups are as defined above. Exemplary heteroaralkyl groups include thienylmethyl, pyridylmethyl, imidazolylmethyl.

'Heteroaryloxy' is heteroaryl-O—, wherein the heteroaryl group is as defined above. Exemplary heteroaryloxy groups include pyrazinyloxy, isothiazolyloxy, oxazolyloxy, pyrazolyloxy, phthalazinyloxy, indolyloxy, quinazolinyloxy, pyridyloxy, thienyloxy.

'Heteroaralkoxy' is heteroaralkyl-O—, wherein the heteroaralkyl group is as defined above. Exemplary heteroaralkoxy groups include thienylmethyloxy, pyridylmethyloxy.

'Alkylcarbonyl' or 'acyl' is ($C_1$-$C_{10}$)alkyl-CO—, wherein the ($C_1$-$C_{10}$)alkyl group is as defined above. Exemplary alkylcarbonyl groups include methylcarbonyl, ethylcarbonyl, propylcarbonyl.

'Alkoxycarbonyl' is ($C_1$-$C_{10}$)alkyl-O—CO—, wherein the ($C_1$-$C_{10}$)alkyl group is as defined above. Exemplary alkoxycarbonyl groups include methoxycarbonyl, ethoxycarbonyl, t-butoxycarbonyl.

'Arylcarbonyl' or 'aroyl' is aryl-CO—, wherein the aryl group is as defined above. Exemplary arylcarbonyl groups include phenylcarbonyl, naphthylcarbonyl.

'Aryloxycarbonyl' is aryl-O—CO—, wherein the aryl group is as defined above. Exemplary aryloxycarbonyl groups include phenoxycarbonyl, naphthyloxycarbonyl.

'Aralkoxycarbonyl' is aryl-($C_1$-$C_6$)alkoxy-CO—, where aryl and ($C_1$-$C_6$)alkoxy are as defined above. Exemplary aralkoxycarbonyl groups include benzyloxycarbonyl, 2-phenethyloxycarbonyl.

'Heteroarylcarbonyl' is heteroaryl-CO—, wherein heteroaryl is as defined above. Exemplary heteroarylcarbonyl groups include pyrazinylcarbonyl, isothiazolylcarbonyl, oxazolylcarbonyl, pyrazolylcarbonyl, pyrrolylcarbonyl, pyridazinylcarbonyl, indolylcarbonyl.

'Alkylsulfonyl' is ($C_1$-$C_{10}$)alkyl-$SO_2$—, wherein the ($C_1$-$C_{10}$)alkyl group is as defined above. Exemplary alkylsulfonyl groups include methylsulfonyl, ethylsulfonyl, propylsulfonyl.

'Arylsulfonyl' is aryl-$SO_2$—, wherein the aryl group is as defined above. Exemplary arylsulfonyl groups include benzenesulfonyl.

'Heteroarylsulfonyl' is heteroaryl-$SO_2$—, wherein heteroaryl is as defined above. Exemplary heteroarylsulfonyl groups include pyrazinylsulfonyl, isothiazolylsulfonyl, oxazolylsulfonyl, pyrazolylsulfonyl, pyrrolylsulfonyl, pyridazinylsulfonyl, phthalazinylsulfonyl, quinazolinylsulfonyl, pyridylsulfonyl, thienylsulfonyl.

'Alkylsulfinyl' is ($C_1$-$C_{10}$)alkyl-SO—, where ($C_1$-$C_{10}$) alkyl is as defined above. Exemplary alkylsulfinyl groups include methylsulfinyl, ethylsulfinyl, propylsulfinyl.

'Arylsulfinyl' is aryl-SO—, wherein the aryl group is as defined above. Exemplary arylsulfonyl groups include phenylsulfinyl.

'Heteroarylsulfinyl' is heteroaryl-SO—, wherein heteroaryl is as defined above. Exemplary heteroarylsulfinyl groups include pyrazinylsulfinyl, isothiazolylsulfinyl, oxazolylsulfinyl, pyrazolylsulfinyl, pyrrolylsulfinyl, pyridazinylsulfinyl, phthalazinylsulfinyl, quinazolinylsulfinyl, pyridylsulfinyl, and thienylsulfinyl.

'Aralkylsulfinyl' is aryl-($C_1$-$C_{10}$)alkyl-SO— group, wherein aryl and ($C_1$-$C_{10}$)alkyl groups are as defined above. Exemplary aralkylsulfinyl groups include benzylsulfinyl, 2-phenethylsulfinyl.

'Alkylthio' is ($C_1$-$C_{10}$)alkyl-S—, wherein ($C_1$-$C_{10}$)alkyl is as defined above. Exemplary alkylthio groups include methylthio, ethylthio, and propylthio.

'Arylthio' is aryl-S—, wherein aryl group is as defined above. Exemplary arylthio groups include phenylthio groups.

'Heteroarylthio' is heteroaryl-S—, wherein heteroaryl is as defined above. Exemplary heteroarylthio groups include pyrazinylthio, isothiazolylthio, oxazolylthio, pyrazolylthio, pyrrolylthio, pyridazinylthio, phthalazinylthio, quinazolinylthio, pyridylthio, and thienylthio.

'Aralkylthio' is aryl-($C_1$-$C_{10}$)alkyl-S— group, wherein aryl and ($C_1$-$C_{10}$)alkyl groups are as defined above. Exemplary aralkylthio groups include benzylthio, and 2-phenethylthio.

'Aryloxyalkyl' is aryl-O—($C_1$-$C_{10}$)alkyl, where aryl and ($C_1$-$C_{10}$)alkyl groups are as defined above. Exemplary aryloxyalkyl groups include phenoxymethyl, phenoxyethyl, and phenoxypropyl.

'Aralkoxyalkyl' is aryl-($C_1$-$C_{10}$)alkyl-O—($C_1$-$C_{10}$)alkyl, where ($C_1$-$C_{10}$)alkyl and aryl groups are as defined above. Exemplary aralkoxyalkyl groups include benzyloxymethyl, benzyloxyethyl, and benzyloxypropyl.

'Fused heteroarylcycloalkyl' is fused heteroaryl and cyclo($C_3$-$C_6$)alkyl, wherein heteroaryl and cyclo($C_3$-$C_6$)alkyl groups are as defined herein. Exemplary fused heteroarylcycloalkyl groups include 5,6,7,8-tetrahydroquinolinyl, and 5,6,7,8-tetrahydroisoquinolyl.

'Fused heteroarylcycloalkenyl' is fused heteroaryl and cyclo($C_3$-$C_6$)alkenyl, wherein heteroaryl and cyclo($C_3$-$C_6$) alkenyl groups are as defined herein. Exemplary fused heteroarylcycloalkenyl groups include 5,6-dihydroquinolyl, 5,6-dihydroisoquinolyl, 5,6-dihydroquinoxalinyl.

'Fused heteroarylheterocyclenyl' is fused heteroaryl and heterocyclenyl, wherein heteroaryl and heterocyclenyl groups are as defined herein. Exemplary fused heteroarylheterocyclenyl groups include 7,8-dihydro[1,7]naphthyridinyl, 1,2-dihydro[2,7]naphthyridinyl.

'Carboxylic acid or its derivatives' may be amides or esters. Exemplary carboxylic acid groups include $CONH_2$, CONHMe, $CONMe_2$, CONHEt, $CONEt_2$, CONHPh, $COOCH_3$, $COOC_2H_5$ or $COOC_3H_7$.

'Sulfonic acid or its derivatives' may be amides or esters. Exemplary sulfonic acid groups include $SO_2NH_2$, $SO_2NHMe$, $SO_2NMe_2$, $SO_2NHCF_3$, $COOCH_3$, $COOC_2H_5$, or $COOC_3H_7$.

As used herein:

$R^a$ is hydrogen, a hydroxy group, a halogen, a nitro group, or an optionally substituted amino group;

$R^b$ is an alkyl group, an alkoxy group, an alkenyl group, or an alkoxyalkyl group;

$R^c$ is a cycloalkenyloxy group, an acyl group, an aryl group, an aralkyl group, a heterocyclyl group, or a heteroaryl group;

$R^{1a}$ is hydrogen, a hydroxy group, a halogen, a nitro group, a carboxy group, a carbamoyl group, or an optionally substituted amino group, an alkyl group, a cycloalkyl group, an alkoxy group, a cycloalkoxy group, an alkenyl group, a cycloalkenyl group, an alkoxyalkyl group, an alkenyloxy group, or a cycloalkenyloxy group;

$R^{1b}$ is an acyl group, an acyloxy group, an aryl group, an aryloxy group, an aroyl group, an aroyloxy group, an aralkyl group, an aralkoxy group, a heterocyclyl group, a heteroaryl group, a heteroaralkyl group, a heteroaryloxy group, a heteroaralkoxy group, an alkoxycarbonyl group, an aryloxycarbonyl group, or a heteroarylcarbonyl group;

$R^{1c}$ is an alkylsulfonyl group, an arylsulfonyl group, a heteroarylsulfonyl group, an aralkylsulfinyl group, an alkylsulfinyl group, an arylsulfinyl group, a heteroarylsulfinyl group, an aralkylsulfinyl group, an alkylthio group, an arylthio group, a heteroarylthio group, an aralkylthio group, an aryloxyalkyl group, carboxylic acid or a derivative thereof, or sulfonic acid or a derivative thereof;

$R^{2a}$ is hydrogen, a hydroxy group, a halogen, a nitro group, a carboxy group, a carbamoyl group, or an optionally substituted amino group, an alkyl group, a cycloalkyl group, an alkoxy group, a cycloalkoxy group, an alkenyl group, a cycloalkenyl group, an alkoxyalkyl group, an alkenyloxy group, or a cycloalkenyloxy group;

$R^{2b}$ is an acyl group, an acyloxy group, an aryl group, an aryloxy group, an aroyl group, an aroyloxy group, an aralkyl group, an aralkoxy group, a heterocyclyl group, a heteroaryl group, a heteroaralkyl group, a heteroaryloxy group, a heteroaralkoxy group, an alkoxycarbonyl group, an aryloxycarbonyl group, or a heteroarylcarbonyl group;

$R^{2c}$ is an alkylsulfonyl group, an arylsulfonyl group, a heteroarylsulfonyl group, an aralkylsulfinyl group, an alkylsulfinyl group, an arylsulfinyl group, a heteroarylsulfinyl group, an aralkylsulfinyl group, an alkylthio group, an arylthio group, a heteroarylthio group, an aralkylthio group, an aryloxyalkyl group, carboxylic acid or a derivative thereof, or sulfonic acid or a derivative thereof;

$R^{3a}$ is hydrogen, a hydroxy group, a halogen, a nitro group, a carboxy group, a carbamoyl group, or an optionally substituted amino group, an alkyl group, a cycloalkyl group, an alkoxy group, a cycloalkoxy group, an alkenyl group, a cycloalkenyl group, an alkoxyalkyl group, an alkenyloxy group, or a cycloalkenyloxy group;

$R^{3b}$ is an acyl group, an acyloxy group, an aryl group, an aryloxy group, an aroyl group, an aroyloxy group, an aralkyl group, an aralkoxy group, a heterocyclyl group, a heteroaryl group, a heteroaralkyl group, a heteroaryloxy group, a heteroaralkoxy group, an alkoxycarbonyl group, an aryloxycarbonyl group, or a heteroarylcarbonyl group;

$R^{3c}$ is an alkylsulfonyl group, an arylsulfonyl group, a heteroarylsulfonyl group, an aralkylsulfinyl group, an alkylsulfinyl group, an arylsulfinyl group, a heteroarylsulfinyl group, an aralkylsulfinyl group, an alkylthio group, an arylthio group, a heteroarylthio group, an aralkylthio group, an aryloxyalkyl group, carboxylic acid or a derivative thereof, or sulfonic acid or a derivative thereof;

$R^{4a}$ is hydrogen, a hydroxy group, a halogen, a nitro group, or an optionally substituted amino group, an alkyl group, a cycloalkyl group, an alkoxy group, a cycloalkoxy group, an alkenyl group, a cycloalkenyl group, an alkoxyalkyl group, an alkenyloxy group, or a cycloalkenyloxy group;

$R^{4b}$ is an acyl group, an acyloxy group, an aryl group, an aryloxy group, aroyl group or an aroyloxy group, an aralkyl group, an aralkenyl group, an aralkynyl group, an aralkoxy group, a heterocyclyl group, a heterocyclenyl group, a heteroaryl group, a heteroaralkyl group, a heteroaryloxy group, or a heteroaralkoxy group;

$R^{4c}$ is an alkoxycarbonyl group, an aryloxycarbonyl group, an aralkoxycarbonyl group, a heteroarylcarbonyl group, an alkylsulfonyl group, an arylsulfonyl group, a heteroarylsulfonyl group, an alkylsulfinyl group, an arylsulfinyl group, or an aralkylsulfinyl group, an alkylthio group, an arylthio group, a heteroarylthio group, an aralkylthio group, a fused heteroarylcycloalkyl group, a fused heteroarylcycloalkenyl group, a fused heteroarylheterocyclenyl group, carboxylic acid or a derivative thereof, or sulfonic acid or a derivative thereof;

$R^{5a}$ is hydrogen, a hydroxy group, a halogen, a nitro group, or an optionally substituted amino group;

$R^{5b}$ is an alkyl group, an alkoxy group, an alkenyl group, or an alkoxyalkyl group;

$R^{5c}$ is a cycloalkenyloxy group, an acyl group, an aryl group, an aralkyl group, a heterocyclyl group, or a heteroaryl group;

$R'^{a}$ is hydrogen, a halogen, a nitro group, an amino group, a mono- or di-substituted amino group, a hydroxy group, an alkoxy group, a carboxy group, a cyano group, an oxo(O=) group, or a thio(S=) group;

$R'^{b}$ is an alkyl group, a cycloalkyl group, an alkoxy group, a haloalkoxy group, a cycloalkyl group, an aryl group, a benzyloxy group, an acyl group, an acyloxy group, an aroyl group, an alkoxycarbonyl group, an aryloxycarbonyl group, a heteroaryl group, a heterocyclyl group, or an aralkyl group;

$R'^{c}$ is an alkylsulfonyl group, an alkylsulfinyl group, an arylsulfonyl group, an arylsulfinyl group, an alkylthio group, an arylthio group, a heteroarylthio group, an aralkylthio group, or a heterocyclyl sulfonyl group;

$R''^{a}$ is hydrogen, a halogen, a nitro group, an amino group, a mono- or di-substituted amino group, a hydroxy group, an alkoxy group, a carboxy group, a cyano group, an oxo(O=) group, or a thio(S=) group;

$R''^{b}$ is an alkyl group, a cycloalkyl group, an alkoxy group, a haloalkoxy group, a cycloalkyl group, an aryl group, a benzyloxy group, an acyl group, an acyloxy group, an aroyl group, an alkoxycarbonyl group, an aryloxycarbonyl group, a heteroaryl group, a heterocyclyl group, or an aralkyl group;

$R''^{c}$ is an alkylsulfonyl group, an alkylsulfinyl group, an arylsulfonyl group, an arylsulfinyl group, an alkylthio group, an arylthio group, a heteroarylthio group, an aralkylthio group, or a heterocyclyl sulfonyl group.

$R^{9a}$ is hydrogen, a halogen, a nitro group, an amino group, a mono- or di-substituted amino group, a hydroxy group, an alkoxy group, a carboxy group, a cyano group, an oxo(O=) group, or a thio(S=) group;

$R^{9b}$ is an alkyl group, a cycloalkyl group, an alkoxy group, a haloalkoxy group, a cycloalkyl group, an aryl group, a benzyloxy group, an acyl group, an acyloxy group, an aroyl group, an alkoxycarbonyl group, an aryloxycarbonyl group, a heteroaryl group, or a heterocyclyl group, an aralkyl group;

$R^{9c}$ is an alkylsulfonyl group, an alkylsulfinyl group, an arylsulfonyl group, an arylsulfinyl group, an alkylthio group, an arylthio group, a heteroarylthio group, an aralkylthio group, or a heterocyclyl sulfonyl group, which is optionally substituted with a halogen, a hydroxyl group, a nitro group, an amino group, an alkyloxy group, or any combination thereof, and wherein the heterocycle group is optionally a substituted morpholinyl group, a thiomorpholinyl group, or a piperzinyl group, wherein the substituent on the heterocyclyl group is a halogen, a nitro group, an amino group, an alkyl group, an alkoxy group, or an aryl group;

$R^{10a}$ is hydrogen, a halogen, a nitro group, an amino group, a mono- or di-substituted amino group, a hydroxy group, an alkoxy group, a carboxy group, a cyano group, an oxo(O=) group, or a thio(S=) group;

$R^{10b}$ is an alkyl group, a cycloalkyl group, an alkoxy group, a haloalkoxy group, a cycloalkyl group, an aryl group, a benzyloxy group, an acyl group, an acyloxy group, an aroyl group, an alkoxycarbonyl group, an aryloxycarbonyl group, a heteroaryl group, a heterocyclyl group, or an aralkyl group;

$R^{10c}$ is an alkylsulfonyl group, an alkylsulfinyl group, an arylsulfonyl group, an arylsulfinyl group, an alkylthio group, an arylthio group, a heteroarylthio group, an aralkylthio group, or a heterocyclyl sulfonyl group, which is optionally substituted with a halogen, a hydroxyl group, a nitro group, an amino group, an alkyloxy group, or any combination thereof, and wherein the heterocycle group is optionally a substituted morpholinyl group, a thiomorpholinyl group, or a piperzinyl group, wherein the substituent on the heterocyclyl group is a halogen, a nitro group, an amino group, an alkyl group, an alkoxy group, or an aryl group.

$R^{11a}$ is hydrogen, a halogen, a nitro group, an amino group, a mono- or di-substituted amino group, a hydroxy group, an alkoxy group, a carboxy group, a cyano group, an oxo(O=) group, or a thio(S=) group;

$R^{11b}$ is an alkyl group, a cycloalkyl group, an alkoxy group, a haloalkoxy group, a cycloalkyl group, an aryl group, a benzyloxy group, an acyl group, an acyloxy group, an aroyl group, an alkoxycarbonyl group, an aryloxycarbonyl group, a heteroaryl group, or a heterocyclyl group, an aralkyl group;

$R^{11c}$ is an alkylsulfonyl group, an alkylsulfinyl group, an arylsulfonyl group, an arylsulfinyl group, an alkylthio group, an arylthio group, a heteroarylthio group, an aralkylthio group, or a heterocyclyl sulfonyl group, which is optionally substituted with a halogen, a hydroxyl group, a nitro group, an amino group, an alkyloxy group, or any combination thereof, and wherein the heterocycle group is optionally a substituted morpholinyl group, a thiomorpholinyl group, or a piperzinyl group, wherein the substituent on the heterocyclyl group is a halogen, a nitro group, an amino group, an alkyl group, an alkoxy group, or an aryl group;

$R^{12a}$ is hydrogen, a halogen, a nitro group, an amino group, a mono- or di-substituted amino group, a hydroxy group, an alkoxy group, a carboxy group, a cyano group, an oxo(O=) group, or a thio(S=) group;

$R^{12b}$ is an alkyl group, a cycloalkyl group, an alkoxy group, a haloalkoxy group, a cycloalkyl group, an aryl group, a benzyloxy group, an acyl group, an acyloxy group, an aroyl group, an alkoxycarbonyl group, an aryloxycarbonyl group, a heteroaryl group, or a heterocyclyl group, an aralkyl group;

$R^{12c}$ is an alkylsulfonyl group, an alkylsulfinyl group, an arylsulfonyl group, an arylsulfinyl group, an alkylthio group, an arylthio group, a heteroarylthio group, an aralkylthio group, or a heterocyclyl sulfonyl group, which is optionally substituted with a halogen, a hydroxyl group, a nitro group, an amino group, an alkyloxy group, or any combination thereof, and wherein the heterocycle group is optionally a substituted morpholinyl group, a thiomorpholinyl group, or a piperzinyl group, wherein the substituent on the heterocyclyl group is a halogen, a nitro group, an amino group, an alkyl group, an alkoxy group, or an aryl group;

$R^{13a}$ is hydrogen, a halogen, a nitro group, an amino group, a mono- or di-substituted amino group, a hydroxy group, an alkoxy group, a carboxy group, a cyano group, an oxo(O=) group, or a thio(S=) group;

$R^{13b}$ is an alkyl group, a cycloalkyl group, an alkoxy group, a haloalkoxy group, a cycloalkyl group, an aryl group, a benzyloxy group, an acyl group, an acyloxy group, an aroyl group, an alkoxycarbonyl group, an aryloxycarbonyl group, a heteroaryl group, or a heterocyclyl group, an aralkyl group;

$R^{13c}$ is an alkylsulfonyl group, an alkylsulfinyl group, an arylsulfonyl group, an arylsulfinyl group, an alkylthio group, an arylthio group, a heteroarylthio group, an aralkylthio group, or a heterocyclyl sulfonyl group, which is optionally substituted with a halogen, a hydroxyl group, a nitro group, an amino group, an alkyloxy group, or any combination thereof, and wherein the heterocycle group is optionally a substituted morpholinyl group, a thiomorpholinyl group, or a piperzinyl group, wherein the substituent on the heterocyclyl group is a halogen, a nitro group, an amino group, an alkyl group, an alkoxy group, or an aryl group;

$R^{14a}$ is hydrogen, a halogen, a nitro group, an amino group, a mono- or di-substituted amino group, a hydroxy group, an alkoxy group, a carboxy group, a cyano group, an oxo(O=) group, or a thio(S=) group;

$R^{14b}$ is an alkyl group, a cycloalkyl group, an alkoxy group, a haloalkoxy group, a cycloalkyl group, an aryl group, a benzyloxy group, an acyl group, an acyloxy group, an aroyl group, an alkoxycarbonyl group, an aryloxycarbonyl group, a heteroaryl group, or a heterocyclyl group, an aralkyl group;

$R^{14c}$ is an alkylsulfonyl group, an alkylsulfinyl group, an arylsulfonyl group, an arylsulfinyl group, an alkylthio group, an arylthio group, a heteroarylthio group, an aralkylthio group, or a heterocyclyl sulfonyl group, which is optionally substituted with a halogen, a hydroxyl group, a nitro group, an amino group, an alkyloxy group, or any combination thereof, and wherein the heterocycle group is optionally a substituted morpholinyl group, a thiomorpholinyl group, or a piperzinyl group, wherein the substituent on the heterocyclyl group is a halogen, a nitro group, an amino group, an alkyl group, an alkoxy group, or an aryl group;

$R^{20a}$ is hydrogen, a halogen, a nitro group, an amino group, a mono- or di-substituted amino group, a hydroxy group, an alkoxy group, a carboxy group, a cyano group, an oxo(O=) group, or a thio(S=) group;

$R^{20b}$ is an alkyl group, a cycloalkyl group, an alkoxy group, a haloalkoxy group, a cycloalkyl group, an aryl group, a benzyloxy group, an acyl group, an acyloxy group, an aroyl group, an alkoxycarbonyl group, an aryloxycarbonyl group, a heteroaryl group, or a heterocyclyl group, an aralkyl group;

$R^{20c}$ is an alkylsulfonyl group, an alkylsulfinyl group, an arylsulfonyl group, an arylsulfinyl group, an alkylthio group, an arylthio group, a heteroarylthio group, an aralkylthio group, or a heterocyclyl sulfonyl group, which is optionally substituted with a halogen, a hydroxyl group, a nitro group, an amino group, an alkyloxy group, or any combination thereof, and wherein the heterocycle group is optionally a substituted morpholinyl group, a thiomorpholinyl group, or a piperzinyl group, wherein the substituent on the heterocyclyl group is a halogen, a nitro group, an amino group, an alkyl group, an alkoxy group, or an aryl group;

$R^{21a}$ is hydrogen, a halogen, a nitro group, an amino group, a mono- or di-substituted amino group, a hydroxy group, an alkoxy group, a carboxy group, a cyano group, an oxo(O=) group, or a thio(S=) group;

$R^{21b}$ is an alkyl group, a cycloalkyl group, an alkoxy group, a haloalkoxy group, a cycloalkyl group, an aryl group, a benzyloxy group, an acyl group, an acyloxy group, an aroyl group, an alkoxycarbonyl group, an aryloxycarbonyl group, a heteroaryl group, a heterocyclyl group, or an aralkyl group;

$R^{21c}$ is an alkylsulfonyl group, an alkylsulfinyl group, an arylsulfonyl group, an arylsulfinyl group, an alkylthio group, an arylthio group, a heteroarylthio group, an aralkylthio group, or a heterocyclyl sulfonyl group, which is optionally substituted with a halogen, a hydroxyl group, a nitro group, an amino group, an alkyloxy group, or any combination thereof, and wherein the heterocycle group is optionally a substituted morpholinyl group, a thiomorpholinyl group, or a piperzinyl group, wherein the substituent on the heterocyclyl group is a halogen, a nitro group, an amino group, an alkyl group, an alkoxy group, or an aryl group.

$G^a$ is —$(CH_2)_s$—, where s is an integer from 0-5;

$G^b$ is —$(CH_2)_s$—CH=CH—$(CH_2)_s$—, where s is an integer from 0-5;

$G^c$ is —(CH$_2$)$_s$—C≡C—(CH$_2$)$_s$—, where s is an integer from 0-5;

$Z^a$ is O; $Z^b$ is NR; $Z^c$ is (—CH$_2$—)$_u$ or S(=O)$_u$, where u is an integer from 0-2;

$E^a$ is O; $E^b$ is S; $E^c$ is NR;

$p^a$ is 0-1; $p^b$ is 2-3; $p^c$ is 4-5;

$v^a$ is 0-1; $v^b$ is 2-3; $v^c$ is 4-5;

$w^a$ is 0; $w^b$ is 1; $w^c$ is 2;

$X^a$ is O; $X^b$ is S; and $X^c$ is —NR.

According to another aspect of the present invention, various compounds of general formula (I) having general formula (II)

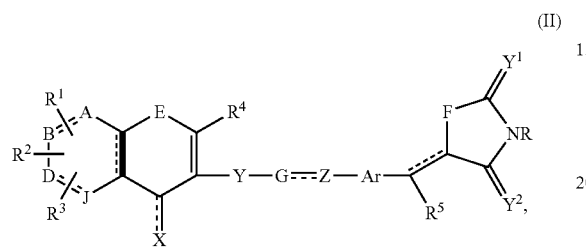

(II)

its tautomeric forms, its stereoisomers, its polymorphs, its pharmaceutically acceptable salts, and its pharmaceutically acceptable solvates are provided. Except as otherwise provided herein, all symbols are as defined above in connection with formula (I).

According to another aspect of the present invention, various compounds of general formula (I) having general formula (III)

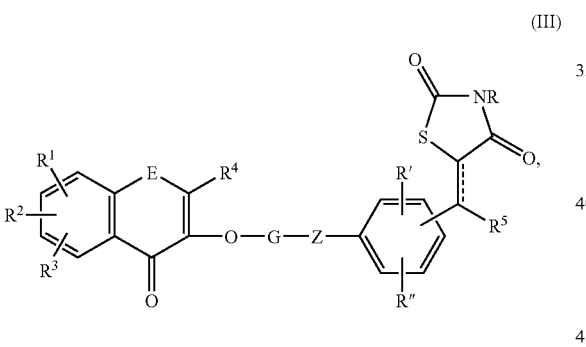

(III)

its tautomeric forms, its stereoisomers, its polymorphs, its pharmaceutically acceptable salts, and its pharmaceutically acceptable solvates are provided. Except as otherwise provided, all symbols are as defined above in connection with formula (I).

R' and R" independently are hydrogen, a halogen, a nitro group, an amino group, a mono- or di-substituted amino group, a hydroxy group, an alkoxy group, a carboxy group, a cyano group, an oxo(O=) group, a thio(S=) group, an alkyl group, a cycloalkyl group, an alkoxy group, a haloalkoxy group, a cycloalkyl group, an aryl group, a benzyloxy group, an acyl group, an acyloxy group, an aroyl group, an alkoxycarbonyl group, an aryloxycarbonyl group, a heteroaryl group, a heterocyclyl group, an aralkyl group, an alkylsulfonyl group, an alkylsulfinyl group, an arylsulfonyl group, an arylsulfinyl group, an alkylthio group, an arylthio group, a heteroarylthio group, an aralkylthio group, or a heterocyclyl sulfonyl group.

In one aspect of the present invention, $R^1$, $R^2$, $R^3$, and $R^5$ are as defined above; $R^4$ is an optionally substituted aryl group, and in some instances, is a phenyl group optionally substituted with a halogen, an alkoxy group, or both; E is O or —NR, where R is as defined above; G is —(CH2)$_s$— or —(CH2)$_s$—CH=CH—(CH2)$_s$—; s is an integer from 1-3; and R' and R" are as defined above, and in some instances, independently are hydrogen, a halogen, a nitro group, an amino group, a mono- or di-substituted amino group, a hydroxy group, an alkoxy group, an alkyl group, a cycloalkyl group, an alkoxy group, an aryl group, or an acyl group.

Numerous compounds having the general formula (III) are contemplated by the present invention. Various configurations of such compounds provided herein are also encompassed by this invention, as provided below.

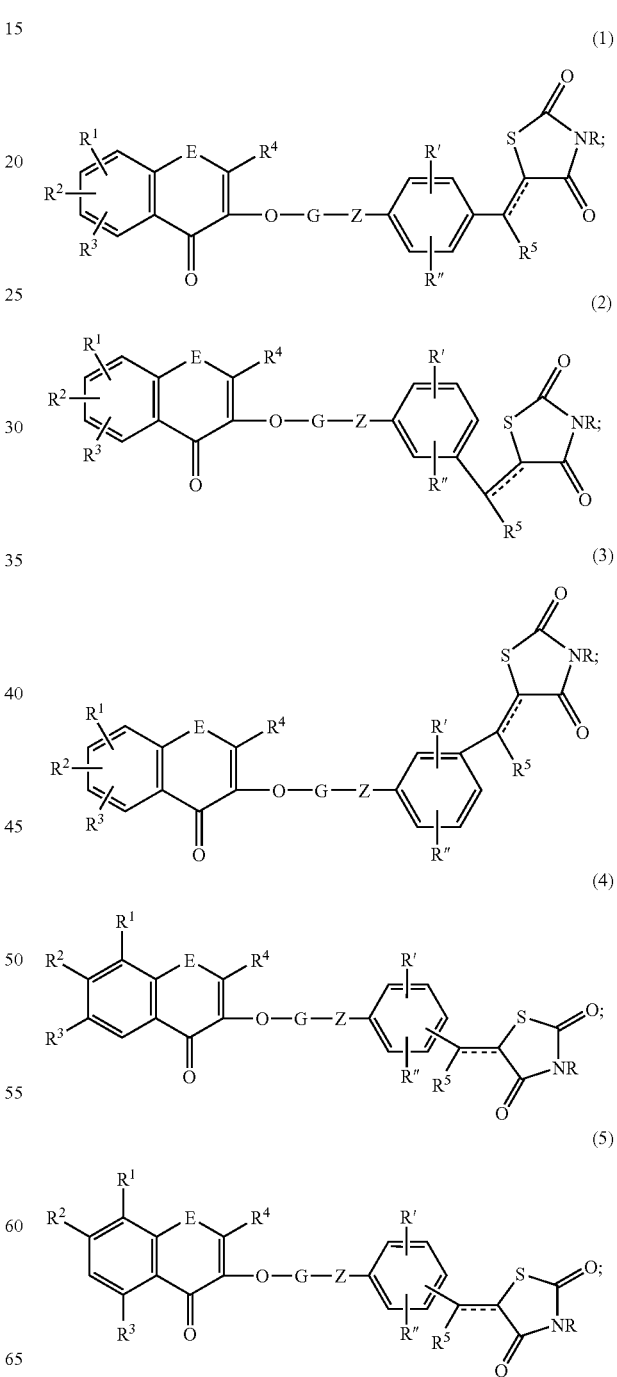

(6)
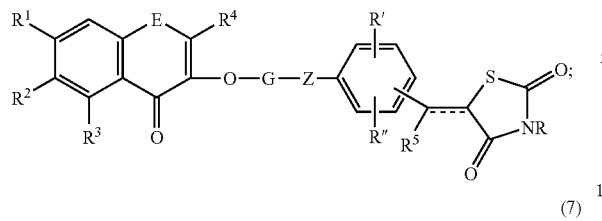
(7)
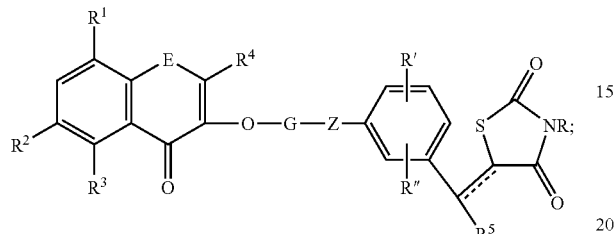
(8)
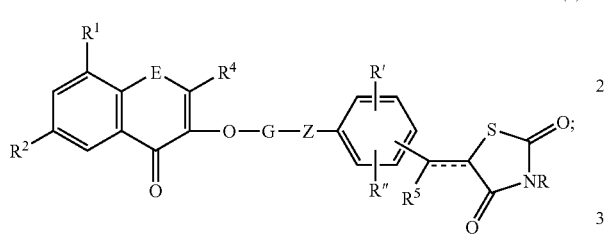
(9)
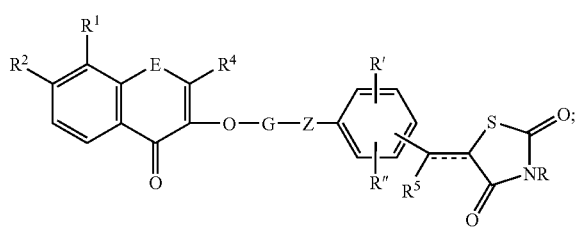
(10)
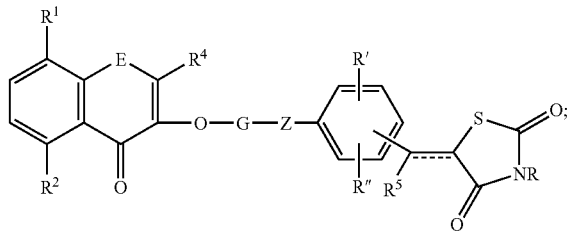
(11)
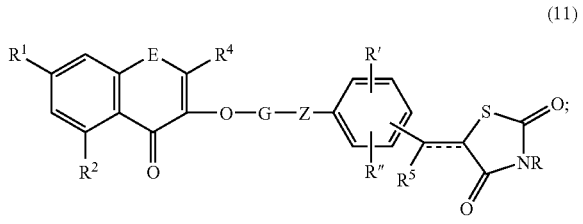
(12)
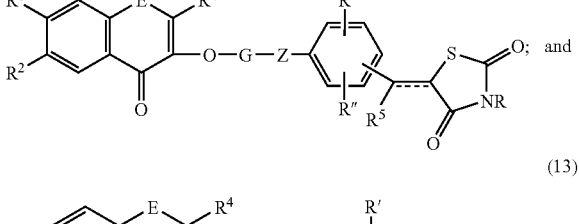
(13)
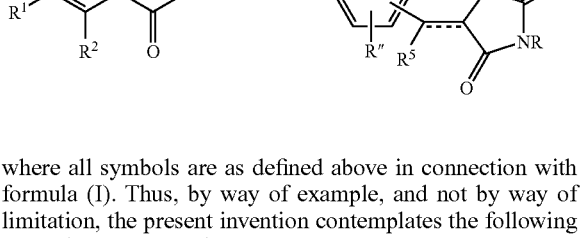
where all symbols are as defined above in connection with formula (I). Thus, by way of example, and not by way of limitation, the present invention contemplates the following exemplary compounds:
(14)
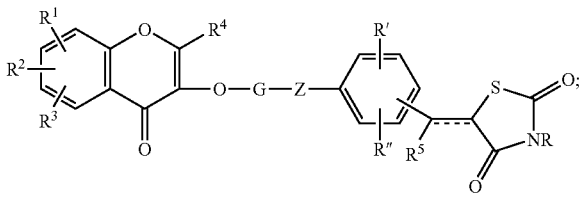
(15)
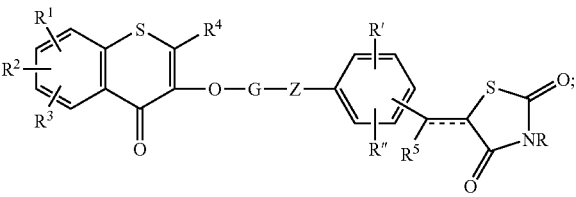
(16)
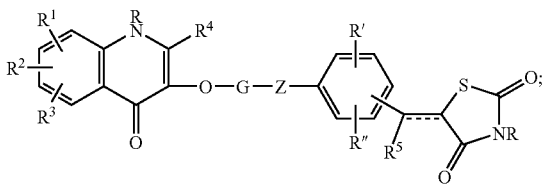
(17)
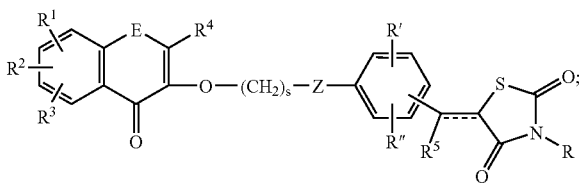

-continued
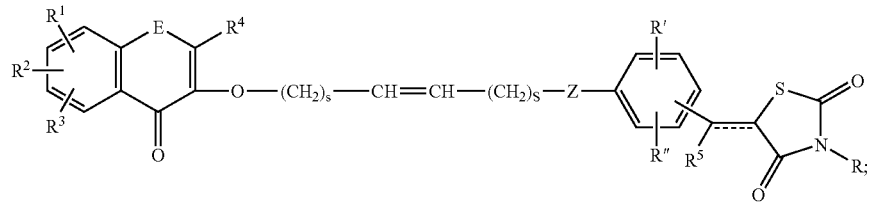
(18)
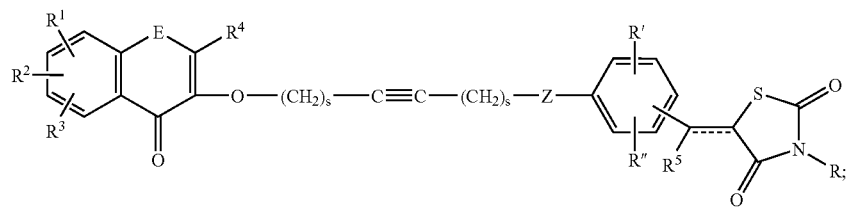
(19)
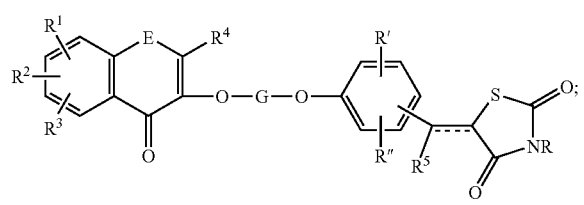
(20)
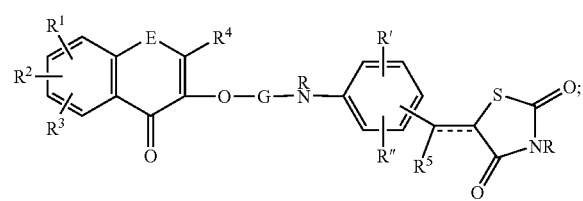
(21)
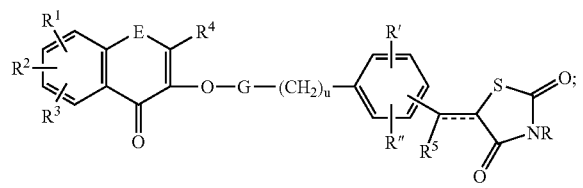
(22)
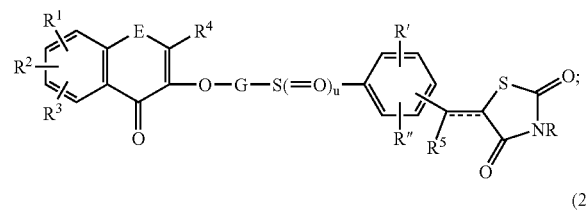
(23)
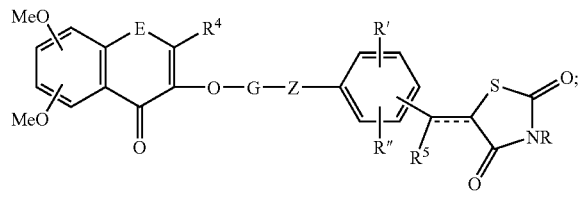
(24)
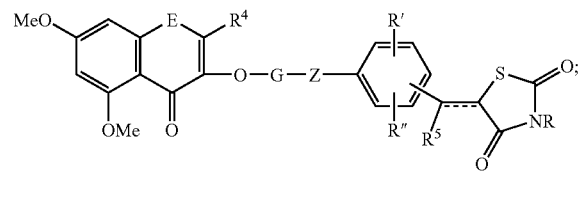
(25)
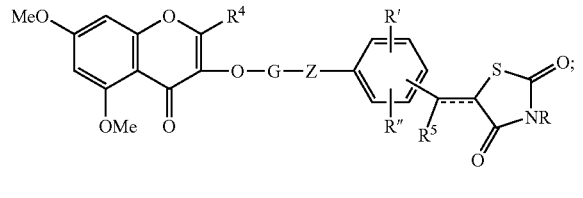
(26)
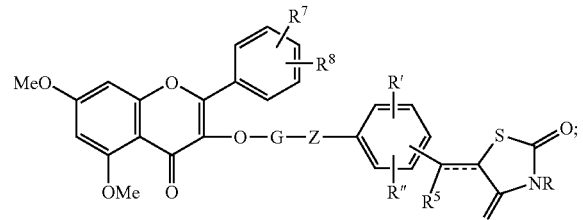
(27)
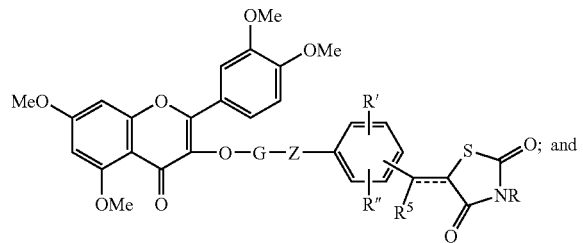
(28)
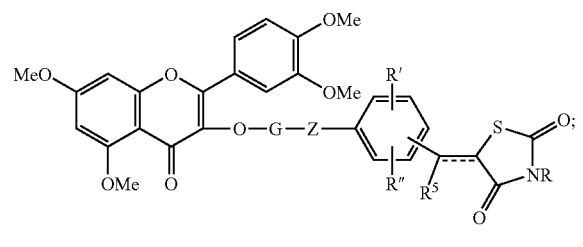
(29)

where all symbols are as defined above in connection with formula (I).

By way of further example, the present invention contemplates various compounds having the following general formula:

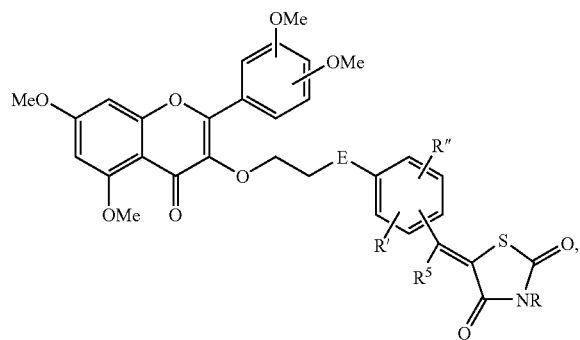

(30)

where all symbols are as defined above in connection with formula (I).

According to various aspects of the present invention, R, $R^5$, R', R", and E of formula (30) are selected to produce various compounds of formula (30-1) through formula (30-243) as follows:

| Formula | R | $R^5$ | R' | R" | E |
|---|---|---|---|---|---|
| 30-1 | $R^a$ | $R^{5a}$ | $R'^a$ | $R''^a$ | $E^a$ |
| 30-2 | $R^b$ | $R^{5a}$ | $R'^a$ | $R''^a$ | $E^a$ |
| 30-3 | $R^c$ | $R^{5a}$ | $R'^a$ | $R''^a$ | $E^a$ |
| 30-4 | $R^a$ | $R^{5b}$ | $R'^a$ | $R''^a$ | $E^a$ |
| 30-5 | $R^b$ | $R^{5b}$ | $R'^a$ | $R''^a$ | $E^a$ |
| 30-6 | $R^c$ | $R^{5b}$ | $R'^a$ | $R''^a$ | $E^a$ |
| 30-7 | $R^a$ | $R^{5c}$ | $R'^a$ | $R''^a$ | $E^a$ |
| 30-8 | $R^b$ | $R^{5c}$ | $R'^a$ | $R''^a$ | $E^a$ |
| 30-9 | $R^c$ | $R^{5c}$ | $R'^a$ | $R''^a$ | $E^a$ |
| 30-10 | $R^a$ | $R^{5a}$ | $R'^b$ | $R''^a$ | $E^a$ |
| 30-11 | $R^b$ | $R^{5a}$ | $R'^b$ | $R''^a$ | $E^a$ |
| 30-12 | $R^c$ | $R^{5a}$ | $R'^b$ | $R''^a$ | $E^a$ |
| 30-13 | $R^a$ | $R^{5b}$ | $R'^b$ | $R''^a$ | $E^a$ |
| 30-14 | $R^b$ | $R^{5b}$ | $R'^b$ | $R''^a$ | $E^a$ |
| 30-15 | $R^c$ | $R^{5b}$ | $R'^b$ | $R''^a$ | $E^a$ |
| 30-16 | $R^a$ | $R^{5c}$ | $R'^b$ | $R''^a$ | $E^a$ |
| 30-17 | $R^b$ | $R^{5c}$ | $R'^b$ | $R''^a$ | $E^a$ |
| 30-18 | $R^c$ | $R^{5c}$ | $R'^b$ | $R''^a$ | $E^a$ |
| 30-19 | $R^a$ | $R^{5a}$ | $R'^c$ | $R''^a$ | $E^a$ |
| 30-20 | $R^b$ | $R^{5a}$ | $R'^c$ | $R''^a$ | $E^a$ |
| 30-21 | $R^c$ | $R^{5a}$ | $R'^c$ | $R''^a$ | $E^a$ |
| 30-22 | $R^a$ | $R^{5b}$ | $R'^c$ | $R''^a$ | $E^a$ |
| 30-23 | $R^b$ | $R^{5b}$ | $R'^c$ | $R''^a$ | $E^a$ |
| 30-24 | $R^c$ | $R^{5b}$ | $R'^c$ | $R''^a$ | $E^a$ |
| 30-25 | $R^a$ | $R^{5c}$ | $R'^c$ | $R''^a$ | $E^a$ |
| 30-26 | $R^b$ | $R^{5c}$ | $R'^c$ | $R''^a$ | $E^a$ |
| 30-27 | $R^c$ | $R^{5c}$ | $R'^c$ | $R''^a$ | $E^a$ |
| 30-28 | $R^a$ | $R^{5a}$ | $R'^a$ | $R''^b$ | $E^a$ |
| 30-29 | $R^b$ | $R^{5a}$ | $R'^a$ | $R''^b$ | $E^a$ |
| 30-30 | $R^c$ | $R^{5a}$ | $R'^a$ | $R''^b$ | $E^a$ |
| 30-31 | $R^a$ | $R^{5b}$ | $R'^a$ | $R''^b$ | $E^a$ |
| 30-32 | $R^b$ | $R^{5b}$ | $R'^a$ | $R''^b$ | $E^a$ |
| 30-33 | $R^c$ | $R^{5b}$ | $R'^a$ | $R''^b$ | $E^a$ |
| 30-34 | $R^a$ | $R^{5c}$ | $R'^a$ | $R''^b$ | $E^a$ |
| 30-35 | $R^b$ | $R^{5c}$ | $R'^a$ | $R''^b$ | $E^a$ |
| 30-36 | $R^c$ | $R^{5c}$ | $R'^a$ | $R''^b$ | $E^a$ |
| 30-37 | $R^a$ | $R^{5a}$ | $R'^b$ | $R''^b$ | $E^a$ |
| 30-38 | $R^b$ | $R^{5a}$ | $R'^b$ | $R''^b$ | $E^a$ |
| 30-39 | $R^c$ | $R^{5a}$ | $R'^b$ | $R''^b$ | $E^a$ |
| 30-40 | $R^a$ | $R^{5b}$ | $R'^b$ | $R''^b$ | $E^a$ |
| 30-41 | $R^b$ | $R^{5b}$ | $R'^b$ | $R''^b$ | $E^a$ |
| 30-42 | $R^c$ | $R^{5b}$ | $R'^b$ | $R''^b$ | $E^a$ |
| 30-43 | $R^a$ | $R^{5c}$ | $R'^b$ | $R''^b$ | $E^a$ |
| 30-44 | $R^b$ | $R^{5c}$ | $R'^b$ | $R''^b$ | $E^a$ |
| 30-45 | $R^c$ | $R^{5c}$ | $R'^b$ | $R''^b$ | $E^a$ |
| 30-46 | $R^a$ | $R^{5a}$ | $R'^c$ | $R''^b$ | $E^a$ |
| 30-47 | $R^b$ | $R^{5a}$ | $R'^c$ | $R''^b$ | $E^a$ |
| 30-48 | $R^c$ | $R^{5a}$ | $R'^c$ | $R''^b$ | $E^a$ |
| 30-49 | $R^a$ | $R^{5b}$ | $R'^c$ | $R''^b$ | $E^a$ |
| 30-50 | $R^b$ | $R^{5b}$ | $R'^c$ | $R''^b$ | $E^a$ |
| 30-51 | $R^c$ | $R^{5b}$ | $R'^c$ | $R''^b$ | $E^a$ |
| 30-52 | $R^a$ | $R^{5c}$ | $R'^c$ | $R''^b$ | $E^a$ |
| 30-53 | $R^b$ | $R^{5c}$ | $R'^c$ | $R''^b$ | $E^a$ |
| 30-54 | $R^c$ | $R^{5c}$ | $R'^c$ | $R''^b$ | $E^a$ |
| 30-55 | $R^a$ | $R^{5a}$ | $R'^a$ | $R''^c$ | $E^a$ |
| 30-56 | $R^b$ | $R^{5a}$ | $R'^a$ | $R''^c$ | $E^a$ |
| 30-57 | $R^c$ | $R^{5a}$ | $R'^a$ | $R''^c$ | $E^a$ |
| 30-58 | $R^a$ | $R^{5b}$ | $R'^a$ | $R''^c$ | $E^a$ |
| 30-59 | $R^b$ | $R^{5b}$ | $R'^a$ | $R''^c$ | $E^a$ |
| 30-60 | $R^c$ | $R^{5b}$ | $R'^a$ | $R''^c$ | $E^a$ |
| 30-61 | $R^a$ | $R^{5c}$ | $R'^a$ | $R''^c$ | $E^a$ |
| 30-62 | $R^b$ | $R^{5c}$ | $R'^a$ | $R''^c$ | $E^a$ |
| 30-63 | $R^c$ | $R^{5c}$ | $R'^a$ | $R''^c$ | $E^a$ |
| 30-64 | $R^a$ | $R^{5a}$ | $R'^b$ | $R''^c$ | $E^a$ |
| 30-65 | $R^b$ | $R^{5a}$ | $R'^b$ | $R''^c$ | $E^a$ |
| 30-66 | $R^c$ | $R^{5a}$ | $R'^b$ | $R''^c$ | $E^a$ |
| 30-67 | $R^a$ | $R^{5b}$ | $R'^b$ | $R''^c$ | $E^a$ |
| 30-68 | $R^b$ | $R^{5b}$ | $R'^b$ | $R''^c$ | $E^a$ |
| 30-69 | $R^c$ | $R^{5b}$ | $R'^b$ | $R''^c$ | $E^a$ |
| 30-70 | $R^a$ | $R^{5c}$ | $R'^b$ | $R''^c$ | $E^a$ |
| 30-71 | $R^b$ | $R^{5c}$ | $R'^b$ | $R''^c$ | $E^a$ |
| 30-72 | $R^c$ | $R^{5c}$ | $R'^b$ | $R''^c$ | $E^a$ |
| 30-73 | $R^a$ | $R^{5a}$ | $R'^c$ | $R''^c$ | $E^a$ |
| 30-74 | $R^b$ | $R^{5a}$ | $R'^c$ | $R''^c$ | $E^a$ |
| 30-75 | $R^c$ | $R^{5a}$ | $R'^c$ | $R''^c$ | $E^a$ |
| 30-76 | $R^a$ | $R^{5b}$ | $R'^c$ | $R''^c$ | $E^a$ |
| 30-77 | $R^b$ | $R^{5b}$ | $R'^c$ | $R''^c$ | $E^a$ |
| 30-78 | $R^c$ | $R^{5b}$ | $R'^c$ | $R''^c$ | $E^a$ |
| 30-79 | $R^a$ | $R^{5c}$ | $R'^c$ | $R''^c$ | $E^a$ |
| 30-80 | $R^b$ | $R^{5c}$ | $R'^c$ | $R''^c$ | $E^a$ |
| 30-81 | $R^c$ | $R^{5c}$ | $R'^c$ | $R''^c$ | $E^a$ |
| 30-82 | $R^a$ | $R^{5a}$ | $R'^a$ | $R''^a$ | $E^b$ |
| 30-83 | $R^b$ | $R^{5a}$ | $R'^a$ | $R''^a$ | $E^b$ |
| 30-84 | $R^c$ | $R^{5a}$ | $R'^a$ | $R''^a$ | $E^b$ |
| 30-85 | $R^a$ | $R^{5b}$ | $R'^a$ | $R''^a$ | $E^b$ |
| 30-86 | $R^b$ | $R^{5b}$ | $R'^a$ | $R''^a$ | $E^b$ |
| 30-87 | $R^c$ | $R^{5b}$ | $R'^a$ | $R''^a$ | $E^b$ |
| 30-88 | $R^a$ | $R^{5c}$ | $R'^a$ | $R''^a$ | $E^b$ |
| 30-89 | $R^b$ | $R^{5c}$ | $R'^a$ | $R''^a$ | $E^b$ |
| 30-90 | $R^c$ | $R^{5c}$ | $R'^a$ | $R''^a$ | $E^b$ |
| 30-91 | $R^a$ | $R^{5a}$ | $R'^b$ | $R''^a$ | $E^b$ |
| 30-92 | $R^b$ | $R^{5a}$ | $R'^b$ | $R''^a$ | $E^b$ |
| 30-93 | $R^c$ | $R^{5a}$ | $R'^b$ | $R''^a$ | $E^b$ |
| 30-94 | $R^a$ | $R^{5b}$ | $R'^b$ | $R''^a$ | $E^b$ |
| 30-95 | $R^b$ | $R^{5b}$ | $R'^b$ | $R''^a$ | $E^b$ |
| 30-96 | $R^c$ | $R^{5b}$ | $R'^b$ | $R''^a$ | $E^b$ |
| 30-97 | $R^a$ | $R^{5c}$ | $R'^b$ | $R''^a$ | $E^b$ |
| 30-98 | $R^b$ | $R^{5c}$ | $R'^b$ | $R''^a$ | $E^b$ |
| 30-99 | $R^c$ | $R^{5c}$ | $R'^b$ | $R''^a$ | $E^b$ |
| 30-100 | $R^a$ | $R^{5a}$ | $R'^c$ | $R''^a$ | $E^b$ |
| 30-101 | $R^b$ | $R^{5a}$ | $R'^c$ | $R''^a$ | $E^b$ |
| 30-102 | $R^c$ | $R^{5a}$ | $R'^c$ | $R''^a$ | $E^b$ |
| 30-103 | $R^a$ | $R^{5b}$ | $R'^c$ | $R''^a$ | $E^b$ |
| 30-104 | $R^b$ | $R^{5b}$ | $R'^c$ | $R''^a$ | $E^b$ |
| 30-105 | $R^c$ | $R^{5b}$ | $R'^c$ | $R''^a$ | $E^b$ |
| 30-106 | $R^a$ | $R^{5c}$ | $R'^c$ | $R''^a$ | $E^b$ |
| 30-107 | $R^b$ | $R^{5c}$ | $R'^c$ | $R''^a$ | $E^b$ |
| 30-108 | $R^c$ | $R^{5c}$ | $R'^c$ | $R''^a$ | $E^b$ |
| 30-109 | $R^a$ | $R^{5a}$ | $R'^a$ | $R''^b$ | $E^b$ |
| 30-110 | $R^b$ | $R^{5a}$ | $R'^a$ | $R''^b$ | $E^b$ |
| 30-111 | $R^c$ | $R^{5a}$ | $R'^a$ | $R''^b$ | $E^b$ |
| 30-112 | $R^a$ | $R^{5b}$ | $R'^a$ | $R''^b$ | $E^b$ |
| 30-113 | $R^b$ | $R^{5b}$ | $R'^a$ | $R''^b$ | $E^b$ |
| 30-114 | $R^c$ | $R^{5b}$ | $R'^a$ | $R''^b$ | $E^b$ |
| 30-115 | $R^a$ | $R^{5c}$ | $R'^a$ | $R''^b$ | $E^b$ |
| 30-116 | $R^b$ | $R^{5c}$ | $R'^a$ | $R''^b$ | $E^b$ |
| 30-117 | $R^c$ | $R^{5c}$ | $R'^a$ | $R''^b$ | $E^b$ |

-continued

| Formula | R | $R^5$ | R' | R" | E |
|---|---|---|---|---|---|
| 30-118 | $R^a$ | $R^{5a}$ | $R'^b$ | $R''^b$ | $E^b$ |
| 30-119 | $R^b$ | $R^{5a}$ | $R'^b$ | $R''^b$ | $E^b$ |
| 30-120 | $R^c$ | $R^{5a}$ | $R'^b$ | $R''^b$ | $E^b$ |
| 30-121 | $R^a$ | $R^{5b}$ | $R'^b$ | $R''^b$ | $E^b$ |
| 30-122 | $R^b$ | $R^{5b}$ | $R'^b$ | $R''^b$ | $E^b$ |
| 30-123 | $R^c$ | $R^{5b}$ | $R'^b$ | $R''^b$ | $E^b$ |
| 30-124 | $R^a$ | $R^{5c}$ | $R'^b$ | $R''^b$ | $E^b$ |
| 30-125 | $R^b$ | $R^{5c}$ | $R'^b$ | $R''^b$ | $E^b$ |
| 30-126 | $R^c$ | $R^{5c}$ | $R'^b$ | $R''^b$ | $E^b$ |
| 30-127 | $R^a$ | $R^{5a}$ | $R'^c$ | $R''^b$ | $E^b$ |
| 30-128 | $R^b$ | $R^{5a}$ | $R'^c$ | $R''^b$ | $E^b$ |
| 30-129 | $R^c$ | $R^{5a}$ | $R'^c$ | $R''^b$ | $E^b$ |
| 30-130 | $R^a$ | $R^{5b}$ | $R'^c$ | $R''^b$ | $E^b$ |
| 30-131 | $R^b$ | $R^{5b}$ | $R'^c$ | $R''^b$ | $E^b$ |
| 30-132 | $R^c$ | $R^{5b}$ | $R'^c$ | $R''^b$ | $E^b$ |
| 30-133 | $R^a$ | $R^{5c}$ | $R'^c$ | $R''^b$ | $E^b$ |
| 30-134 | $R^b$ | $R^{5c}$ | $R'^c$ | $R''^b$ | $E^b$ |
| 30-135 | $R^c$ | $R^{5c}$ | $R'^c$ | $R''^b$ | $E^b$ |
| 30-136 | $R^a$ | $R^{5a}$ | $R'^a$ | $R''^c$ | $E^b$ |
| 30-137 | $R^b$ | $R^{5a}$ | $R'^a$ | $R''^c$ | $E^b$ |
| 30-138 | $R^c$ | $R^{5a}$ | $R'^a$ | $R''^c$ | $E^b$ |
| 30-139 | $R^a$ | $R^{5b}$ | $R'^a$ | $R''^c$ | $E^b$ |
| 30-140 | $R^b$ | $R^{5b}$ | $R'^a$ | $R''^c$ | $E^b$ |
| 30-141 | $R^c$ | $R^{5b}$ | $R'^a$ | $R''^c$ | $E^b$ |
| 30-142 | $R^a$ | $R^{5c}$ | $R'^a$ | $R''^c$ | $E^b$ |
| 30-143 | $R^b$ | $R^{5c}$ | $R'^a$ | $R''^c$ | $E^b$ |
| 30-144 | $R^c$ | $R^{5c}$ | $R'^a$ | $R''^c$ | $E^b$ |
| 30-145 | $R^a$ | $R^{5a}$ | $R'^b$ | $R''^c$ | $E^b$ |
| 30-146 | $R^b$ | $R^{5a}$ | $R'^b$ | $R''^c$ | $E^b$ |
| 30-147 | $R^c$ | $R^{5a}$ | $R'^b$ | $R''^c$ | $E^b$ |
| 30-148 | $R^a$ | $R^{5b}$ | $R'^b$ | $R''^c$ | $E^b$ |
| 30-149 | $R^b$ | $R^{5b}$ | $R'^b$ | $R''^c$ | $E^b$ |
| 30-150 | $R^c$ | $R^{5b}$ | $R'^b$ | $R''^c$ | $E^b$ |
| 30-151 | $R^a$ | $R^{5c}$ | $R'^b$ | $R''^c$ | $E^b$ |
| 30-152 | $R^b$ | $R^{5c}$ | $R'^b$ | $R''^c$ | $E^b$ |
| 30-153 | $R^c$ | $R^{5c}$ | $R'^b$ | $R''^c$ | $E^b$ |
| 30-154 | $R^a$ | $R^{5a}$ | $R'^c$ | $R''^c$ | $E^b$ |
| 30-155 | $R^b$ | $R^{5a}$ | $R'^c$ | $R''^c$ | $E^b$ |
| 30-156 | $R^c$ | $R^{5a}$ | $R'^c$ | $R''^c$ | $E^b$ |
| 30-157 | $R^a$ | $R^{5b}$ | $R'^c$ | $R''^c$ | $E^b$ |
| 30-158 | $R^b$ | $R^{5b}$ | $R'^c$ | $R''^c$ | $E^b$ |
| 30-159 | $R^c$ | $R^{5b}$ | $R'^c$ | $R''^c$ | $E^b$ |
| 30-160 | $R^a$ | $R^{5c}$ | $R'^c$ | $R''^c$ | $E^b$ |
| 30-161 | $R^b$ | $R^{5c}$ | $R'^c$ | $R''^c$ | $E^b$ |
| 30-162 | $R^c$ | $R^{5c}$ | $R'^c$ | $R''^c$ | $E^b$ |
| 30-163 | $R^a$ | $R^{5a}$ | $R'^a$ | $R''^a$ | $E^c$ |
| 30-164 | $R^b$ | $R^{5a}$ | $R'^a$ | $R''^a$ | $E^c$ |
| 30-165 | $R^c$ | $R^{5a}$ | $R'^a$ | $R''^a$ | $E^c$ |
| 30-166 | $R^a$ | $R^{5b}$ | $R'^a$ | $R''^a$ | $E^c$ |
| 30-167 | $R^b$ | $R^{5b}$ | $R'^a$ | $R''^a$ | $E^c$ |
| 30-168 | $R^c$ | $R^{5b}$ | $R'^a$ | $R''^a$ | $E^c$ |
| 30-169 | $R^a$ | $R^{5c}$ | $R'^a$ | $R''^a$ | $E^c$ |
| 30-170 | $R^b$ | $R^{5c}$ | $R'^a$ | $R''^a$ | $E^c$ |
| 30-171 | $R^c$ | $R^{5c}$ | $R'^a$ | $R''^a$ | $E^c$ |
| 30-172 | $R^a$ | $R^{5a}$ | $R'^b$ | $R''^a$ | $E^c$ |
| 30-173 | $R^b$ | $R^{5a}$ | $R'^b$ | $R''^a$ | $E^c$ |
| 30-174 | $R^c$ | $R^{5a}$ | $R'^b$ | $R''^a$ | $E^c$ |
| 30-175 | $R^a$ | $R^{5b}$ | $R'^b$ | $R''^a$ | $E^c$ |
| 30-176 | $R^b$ | $R^{5b}$ | $R'^b$ | $R''^a$ | $E^c$ |
| 30-177 | $R^c$ | $R^{5b}$ | $R'^b$ | $R''^a$ | $E^c$ |
| 30-178 | $R^a$ | $R^{5c}$ | $R'^b$ | $R''^a$ | $E^c$ |
| 30-179 | $R^b$ | $R^{5c}$ | $R'^b$ | $R''^a$ | $E^c$ |
| 30-180 | $R^c$ | $R^{5c}$ | $R'^b$ | $R''^a$ | $E^c$ |
| 30-181 | $R^a$ | $R^{5a}$ | $R'^c$ | $R''^a$ | $E^c$ |
| 30-182 | $R^b$ | $R^{5a}$ | $R'^c$ | $R''^a$ | $E^c$ |
| 30-183 | $R^c$ | $R^{5a}$ | $R'^c$ | $R''^a$ | $E^c$ |
| 30-184 | $R^a$ | $R^{5b}$ | $R'^c$ | $R''^a$ | $E^c$ |
| 30-185 | $R^b$ | $R^{5b}$ | $R'^c$ | $R''^a$ | $E^c$ |
| 30-186 | $R^c$ | $R^{5b}$ | $R'^c$ | $R''^a$ | $E^c$ |
| 30-187 | $R^a$ | $R^{5c}$ | $R'^c$ | $R''^a$ | $E^c$ |
| 30-188 | $R^b$ | $R^{5c}$ | $R'^c$ | $R''^a$ | $E^c$ |
| 30-189 | $R^c$ | $R^{5c}$ | $R'^c$ | $R''^a$ | $E^c$ |
| 30-190 | $R^a$ | $R^{5a}$ | $R'^a$ | $R''^b$ | $E^c$ |
| 30-191 | $R^b$ | $R^{5a}$ | $R'^a$ | $R''^b$ | $E^c$ |
| 30-192 | $R^c$ | $R^{5a}$ | $R'^a$ | $R''^b$ | $E^c$ |
| 30-193 | $R^a$ | $R^{5b}$ | $R'^a$ | $R''^b$ | $E^c$ |
| 30-194 | $R^b$ | $R^{5b}$ | $R'^a$ | $R''^b$ | $E^c$ |
| 30-195 | $R^c$ | $R^{5b}$ | $R'^a$ | $R''^b$ | $E^c$ |
| 30-196 | $R^a$ | $R^{5c}$ | $R'^a$ | $R''^b$ | $E^c$ |
| 30-197 | $R^b$ | $R^{5c}$ | $R'^a$ | $R''^b$ | $E^c$ |
| 30-198 | $R^c$ | $R^{5c}$ | $R'^a$ | $R''^b$ | $E^c$ |
| 30-199 | $R^a$ | $R^{5a}$ | $R'^b$ | $R''^b$ | $E^c$ |
| 30-200 | $R^b$ | $R^{5a}$ | $R'^b$ | $R''^b$ | $E^c$ |
| 30-201 | $R^c$ | $R^{5a}$ | $R'^b$ | $R''^b$ | $E^c$ |
| 30-202 | $R^a$ | $R^{5b}$ | $R'^b$ | $R''^b$ | $E^c$ |
| 30-203 | $R^b$ | $R^{5b}$ | $R'^b$ | $R''^b$ | $E^c$ |
| 30-204 | $R^c$ | $R^{5b}$ | $R'^b$ | $R''^b$ | $E^c$ |
| 30-205 | $R^a$ | $R^{5c}$ | $R'^b$ | $R''^b$ | $E^c$ |
| 30-206 | $R^b$ | $R^{5c}$ | $R'^b$ | $R''^b$ | $E^c$ |
| 30-207 | $R^c$ | $R^{5c}$ | $R'^b$ | $R''^b$ | $E^c$ |
| 30-208 | $R^a$ | $R^{5a}$ | $R'^c$ | $R''^b$ | $E^c$ |
| 30-209 | $R^b$ | $R^{5a}$ | $R'^c$ | $R''^b$ | $E^c$ |
| 30-210 | $R^c$ | $R^{5a}$ | $R'^c$ | $R''^b$ | $E^c$ |
| 30-211 | $R^a$ | $R^{5b}$ | $R'^c$ | $R''^b$ | $E^c$ |
| 30-212 | $R^b$ | $R^{5b}$ | $R'^c$ | $R''^b$ | $E^c$ |
| 30-213 | $R^c$ | $R^{5b}$ | $R'^c$ | $R''^b$ | $E^c$ |
| 30-214 | $R^a$ | $R^{5c}$ | $R'^c$ | $R''^b$ | $E^c$ |
| 30-215 | $R^b$ | $R^{5c}$ | $R'^c$ | $R''^b$ | $E^c$ |
| 30-216 | $R^c$ | $R^{5c}$ | $R'^c$ | $R''^b$ | $E^c$ |
| 30-217 | $R^a$ | $R^{5a}$ | $R'^a$ | $R''^c$ | $E^c$ |
| 30-218 | $R^b$ | $R^{5a}$ | $R'^a$ | $R''^c$ | $E^c$ |
| 30-219 | $R^c$ | $R^{5a}$ | $R'^a$ | $R''^c$ | $E^c$ |
| 30-220 | $R^a$ | $R^{5b}$ | $R'^a$ | $R''^c$ | $E^c$ |
| 30-221 | $R^b$ | $R^{5b}$ | $R'^a$ | $R''^c$ | $E^c$ |
| 30-222 | $R^c$ | $R^{5b}$ | $R'^a$ | $R''^c$ | $E^c$ |
| 30-223 | $R^a$ | $R^{5c}$ | $R'^a$ | $R''^c$ | $E^c$ |
| 30-224 | $R^b$ | $R^{5c}$ | $R'^a$ | $R''^c$ | $E^c$ |
| 30-225 | $R^c$ | $R^{5c}$ | $R'^a$ | $R''^c$ | $E^c$ |
| 30-226 | $R^a$ | $R^{5a}$ | $R'^b$ | $R''^c$ | $E^c$ |
| 30-227 | $R^b$ | $R^{5a}$ | $R'^b$ | $R''^c$ | $E^c$ |
| 30-228 | $R^c$ | $R^{5a}$ | $R'^b$ | $R''^c$ | $E^c$ |
| 30-229 | $R^a$ | $R^{5b}$ | $R'^b$ | $R''^c$ | $E^c$ |
| 30-230 | $R^b$ | $R^{5b}$ | $R'^b$ | $R''^c$ | $E^c$ |
| 30-231 | $R^c$ | $R^{5b}$ | $R'^b$ | $R''^c$ | $E^c$ |
| 30-232 | $R^a$ | $R^{5c}$ | $R'^b$ | $R''^c$ | $E^c$ |
| 30-233 | $R^b$ | $R^{5c}$ | $R'^b$ | $R''^c$ | $E^c$ |
| 30-234 | $R^c$ | $R^{5c}$ | $R'^b$ | $R''^c$ | $E^c$ |
| 30-235 | $R^a$ | $R^{5a}$ | $R'^c$ | $R''^c$ | $E^c$ |
| 30-236 | $R^b$ | $R^{5a}$ | $R'^c$ | $R''^c$ | $E^c$ |
| 30-237 | $R^c$ | $R^{5a}$ | $R'^c$ | $R''^c$ | $E^c$ |
| 30-238 | $R^a$ | $R^{5b}$ | $R'^c$ | $R''^c$ | $E^c$ |
| 30-239 | $R^b$ | $R^{5b}$ | $R'^c$ | $R''^c$ | $E^c$ |
| 30-240 | $R^c$ | $R^{5b}$ | $R'^c$ | $R''^c$ | $E^c$ |
| 30-241 | $R^a$ | $R^{5c}$ | $R'^c$ | $R''^c$ | $E^c$ |
| 30-242 | $R^b$ | $R^{5c}$ | $R'^c$ | $R''^c$ | $E^c$ |
| 30-243 | $R^c$ | $R^{5c}$ | $R'^c$ | $R''^c$ | $E^c$ | where all symbols are as defined above.

In one aspect of formula (30) of the present invention, R is hydrogen, a hydroxy group, a halogen, a nitro group, or an optionally substituted amino group; $R^5$ is hydrogen, a hydroxy group, a halogen, a nitro group, an optionally substituted amino group, an alkyl group, an alkoxy group, an alkenyl group, or an alkoxyalkyl group; R' and R" independently are hydrogen, a halogen, a nitro group, an amino group, a mono- or di-substituted amino group, an alkyl group, a cycloalkyl group, an alkoxy group, a haloalkoxy group, a cycloalkyl group, an aryl group, or a benzyloxy group; and E is O, S, or NH.

In another aspect of formula (30) of the present invention, R is hydrogen, an alkyl group, potassium, or sodium; $R^5$ is hydrogen or an alkyl group; and all other symbols are as defined above in connection with formula (I);

In another aspect of formula (30) of the present invention, E is O, S, or NH; R' and R? independently are —H, —Cl, —Br, or —CH$_3$; $R^5$ is —H, —CH$_3$, or —CH$_2$CH$_2$CH$_3$; and R is —H, K, or Na.

Examples of compounds of formula (30) include, but are not limited to:
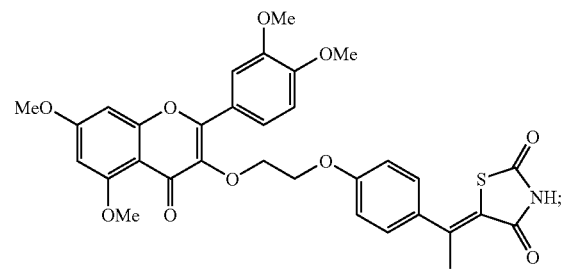

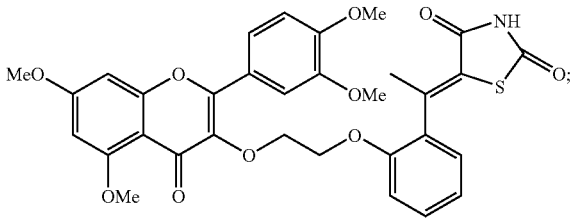
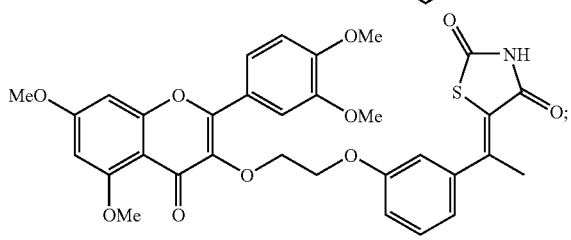
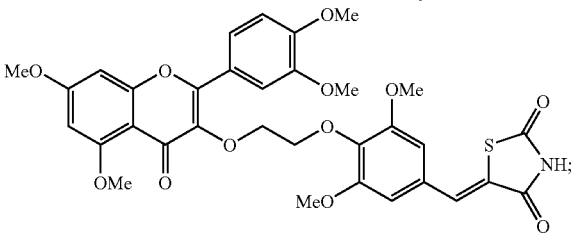
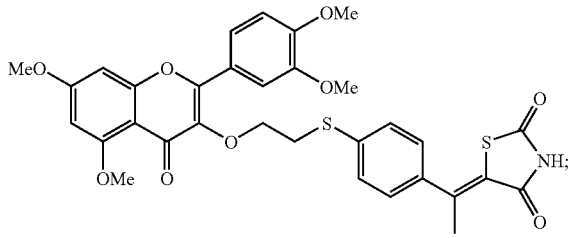
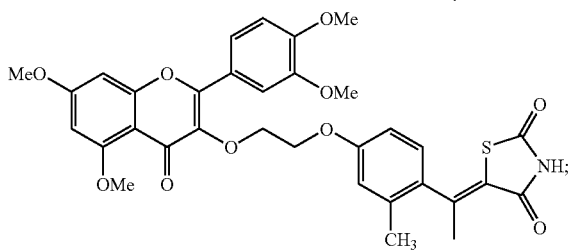
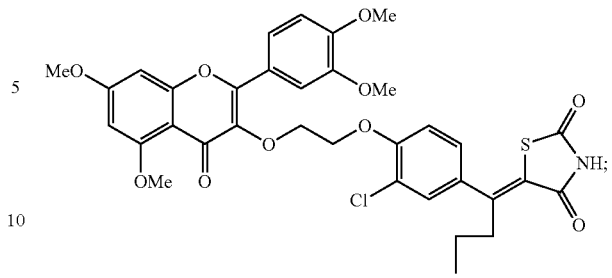
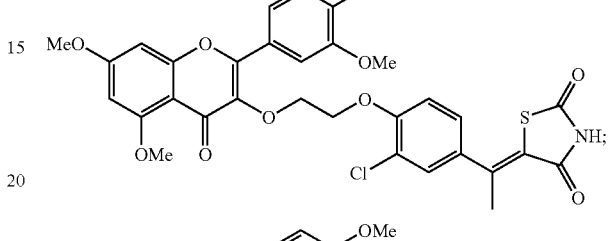
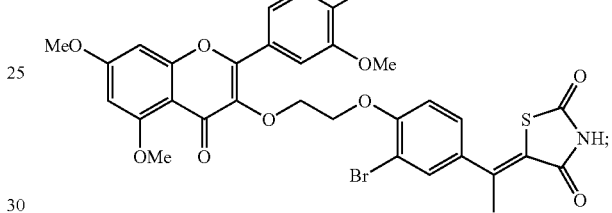
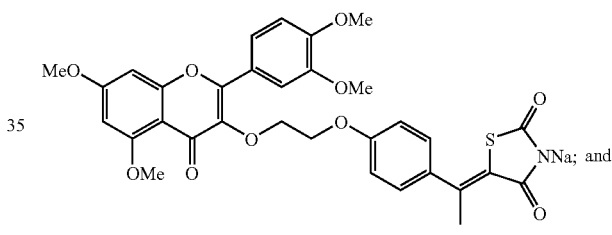
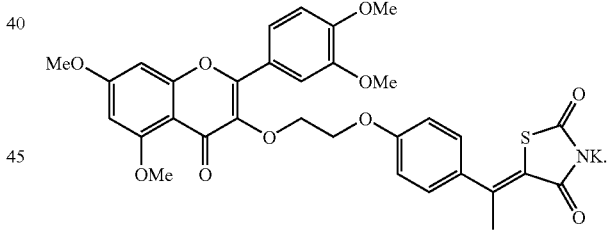
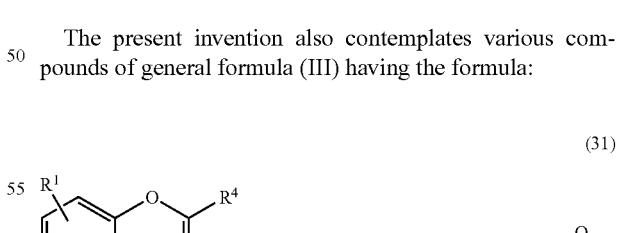
The present invention also contemplates various compounds of general formula (III) having the formula:
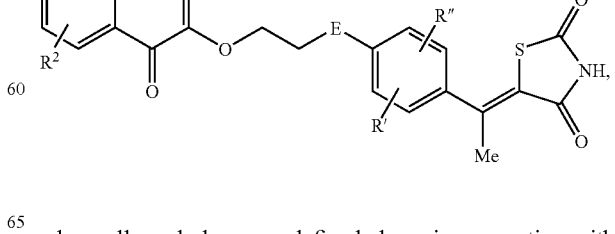
(31)
where all symbols are as defined above in connection with formula (I).

According to various aspects of the present invention, $R^1$, $R^2$, $R^4$, E, R', and R" of formula (31) are selected to produce various compounds of formula (31-1) to (31-729) as follows:

| Formula | $R^1$ | $R^2$ | $R^4$ | E | R' | R" |
|---|---|---|---|---|---|---|
| 31-1 | $R^{1a}$ | $R^{2a}$ | $R^{4a}$ | $E^a$ | $R'^a$ | $R''^a$ |
| 31-2 | $R^{1b}$ | $R^{2a}$ | $R^{4a}$ | $E^a$ | $R'^a$ | $R''^a$ |
| 31-3 | $R^{1c}$ | $R^{2a}$ | $R^{4a}$ | $E^a$ | $R'^a$ | $R''^a$ |
| 31-4 | $R^{1a}$ | $R^{2b}$ | $R^{4a}$ | $E^a$ | $R'^a$ | $R''^a$ |
| 31-5 | $R^{1b}$ | $R^{2b}$ | $R^{4a}$ | $E^a$ | $R'^a$ | $R''^a$ |
| 31-6 | $R^{1c}$ | $R^{2b}$ | $R^{4a}$ | $E^a$ | $R'^a$ | $R''^a$ |
| 31-7 | $R^{1a}$ | $R^{2c}$ | $R^{4a}$ | $E^a$ | $R'^a$ | $R''^a$ |
| 31-8 | $R^{1b}$ | $R^{2c}$ | $R^{4a}$ | $E^a$ | $R'^a$ | $R''^a$ |
| 31-9 | $R^{1c}$ | $R^{2c}$ | $R^{4a}$ | $E^a$ | $R'^a$ | $R''^a$ |
| 31-10 | $R^{1a}$ | $R^{2a}$ | $R^{4b}$ | $E^a$ | $R'^a$ | $R''^a$ |
| 31-11 | $R^{1b}$ | $R^{2a}$ | $R^{4b}$ | $E^a$ | $R'^a$ | $R''^a$ |
| 31-12 | $R^{1c}$ | $R^{2a}$ | $R^{4b}$ | $E^a$ | $R'^a$ | $R''^a$ |
| 31-13 | $R^{1a}$ | $R^{2b}$ | $R^{4b}$ | $E^a$ | $R'^a$ | $R''^a$ |
| 31-14 | $R^{1b}$ | $R^{2b}$ | $R^{4b}$ | $E^a$ | $R'^a$ | $R''^a$ |
| 31-15 | $R^{1c}$ | $R^{2b}$ | $R^{4b}$ | $E^a$ | $R'^a$ | $R''^a$ |
| 31-16 | $R^{1a}$ | $R^{2c}$ | $R^{4b}$ | $E^a$ | $R'^a$ | $R''^a$ |
| 31-17 | $R^{1b}$ | $R^{2c}$ | $R^{4b}$ | $E^a$ | $R'^a$ | $R''^a$ |
| 31-18 | $R^{1c}$ | $R^{2c}$ | $R^{4b}$ | $E^a$ | $R'^a$ | $R''^a$ |
| 31-19 | $R^{1a}$ | $R^{2a}$ | $R^{4c}$ | $E^a$ | $R'^a$ | $R''^a$ |
| 31-20 | $R^{1b}$ | $R^{2a}$ | $R^{4c}$ | $E^a$ | $R'^a$ | $R''^a$ |
| 31-21 | $R^{1c}$ | $R^{2a}$ | $R^{4c}$ | $E^a$ | $R'^a$ | $R''^a$ |
| 31-22 | $R^{1a}$ | $R^{2b}$ | $R^{4c}$ | $E^a$ | $R'^a$ | $R''^a$ |
| 31-23 | $R^{1b}$ | $R^{2b}$ | $R^{4c}$ | $E^a$ | $R'^a$ | $R''^a$ |
| 31-24 | $R^{1c}$ | $R^{2b}$ | $R^{4c}$ | $E^a$ | $R'^a$ | $R''^a$ |
| 31-25 | $R^{1a}$ | $R^{2c}$ | $R^{4c}$ | $E^a$ | $R'^a$ | $R''^a$ |
| 31-26 | $R^{1b}$ | $R^{2c}$ | $R^{4c}$ | $E^a$ | $R'^a$ | $R''^a$ |
| 31-27 | $R^{1c}$ | $R^{2c}$ | $R^{4c}$ | $E^a$ | $R'^a$ | $R''^a$ |
| 31-28 | $R^{1a}$ | $R^{2a}$ | $R^{4a}$ | $E^b$ | $R'^a$ | $R''^a$ |
| 31-29 | $R^{1b}$ | $R^{2a}$ | $R^{4a}$ | $E^b$ | $R'^a$ | $R''^a$ |
| 31-30 | $R^{1c}$ | $R^{2a}$ | $R^{4a}$ | $E^b$ | $R'^a$ | $R''^a$ |
| 31-31 | $R^{1a}$ | $R^{2b}$ | $R^{4a}$ | $E^b$ | $R'^a$ | $R''^a$ |
| 31-32 | $R^{1b}$ | $R^{2b}$ | $R^{4a}$ | $E^b$ | $R'^a$ | $R''^a$ |
| 31-33 | $R^{1c}$ | $R^{2b}$ | $R^{4a}$ | $E^b$ | $R'^a$ | $R''^a$ |
| 31-34 | $R^{1a}$ | $R^{2c}$ | $R^{4a}$ | $E^b$ | $R'^a$ | $R''^a$ |
| 31-35 | $R^{1b}$ | $R^{2c}$ | $R^{4a}$ | $E^b$ | $R'^a$ | $R''^a$ |
| 31-36 | $R^{1c}$ | $R^{2c}$ | $R^{4a}$ | $E^b$ | $R'^a$ | $R''^a$ |
| 31-37 | $R^{1a}$ | $R^{2a}$ | $R^{4b}$ | $E^b$ | $R'^a$ | $R''^a$ |
| 31-38 | $R^{1b}$ | $R^{2a}$ | $R^{4b}$ | $E^b$ | $R'^a$ | $R''^a$ |
| 31-39 | $R^{1c}$ | $R^{2a}$ | $R^{4b}$ | $E^b$ | $R'^a$ | $R''^a$ |
| 31-40 | $R^{1a}$ | $R^{2b}$ | $R^{4b}$ | $E^b$ | $R'^a$ | $R''^a$ |
| 31-41 | $R^{1b}$ | $R^{2b}$ | $R^{4b}$ | $E^b$ | $R'^a$ | $R''^a$ |
| 31-42 | $R^{1c}$ | $R^{2b}$ | $R^{4b}$ | $E^b$ | $R'^a$ | $R''^a$ |
| 31-43 | $R^{1a}$ | $R^{2c}$ | $R^{4b}$ | $E^b$ | $R'^a$ | $R''^a$ |
| 31-44 | $R^{1b}$ | $R^{2c}$ | $R^{4b}$ | $E^b$ | $R'^a$ | $R''^a$ |
| 31-45 | $R^{1c}$ | $R^{2c}$ | $R^{4b}$ | $E^b$ | $R'^a$ | $R''^a$ |
| 31-46 | $R^{1a}$ | $R^{2a}$ | $R^{4c}$ | $E^b$ | $R'^a$ | $R''^a$ |
| 31-47 | $R^{1b}$ | $R^{2a}$ | $R^{4c}$ | $E^b$ | $R'^a$ | $R''^a$ |
| 31-48 | $R^{1c}$ | $R^{2a}$ | $R^{4c}$ | $E^b$ | $R'^a$ | $R''^a$ |
| 31-49 | $R^{1a}$ | $R^{2b}$ | $R^{4c}$ | $E^b$ | $R'^a$ | $R''^a$ |
| 31-50 | $R^{1b}$ | $R^{2b}$ | $R^{4c}$ | $E^b$ | $R'^a$ | $R''^a$ |
| 31-51 | $R^{1c}$ | $R^{2b}$ | $R^{4c}$ | $E^b$ | $R'^a$ | $R''^a$ |
| 31-52 | $R^{1a}$ | $R^{2c}$ | $R^{4c}$ | $E^b$ | $R'^a$ | $R''^a$ |
| 31-53 | $R^{1b}$ | $R^{2c}$ | $R^{4c}$ | $E^b$ | $R'^a$ | $R''^a$ |
| 31-54 | $R^{1c}$ | $R^{2c}$ | $R^{4c}$ | $E^b$ | $R'^a$ | $R''^a$ |
| 31-55 | $R^{1a}$ | $R^{2a}$ | $R^{4a}$ | $E^c$ | $R'^a$ | $R''^a$ |
| 31-56 | $R^{1b}$ | $R^{2a}$ | $R^{4a}$ | $E^c$ | $R'^a$ | $R''^a$ |
| 31-57 | $R^{1c}$ | $R^{2a}$ | $R^{4a}$ | $E^c$ | $R'^a$ | $R''^a$ |
| 31-58 | $R^{1a}$ | $R^{2b}$ | $R^{4a}$ | $E^c$ | $R'^a$ | $R''^a$ |
| 31-59 | $R^{1b}$ | $R^{2b}$ | $R^{4a}$ | $E^c$ | $R'^a$ | $R''^a$ |
| 31-60 | $R^{1c}$ | $R^{2b}$ | $R^{4a}$ | $E^c$ | $R'^a$ | $R''^a$ |
| 31-61 | $R^{1a}$ | $R^{2c}$ | $R^{4a}$ | $E^c$ | $R'^a$ | $R''^a$ |
| 31-62 | $R^{1b}$ | $R^{2c}$ | $R^{4a}$ | $E^c$ | $R'^a$ | $R''^a$ |
| 31-63 | $R^{1c}$ | $R^{2c}$ | $R^{4a}$ | $E^c$ | $R'^a$ | $R''^a$ |
| 31-64 | $R^{1a}$ | $R^{2a}$ | $R^{4b}$ | $E^c$ | $R'^a$ | $R''^a$ |
| 31-65 | $R^{1b}$ | $R^{2a}$ | $R^{4b}$ | $E^c$ | $R'^a$ | $R''^a$ |
| 31-66 | $R^{1c}$ | $R^{2a}$ | $R^{4b}$ | $E^c$ | $R'^a$ | $R''^a$ |
| 31-67 | $R^{1a}$ | $R^{2b}$ | $R^{4b}$ | $E^c$ | $R'^a$ | $R''^a$ |
| 31-68 | $R^{1b}$ | $R^{2b}$ | $R^{4b}$ | $E^c$ | $R'^a$ | $R''^a$ |
| 31-69 | $R^{1c}$ | $R^{2b}$ | $R^{4b}$ | $E^c$ | $R'^a$ | $R''^a$ |
| 31-70 | $R^{1a}$ | $R^{2c}$ | $R^{4b}$ | $E^c$ | $R'^a$ | $R''^a$ |
| 31-71 | $R^{1b}$ | $R^{2c}$ | $R^{4b}$ | $E^c$ | $R'^a$ | $R''^a$ |
| 31-72 | $R^{1c}$ | $R^{2c}$ | $R^{4b}$ | $E^c$ | $R'^a$ | $R''^a$ |
| 31-73 | $R^{1a}$ | $R^{2a}$ | $R^{4c}$ | $E^c$ | $R'^a$ | $R''^a$ |
| 31-74 | $R^{1b}$ | $R^{2a}$ | $R^{4c}$ | $E^c$ | $R'^a$ | $R''^a$ |
| 31-75 | $R^{1c}$ | $R^{2a}$ | $R^{4c}$ | $E^c$ | $R'^a$ | $R''^a$ |
| 31-76 | $R^{1a}$ | $R^{2b}$ | $R^{4c}$ | $E^c$ | $R'^a$ | $R''^a$ |
| 31-77 | $R^{1b}$ | $R^{2b}$ | $R^{4c}$ | $E^c$ | $R'^a$ | $R''^a$ |
| 31-78 | $R^{1c}$ | $R^{2b}$ | $R^{4c}$ | $E^c$ | $R'^a$ | $R''^a$ |
| 31-79 | $R^{1a}$ | $R^{2c}$ | $R^{4c}$ | $E^c$ | $R'^a$ | $R''^a$ |
| 31-80 | $R^{1b}$ | $R^{2c}$ | $R^{4c}$ | $E^c$ | $R'^a$ | $R''^a$ |
| 31-81 | $R^{1c}$ | $R^{2c}$ | $R^{4c}$ | $E^c$ | $R'^a$ | $R''^a$ |
| 31-82 | $R^{1a}$ | $R^{2a}$ | $R^{4a}$ | $E^a$ | $R'^b$ | $R''^a$ |
| 31-83 | $R^{1b}$ | $R^{2a}$ | $R^{4a}$ | $E^a$ | $R'^b$ | $R''^a$ |
| 31-84 | $R^{1c}$ | $R^{2a}$ | $R^{4a}$ | $E^a$ | $R'^b$ | $R''^a$ |
| 31-85 | $R^{1a}$ | $R^{2b}$ | $R^{4a}$ | $E^a$ | $R'^b$ | $R''^a$ |
| 31-86 | $R^{1b}$ | $R^{2b}$ | $R^{4a}$ | $E^a$ | $R'^b$ | $R''^a$ |
| 31-87 | $R^{1c}$ | $R^{2b}$ | $R^{4a}$ | $E^a$ | $R'^b$ | $R''^a$ |
| 31-88 | $R^{1a}$ | $R^{2c}$ | $R^{4a}$ | $E^a$ | $R'^b$ | $R''^a$ |
| 31-89 | $R^{1b}$ | $R^{2c}$ | $R^{4a}$ | $E^a$ | $R'^b$ | $R''^a$ |
| 31-90 | $R^{1c}$ | $R^{2c}$ | $R^{4a}$ | $E^a$ | $R'^b$ | $R''^a$ |
| 31-91 | $R^{1a}$ | $R^{2a}$ | $R^{4b}$ | $E^a$ | $R'^b$ | $R''^a$ |
| 31-92 | $R^{1b}$ | $R^{2a}$ | $R^{4b}$ | $E^a$ | $R'^b$ | $R''^a$ |
| 31-93 | $R^{1c}$ | $R^{2a}$ | $R^{4b}$ | $E^a$ | $R'^b$ | $R''^a$ |
| 31-94 | $R^{1a}$ | $R^{2b}$ | $R^{4b}$ | $E^a$ | $R'^b$ | $R''^a$ |
| 31-95 | $R^{1b}$ | $R^{2b}$ | $R^{4b}$ | $E^a$ | $R'^b$ | $R''^a$ |
| 31-96 | $R^{1c}$ | $R^{2b}$ | $R^{4b}$ | $E^a$ | $R'^b$ | $R''^a$ |
| 31-97 | $R^{1a}$ | $R^{2c}$ | $R^{4b}$ | $E^a$ | $R'^b$ | $R''^a$ |
| 31-98 | $R^{1b}$ | $R^{2c}$ | $R^{4b}$ | $E^a$ | $R'^b$ | $R''^a$ |
| 31-99 | $R^{1c}$ | $R^{2c}$ | $R^{4b}$ | $E^a$ | $R'^b$ | $R''^a$ |
| 31-100 | $R^{1a}$ | $R^{2a}$ | $R^{4c}$ | $E^a$ | $R'^b$ | $R''^a$ |
| 31-101 | $R^{1b}$ | $R^{2a}$ | $R^{4c}$ | $E^a$ | $R'^b$ | $R''^a$ |
| 31-102 | $R^{1c}$ | $R^{2a}$ | $R^{4c}$ | $E^a$ | $R'^b$ | $R''^a$ |
| 31-103 | $R^{1a}$ | $R^{2b}$ | $R^{4c}$ | $E^a$ | $R'^b$ | $R''^a$ |
| 31-104 | $R^{1b}$ | $R^{2b}$ | $R^{4c}$ | $E^a$ | $R'^b$ | $R''^a$ |
| 31-105 | $R^{1c}$ | $R^{2b}$ | $R^{4c}$ | $E^a$ | $R'^b$ | $R''^a$ |
| 31-106 | $R^{1a}$ | $R^{2c}$ | $R^{4c}$ | $E^a$ | $R'^b$ | $R''^a$ |
| 31-107 | $R^{1b}$ | $R^{2c}$ | $R^{4c}$ | $E^a$ | $R'^b$ | $R''^a$ |
| 31-108 | $R^{1c}$ | $R^{2c}$ | $R^{4c}$ | $E^a$ | $R'^b$ | $R''^a$ |
| 31-109 | $R^{1a}$ | $R^{2a}$ | $R^{4a}$ | $E^b$ | $R'^b$ | $R''^a$ |
| 31-110 | $R^{1b}$ | $R^{2a}$ | $R^{4a}$ | $E^b$ | $R'^b$ | $R''^a$ |
| 31-111 | $R^{1c}$ | $R^{2a}$ | $R^{4a}$ | $E^b$ | $R'^b$ | $R''^a$ |
| 31-112 | $R^{1a}$ | $R^{2b}$ | $R^{4a}$ | $E^b$ | $R'^b$ | $R''^a$ |
| 31-113 | $R^{1b}$ | $R^{2b}$ | $R^{4a}$ | $E^b$ | $R'^b$ | $R''^a$ |
| 31-114 | $R^{1c}$ | $R^{2b}$ | $R^{4a}$ | $E^b$ | $R'^b$ | $R''^a$ |
| 31-115 | $R^{1a}$ | $R^{2c}$ | $R^{4a}$ | $E^b$ | $R'^b$ | $R''^a$ |
| 31-116 | $R^{1b}$ | $R^{2c}$ | $R^{4a}$ | $E^b$ | $R'^b$ | $R''^a$ |
| 31-117 | $R^{1c}$ | $R^{2c}$ | $R^{4a}$ | $E^b$ | $R'^b$ | $R''^a$ |
| 31-118 | $R^{1a}$ | $R^{2a}$ | $R^{4b}$ | $E^b$ | $R'^b$ | $R''^a$ |
| 31-119 | $R^{1b}$ | $R^{2a}$ | $R^{4b}$ | $E^b$ | $R'^b$ | $R''^a$ |
| 31-120 | $R^{1c}$ | $R^{2a}$ | $R^{4b}$ | $E^b$ | $R'^b$ | $R''^a$ |
| 31-121 | $R^{1a}$ | $R^{2b}$ | $R^{4b}$ | $E^b$ | $R'^b$ | $R''^a$ |
| 31-122 | $R^{1b}$ | $R^{2b}$ | $R^{4b}$ | $E^b$ | $R'^b$ | $R''^a$ |
| 31-123 | $R^{1c}$ | $R^{2b}$ | $R^{4b}$ | $E^b$ | $R'^b$ | $R''^a$ |
| 31-124 | $R^{1a}$ | $R^{2c}$ | $R^{4b}$ | $E^b$ | $R'^b$ | $R''^a$ |
| 31-125 | $R^{1b}$ | $R^{2c}$ | $R^{4b}$ | $E^b$ | $R'^b$ | $R''^a$ |
| 31-126 | $R^{1c}$ | $R^{2c}$ | $R^{4b}$ | $E^b$ | $R'^b$ | $R''^a$ |
| 31-127 | $R^{1a}$ | $R^{2a}$ | $R^{4c}$ | $E^b$ | $R'^b$ | $R''^a$ |
| 31-128 | $R^{1b}$ | $R^{2a}$ | $R^{4c}$ | $E^b$ | $R'^b$ | $R''^a$ |
| 31-129 | $R^{1c}$ | $R^{2a}$ | $R^{4c}$ | $E^b$ | $R'^b$ | $R''^a$ |
| 31-130 | $R^{1a}$ | $R^{2b}$ | $R^{4c}$ | $E^b$ | $R'^b$ | $R''^a$ |
| 31-131 | $R^{1b}$ | $R^{2b}$ | $R^{4c}$ | $E^b$ | $R'^b$ | $R''^a$ |
| 31-132 | $R^{1c}$ | $R^{2b}$ | $R^{4c}$ | $E^b$ | $R'^b$ | $R''^a$ |
| 31-133 | $R^{1a}$ | $R^{2c}$ | $R^{4c}$ | $E^b$ | $R'^b$ | $R''^a$ |
| 31-134 | $R^{1b}$ | $R^{2c}$ | $R^{4c}$ | $E^b$ | $R'^b$ | $R''^a$ |
| 31-135 | $R^{1c}$ | $R^{2c}$ | $R^{4c}$ | $E^b$ | $R'^b$ | $R''^a$ |
| 31-136 | $R^{1a}$ | $R^{2a}$ | $R^{4a}$ | $E^c$ | $R'^b$ | $R''^a$ |
| 31-137 | $R^{1b}$ | $R^{2a}$ | $R^{4a}$ | $E^c$ | $R'^b$ | $R''^a$ |
| 31-138 | $R^{1c}$ | $R^{2a}$ | $R^{4a}$ | $E^c$ | $R'^b$ | $R''^a$ |
| 31-139 | $R^{1a}$ | $R^{2b}$ | $R^{4a}$ | $E^c$ | $R'^b$ | $R''^a$ |
| 31-140 | $R^{1b}$ | $R^{2b}$ | $R^{4a}$ | $E^c$ | $R'^b$ | $R''^a$ |
| 31-141 | $R^{1c}$ | $R^{2b}$ | $R^{4a}$ | $E^c$ | $R'^b$ | $R''^a$ |
| 31-142 | $R^{1a}$ | $R^{2c}$ | $R^{4a}$ | $E^c$ | $R'^b$ | $R''^a$ |
| 31-143 | $R^{1b}$ | $R^{2c}$ | $R^{4a}$ | $E^c$ | $R'^b$ | $R''^a$ |
| 31-144 | $R^{1c}$ | $R^{2c}$ | $R^{4a}$ | $E^c$ | $R'^b$ | $R''^a$ |
| 31-145 | $R^{1a}$ | $R^{2a}$ | $R^{4b}$ | $E^c$ | $R'^b$ | $R''^a$ |
| 31-146 | $R^{1b}$ | $R^{2a}$ | $R^{4b}$ | $E^c$ | $R'^b$ | $R''^a$ |
| 31-147 | $R^{1c}$ | $R^{2a}$ | $R^{4b}$ | $E^c$ | $R'^b$ | $R''^a$ |
| 31-148 | $R^{1a}$ | $R^{2b}$ | $R^{4b}$ | $E^c$ | $R'^b$ | $R''^a$ |
| 31-149 | $R^{1b}$ | $R^{2b}$ | $R^{4b}$ | $E^c$ | $R'^b$ | $R''^a$ |
| 31-150 | $R^{1c}$ | $R^{2b}$ | $R^{4b}$ | $E^c$ | $R'^b$ | $R''^a$ |

-continued

| Formula | $R^1$ | $R^2$ | $R^4$ | E | R' | R" |
|---|---|---|---|---|---|---|
| 31-151 | $R^{1a}$ | $R^{2c}$ | $R^{4b}$ | $E^c$ | $R'^b$ | $R''^a$ |
| 31-152 | $R^{1b}$ | $R^{2c}$ | $R^{4b}$ | $E^c$ | $R'^b$ | $R''^a$ |
| 31-153 | $R^{1c}$ | $R^{2c}$ | $R^{4b}$ | $E^c$ | $R'^b$ | $R''^a$ |
| 31-154 | $R^{1a}$ | $R^{2a}$ | $R^{4c}$ | $E^c$ | $R'^b$ | $R''^a$ |
| 31-155 | $R^{1b}$ | $R^{2a}$ | $R^{4c}$ | $E^c$ | $R'^b$ | $R''^a$ |
| 31-156 | $R^{1c}$ | $R^{2a}$ | $R^{4c}$ | $E^c$ | $R'^b$ | $R''^a$ |
| 31-157 | $R^{1a}$ | $R^{2b}$ | $R^{4c}$ | $E^c$ | $R'^b$ | $R''^a$ |
| 31-158 | $R^{1b}$ | $R^{2b}$ | $R^{4c}$ | $E^c$ | $R'^b$ | $R''^a$ |
| 31-159 | $R^{1c}$ | $R^{2b}$ | $R^{4c}$ | $E^c$ | $R'^b$ | $R''^a$ |
| 31-160 | $R^{1a}$ | $R^{2c}$ | $R^{4c}$ | $E^c$ | $R'^b$ | $R''^a$ |
| 31-161 | $R^{1b}$ | $R^{2c}$ | $R^{4c}$ | $E^c$ | $R'^b$ | $R''^a$ |
| 31-162 | $R^{1c}$ | $R^{2c}$ | $R^{4c}$ | $E^c$ | $R'^b$ | $R''^a$ |
| 31-163 | $R^{1a}$ | $R^{2a}$ | $R^{4a}$ | $E^a$ | $R'^c$ | $R''^a$ |
| 31-164 | $R^{1b}$ | $R^{2a}$ | $R^{4a}$ | $E^a$ | $R'^c$ | $R''^a$ |
| 31-165 | $R^{1c}$ | $R^{2a}$ | $R^{4a}$ | $E^a$ | $R'^c$ | $R''^a$ |
| 31-166 | $R^{1a}$ | $R^{2b}$ | $R^{4a}$ | $E^a$ | $R'^c$ | $R''^a$ |
| 31-167 | $R^{1b}$ | $R^{2b}$ | $R^{4a}$ | $E^a$ | $R'^c$ | $R''^a$ |
| 31-168 | $R^{1c}$ | $R^{2b}$ | $R^{4a}$ | $E^a$ | $R'^c$ | $R''^a$ |
| 31-169 | $R^{1a}$ | $R^{2c}$ | $R^{4a}$ | $E^a$ | $R'^c$ | $R''^a$ |
| 31-170 | $R^{1b}$ | $R^{2c}$ | $R^{4a}$ | $E^a$ | $R'^c$ | $R''^a$ |
| 31-171 | $R^{1c}$ | $R^{2c}$ | $R^{4a}$ | $E^a$ | $R'^c$ | $R''^a$ |
| 31-172 | $R^{1a}$ | $R^{2a}$ | $R^{4b}$ | $E^a$ | $R'^c$ | $R''^a$ |
| 31-173 | $R^{1b}$ | $R^{2a}$ | $R^{4b}$ | $E^a$ | $R'^c$ | $R''^a$ |
| 31-174 | $R^{1c}$ | $R^{2a}$ | $R^{4b}$ | $E^a$ | $R'^c$ | $R''^a$ |
| 31-175 | $R^{1a}$ | $R^{2b}$ | $R^{4b}$ | $E^a$ | $R'^c$ | $R''^a$ |
| 31-176 | $R^{1b}$ | $R^{2b}$ | $R^{4b}$ | $E^a$ | $R'^c$ | $R''^a$ |
| 31-177 | $R^{1c}$ | $R^{2b}$ | $R^{4b}$ | $E^a$ | $R'^c$ | $R''^a$ |
| 31-178 | $R^{1a}$ | $R^{2c}$ | $R^{4b}$ | $E^a$ | $R'^c$ | $R''^a$ |
| 31-179 | $R^{1b}$ | $R^{2c}$ | $R^{4b}$ | $E^a$ | $R'^c$ | $R''^a$ |
| 31-180 | $R^{1c}$ | $R^{2c}$ | $R^{4b}$ | $E^a$ | $R'^c$ | $R''^a$ |
| 31-181 | $R^{1a}$ | $R^{2a}$ | $R^{4c}$ | $E^a$ | $R'^c$ | $R''^a$ |
| 31-182 | $R^{1b}$ | $R^{2a}$ | $R^{4c}$ | $E^a$ | $R'^c$ | $R''^a$ |
| 31-183 | $R^{1c}$ | $R^{2a}$ | $R^{4c}$ | $E^a$ | $R'^c$ | $R''^a$ |
| 31-184 | $R^{1a}$ | $R^{2b}$ | $R^{4c}$ | $E^a$ | $R'^c$ | $R''^a$ |
| 31-185 | $R^{1b}$ | $R^{2b}$ | $R^{4c}$ | $E^a$ | $R'^c$ | $R''^a$ |
| 31-186 | $R^{1c}$ | $R^{2b}$ | $R^{4c}$ | $E^a$ | $R'^c$ | $R''^a$ |
| 31-187 | $R^{1a}$ | $R^{2c}$ | $R^{4c}$ | $E^a$ | $R'^c$ | $R''^a$ |
| 31-188 | $R^{1b}$ | $R^{2c}$ | $R^{4c}$ | $E^a$ | $R'^c$ | $R''^a$ |
| 31-189 | $R^{1c}$ | $R^{2c}$ | $R^{4c}$ | $E^a$ | $R'^c$ | $R''^a$ |
| 31-190 | $R^{1a}$ | $R^{2a}$ | $R^{4a}$ | $E^b$ | $R'^c$ | $R''^a$ |
| 31-191 | $R^{1b}$ | $R^{2a}$ | $R^{4a}$ | $E^b$ | $R'^c$ | $R''^a$ |
| 31-192 | $R^{1c}$ | $R^{2a}$ | $R^{4a}$ | $E^b$ | $R'^c$ | $R''^a$ |
| 31-193 | $R^{1a}$ | $R^{2b}$ | $R^{4a}$ | $E^b$ | $R'^c$ | $R''^a$ |
| 31-194 | $R^{1b}$ | $R^{2b}$ | $R^{4a}$ | $E^b$ | $R'^c$ | $R''^a$ |
| 31-195 | $R^{1c}$ | $R^{2b}$ | $R^{4a}$ | $E^b$ | $R'^c$ | $R''^a$ |
| 31-196 | $R^{1a}$ | $R^{2c}$ | $R^{4a}$ | $E^b$ | $R'^c$ | $R''^a$ |
| 31-197 | $R^{1b}$ | $R^{2c}$ | $R^{4a}$ | $E^b$ | $R'^c$ | $R''^a$ |
| 31-198 | $R^{1c}$ | $R^{2c}$ | $R^{4a}$ | $E^b$ | $R'^c$ | $R''^a$ |
| 31-199 | $R^{1a}$ | $R^{2a}$ | $R^{4b}$ | $E^b$ | $R'^c$ | $R''^a$ |
| 31-200 | $R^{1b}$ | $R^{2a}$ | $R^{4b}$ | $E^b$ | $R'^c$ | $R''^a$ |
| 31-201 | $R^{1c}$ | $R^{2a}$ | $R^{4b}$ | $E^b$ | $R'^c$ | $R''^a$ |
| 31-202 | $R^{1a}$ | $R^{2b}$ | $R^{4b}$ | $E^b$ | $R'^c$ | $R''^a$ |
| 31-203 | $R^{1b}$ | $R^{2b}$ | $R^{4b}$ | $E^b$ | $R'^c$ | $R''^a$ |
| 31-204 | $R^{1c}$ | $R^{2b}$ | $R^{4b}$ | $E^b$ | $R'^c$ | $R''^a$ |
| 31-205 | $R^{1a}$ | $R^{2c}$ | $R^{4b}$ | $E^b$ | $R'^c$ | $R''^a$ |
| 31-206 | $R^{1b}$ | $R^{2c}$ | $R^{4b}$ | $E^b$ | $R'^c$ | $R''^a$ |
| 31-207 | $R^{1c}$ | $R^{2c}$ | $R^{4b}$ | $E^b$ | $R'^c$ | $R''^a$ |
| 31-208 | $R^{1a}$ | $R^{2a}$ | $R^{4c}$ | $E^b$ | $R'^c$ | $R''^a$ |
| 31-209 | $R^{1b}$ | $R^{2a}$ | $R^{4c}$ | $E^b$ | $R'^c$ | $R''^a$ |
| 31-210 | $R^{1c}$ | $R^{2a}$ | $R^{4c}$ | $E^b$ | $R'^c$ | $R''^a$ |
| 31-211 | $R^{1a}$ | $R^{2b}$ | $R^{4c}$ | $E^b$ | $R'^c$ | $R''^a$ |
| 31-212 | $R^{1b}$ | $R^{2b}$ | $R^{4c}$ | $E^b$ | $R'^c$ | $R''^a$ |
| 31-213 | $R^{1c}$ | $R^{2b}$ | $R^{4c}$ | $E^b$ | $R'^c$ | $R''^a$ |
| 31-214 | $R^{1a}$ | $R^{2c}$ | $R^{4c}$ | $E^b$ | $R'^c$ | $R''^a$ |
| 31-215 | $R^{1b}$ | $R^{2c}$ | $R^{4c}$ | $E^b$ | $R'^c$ | $R''^a$ |
| 31-216 | $R^{1c}$ | $R^{2c}$ | $R^{4c}$ | $E^b$ | $R'^c$ | $R''^a$ |
| 31-217 | $R^{1a}$ | $R^{2a}$ | $R^{4a}$ | $E^c$ | $R'^c$ | $R''^a$ |
| 31-218 | $R^{1b}$ | $R^{2a}$ | $R^{4a}$ | $E^c$ | $R'^c$ | $R''^a$ |
| 31-219 | $R^{1c}$ | $R^{2a}$ | $R^{4a}$ | $E^c$ | $R'^c$ | $R''^a$ |
| 31-220 | $R^{1a}$ | $R^{2b}$ | $R^{4a}$ | $E^c$ | $R'^c$ | $R''^a$ |
| 31-221 | $R^{1b}$ | $R^{2b}$ | $R^{4a}$ | $E^c$ | $R'^c$ | $R''^a$ |
| 31-222 | $R^{1c}$ | $R^{2b}$ | $R^{4a}$ | $E^c$ | $R'^c$ | $R''^a$ |
| 31-223 | $R^{1a}$ | $R^{2c}$ | $R^{4a}$ | $E^c$ | $R'^c$ | $R''^a$ |
| 31-224 | $R^{1b}$ | $R^{2c}$ | $R^{4a}$ | $E^c$ | $R'^c$ | $R''^a$ |
| 31-225 | $R^{1c}$ | $R^{2c}$ | $R^{4a}$ | $E^c$ | $R'^c$ | $R''^a$ |
| 31-226 | $R^{1a}$ | $R^{2a}$ | $R^{4b}$ | $E^c$ | $R'^c$ | $R''^a$ |
| 31-227 | $R^{1b}$ | $R^{2a}$ | $R^{4b}$ | $E^c$ | $R'^c$ | $R''^a$ |
| 31-228 | $R^{1c}$ | $R^{2a}$ | $R^{4b}$ | $E^c$ | $R'^c$ | $R''^a$ |
| 31-229 | $R^{1a}$ | $R^{2b}$ | $R^{4b}$ | $E^c$ | $R'^c$ | $R''^a$ |
| 31-230 | $R^{1b}$ | $R^{2b}$ | $R^{4b}$ | $E^c$ | $R'^c$ | $R''^a$ |
| 31-231 | $R^{1c}$ | $R^{2b}$ | $R^{4b}$ | $E^c$ | $R'^c$ | $R''^a$ |
| 31-232 | $R^{1a}$ | $R^{2c}$ | $R^{4b}$ | $E^c$ | $R'^c$ | $R''^a$ |
| 31-233 | $R^{1b}$ | $R^{2c}$ | $R^{4b}$ | $E^c$ | $R'^c$ | $R''^a$ |
| 31-234 | $R^{1c}$ | $R^{2c}$ | $R^{4b}$ | $E^c$ | $R'^c$ | $R''^a$ |
| 31-235 | $R^{1a}$ | $R^{2a}$ | $R^{4c}$ | $E^c$ | $R'^c$ | $R''^a$ |
| 31-236 | $R^{1b}$ | $R^{2a}$ | $R^{4c}$ | $E^c$ | $R'^c$ | $R''^a$ |
| 31-237 | $R^{1c}$ | $R^{2a}$ | $R^{4c}$ | $E^c$ | $R'^c$ | $R''^a$ |
| 31-238 | $R^{1a}$ | $R^{2b}$ | $R^{4c}$ | $E^c$ | $R'^c$ | $R''^a$ |
| 31-239 | $R^{1b}$ | $R^{2b}$ | $R^{4c}$ | $E^c$ | $R'^c$ | $R''^a$ |
| 31-240 | $R^{1c}$ | $R^{2b}$ | $R^{4c}$ | $E^c$ | $R'^c$ | $R''^a$ |
| 31-241 | $R^{1a}$ | $R^{2c}$ | $R^{4c}$ | $E^c$ | $R'^c$ | $R''^a$ |
| 31-242 | $R^{1b}$ | $R^{2c}$ | $R^{4c}$ | $E^c$ | $R'^c$ | $R''^a$ |
| 31-243 | $R^{1c}$ | $R^{2c}$ | $R^{4c}$ | $E^c$ | $R'^c$ | $R''^a$ |
| 31-244 | $R^{1a}$ | $R^{2a}$ | $R^{4a}$ | $E^a$ | $R'^a$ | $R''^b$ |
| 31-245 | $R^{1b}$ | $R^{2a}$ | $R^{4a}$ | $E^a$ | $R'^a$ | $R''^b$ |
| 31-246 | $R^{1c}$ | $R^{2a}$ | $R^{4a}$ | $E^a$ | $R'^a$ | $R''^b$ |
| 31-247 | $R^{1a}$ | $R^{2b}$ | $R^{4a}$ | $E^a$ | $R'^a$ | $R''^b$ |
| 31-248 | $R^{1b}$ | $R^{2b}$ | $R^{4a}$ | $E^a$ | $R'^a$ | $R''^b$ |
| 31-249 | $R^{1c}$ | $R^{2b}$ | $R^{4a}$ | $E^a$ | $R'^a$ | $R''^b$ |
| 31-250 | $R^{1a}$ | $R^{2c}$ | $R^{4a}$ | $E^a$ | $R'^a$ | $R''^b$ |
| 31-251 | $R^{1b}$ | $R^{2c}$ | $R^{4a}$ | $E^a$ | $R'^a$ | $R''^b$ |
| 31-252 | $R^{1c}$ | $R^{2c}$ | $R^{4a}$ | $E^a$ | $R'^a$ | $R''^b$ |
| 31-253 | $R^{1a}$ | $R^{2a}$ | $R^{4b}$ | $E^a$ | $R'^a$ | $R''^b$ |
| 31-254 | $R^{1b}$ | $R^{2a}$ | $R^{4b}$ | $E^a$ | $R'^a$ | $R''^b$ |
| 31-255 | $R^{1c}$ | $R^{2a}$ | $R^{4b}$ | $E^a$ | $R'^a$ | $R''^b$ |
| 31-256 | $R^{1a}$ | $R^{2b}$ | $R^{4b}$ | $E^a$ | $R'^a$ | $R''^b$ |
| 31-257 | $R^{1b}$ | $R^{2b}$ | $R^{4b}$ | $E^a$ | $R'^a$ | $R''^b$ |
| 31-258 | $R^{1c}$ | $R^{2b}$ | $R^{4b}$ | $E^a$ | $R'^a$ | $R''^b$ |
| 31-259 | $R^{1a}$ | $R^{2c}$ | $R^{4b}$ | $E^a$ | $R'^a$ | $R''^b$ |
| 31-260 | $R^{1b}$ | $R^{2c}$ | $R^{4b}$ | $E^a$ | $R'^a$ | $R''^b$ |
| 31-261 | $R^{1c}$ | $R^{2c}$ | $R^{4b}$ | $E^a$ | $R'^a$ | $R''^b$ |
| 31-262 | $R^{1a}$ | $R^{2a}$ | $R^{4c}$ | $E^a$ | $R'^a$ | $R''^b$ |
| 31-263 | $R^{1b}$ | $R^{2a}$ | $R^{4c}$ | $E^a$ | $R'^a$ | $R''^b$ |
| 31-264 | $R^{1c}$ | $R^{2a}$ | $R^{4c}$ | $E^a$ | $R'^a$ | $R''^b$ |
| 31-265 | $R^{1a}$ | $R^{2b}$ | $R^{4c}$ | $E^a$ | $R'^a$ | $R''^b$ |
| 31-266 | $R^{1b}$ | $R^{2b}$ | $R^{4c}$ | $E^a$ | $R'^a$ | $R''^b$ |
| 31-267 | $R^{1c}$ | $R^{2b}$ | $R^{4c}$ | $E^a$ | $R'^a$ | $R''^b$ |
| 31-268 | $R^{1a}$ | $R^{2c}$ | $R^{4c}$ | $E^a$ | $R'^a$ | $R''^b$ |
| 31-269 | $R^{1b}$ | $R^{2c}$ | $R^{4c}$ | $E^a$ | $R'^a$ | $R''^b$ |
| 31-270 | $R^{1c}$ | $R^{2c}$ | $R^{4c}$ | $E^a$ | $R'^a$ | $R''^b$ |
| 31-271 | $R^{1a}$ | $R^{2a}$ | $R^{4a}$ | $E^b$ | $R'^a$ | $R''^b$ |
| 31-272 | $R^{1b}$ | $R^{2a}$ | $R^{4a}$ | $E^b$ | $R'^a$ | $R''^b$ |
| 31-273 | $R^{1c}$ | $R^{2a}$ | $R^{4a}$ | $E^b$ | $R'^a$ | $R''^b$ |
| 31-274 | $R^{1a}$ | $R^{2b}$ | $R^{4a}$ | $E^b$ | $R'^a$ | $R''^b$ |
| 31-275 | $R^{1b}$ | $R^{2b}$ | $R^{4a}$ | $E^b$ | $R'^a$ | $R''^b$ |
| 31-276 | $R^{1c}$ | $R^{2b}$ | $R^{4a}$ | $E^b$ | $R'^a$ | $R''^b$ |
| 31-277 | $R^{1a}$ | $R^{2c}$ | $R^{4a}$ | $E^b$ | $R'^a$ | $R''^b$ |
| 31-278 | $R^{1b}$ | $R^{2c}$ | $R^{4a}$ | $E^b$ | $R'^a$ | $R''^b$ |
| 31-279 | $R^{1c}$ | $R^{2c}$ | $R^{4a}$ | $E^b$ | $R'^a$ | $R''^b$ |
| 31-280 | $R^{1a}$ | $R^{2a}$ | $R^{4b}$ | $E^b$ | $R'^a$ | $R''^b$ |
| 31-281 | $R^{1b}$ | $R^{2a}$ | $R^{4b}$ | $E^b$ | $R'^a$ | $R''^b$ |
| 31-282 | $R^{1c}$ | $R^{2a}$ | $R^{4b}$ | $E^b$ | $R'^a$ | $R''^b$ |
| 31-283 | $R^{1a}$ | $R^{2b}$ | $R^{4b}$ | $E^b$ | $R'^a$ | $R''^b$ |
| 31-284 | $R^{1b}$ | $R^{2b}$ | $R^{4b}$ | $E^b$ | $R'^a$ | $R''^b$ |
| 31-285 | $R^{1c}$ | $R^{2b}$ | $R^{4b}$ | $E^b$ | $R'^a$ | $R''^b$ |
| 31-286 | $R^{1a}$ | $R^{2c}$ | $R^{4b}$ | $E^b$ | $R'^a$ | $R''^b$ |
| 31-287 | $R^{1b}$ | $R^{2c}$ | $R^{4b}$ | $E^b$ | $R'^a$ | $R''^b$ |
| 31-288 | $R^{1c}$ | $R^{2c}$ | $R^{4b}$ | $E^b$ | $R'^a$ | $R''^b$ |
| 31-289 | $R^{1a}$ | $R^{2a}$ | $R^{4c}$ | $E^b$ | $R'^a$ | $R''^b$ |
| 31-290 | $R^{1b}$ | $R^{2a}$ | $R^{4c}$ | $E^b$ | $R'^a$ | $R''^b$ |
| 31-291 | $R^{1c}$ | $R^{2a}$ | $R^{4c}$ | $E^b$ | $R'^a$ | $R''^b$ |
| 31-292 | $R^{1a}$ | $R^{2b}$ | $R^{4c}$ | $E^b$ | $R'^a$ | $R''^b$ |
| 31-293 | $R^{1b}$ | $R^{2b}$ | $R^{4c}$ | $E^b$ | $R'^a$ | $R''^b$ |
| 31-294 | $R^{1c}$ | $R^{2b}$ | $R^{4c}$ | $E^b$ | $R'^a$ | $R''^b$ |
| 31-295 | $R^{1a}$ | $R^{2c}$ | $R^{4c}$ | $E^b$ | $R'^a$ | $R''^b$ |
| 31-296 | $R^{1b}$ | $R^{2c}$ | $R^{4c}$ | $E^b$ | $R'^a$ | $R''^b$ |
| 31-297 | $R^{1c}$ | $R^{2c}$ | $R^{4c}$ | $E^b$ | $R'^a$ | $R''^b$ |
| 31-298 | $R^{1a}$ | $R^{2a}$ | $R^{4a}$ | $E^c$ | $R'^a$ | $R''^b$ |
| 31-299 | $R^{1b}$ | $R^{2a}$ | $R^{4a}$ | $E^c$ | $R'^a$ | $R''^b$ |
| 31-300 | $R^{1c}$ | $R^{2a}$ | $R^{4a}$ | $E^c$ | $R'^a$ | $R''^b$ |
| 31-301 | $R^{1a}$ | $R^{2b}$ | $R^{4a}$ | $E^c$ | $R'^a$ | $R''^b$ |
| 31-302 | $R^{1b}$ | $R^{2b}$ | $R^{4a}$ | $E^c$ | $R'^a$ | $R''^b$ |
| 31-303 | $R^{1c}$ | $R^{2b}$ | $R^{4a}$ | $E^c$ | $R'^a$ | $R''^b$ |
| 31-304 | $R^{1a}$ | $R^{2c}$ | $R^{4a}$ | $E^c$ | $R'^a$ | $R''^b$ |

-continued

| Formula | R¹ | R² | R⁴ | E | R' | R" |
|---|---|---|---|---|---|---|
| 31-305 | R¹ᵇ | R²ᶜ | R⁴ᵃ | Eᶜ | R'ᵃ | R"ᵇ |
| 31-306 | R¹ᶜ | R²ᶜ | R⁴ᵃ | Eᶜ | R'ᵃ | R"ᵇ |
| 31-307 | R¹ᵃ | R²ᵃ | R⁴ᵇ | Eᶜ | R'ᵃ | R"ᵇ |
| 31-308 | R¹ᵇ | R²ᵃ | R⁴ᵇ | Eᶜ | R'ᵃ | R"ᵇ |
| 31-309 | R¹ᶜ | R²ᵃ | R⁴ᵇ | Eᶜ | R'ᵃ | R"ᵇ |
| 31-310 | R¹ᵃ | R²ᵇ | R⁴ᵇ | Eᶜ | R'ᵃ | R"ᵇ |
| 31-311 | R¹ᵇ | R²ᵇ | R⁴ᵇ | Eᶜ | R'ᵃ | R"ᵇ |
| 31-312 | R¹ᶜ | R²ᵇ | R⁴ᵇ | Eᶜ | R'ᵃ | R"ᵇ |
| 31-313 | R¹ᵃ | R²ᶜ | R⁴ᵇ | Eᶜ | R'ᵃ | R"ᵇ |
| 31-314 | R¹ᵇ | R²ᶜ | R⁴ᵇ | Eᶜ | R'ᵃ | R"ᵇ |
| 31-315 | R¹ᶜ | R²ᶜ | R⁴ᵇ | Eᶜ | R'ᵃ | R"ᵇ |
| 31-316 | R¹ᵃ | R²ᵃ | R⁴ᶜ | Eᶜ | R'ᵃ | R"ᵇ |
| 31-317 | R¹ᵇ | R²ᵃ | R⁴ᶜ | Eᶜ | R'ᵃ | R"ᵇ |
| 31-318 | R¹ᶜ | R²ᵃ | R⁴ᶜ | Eᶜ | R'ᵃ | R"ᵇ |
| 31-319 | R¹ᵃ | R²ᵇ | R⁴ᶜ | Eᶜ | R'ᵃ | R"ᵇ |
| 31-320 | R¹ᵇ | R²ᵇ | R⁴ᶜ | Eᶜ | R'ᵃ | R"ᵇ |
| 31-321 | R¹ᶜ | R²ᵇ | R⁴ᶜ | Eᶜ | R'ᵃ | R"ᵇ |
| 31-322 | R¹ᵃ | R²ᶜ | R⁴ᶜ | Eᶜ | R'ᵃ | R"ᵇ |
| 31-323 | R¹ᵇ | R²ᶜ | R⁴ᶜ | Eᶜ | R'ᵃ | R"ᵇ |
| 31-324 | R¹ᶜ | R²ᶜ | R⁴ᶜ | Eᶜ | R'ᵃ | R"ᵇ |
| 31-325 | R¹ᵃ | R²ᵃ | R⁴ᵃ | Eᵃ | R'ᵇ | R"ᵇ |
| 31-326 | R¹ᵇ | R²ᵃ | R⁴ᵃ | Eᵃ | R'ᵇ | R"ᵇ |
| 31-327 | R¹ᶜ | R²ᵃ | R⁴ᵃ | Eᵃ | R'ᵇ | R"ᵇ |
| 31-328 | R¹ᵃ | R²ᵇ | R⁴ᵃ | Eᵃ | R'ᵇ | R"ᵇ |
| 31-329 | R¹ᵇ | R²ᵇ | R⁴ᵃ | Eᵃ | R'ᵇ | R"ᵇ |
| 31-330 | R¹ᶜ | R²ᵇ | R⁴ᵃ | Eᵃ | R'ᵇ | R"ᵇ |
| 31-331 | R¹ᵃ | R²ᶜ | R⁴ᵃ | Eᵃ | R'ᵇ | R"ᵇ |
| 31-332 | R¹ᵇ | R²ᶜ | R⁴ᵃ | Eᵃ | R'ᵇ | R"ᵇ |
| 31-333 | R¹ᶜ | R²ᶜ | R⁴ᵃ | Eᵃ | R'ᵇ | R"ᵇ |
| 31-334 | R¹ᵃ | R²ᵃ | R⁴ᵇ | Eᵃ | R'ᵇ | R"ᵇ |
| 31-335 | R¹ᵇ | R²ᵃ | R⁴ᵇ | Eᵃ | R'ᵇ | R"ᵇ |
| 31-336 | R¹ᶜ | R²ᵃ | R⁴ᵇ | Eᵃ | R'ᵇ | R"ᵇ |
| 31-337 | R¹ᵃ | R²ᵇ | R⁴ᵇ | Eᵃ | R'ᵇ | R"ᵇ |
| 31-338 | R¹ᵇ | R²ᵇ | R⁴ᵇ | Eᵃ | R'ᵇ | R"ᵇ |
| 31-339 | R¹ᶜ | R²ᵇ | R⁴ᵇ | Eᵃ | R'ᵇ | R"ᵇ |
| 31-340 | R¹ᵃ | R²ᶜ | R⁴ᵇ | Eᵃ | R'ᵇ | R"ᵇ |
| 31-341 | R¹ᵇ | R²ᶜ | R⁴ᵇ | Eᵃ | R'ᵇ | R"ᵇ |
| 31-342 | R¹ᶜ | R²ᶜ | R⁴ᵇ | Eᵃ | R'ᵇ | R"ᵇ |
| 31-343 | R¹ᵃ | R²ᵃ | R⁴ᶜ | Eᵃ | R'ᵇ | R"ᵇ |
| 31-344 | R¹ᵇ | R²ᵃ | R⁴ᶜ | Eᵃ | R'ᵇ | R"ᵇ |
| 31-345 | R¹ᶜ | R²ᵃ | R⁴ᶜ | Eᵃ | R'ᵇ | R"ᵇ |
| 31-346 | R¹ᵃ | R²ᵇ | R⁴ᶜ | Eᵃ | R'ᵇ | R"ᵇ |
| 31-347 | R¹ᵇ | R²ᵇ | R⁴ᶜ | Eᵃ | R'ᵇ | R"ᵇ |
| 31-348 | R¹ᶜ | R²ᵇ | R⁴ᶜ | Eᵃ | R'ᵇ | R"ᵇ |
| 31-349 | R¹ᵃ | R²ᶜ | R⁴ᶜ | Eᵃ | R'ᵇ | R"ᵇ |
| 31-350 | R¹ᵇ | R²ᶜ | R⁴ᶜ | Eᵃ | R'ᵇ | R"ᵇ |
| 31-351 | R¹ᶜ | R²ᶜ | R⁴ᶜ | Eᵃ | R'ᵇ | R"ᵇ |
| 31-352 | R¹ᵃ | R²ᵃ | R⁴ᵃ | Eᵇ | R'ᵇ | R"ᵇ |
| 31-353 | R¹ᵇ | R²ᵃ | R⁴ᵃ | Eᵇ | R'ᵇ | R"ᵇ |
| 31-354 | R¹ᶜ | R²ᵃ | R⁴ᵃ | Eᵇ | R'ᵇ | R"ᵇ |
| 31-355 | R¹ᵃ | R²ᵇ | R⁴ᵃ | Eᵇ | R'ᵇ | R"ᵇ |
| 31-356 | R¹ᵇ | R²ᵇ | R⁴ᵃ | Eᵇ | R'ᵇ | R"ᵇ |
| 31-357 | R¹ᶜ | R²ᵇ | R⁴ᵃ | Eᵇ | R'ᵇ | R"ᵇ |
| 31-358 | R¹ᵃ | R²ᶜ | R⁴ᵃ | Eᵇ | R'ᵇ | R"ᵇ |
| 31-359 | R¹ᵇ | R²ᶜ | R⁴ᵃ | Eᵇ | R'ᵇ | R"ᵇ |
| 31-360 | R¹ᶜ | R²ᶜ | R⁴ᵃ | Eᵇ | R'ᵇ | R"ᵇ |
| 31-361 | R¹ᵃ | R²ᵃ | R⁴ᵇ | Eᵇ | R'ᵇ | R"ᵇ |
| 31-362 | R¹ᵇ | R²ᵃ | R⁴ᵇ | Eᵇ | R'ᵇ | R"ᵇ |
| 31-363 | R¹ᶜ | R²ᵃ | R⁴ᵇ | Eᵇ | R'ᵇ | R"ᵇ |
| 31-364 | R¹ᵃ | R²ᵇ | R⁴ᵇ | Eᵇ | R'ᵇ | R"ᵇ |
| 31-365 | R¹ᵇ | R²ᵇ | R⁴ᵇ | Eᵇ | R'ᵇ | R"ᵇ |
| 31-366 | R¹ᶜ | R²ᵇ | R⁴ᵇ | Eᵇ | R'ᵇ | R"ᵇ |
| 31-367 | R¹ᵃ | R²ᶜ | R⁴ᵇ | Eᵇ | R'ᵇ | R"ᵇ |
| 31-368 | R¹ᵇ | R²ᶜ | R⁴ᵇ | Eᵇ | R'ᵇ | R"ᵇ |
| 31-369 | R¹ᶜ | R²ᶜ | R⁴ᵇ | Eᵇ | R'ᵇ | R"ᵇ |
| 31-370 | R¹ᵃ | R²ᵃ | R⁴ᶜ | Eᵇ | R'ᵇ | R"ᵇ |
| 31-371 | R¹ᵇ | R²ᵃ | R⁴ᶜ | Eᵇ | R'ᵇ | R"ᵇ |
| 31-372 | R¹ᶜ | R²ᵃ | R⁴ᶜ | Eᵇ | R'ᵇ | R"ᵇ |
| 31-373 | R¹ᵃ | R²ᵇ | R⁴ᶜ | Eᵇ | R'ᵇ | R"ᵇ |
| 31-374 | R¹ᵇ | R²ᵇ | R⁴ᶜ | Eᵇ | R'ᵇ | R"ᵇ |
| 31-375 | R¹ᶜ | R²ᵇ | R⁴ᶜ | Eᵇ | R'ᵇ | R"ᵇ |
| 31-376 | R¹ᵃ | R²ᶜ | R⁴ᶜ | Eᵇ | R'ᵇ | R"ᵇ |
| 31-377 | R¹ᵇ | R²ᶜ | R⁴ᶜ | Eᵇ | R'ᵇ | R"ᵇ |
| 31-378 | R¹ᶜ | R²ᶜ | R⁴ᶜ | Eᵇ | R'ᵇ | R"ᵇ |
| 31-379 | R¹ᵃ | R²ᵃ | R⁴ᵃ | Eᶜ | R'ᵇ | R"ᵇ |
| 31-380 | R¹ᵇ | R²ᵃ | R⁴ᵃ | Eᶜ | R'ᵇ | R"ᵇ |
| 31-381 | R¹ᶜ | R²ᵃ | R⁴ᵃ | Eᶜ | R'ᵇ | R"ᵇ |
| 31-382 | R¹ᵃ | R²ᵇ | R⁴ᵃ | Eᶜ | R'ᵇ | R"ᵇ |
| 31-383 | R¹ᵇ | R²ᵇ | R⁴ᵃ | Eᶜ | R'ᵇ | R"ᵇ |
| 31-384 | R¹ᶜ | R²ᵇ | R⁴ᵃ | Eᶜ | R'ᵇ | R"ᵇ |
| 31-385 | R¹ᵃ | R²ᶜ | R⁴ᵃ | Eᶜ | R'ᵇ | R"ᵇ |
| 31-386 | R¹ᵇ | R²ᶜ | R⁴ᵃ | Eᶜ | R'ᵇ | R"ᵇ |
| 31-387 | R¹ᶜ | R²ᶜ | R⁴ᵃ | Eᶜ | R'ᵇ | R"ᵇ |
| 31-388 | R¹ᵃ | R²ᵃ | R⁴ᵇ | Eᶜ | R'ᵇ | R"ᵇ |
| 31-389 | R¹ᵇ | R²ᵃ | R⁴ᵇ | Eᶜ | R'ᵇ | R"ᵇ |
| 31-390 | R¹ᶜ | R²ᵃ | R⁴ᵇ | Eᶜ | R'ᵇ | R"ᵇ |
| 31-391 | R¹ᵃ | R²ᵇ | R⁴ᵇ | Eᶜ | R'ᵇ | R"ᵇ |
| 31-392 | R¹ᵇ | R²ᵇ | R⁴ᵇ | Eᶜ | R'ᵇ | R"ᵇ |
| 31-393 | R¹ᶜ | R²ᵇ | R⁴ᵇ | Eᶜ | R'ᵇ | R"ᵇ |
| 31-394 | R¹ᵃ | R²ᶜ | R⁴ᵇ | Eᶜ | R'ᵇ | R"ᵇ |
| 31-395 | R¹ᵇ | R²ᶜ | R⁴ᵇ | Eᶜ | R'ᵇ | R"ᵇ |
| 31-396 | R¹ᶜ | R²ᶜ | R⁴ᵇ | Eᶜ | R'ᵇ | R"ᵇ |
| 31-397 | R¹ᵃ | R²ᵃ | R⁴ᶜ | Eᶜ | R'ᵇ | R"ᵇ |
| 31-398 | R¹ᵇ | R²ᵃ | R⁴ᶜ | Eᶜ | R'ᵇ | R"ᵇ |
| 31-399 | R¹ᶜ | R²ᵃ | R⁴ᶜ | Eᶜ | R'ᵇ | R"ᵇ |
| 31-400 | R¹ᵃ | R²ᵇ | R⁴ᶜ | Eᶜ | R'ᵇ | R"ᵇ |
| 31-401 | R¹ᵇ | R²ᵇ | R⁴ᶜ | Eᶜ | R'ᵇ | R"ᵇ |
| 31-402 | R¹ᶜ | R²ᵇ | R⁴ᶜ | Eᶜ | R'ᵇ | R"ᵇ |
| 31-403 | R¹ᵃ | R²ᶜ | R⁴ᶜ | Eᶜ | R'ᵇ | R"ᵇ |
| 31-404 | R¹ᵇ | R²ᶜ | R⁴ᶜ | Eᶜ | R'ᵇ | R"ᵇ |
| 31-405 | R¹ᶜ | R²ᶜ | R⁴ᶜ | Eᶜ | R'ᵇ | R"ᵇ |
| 31-406 | R¹ᵃ | R²ᵃ | R⁴ᵃ | Eᵃ | R'ᶜ | R"ᵇ |
| 31-407 | R¹ᵇ | R²ᵃ | R⁴ᵃ | Eᵃ | R'ᶜ | R"ᵇ |
| 31-408 | R¹ᶜ | R²ᵃ | R⁴ᵃ | Eᵃ | R'ᶜ | R"ᵇ |
| 31-409 | R¹ᵃ | R²ᵇ | R⁴ᵃ | Eᵃ | R'ᶜ | R"ᵇ |
| 31-410 | R¹ᵇ | R²ᵇ | R⁴ᵃ | Eᵃ | R'ᶜ | R"ᵇ |
| 31-411 | R¹ᶜ | R²ᵇ | R⁴ᵃ | Eᵃ | R'ᶜ | R"ᵇ |
| 31-412 | R¹ᵃ | R²ᶜ | R⁴ᵃ | Eᵃ | R'ᶜ | R"ᵇ |
| 31-413 | R¹ᵇ | R²ᶜ | R⁴ᵃ | Eᵃ | R'ᶜ | R"ᵇ |
| 31-414 | R¹ᶜ | R²ᶜ | R⁴ᵃ | Eᵃ | R'ᶜ | R"ᵇ |
| 31-415 | R¹ᵃ | R²ᵃ | R⁴ᵇ | Eᵃ | R'ᶜ | R"ᵇ |
| 31-416 | R¹ᵇ | R²ᵃ | R⁴ᵇ | Eᵃ | R'ᶜ | R"ᵇ |
| 31-417 | R¹ᶜ | R²ᵃ | R⁴ᵇ | Eᵃ | R'ᶜ | R"ᵇ |
| 31-418 | R¹ᵃ | R²ᵇ | R⁴ᵇ | Eᵃ | R'ᶜ | R"ᵇ |
| 31-419 | R¹ᵇ | R²ᵇ | R⁴ᵇ | Eᵃ | R'ᶜ | R"ᵇ |
| 31-420 | R¹ᶜ | R²ᵇ | R⁴ᵇ | Eᵃ | R'ᶜ | R"ᵇ |
| 31-421 | R¹ᵃ | R²ᶜ | R⁴ᵇ | Eᵃ | R'ᶜ | R"ᵇ |
| 31-422 | R¹ᵇ | R²ᶜ | R⁴ᵇ | Eᵃ | R'ᶜ | R"ᵇ |
| 31-423 | R¹ᶜ | R²ᶜ | R⁴ᵇ | Eᵃ | R'ᶜ | R"ᵇ |
| 31-424 | R¹ᵃ | R²ᵃ | R⁴ᶜ | Eᵃ | R'ᶜ | R"ᵇ |
| 31-425 | R¹ᵇ | R²ᵃ | R⁴ᶜ | Eᵃ | R'ᶜ | R"ᵇ |
| 31-426 | R¹ᶜ | R²ᵃ | R⁴ᶜ | Eᵃ | R'ᶜ | R"ᵇ |
| 31-427 | R¹ᵃ | R²ᵇ | R⁴ᶜ | Eᵃ | R'ᶜ | R"ᵇ |
| 31-428 | R¹ᵇ | R²ᵇ | R⁴ᶜ | Eᵃ | R'ᶜ | R"ᵇ |
| 31-429 | R¹ᶜ | R²ᵇ | R⁴ᶜ | Eᵃ | R'ᶜ | R"ᵇ |
| 31-430 | R¹ᵃ | R²ᶜ | R⁴ᶜ | Eᵃ | R'ᶜ | R"ᵇ |
| 31-431 | R¹ᵇ | R²ᶜ | R⁴ᶜ | Eᵃ | R'ᶜ | R"ᵇ |
| 31-432 | R¹ᶜ | R²ᶜ | R⁴ᶜ | Eᵃ | R'ᶜ | R"ᵇ |
| 31-433 | R¹ᵃ | R²ᵃ | R⁴ᵃ | Eᵇ | R'ᶜ | R"ᵇ |
| 31-434 | R¹ᵇ | R²ᵃ | R⁴ᵃ | Eᵇ | R'ᶜ | R"ᵇ |
| 31-435 | R¹ᶜ | R²ᵃ | R⁴ᵃ | Eᵇ | R'ᶜ | R"ᵇ |
| 31-436 | R¹ᵃ | R²ᵇ | R⁴ᵃ | Eᵇ | R'ᶜ | R"ᵇ |
| 31-437 | R¹ᵇ | R²ᵇ | R⁴ᵃ | Eᵇ | R'ᶜ | R"ᵇ |
| 31-438 | R¹ᶜ | R²ᵇ | R⁴ᵃ | Eᵇ | R'ᶜ | R"ᵇ |
| 31-439 | R¹ᵃ | R²ᶜ | R⁴ᵃ | Eᵇ | R'ᶜ | R"ᵇ |
| 31-440 | R¹ᵇ | R²ᶜ | R⁴ᵃ | Eᵇ | R'ᶜ | R"ᵇ |
| 31-441 | R¹ᶜ | R²ᶜ | R⁴ᵃ | Eᵇ | R'ᶜ | R"ᵇ |
| 31-442 | R¹ᵃ | R²ᵃ | R⁴ᵇ | Eᵇ | R'ᶜ | R"ᵇ |
| 31-443 | R¹ᵇ | R²ᵃ | R⁴ᵇ | Eᵇ | R'ᶜ | R"ᵇ |
| 31-444 | R¹ᶜ | R²ᵃ | R⁴ᵇ | Eᵇ | R'ᶜ | R"ᵇ |
| 31-445 | R¹ᵃ | R²ᵇ | R⁴ᵇ | Eᵇ | R'ᶜ | R"ᵇ |
| 31-446 | R¹ᵇ | R²ᵇ | R⁴ᵇ | Eᵇ | R'ᶜ | R"ᵇ |
| 31-447 | R¹ᶜ | R²ᵇ | R⁴ᵇ | Eᵇ | R'ᶜ | R"ᵇ |
| 31-448 | R¹ᵃ | R²ᶜ | R⁴ᵇ | Eᵇ | R'ᶜ | R"ᵇ |
| 31-449 | R¹ᵇ | R²ᶜ | R⁴ᵇ | Eᵇ | R'ᶜ | R"ᵇ |
| 31-450 | R¹ᶜ | R²ᶜ | R⁴ᵇ | Eᵇ | R'ᶜ | R"ᵇ |
| 31-451 | R¹ᵃ | R²ᵃ | R⁴ᶜ | Eᵇ | R'ᶜ | R"ᵇ |
| 31-452 | R¹ᵇ | R²ᵃ | R⁴ᶜ | Eᵇ | R'ᶜ | R"ᵇ |
| 31-453 | R¹ᶜ | R²ᵃ | R⁴ᶜ | Eᵇ | R'ᶜ | R"ᵇ |
| 31-454 | R¹ᵃ | R²ᵇ | R⁴ᶜ | Eᵇ | R'ᶜ | R"ᵇ |
| 31-455 | R¹ᵇ | R²ᵇ | R⁴ᶜ | Eᵇ | R'ᶜ | R"ᵇ |
| 31-456 | R¹ᶜ | R²ᵇ | R⁴ᶜ | Eᵇ | R'ᶜ | R"ᵇ |
| 31-457 | R¹ᵃ | R²ᶜ | R⁴ᶜ | Eᵇ | R'ᶜ | R"ᵇ |
| 31-458 | R¹ᵇ | R²ᶜ | R⁴ᶜ | Eᵇ | R'ᶜ | R"ᵇ |

| Formula | R$^1$ | R$^2$ | R$^4$ | E | R' | R" |
|---|---|---|---|---|---|---|
| 31-459 | R$^{1c}$ | R$^{2c}$ | R$^{4c}$ | E$^b$ | R'$^c$ | R"$^b$ |
| 31-460 | R$^{1a}$ | R$^{2a}$ | R$^{4a}$ | E$^c$ | R'$^c$ | R"$^b$ |
| 31-461 | R$^{1b}$ | R$^{2a}$ | R$^{4a}$ | E$^c$ | R'$^c$ | R"$^b$ |
| 31-462 | R$^{1c}$ | R$^{2a}$ | R$^{4a}$ | E$^c$ | R'$^c$ | R"$^b$ |
| 31-463 | R$^{1a}$ | R$^{2b}$ | R$^{4a}$ | E$^c$ | R'$^c$ | R"$^b$ |
| 31-464 | R$^{1b}$ | R$^{2b}$ | R$^{4a}$ | E$^c$ | R'$^c$ | R"$^b$ |
| 31-465 | R$^{1c}$ | R$^{2b}$ | R$^{4a}$ | E$^c$ | R'$^c$ | R"$^b$ |
| 31-466 | R$^{1a}$ | R$^{2c}$ | R$^{4a}$ | E$^c$ | R'$^c$ | R"$^b$ |
| 31-467 | R$^{1b}$ | R$^{2c}$ | R$^{4a}$ | E$^c$ | R'$^c$ | R"$^b$ |
| 31-468 | R$^{1c}$ | R$^{2c}$ | R$^{4a}$ | E$^c$ | R'$^c$ | R"$^b$ |
| 31-469 | R$^{1a}$ | R$^{2a}$ | R$^{4b}$ | E$^c$ | R'$^c$ | R"$^b$ |
| 31-470 | R$^{1b}$ | R$^{2a}$ | R$^{4b}$ | E$^c$ | R'$^c$ | R"$^b$ |
| 31-471 | R$^{1c}$ | R$^{2a}$ | R$^{4b}$ | E$^c$ | R'$^c$ | R"$^b$ |
| 31-472 | R$^{1a}$ | R$^{2b}$ | R$^{4b}$ | E$^c$ | R'$^c$ | R"$^b$ |
| 31-473 | R$^{1b}$ | R$^{2b}$ | R$^{4b}$ | E$^c$ | R'$^c$ | R"$^b$ |
| 31-474 | R$^{1c}$ | R$^{2b}$ | R$^{4b}$ | E$^c$ | R'$^c$ | R"$^b$ |
| 31-475 | R$^{1a}$ | R$^{2c}$ | R$^{4b}$ | E$^c$ | R'$^c$ | R"$^b$ |
| 31-476 | R$^{1b}$ | R$^{2c}$ | R$^{4b}$ | E$^c$ | R'$^c$ | R"$^b$ |
| 31-477 | R$^{1c}$ | R$^{2c}$ | R$^{4b}$ | E$^c$ | R'$^c$ | R"$^b$ |
| 31-478 | R$^{1a}$ | R$^{2a}$ | R$^{4c}$ | E$^c$ | R'$^c$ | R"$^b$ |
| 31-479 | R$^{1b}$ | R$^{2a}$ | R$^{4c}$ | E$^c$ | R'$^c$ | R"$^b$ |
| 31-480 | R$^{1c}$ | R$^{2a}$ | R$^{4c}$ | E$^c$ | R'$^c$ | R"$^b$ |
| 31-481 | R$^{1a}$ | R$^{2b}$ | R$^{4c}$ | E$^c$ | R'$^c$ | R"$^b$ |
| 31-482 | R$^{1b}$ | R$^{2b}$ | R$^{4c}$ | E$^c$ | R'$^c$ | R"$^b$ |
| 31-483 | R$^{1c}$ | R$^{2b}$ | R$^{4c}$ | E$^c$ | R'$^c$ | R"$^b$ |
| 31-484 | R$^{1a}$ | R$^{2c}$ | R$^{4c}$ | E$^c$ | R'$^c$ | R"$^b$ |
| 31-485 | R$^{1b}$ | R$^{2c}$ | R$^{4c}$ | E$^c$ | R'$^c$ | R"$^b$ |
| 31-486 | R$^{1c}$ | R$^{2c}$ | R$^{4c}$ | E$^c$ | R'$^c$ | R"$^b$ |
| 31-487 | R$^{1a}$ | R$^{2a}$ | R$^{4a}$ | E$^a$ | R'$^a$ | R"$^c$ |
| 31-488 | R$^{1b}$ | R$^{2a}$ | R$^{4a}$ | E$^a$ | R'$^a$ | R"$^c$ |
| 31-489 | R$^{1c}$ | R$^{2a}$ | R$^{4a}$ | E$^a$ | R'$^a$ | R"$^c$ |
| 31-490 | R$^{1a}$ | R$^{2b}$ | R$^{4a}$ | E$^a$ | R'$^a$ | R"$^c$ |
| 31-491 | R$^{1b}$ | R$^{2b}$ | R$^{4a}$ | E$^a$ | R'$^a$ | R"$^c$ |
| 31-492 | R$^{1c}$ | R$^{2b}$ | R$^{4a}$ | E$^a$ | R'$^a$ | R"$^c$ |
| 31-493 | R$^{1a}$ | R$^{2c}$ | R$^{4a}$ | E$^a$ | R'$^a$ | R"$^c$ |
| 31-494 | R$^{1b}$ | R$^{2c}$ | R$^{4a}$ | E$^a$ | R'$^a$ | R"$^c$ |
| 31-495 | R$^{1c}$ | R$^{2c}$ | R$^{4a}$ | E$^a$ | R'$^a$ | R"$^c$ |
| 31-496 | R$^{1a}$ | R$^{2a}$ | R$^{4b}$ | E$^a$ | R'$^a$ | R"$^c$ |
| 31-497 | R$^{1b}$ | R$^{2a}$ | R$^{4b}$ | E$^a$ | R'$^a$ | R"$^c$ |
| 31-498 | R$^{1c}$ | R$^{2a}$ | R$^{4b}$ | E$^a$ | R'$^a$ | R"$^c$ |
| 31-499 | R$^{1a}$ | R$^{2b}$ | R$^{4b}$ | E$^a$ | R'$^a$ | R"$^c$ |
| 31-500 | R$^{1b}$ | R$^{2b}$ | R$^{4b}$ | E$^a$ | R'$^a$ | R"$^c$ |
| 31-501 | R$^{1c}$ | R$^{2b}$ | R$^{4b}$ | E$^a$ | R'$^a$ | R"$^c$ |
| 31-502 | R$^{1a}$ | R$^{2c}$ | R$^{4b}$ | E$^a$ | R'$^a$ | R"$^c$ |
| 31-503 | R$^{1b}$ | R$^{2c}$ | R$^{4b}$ | E$^a$ | R'$^a$ | R"$^c$ |
| 31-504 | R$^{1c}$ | R$^{2c}$ | R$^{4b}$ | E$^a$ | R'$^a$ | R"$^c$ |
| 31-505 | R$^{1a}$ | R$^{2a}$ | R$^{4c}$ | E$^a$ | R'$^a$ | R"$^c$ |
| 31-506 | R$^{1b}$ | R$^{2a}$ | R$^{4c}$ | E$^a$ | R'$^a$ | R"$^c$ |
| 31-507 | R$^{1c}$ | R$^{2a}$ | R$^{4c}$ | E$^a$ | R'$^a$ | R"$^c$ |
| 31-508 | R$^{1a}$ | R$^{2b}$ | R$^{4c}$ | E$^a$ | R'$^a$ | R"$^c$ |
| 31-509 | R$^{1b}$ | R$^{2b}$ | R$^{4c}$ | E$^a$ | R'$^a$ | R"$^c$ |
| 31-510 | R$^{1c}$ | R$^{2b}$ | R$^{4c}$ | E$^a$ | R'$^a$ | R"$^c$ |
| 31-511 | R$^{1a}$ | R$^{2c}$ | R$^{4c}$ | E$^a$ | R'$^a$ | R"$^c$ |
| 31-512 | R$^{1b}$ | R$^{2c}$ | R$^{4c}$ | E$^a$ | R'$^a$ | R"$^c$ |
| 31-513 | R$^{1c}$ | R$^{2c}$ | R$^{4c}$ | E$^a$ | R'$^a$ | R"$^c$ |
| 31-514 | R$^{1a}$ | R$^{2a}$ | R$^{4a}$ | E$^b$ | R'$^a$ | R"$^c$ |
| 31-515 | R$^{1b}$ | R$^{2a}$ | R$^{4a}$ | E$^b$ | R'$^a$ | R"$^c$ |
| 31-516 | R$^{1c}$ | R$^{2a}$ | R$^{4a}$ | E$^b$ | R'$^a$ | R"$^c$ |
| 31-517 | R$^{1a}$ | R$^{2b}$ | R$^{4a}$ | E$^b$ | R'$^a$ | R"$^c$ |
| 31-518 | R$^{1b}$ | R$^{2b}$ | R$^{4a}$ | E$^b$ | R'$^a$ | R"$^c$ |
| 31-519 | R$^{1c}$ | R$^{2b}$ | R$^{4a}$ | E$^b$ | R'$^a$ | R"$^c$ |
| 31-520 | R$^{1a}$ | R$^{2c}$ | R$^{4a}$ | E$^b$ | R'$^a$ | R"$^c$ |
| 31-521 | R$^{1b}$ | R$^{2c}$ | R$^{4a}$ | E$^b$ | R'$^a$ | R"$^c$ |
| 31-522 | R$^{1c}$ | R$^{2c}$ | R$^{4a}$ | E$^b$ | R'$^a$ | R"$^c$ |
| 31-523 | R$^{1a}$ | R$^{2a}$ | R$^{4b}$ | E$^b$ | R'$^a$ | R"$^c$ |
| 31-524 | R$^{1b}$ | R$^{2a}$ | R$^{4b}$ | E$^b$ | R'$^a$ | R"$^c$ |
| 31-525 | R$^{1c}$ | R$^{2a}$ | R$^{4b}$ | E$^b$ | R'$^a$ | R"$^c$ |
| 31-526 | R$^{1a}$ | R$^{2b}$ | R$^{4b}$ | E$^b$ | R'$^a$ | R"$^c$ |
| 31-527 | R$^{1b}$ | R$^{2b}$ | R$^{4b}$ | E$^b$ | R'$^a$ | R"$^c$ |
| 31-528 | R$^{1c}$ | R$^{2b}$ | R$^{4b}$ | E$^b$ | R'$^a$ | R"$^c$ |
| 31-529 | R$^{1a}$ | R$^{2c}$ | R$^{4b}$ | E$^b$ | R'$^a$ | R"$^c$ |
| 31-530 | R$^{1b}$ | R$^{2c}$ | R$^{4b}$ | E$^b$ | R'$^a$ | R"$^c$ |
| 31-531 | R$^{1c}$ | R$^{2c}$ | R$^{4b}$ | E$^b$ | R'$^a$ | R"$^c$ |
| 31-532 | R$^{1a}$ | R$^{2a}$ | R$^{4c}$ | E$^b$ | R'$^a$ | R"$^c$ |
| 31-533 | R$^{1b}$ | R$^{2a}$ | R$^{4c}$ | E$^b$ | R'$^a$ | R"$^c$ |
| 31-534 | R$^{1c}$ | R$^{2a}$ | R$^{4c}$ | E$^b$ | R'$^a$ | R"$^c$ |
| 31-535 | R$^{1a}$ | R$^{2b}$ | R$^{4c}$ | E$^b$ | R'$^a$ | R"$^c$ |
| 31-536 | R$^{1b}$ | R$^{2b}$ | R$^{4c}$ | E$^b$ | R'$^a$ | R"$^c$ |
| 31-537 | R$^{1c}$ | R$^{2b}$ | R$^{4c}$ | E$^b$ | R'$^a$ | R"$^c$ |
| 31-538 | R$^{1a}$ | R$^{2c}$ | R$^{4c}$ | E$^b$ | R'$^a$ | R"$^c$ |
| 31-539 | R$^{1b}$ | R$^{2c}$ | R$^{4c}$ | E$^b$ | R'$^a$ | R"$^c$ |
| 31-540 | R$^{1c}$ | R$^{2c}$ | R$^{4c}$ | E$^b$ | R'$^a$ | R"$^c$ |
| 31-541 | R$^{1a}$ | R$^{2a}$ | R$^{4a}$ | E$^c$ | R'$^a$ | R"$^c$ |
| 31-542 | R$^{1b}$ | R$^{2a}$ | R$^{4a}$ | E$^c$ | R'$^a$ | R"$^c$ |
| 31-543 | R$^{1c}$ | R$^{2a}$ | R$^{4a}$ | E$^c$ | R'$^a$ | R"$^c$ |
| 31-544 | R$^{1a}$ | R$^{2b}$ | R$^{4a}$ | E$^c$ | R'$^a$ | R"$^c$ |
| 31-545 | R$^{1b}$ | R$^{2b}$ | R$^{4a}$ | E$^c$ | R'$^a$ | R"$^c$ |
| 31-546 | R$^{1c}$ | R$^{2b}$ | R$^{4a}$ | E$^c$ | R'$^a$ | R"$^c$ |
| 31-547 | R$^{1a}$ | R$^{2c}$ | R$^{4a}$ | E$^c$ | R'$^a$ | R"$^c$ |
| 31-548 | R$^{1b}$ | R$^{2c}$ | R$^{4a}$ | E$^c$ | R'$^a$ | R"$^c$ |
| 31-549 | R$^{1c}$ | R$^{2c}$ | R$^{4a}$ | E$^c$ | R'$^a$ | R"$^c$ |
| 31-550 | R$^{1a}$ | R$^{2a}$ | R$^{4b}$ | E$^c$ | R'$^a$ | R"$^c$ |
| 31-551 | R$^{1b}$ | R$^{2a}$ | R$^{4b}$ | E$^c$ | R'$^a$ | R"$^c$ |
| 31-552 | R$^{1c}$ | R$^{2a}$ | R$^{4b}$ | E$^c$ | R'$^a$ | R"$^c$ |
| 31-553 | R$^{1a}$ | R$^{2b}$ | R$^{4b}$ | E$^c$ | R'$^a$ | R"$^c$ |
| 31-554 | R$^{1b}$ | R$^{2b}$ | R$^{4b}$ | E$^c$ | R'$^a$ | R"$^c$ |
| 31-555 | R$^{1c}$ | R$^{2b}$ | R$^{4b}$ | E$^c$ | R'$^a$ | R"$^c$ |
| 31-556 | R$^{1a}$ | R$^{2c}$ | R$^{4b}$ | E$^c$ | R'$^a$ | R"$^c$ |
| 31-557 | R$^{1b}$ | R$^{2c}$ | R$^{4b}$ | E$^c$ | R'$^a$ | R"$^c$ |
| 31-558 | R$^{1c}$ | R$^{2c}$ | R$^{4b}$ | E$^c$ | R'$^a$ | R"$^c$ |
| 31-559 | R$^{1a}$ | R$^{2a}$ | R$^{4c}$ | E$^c$ | R'$^a$ | R"$^c$ |
| 31-560 | R$^{1b}$ | R$^{2a}$ | R$^{4c}$ | E$^c$ | R'$^a$ | R"$^c$ |
| 31-561 | R$^{1c}$ | R$^{2a}$ | R$^{4c}$ | E$^c$ | R'$^a$ | R"$^c$ |
| 31-562 | R$^{1a}$ | R$^{2b}$ | R$^{4c}$ | E$^c$ | R'$^a$ | R"$^c$ |
| 31-563 | R$^{1b}$ | R$^{2b}$ | R$^{4c}$ | E$^c$ | R'$^a$ | R"$^c$ |
| 31-564 | R$^{1c}$ | R$^{2b}$ | R$^{4c}$ | E$^c$ | R'$^a$ | R"$^c$ |
| 31-565 | R$^{1a}$ | R$^{2c}$ | R$^{4c}$ | E$^c$ | R'$^a$ | R"$^c$ |
| 31-566 | R$^{1b}$ | R$^{2c}$ | R$^{4c}$ | E$^c$ | R'$^a$ | R"$^c$ |
| 31-567 | R$^{1c}$ | R$^{2c}$ | R$^{4c}$ | E$^c$ | R'$^a$ | R"$^c$ |
| 31-568 | R$^{1a}$ | R$^{2a}$ | R$^{4a}$ | E$^a$ | R'$^b$ | R"$^c$ |
| 31-569 | R$^{1b}$ | R$^{2a}$ | R$^{4a}$ | E$^a$ | R'$^b$ | R"$^c$ |
| 31-570 | R$^{1c}$ | R$^{2a}$ | R$^{4a}$ | E$^a$ | R'$^b$ | R"$^c$ |
| 31-571 | R$^{1a}$ | R$^{2b}$ | R$^{4a}$ | E$^a$ | R'$^b$ | R"$^c$ |
| 31-572 | R$^{1b}$ | R$^{2b}$ | R$^{4a}$ | E$^a$ | R'$^b$ | R"$^c$ |
| 31-573 | R$^{1c}$ | R$^{2b}$ | R$^{4a}$ | E$^a$ | R'$^b$ | R"$^c$ |
| 31-574 | R$^{1a}$ | R$^{2c}$ | R$^{4a}$ | E$^a$ | R'$^b$ | R"$^c$ |
| 31-575 | R$^{1b}$ | R$^{2c}$ | R$^{4a}$ | E$^a$ | R'$^b$ | R"$^c$ |
| 31-576 | R$^{1c}$ | R$^{2c}$ | R$^{4a}$ | E$^a$ | R'$^b$ | R"$^c$ |
| 31-577 | R$^{1a}$ | R$^{2a}$ | R$^{4b}$ | E$^a$ | R'$^b$ | R"$^c$ |
| 31-578 | R$^{1b}$ | R$^{2a}$ | R$^{4b}$ | E$^a$ | R'$^b$ | R"$^c$ |
| 31-579 | R$^{1c}$ | R$^{2a}$ | R$^{4b}$ | E$^a$ | R'$^b$ | R"$^c$ |
| 31-580 | R$^{1a}$ | R$^{2b}$ | R$^{4b}$ | E$^a$ | R'$^b$ | R"$^c$ |
| 31-581 | R$^{1b}$ | R$^{2b}$ | R$^{4b}$ | E$^a$ | R'$^b$ | R"$^c$ |
| 31-582 | R$^{1c}$ | R$^{2b}$ | R$^{4b}$ | E$^a$ | R'$^b$ | R"$^c$ |
| 31-583 | R$^{1a}$ | R$^{2c}$ | R$^{4b}$ | E$^a$ | R'$^b$ | R"$^c$ |
| 31-584 | R$^{1b}$ | R$^{2c}$ | R$^{4b}$ | E$^a$ | R'$^b$ | R"$^c$ |
| 31-585 | R$^{1c}$ | R$^{2c}$ | R$^{4b}$ | E$^a$ | R'$^b$ | R"$^c$ |
| 31-586 | R$^{1a}$ | R$^{2a}$ | R$^{4c}$ | E$^a$ | R'$^b$ | R"$^c$ |
| 31-587 | R$^{1b}$ | R$^{2a}$ | R$^{4c}$ | E$^a$ | R'$^b$ | R"$^c$ |
| 31-588 | R$^{1c}$ | R$^{2a}$ | R$^{4c}$ | E$^a$ | R'$^b$ | R"$^c$ |
| 31-589 | R$^{1a}$ | R$^{2b}$ | R$^{4c}$ | E$^a$ | R'$^b$ | R"$^c$ |
| 31-590 | R$^{1b}$ | R$^{2b}$ | R$^{4c}$ | E$^a$ | R'$^b$ | R"$^c$ |
| 31-591 | R$^{1c}$ | R$^{2b}$ | R$^{4c}$ | E$^a$ | R'$^b$ | R"$^c$ |
| 31-592 | R$^{1a}$ | R$^{2c}$ | R$^{4c}$ | E$^a$ | R'$^b$ | R"$^c$ |
| 31-593 | R$^{1b}$ | R$^{2c}$ | R$^{4c}$ | E$^a$ | R'$^b$ | R"$^c$ |
| 31-594 | R$^{1c}$ | R$^{2c}$ | R$^{4c}$ | E$^a$ | R'$^b$ | R"$^c$ |
| 31-595 | R$^{1a}$ | R$^{2a}$ | R$^{4a}$ | E$^b$ | R'$^b$ | R"$^c$ |
| 31-596 | R$^{1b}$ | R$^{2a}$ | R$^{4a}$ | E$^b$ | R'$^b$ | R"$^c$ |
| 31-597 | R$^{1c}$ | R$^{2a}$ | R$^{4a}$ | E$^b$ | R'$^b$ | R"$^c$ |
| 31-598 | R$^{1a}$ | R$^{2b}$ | R$^{4a}$ | E$^b$ | R'$^b$ | R"$^c$ |
| 31-599 | R$^{1b}$ | R$^{2b}$ | R$^{4a}$ | E$^b$ | R'$^b$ | R"$^c$ |
| 31-600 | R$^{1c}$ | R$^{2b}$ | R$^{4a}$ | E$^b$ | R'$^b$ | R"$^c$ |
| 31-601 | R$^{1a}$ | R$^{2c}$ | R$^{4a}$ | E$^b$ | R'$^b$ | R"$^c$ |
| 31-602 | R$^{1b}$ | R$^{2c}$ | R$^{4a}$ | E$^b$ | R'$^b$ | R"$^c$ |
| 31-603 | R$^{1c}$ | R$^{2c}$ | R$^{4a}$ | E$^b$ | R'$^b$ | R"$^c$ |
| 31-604 | R$^{1a}$ | R$^{2a}$ | R$^{4b}$ | E$^b$ | R'$^b$ | R"$^c$ |
| 31-605 | R$^{1b}$ | R$^{2a}$ | R$^{4b}$ | E$^b$ | R'$^b$ | R"$^c$ |
| 31-606 | R$^{1c}$ | R$^{2a}$ | R$^{4b}$ | E$^b$ | R'$^b$ | R"$^c$ |
| 31-607 | R$^{1a}$ | R$^{2b}$ | R$^{4b}$ | E$^b$ | R'$^b$ | R"$^c$ |
| 31-608 | R$^{1b}$ | R$^{2b}$ | R$^{4b}$ | E$^b$ | R'$^b$ | R"$^c$ |
| 31-609 | R$^{1c}$ | R$^{2b}$ | R$^{4b}$ | E$^b$ | R'$^b$ | R"$^c$ |
| 31-610 | R$^{1a}$ | R$^{2c}$ | R$^{4b}$ | E$^b$ | R'$^b$ | R"$^c$ |
| 31-611 | R$^{1b}$ | R$^{2c}$ | R$^{4b}$ | E$^b$ | R'$^b$ | R"$^c$ |
| 31-612 | R$^{1c}$ | R$^{2c}$ | R$^{4b}$ | E$^b$ | R'$^b$ | R"$^c$ |

| Formula | $R^1$ | $R^2$ | $R^4$ | E | R' | R" |
|---|---|---|---|---|---|---|
| 31-613 | $R^{1a}$ | $R^{2a}$ | $R^{4c}$ | $E^b$ | $R'^b$ | $R''^c$ |
| 31-614 | $R^{1b}$ | $R^{2a}$ | $R^{4c}$ | $E^b$ | $R'^b$ | $R''^c$ |
| 31-615 | $R^{1c}$ | $R^{2a}$ | $R^{4c}$ | $E^b$ | $R'^b$ | $R''^c$ |
| 31-616 | $R^{1a}$ | $R^{2b}$ | $R^{4c}$ | $E^b$ | $R'^b$ | $R''^c$ |
| 31-617 | $R^{1b}$ | $R^{2b}$ | $R^{4c}$ | $E^b$ | $R'^b$ | $R''^c$ |
| 31-618 | $R^{1c}$ | $R^{2b}$ | $R^{4c}$ | $E^b$ | $R'^b$ | $R''^c$ |
| 31-619 | $R^{1a}$ | $R^{2c}$ | $R^{4c}$ | $E^b$ | $R'^b$ | $R''^c$ |
| 31-620 | $R^{1b}$ | $R^{2c}$ | $R^{4c}$ | $E^b$ | $R'^b$ | $R''^c$ |
| 31-621 | $R^{1c}$ | $R^{2c}$ | $R^{4c}$ | $E^b$ | $R'^b$ | $R''^c$ |
| 31-622 | $R^{1a}$ | $R^{2a}$ | $R^{4a}$ | $E^c$ | $R'^b$ | $R''^c$ |
| 31-623 | $R^{1b}$ | $R^{2a}$ | $R^{4a}$ | $E^c$ | $R'^b$ | $R''^c$ |
| 31-624 | $R^{1c}$ | $R^{2a}$ | $R^{4a}$ | $E^c$ | $R'^b$ | $R''^c$ |
| 31-625 | $R^{1a}$ | $R^{2b}$ | $R^{4a}$ | $E^c$ | $R'^b$ | $R''^c$ |
| 31-626 | $R^{1b}$ | $R^{2b}$ | $R^{4a}$ | $E^c$ | $R'^b$ | $R''^c$ |
| 31-627 | $R^{1c}$ | $R^{2b}$ | $R^{4a}$ | $E^c$ | $R'^b$ | $R''^c$ |
| 31-628 | $R^{1a}$ | $R^{2c}$ | $R^{4a}$ | $E^c$ | $R'^b$ | $R''^c$ |
| 31-629 | $R^{1b}$ | $R^{2c}$ | $R^{4a}$ | $E^c$ | $R'^b$ | $R''^c$ |
| 31-630 | $R^{1c}$ | $R^{2c}$ | $R^{4a}$ | $E^c$ | $R'^b$ | $R''^c$ |
| 31-631 | $R^{1a}$ | $R^{2a}$ | $R^{4b}$ | $E^c$ | $R'^b$ | $R''^c$ |
| 31-632 | $R^{1b}$ | $R^{2a}$ | $R^{4b}$ | $E^c$ | $R'^b$ | $R''^c$ |
| 31-633 | $R^{1c}$ | $R^{2a}$ | $R^{4b}$ | $E^c$ | $R'^b$ | $R''^c$ |
| 31-634 | $R^{1a}$ | $R^{2b}$ | $R^{4b}$ | $E^c$ | $R'^b$ | $R''^c$ |
| 31-635 | $R^{1b}$ | $R^{2b}$ | $R^{4b}$ | $E^c$ | $R'^b$ | $R''^c$ |
| 31-636 | $R^{1c}$ | $R^{2b}$ | $R^{4b}$ | $E^c$ | $R'^b$ | $R''^c$ |
| 31-637 | $R^{1a}$ | $R^{2c}$ | $R^{4b}$ | $E^c$ | $R'^b$ | $R''^c$ |
| 31-638 | $R^{1b}$ | $R^{2c}$ | $R^{4b}$ | $E^c$ | $R'^b$ | $R''^c$ |
| 31-639 | $R^{1c}$ | $R^{2c}$ | $R^{4b}$ | $E^c$ | $R'^b$ | $R''^c$ |
| 31-640 | $R^{1a}$ | $R^{2a}$ | $R^{4c}$ | $E^c$ | $R'^b$ | $R''^c$ |
| 31-641 | $R^{1b}$ | $R^{2a}$ | $R^{4c}$ | $E^c$ | $R'^b$ | $R''^c$ |
| 31-642 | $R^{1c}$ | $R^{2a}$ | $R^{4c}$ | $E^c$ | $R'^b$ | $R''^c$ |
| 31-643 | $R^{1a}$ | $R^{2b}$ | $R^{4c}$ | $E^c$ | $R'^b$ | $R''^c$ |
| 31-644 | $R^{1b}$ | $R^{2b}$ | $R^{4c}$ | $E^c$ | $R'^b$ | $R''^c$ |
| 31-645 | $R^{1c}$ | $R^{2b}$ | $R^{4c}$ | $E^c$ | $R'^b$ | $R''^c$ |
| 31-646 | $R^{1a}$ | $R^{2c}$ | $R^{4c}$ | $E^c$ | $R'^b$ | $R''^c$ |
| 31-647 | $R^{1b}$ | $R^{2c}$ | $R^{4c}$ | $E^c$ | $R'^b$ | $R''^c$ |
| 31-648 | $R^{1c}$ | $R^{2c}$ | $R^{4c}$ | $E^c$ | $R'^b$ | $R''^c$ |
| 31-649 | $R^{1a}$ | $R^{2a}$ | $R^{4a}$ | $E^a$ | $R'^c$ | $R''^c$ |
| 31-650 | $R^{1b}$ | $R^{2a}$ | $R^{4a}$ | $E^a$ | $R'^c$ | $R''^c$ |
| 31-651 | $R^{1c}$ | $R^{2a}$ | $R^{4a}$ | $E^a$ | $R'^c$ | $R''^c$ |
| 31-652 | $R^{1a}$ | $R^{2b}$ | $R^{4a}$ | $E^a$ | $R'^c$ | $R''^c$ |
| 31-653 | $R^{1b}$ | $R^{2b}$ | $R^{4a}$ | $E^a$ | $R'^c$ | $R''^c$ |
| 31-654 | $R^{1c}$ | $R^{2b}$ | $R^{4a}$ | $E^a$ | $R'^c$ | $R''^c$ |
| 31-655 | $R^{1a}$ | $R^{2c}$ | $R^{4a}$ | $E^a$ | $R'^c$ | $R''^c$ |
| 31-656 | $R^{1b}$ | $R^{2c}$ | $R^{4a}$ | $E^a$ | $R'^c$ | $R''^c$ |
| 31-657 | $R^{1c}$ | $R^{2c}$ | $R^{4a}$ | $E^a$ | $R'^c$ | $R''^c$ |
| 31-658 | $R^{1a}$ | $R^{2a}$ | $R^{4b}$ | $E^a$ | $R'^c$ | $R''^c$ |
| 31-659 | $R^{1b}$ | $R^{2a}$ | $R^{4b}$ | $E^a$ | $R'^c$ | $R''^c$ |
| 31-660 | $R^{1c}$ | $R^{2a}$ | $R^{4b}$ | $E^a$ | $R'^c$ | $R''^c$ |
| 31-661 | $R^{1a}$ | $R^{2b}$ | $R^{4b}$ | $E^a$ | $R'^c$ | $R''^c$ |
| 31-662 | $R^{1b}$ | $R^{2b}$ | $R^{4b}$ | $E^a$ | $R'^c$ | $R''^c$ |
| 31-663 | $R^{1c}$ | $R^{2b}$ | $R^{4b}$ | $E^a$ | $R'^c$ | $R''^c$ |
| 31-664 | $R^{1a}$ | $R^{2c}$ | $R^{4b}$ | $E^a$ | $R'^c$ | $R''^c$ |
| 31-665 | $R^{1b}$ | $R^{2c}$ | $R^{4b}$ | $E^a$ | $R'^c$ | $R''^c$ |
| 31-666 | $R^{1c}$ | $R^{2c}$ | $R^{4b}$ | $E^a$ | $R'^c$ | $R''^c$ |
| 31-667 | $R^{1a}$ | $R^{2a}$ | $R^{4c}$ | $E^a$ | $R'^c$ | $R''^c$ |
| 31-668 | $R^{1b}$ | $R^{2a}$ | $R^{4c}$ | $E^a$ | $R'^c$ | $R''^c$ |
| 31-669 | $R^{1c}$ | $R^{2a}$ | $R^{4c}$ | $E^a$ | $R'^c$ | $R''^c$ |
| 31-670 | $R^{1a}$ | $R^{2b}$ | $R^{4c}$ | $E^a$ | $R'^c$ | $R''^c$ |
| 31-671 | $R^{1b}$ | $R^{2b}$ | $R^{4c}$ | $E^a$ | $R'^c$ | $R''^c$ |
| 31-672 | $R^{1c}$ | $R^{2b}$ | $R^{4c}$ | $E^a$ | $R'^c$ | $R''^c$ |
| 31-673 | $R^{1a}$ | $R^{2c}$ | $R^{4c}$ | $E^a$ | $R'^c$ | $R''^c$ |
| 31-674 | $R^{1b}$ | $R^{2c}$ | $R^{4c}$ | $E^a$ | $R'^c$ | $R''^c$ |
| 31-675 | $R^{1c}$ | $R^{2c}$ | $R^{4c}$ | $E^a$ | $R'^c$ | $R''^c$ |
| 31-676 | $R^{1a}$ | $R^{2a}$ | $R^{4a}$ | $E^b$ | $R'^c$ | $R''^c$ |
| 31-677 | $R^{1b}$ | $R^{2a}$ | $R^{4a}$ | $E^b$ | $R'^c$ | $R''^c$ |
| 31-678 | $R^{1c}$ | $R^{2a}$ | $R^{4a}$ | $E^b$ | $R'^c$ | $R''^c$ |
| 31-679 | $R^{1a}$ | $R^{2b}$ | $R^{4a}$ | $E^b$ | $R'^c$ | $R''^c$ |
| 31-680 | $R^{1b}$ | $R^{2b}$ | $R^{4a}$ | $E^b$ | $R'^c$ | $R''^c$ |
| 31-681 | $R^{1c}$ | $R^{2b}$ | $R^{4a}$ | $E^b$ | $R'^c$ | $R''^c$ |
| 31-682 | $R^{1a}$ | $R^{2c}$ | $R^{4a}$ | $E^b$ | $R'^c$ | $R''^c$ |
| 31-683 | $R^{1b}$ | $R^{2c}$ | $R^{4a}$ | $E^b$ | $R'^c$ | $R''^c$ |
| 31-684 | $R^{1c}$ | $R^{2c}$ | $R^{4a}$ | $E^b$ | $R'^c$ | $R''^c$ |
| 31-685 | $R^{1a}$ | $R^{2a}$ | $R^{4b}$ | $E^b$ | $R'^c$ | $R''^c$ |
| 31-686 | $R^{1b}$ | $R^{2a}$ | $R^{4b}$ | $E^b$ | $R'^c$ | $R''^c$ |
| 31-687 | $R^{1c}$ | $R^{2a}$ | $R^{4b}$ | $E^b$ | $R'^c$ | $R''^c$ |
| 31-688 | $R^{1a}$ | $R^{2b}$ | $R^{4b}$ | $E^b$ | $R'^c$ | $R''^c$ |
| 31-689 | $R^{1b}$ | $R^{2b}$ | $R^{4b}$ | $E^b$ | $R'^c$ | $R''^c$ |
| 31-690 | $R^{1c}$ | $R^{2b}$ | $R^{4b}$ | $E^b$ | $R'^c$ | $R''^c$ |
| 31-691 | $R^{1a}$ | $R^{2c}$ | $R^{4b}$ | $E^b$ | $R'^c$ | $R''^c$ |
| 31-692 | $R^{1b}$ | $R^{2c}$ | $R^{4b}$ | $E^b$ | $R'^c$ | $R''^c$ |
| 31-693 | $R^{1c}$ | $R^{2c}$ | $R^{4b}$ | $E^b$ | $R'^c$ | $R''^c$ |
| 31-694 | $R^{1a}$ | $R^{2a}$ | $R^{4c}$ | $E^b$ | $R'^c$ | $R''^c$ |
| 31-695 | $R^{1b}$ | $R^{2a}$ | $R^{4c}$ | $E^b$ | $R'^c$ | $R''^c$ |
| 31-696 | $R^{1c}$ | $R^{2a}$ | $R^{4c}$ | $E^b$ | $R'^c$ | $R''^c$ |
| 31-697 | $R^{1a}$ | $R^{2b}$ | $R^{4c}$ | $E^b$ | $R'^c$ | $R''^c$ |
| 31-698 | $R^{1b}$ | $R^{2b}$ | $R^{4c}$ | $E^b$ | $R'^c$ | $R''^c$ |
| 31-699 | $R^{1c}$ | $R^{2b}$ | $R^{4c}$ | $E^b$ | $R'^c$ | $R''^c$ |
| 31-700 | $R^{1a}$ | $R^{2c}$ | $R^{4c}$ | $E^b$ | $R'^c$ | $R''^c$ |
| 31-701 | $R^{1b}$ | $R^{2c}$ | $R^{4c}$ | $E^b$ | $R'^c$ | $R''^c$ |
| 31-702 | $R^{1c}$ | $R^{2c}$ | $R^{4c}$ | $E^b$ | $R'^c$ | $R''^c$ |
| 31-703 | $R^{1a}$ | $R^{2a}$ | $R^{4a}$ | $E^c$ | $R'^c$ | $R''^c$ |
| 31-704 | $R^{1b}$ | $R^{2a}$ | $R^{4a}$ | $E^c$ | $R'^c$ | $R''^c$ |
| 31-705 | $R^{1c}$ | $R^{2a}$ | $R^{4a}$ | $E^c$ | $R'^c$ | $R''^c$ |
| 31-706 | $R^{1a}$ | $R^{2b}$ | $R^{4a}$ | $E^c$ | $R'^c$ | $R''^c$ |
| 31-707 | $R^{1b}$ | $R^{2b}$ | $R^{4a}$ | $E^c$ | $R'^c$ | $R''^c$ |
| 31-708 | $R^{1c}$ | $R^{2b}$ | $R^{4a}$ | $E^c$ | $R'^c$ | $R''^c$ |
| 31-709 | $R^{1a}$ | $R^{2c}$ | $R^{4a}$ | $E^c$ | $R'^c$ | $R''^c$ |
| 31-710 | $R^{1b}$ | $R^{2c}$ | $R^{4a}$ | $E^c$ | $R'^c$ | $R''^c$ |
| 31-711 | $R^{1c}$ | $R^{2c}$ | $R^{4a}$ | $E^c$ | $R'^c$ | $R''^c$ |
| 31-712 | $R^{1a}$ | $R^{2a}$ | $R^{4b}$ | $E^c$ | $R'^c$ | $R''^c$ |
| 31-713 | $R^{1b}$ | $R^{2a}$ | $R^{4b}$ | $E^c$ | $R'^c$ | $R''^c$ |
| 31-714 | $R^{1c}$ | $R^{2a}$ | $R^{4b}$ | $E^c$ | $R'^c$ | $R''^c$ |
| 31-715 | $R^{1a}$ | $R^{2b}$ | $R^{4b}$ | $E^c$ | $R'^c$ | $R''^c$ |
| 31-716 | $R^{1b}$ | $R^{2b}$ | $R^{4b}$ | $E^c$ | $R'^c$ | $R''^c$ |
| 31-717 | $R^{1c}$ | $R^{2b}$ | $R^{4b}$ | $E^c$ | $R'^c$ | $R''^c$ |
| 31-718 | $R^{1a}$ | $R^{2c}$ | $R^{4b}$ | $E^c$ | $R'^c$ | $R''^c$ |
| 31-719 | $R^{1b}$ | $R^{2c}$ | $R^{4b}$ | $E^c$ | $R'^c$ | $R''^c$ |
| 31-720 | $R^{1c}$ | $R^{2c}$ | $R^{4b}$ | $E^c$ | $R'^c$ | $R''^c$ |
| 31-721 | $R^{1a}$ | $R^{2a}$ | $R^{4c}$ | $E^c$ | $R'^c$ | $R''^c$ |
| 31-722 | $R^{1b}$ | $R^{2a}$ | $R^{4c}$ | $E^c$ | $R'^c$ | $R''^c$ |
| 31-723 | $R^{1c}$ | $R^{2a}$ | $R^{4c}$ | $E^c$ | $R'^c$ | $R''^c$ |
| 31-724 | $R^{1a}$ | $R^{2b}$ | $R^{4c}$ | $E^c$ | $R'^c$ | $R''^c$ |
| 31-725 | $R^{1b}$ | $R^{2b}$ | $R^{4c}$ | $E^c$ | $R'^c$ | $R''^c$ |
| 31-726 | $R^{1c}$ | $R^{2b}$ | $R^{4c}$ | $E^c$ | $R'^c$ | $R''^c$ |
| 31-727 | $R^{1a}$ | $R^{2c}$ | $R^{4c}$ | $E^c$ | $R'^c$ | $R''^c$ |
| 31-728 | $R^{1b}$ | $R^{2c}$ | $R^{4c}$ | $E^c$ | $R'^c$ | $R''^c$ |
| 31-729 | $R^{1c}$ | $R^{2c}$ | $R^{4c}$ | $E^c$ | $R'^c$ | $R''^c$ | where all symbols are as defined above.

In one aspect of formula (31) of the present invention, $R^1$ and $R^2$ independently are hydrogen, a hydroxy group, a halogen, a nitro group, a carboxy group, a carbamoyl group, or an optionally substituted amino group, an alkyl group, a cycloalkyl group, an alkoxy group, a cycloalkoxy group, an alkenyl group, a cycloalkenyl group, an alkoxyalkyl group, an alkenyloxy group, or a cycloalkenyloxy group; $R^4$ is hydrogen, a hydroxy group, a halogen, a nitro group, or an optionally substituted amino group, an alkyl group, a cycloalkyl group, an alkoxy group, a cycloalkoxy group, an alkenyl group, a cycloalkenyl group, an alkoxyalkyl group, an alkenyloxy group, a cycloalkenyloxy group; an acyl group, an acyloxy group, an aryl group, an aryloxy group, aroyl group or an aroyloxy group, an aralkyl group, an aralkenyl group, an aralkynyl group, an aralkoxy group, a heterocyclyl group, a heterocyclenyl group, a heteroaryl group, a heteroaralkyl group, a heteroaryloxy group, or a heteroaralkoxy group; R' and R" independently are hydrogen, a halogen, a nitro group, an amino group, a mono- or di-substituted amino group, a hydroxy group, an alkoxy group, a carboxy group, a cyano group, an oxo(O=) group, a thio(S=) group, an alkyl group, a cycloalkyl group, an alkoxy group, a haloalkoxy group, a cycloalkyl group, an aryl group, a benzyloxy group, an acyl group, an acyloxy group, an aroyl group, an alkoxycarbonyl group, an aryloxycarbonyl group, a heteroaryl group, a heterocyclyl group, or an aralkyl group; and all other symbols are as defined above in connection with formula (I).

In another aspect of formula (31) of the present invention, $R^1$ is hydrogen, a hydroxy group, a halogen, a nitro group, a carboxy group, a carbamoyl group, or an optionally substituted amino group, an alkyl group, a cycloalkyl group, an alkoxy group; $R^2$ is hydrogen, a hydroxy group, a halogen, a nitro group, a carboxy group, a carbamoyl group, or an optionally substituted amino group, an alkyl group, a cycloalkyl group, an alkoxy group; $R^4$ is a substituted or unsubstituted aryl group, R' is hydrogen, a halogen, or an alkyl group; and R" is hydrogen, a halogen, or an alkyl group; and all other symbols are as defined above in connection with formula (I).

In yet another aspect of formula (31) of the present invention, $R^1$ is hydrogen or an alkoxy group; $R^2$ is hydrogen or an alkoxy group; $R^4$ is a substituted or unsubstituted aryl group, R' is hydrogen, a halogen, or an alkyl group; R" is hydrogen, a halogen, or an alkyl group; and E is O, S, or NH.

In still another aspect of formula (31) of the present invention, $R^1$ is —H or —OCH$_3$; $R^2$ is —H or —OCH$_3$; $R^4$ is a substituted aryl group, R' is —H, —Cl, —Br, or —CH$_3$; and R" is —H, —Cl, —Br, or —CH$_3$; and E is O, S, or NH.

The present invention further contemplates various compounds of general formula (III) having the general formula:

(32)

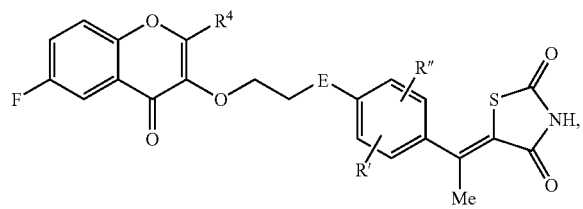

where all symbols are as defined above in connection with formula (I).

According to various aspects the present invention, $R^4$, R', and R" of formula (32) are selected to produce various compounds of formula (32-1) through formula (32-27) as follows:

| Formula | $R^4$ | R' | R" |
| --- | --- | --- | --- |
| 32-1 | $R^{4a}$ | $R'^a$ | $R''^a$ |
| 32-2 | $R^{4b}$ | $R'^a$ | $R''^a$ |
| 32-3 | $R^{4c}$ | $R'^a$ | $R''^a$ |
| 32-4 | $R^{4a}$ | $R'^b$ | $R''^a$ |
| 32-5 | $R^{4b}$ | $R'^b$ | $R''^a$ |
| 32-6 | $R^{4c}$ | $R'^b$ | $R''^a$ |
| 32-7 | $R^{4a}$ | $R'^c$ | $R''^a$ |
| 32-8 | $R^{4b}$ | $R'^c$ | $R''^a$ |
| 32-9 | $R^{4c}$ | $R'^c$ | $R''^a$ |
| 32-10 | $R^{4a}$ | $R'^a$ | $R''^b$ |
| 32-11 | $R^{4b}$ | $R'^a$ | $R''^b$ |
| 32-12 | $R^{4c}$ | $R'^a$ | $R''^b$ |
| 32-13 | $R^{4a}$ | $R'^b$ | $R''^b$ |
| 32-14 | $R^{4b}$ | $R'^b$ | $R''^b$ |
| 32-15 | $R^{4c}$ | $R'^b$ | $R''^b$ |
| 32-16 | $R^{4a}$ | $R'^c$ | $R''^b$ |
| 32-17 | $R^{4b}$ | $R'^c$ | $R''^b$ |
| 32-18 | $R^{4c}$ | $R'^c$ | $R''^b$ |
| 32-19 | $R^{4a}$ | $R'^a$ | $R''^c$ |
| 32-20 | $R^{4b}$ | $R'^a$ | $R''^c$ |
| 32-21 | $R^{4c}$ | $R'^a$ | $R''^c$ |
| 32-22 | $R^{4a}$ | $R'^b$ | $R''^c$ |
| 32-23 | $R^{4b}$ | $R'^b$ | $R''^c$ |
| 32-24 | $R^{4c}$ | $R'^b$ | $R''^c$ |
| 32-25 | $R^{4a}$ | $R'^c$ | $R''^c$ |
| 32-26 | $R^{4b}$ | $R'^c$ | $R''^c$ |
| 32-27 | $R^{4c}$ | $R'^c$ | $R''^c$ | where all symbols are as defined above.

In one aspect of the present invention, $R^4$ is hydrogen, a hydroxy group, a halogen, a nitro group, an optionally substituted amino group, an alkyl group, a cycloalkyl group, an alkoxy group, or a cycloalkoxy group; R' is hydrogen, a halogen, a nitro group, an amino group, a mono- or di-substituted amino group, a hydroxy group, an alkoxy group, a carboxy group, a cyano group, an oxo(O═) group, a thio(S═) group, an alkyl group, a cycloalkyl group, an alkoxy group, a haloalkoxy group, a cycloalkyl group, an aryl group, or a benzyloxy group; R" is hydrogen, a halogen, a nitro group, an amino group, a mono- or di-substituted amino group, a hydroxy group, an alkoxy group, a carboxy group, a cyano group, an oxo(O═) group, a thio(S═) group, an alkyl group, a cycloalkyl group, an alkoxy group, a haloalkoxy group, a cycloalkyl group, an aryl group, or a benzyloxy group; and all other symbols are as defined above in connection with formula (I).

In another aspect of the present invention, $R^4$ is an alkenyl group, a cycloalkenyl group, an alkoxyalkyl group, an alkenyloxy group, a cycloalkenyloxy group, an acyl group, an acyloxy group, an aryl group, an aryloxy group, an aroyl group, an aroyloxy group, an aralkyl group, an aralkenyl group, an aralkynyl group, or an aralkoxy group; R' is hydrogen, a halogen, a nitro group, an amino group, a mono- or di-substituted amino group, a hydroxy group, an alkoxy group, a carboxy group, a cyano group, an oxo(O═) group, a thio(S═) group, an alkyl group, a cycloalkyl group, an alkoxy group, a haloalkoxy group, a cycloalkyl group, an aryl group, or a benzyloxy group; R" is hydrogen, a halogen, a nitro group, an amino group, a mono- or di-substituted amino group, a hydroxy group, an alkoxy group, a carboxy group, a cyano group, an oxo(O═) group, a thio(S═) group, an alkyl group, a cycloalkyl group, an alkoxy group, a haloalkoxy group, a cycloalkyl group, an aryl group, or a benzyloxy group; and all other symbols are as defined above in connection with formula (I).

In one aspect of the present invention, E is O or —NR; $R^4$ is

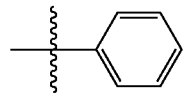

optionally substituted with an alkyl group or an alkoxy group,

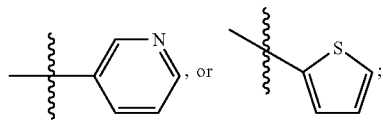

and R' and R? are defined as above. Examples of such compounds include, but are not limited to:

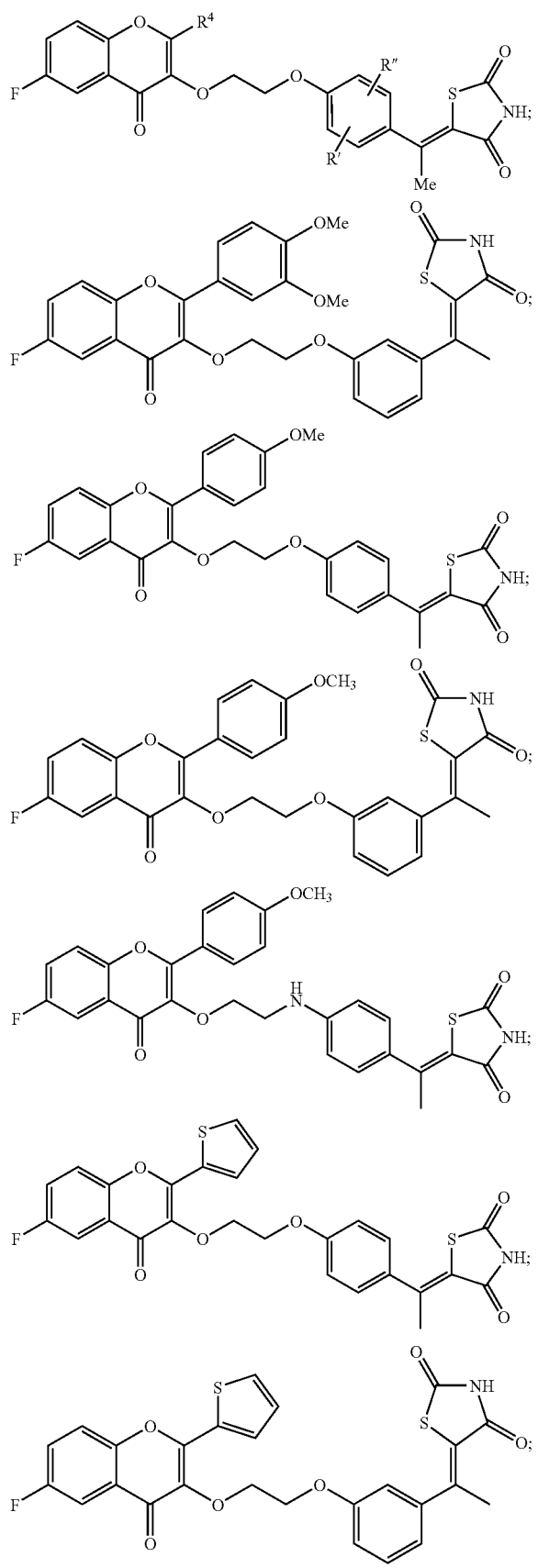
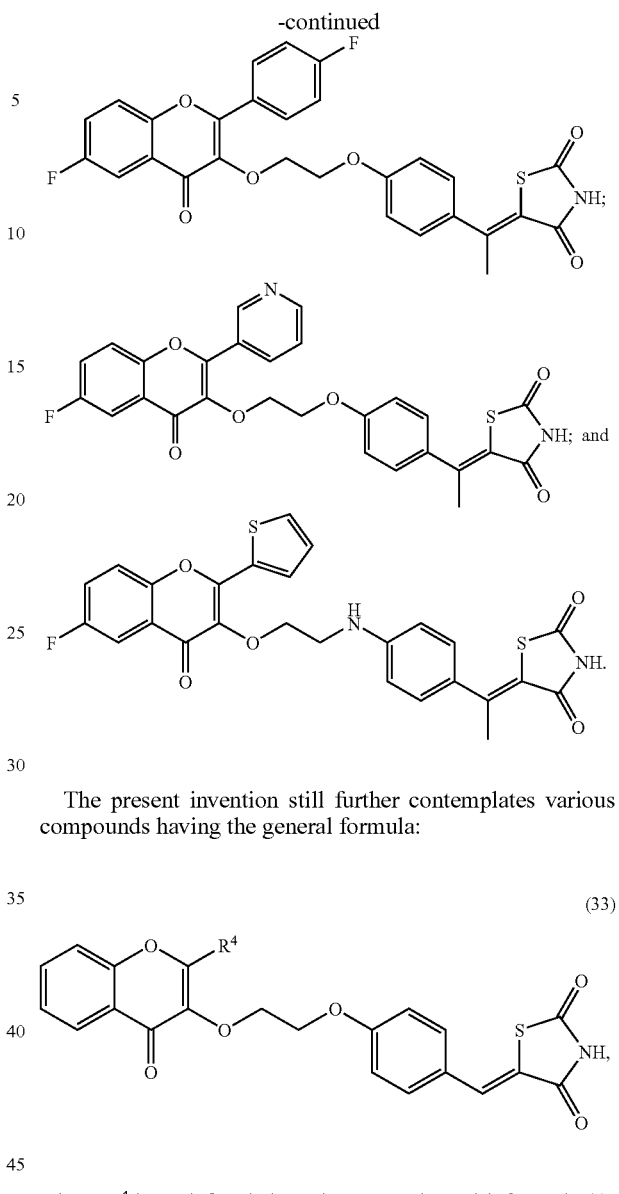

The present invention still further contemplates various compounds having the general formula:

(33)

where $R^4$ is as defined above in connection with formula (I).

In one aspect of formula (33) of the present invention, $R^4$ is hydrogen, a hydroxy group, a halogen, a nitro group, or an optionally substituted amino group, an alkyl group, a cycloalkyl group, an alkoxy group, a cycloalkoxy group, an alkenyl group, a cycloalkenyl group, an alkoxyalkyl group, an alkenyloxy group, or a cycloalkenyloxy group.

In another aspect of formula (33) of the present invention, $R^4$ is an acyl group, an acyloxy group, an aryl group, an aryloxy group, aroyl group or an aroyloxy group, an aralkyl group, an aralkenyl group, an aralkynyl group, an aralkoxy group, a heterocyclyl group, a heterocyclenyl group, a heteroaryl group, a heteroaralkyl group, a heteroaryloxy group, or a heteroaralkoxy group.

In yet another aspect of formula (33) of the present invention, $R^4$ is an alkoxycarbonyl group, an aryloxycarbonyl group, an aralkoxycarbonyl group, a heteroarylcarbonyl group, an alkylsulfonyl group, an arylsulfonyl group, a heteroarylsulfonyl group, an alkylsulfinyl group, an arylsulfinyl group, or an aralkylsulfinyl group, an alkylthio group, an arylthio group, a heteroarylthio group, an aralkylthio group, a fused heteroarylcycloalkyl group, a fused heteroarylcycloalkenyl group, a fused heteroarylheterocyclenyl group, carboxylic acid or a derivative thereof, or sulfonic acid or a derivative thereof.

In still another aspect of formula (33) of the present invention, $R^4$ is

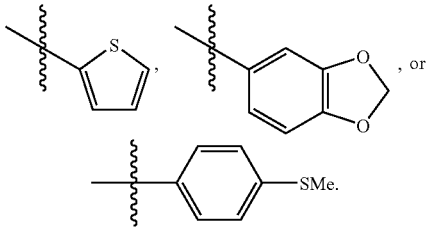

Examples of such compounds include, but are not limited to:

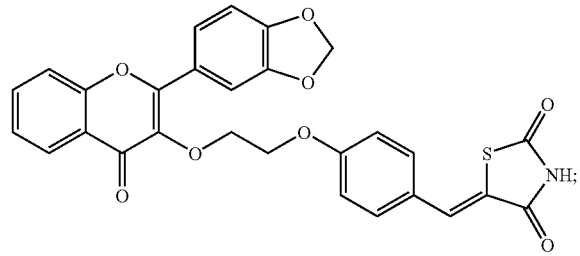

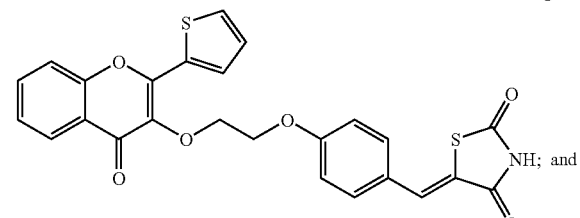

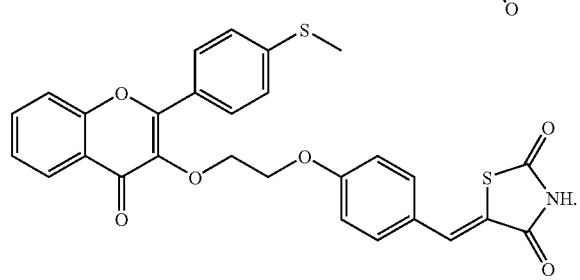

The present invention further still contemplates various compounds having the general formula:

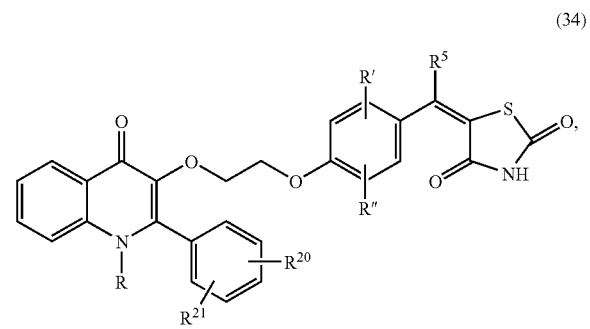

(34)

where all symbols are as defined above in connection with formula (I).

where $R^{20}$ and $R^{21}$ independently are hydrogen, a halogen, a nitro group, an amino group, a mono- or di-substituted amino group, a hydroxy group, an alkoxy group, a carboxy group, a cyano group, an oxo(O=) group, a thio(S=) group, an alkyl group, a cycloalkyl group, an alkoxy group, a haloalkoxy group, a cycloalkyl group, an aryl group, a benzyloxy group, an acyl group, an acyloxy group, an aroyl group, an alkoxycarbonyl group, an aryloxycarbonyl group, a heteroaryl group, a heterocyclyl group, an aralkyl group, an alkylsulfonyl group, an alkylsulfinyl group, an arylsulfonyl group, an arylsulfinyl group, an alkylthio group, an arylthio group, a heteroarylthio group, an aralkylthio group, or a heterocyclyl sulfonyl group, which is optionally substituted with a halogen, a hydroxyl group, a nitro group, an amino group, an alkyloxy group, or any combination thereof, and wherein the heterocycle group is optionally a substituted morpholinyl group, a thiomorpholinyl group, or a piperzinyl group, wherein the substituent on the heterocyclyl group is a halogen, a nitro group, an amino group, an alkyl group, an alkoxy group, or an aryl group; and all other symbols are as defined above.

According to various aspects of the present invention, R, $R^5$, $R^{20}$, $R^{21}$, R' and R" of formula (34) are selected to produce various compounds of formula (34-1) through formula (34-729) as follows:

| Formula | R | $R^5$ | $R^{20}$ | $R^{21}$ | R' | R" |
|---|---|---|---|---|---|---|
| 34-1 | $R^a$ | $R^{5a}$ | $R^{20a}$ | $R^{21a}$ | $R'^a$ | $R''^a$ |
| 34-2 | $R^b$ | $R^{5a}$ | $R^{20a}$ | $R^{21a}$ | $R'^a$ | $R''^a$ |
| 34-3 | $R^c$ | $R^{5a}$ | $R^{20a}$ | $R^{21a}$ | $R'^a$ | $R''^a$ |
| 34-4 | $R^a$ | $R^{5b}$ | $R^{20a}$ | $R^{21a}$ | $R'^a$ | $R''^a$ |
| 34-5 | $R^b$ | $R^{5b}$ | $R^{20a}$ | $R^{21a}$ | $R'^a$ | $R''^a$ |
| 34-6 | $R^c$ | $R^{5b}$ | $R^{20a}$ | $R^{21a}$ | $R'^a$ | $R''^a$ |
| 34-7 | $R^a$ | $R^{5c}$ | $R^{20a}$ | $R^{21a}$ | $R'^a$ | $R''^a$ |
| 34-8 | $R^b$ | $R^{5c}$ | $R^{20a}$ | $R^{21a}$ | $R'^a$ | $R''^a$ |
| 34-9 | $R^c$ | $R^{5c}$ | $R^{20a}$ | $R^{21a}$ | $R'^a$ | $R''^a$ |
| 34-10 | $R^a$ | $R^{5a}$ | $R^{20b}$ | $R^{21a}$ | $R'^a$ | $R''^a$ |
| 34-11 | $R^b$ | $R^{5a}$ | $R^{20b}$ | $R^{21a}$ | $R'^a$ | $R''^a$ |
| 34-12 | $R^c$ | $R^{5a}$ | $R^{20b}$ | $R^{21a}$ | $R'^a$ | $R''^a$ |
| 34-13 | $R^a$ | $R^{5b}$ | $R^{20b}$ | $R^{21a}$ | $R'^a$ | $R''^a$ |
| 34-14 | $R^b$ | $R^{5b}$ | $R^{20b}$ | $R^{21a}$ | $R'^a$ | $R''^a$ |
| 34-15 | $R^c$ | $R^{5b}$ | $R^{20b}$ | $R^{21a}$ | $R'^a$ | $R''^a$ |
| 34-16 | $R^a$ | $R^{5c}$ | $R^{20b}$ | $R^{21a}$ | $R'^a$ | $R''^a$ |
| 34-17 | $R^b$ | $R^{5c}$ | $R^{20b}$ | $R^{21a}$ | $R'^a$ | $R''^a$ |
| 34-18 | $R^c$ | $R^{5c}$ | $R^{20b}$ | $R^{21a}$ | $R'^a$ | $R''^a$ |
| 34-19 | $R^a$ | $R^{5a}$ | $R^{20c}$ | $R^{21a}$ | $R'^a$ | $R''^a$ |
| 34-20 | $R^b$ | $R^{5a}$ | $R^{20c}$ | $R^{21a}$ | $R'^a$ | $R''^a$ |
| 34-21 | $R^c$ | $R^{5a}$ | $R^{20c}$ | $R^{21a}$ | $R'^a$ | $R''^a$ |
| 34-22 | $R^a$ | $R^{5b}$ | $R^{20c}$ | $R^{21a}$ | $R'^a$ | $R''^a$ |
| 34-23 | $R^b$ | $R^{5b}$ | $R^{20c}$ | $R^{21a}$ | $R'^a$ | $R''^a$ |
| 34-24 | $R^c$ | $R^{5b}$ | $R^{20c}$ | $R^{21a}$ | $R'^a$ | $R''^a$ |
| 34-25 | $R^a$ | $R^{5c}$ | $R^{20c}$ | $R^{21a}$ | $R'^a$ | $R''^a$ |
| 34-26 | $R^b$ | $R^{5c}$ | $R^{20c}$ | $R^{21a}$ | $R'^a$ | $R''^a$ |
| 34-27 | $R^c$ | $R^{5c}$ | $R^{20c}$ | $R^{21a}$ | $R'^a$ | $R''^a$ |
| 34-28 | $R^a$ | $R^{5a}$ | $R^{20a}$ | $R^{21b}$ | $R'^a$ | $R''^a$ |
| 34-29 | $R^b$ | $R^{5a}$ | $R^{20a}$ | $R^{21b}$ | $R'^a$ | $R''^a$ |
| 34-30 | $R^c$ | $R^{5a}$ | $R^{20a}$ | $R^{21b}$ | $R'^a$ | $R''^a$ |
| 34-31 | $R^a$ | $R^{5b}$ | $R^{20a}$ | $R^{21b}$ | $R'^a$ | $R''^a$ |
| 34-32 | $R^b$ | $R^{5b}$ | $R^{20a}$ | $R^{21b}$ | $R'^a$ | $R''^a$ |
| 34-33 | $R^c$ | $R^{5b}$ | $R^{20a}$ | $R^{21b}$ | $R'^a$ | $R''^a$ |
| 34-34 | $R^a$ | $R^{5c}$ | $R^{20a}$ | $R^{21b}$ | $R'^a$ | $R''^a$ |
| 34-35 | $R^b$ | $R^{5c}$ | $R^{20a}$ | $R^{21b}$ | $R'^a$ | $R''^a$ |
| 34-36 | $R^c$ | $R^{5c}$ | $R^{20a}$ | $R^{21b}$ | $R'^a$ | $R''^a$ |
| 34-37 | $R^a$ | $R^{5a}$ | $R^{20b}$ | $R^{21b}$ | $R'^a$ | $R''^a$ |
| 34-38 | $R^b$ | $R^{5a}$ | $R^{20b}$ | $R^{21b}$ | $R'^a$ | $R''^a$ |
| 34-39 | $R^c$ | $R^{5a}$ | $R^{20b}$ | $R^{21b}$ | $R'^a$ | $R''^a$ |
| 34-40 | $R^a$ | $R^{5b}$ | $R^{20b}$ | $R^{21b}$ | $R'^a$ | $R''^a$ |
| 34-41 | $R^b$ | $R^{5b}$ | $R^{20b}$ | $R^{21b}$ | $R'^a$ | $R''^a$ |
| 34-42 | $R^c$ | $R^{5b}$ | $R^{20b}$ | $R^{21b}$ | $R'^a$ | $R''^a$ |
| 34-43 | $R^a$ | $R^{5c}$ | $R^{20b}$ | $R^{21b}$ | $R'^a$ | $R''^a$ |
| 34-44 | $R^b$ | $R^{5c}$ | $R^{20b}$ | $R^{21b}$ | $R'^a$ | $R''^a$ |
| 34-45 | $R^c$ | $R^{5c}$ | $R^{20b}$ | $R^{21b}$ | $R'^a$ | $R''^a$ |

| Formula | R | $R^5$ | $R^{20}$ | $R^{21}$ | R' | R" |
|---|---|---|---|---|---|---|
| 34-46 | $R^a$ | $R^{5a}$ | $R^{20c}$ | $R^{21b}$ | $R'^a$ | $R''^a$ |
| 34-47 | $R^b$ | $R^{5a}$ | $R^{20c}$ | $R^{21b}$ | $R'^a$ | $R''^a$ |
| 34-48 | $R^c$ | $R^{5a}$ | $R^{20c}$ | $R^{21b}$ | $R'^a$ | $R''^a$ |
| 34-49 | $R^a$ | $R^{5b}$ | $R^{20c}$ | $R^{21b}$ | $R'^a$ | $R''^a$ |
| 34-50 | $R^b$ | $R^{5b}$ | $R^{20c}$ | $R^{21b}$ | $R'^a$ | $R''^a$ |
| 34-51 | $R^c$ | $R^{5b}$ | $R^{20c}$ | $R^{21b}$ | $R'^a$ | $R''^a$ |
| 34-52 | $R^a$ | $R^{5c}$ | $R^{20c}$ | $R^{21b}$ | $R'^a$ | $R''^a$ |
| 34-53 | $R^b$ | $R^{5c}$ | $R^{20c}$ | $R^{21b}$ | $R'^a$ | $R''^a$ |
| 34-54 | $R^c$ | $R^{5c}$ | $R^{20c}$ | $R^{21b}$ | $R'^a$ | $R''^a$ |
| 34-55 | $R^a$ | $R^{5a}$ | $R^{20a}$ | $R^{21c}$ | $R'^a$ | $R''^a$ |
| 34-56 | $R^b$ | $R^{5a}$ | $R^{20a}$ | $R^{21c}$ | $R'^a$ | $R''^a$ |
| 34-57 | $R^c$ | $R^{5a}$ | $R^{20a}$ | $R^{21c}$ | $R'^a$ | $R''^a$ |
| 34-58 | $R^a$ | $R^{5b}$ | $R^{20a}$ | $R^{21c}$ | $R'^a$ | $R''^a$ |
| 34-59 | $R^b$ | $R^{5b}$ | $R^{20a}$ | $R^{21c}$ | $R'^a$ | $R''^a$ |
| 34-60 | $R^c$ | $R^{5b}$ | $R^{20a}$ | $R^{21c}$ | $R'^a$ | $R''^a$ |
| 34-61 | $R^a$ | $R^{5c}$ | $R^{20a}$ | $R^{21c}$ | $R'^a$ | $R''^a$ |
| 34-62 | $R^b$ | $R^{5c}$ | $R^{20a}$ | $R^{21c}$ | $R'^a$ | $R''^a$ |
| 34-63 | $R^c$ | $R^{5c}$ | $R^{20a}$ | $R^{21c}$ | $R'^a$ | $R''^a$ |
| 34-64 | $R^a$ | $R^{5a}$ | $R^{20b}$ | $R^{21c}$ | $R'^a$ | $R''^a$ |
| 34-65 | $R^b$ | $R^{5a}$ | $R^{20b}$ | $R^{21c}$ | $R'^a$ | $R''^a$ |
| 34-66 | $R^c$ | $R^{5a}$ | $R^{20b}$ | $R^{21c}$ | $R'^a$ | $R''^a$ |
| 34-67 | $R^a$ | $R^{5b}$ | $R^{20b}$ | $R^{21c}$ | $R'^a$ | $R''^a$ |
| 34-68 | $R^b$ | $R^{5b}$ | $R^{20b}$ | $R^{21c}$ | $R'^a$ | $R''^a$ |
| 34-69 | $R^c$ | $R^{5b}$ | $R^{20b}$ | $R^{21c}$ | $R'^a$ | $R''^a$ |
| 34-70 | $R^a$ | $R^{5c}$ | $R^{20b}$ | $R^{21c}$ | $R'^a$ | $R''^a$ |
| 34-71 | $R^b$ | $R^{5c}$ | $R^{20b}$ | $R^{21c}$ | $R'^a$ | $R''^a$ |
| 34-72 | $R^c$ | $R^{5c}$ | $R^{20b}$ | $R^{21c}$ | $R'^a$ | $R''^a$ |
| 34-73 | $R^a$ | $R^{5a}$ | $R^{20c}$ | $R^{21c}$ | $R'^a$ | $R''^a$ |
| 34-74 | $R^b$ | $R^{5a}$ | $R^{20c}$ | $R^{21c}$ | $R'^a$ | $R''^a$ |
| 34-75 | $R^c$ | $R^{5a}$ | $R^{20c}$ | $R^{21c}$ | $R'^a$ | $R''^a$ |
| 34-76 | $R^a$ | $R^{5b}$ | $R^{20c}$ | $R^{21c}$ | $R'^a$ | $R''^a$ |
| 34-77 | $R^b$ | $R^{5b}$ | $R^{20c}$ | $R^{21c}$ | $R'^a$ | $R''^a$ |
| 34-78 | $R^c$ | $R^{5b}$ | $R^{20c}$ | $R^{21c}$ | $R'^a$ | $R''^a$ |
| 34-79 | $R^a$ | $R^{5c}$ | $R^{20c}$ | $R^{21c}$ | $R'^a$ | $R''^a$ |
| 34-80 | $R^b$ | $R^{5c}$ | $R^{20c}$ | $R^{21c}$ | $R'^a$ | $R''^a$ |
| 34-81 | $R^c$ | $R^{5c}$ | $R^{20c}$ | $R^{21c}$ | $R'^a$ | $R''^a$ |
| 34-82 | $R^a$ | $R^{5a}$ | $R^{20a}$ | $R^{21a}$ | $R'^b$ | $R''^a$ |
| 34-83 | $R^b$ | $R^{5a}$ | $R^{20a}$ | $R^{21a}$ | $R'^b$ | $R''^a$ |
| 34-84 | $R^c$ | $R^{5a}$ | $R^{20a}$ | $R^{21a}$ | $R'^b$ | $R''^a$ |
| 34-85 | $R^a$ | $R^{5b}$ | $R^{20a}$ | $R^{21a}$ | $R'^b$ | $R''^a$ |
| 34-86 | $R^b$ | $R^{5b}$ | $R^{20a}$ | $R^{21a}$ | $R'^b$ | $R''^a$ |
| 34-87 | $R^c$ | $R^{5b}$ | $R^{20a}$ | $R^{21a}$ | $R'^b$ | $R''^a$ |
| 34-88 | $R^a$ | $R^{5c}$ | $R^{20a}$ | $R^{21a}$ | $R'^b$ | $R''^a$ |
| 34-89 | $R^b$ | $R^{5c}$ | $R^{20a}$ | $R^{21a}$ | $R'^b$ | $R''^a$ |
| 34-90 | $R^c$ | $R^{5c}$ | $R^{20a}$ | $R^{21a}$ | $R'^b$ | $R''^a$ |
| 34-91 | $R^a$ | $R^{5a}$ | $R^{20b}$ | $R^{21a}$ | $R'^b$ | $R''^a$ |
| 34-92 | $R^b$ | $R^{5a}$ | $R^{20b}$ | $R^{21a}$ | $R'^b$ | $R''^a$ |
| 34-93 | $R^c$ | $R^{5a}$ | $R^{20b}$ | $R^{21a}$ | $R'^b$ | $R''^a$ |
| 34-94 | $R^a$ | $R^{5b}$ | $R^{20b}$ | $R^{21a}$ | $R'^b$ | $R''^a$ |
| 34-95 | $R^b$ | $R^{5b}$ | $R^{20b}$ | $R^{21a}$ | $R'^b$ | $R''^a$ |
| 34-96 | $R^c$ | $R^{5b}$ | $R^{20b}$ | $R^{21a}$ | $R'^b$ | $R''^a$ |
| 34-97 | $R^a$ | $R^{5c}$ | $R^{20b}$ | $R^{21a}$ | $R'^b$ | $R''^a$ |
| 34-98 | $R^b$ | $R^{5c}$ | $R^{20b}$ | $R^{21a}$ | $R'^b$ | $R''^a$ |
| 34-99 | $R^c$ | $R^{5c}$ | $R^{20b}$ | $R^{21a}$ | $R'^b$ | $R''^a$ |
| 34-100 | $R^a$ | $R^{5a}$ | $R^{20c}$ | $R^{21a}$ | $R'^b$ | $R''^a$ |
| 34-101 | $R^b$ | $R^{5a}$ | $R^{20c}$ | $R^{21a}$ | $R'^b$ | $R''^a$ |
| 34-102 | $R^c$ | $R^{5a}$ | $R^{20c}$ | $R^{21a}$ | $R'^b$ | $R''^a$ |
| 34-103 | $R^a$ | $R^{5b}$ | $R^{20c}$ | $R^{21a}$ | $R'^b$ | $R''^a$ |
| 34-104 | $R^b$ | $R^{5b}$ | $R^{20c}$ | $R^{21a}$ | $R'^b$ | $R''^a$ |
| 34-105 | $R^c$ | $R^{5b}$ | $R^{20c}$ | $R^{21a}$ | $R'^b$ | $R''^a$ |
| 34-106 | $R^a$ | $R^{5c}$ | $R^{20c}$ | $R^{21a}$ | $R'^b$ | $R''^a$ |
| 34-107 | $R^b$ | $R^{5c}$ | $R^{20c}$ | $R^{21a}$ | $R'^b$ | $R''^a$ |
| 34-108 | $R^c$ | $R^{5c}$ | $R^{20c}$ | $R^{21a}$ | $R'^b$ | $R''^a$ |
| 34-109 | $R^a$ | $R^{5a}$ | $R^{20a}$ | $R^{21b}$ | $R'^b$ | $R''^a$ |
| 34-110 | $R^b$ | $R^{5a}$ | $R^{20a}$ | $R^{21b}$ | $R'^b$ | $R''^a$ |
| 34-111 | $R^c$ | $R^{5a}$ | $R^{20a}$ | $R^{21b}$ | $R'^b$ | $R''^a$ |
| 34-112 | $R^a$ | $R^{5b}$ | $R^{20a}$ | $R^{21b}$ | $R'^b$ | $R''^a$ |
| 34-113 | $R^b$ | $R^{5b}$ | $R^{20a}$ | $R^{21b}$ | $R'^b$ | $R''^a$ |
| 34-114 | $R^c$ | $R^{5b}$ | $R^{20a}$ | $R^{21b}$ | $R'^b$ | $R''^a$ |
| 34-115 | $R^a$ | $R^{5c}$ | $R^{20a}$ | $R^{21b}$ | $R'^b$ | $R''^a$ |
| 34-116 | $R^b$ | $R^{5c}$ | $R^{20a}$ | $R^{21b}$ | $R'^b$ | $R''^a$ |
| 34-117 | $R^c$ | $R^{5c}$ | $R^{20a}$ | $R^{21b}$ | $R'^b$ | $R''^a$ |
| 34-118 | $R^a$ | $R^{5a}$ | $R^{20b}$ | $R^{21b}$ | $R'^b$ | $R''^a$ |
| 34-119 | $R^b$ | $R^{5a}$ | $R^{20b}$ | $R^{21b}$ | $R'^b$ | $R''^a$ |
| 34-120 | $R^c$ | $R^{5a}$ | $R^{20b}$ | $R^{21b}$ | $R'^b$ | $R''^a$ |
| 34-121 | $R^a$ | $R^{5b}$ | $R^{20b}$ | $R^{21b}$ | $R'^b$ | $R''^a$ |
| 34-122 | $R^b$ | $R^{5b}$ | $R^{20b}$ | $R^{21b}$ | $R'^b$ | $R''^a$ |
| 34-123 | $R^c$ | $R^{5b}$ | $R^{20b}$ | $R^{21b}$ | $R'^b$ | $R''^a$ |
| 34-124 | $R^a$ | $R^{5c}$ | $R^{20b}$ | $R^{21b}$ | $R'^b$ | $R''^a$ |
| 34-125 | $R^b$ | $R^{5c}$ | $R^{20b}$ | $R^{21b}$ | $R'^b$ | $R''^a$ |
| 34-126 | $R^c$ | $R^{5c}$ | $R^{20b}$ | $R^{21b}$ | $R'^b$ | $R''^a$ |
| 34-127 | $R^a$ | $R^{5a}$ | $R^{20c}$ | $R^{21b}$ | $R'^b$ | $R''^a$ |
| 34-128 | $R^b$ | $R^{5a}$ | $R^{20c}$ | $R^{21b}$ | $R'^b$ | $R''^a$ |
| 34-129 | $R^c$ | $R^{5a}$ | $R^{20c}$ | $R^{21b}$ | $R'^b$ | $R''^a$ |
| 34-130 | $R^a$ | $R^{5b}$ | $R^{20c}$ | $R^{21b}$ | $R'^b$ | $R''^a$ |
| 34-131 | $R^b$ | $R^{5b}$ | $R^{20c}$ | $R^{21b}$ | $R'^b$ | $R''^a$ |
| 34-132 | $R^c$ | $R^{5b}$ | $R^{20c}$ | $R^{21b}$ | $R'^b$ | $R''^a$ |
| 34-133 | $R^a$ | $R^{5c}$ | $R^{20c}$ | $R^{21b}$ | $R'^b$ | $R''^a$ |
| 34-134 | $R^b$ | $R^{5c}$ | $R^{20c}$ | $R^{21b}$ | $R'^b$ | $R''^a$ |
| 34-135 | $R^c$ | $R^{5c}$ | $R^{20c}$ | $R^{21b}$ | $R'^b$ | $R''^a$ |
| 34-136 | $R^a$ | $R^{5a}$ | $R^{20a}$ | $R^{21c}$ | $R'^b$ | $R''^a$ |
| 34-137 | $R^b$ | $R^{5a}$ | $R^{20a}$ | $R^{21c}$ | $R'^b$ | $R''^a$ |
| 34-138 | $R^c$ | $R^{5a}$ | $R^{20a}$ | $R^{21c}$ | $R'^b$ | $R''^a$ |
| 34-139 | $R^a$ | $R^{5b}$ | $R^{20a}$ | $R^{21c}$ | $R'^b$ | $R''^a$ |
| 34-140 | $R^b$ | $R^{5b}$ | $R^{20a}$ | $R^{21c}$ | $R'^b$ | $R''^a$ |
| 34-141 | $R^c$ | $R^{5b}$ | $R^{20a}$ | $R^{21c}$ | $R'^b$ | $R''^a$ |
| 34-142 | $R^a$ | $R^{5c}$ | $R^{20a}$ | $R^{21c}$ | $R'^b$ | $R''^a$ |
| 34-143 | $R^b$ | $R^{5c}$ | $R^{20a}$ | $R^{21c}$ | $R'^b$ | $R''^a$ |
| 34-144 | $R^c$ | $R^{5c}$ | $R^{20a}$ | $R^{21c}$ | $R'^b$ | $R''^a$ |
| 34-145 | $R^a$ | $R^{5a}$ | $R^{20b}$ | $R^{21c}$ | $R'^b$ | $R''^a$ |
| 34-146 | $R^b$ | $R^{5a}$ | $R^{20b}$ | $R^{21c}$ | $R'^b$ | $R''^a$ |
| 34-147 | $R^c$ | $R^{5a}$ | $R^{20b}$ | $R^{21c}$ | $R'^b$ | $R''^a$ |
| 34-148 | $R^a$ | $R^{5b}$ | $R^{20b}$ | $R^{21c}$ | $R'^b$ | $R''^a$ |
| 34-149 | $R^b$ | $R^{5b}$ | $R^{20b}$ | $R^{21c}$ | $R'^b$ | $R''^a$ |
| 34-150 | $R^c$ | $R^{5b}$ | $R^{20b}$ | $R^{21c}$ | $R'^b$ | $R''^a$ |
| 34-151 | $R^a$ | $R^{5c}$ | $R^{20b}$ | $R^{21c}$ | $R'^b$ | $R''^a$ |
| 34-152 | $R^b$ | $R^{5c}$ | $R^{20b}$ | $R^{21c}$ | $R'^b$ | $R''^a$ |
| 34-153 | $R^c$ | $R^{5c}$ | $R^{20b}$ | $R^{21c}$ | $R'^b$ | $R''^a$ |
| 34-154 | $R^a$ | $R^{5a}$ | $R^{20c}$ | $R^{21c}$ | $R'^b$ | $R''^a$ |
| 34-155 | $R^b$ | $R^{5a}$ | $R^{20c}$ | $R^{21c}$ | $R'^b$ | $R''^a$ |
| 34-156 | $R^c$ | $R^{5a}$ | $R^{20c}$ | $R^{21c}$ | $R'^b$ | $R''^a$ |
| 34-157 | $R^a$ | $R^{5b}$ | $R^{20c}$ | $R^{21c}$ | $R'^b$ | $R''^a$ |
| 34-158 | $R^b$ | $R^{5b}$ | $R^{20c}$ | $R^{21c}$ | $R'^b$ | $R''^a$ |
| 34-159 | $R^c$ | $R^{5b}$ | $R^{20c}$ | $R^{21c}$ | $R'^b$ | $R''^a$ |
| 34-160 | $R^a$ | $R^{5c}$ | $R^{20c}$ | $R^{21c}$ | $R'^b$ | $R''^a$ |
| 34-161 | $R^b$ | $R^{5c}$ | $R^{20c}$ | $R^{21c}$ | $R'^b$ | $R''^a$ |
| 34-162 | $R^c$ | $R^{5c}$ | $R^{20c}$ | $R^{21c}$ | $R'^b$ | $R''^a$ |
| 34-163 | $R^a$ | $R^{5a}$ | $R^{20a}$ | $R^{21a}$ | $R'^c$ | $R''^a$ |
| 34-164 | $R^b$ | $R^{5a}$ | $R^{20a}$ | $R^{21a}$ | $R'^c$ | $R''^a$ |
| 34-165 | $R^c$ | $R^{5a}$ | $R^{20a}$ | $R^{21a}$ | $R'^c$ | $R''^a$ |
| 34-166 | $R^a$ | $R^{5b}$ | $R^{20a}$ | $R^{21a}$ | $R'^c$ | $R''^a$ |
| 34-167 | $R^b$ | $R^{5b}$ | $R^{20a}$ | $R^{21a}$ | $R'^c$ | $R''^a$ |
| 34-168 | $R^c$ | $R^{5b}$ | $R^{20a}$ | $R^{21a}$ | $R'^c$ | $R''^a$ |
| 34-169 | $R^a$ | $R^{5c}$ | $R^{20a}$ | $R^{21a}$ | $R'^c$ | $R''^a$ |
| 34-170 | $R^b$ | $R^{5c}$ | $R^{20a}$ | $R^{21a}$ | $R'^c$ | $R''^a$ |
| 34-171 | $R^c$ | $R^{5c}$ | $R^{20a}$ | $R^{21a}$ | $R'^c$ | $R''^a$ |
| 34-172 | $R^a$ | $R^{5a}$ | $R^{20b}$ | $R^{21a}$ | $R'^c$ | $R''^a$ |
| 34-173 | $R^b$ | $R^{5a}$ | $R^{20b}$ | $R^{21a}$ | $R'^c$ | $R''^a$ |
| 34-174 | $R^c$ | $R^{5a}$ | $R^{20b}$ | $R^{21a}$ | $R'^c$ | $R''^a$ |
| 34-175 | $R^a$ | $R^{5b}$ | $R^{20b}$ | $R^{21a}$ | $R'^c$ | $R''^a$ |
| 34-176 | $R^b$ | $R^{5b}$ | $R^{20b}$ | $R^{21a}$ | $R'^c$ | $R''^a$ |
| 34-177 | $R^c$ | $R^{5b}$ | $R^{20b}$ | $R^{21a}$ | $R'^c$ | $R''^a$ |
| 34-178 | $R^a$ | $R^{5c}$ | $R^{20b}$ | $R^{21a}$ | $R'^c$ | $R''^a$ |
| 34-179 | $R^b$ | $R^{5c}$ | $R^{20b}$ | $R^{21a}$ | $R'^c$ | $R''^a$ |
| 34-180 | $R^c$ | $R^{5c}$ | $R^{20b}$ | $R^{21a}$ | $R'^c$ | $R''^a$ |
| 34-181 | $R^a$ | $R^{5a}$ | $R^{20c}$ | $R^{21a}$ | $R'^c$ | $R''^a$ |
| 34-182 | $R^b$ | $R^{5a}$ | $R^{20c}$ | $R^{21a}$ | $R'^c$ | $R''^a$ |
| 34-183 | $R^c$ | $R^{5a}$ | $R^{20c}$ | $R^{21a}$ | $R'^c$ | $R''^a$ |
| 34-184 | $R^a$ | $R^{5b}$ | $R^{20c}$ | $R^{21a}$ | $R'^c$ | $R''^a$ |
| 34-185 | $R^b$ | $R^{5b}$ | $R^{20c}$ | $R^{21a}$ | $R'^c$ | $R''^a$ |
| 34-186 | $R^c$ | $R^{5b}$ | $R^{20c}$ | $R^{21a}$ | $R'^c$ | $R''^a$ |
| 34-187 | $R^a$ | $R^{5c}$ | $R^{20c}$ | $R^{21a}$ | $R'^c$ | $R''^a$ |
| 34-188 | $R^b$ | $R^{5c}$ | $R^{20c}$ | $R^{21a}$ | $R'^c$ | $R''^a$ |
| 34-189 | $R^c$ | $R^{5c}$ | $R^{20c}$ | $R^{21a}$ | $R'^c$ | $R''^a$ |
| 34-190 | $R^a$ | $R^{5a}$ | $R^{20a}$ | $R^{21b}$ | $R'^c$ | $R''^a$ |
| 34-191 | $R^b$ | $R^{5a}$ | $R^{20a}$ | $R^{21b}$ | $R'^c$ | $R''^a$ |
| 34-192 | $R^c$ | $R^{5a}$ | $R^{20a}$ | $R^{21b}$ | $R'^c$ | $R''^a$ |
| 34-193 | $R^a$ | $R^{5b}$ | $R^{20a}$ | $R^{21b}$ | $R'^c$ | $R''^a$ |
| 34-194 | $R^b$ | $R^{5b}$ | $R^{20a}$ | $R^{21b}$ | $R'^c$ | $R''^a$ |
| 34-195 | $R^c$ | $R^{5b}$ | $R^{20a}$ | $R^{21b}$ | $R'^c$ | $R''^a$ |
| 34-196 | $R^a$ | $R^{5c}$ | $R^{20a}$ | $R^{21b}$ | $R'^c$ | $R''^a$ |
| 34-197 | $R^b$ | $R^{5c}$ | $R^{20a}$ | $R^{21b}$ | $R'^c$ | $R''^a$ |
| 34-198 | $R^c$ | $R^{5c}$ | $R^{20a}$ | $R^{21b}$ | $R'^c$ | $R''^a$ |
| 34-199 | $R^a$ | $R^{5a}$ | $R^{20b}$ | $R^{21b}$ | $R'^c$ | $R''^a$ |

| Formula | R | $R^5$ | $R^{20}$ | $R^{21}$ | R' | R'' |
|---|---|---|---|---|---|---|
| 34-200 | $R^b$ | $R^{5a}$ | $R^{20b}$ | $R^{21b}$ | $R'^c$ | $R''^a$ |
| 34-201 | $R^c$ | $R^{5a}$ | $R^{20b}$ | $R^{21b}$ | $R'^c$ | $R''^a$ |
| 34-202 | $R^a$ | $R^{5b}$ | $R^{20b}$ | $R^{21b}$ | $R'^c$ | $R''^a$ |
| 34-203 | $R^b$ | $R^{5b}$ | $R^{20b}$ | $R^{21b}$ | $R'^c$ | $R''^a$ |
| 34-204 | $R^c$ | $R^{5b}$ | $R^{20b}$ | $R^{21b}$ | $R'^c$ | $R''^a$ |
| 34-205 | $R^a$ | $R^{5c}$ | $R^{20b}$ | $R^{21b}$ | $R'^c$ | $R''^a$ |
| 34-206 | $R^b$ | $R^{5c}$ | $R^{20b}$ | $R^{21b}$ | $R'^c$ | $R''^a$ |
| 34-207 | $R^c$ | $R^{5c}$ | $R^{20b}$ | $R^{21b}$ | $R'^c$ | $R''^a$ |
| 34-208 | $R^a$ | $R^{5a}$ | $R^{20c}$ | $R^{21b}$ | $R'^c$ | $R''^a$ |
| 34-209 | $R^b$ | $R^{5a}$ | $R^{20c}$ | $R^{21b}$ | $R'^c$ | $R''^a$ |
| 34-210 | $R^c$ | $R^{5a}$ | $R^{20c}$ | $R^{21b}$ | $R'^c$ | $R''^a$ |
| 34-211 | $R^a$ | $R^{5b}$ | $R^{20c}$ | $R^{21b}$ | $R'^c$ | $R''^a$ |
| 34-212 | $R^b$ | $R^{5b}$ | $R^{20c}$ | $R^{21b}$ | $R'^c$ | $R''^a$ |
| 34-213 | $R^c$ | $R^{5b}$ | $R^{20c}$ | $R^{21b}$ | $R'^c$ | $R''^a$ |
| 34-214 | $R^a$ | $R^{5c}$ | $R^{20c}$ | $R^{21b}$ | $R'^c$ | $R''^a$ |
| 34-215 | $R^b$ | $R^{5c}$ | $R^{20c}$ | $R^{21b}$ | $R'^c$ | $R''^a$ |
| 34-216 | $R^c$ | $R^{5c}$ | $R^{20c}$ | $R^{21b}$ | $R'^c$ | $R''^a$ |
| 34-217 | $R^a$ | $R^{5a}$ | $R^{20a}$ | $R^{21c}$ | $R'^c$ | $R''^a$ |
| 34-218 | $R^b$ | $R^{5a}$ | $R^{20a}$ | $R^{21c}$ | $R'^c$ | $R''^a$ |
| 34-219 | $R^c$ | $R^{5a}$ | $R^{20a}$ | $R^{21c}$ | $R'^c$ | $R''^a$ |
| 34-220 | $R^a$ | $R^{5b}$ | $R^{20a}$ | $R^{21c}$ | $R'^c$ | $R''^a$ |
| 34-221 | $R^b$ | $R^{5b}$ | $R^{20a}$ | $R^{21c}$ | $R'^c$ | $R''^a$ |
| 34-222 | $R^c$ | $R^{5b}$ | $R^{20a}$ | $R^{21c}$ | $R'^c$ | $R''^a$ |
| 34-223 | $R^a$ | $R^{5c}$ | $R^{20a}$ | $R^{21c}$ | $R'^c$ | $R''^a$ |
| 34-224 | $R^b$ | $R^{5c}$ | $R^{20a}$ | $R^{21c}$ | $R'^c$ | $R''^a$ |
| 34-225 | $R^c$ | $R^{5c}$ | $R^{20a}$ | $R^{21c}$ | $R'^c$ | $R''^a$ |
| 34-226 | $R^a$ | $R^{5a}$ | $R^{20b}$ | $R^{21c}$ | $R'^c$ | $R''^a$ |
| 34-227 | $R^b$ | $R^{5a}$ | $R^{20b}$ | $R^{21c}$ | $R'^c$ | $R''^a$ |
| 34-228 | $R^c$ | $R^{5a}$ | $R^{20b}$ | $R^{21c}$ | $R'^c$ | $R''^a$ |
| 34-229 | $R^a$ | $R^{5b}$ | $R^{20b}$ | $R^{21c}$ | $R'^c$ | $R''^a$ |
| 34-230 | $R^b$ | $R^{5b}$ | $R^{20b}$ | $R^{21c}$ | $R'^c$ | $R''^a$ |
| 34-231 | $R^c$ | $R^{5b}$ | $R^{20b}$ | $R^{21c}$ | $R'^c$ | $R''^a$ |
| 34-232 | $R^a$ | $R^{5c}$ | $R^{20b}$ | $R^{21c}$ | $R'^c$ | $R''^a$ |
| 34-233 | $R^b$ | $R^{5c}$ | $R^{20b}$ | $R^{21c}$ | $R'^c$ | $R''^a$ |
| 34-234 | $R^c$ | $R^{5c}$ | $R^{20b}$ | $R^{21c}$ | $R'^c$ | $R''^a$ |
| 34-235 | $R^a$ | $R^{5a}$ | $R^{20c}$ | $R^{21c}$ | $R'^c$ | $R''^a$ |
| 34-236 | $R^b$ | $R^{5a}$ | $R^{20c}$ | $R^{21c}$ | $R'^c$ | $R''^a$ |
| 34-237 | $R^c$ | $R^{5a}$ | $R^{20c}$ | $R^{21c}$ | $R'^c$ | $R''^a$ |
| 34-238 | $R^a$ | $R^{5b}$ | $R^{20c}$ | $R^{21c}$ | $R'^c$ | $R''^a$ |
| 34-239 | $R^b$ | $R^{5b}$ | $R^{20c}$ | $R^{21c}$ | $R'^c$ | $R''^a$ |
| 34-240 | $R^c$ | $R^{5b}$ | $R^{20c}$ | $R^{21c}$ | $R'^c$ | $R''^a$ |
| 34-241 | $R^a$ | $R^{5c}$ | $R^{20c}$ | $R^{21c}$ | $R'^c$ | $R''^a$ |
| 34-242 | $R^b$ | $R^{5c}$ | $R^{20c}$ | $R^{21c}$ | $R'^c$ | $R''^a$ |
| 34-243 | $R^c$ | $R^{5c}$ | $R^{20c}$ | $R^{21c}$ | $R'^c$ | $R''^a$ |
| 34-244 | $R^a$ | $R^{5a}$ | $R^{20a}$ | $R^{21a}$ | $R'^a$ | $R''^b$ |
| 34-245 | $R^b$ | $R^{5a}$ | $R^{20a}$ | $R^{21a}$ | $R'^a$ | $R''^b$ |
| 34-246 | $R^c$ | $R^{5a}$ | $R^{20a}$ | $R^{21a}$ | $R'^a$ | $R''^b$ |
| 34-247 | $R^a$ | $R^{5b}$ | $R^{20a}$ | $R^{21a}$ | $R'^a$ | $R''^b$ |
| 34-248 | $R^b$ | $R^{5b}$ | $R^{20a}$ | $R^{21a}$ | $R'^a$ | $R''^b$ |
| 34-249 | $R^c$ | $R^{5b}$ | $R^{20a}$ | $R^{21a}$ | $R'^a$ | $R''^b$ |
| 34-250 | $R^a$ | $R^{5c}$ | $R^{20a}$ | $R^{21a}$ | $R'^a$ | $R''^b$ |
| 34-251 | $R^b$ | $R^{5c}$ | $R^{20a}$ | $R^{21a}$ | $R'^a$ | $R''^b$ |
| 34-252 | $R^c$ | $R^{5c}$ | $R^{20a}$ | $R^{21a}$ | $R'^a$ | $R''^b$ |
| 34-253 | $R^a$ | $R^{5a}$ | $R^{20b}$ | $R^{21a}$ | $R'^a$ | $R''^b$ |
| 34-254 | $R^b$ | $R^{5a}$ | $R^{20b}$ | $R^{21a}$ | $R'^a$ | $R''^b$ |
| 34-255 | $R^c$ | $R^{5a}$ | $R^{20b}$ | $R^{21a}$ | $R'^a$ | $R''^b$ |
| 34-256 | $R^a$ | $R^{5b}$ | $R^{20b}$ | $R^{21a}$ | $R'^a$ | $R''^b$ |
| 34-257 | $R^b$ | $R^{5b}$ | $R^{20b}$ | $R^{21a}$ | $R'^a$ | $R''^b$ |
| 34-258 | $R^c$ | $R^{5b}$ | $R^{20b}$ | $R^{21a}$ | $R'^a$ | $R''^b$ |
| 34-259 | $R^a$ | $R^{5c}$ | $R^{20b}$ | $R^{21a}$ | $R'^a$ | $R''^b$ |
| 34-260 | $R^b$ | $R^{5c}$ | $R^{20b}$ | $R^{21a}$ | $R'^a$ | $R''^b$ |
| 34-261 | $R^c$ | $R^{5c}$ | $R^{20b}$ | $R^{21a}$ | $R'^a$ | $R''^b$ |
| 34-262 | $R^a$ | $R^{5a}$ | $R^{20c}$ | $R^{21a}$ | $R'^a$ | $R''^b$ |
| 34-263 | $R^b$ | $R^{5a}$ | $R^{20c}$ | $R^{21a}$ | $R'^a$ | $R''^b$ |
| 34-264 | $R^c$ | $R^{5a}$ | $R^{20c}$ | $R^{21a}$ | $R'^a$ | $R''^b$ |
| 34-265 | $R^a$ | $R^{5b}$ | $R^{20c}$ | $R^{21a}$ | $R'^a$ | $R''^b$ |
| 34-266 | $R^b$ | $R^{5b}$ | $R^{20c}$ | $R^{21a}$ | $R'^a$ | $R''^b$ |
| 34-267 | $R^c$ | $R^{5b}$ | $R^{20c}$ | $R^{21a}$ | $R'^a$ | $R''^b$ |
| 34-268 | $R^a$ | $R^{5c}$ | $R^{20c}$ | $R^{21a}$ | $R'^a$ | $R''^b$ |
| 34-269 | $R^b$ | $R^{5c}$ | $R^{20c}$ | $R^{21a}$ | $R'^a$ | $R''^b$ |
| 34-270 | $R^c$ | $R^{5c}$ | $R^{20c}$ | $R^{21a}$ | $R'^a$ | $R''^b$ |
| 34-271 | $R^a$ | $R^{5a}$ | $R^{20a}$ | $R^{21b}$ | $R'^a$ | $R''^b$ |
| 34-272 | $R^b$ | $R^{5a}$ | $R^{20a}$ | $R^{21b}$ | $R'^a$ | $R''^b$ |
| 34-273 | $R^c$ | $R^{5a}$ | $R^{20a}$ | $R^{21b}$ | $R'^a$ | $R''^b$ |
| 34-274 | $R^a$ | $R^{5b}$ | $R^{20a}$ | $R^{21b}$ | $R'^a$ | $R''^b$ |
| 34-275 | $R^b$ | $R^{5b}$ | $R^{20a}$ | $R^{21b}$ | $R'^a$ | $R''^b$ |
| 34-276 | $R^c$ | $R^{5b}$ | $R^{20a}$ | $R^{21b}$ | $R'^a$ | $R''^b$ |
| 34-277 | $R^a$ | $R^{5c}$ | $R^{20a}$ | $R^{21b}$ | $R'^a$ | $R''^b$ |
| 34-278 | $R^b$ | $R^{5c}$ | $R^{20a}$ | $R^{21b}$ | $R'^a$ | $R''^b$ |
| 34-279 | $R^c$ | $R^{5c}$ | $R^{20a}$ | $R^{21b}$ | $R'^a$ | $R''^b$ |
| 34-280 | $R^a$ | $R^{5a}$ | $R^{20b}$ | $R^{21b}$ | $R'^a$ | $R''^b$ |
| 34-281 | $R^b$ | $R^{5a}$ | $R^{20b}$ | $R^{21b}$ | $R'^a$ | $R''^b$ |
| 34-282 | $R^c$ | $R^{5a}$ | $R^{20b}$ | $R^{21b}$ | $R'^a$ | $R''^b$ |
| 34-283 | $R^a$ | $R^{5b}$ | $R^{20b}$ | $R^{21b}$ | $R'^a$ | $R''^b$ |
| 34-284 | $R^b$ | $R^{5b}$ | $R^{20b}$ | $R^{21b}$ | $R'^a$ | $R''^b$ |
| 34-285 | $R^c$ | $R^{5b}$ | $R^{20b}$ | $R^{21b}$ | $R'^a$ | $R''^b$ |
| 34-286 | $R^a$ | $R^{5c}$ | $R^{20b}$ | $R^{21b}$ | $R'^a$ | $R''^b$ |
| 34-287 | $R^b$ | $R^{5c}$ | $R^{20b}$ | $R^{21b}$ | $R'^a$ | $R''^b$ |
| 34-288 | $R^c$ | $R^{5c}$ | $R^{20b}$ | $R^{21b}$ | $R'^a$ | $R''^b$ |
| 34-289 | $R^a$ | $R^{5a}$ | $R^{20c}$ | $R^{21b}$ | $R'^a$ | $R''^b$ |
| 34-290 | $R^b$ | $R^{5a}$ | $R^{20c}$ | $R^{21b}$ | $R'^a$ | $R''^b$ |
| 34-291 | $R^c$ | $R^{5a}$ | $R^{20c}$ | $R^{21b}$ | $R'^a$ | $R''^b$ |
| 34-292 | $R^a$ | $R^{5b}$ | $R^{20c}$ | $R^{21b}$ | $R'^a$ | $R''^b$ |
| 34-293 | $R^b$ | $R^{5b}$ | $R^{20c}$ | $R^{21b}$ | $R'^a$ | $R''^b$ |
| 34-294 | $R^c$ | $R^{5b}$ | $R^{20c}$ | $R^{21b}$ | $R'^a$ | $R''^b$ |
| 34-295 | $R^a$ | $R^{5c}$ | $R^{20c}$ | $R^{21b}$ | $R'^a$ | $R''^b$ |
| 34-296 | $R^b$ | $R^{5c}$ | $R^{20c}$ | $R^{21b}$ | $R'^a$ | $R''^b$ |
| 34-297 | $R^c$ | $R^{5c}$ | $R^{20c}$ | $R^{21b}$ | $R'^a$ | $R''^b$ |
| 34-298 | $R^a$ | $R^{5a}$ | $R^{20a}$ | $R^{21c}$ | $R'^a$ | $R''^b$ |
| 34-299 | $R^b$ | $R^{5a}$ | $R^{20a}$ | $R^{21c}$ | $R'^a$ | $R''^b$ |
| 34-300 | $R^c$ | $R^{5a}$ | $R^{20a}$ | $R^{21c}$ | $R'^a$ | $R''^b$ |
| 34-301 | $R^a$ | $R^{5b}$ | $R^{20a}$ | $R^{21c}$ | $R'^a$ | $R''^b$ |
| 34-302 | $R^b$ | $R^{5b}$ | $R^{20a}$ | $R^{21c}$ | $R'^a$ | $R''^b$ |
| 34-303 | $R^c$ | $R^{5b}$ | $R^{20a}$ | $R^{21c}$ | $R'^a$ | $R''^b$ |
| 34-304 | $R^a$ | $R^{5c}$ | $R^{20a}$ | $R^{21c}$ | $R'^a$ | $R''^b$ |
| 34-305 | $R^b$ | $R^{5c}$ | $R^{20a}$ | $R^{21c}$ | $R'^a$ | $R''^b$ |
| 34-306 | $R^c$ | $R^{5c}$ | $R^{20a}$ | $R^{21c}$ | $R'^a$ | $R''^b$ |
| 34-307 | $R^a$ | $R^{5a}$ | $R^{20b}$ | $R^{21c}$ | $R'^a$ | $R''^b$ |
| 34-308 | $R^b$ | $R^{5a}$ | $R^{20b}$ | $R^{21c}$ | $R'^a$ | $R''^b$ |
| 34-309 | $R^c$ | $R^{5a}$ | $R^{20b}$ | $R^{21c}$ | $R'^a$ | $R''^b$ |
| 34-310 | $R^a$ | $R^{5b}$ | $R^{20b}$ | $R^{21c}$ | $R'^a$ | $R''^b$ |
| 34-311 | $R^b$ | $R^{5b}$ | $R^{20b}$ | $R^{21c}$ | $R'^a$ | $R''^b$ |
| 34-312 | $R^c$ | $R^{5b}$ | $R^{20b}$ | $R^{21c}$ | $R'^a$ | $R''^b$ |
| 34-313 | $R^a$ | $R^{5c}$ | $R^{20b}$ | $R^{21c}$ | $R'^a$ | $R''^b$ |
| 34-314 | $R^b$ | $R^{5c}$ | $R^{20b}$ | $R^{21c}$ | $R'^a$ | $R''^b$ |
| 34-315 | $R^c$ | $R^{5c}$ | $R^{20b}$ | $R^{21c}$ | $R'^a$ | $R''^b$ |
| 34-316 | $R^a$ | $R^{5a}$ | $R^{20c}$ | $R^{21c}$ | $R'^a$ | $R''^b$ |
| 34-317 | $R^b$ | $R^{5a}$ | $R^{20c}$ | $R^{21c}$ | $R'^a$ | $R''^b$ |
| 34-318 | $R^c$ | $R^{5a}$ | $R^{20c}$ | $R^{21c}$ | $R'^a$ | $R''^b$ |
| 34-319 | $R^a$ | $R^{5b}$ | $R^{20c}$ | $R^{21c}$ | $R'^a$ | $R''^b$ |
| 34-320 | $R^b$ | $R^{5b}$ | $R^{20c}$ | $R^{21c}$ | $R'^a$ | $R''^b$ |
| 34-321 | $R^c$ | $R^{5b}$ | $R^{20c}$ | $R^{21c}$ | $R'^a$ | $R''^b$ |
| 34-322 | $R^a$ | $R^{5c}$ | $R^{20c}$ | $R^{21c}$ | $R'^a$ | $R''^b$ |
| 34-323 | $R^b$ | $R^{5c}$ | $R^{20c}$ | $R^{21c}$ | $R'^a$ | $R''^b$ |
| 34-324 | $R^c$ | $R^{5c}$ | $R^{20c}$ | $R^{21c}$ | $R'^a$ | $R''^b$ |
| 34-325 | $R^a$ | $R^{5a}$ | $R^{20a}$ | $R^{21a}$ | $R'^b$ | $R''^b$ |
| 34-326 | $R^b$ | $R^{5a}$ | $R^{20a}$ | $R^{21a}$ | $R'^b$ | $R''^b$ |
| 34-327 | $R^c$ | $R^{5a}$ | $R^{20a}$ | $R^{21a}$ | $R'^b$ | $R''^b$ |
| 34-328 | $R^a$ | $R^{5b}$ | $R^{20a}$ | $R^{21a}$ | $R'^b$ | $R''^b$ |
| 34-329 | $R^b$ | $R^{5b}$ | $R^{20a}$ | $R^{21a}$ | $R'^b$ | $R''^b$ |
| 34-330 | $R^c$ | $R^{5b}$ | $R^{20a}$ | $R^{21a}$ | $R'^b$ | $R''^b$ |
| 34-331 | $R^a$ | $R^{5c}$ | $R^{20a}$ | $R^{21a}$ | $R'^b$ | $R''^b$ |
| 34-332 | $R^b$ | $R^{5c}$ | $R^{20a}$ | $R^{21a}$ | $R'^b$ | $R''^b$ |
| 34-333 | $R^c$ | $R^{5c}$ | $R^{20a}$ | $R^{21a}$ | $R'^b$ | $R''^b$ |
| 34-334 | $R^a$ | $R^{5a}$ | $R^{20b}$ | $R^{21a}$ | $R'^b$ | $R''^b$ |
| 34-335 | $R^b$ | $R^{5a}$ | $R^{20b}$ | $R^{21a}$ | $R'^b$ | $R''^b$ |
| 34-336 | $R^c$ | $R^{5a}$ | $R^{20b}$ | $R^{21a}$ | $R'^b$ | $R''^b$ |
| 34-337 | $R^a$ | $R^{5b}$ | $R^{20b}$ | $R^{21a}$ | $R'^b$ | $R''^b$ |
| 34-338 | $R^b$ | $R^{5b}$ | $R^{20b}$ | $R^{21a}$ | $R'^b$ | $R''^b$ |
| 34-339 | $R^c$ | $R^{5b}$ | $R^{20b}$ | $R^{21a}$ | $R'^b$ | $R''^b$ |
| 34-340 | $R^a$ | $R^{5c}$ | $R^{20b}$ | $R^{21a}$ | $R'^b$ | $R''^b$ |
| 34-341 | $R^b$ | $R^{5c}$ | $R^{20b}$ | $R^{21a}$ | $R'^b$ | $R''^b$ |
| 34-342 | $R^c$ | $R^{5c}$ | $R^{20b}$ | $R^{21a}$ | $R'^b$ | $R''^b$ |
| 34-343 | $R^a$ | $R^{5a}$ | $R^{20c}$ | $R^{21a}$ | $R'^b$ | $R''^b$ |
| 34-344 | $R^b$ | $R^{5a}$ | $R^{20c}$ | $R^{21a}$ | $R'^b$ | $R''^b$ |
| 34-345 | $R^c$ | $R^{5a}$ | $R^{20c}$ | $R^{21a}$ | $R'^b$ | $R''^b$ |
| 34-346 | $R^a$ | $R^{5b}$ | $R^{20c}$ | $R^{21a}$ | $R'^b$ | $R''^b$ |
| 34-347 | $R^b$ | $R^{5b}$ | $R^{20c}$ | $R^{21a}$ | $R'^b$ | $R''^b$ |
| 34-348 | $R^c$ | $R^{5b}$ | $R^{20c}$ | $R^{21a}$ | $R'^b$ | $R''^b$ |
| 34-349 | $R^a$ | $R^{5c}$ | $R^{20c}$ | $R^{21a}$ | $R'^b$ | $R''^b$ |
| 34-350 | $R^b$ | $R^{5c}$ | $R^{20c}$ | $R^{21a}$ | $R'^b$ | $R''^b$ |
| 34-351 | $R^c$ | $R^{5c}$ | $R^{20c}$ | $R^{21a}$ | $R'^b$ | $R''^b$ |
| 34-352 | $R^a$ | $R^{5a}$ | $R^{20a}$ | $R^{21b}$ | $R'^b$ | $R''^b$ |
| 34-353 | $R^b$ | $R^{5a}$ | $R^{20a}$ | $R^{21b}$ | $R'^b$ | $R''^b$ |

-continued

| Formula | R | $R^5$ | $R^{20}$ | $R^{21}$ | R' | R" |
|---|---|---|---|---|---|---|
| 34-354 | $R^c$ | $R^{5a}$ | $R^{20a}$ | $R^{21b}$ | $R'^b$ | $R''^b$ |
| 34-355 | $R^a$ | $R^{5b}$ | $R^{20a}$ | $R^{21b}$ | $R'^b$ | $R''^b$ |
| 34-356 | $R^b$ | $R^{5b}$ | $R^{20a}$ | $R^{21b}$ | $R'^b$ | $R''^b$ |
| 34-357 | $R^c$ | $R^{5b}$ | $R^{20a}$ | $R^{21b}$ | $R'^b$ | $R''^b$ |
| 34-358 | $R^a$ | $R^{5c}$ | $R^{20a}$ | $R^{21b}$ | $R'^b$ | $R''^b$ |
| 34-359 | $R^b$ | $R^{5c}$ | $R^{20a}$ | $R^{21b}$ | $R'^b$ | $R''^b$ |
| 34-360 | $R^c$ | $R^{5c}$ | $R^{20a}$ | $R^{21b}$ | $R'^b$ | $R''^b$ |
| 34-361 | $R^a$ | $R^{5a}$ | $R^{20b}$ | $R^{21b}$ | $R'^b$ | $R''^b$ |
| 34-362 | $R^b$ | $R^{5a}$ | $R^{20b}$ | $R^{21b}$ | $R'^b$ | $R''^b$ |
| 34-363 | $R^c$ | $R^{5a}$ | $R^{20b}$ | $R^{21b}$ | $R'^b$ | $R''^b$ |
| 34-364 | $R^a$ | $R^{5b}$ | $R^{20b}$ | $R^{21b}$ | $R'^b$ | $R''^b$ |
| 34-365 | $R^b$ | $R^{5b}$ | $R^{20b}$ | $R^{21b}$ | $R'^b$ | $R''^b$ |
| 34-366 | $R^c$ | $R^{5b}$ | $R^{20b}$ | $R^{21b}$ | $R'^b$ | $R''^b$ |
| 34-367 | $R^a$ | $R^{5c}$ | $R^{20b}$ | $R^{21b}$ | $R'^b$ | $R''^b$ |
| 34-368 | $R^b$ | $R^{5c}$ | $R^{20b}$ | $R^{21b}$ | $R'^b$ | $R''^b$ |
| 34-369 | $R^c$ | $R^{5c}$ | $R^{20b}$ | $R^{21b}$ | $R'^b$ | $R''^b$ |
| 34-370 | $R^a$ | $R^{5a}$ | $R^{20c}$ | $R^{21b}$ | $R'^b$ | $R''^b$ |
| 34-371 | $R^b$ | $R^{5a}$ | $R^{20c}$ | $R^{21b}$ | $R'^b$ | $R''^b$ |
| 34-372 | $R^c$ | $R^{5a}$ | $R^{20c}$ | $R^{21b}$ | $R'^b$ | $R''^b$ |
| 34-373 | $R^a$ | $R^{5b}$ | $R^{20c}$ | $R^{21b}$ | $R'^b$ | $R''^b$ |
| 34-374 | $R^b$ | $R^{5b}$ | $R^{20c}$ | $R^{21b}$ | $R'^b$ | $R''^b$ |
| 34-375 | $R^c$ | $R^{5b}$ | $R^{20c}$ | $R^{21b}$ | $R'^b$ | $R''^b$ |
| 34-376 | $R^a$ | $R^{5c}$ | $R^{20c}$ | $R^{21b}$ | $R'^b$ | $R''^b$ |
| 34-377 | $R^b$ | $R^{5c}$ | $R^{20c}$ | $R^{21b}$ | $R'^b$ | $R''^b$ |
| 34-378 | $R^c$ | $R^{5c}$ | $R^{20c}$ | $R^{21b}$ | $R'^b$ | $R''^b$ |
| 34-379 | $R^a$ | $R^{5a}$ | $R^{20a}$ | $R^{21c}$ | $R'^b$ | $R''^b$ |
| 34-380 | $R^b$ | $R^{5a}$ | $R^{20a}$ | $R^{21c}$ | $R'^b$ | $R''^b$ |
| 34-381 | $R^c$ | $R^{5a}$ | $R^{20a}$ | $R^{21c}$ | $R'^b$ | $R''^b$ |
| 34-382 | $R^a$ | $R^{5b}$ | $R^{20a}$ | $R^{21c}$ | $R'^b$ | $R''^b$ |
| 34-383 | $R^b$ | $R^{5b}$ | $R^{20a}$ | $R^{21c}$ | $R'^b$ | $R''^b$ |
| 34-384 | $R^c$ | $R^{5b}$ | $R^{20a}$ | $R^{21c}$ | $R'^b$ | $R''^b$ |
| 34-385 | $R^a$ | $R^{5c}$ | $R^{20a}$ | $R^{21c}$ | $R'^b$ | $R''^b$ |
| 34-386 | $R^b$ | $R^{5c}$ | $R^{20a}$ | $R^{21c}$ | $R'^b$ | $R''^b$ |
| 34-387 | $R^c$ | $R^{5c}$ | $R^{20a}$ | $R^{21c}$ | $R'^b$ | $R''^b$ |
| 34-388 | $R^a$ | $R^{5a}$ | $R^{20b}$ | $R^{21c}$ | $R'^b$ | $R''^b$ |
| 34-389 | $R^b$ | $R^{5a}$ | $R^{20b}$ | $R^{21c}$ | $R'^b$ | $R''^b$ |
| 34-390 | $R^c$ | $R^{5a}$ | $R^{20b}$ | $R^{21c}$ | $R'^b$ | $R''^b$ |
| 34-391 | $R^a$ | $R^{5b}$ | $R^{20b}$ | $R^{21c}$ | $R'^b$ | $R''^b$ |
| 34-392 | $R^b$ | $R^{5b}$ | $R^{20b}$ | $R^{21c}$ | $R'^b$ | $R''^b$ |
| 34-393 | $R^c$ | $R^{5b}$ | $R^{20b}$ | $R^{21c}$ | $R'^b$ | $R''^b$ |
| 34-394 | $R^a$ | $R^{5c}$ | $R^{20b}$ | $R^{21c}$ | $R'^b$ | $R''^b$ |
| 34-395 | $R^b$ | $R^{5c}$ | $R^{20b}$ | $R^{21c}$ | $R'^b$ | $R''^b$ |
| 34-396 | $R^c$ | $R^{5c}$ | $R^{20b}$ | $R^{21c}$ | $R'^b$ | $R''^b$ |
| 34-397 | $R^a$ | $R^{5a}$ | $R^{20c}$ | $R^{21c}$ | $R'^b$ | $R''^b$ |
| 34-398 | $R^b$ | $R^{5a}$ | $R^{20c}$ | $R^{21c}$ | $R'^b$ | $R''^b$ |
| 34-399 | $R^c$ | $R^{5a}$ | $R^{20c}$ | $R^{21c}$ | $R'^b$ | $R''^b$ |
| 34-400 | $R^a$ | $R^{5b}$ | $R^{20c}$ | $R^{21c}$ | $R'^b$ | $R''^b$ |
| 34-401 | $R^b$ | $R^{5b}$ | $R^{20c}$ | $R^{21c}$ | $R'^b$ | $R''^b$ |
| 34-402 | $R^c$ | $R^{5b}$ | $R^{20c}$ | $R^{21c}$ | $R'^b$ | $R''^b$ |
| 34-403 | $R^a$ | $R^{5c}$ | $R^{20c}$ | $R^{21c}$ | $R'^b$ | $R''^b$ |
| 34-404 | $R^b$ | $R^{5c}$ | $R^{20c}$ | $R^{21c}$ | $R'^b$ | $R''^b$ |
| 34-405 | $R^c$ | $R^{5c}$ | $R^{20c}$ | $R^{21c}$ | $R'^b$ | $R''^b$ |
| 34-406 | $R^a$ | $R^{5a}$ | $R^{20a}$ | $R^{21a}$ | $R'^c$ | $R''^b$ |
| 34-407 | $R^b$ | $R^{5a}$ | $R^{20a}$ | $R^{21a}$ | $R'^c$ | $R''^b$ |
| 34-408 | $R^c$ | $R^{5a}$ | $R^{20a}$ | $R^{21a}$ | $R'^c$ | $R''^b$ |
| 34-409 | $R^a$ | $R^{5b}$ | $R^{20a}$ | $R^{21a}$ | $R'^c$ | $R''^b$ |
| 34-410 | $R^b$ | $R^{5b}$ | $R^{20a}$ | $R^{21a}$ | $R'^c$ | $R''^b$ |
| 34-411 | $R^c$ | $R^{5b}$ | $R^{20a}$ | $R^{21a}$ | $R'^c$ | $R''^b$ |
| 34-412 | $R^a$ | $R^{5c}$ | $R^{20a}$ | $R^{21a}$ | $R'^c$ | $R''^b$ |
| 34-413 | $R^b$ | $R^{5c}$ | $R^{20a}$ | $R^{21a}$ | $R'^c$ | $R''^b$ |
| 34-414 | $R^c$ | $R^{5c}$ | $R^{20a}$ | $R^{21a}$ | $R'^c$ | $R''^b$ |
| 34-415 | $R^a$ | $R^{5a}$ | $R^{20b}$ | $R^{21a}$ | $R'^c$ | $R''^b$ |
| 34-416 | $R^b$ | $R^{5a}$ | $R^{20b}$ | $R^{21a}$ | $R'^c$ | $R''^b$ |
| 34-417 | $R^c$ | $R^{5a}$ | $R^{20b}$ | $R^{21a}$ | $R'^c$ | $R''^b$ |
| 34-418 | $R^a$ | $R^{5b}$ | $R^{20b}$ | $R^{21a}$ | $R'^c$ | $R''^b$ |
| 34-419 | $R^b$ | $R^{5b}$ | $R^{20b}$ | $R^{21a}$ | $R'^c$ | $R''^b$ |
| 34-420 | $R^c$ | $R^{5b}$ | $R^{20b}$ | $R^{21a}$ | $R'^c$ | $R''^b$ |
| 34-421 | $R^a$ | $R^{5c}$ | $R^{20b}$ | $R^{21a}$ | $R'^c$ | $R''^b$ |
| 34-422 | $R^b$ | $R^{5c}$ | $R^{20b}$ | $R^{21a}$ | $R'^c$ | $R''^b$ |
| 34-423 | $R^c$ | $R^{5c}$ | $R^{20b}$ | $R^{21a}$ | $R'^c$ | $R''^b$ |
| 34-424 | $R^a$ | $R^{5a}$ | $R^{20c}$ | $R^{21a}$ | $R'^c$ | $R''^b$ |
| 34-425 | $R^b$ | $R^{5a}$ | $R^{20c}$ | $R^{21a}$ | $R'^c$ | $R''^b$ |
| 34-426 | $R^c$ | $R^{5a}$ | $R^{20c}$ | $R^{21a}$ | $R'^c$ | $R''^b$ |
| 34-427 | $R^a$ | $R^{5b}$ | $R^{20c}$ | $R^{21a}$ | $R'^c$ | $R''^b$ |
| 34-428 | $R^b$ | $R^{5b}$ | $R^{20c}$ | $R^{21a}$ | $R'^c$ | $R''^b$ |
| 34-429 | $R^c$ | $R^{5b}$ | $R^{20c}$ | $R^{21a}$ | $R'^c$ | $R''^b$ |
| 34-430 | $R^a$ | $R^{5c}$ | $R^{20c}$ | $R^{21a}$ | $R'^c$ | $R''^b$ |
| 34-431 | $R^b$ | $R^{5c}$ | $R^{20c}$ | $R^{21a}$ | $R'^c$ | $R''^b$ |
| 34-432 | $R^c$ | $R^{5c}$ | $R^{20c}$ | $R^{21a}$ | $R'^c$ | $R''^b$ |
| 34-433 | $R^a$ | $R^{5a}$ | $R^{20a}$ | $R^{21b}$ | $R'^c$ | $R''^b$ |
| 34-434 | $R^b$ | $R^{5a}$ | $R^{20a}$ | $R^{21b}$ | $R'^c$ | $R''^b$ |
| 34-435 | $R^c$ | $R^{5a}$ | $R^{20a}$ | $R^{21b}$ | $R'^c$ | $R''^b$ |
| 34-436 | $R^a$ | $R^{5b}$ | $R^{20a}$ | $R^{21b}$ | $R'^c$ | $R''^b$ |
| 34-437 | $R^b$ | $R^{5b}$ | $R^{20a}$ | $R^{21b}$ | $R'^c$ | $R''^b$ |
| 34-438 | $R^c$ | $R^{5b}$ | $R^{20a}$ | $R^{21b}$ | $R'^c$ | $R''^b$ |
| 34-439 | $R^a$ | $R^{5c}$ | $R^{20a}$ | $R^{21b}$ | $R'^c$ | $R''^b$ |
| 34-440 | $R^b$ | $R^{5c}$ | $R^{20a}$ | $R^{21b}$ | $R'^c$ | $R''^b$ |
| 34-441 | $R^c$ | $R^{5c}$ | $R^{20a}$ | $R^{21b}$ | $R'^c$ | $R''^b$ |
| 34-442 | $R^a$ | $R^{5a}$ | $R^{20b}$ | $R^{21b}$ | $R'^c$ | $R''^b$ |
| 34-443 | $R^b$ | $R^{5a}$ | $R^{20b}$ | $R^{21b}$ | $R'^c$ | $R''^b$ |
| 34-444 | $R^c$ | $R^{5a}$ | $R^{20b}$ | $R^{21b}$ | $R'^c$ | $R''^b$ |
| 34-445 | $R^a$ | $R^{5b}$ | $R^{20b}$ | $R^{21b}$ | $R'^c$ | $R''^b$ |
| 34-446 | $R^b$ | $R^{5b}$ | $R^{20b}$ | $R^{21b}$ | $R'^c$ | $R''^b$ |
| 34-447 | $R^c$ | $R^{5b}$ | $R^{20b}$ | $R^{21b}$ | $R'^c$ | $R''^b$ |
| 34-448 | $R^a$ | $R^{5c}$ | $R^{20b}$ | $R^{21b}$ | $R'^c$ | $R''^b$ |
| 34-449 | $R^b$ | $R^{5c}$ | $R^{20b}$ | $R^{21b}$ | $R'^c$ | $R''^b$ |
| 34-450 | $R^c$ | $R^{5c}$ | $R^{20b}$ | $R^{21b}$ | $R'^c$ | $R''^b$ |
| 34-451 | $R^a$ | $R^{5a}$ | $R^{20c}$ | $R^{21b}$ | $R'^c$ | $R''^b$ |
| 34-452 | $R^b$ | $R^{5a}$ | $R^{20c}$ | $R^{21b}$ | $R'^c$ | $R''^b$ |
| 34-453 | $R^c$ | $R^{5a}$ | $R^{20c}$ | $R^{21b}$ | $R'^c$ | $R''^b$ |
| 34-454 | $R^a$ | $R^{5b}$ | $R^{20c}$ | $R^{21b}$ | $R'^c$ | $R''^b$ |
| 34-455 | $R^b$ | $R^{5b}$ | $R^{20c}$ | $R^{21b}$ | $R'^c$ | $R''^b$ |
| 34-456 | $R^c$ | $R^{5b}$ | $R^{20c}$ | $R^{21b}$ | $R'^c$ | $R''^b$ |
| 34-457 | $R^a$ | $R^{5c}$ | $R^{20c}$ | $R^{21b}$ | $R'^c$ | $R''^b$ |
| 34-458 | $R^b$ | $R^{5c}$ | $R^{20c}$ | $R^{21b}$ | $R'^c$ | $R''^b$ |
| 34-459 | $R^c$ | $R^{5c}$ | $R^{20c}$ | $R^{21b}$ | $R'^c$ | $R''^b$ |
| 34-460 | $R^a$ | $R^{5a}$ | $R^{20a}$ | $R^{21c}$ | $R'^c$ | $R''^b$ |
| 34-461 | $R^b$ | $R^{5a}$ | $R^{20a}$ | $R^{21c}$ | $R'^c$ | $R''^b$ |
| 34-462 | $R^c$ | $R^{5a}$ | $R^{20a}$ | $R^{21c}$ | $R'^c$ | $R''^b$ |
| 34-463 | $R^a$ | $R^{5b}$ | $R^{20a}$ | $R^{21c}$ | $R'^c$ | $R''^b$ |
| 34-464 | $R^b$ | $R^{5b}$ | $R^{20a}$ | $R^{21c}$ | $R'^c$ | $R''^b$ |
| 34-465 | $R^c$ | $R^{5b}$ | $R^{20a}$ | $R^{21c}$ | $R'^c$ | $R''^b$ |
| 34-466 | $R^a$ | $R^{5c}$ | $R^{20a}$ | $R^{21c}$ | $R'^c$ | $R''^b$ |
| 34-467 | $R^b$ | $R^{5c}$ | $R^{20a}$ | $R^{21c}$ | $R'^c$ | $R''^b$ |
| 34-468 | $R^c$ | $R^{5c}$ | $R^{20a}$ | $R^{21c}$ | $R'^c$ | $R''^b$ |
| 34-469 | $R^a$ | $R^{5a}$ | $R^{20b}$ | $R^{21c}$ | $R'^c$ | $R''^b$ |
| 34-470 | $R^b$ | $R^{5a}$ | $R^{20b}$ | $R^{21c}$ | $R'^c$ | $R''^b$ |
| 34-471 | $R^c$ | $R^{5a}$ | $R^{20b}$ | $R^{21c}$ | $R'^c$ | $R''^b$ |
| 34-472 | $R^a$ | $R^{5b}$ | $R^{20b}$ | $R^{21c}$ | $R'^c$ | $R''^b$ |
| 34-473 | $R^b$ | $R^{5b}$ | $R^{20b}$ | $R^{21c}$ | $R'^c$ | $R''^b$ |
| 34-474 | $R^c$ | $R^{5b}$ | $R^{20b}$ | $R^{21c}$ | $R'^c$ | $R''^b$ |
| 34-475 | $R^a$ | $R^{5c}$ | $R^{20b}$ | $R^{21c}$ | $R'^c$ | $R''^b$ |
| 34-476 | $R^b$ | $R^{5c}$ | $R^{20b}$ | $R^{21c}$ | $R'^c$ | $R''^b$ |
| 34-477 | $R^c$ | $R^{5c}$ | $R^{20b}$ | $R^{21c}$ | $R'^c$ | $R''^b$ |
| 34-478 | $R^a$ | $R^{5a}$ | $R^{20c}$ | $R^{21c}$ | $R'^c$ | $R''^b$ |
| 34-479 | $R^b$ | $R^{5a}$ | $R^{20c}$ | $R^{21c}$ | $R'^c$ | $R''^b$ |
| 34-480 | $R^c$ | $R^{5a}$ | $R^{20c}$ | $R^{21c}$ | $R'^c$ | $R''^b$ |
| 34-481 | $R^a$ | $R^{5b}$ | $R^{20c}$ | $R^{21c}$ | $R'^c$ | $R''^b$ |
| 34-482 | $R^b$ | $R^{5b}$ | $R^{20c}$ | $R^{21c}$ | $R'^c$ | $R''^b$ |
| 34-483 | $R^c$ | $R^{5b}$ | $R^{20c}$ | $R^{21c}$ | $R'^c$ | $R''^b$ |
| 34-484 | $R^a$ | $R^{5c}$ | $R^{20c}$ | $R^{21c}$ | $R'^c$ | $R''^b$ |
| 34-485 | $R^b$ | $R^{5c}$ | $R^{20c}$ | $R^{21c}$ | $R'^c$ | $R''^b$ |
| 34-486 | $R^c$ | $R^{5c}$ | $R^{20c}$ | $R^{21c}$ | $R'^c$ | $R''^b$ |
| 34-487 | $R^a$ | $R^{5a}$ | $R^{20a}$ | $R^{21a}$ | $R'^a$ | $R''^c$ |
| 34-488 | $R^b$ | $R^{5a}$ | $R^{20a}$ | $R^{21a}$ | $R'^a$ | $R''^c$ |
| 34-489 | $R^c$ | $R^{5a}$ | $R^{20a}$ | $R^{21a}$ | $R'^a$ | $R''^c$ |
| 34-490 | $R^a$ | $R^{5b}$ | $R^{20a}$ | $R^{21a}$ | $R'^a$ | $R''^c$ |
| 34-491 | $R^b$ | $R^{5b}$ | $R^{20a}$ | $R^{21a}$ | $R'^a$ | $R''^c$ |
| 34-492 | $R^c$ | $R^{5b}$ | $R^{20a}$ | $R^{21a}$ | $R'^a$ | $R''^c$ |
| 34-493 | $R^a$ | $R^{5c}$ | $R^{20a}$ | $R^{21a}$ | $R'^a$ | $R''^c$ |
| 34-494 | $R^b$ | $R^{5c}$ | $R^{20a}$ | $R^{21a}$ | $R'^a$ | $R''^c$ |
| 34-495 | $R^c$ | $R^{5c}$ | $R^{20a}$ | $R^{21a}$ | $R'^a$ | $R''^c$ |
| 34-496 | $R^a$ | $R^{5a}$ | $R^{20b}$ | $R^{21a}$ | $R'^a$ | $R''^c$ |
| 34-497 | $R^b$ | $R^{5a}$ | $R^{20b}$ | $R^{21a}$ | $R'^a$ | $R''^c$ |
| 34-498 | $R^c$ | $R^{5a}$ | $R^{20b}$ | $R^{21a}$ | $R'^a$ | $R''^c$ |
| 34-499 | $R^a$ | $R^{5b}$ | $R^{20b}$ | $R^{21a}$ | $R'^a$ | $R''^c$ |
| 34-500 | $R^b$ | $R^{5b}$ | $R^{20b}$ | $R^{21a}$ | $R'^a$ | $R''^c$ |
| 34-501 | $R^c$ | $R^{5b}$ | $R^{20b}$ | $R^{21a}$ | $R'^a$ | $R''^c$ |
| 34-502 | $R^a$ | $R^{5c}$ | $R^{20b}$ | $R^{21a}$ | $R'^a$ | $R''^c$ |
| 34-503 | $R^b$ | $R^{5c}$ | $R^{20b}$ | $R^{21a}$ | $R'^a$ | $R''^c$ |
| 34-504 | $R^c$ | $R^{5c}$ | $R^{20b}$ | $R^{21a}$ | $R'^a$ | $R''^c$ |
| 34-505 | $R^a$ | $R^{5a}$ | $R^{20c}$ | $R^{21a}$ | $R'^a$ | $R''^c$ |
| 34-506 | $R^b$ | $R^{5a}$ | $R^{20c}$ | $R^{21a}$ | $R'^a$ | $R''^c$ |
| 34-507 | $R^c$ | $R^{5a}$ | $R^{20c}$ | $R^{21a}$ | $R'^a$ | $R''^c$ |

-continued

| Formula | R | $R^5$ | $R^{20}$ | $R^{21}$ | R' | R" |
|---|---|---|---|---|---|---|
| 34-508 | $R^a$ | $R^{5b}$ | $R^{20c}$ | $R^{21a}$ | $R'^a$ | $R''^c$ |
| 34-509 | $R^b$ | $R^{5b}$ | $R^{20c}$ | $R^{21a}$ | $R'^a$ | $R''^c$ |
| 34-510 | $R^c$ | $R^{5b}$ | $R^{20c}$ | $R^{21a}$ | $R'^a$ | $R''^c$ |
| 34-511 | $R^a$ | $R^{5c}$ | $R^{20c}$ | $R^{21a}$ | $R'^a$ | $R''^c$ |
| 34-512 | $R^b$ | $R^{5c}$ | $R^{20c}$ | $R^{21a}$ | $R'^a$ | $R''^c$ |
| 34-513 | $R^c$ | $R^{5c}$ | $R^{20c}$ | $R^{21a}$ | $R'^a$ | $R''^c$ |
| 34-514 | $R^a$ | $R^{5a}$ | $R^{20a}$ | $R^{21b}$ | $R'^a$ | $R''^c$ |
| 34-515 | $R^b$ | $R^{5a}$ | $R^{20a}$ | $R^{21b}$ | $R'^a$ | $R''^c$ |
| 34-516 | $R^c$ | $R^{5a}$ | $R^{20a}$ | $R^{21b}$ | $R'^a$ | $R''^c$ |
| 34-517 | $R^a$ | $R^{5b}$ | $R^{20a}$ | $R^{21b}$ | $R'^a$ | $R''^c$ |
| 34-518 | $R^b$ | $R^{5b}$ | $R^{20a}$ | $R^{21b}$ | $R'^a$ | $R''^c$ |
| 34-519 | $R^c$ | $R^{5b}$ | $R^{20a}$ | $R^{21b}$ | $R'^a$ | $R''^c$ |
| 34-520 | $R^a$ | $R^{5c}$ | $R^{20a}$ | $R^{21b}$ | $R'^a$ | $R''^c$ |
| 34-521 | $R^b$ | $R^{5c}$ | $R^{20a}$ | $R^{21b}$ | $R'^a$ | $R''^c$ |
| 34-522 | $R^c$ | $R^{5c}$ | $R^{20a}$ | $R^{21b}$ | $R'^a$ | $R''^c$ |
| 34-523 | $R^a$ | $R^{5a}$ | $R^{20b}$ | $R^{21b}$ | $R'^a$ | $R''^c$ |
| 34-524 | $R^b$ | $R^{5a}$ | $R^{20b}$ | $R^{21b}$ | $R'^a$ | $R''^c$ |
| 34-525 | $R^c$ | $R^{5a}$ | $R^{20b}$ | $R^{21b}$ | $R'^a$ | $R''^c$ |
| 34-526 | $R^a$ | $R^{5b}$ | $R^{20b}$ | $R^{21b}$ | $R'^a$ | $R''^c$ |
| 34-527 | $R^b$ | $R^{5b}$ | $R^{20b}$ | $R^{21b}$ | $R'^a$ | $R''^c$ |
| 34-528 | $R^c$ | $R^{5b}$ | $R^{20b}$ | $R^{21b}$ | $R'^a$ | $R''^c$ |
| 34-529 | $R^a$ | $R^{5c}$ | $R^{20b}$ | $R^{21b}$ | $R'^a$ | $R''^c$ |
| 34-530 | $R^b$ | $R^{5c}$ | $R^{20b}$ | $R^{21b}$ | $R'^a$ | $R''^c$ |
| 34-531 | $R^c$ | $R^{5c}$ | $R^{20b}$ | $R^{21b}$ | $R'^a$ | $R''^c$ |
| 34-532 | $R^a$ | $R^{5a}$ | $R^{20c}$ | $R^{21b}$ | $R'^a$ | $R''^c$ |
| 34-533 | $R^b$ | $R^{5a}$ | $R^{20c}$ | $R^{21b}$ | $R'^a$ | $R''^c$ |
| 34-534 | $R^c$ | $R^{5a}$ | $R^{20c}$ | $R^{21b}$ | $R'^a$ | $R''^c$ |
| 34-535 | $R^a$ | $R^{5b}$ | $R^{20c}$ | $R^{21b}$ | $R'^a$ | $R''^c$ |
| 34-536 | $R^b$ | $R^{5b}$ | $R^{20c}$ | $R^{21b}$ | $R'^a$ | $R''^c$ |
| 34-537 | $R^c$ | $R^{5b}$ | $R^{20c}$ | $R^{21b}$ | $R'^a$ | $R''^c$ |
| 34-538 | $R^a$ | $R^{5c}$ | $R^{20c}$ | $R^{21b}$ | $R'^a$ | $R''^c$ |
| 34-539 | $R^b$ | $R^{5c}$ | $R^{20c}$ | $R^{21b}$ | $R'^a$ | $R''^c$ |
| 34-540 | $R^c$ | $R^{5c}$ | $R^{20c}$ | $R^{21b}$ | $R'^a$ | $R''^c$ |
| 34-541 | $R^a$ | $R^{5a}$ | $R^{20a}$ | $R^{21c}$ | $R'^a$ | $R''^c$ |
| 34-542 | $R^b$ | $R^{5a}$ | $R^{20a}$ | $R^{21c}$ | $R'^a$ | $R''^c$ |
| 34-543 | $R^c$ | $R^{5a}$ | $R^{20a}$ | $R^{21c}$ | $R'^a$ | $R''^c$ |
| 34-544 | $R^a$ | $R^{5b}$ | $R^{20a}$ | $R^{21c}$ | $R'^a$ | $R''^c$ |
| 34-545 | $R^b$ | $R^{5b}$ | $R^{20a}$ | $R^{21c}$ | $R'^a$ | $R''^c$ |
| 34-546 | $R^c$ | $R^{5b}$ | $R^{20a}$ | $R^{21c}$ | $R'^a$ | $R''^c$ |
| 34-547 | $R^a$ | $R^{5c}$ | $R^{20a}$ | $R^{21c}$ | $R'^a$ | $R''^c$ |
| 34-548 | $R^b$ | $R^{5c}$ | $R^{20a}$ | $R^{21c}$ | $R'^a$ | $R''^c$ |
| 34-549 | $R^c$ | $R^{5c}$ | $R^{20a}$ | $R^{21c}$ | $R'^a$ | $R''^c$ |
| 34-550 | $R^a$ | $R^{5a}$ | $R^{20b}$ | $R^{21c}$ | $R'^a$ | $R''^c$ |
| 34-551 | $R^b$ | $R^{5a}$ | $R^{20b}$ | $R^{21c}$ | $R'^a$ | $R''^c$ |
| 34-552 | $R^c$ | $R^{5a}$ | $R^{20b}$ | $R^{21c}$ | $R'^a$ | $R''^c$ |
| 34-553 | $R^a$ | $R^{5b}$ | $R^{20b}$ | $R^{21c}$ | $R'^a$ | $R''^c$ |
| 34-554 | $R^b$ | $R^{5b}$ | $R^{20b}$ | $R^{21c}$ | $R'^a$ | $R''^c$ |
| 34-555 | $R^c$ | $R^{5b}$ | $R^{20b}$ | $R^{21c}$ | $R'^a$ | $R''^c$ |
| 34-556 | $R^a$ | $R^{5c}$ | $R^{20b}$ | $R^{21c}$ | $R'^a$ | $R''^c$ |
| 34-557 | $R^b$ | $R^{5c}$ | $R^{20b}$ | $R^{21c}$ | $R'^a$ | $R''^c$ |
| 34-558 | $R^c$ | $R^{5c}$ | $R^{20b}$ | $R^{21c}$ | $R'^a$ | $R''^c$ |
| 34-559 | $R^a$ | $R^{5a}$ | $R^{20c}$ | $R^{21c}$ | $R'^a$ | $R''^c$ |
| 34-560 | $R^b$ | $R^{5a}$ | $R^{20c}$ | $R^{21c}$ | $R'^a$ | $R''^c$ |
| 34-561 | $R^c$ | $R^{5a}$ | $R^{20c}$ | $R^{21c}$ | $R'^a$ | $R''^c$ |
| 34-562 | $R^a$ | $R^{5b}$ | $R^{20c}$ | $R^{21c}$ | $R'^a$ | $R''^c$ |
| 34-563 | $R^b$ | $R^{5b}$ | $R^{20c}$ | $R^{21c}$ | $R'^a$ | $R''^c$ |
| 34-564 | $R^c$ | $R^{5b}$ | $R^{20c}$ | $R^{21c}$ | $R'^a$ | $R''^c$ |
| 34-565 | $R^a$ | $R^{5c}$ | $R^{20c}$ | $R^{21c}$ | $R'^a$ | $R''^c$ |
| 34-566 | $R^b$ | $R^{5c}$ | $R^{20c}$ | $R^{21c}$ | $R'^a$ | $R''^c$ |
| 34-567 | $R^c$ | $R^{5c}$ | $R^{20c}$ | $R^{21c}$ | $R'^a$ | $R''^c$ |
| 34-568 | $R^a$ | $R^{5a}$ | $R^{20a}$ | $R^{21a}$ | $R'^b$ | $R''^c$ |
| 34-569 | $R^b$ | $R^{5a}$ | $R^{20a}$ | $R^{21a}$ | $R'^b$ | $R''^c$ |
| 34-570 | $R^c$ | $R^{5a}$ | $R^{20a}$ | $R^{21a}$ | $R'^b$ | $R''^c$ |
| 34-571 | $R^a$ | $R^{5b}$ | $R^{20a}$ | $R^{21a}$ | $R'^b$ | $R''^c$ |
| 34-572 | $R^b$ | $R^{5b}$ | $R^{20a}$ | $R^{21a}$ | $R'^b$ | $R''^c$ |
| 34-573 | $R^c$ | $R^{5b}$ | $R^{20a}$ | $R^{21a}$ | $R'^b$ | $R''^c$ |
| 34-574 | $R^a$ | $R^{5c}$ | $R^{20a}$ | $R^{21a}$ | $R'^b$ | $R''^c$ |
| 34-575 | $R^b$ | $R^{5c}$ | $R^{20a}$ | $R^{21a}$ | $R'^b$ | $R''^c$ |
| 34-576 | $R^c$ | $R^{5c}$ | $R^{20a}$ | $R^{21a}$ | $R'^b$ | $R''^c$ |
| 34-577 | $R^a$ | $R^{5a}$ | $R^{20b}$ | $R^{21a}$ | $R'^b$ | $R''^c$ |
| 34-578 | $R^b$ | $R^{5a}$ | $R^{20b}$ | $R^{21a}$ | $R'^b$ | $R''^c$ |
| 34-579 | $R^c$ | $R^{5a}$ | $R^{20b}$ | $R^{21a}$ | $R'^b$ | $R''^c$ |
| 34-580 | $R^a$ | $R^{5b}$ | $R^{20b}$ | $R^{21a}$ | $R'^b$ | $R''^c$ |
| 34-581 | $R^b$ | $R^{5b}$ | $R^{20b}$ | $R^{21a}$ | $R'^b$ | $R''^c$ |
| 34-582 | $R^c$ | $R^{5b}$ | $R^{20b}$ | $R^{21a}$ | $R'^b$ | $R''^c$ |
| 34-583 | $R^a$ | $R^{5c}$ | $R^{20b}$ | $R^{21a}$ | $R'^b$ | $R''^c$ |
| 34-584 | $R^b$ | $R^{5c}$ | $R^{20b}$ | $R^{21a}$ | $R'^b$ | $R''^c$ |
| 34-585 | $R^c$ | $R^{5c}$ | $R^{20b}$ | $R^{21a}$ | $R'^b$ | $R''^c$ |
| 34-586 | $R^a$ | $R^{5a}$ | $R^{20c}$ | $R^{21a}$ | $R'^b$ | $R''^c$ |
| 34-587 | $R^b$ | $R^{5a}$ | $R^{20c}$ | $R^{21a}$ | $R'^b$ | $R''^c$ |
| 34-588 | $R^c$ | $R^{5a}$ | $R^{20c}$ | $R^{21a}$ | $R'^b$ | $R''^c$ |
| 34-589 | $R^a$ | $R^{5b}$ | $R^{20c}$ | $R^{21a}$ | $R'^b$ | $R''^c$ |
| 34-590 | $R^b$ | $R^{5b}$ | $R^{20c}$ | $R^{21a}$ | $R'^b$ | $R''^c$ |
| 34-591 | $R^c$ | $R^{5b}$ | $R^{20c}$ | $R^{21a}$ | $R'^b$ | $R''^c$ |
| 34-592 | $R^a$ | $R^{5c}$ | $R^{20c}$ | $R^{21a}$ | $R'^b$ | $R''^c$ |
| 34-593 | $R^b$ | $R^{5c}$ | $R^{20c}$ | $R^{21a}$ | $R'^b$ | $R''^c$ |
| 34-594 | $R^c$ | $R^{5c}$ | $R^{20c}$ | $R^{21a}$ | $R'^b$ | $R''^c$ |
| 34-595 | $R^a$ | $R^{5a}$ | $R^{20a}$ | $R^{21b}$ | $R'^b$ | $R''^c$ |
| 34-596 | $R^b$ | $R^{5a}$ | $R^{20a}$ | $R^{21b}$ | $R'^b$ | $R''^c$ |
| 34-597 | $R^c$ | $R^{5a}$ | $R^{20a}$ | $R^{21b}$ | $R'^b$ | $R''^c$ |
| 34-598 | $R^a$ | $R^{5b}$ | $R^{20a}$ | $R^{21b}$ | $R'^b$ | $R''^c$ |
| 34-599 | $R^b$ | $R^{5b}$ | $R^{20a}$ | $R^{21b}$ | $R'^b$ | $R''^c$ |
| 34-600 | $R^c$ | $R^{5b}$ | $R^{20a}$ | $R^{21b}$ | $R'^b$ | $R''^c$ |
| 34-601 | $R^a$ | $R^{5c}$ | $R^{20a}$ | $R^{21b}$ | $R'^b$ | $R''^c$ |
| 34-602 | $R^b$ | $R^{5c}$ | $R^{20a}$ | $R^{21b}$ | $R'^b$ | $R''^c$ |
| 34-603 | $R^c$ | $R^{5c}$ | $R^{20a}$ | $R^{21b}$ | $R'^b$ | $R''^c$ |
| 34-604 | $R^a$ | $R^{5a}$ | $R^{20b}$ | $R^{21b}$ | $R'^b$ | $R''^c$ |
| 34-605 | $R^b$ | $R^{5a}$ | $R^{20b}$ | $R^{21b}$ | $R'^b$ | $R''^c$ |
| 34-606 | $R^c$ | $R^{5a}$ | $R^{20b}$ | $R^{21b}$ | $R'^b$ | $R''^c$ |
| 34-607 | $R^a$ | $R^{5b}$ | $R^{20b}$ | $R^{21b}$ | $R'^b$ | $R''^c$ |
| 34-608 | $R^b$ | $R^{5b}$ | $R^{20b}$ | $R^{21b}$ | $R'^b$ | $R''^c$ |
| 34-609 | $R^c$ | $R^{5b}$ | $R^{20b}$ | $R^{21b}$ | $R'^b$ | $R''^c$ |
| 34-610 | $R^a$ | $R^{5c}$ | $R^{20b}$ | $R^{21b}$ | $R'^b$ | $R''^c$ |
| 34-611 | $R^b$ | $R^{5c}$ | $R^{20b}$ | $R^{21b}$ | $R'^b$ | $R''^c$ |
| 34-612 | $R^c$ | $R^{5c}$ | $R^{20b}$ | $R^{21b}$ | $R'^b$ | $R''^c$ |
| 34-613 | $R^a$ | $R^{5a}$ | $R^{20c}$ | $R^{21b}$ | $R'^b$ | $R''^c$ |
| 34-614 | $R^b$ | $R^{5a}$ | $R^{20c}$ | $R^{21b}$ | $R'^b$ | $R''^c$ |
| 34-615 | $R^c$ | $R^{5a}$ | $R^{20c}$ | $R^{21b}$ | $R'^b$ | $R''^c$ |
| 34-616 | $R^a$ | $R^{5b}$ | $R^{20c}$ | $R^{21b}$ | $R'^b$ | $R''^c$ |
| 34-617 | $R^b$ | $R^{5b}$ | $R^{20c}$ | $R^{21b}$ | $R'^b$ | $R''^c$ |
| 34-618 | $R^c$ | $R^{5b}$ | $R^{20c}$ | $R^{21b}$ | $R'^b$ | $R''^c$ |
| 34-619 | $R^a$ | $R^{5c}$ | $R^{20c}$ | $R^{21b}$ | $R'^b$ | $R''^c$ |
| 34-620 | $R^b$ | $R^{5c}$ | $R^{20c}$ | $R^{21b}$ | $R'^b$ | $R''^c$ |
| 34-621 | $R^c$ | $R^{5c}$ | $R^{20c}$ | $R^{21b}$ | $R'^b$ | $R''^c$ |
| 34-622 | $R^a$ | $R^{5a}$ | $R^{20a}$ | $R^{21c}$ | $R'^b$ | $R''^c$ |
| 34-623 | $R^b$ | $R^{5a}$ | $R^{20a}$ | $R^{21c}$ | $R'^b$ | $R''^c$ |
| 34-624 | $R^c$ | $R^{5a}$ | $R^{20a}$ | $R^{21c}$ | $R'^b$ | $R''^c$ |
| 34-625 | $R^a$ | $R^{5b}$ | $R^{20a}$ | $R^{21c}$ | $R'^b$ | $R''^c$ |
| 34-626 | $R^b$ | $R^{5b}$ | $R^{20a}$ | $R^{21c}$ | $R'^b$ | $R''^c$ |
| 34-627 | $R^c$ | $R^{5b}$ | $R^{20a}$ | $R^{21c}$ | $R'^b$ | $R''^c$ |
| 34-628 | $R^a$ | $R^{5c}$ | $R^{20a}$ | $R^{21c}$ | $R'^b$ | $R''^c$ |
| 34-629 | $R^b$ | $R^{5c}$ | $R^{20a}$ | $R^{21c}$ | $R'^b$ | $R''^c$ |
| 34-630 | $R^c$ | $R^{5c}$ | $R^{20a}$ | $R^{21c}$ | $R'^b$ | $R''^c$ |
| 34-631 | $R^a$ | $R^{5a}$ | $R^{20b}$ | $R^{21c}$ | $R'^b$ | $R''^c$ |
| 34-632 | $R^b$ | $R^{5a}$ | $R^{20b}$ | $R^{21c}$ | $R'^b$ | $R''^c$ |
| 34-633 | $R^c$ | $R^{5a}$ | $R^{20b}$ | $R^{21c}$ | $R'^b$ | $R''^c$ |
| 34-634 | $R^a$ | $R^{5b}$ | $R^{20b}$ | $R^{21c}$ | $R'^b$ | $R''^c$ |
| 34-635 | $R^b$ | $R^{5b}$ | $R^{20b}$ | $R^{21c}$ | $R'^b$ | $R''^c$ |
| 34-636 | $R^c$ | $R^{5b}$ | $R^{20b}$ | $R^{21c}$ | $R'^b$ | $R''^c$ |
| 34-637 | $R^a$ | $R^{5c}$ | $R^{20b}$ | $R^{21c}$ | $R'^b$ | $R''^c$ |
| 34-638 | $R^b$ | $R^{5c}$ | $R^{20b}$ | $R^{21c}$ | $R'^b$ | $R''^c$ |
| 34-639 | $R^c$ | $R^{5c}$ | $R^{20b}$ | $R^{21c}$ | $R'^b$ | $R''^c$ |
| 34-640 | $R^a$ | $R^{5a}$ | $R^{20c}$ | $R^{21c}$ | $R'^b$ | $R''^c$ |
| 34-641 | $R^b$ | $R^{5a}$ | $R^{20c}$ | $R^{21c}$ | $R'^b$ | $R''^c$ |
| 34-642 | $R^c$ | $R^{5a}$ | $R^{20c}$ | $R^{21c}$ | $R'^b$ | $R''^c$ |
| 34-643 | $R^a$ | $R^{5b}$ | $R^{20c}$ | $R^{21c}$ | $R'^b$ | $R''^c$ |
| 34-644 | $R^b$ | $R^{5b}$ | $R^{20c}$ | $R^{21c}$ | $R'^b$ | $R''^c$ |
| 34-645 | $R^c$ | $R^{5b}$ | $R^{20c}$ | $R^{21c}$ | $R'^b$ | $R''^c$ |
| 34-646 | $R^a$ | $R^{5c}$ | $R^{20c}$ | $R^{21c}$ | $R'^b$ | $R''^c$ |
| 34-647 | $R^b$ | $R^{5c}$ | $R^{20c}$ | $R^{21c}$ | $R'^b$ | $R''^c$ |
| 34-648 | $R^c$ | $R^{5c}$ | $R^{20c}$ | $R^{21c}$ | $R'^b$ | $R''^c$ |
| 34-649 | $R^a$ | $R^{5a}$ | $R^{20a}$ | $R^{21a}$ | $R'^c$ | $R''^c$ |
| 34-650 | $R^b$ | $R^{5a}$ | $R^{20a}$ | $R^{21a}$ | $R'^c$ | $R''^c$ |
| 34-651 | $R^c$ | $R^{5a}$ | $R^{20a}$ | $R^{21a}$ | $R'^c$ | $R''^c$ |
| 34-652 | $R^a$ | $R^{5b}$ | $R^{20a}$ | $R^{21a}$ | $R'^c$ | $R''^c$ |
| 34-653 | $R^b$ | $R^{5b}$ | $R^{20a}$ | $R^{21a}$ | $R'^c$ | $R''^c$ |
| 34-654 | $R^c$ | $R^{5b}$ | $R^{20a}$ | $R^{21a}$ | $R'^c$ | $R''^c$ |
| 34-655 | $R^a$ | $R^{5c}$ | $R^{20a}$ | $R^{21a}$ | $R'^c$ | $R''^c$ |
| 34-656 | $R^b$ | $R^{5c}$ | $R^{20a}$ | $R^{21a}$ | $R'^c$ | $R''^c$ |
| 34-657 | $R^c$ | $R^{5c}$ | $R^{20a}$ | $R^{21a}$ | $R'^c$ | $R''^c$ |
| 34-658 | $R^a$ | $R^{5a}$ | $R^{20b}$ | $R^{21a}$ | $R'^c$ | $R''^c$ |
| 34-659 | $R^b$ | $R^{5a}$ | $R^{20b}$ | $R^{21a}$ | $R'^c$ | $R''^c$ |
| 34-660 | $R^c$ | $R^{5a}$ | $R^{20b}$ | $R^{21a}$ | $R'^c$ | $R''^c$ |
| 34-661 | $R^a$ | $R^{5b}$ | $R^{20b}$ | $R^{21a}$ | $R'^c$ | $R''^c$ |

-continued

| Formula | R | $R^5$ | $R^{20}$ | $R^{21}$ | R' | R" |
|---|---|---|---|---|---|---|
| 34-662 | $R^b$ | $R^{5b}$ | $R^{20b}$ | $R^{21a}$ | $R'^c$ | $R''^c$ |
| 34-663 | $R^c$ | $R^{5b}$ | $R^{20b}$ | $R^{21a}$ | $R'^c$ | $R''^c$ |
| 34-664 | $R^a$ | $R^{5c}$ | $R^{20b}$ | $R^{21a}$ | $R'^c$ | $R''^c$ |
| 34-665 | $R^b$ | $R^{5c}$ | $R^{20b}$ | $R^{21a}$ | $R'^c$ | $R''^c$ |
| 34-666 | $R^c$ | $R^{5c}$ | $R^{20b}$ | $R^{21a}$ | $R'^c$ | $R''^c$ |
| 34-667 | $R^a$ | $R^{5a}$ | $R^{20c}$ | $R^{21a}$ | $R'^c$ | $R''^c$ |
| 34-668 | $R^b$ | $R^{5a}$ | $R^{20c}$ | $R^{21a}$ | $R'^c$ | $R''^c$ |
| 34-669 | $R^c$ | $R^{5a}$ | $R^{20c}$ | $R^{21a}$ | $R'^c$ | $R''^c$ |
| 34-670 | $R^a$ | $R^{5b}$ | $R^{20c}$ | $R^{21a}$ | $R'^c$ | $R''^c$ |
| 34-671 | $R^b$ | $R^{5b}$ | $R^{20c}$ | $R^{21a}$ | $R'^c$ | $R''^c$ |
| 34-672 | $R^c$ | $R^{5b}$ | $R^{20c}$ | $R^{21a}$ | $R'^c$ | $R''^c$ |
| 34-673 | $R^a$ | $R^{5c}$ | $R^{20c}$ | $R^{21a}$ | $R'^c$ | $R''^c$ |
| 34-674 | $R^b$ | $R^{5c}$ | $R^{20c}$ | $R^{21a}$ | $R'^c$ | $R''^c$ |
| 34-675 | $R^c$ | $R^{5c}$ | $R^{20c}$ | $R^{21a}$ | $R'^c$ | $R''^c$ |
| 34-676 | $R^a$ | $R^{5a}$ | $R^{20a}$ | $R^{21b}$ | $R'^c$ | $R''^c$ |
| 34-677 | $R^b$ | $R^{5a}$ | $R^{20a}$ | $R^{21b}$ | $R'^c$ | $R''^c$ |
| 34-678 | $R^c$ | $R^{5a}$ | $R^{20a}$ | $R^{21b}$ | $R'^c$ | $R''^c$ |
| 34-679 | $R^a$ | $R^{5b}$ | $R^{20a}$ | $R^{21b}$ | $R'^c$ | $R''^c$ |
| 34-680 | $R^b$ | $R^{5b}$ | $R^{20a}$ | $R^{21b}$ | $R'^c$ | $R''^c$ |
| 34-681 | $R^c$ | $R^{5b}$ | $R^{20a}$ | $R^{21b}$ | $R'^c$ | $R''^c$ |
| 34-682 | $R^a$ | $R^{5c}$ | $R^{20a}$ | $R^{21b}$ | $R'^c$ | $R''^c$ |
| 34-683 | $R^b$ | $R^{5c}$ | $R^{20a}$ | $R^{21b}$ | $R'^c$ | $R''^c$ |
| 34-684 | $R^c$ | $R^{5c}$ | $R^{20a}$ | $R^{21b}$ | $R'^c$ | $R''^c$ |
| 34-685 | $R^a$ | $R^{5a}$ | $R^{20b}$ | $R^{21b}$ | $R'^c$ | $R''^c$ |
| 34-686 | $R^b$ | $R^{5a}$ | $R^{20b}$ | $R^{21b}$ | $R'^c$ | $R''^c$ |
| 34-687 | $R^c$ | $R^{5a}$ | $R^{20b}$ | $R^{21b}$ | $R'^c$ | $R''^c$ |
| 34-688 | $R^a$ | $R^{5b}$ | $R^{20b}$ | $R^{21b}$ | $R'^c$ | $R''^c$ |
| 34-689 | $R^b$ | $R^{5b}$ | $R^{20b}$ | $R^{21b}$ | $R'^c$ | $R''^c$ |
| 34-690 | $R^c$ | $R^{5b}$ | $R^{20b}$ | $R^{21b}$ | $R'^c$ | $R''^c$ |
| 34-691 | $R^a$ | $R^{5c}$ | $R^{20b}$ | $R^{21b}$ | $R'^c$ | $R''^c$ |
| 34-692 | $R^b$ | $R^{5c}$ | $R^{20b}$ | $R^{21b}$ | $R'^c$ | $R''^c$ |
| 34-693 | $R^c$ | $R^{5c}$ | $R^{20b}$ | $R^{21b}$ | $R'^c$ | $R''^c$ |
| 34-694 | $R^a$ | $R^{5a}$ | $R^{20c}$ | $R^{21b}$ | $R'^c$ | $R''^c$ |
| 34-695 | $R^b$ | $R^{5a}$ | $R^{20c}$ | $R^{21b}$ | $R'^c$ | $R''^c$ |
| 34-696 | $R^c$ | $R^{5a}$ | $R^{20c}$ | $R^{21b}$ | $R'^c$ | $R''^c$ |
| 34-697 | $R^a$ | $R^{5b}$ | $R^{20c}$ | $R^{21b}$ | $R'^c$ | $R''^c$ |
| 34-698 | $R^b$ | $R^{5b}$ | $R^{20c}$ | $R^{21b}$ | $R'^c$ | $R''^c$ |
| 34-699 | $R^c$ | $R^{5b}$ | $R^{20c}$ | $R^{21b}$ | $R'^c$ | $R''^c$ |
| 34-700 | $R^a$ | $R^{5c}$ | $R^{20c}$ | $R^{21b}$ | $R'^c$ | $R''^c$ |
| 34-701 | $R^b$ | $R^{5c}$ | $R^{20c}$ | $R^{21b}$ | $R'^c$ | $R''^c$ |
| 34-702 | $R^c$ | $R^{5c}$ | $R^{20c}$ | $R^{21b}$ | $R'^c$ | $R''^c$ |
| 34-703 | $R^a$ | $R^{5a}$ | $R^{20a}$ | $R^{21c}$ | $R'^c$ | $R''^c$ |
| 34-704 | $R^b$ | $R^{5a}$ | $R^{20a}$ | $R^{21c}$ | $R'^c$ | $R''^c$ |
| 34-705 | $R^c$ | $R^{5a}$ | $R^{20a}$ | $R^{21c}$ | $R'^c$ | $R''^c$ |
| 34-706 | $R^a$ | $R^{5b}$ | $R^{20a}$ | $R^{21c}$ | $R'^c$ | $R''^c$ |
| 34-707 | $R^b$ | $R^{5b}$ | $R^{20a}$ | $R^{21c}$ | $R'^c$ | $R''^c$ |
| 34-708 | $R^c$ | $R^{5b}$ | $R^{20a}$ | $R^{21c}$ | $R'^c$ | $R''^c$ |
| 34-709 | $R^a$ | $R^{5c}$ | $R^{20a}$ | $R^{21c}$ | $R'^c$ | $R''^c$ |
| 34-710 | $R^b$ | $R^{5c}$ | $R^{20a}$ | $R^{21c}$ | $R'^c$ | $R''^c$ |
| 34-711 | $R^c$ | $R^{5c}$ | $R^{20a}$ | $R^{21c}$ | $R'^c$ | $R''^c$ |
| 34-712 | $R^a$ | $R^{5a}$ | $R^{20b}$ | $R^{21c}$ | $R'^c$ | $R''^c$ |
| 34-713 | $R^b$ | $R^{5a}$ | $R^{20b}$ | $R^{21c}$ | $R'^c$ | $R''^c$ |
| 34-714 | $R^c$ | $R^{5a}$ | $R^{20b}$ | $R^{21c}$ | $R'^c$ | $R''^c$ |
| 34-715 | $R^a$ | $R^{5b}$ | $R^{20b}$ | $R^{21c}$ | $R'^c$ | $R''^c$ |
| 34-716 | $R^b$ | $R^{5b}$ | $R^{20b}$ | $R^{21c}$ | $R'^c$ | $R''^c$ |
| 34-717 | $R^c$ | $R^{5b}$ | $R^{20b}$ | $R^{21c}$ | $R'^c$ | $R''^c$ |
| 34-718 | $R^a$ | $R^{5c}$ | $R^{20b}$ | $R^{21c}$ | $R'^c$ | $R''^c$ |
| 34-719 | $R^b$ | $R^{5c}$ | $R^{20b}$ | $R^{21c}$ | $R'^c$ | $R''^c$ |
| 34-720 | $R^c$ | $R^{5c}$ | $R^{20b}$ | $R^{21c}$ | $R'^c$ | $R''^c$ |
| 34-721 | $R^a$ | $R^{5a}$ | $R^{20c}$ | $R^{21c}$ | $R'^c$ | $R''^c$ |
| 34-722 | $R^b$ | $R^{5a}$ | $R^{20c}$ | $R^{21c}$ | $R'^c$ | $R''^c$ |
| 34-723 | $R^c$ | $R^{5a}$ | $R^{20c}$ | $R^{21c}$ | $R'^c$ | $R''^c$ |
| 34-724 | $R^a$ | $R^{5b}$ | $R^{20c}$ | $R^{21c}$ | $R'^c$ | $R''^c$ |
| 34-725 | $R^b$ | $R^{5b}$ | $R^{20c}$ | $R^{21c}$ | $R'^c$ | $R''^c$ |
| 34-726 | $R^c$ | $R^{5b}$ | $R^{20c}$ | $R^{21c}$ | $R'^c$ | $R''^c$ |
| 34-727 | $R^a$ | $R^{5c}$ | $R^{20c}$ | $R^{21c}$ | $R'^c$ | $R''^c$ |
| 34-728 | $R^b$ | $R^{5c}$ | $R^{20c}$ | $R^{21c}$ | $R'^c$ | $R''^c$ |
| 34-729 | $R^c$ | $R^{5c}$ | $R^{20c}$ | $R^{21c}$ | $R'^c$ | $R''^c$ | where all symbols are as defined above.

In one aspect of formula (34) of the present invention, R is hydrogen, a hydroxy group, a halogen, a nitro group, an optionally substituted amino group, an alkyl group, an alkoxy group, an alkenyl group, or an alkoxyalkyl group; $R^5$ is hydrogen, a hydroxy group, a halogen, a nitro group, an optionally substituted amino group, an alkyl group, an alkoxy group, an alkenyl group, or an alkoxyalkyl group; R' and R? independently are hydrogen, a halogen, a nitro group, an amino group, a mono- or di-substituted amino group; a hydroxy group, an alkoxy group, a carboxy group, a cyano group, an oxo(O=) group, a thio(S=) group; an alkyl group, a cycloalkyl group, an alkoxy group, a haloalkoxy group, a cycloalkyl group, an aryl group, or a benzyloxy group; and $R^{20}$ and $R^{21}$ independently are hydrogen, a halogen, a nitro group, an amino group, a mono- or di-substituted amino group, a hydroxy group, an alkoxy group, a carboxy group, a cyano group, an oxo(O=) group, a thio(S=) group; an alkyl group, a cycloalkyl group, an alkoxy group, a haloalkoxy group, a cycloalkyl group, an aryl group, a benzyloxy group, an acyl group, an acyloxy group, an aroyl group, an alkoxycarbonyl group, an aryloxycarbonyl group, a heteroaryl group, a heterocyclyl group, or an aralkyl group.

In another aspect of formula (34) of the present invention, R is hydrogen or an alkyl group; $R^5$ is hydrogen or an alkyl group; R' and R? independently are hydrogen or a halogen; $R^{20}$ is hydrogen or a halogen; and $R^{21}$ is hydrogen or a halogen.

In yet another aspect of formula (34) of the present invention, R is —H, $CH_3$, or $CH_2CH_3$; $R^5$ is —H or $CH_3$; R' and R? independently are —H, —F, or —Cl; $R^{20}$ is —H, —F, —Cl, or —Br; and $R^{21}$ is —H, $CH_3$, or —F. Exemplary compounds include, but are not limited to:

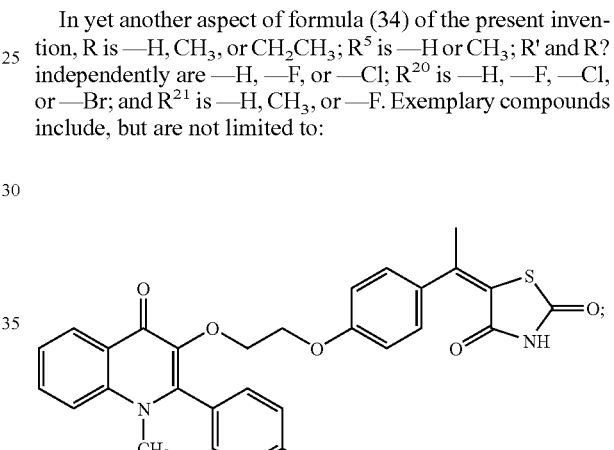

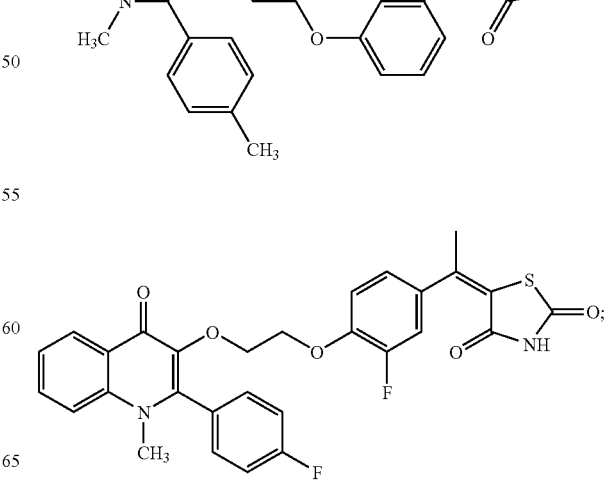

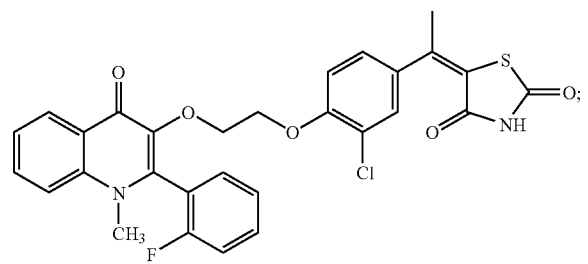
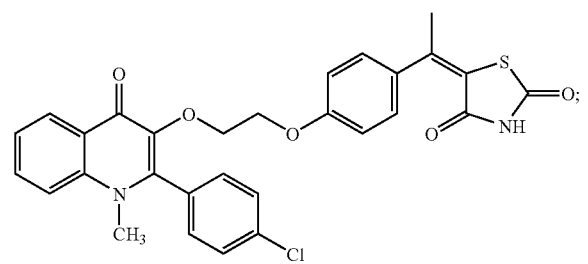
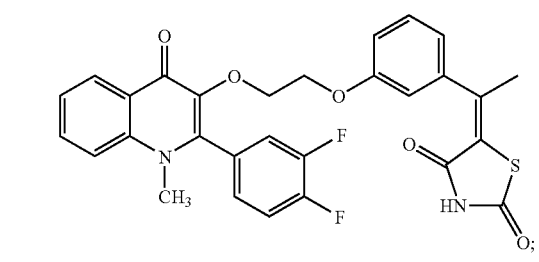
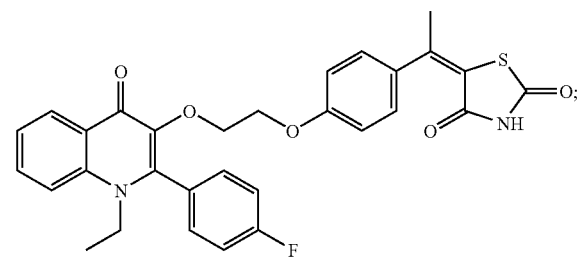
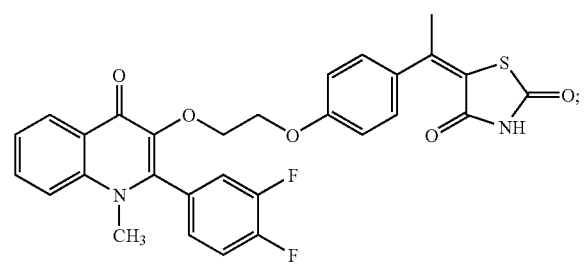
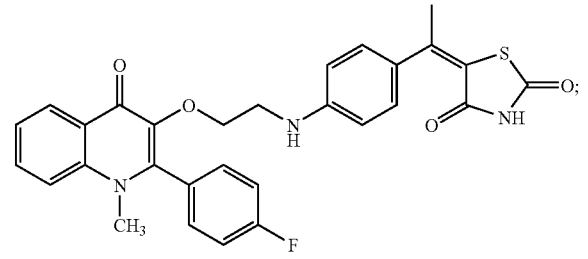
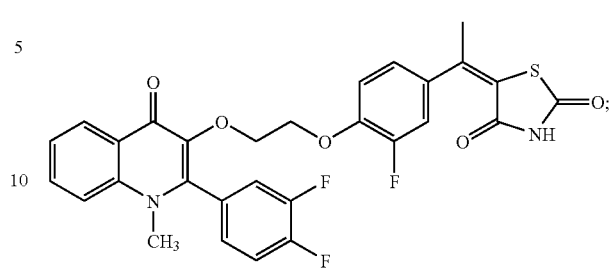
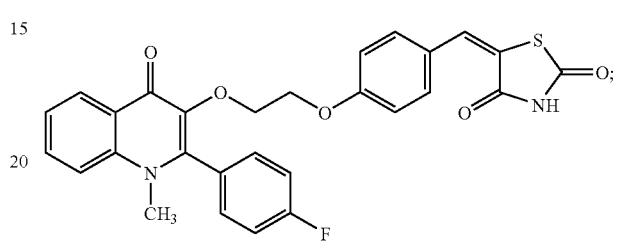

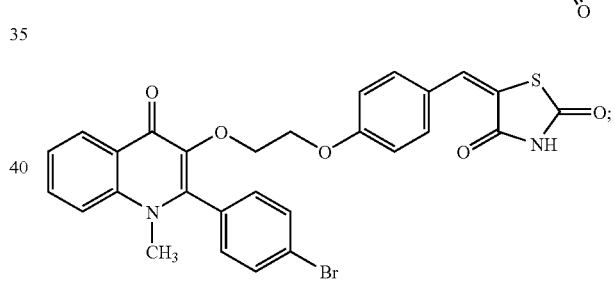
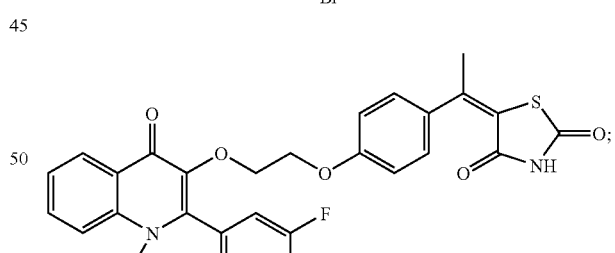
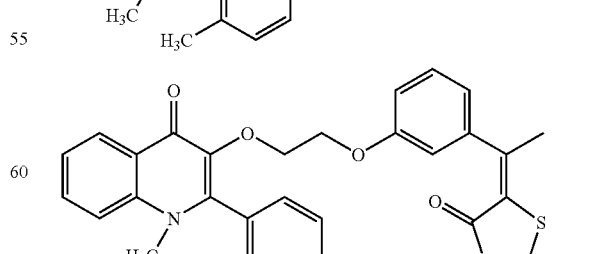
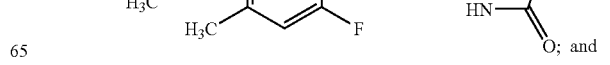

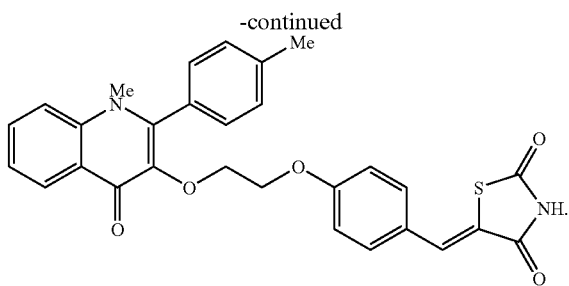

The present invention also contemplates various compounds having the general formula:

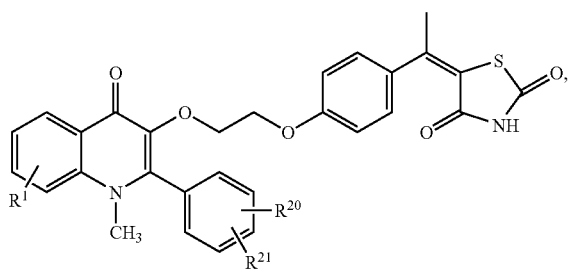

(35)

where all symbols are as defined above in connection with formula (I).

where $R^{20}$ and $R^{21}$ independently are hydrogen, a halogen, a nitro group, an amino group, a mono- or di-substituted amino group, a hydroxy group, an alkoxy group, a carboxy group, a cyano group, an oxo(O=) group, a thio(S=) group, an alkyl group, a cycloalkyl group, an alkoxy group, a haloalkoxy group, a cycloalkyl group, an aryl group, a benzyloxy group, an acyl group, an acyloxy group, an aroyl group, an alkoxycarbonyl group, an aryloxycarbonyl group, a heteroaryl group, a heterocyclyl group, an aralkyl group, an alkylsulfonyl group, an alkylsulfinyl group, an arylsulfonyl group, an arylsulfinyl group, an alkylthio group, an arylthio group, a heteroarylthio group, an aralkylthio group, or a heterocyclyl sulfonyl group, which is optionally substituted with a halogen, a hydroxyl group, a nitro group, an amino group, an alkyloxy group, or any combination thereof, and wherein the heterocycle group is optionally a substituted morpholinyl group, a thiomorpholinyl group, or a piperzinyl group, wherein the substituent on the heterocyclyl group is a halogen, a nitro group, an amino group, an alkyl group, an alkoxy group, or an aryl group; and $R^1$ is defined above.

According to some variations of the present invention, $R^1$, $R^{20}$, and $R^{21}$ of formula (35) are selected to produce various compounds of formula (35-1) to formula (35-27) as follows:

| Formula | $R^1$ | $R^{20}$ | $R^{21}$ |
|---|---|---|---|
| 35-1 | $R^{1a}$ | $R^{20a}$ | $R^{21a}$ |
| 35-2 | $R^{1b}$ | $R^{20a}$ | $R^{21a}$ |
| 35-3 | $R^{1c}$ | $R^{20a}$ | $R^{21a}$ |
| 35-4 | $R^{1a}$ | $R^{20b}$ | $R^{21a}$ |
| 35-5 | $R^{1b}$ | $R^{20b}$ | $R^{21a}$ |
| 35-6 | $R^{1c}$ | $R^{20b}$ | $R^{21a}$ |
| 35-7 | $R^{1a}$ | $R^{20c}$ | $R^{21a}$ |
| 35-8 | $R^{1b}$ | $R^{20c}$ | $R^{21a}$ |
| 35-9 | $R^{1c}$ | $R^{20c}$ | $R^{21a}$ |
| 35-10 | $R^{1a}$ | $R^{20a}$ | $R^{21b}$ |
| 35-11 | $R^{1b}$ | $R^{20a}$ | $R^{21b}$ |
| 35-12 | $R^{1c}$ | $R^{20a}$ | $R^{21b}$ |
| 35-13 | $R^{1a}$ | $R^{20b}$ | $R^{21b}$ |
| 35-14 | $R^{1b}$ | $R^{20b}$ | $R^{21b}$ |
| 35-15 | $R^{1c}$ | $R^{20b}$ | $R^{21b}$ |
| 35-16 | $R^{1a}$ | $R^{20c}$ | $R^{21b}$ |
| 35-17 | $R^{1b}$ | $R^{20c}$ | $R^{21b}$ |
| 35-18 | $R^{1c}$ | $R^{20c}$ | $R^{21b}$ |
| 35-19 | $R^{1a}$ | $R^{20a}$ | $R^{21c}$ |
| 35-20 | $R^{1b}$ | $R^{20a}$ | $R^{21c}$ |
| 35-21 | $R^{1c}$ | $R^{20a}$ | $R^{21c}$ |
| 35-22 | $R^{1a}$ | $R^{20b}$ | $R^{21c}$ |
| 35-23 | $R^{1b}$ | $R^{20b}$ | $R^{21c}$ |
| 35-24 | $R^{1c}$ | $R^{20b}$ | $R^{21c}$ |
| 35-25 | $R^{1a}$ | $R^{20c}$ | $R^{21c}$ |
| 35-26 | $R^{1b}$ | $R^{20c}$ | $R^{21c}$ |
| 35-27 | $R^{1c}$ | $R^{20c}$ | $R^{21c}$ | where all symbols are as defined above.

In one aspect of formula (35) of the present invention, $R^1$ is hydrogen, a hydroxy group, a halogen, a nitro group, a carboxy group, a carbamoyl group, an optionally s substituted amino group, an alkyl group, a cycloalkyl group, an alkoxy group, a cycloalkoxy group, an alkenyl group, a cycloalkenyl group, an alkoxyalkyl group, an alkenyloxy group, or a cycloalkenyloxy group; $R^{20}$ is hydrogen, a halogen, a nitro group, an amino group, a mono- or di-substituted amino group, a hydroxy group, an alkoxy group, a carboxy group, a cyano group, an oxo(O=) group, or a thio(S=) group; and $R^{21}$ is hydrogen, a halogen, a nitro group, an amino group, a mono- or di-substituted amino group, a hydroxy group, an alkoxy group, a carboxy group, a cyano group, an oxo(O=) group, or a thio(S=) group.

In another aspect of formula (35) of of the present invention, $R^1$ is a halogen, $R^{20}$ is hydrogen or a halogen, and $R^{21}$ is hydrogen or a halogen.

In yet another aspect of of formula (35) of the present invention, $R^1$ is Cl or F, $R^{20}$ is —H or —F, and $R^{21}$ is —F.

Exemplary compounds of formula (35) include, but are not limited to:

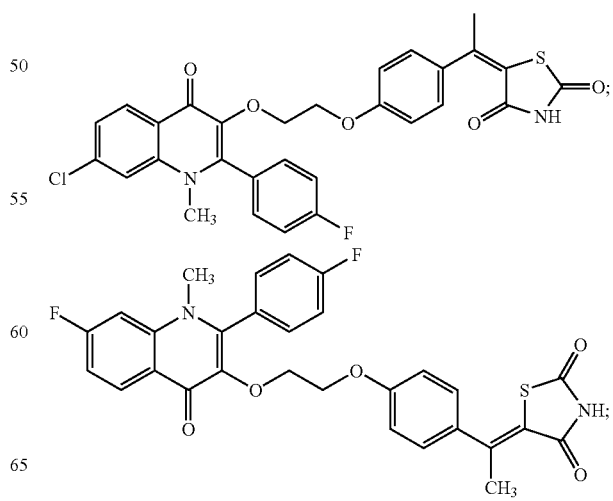

-continued

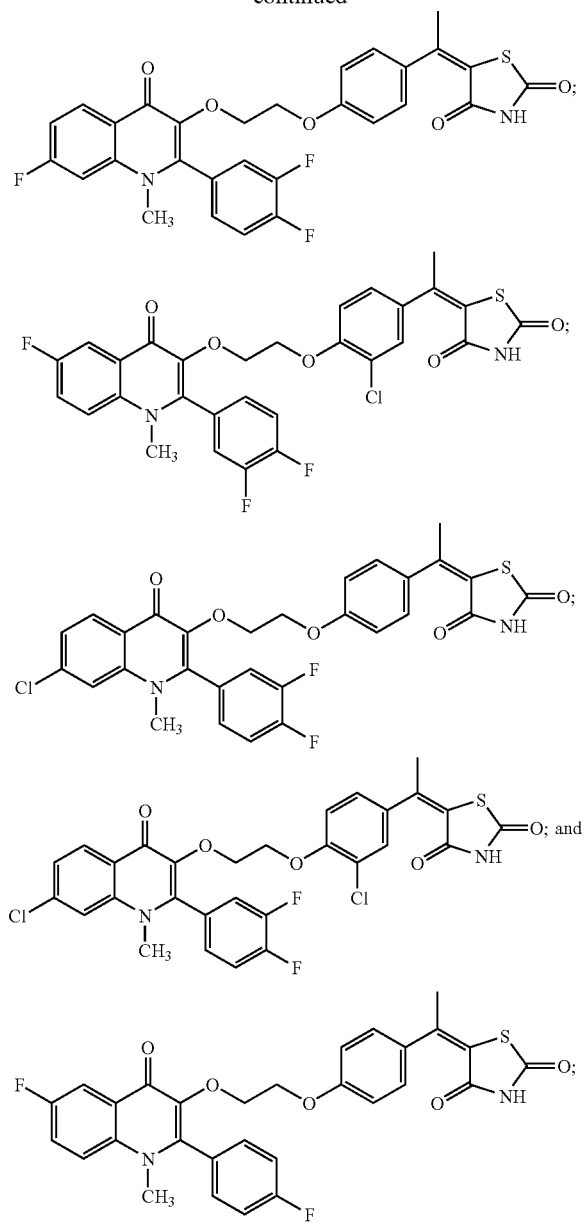

The present invention further contemplates various compounds having the general formula:

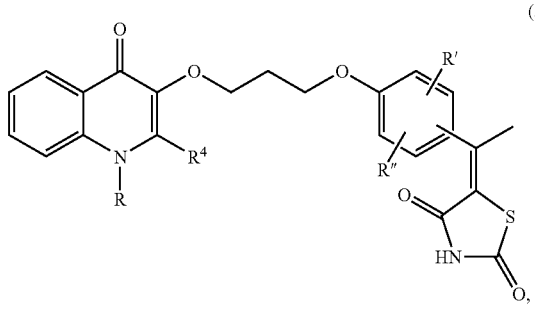
(36)

where all symbols are as defined above in connection with formula (I).

According to some variations of the present invention, R, $R^4$, R' and R" of formula (36) are selected to produce compounds of formula (36-1) through formula (36-81) as follows:

| Formula | R | $R^4$ | R' | R" |
|---|---|---|---|---|
| 36-1 | $R^a$ | $R^{4a}$ | $R'^a$ | $R''^a$ |
| 36-2 | $R^b$ | $R^{4a}$ | $R'^a$ | $R''^a$ |
| 36-3 | $R^c$ | $R^{4a}$ | $R'^a$ | $R''^a$ |
| 36-4 | $R^a$ | $R^{4b}$ | $R'^a$ | $R''^a$ |
| 36-5 | $R^b$ | $R^{4b}$ | $R'^a$ | $R''^a$ |
| 36-6 | $R^c$ | $R^{4b}$ | $R'^a$ | $R''^a$ |
| 36-7 | $R^a$ | $R^{4c}$ | $R'^a$ | $R''^a$ |
| 36-8 | $R^b$ | $R^{4c}$ | $R'^a$ | $R''^a$ |
| 36-9 | $R^c$ | $R^{4c}$ | $R'^a$ | $R''^a$ |
| 36-10 | $R^a$ | $R^{4a}$ | $R'^b$ | $R''^a$ |
| 36-11 | $R^b$ | $R^{4a}$ | $R'^b$ | $R''^a$ |
| 36-12 | $R^c$ | $R^{4a}$ | $R'^b$ | $R''^a$ |
| 36-13 | $R^a$ | $R^{4b}$ | $R'^b$ | $R''^a$ |
| 36-14 | $R^b$ | $R^{4b}$ | $R'^b$ | $R''^a$ |
| 36-15 | $R^c$ | $R^{4b}$ | $R'^b$ | $R''^a$ |
| 36-16 | $R^a$ | $R^{4c}$ | $R'^b$ | $R''^a$ |
| 36-17 | $R^b$ | $R^{4c}$ | $R'^b$ | $R''^a$ |
| 36-18 | $R^c$ | $R^{4c}$ | $R'^b$ | $R''^a$ |
| 36-19 | $R^a$ | $R^{4a}$ | $R'^c$ | $R''^a$ |
| 36-20 | $R^b$ | $R^{4a}$ | $R'^c$ | $R''^a$ |
| 36-21 | $R^c$ | $R^{4a}$ | $R'^c$ | $R''^a$ |
| 36-22 | $R^a$ | $R^{4b}$ | $R'^c$ | $R''^a$ |
| 36-23 | $R^b$ | $R^{4b}$ | $R'^c$ | $R''^a$ |
| 36-24 | $R^c$ | $R^{4b}$ | $R'^c$ | $R''^a$ |
| 36-25 | $R^a$ | $R^{4c}$ | $R'^c$ | $R''^a$ |
| 36-26 | $R^b$ | $R^{4c}$ | $R'^c$ | $R''^a$ |
| 36-27 | $R^c$ | $R^{4c}$ | $R'^c$ | $R''^a$ |
| 36-28 | $R^a$ | $R^{4a}$ | $R'^a$ | $R''^b$ |
| 36-29 | $R^b$ | $R^{4a}$ | $R'^a$ | $R''^b$ |
| 36-30 | $R^c$ | $R^{4a}$ | $R'^a$ | $R''^b$ |
| 36-31 | $R^a$ | $R^{4b}$ | $R'^a$ | $R''^b$ |
| 36-32 | $R^b$ | $R^{4b}$ | $R'^a$ | $R''^b$ |
| 36-33 | $R^c$ | $R^{4b}$ | $R'^a$ | $R''^b$ |
| 36-34 | $R^a$ | $R^{4c}$ | $R'^a$ | $R''^b$ |
| 36-35 | $R^b$ | $R^{4c}$ | $R'^a$ | $R''^b$ |
| 36-36 | $R^c$ | $R^{4c}$ | $R'^a$ | $R''^b$ |
| 36-37 | $R^a$ | $R^{4a}$ | $R'^b$ | $R''^b$ |
| 36-38 | $R^b$ | $R^{4a}$ | $R'^b$ | $R''^b$ |
| 36-39 | $R^c$ | $R^{4a}$ | $R'^b$ | $R''^b$ |
| 36-40 | $R^a$ | $R^{4b}$ | $R'^b$ | $R''^b$ |
| 36-41 | $R^b$ | $R^{4b}$ | $R'^b$ | $R''^b$ |
| 36-42 | $R^c$ | $R^{4b}$ | $R'^b$ | $R''^b$ |
| 36-43 | $R^a$ | $R^{4c}$ | $R'^b$ | $R''^b$ |
| 36-44 | $R^b$ | $R^{4c}$ | $R'^b$ | $R''^b$ |
| 36-45 | $R^c$ | $R^{4c}$ | $R'^b$ | $R''^b$ |
| 36-46 | $R^a$ | $R^{4a}$ | $R'^c$ | $R''^b$ |
| 36-47 | $R^b$ | $R^{4a}$ | $R'^c$ | $R''^b$ |
| 36-48 | $R^c$ | $R^{4a}$ | $R'^c$ | $R''^b$ |
| 36-49 | $R^a$ | $R^{4b}$ | $R'^c$ | $R''^b$ |
| 36-50 | $R^b$ | $R^{4b}$ | $R'^c$ | $R''^b$ |
| 36-51 | $R^c$ | $R^{4b}$ | $R'^c$ | $R''^b$ |
| 36-52 | $R^a$ | $R^{4c}$ | $R'^c$ | $R''^b$ |
| 36-53 | $R^b$ | $R^{4c}$ | $R'^c$ | $R''^b$ |
| 36-54 | $R^c$ | $R^{4c}$ | $R'^c$ | $R''^b$ |
| 36-55 | $R^a$ | $R^{4a}$ | $R'^a$ | $R''^c$ |
| 36-56 | $R^b$ | $R^{4a}$ | $R'^a$ | $R''^c$ |
| 36-57 | $R^c$ | $R^{4a}$ | $R'^a$ | $R''^c$ |
| 36-58 | $R^a$ | $R^{4b}$ | $R'^a$ | $R''^c$ |
| 36-59 | $R^b$ | $R^{4b}$ | $R'^a$ | $R''^c$ |
| 36-60 | $R^c$ | $R^{4b}$ | $R'^a$ | $R''^c$ |
| 36-61 | $R^a$ | $R^{4c}$ | $R'^a$ | $R''^c$ |
| 36-62 | $R^b$ | $R^{4c}$ | $R'^a$ | $R''^c$ |
| 36-63 | $R^c$ | $R^{4c}$ | $R'^a$ | $R''^c$ |
| 36-64 | $R^a$ | $R^{4a}$ | $R'^b$ | $R''^c$ |
| 36-65 | $R^b$ | $R^{4a}$ | $R'^b$ | $R''^c$ |
| 36-66 | $R^c$ | $R^{4a}$ | $R'^b$ | $R''^c$ |
| 36-67 | $R^a$ | $R^{4b}$ | $R'^b$ | $R''^c$ |
| 36-68 | $R^b$ | $R^{4b}$ | $R'^b$ | $R''^c$ |
| 36-69 | $R^c$ | $R^{4b}$ | $R'^b$ | $R''^c$ |
| 36-70 | $R^a$ | $R^{4c}$ | $R'^b$ | $R''^c$ |

-continued

| Formula | R | R⁴ | R' | R" |
|---|---|---|---|---|
| 36-71 | R$^b$ | R$^{4c}$ | R'$^b$ | R"$^c$ |
| 36-72 | R$^c$ | R$^{4c}$ | R'$^b$ | R"$^c$ |
| 36-73 | R$^a$ | R$^{4a}$ | R'$^c$ | R"$^c$ |
| 36-74 | R$^b$ | R$^{4a}$ | R'$^c$ | R"$^c$ |
| 36-75 | R$^c$ | R$^{4a}$ | R'$^c$ | R"$^c$ |
| 36-76 | R$^a$ | R$^{4b}$ | R'$^c$ | R"$^c$ |
| 36-77 | R$^b$ | R$^{4b}$ | R'$^c$ | R"$^c$ |
| 36-78 | R$^c$ | R$^{4b}$ | R'$^c$ | R"$^c$ |
| 36-79 | R$^a$ | R$^{4c}$ | R'$^c$ | R"$^c$ |
| 36-80 | R$^b$ | R$^{4c}$ | R'$^c$ | R"$^c$ |
| 36-81 | R$^c$ | R$^{4c}$ | R'$^c$ | R"$^c$ | where all symbols are as defined above.

In one aspect of formula (36) of the present invention, R is hydrogen, a hydroxy group, a halogen, a nitro group, an optionally substituted amino group, an alkyl group, an alkoxy group, an alkenyl group, or an alkoxyalkyl group; R⁴ is an alkenyl group, a cycloalkenyl group, an alkoxyalkyl group, an alkenyloxy group, a cycloalkenyloxy group, an acyl group or an acyloxy group, an aryl group, an aryloxy group, an aroyl group, an aroyloxy group, an aralkyl group, an aralkenyl group, an aralkynyl group, an aralkoxy group, a heterocyclyl group, a heterocyclenyl group, a heteroaryl group, a heteroaralkyl group, a heteroaryloxy group, or a heteroaralkoxy group; and R' and R" independently are hydrogen, a halogen, a nitro group, an amino group, a mono- or di-substituted amino group; a hydroxy group, an alkoxy group, a carboxy group, a cyano group, an oxo(O═) group, a thio(S═) group; an alkyl group, a cycloalkyl group, an alkoxy group, a haloalkoxy group, a cycloalkyl group, an aryl group, or a benzyloxy group.

In another aspect of formula (36) of the present invention, R is hydrogen or an alkyl group; R⁴ is a cycloalkenyl group, a cycloalkenyloxy group, an acyl group or an acyloxy group, an aryl group, an aryloxy group, an aroyl group, an aroyloxy group, an aralkyl group, an aralkenyl group, an aralkynyl group, an aralkoxy group, a heterocyclyl group, a heterocyclenyl group, a heteroaryl group, a heteroaralkyl group, a heteroaryloxy group, or a heteroaralkoxy group; and R' and R" independently are hydrogen or a halogen.

In yet another aspect of formula (36) of the present invention, R is —H or CH₃; R⁴ is a halogen substituted aryl group; and R' and R" independently are —H or —Cl; and all other symbols are as defined above in connection with formula (I).

Examples of compounds of formula (36) include, but are not limited to:

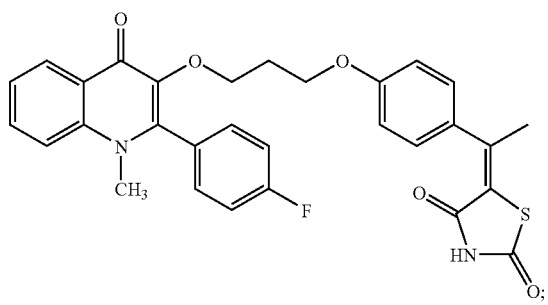

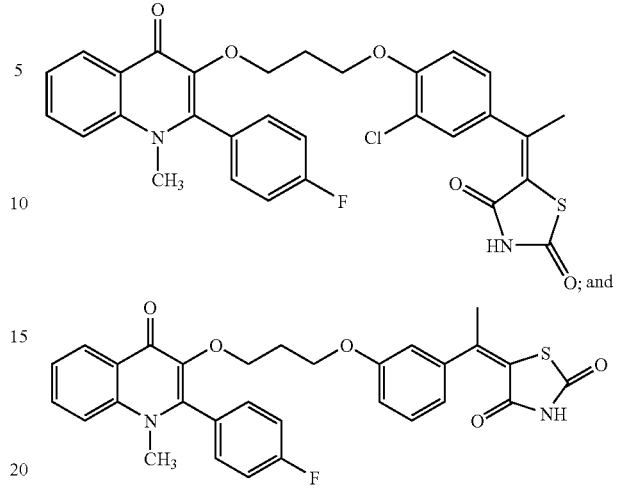

The present invention also contemplates various compounds having the general formula:

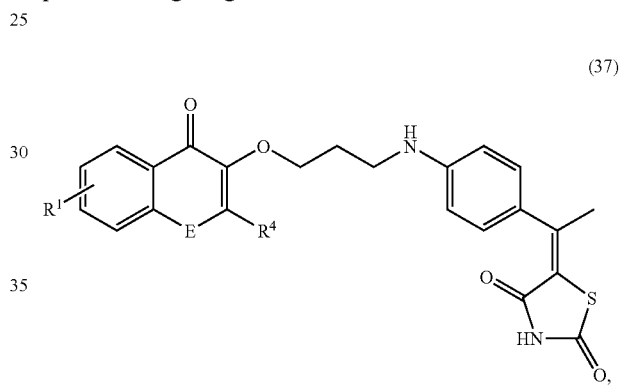

(37)

where all symbols are as defined above in connection with formula (I).

According to some variations of the present invention, E, R¹, and R⁴ of formula (37) are selected to produce compounds of formula (37-1) through formula (37-27):

| Formula | E | R¹ | R⁴ |
|---|---|---|---|
| 37-1 | E$^a$ | R$^{1a}$ | R$^{4a}$ |
| 37-2 | E$^b$ | R$^{1a}$ | R$^{4a}$ |
| 37-3 | E$^c$ | R$^{1a}$ | R$^{4a}$ |
| 37-4 | E$^a$ | R$^{1b}$ | R$^{4a}$ |
| 37-5 | E$^b$ | R$^{1b}$ | R$^{4a}$ |
| 37-6 | E$^c$ | R$^{1b}$ | R$^{4a}$ |
| 37-7 | E$^a$ | R$^{1c}$ | R$^{4a}$ |
| 37-8 | E$^b$ | R$^{1c}$ | R$^{4a}$ |
| 37-9 | E$^c$ | R$^{1c}$ | R$^{4a}$ |
| 37-10 | E$^a$ | R$^{1a}$ | R$^{4b}$ |
| 37-11 | E$^b$ | R$^{1a}$ | R$^{4b}$ |
| 37-12 | E$^c$ | R$^{1a}$ | R$^{4b}$ |
| 37-13 | E$^a$ | R$^{1b}$ | R$^{4b}$ |
| 37-14 | E$^b$ | R$^{1b}$ | R$^{4b}$ |
| 37-15 | E$^c$ | R$^{1b}$ | R$^{4b}$ |
| 37-16 | E$^a$ | R$^{1c}$ | R$^{4b}$ |
| 37-17 | E$^b$ | R$^{1c}$ | R$^{4b}$ |
| 37-18 | E$^c$ | R$^{1c}$ | R$^{4b}$ |
| 37-19 | E$^a$ | R$^{1a}$ | R$^{4c}$ |
| 37-20 | E$^b$ | R$^{1a}$ | R$^{4c}$ |

-continued

| Formula | E | $R^1$ | $R^4$ |
|---|---|---|---|
| 37-21 | $E^c$ | $R^{1a}$ | $R^{4c}$ |
| 37-22 | $E^a$ | $R^{1b}$ | $R^{4c}$ |
| 37-23 | $E^b$ | $R^{1b}$ | $R^{4c}$ |
| 37-24 | $E^c$ | $R^{1b}$ | $R^{4c}$ |
| 37-25 | $E^a$ | $R1^c$ | $R^{4c}$ |
| 37-26 | $E^b$ | $R^{1c}$ | $R^{4c}$ |
| 37-27 | $E^c$ | $R^{1c}$ | $R^{4c}$ | where all symbols are as defined above.

In one aspect of formula (37) of the present invention, $R^1$ is hydrogen, a hydroxy group, a halogen, a nitro group, a carboxy group, a carbamoyl group, an optionally substituted amino group, an alkyl group, a cycloalkyl group, an alkoxy group, a cycloalkoxy group, an alkenyl group, a cycloalkenyl group, an alkoxyalkyl group, an alkenyloxy group, or a cycloalkenyloxy group; $R^4$ is an alkenyl group, a cycloalkenyl group, an alkoxyalkyl group, an alkenyloxy group, a cycloalkenyloxy group, an acyl group or an acyloxy group, an aryl group, an aryloxy group, an aroyl group, an aroyloxy group, an aralkyl group, an aralkenyl group, an aralkynyl group, an aralkoxy group, a heterocyclyl group, a heterocyclenyl group, a heteroaryl group, a heteroaralkyl group, a heteroaryloxy group, or a heteroaralkoxy group; and all other symbols are as defined above in connection with formula (I).

In another aspect of formula (37) of the present invention, $R^1$ is hydrogen, a hydroxy group, a halogen, a nitro group, a carboxy group, a carbamoyl group, an optionally substituted amino group, or an alkyl group; $R^4$ is a cycloalkenyl group, a cycloalkenyloxy group, an acyl group or an acyloxy group, an aryl group, an aryloxy group, an aroyl group, an aroyloxy group, an aralkyl group, an aralkenyl group, an aralkynyl group, an aralkoxy group, a heterocyclyl group, a heterocyclenyl group, a heteroaryl group, a heteroaralkyl group, a heteroaryloxy group, or a heteroaralkoxy group; and all other symbols are as defined above in connection with formula (I).

In yet another aspect of formula (37) of the present invention, $R^1$ is hydrogen, a halogen, or an alkoxy group; $R^4$ is a cycloalkenyl group, a cycloalkenyloxy group, an acyl group or an acyloxy group, an aryl group, an aryloxy group, an aroyl group, an aroyloxy group, an aralkyl group, an aralkenyl group, an aralkynyl group, an aralkoxy group, a heterocyclyl group, a heterocyclenyl group, a heteroaryl group, a heteroaralkyl group, a heteroaryloxy group, or a heteroaralkoxy group; and all other symbols are as defined above in connection with formula (I).

In still another aspect of formula (37) of the present invention, $R^1$ is hydrogen, a halogen, or an alkoxy group; E is O or —NR; and $R^4$ is

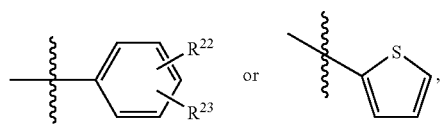

where $R^{22}$ and $R^{23}$ independently are hydrogen, a halogen, a nitro group, an amino group, a mono- or di-substituted amino group, a hydroxy group, an alkoxy group, a carboxy group, a cyano group, an oxo(O=) group, a thio(S=) group, an alkyl group, a cycloalkyl group, an alkoxy group, a haloalkoxy group, a cycloalkyl group, an aryl group, a benzyloxy group, an acyl group, an acyloxy group, an aroyl group, an alkoxycarbonyl group, an aryloxycarbonyl group, a heteroaryl group, a heterocyclyl group, an aralkyl group, an alkylsulfonyl group, an alkylsulfinyl group, an arylsulfonyl group, an arylsulfinyl group, an alkylthio group, an arylthio group, a heteroarylthio group, an aralkylthio group, or a heterocyclyl sulfonyl group, which is optionally substituted with a halogen, a hydroxyl group, a nitro group, an amino group, an alkyloxy group, or any combination thereof, and wherein the heterocycle group is optionally a substituted morpholinyl group, a thiomorpholinyl group, or a piperzinyl group, wherein the substituent on the heterocyclyl group is a halogen, a nitro group, an amino group, an alkyl group, an alkoxy group, or an aryl group; and all other symbols are as defined above in connection with formula (I).

In still another aspect of formula (37) of the present invention, $R^1$ is hydrogen or a halogen; E is O or NMe; $R^4$ is a substituted aryl group or a heterocycyl group; $R^{22}$ is hydrogen or an alkoxy group; $R^{22}$ is hydrogen or an alkoxy group; and all other symbols are as defined above in connection with formula (I).

In yet a further aspect of formula (37) of the present invention, $R^1$ is —H, —F, or MeO; E is O or NMe; $R^4$ is

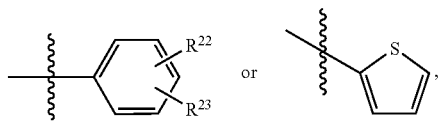

where $R^{22}$ is —H or OMe; and $R^{23}$ is —F or OMe.

An exemplary compound includes, but is not limited to:

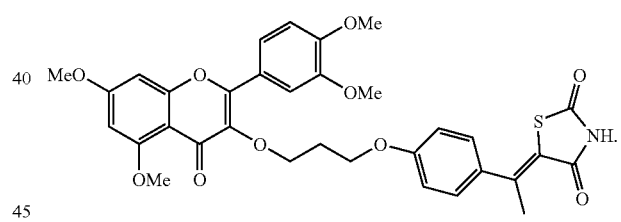

According to another aspect of the present invention, various compounds of general formula (I) having general formula (IV)

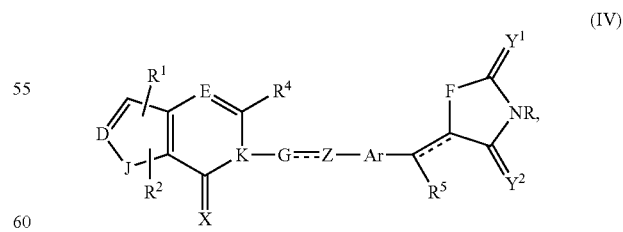

(IV)

its tautomeric forms, its stereoisomers, its polymorphs, its pharmaceutically acceptable salts, and its pharmaceutically acceptable solvates are provided. Except as otherwise provided herein, all symbols are as defined above in connection with formula (I).

A multitude of compounds having the general formula (IV) are contemplated by the present invention. Examples of such compounds include, but are not limited to:
(38)
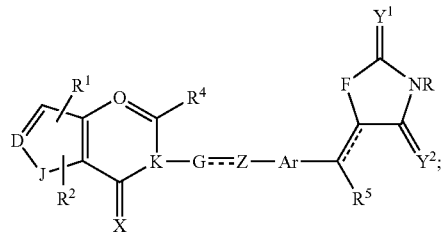
(39)
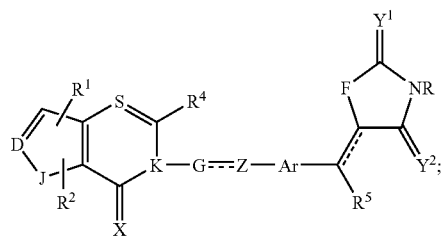
(40)
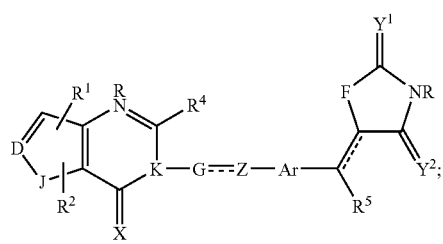
(41)
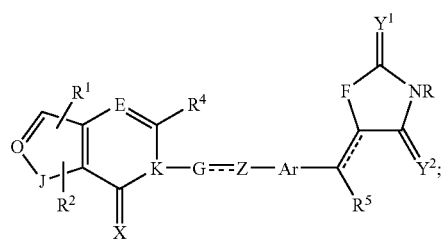
(42)
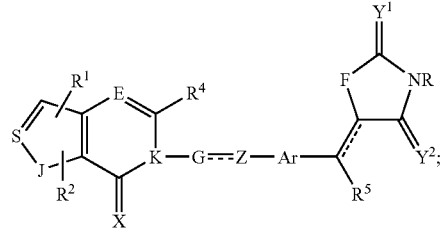
(43)
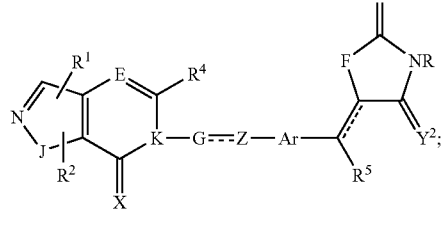
-continued
(44)
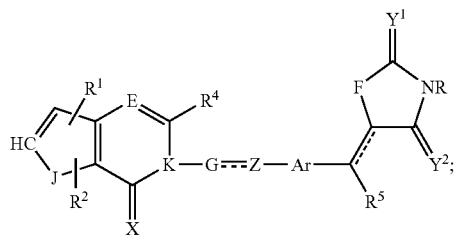
(45)
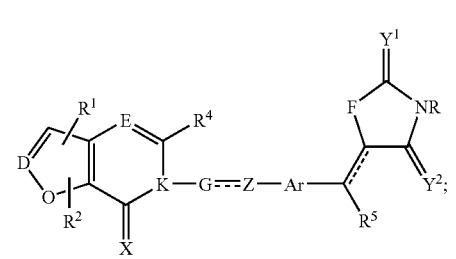
(46)
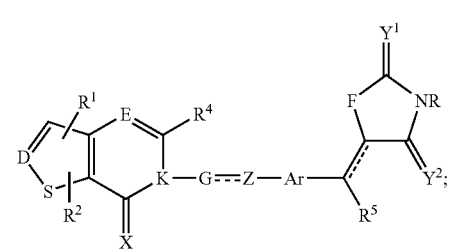
(47)
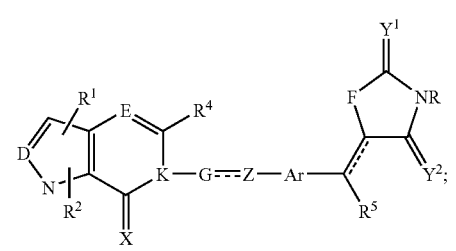
(48)
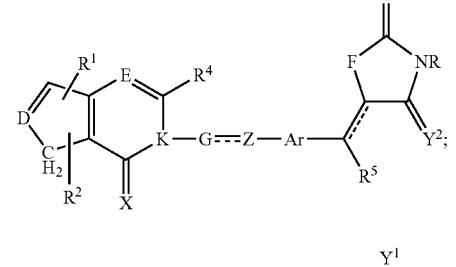
(49)
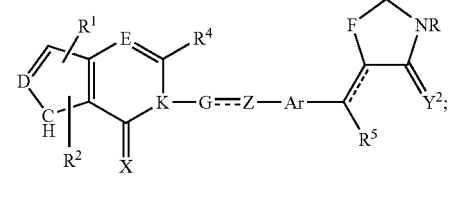

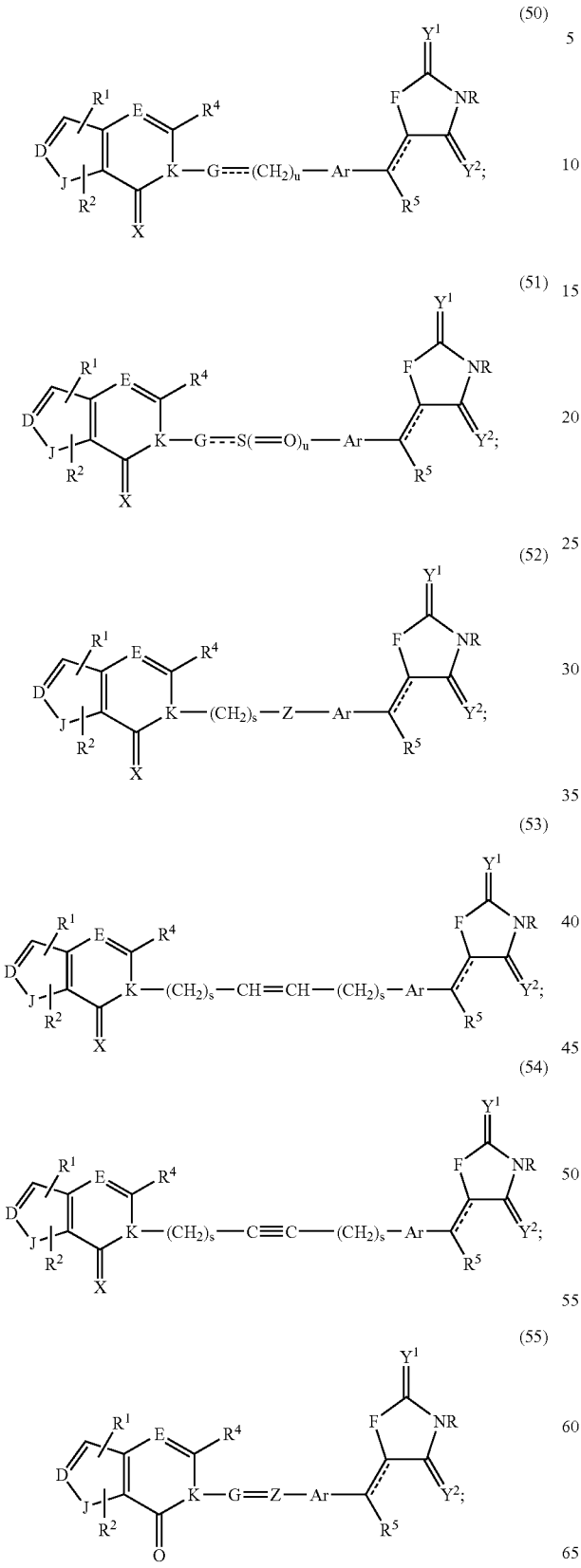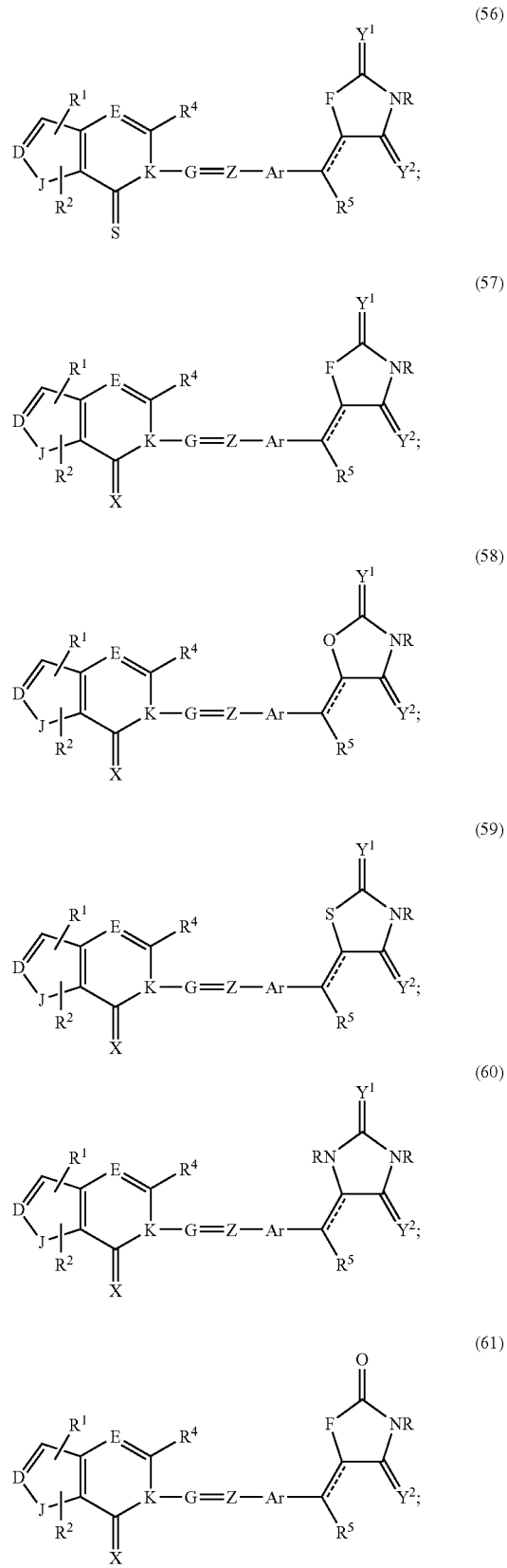

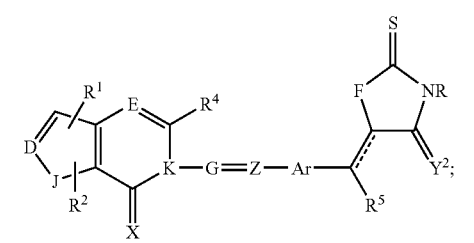
(62)
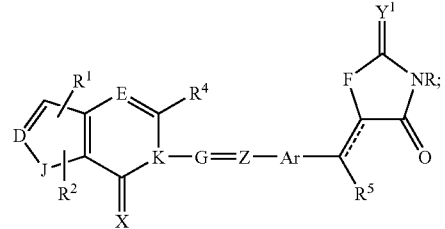
(63)
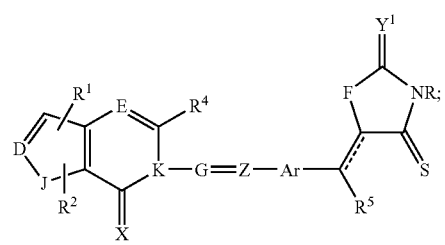
(64)
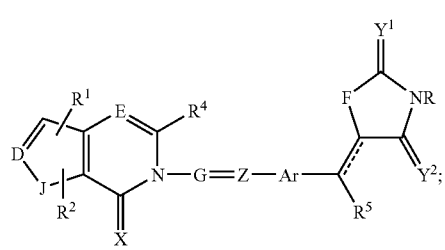
(65)
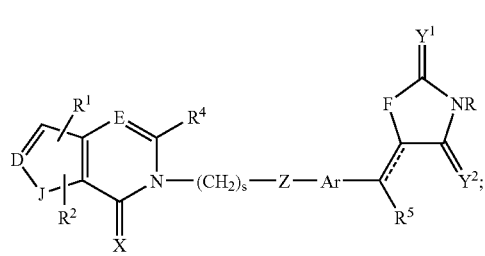
(66)
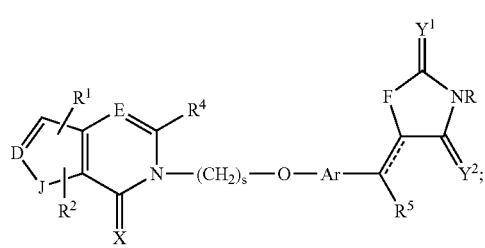
(67)
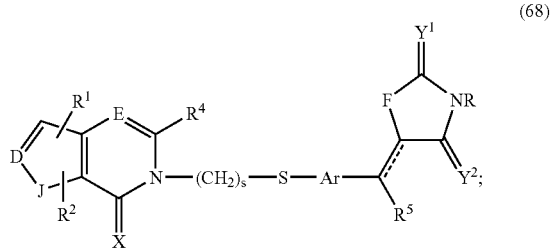
(68)
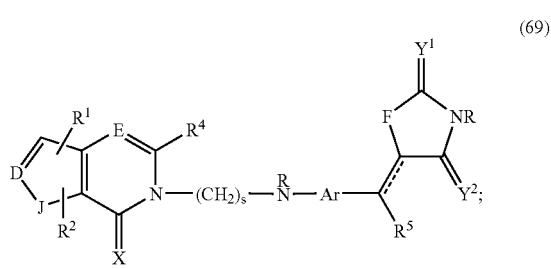
(69)
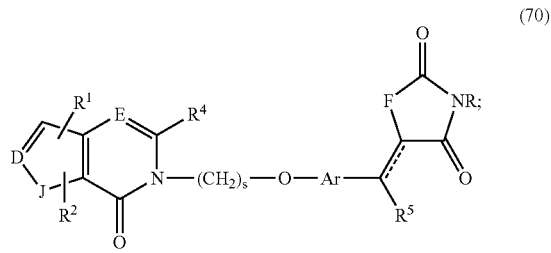
(70)
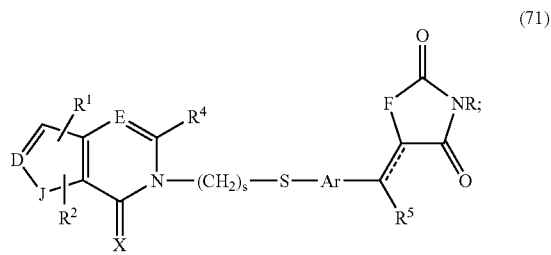
(71)
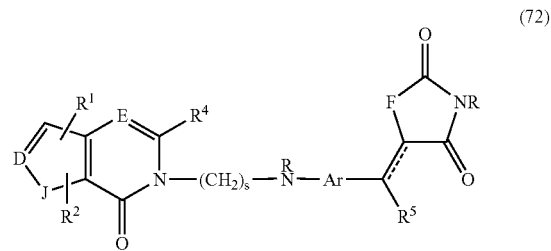
(72)
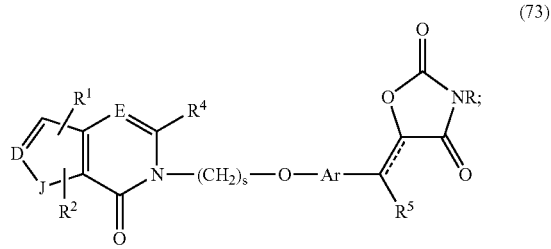
(73)

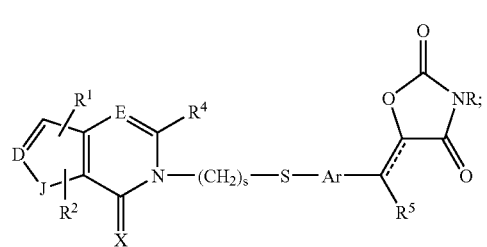 (74)
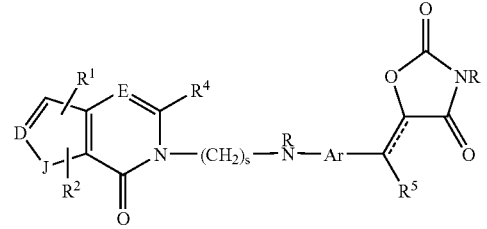 (75)
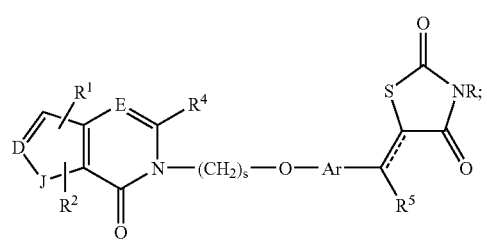 (76)
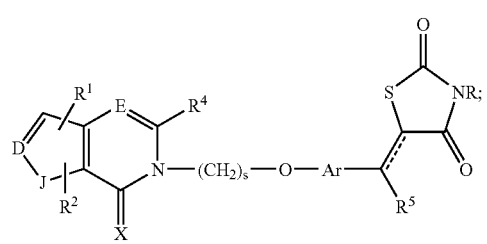 (77)
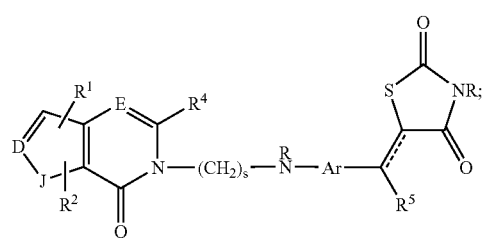 (78)
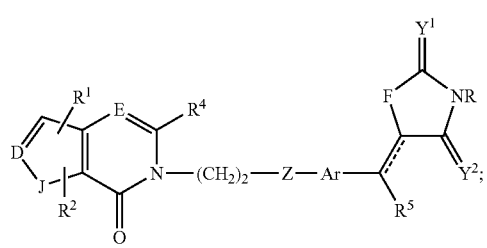 (79)
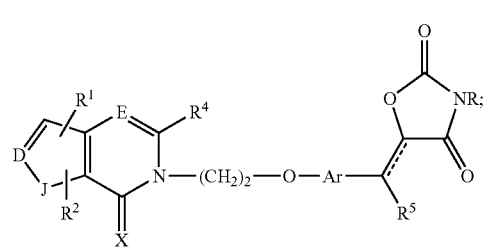 (80)
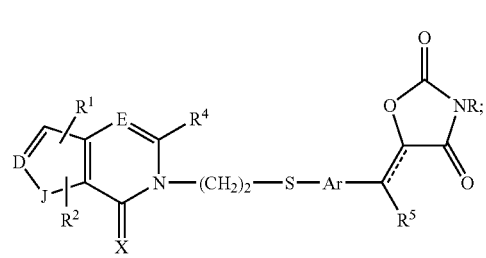 (81)
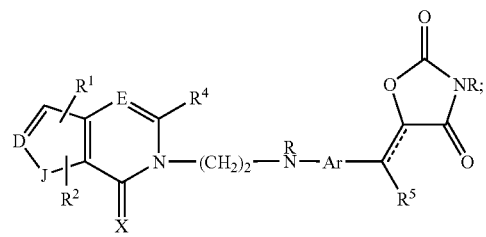 (82)
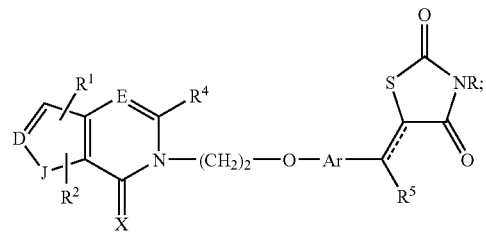 (83)
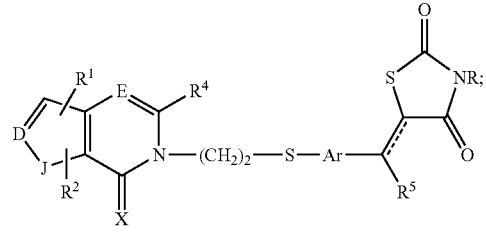 (84)
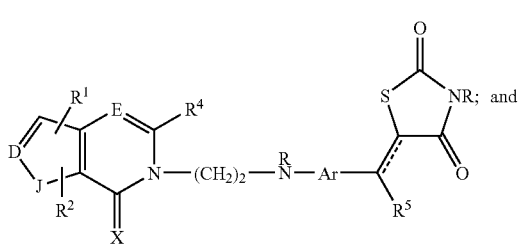 (85)

-continued

(86)
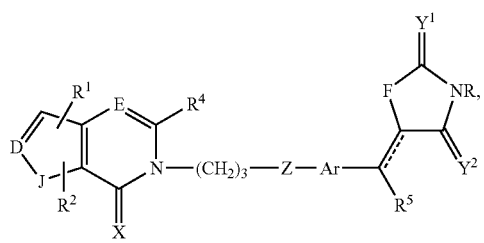

where all symbols are as defined above in connection with formula I.

Thus, for example, the present invention encompasses various compounds of general compound (IV) having the formula:

(87)
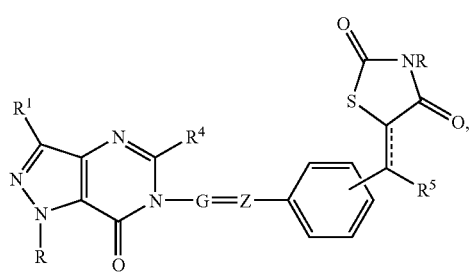

where all symbols are as defined above in connection with formula (I). It should be understood that while various configurations are provided herein, other configurations are contemplated by the present invention. Thus, compounds having the general formula:

(88)
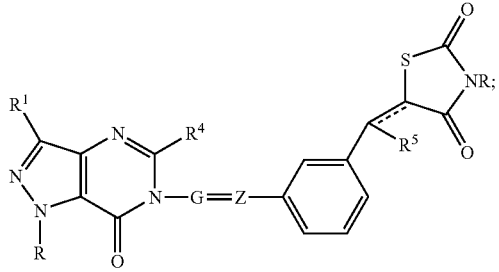

-continued

(89)
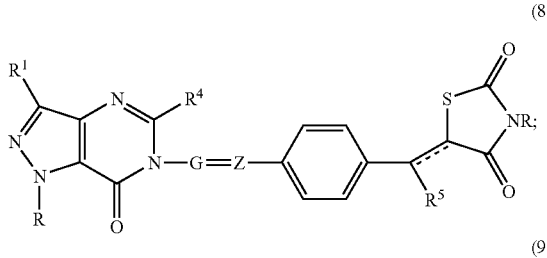

(90)
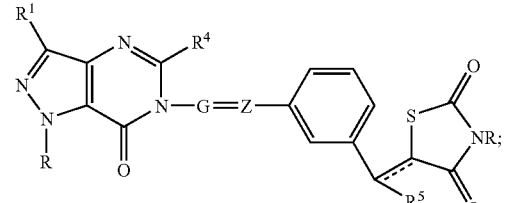

(91)
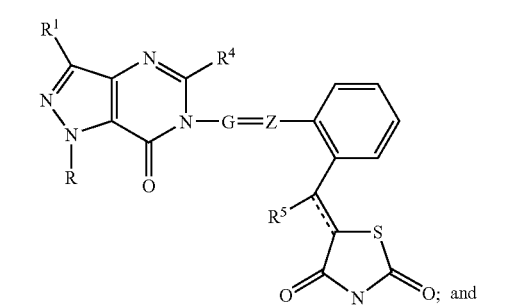

(92)
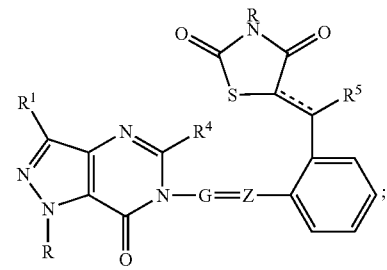

where all symbols are as defined above in connection with formula (I), are also contemplated hereby.

According to some variations of the present invention, R, $R^1$, $R^4$, G, and Z of formulae (88), (89), (90), (91), (92) are selected to produce compounds of formulae (88-1), (89-1), (90-1), (91-1), and (92-1) through formulae (88-729), (89-729), (90-729), (91-729), and (92-729) as follows:

| Formulae | | | | | R | $R^1$ | $R^4$ | $R^5$ | G | Z |
|---|---|---|---|---|---|---|---|---|---|---|
| 88-1 | 89-1 | 90-1 | 91-1 | 92-1 | $R^a$ | $R^{1a}$ | $R^{4a}$ | $R^{5a}$ | $G^a$ | $Z^a$ |
| 88-2 | 89-2 | 90-2 | 91-2 | 92-2 | $R^b$ | $R^{1a}$ | $R^{4a}$ | $R^{5a}$ | $G^a$ | $Z^a$ |
| 88-3 | 89-3 | 90-3 | 91-3 | 92-3 | $R^c$ | $R^{1a}$ | $R^{4a}$ | $R^{5a}$ | $G^a$ | $Z^a$ |
| 88-4 | 89-4 | 90-4 | 91-4 | 92-4 | $R^a$ | $R^{1b}$ | $R^{4a}$ | $R^{5a}$ | $G^a$ | $Z^a$ |
| 88-5 | 89-5 | 90-5 | 91-5 | 92-5 | $R^b$ | $R^{1b}$ | $R^{4a}$ | $R^{5a}$ | $G^a$ | $Z^a$ |
| 88-6 | 89-6 | 90-6 | 91-6 | 92-6 | $R^c$ | $R^{1b}$ | $R^{4a}$ | $R^{5a}$ | $G^a$ | $Z^a$ |
| 88-7 | 89-7 | 90-7 | 91-7 | 92-7 | $R^a$ | $R^{1c}$ | $R^{4a}$ | $R^{5a}$ | $G^a$ | $Z^a$ |
| 88-8 | 89-8 | 90-8 | 91-8 | 92-8 | $R^b$ | $R^{1c}$ | $R^{4a}$ | $R^{5a}$ | $G^a$ | $Z^a$ |
| 88-9 | 89-9 | 90-9 | 91-9 | 92-9 | $R^c$ | $R^{1c}$ | $R^{4a}$ | $R^{5a}$ | $G^a$ | $Z^a$ |
| 88-10 | 89-10 | 90-10 | 91-10 | 92-10 | $R^a$ | $R^{1a}$ | $R^{4b}$ | $R^{5a}$ | $G^a$ | $Z^a$ |
| 88-11 | 89-11 | 90-11 | 91-11 | 92-11 | $R^b$ | $R^{1a}$ | $R^{4b}$ | $R^{5a}$ | $G^a$ | $Z^a$ |

-continued

| | | Formulae | | | R | R$^1$ | R$^4$ | R$^5$ | G | Z |
|---|---|---|---|---|---|---|---|---|---|---|
| 88-12 | 89-12 | 90-12 | 91-12 | 92-12 | R$^c$ | R$^{1a}$ | R$^{4b}$ | R$^{5a}$ | G$^a$ | Z$^a$ |
| 88-13 | 89-13 | 90-13 | 91-13 | 92-13 | R$^a$ | R$^{1b}$ | R$^{4b}$ | R$^{5a}$ | G$^a$ | Z$^a$ |
| 88-14 | 89-14 | 90-14 | 91-14 | 92-14 | R$^b$ | R$^{1b}$ | R$^{4b}$ | R$^{5a}$ | G$^a$ | Z$^a$ |
| 88-15 | 89-15 | 90-15 | 91-15 | 92-15 | R$^c$ | R$^{1b}$ | R$^{4b}$ | R$^{5a}$ | G$^a$ | Z$^a$ |
| 88-16 | 89-16 | 90-16 | 91-16 | 92-16 | R$^a$ | R$^{1c}$ | R$^{4b}$ | R$^{5a}$ | G$^a$ | Z$^a$ |
| 88-17 | 89-17 | 90-17 | 91-17 | 92-17 | R$^b$ | R$^{1c}$ | R$^{4b}$ | R$^{5a}$ | G$^a$ | Z$^a$ |
| 88-18 | 89-18 | 90-18 | 91-18 | 92-18 | R$^c$ | R$^{1c}$ | R$^{4b}$ | R$^{5a}$ | G$^a$ | Z$^a$ |
| 88-19 | 89-19 | 90-19 | 91-19 | 92-19 | R$^a$ | R$^{1a}$ | R$^{4c}$ | R$^{5a}$ | G$^a$ | Z$^a$ |
| 88-20 | 89-20 | 90-20 | 91-20 | 92-20 | R$^b$ | R$^{1a}$ | R$^{4c}$ | R$^{5a}$ | G$^a$ | Z$^a$ |
| 88-21 | 89-21 | 90-21 | 91-21 | 92-21 | R$^c$ | R$^{1a}$ | R$^{4c}$ | R$^{5a}$ | G$^a$ | Z$^a$ |
| 88-22 | 89-22 | 90-22 | 91-22 | 92-22 | R$^a$ | R$^{1b}$ | R$^{4c}$ | R$^{5a}$ | G$^a$ | Z$^a$ |
| 88-23 | 89-23 | 90-23 | 91-23 | 92-23 | R$^b$ | R$^{1b}$ | R$^{4c}$ | R$^{5a}$ | G$^a$ | Z$^a$ |
| 88-24 | 89-24 | 90-24 | 91-24 | 92-24 | R$^c$ | R$^{1b}$ | R$^{4c}$ | R$^{5a}$ | G$^a$ | Z$^a$ |
| 88-25 | 89-25 | 90-25 | 91-25 | 92-25 | R$^a$ | R$^{1c}$ | R$^{4c}$ | R$^{5a}$ | G$^a$ | Z$^a$ |
| 88-26 | 89-26 | 90-26 | 91-26 | 92-26 | R$^b$ | R$^{1c}$ | R$^{4c}$ | R$^{5a}$ | G$^a$ | Z$^a$ |
| 88-27 | 89-27 | 90-27 | 91-27 | 92-27 | R$^c$ | R$^{1c}$ | R$^{4c}$ | R$^{5a}$ | G$^a$ | Z$^a$ |
| 88-28 | 89-28 | 90-28 | 91-28 | 92-28 | R$^a$ | R$^{1a}$ | R$^{4a}$ | R$^{5b}$ | G$^a$ | Z$^a$ |
| 88-29 | 89-29 | 90-29 | 91-29 | 92-29 | R$^b$ | R$^{1a}$ | R$^{4a}$ | R$^{5b}$ | G$^a$ | Z$^a$ |
| 88-30 | 89-30 | 90-30 | 91-30 | 92-30 | R$^c$ | R$^{1a}$ | R$^{4a}$ | R$^{5b}$ | G$^a$ | Z$^a$ |
| 88-31 | 89-31 | 90-31 | 91-31 | 92-31 | R$^a$ | R$^{1b}$ | R$^{4a}$ | R$^{5b}$ | G$^a$ | Z$^a$ |
| 88-32 | 89-32 | 90-32 | 91-32 | 92-32 | R$^b$ | R$^{1b}$ | R$^{4a}$ | R$^{5b}$ | G$^a$ | Z$^a$ |
| 88-33 | 89-33 | 90-33 | 91-33 | 92-33 | R$^c$ | R$^{1b}$ | R$^{4a}$ | R$^{5b}$ | G$^a$ | Z$^a$ |
| 88-34 | 89-34 | 90-34 | 91-34 | 92-34 | R$^a$ | R$^{1c}$ | R$^{4a}$ | R$^{5b}$ | G$^a$ | Z$^a$ |
| 88-35 | 89-35 | 90-35 | 91-35 | 92-35 | R$^b$ | R$^{1c}$ | R$^{4a}$ | R$^{5b}$ | G$^a$ | Z$^a$ |
| 88-36 | 89-36 | 90-36 | 91-36 | 92-36 | R$^c$ | R$^{1c}$ | R$^{4a}$ | R$^{5b}$ | G$^a$ | Z$^a$ |
| 88-37 | 89-37 | 90-37 | 91-37 | 92-37 | R$^a$ | R$^{1a}$ | R$^{4b}$ | R$^{5b}$ | G$^a$ | Z$^a$ |
| 88-38 | 89-38 | 90-38 | 91-38 | 92-38 | R$^b$ | R$^{1a}$ | R$^{4b}$ | R$^{5b}$ | G$^a$ | Z$^a$ |
| 88-39 | 89-39 | 90-39 | 91-39 | 92-39 | R$^c$ | R$^{1a}$ | R$^{4b}$ | R$^{5b}$ | G$^a$ | Z$^a$ |
| 88-40 | 89-40 | 90-40 | 91-40 | 92-40 | R$^a$ | R$^{1b}$ | R$^{4b}$ | R$^{5b}$ | G$^a$ | Z$^a$ |
| 88-41 | 89-41 | 90-41 | 91-41 | 92-41 | R$^b$ | R$^{1b}$ | R$^{4b}$ | R$^{5b}$ | G$^a$ | Z$^a$ |
| 88-42 | 89-42 | 90-42 | 91-42 | 92-42 | R$^c$ | R$^{1b}$ | R$^{4b}$ | R$^{5b}$ | G$^a$ | Z$^a$ |
| 88-43 | 89-43 | 90-43 | 91-43 | 92-43 | R$^a$ | R$^{1c}$ | R$^{4b}$ | R$^{5b}$ | G$^a$ | Z$^a$ |
| 88-44 | 89-44 | 90-44 | 91-44 | 92-44 | R$^b$ | R$^{1c}$ | R$^{4b}$ | R$^{5b}$ | G$^a$ | Z$^a$ |
| 88-45 | 89-45 | 90-45 | 91-45 | 92-45 | R$^c$ | R$^{1c}$ | R$^{4b}$ | R$^{5b}$ | G$^a$ | Z$^a$ |
| 88-46 | 89-46 | 90-46 | 91-46 | 92-46 | R$^a$ | R$^{1a}$ | R$^{4c}$ | R$^{5b}$ | G$^a$ | Z$^a$ |
| 88-47 | 89-47 | 90-47 | 91-47 | 92-47 | R$^b$ | R$^{1a}$ | R$^{4c}$ | R$^{5b}$ | G$^a$ | Z$^a$ |
| 88-48 | 89-48 | 90-48 | 91-48 | 92-48 | R$^c$ | R$^{1a}$ | R$^{4c}$ | R$^{5b}$ | G$^a$ | Z$^a$ |
| 88-49 | 89-49 | 90-49 | 91-49 | 92-49 | R$^a$ | R$^{1b}$ | R$^{4c}$ | R$^{5b}$ | G$^a$ | Z$^a$ |
| 88-50 | 89-50 | 90-50 | 91-50 | 92-50 | R$^b$ | R$^{1b}$ | R$^{4c}$ | R$^{5b}$ | G$^a$ | Z$^a$ |
| 88-51 | 89-51 | 90-51 | 91-51 | 92-51 | R$^c$ | R$^{1b}$ | R$^{4c}$ | R$^{5b}$ | G$^a$ | Z$^a$ |
| 88-52 | 89-52 | 90-52 | 91-52 | 92-52 | R$^a$ | R$^{1c}$ | R$^{4c}$ | R$^{5b}$ | G$^a$ | Z$^a$ |
| 88-53 | 89-53 | 90-53 | 91-53 | 92-53 | R$^b$ | R$^{1c}$ | R$^{4c}$ | R$^{5b}$ | G$^a$ | Z$^a$ |
| 88-54 | 89-54 | 90-54 | 91-54 | 92-54 | R$^c$ | R$^{1c}$ | R$^{4c}$ | R$^{5b}$ | G$^a$ | Z$^a$ |
| 88-55 | 89-55 | 90-55 | 91-55 | 92-55 | R$^a$ | R$^{1a}$ | R$^{4a}$ | R$^{5c}$ | G$^a$ | Z$^a$ |
| 88-56 | 89-56 | 90-56 | 91-56 | 92-56 | R$^b$ | R$^{1a}$ | R$^{4a}$ | R$^{5c}$ | G$^a$ | Z$^a$ |
| 88-57 | 89-57 | 90-57 | 91-57 | 92-57 | R$^c$ | R$^{1a}$ | R$^{4a}$ | R$^{5c}$ | G$^a$ | Z$^a$ |
| 88-58 | 89-58 | 90-58 | 91-58 | 92-58 | R$^a$ | R$^{1b}$ | R$^{4a}$ | R$^{5c}$ | G$^a$ | Z$^a$ |
| 88-59 | 89-59 | 90-59 | 91-59 | 92-59 | R$^b$ | R$^{1b}$ | R$^{4a}$ | R$^{5c}$ | G$^a$ | Z$^a$ |
| 88-60 | 89-60 | 90-60 | 91-60 | 92-60 | R$^c$ | R$^{1b}$ | R$^{4a}$ | R$^{5c}$ | G$^a$ | Z$^a$ |
| 88-61 | 89-61 | 90-61 | 91-61 | 92-61 | R$^a$ | R$^{1c}$ | R$^{4a}$ | R$^{5c}$ | G$^a$ | Z$^a$ |
| 88-62 | 89-62 | 90-62 | 91-62 | 92-62 | R$^b$ | R$^{1c}$ | R$^{4a}$ | R$^{5c}$ | G$^a$ | Z$^a$ |
| 88-63 | 89-63 | 90-63 | 91-63 | 92-63 | R$^c$ | R$^{1c}$ | R$^{4a}$ | R$^{5c}$ | G$^a$ | Z$^a$ |
| 88-64 | 89-64 | 90-64 | 91-64 | 92-64 | R$^a$ | R$^{1a}$ | R$^{4b}$ | R$^{5c}$ | G$^a$ | Z$^a$ |
| 88-65 | 89-65 | 90-65 | 91-65 | 92-65 | R$^b$ | R$^{1a}$ | R$^{4b}$ | R$^{5c}$ | G$^a$ | Z$^a$ |
| 88-66 | 89-66 | 90-66 | 91-66 | 92-66 | R$^c$ | R$^{1a}$ | R$^{4b}$ | R$^{5c}$ | G$^a$ | Z$^a$ |
| 88-67 | 89-67 | 90-67 | 91-67 | 92-67 | R$^a$ | R$^{1b}$ | R$^{4b}$ | R$^{5c}$ | G$^a$ | Z$^a$ |
| 88-68 | 89-68 | 90-68 | 91-68 | 92-68 | R$^b$ | R$^{1b}$ | R$^{4b}$ | R$^{5c}$ | G$^a$ | Z$^a$ |
| 88-69 | 89-69 | 90-69 | 91-69 | 92-69 | R$^c$ | R$^{1b}$ | R$^{4b}$ | R$^{5c}$ | G$^a$ | Z$^a$ |
| 88-70 | 89-70 | 90-70 | 91-70 | 92-70 | R$^a$ | R$^{1c}$ | R$^{4b}$ | R$^{5c}$ | G$^a$ | Z$^a$ |
| 88-71 | 89-71 | 90-71 | 91-71 | 92-71 | R$^b$ | R$^{1c}$ | R$^{4b}$ | R$^{5c}$ | G$^a$ | Z$^a$ |
| 88-72 | 89-72 | 90-72 | 91-72 | 92-72 | R$^c$ | R$^{1c}$ | R$^{4b}$ | R$^{5c}$ | G$^a$ | Z$^a$ |
| 88-73 | 89-73 | 90-73 | 91-73 | 92-73 | R$^a$ | R$^{1a}$ | R$^{4c}$ | R$^{5c}$ | G$^a$ | Z$^a$ |
| 88-74 | 89-74 | 90-74 | 91-74 | 92-74 | R$^b$ | R$^{1a}$ | R$^{4c}$ | R$^{5c}$ | G$^a$ | Z$^a$ |
| 88-75 | 89-75 | 90-75 | 91-75 | 92-75 | R$^c$ | R$^{1a}$ | R$^{4c}$ | R$^{5c}$ | G$^a$ | Z$^a$ |
| 88-76 | 89-76 | 90-76 | 91-76 | 92-76 | R$^a$ | R$^{1b}$ | R$^{4c}$ | R$^{5c}$ | G$^a$ | Z$^a$ |
| 88-77 | 89-77 | 90-77 | 91-77 | 92-77 | R$^b$ | R$^{1b}$ | R$^{4c}$ | R$^{5c}$ | G$^a$ | Z$^a$ |
| 88-78 | 89-78 | 90-78 | 91-78 | 92-78 | R$^c$ | R$^{1b}$ | R$^{4c}$ | R$^{5c}$ | G$^a$ | Z$^a$ |
| 88-79 | 89-79 | 90-79 | 91-79 | 92-79 | R$^a$ | R$^{1c}$ | R$^{4c}$ | R$^{5c}$ | G$^a$ | Z$^a$ |
| 88-80 | 89-80 | 90-80 | 91-80 | 92-80 | R$^b$ | R$^{1c}$ | R$^{4c}$ | R$^{5c}$ | G$^a$ | Z$^a$ |
| 88-81 | 89-81 | 90-81 | 91-81 | 92-81 | R$^c$ | R$^{1c}$ | R$^{4c}$ | R$^{5c}$ | G$^a$ | Z$^a$ |
| 88-82 | 89-82 | 90-82 | 91-82 | 92-82 | R$^a$ | R$^{1a}$ | R$^{4a}$ | R$^{5a}$ | G$^b$ | Z$^a$ |
| 88-83 | 89-83 | 90-83 | 91-83 | 92-83 | R$^b$ | R$^{1a}$ | R$^{4a}$ | R$^{5a}$ | G$^b$ | Z$^a$ |
| 88-84 | 89-84 | 90-84 | 91-84 | 92-84 | R$^c$ | R$^{1a}$ | R$^{4a}$ | R$^{5a}$ | G$^b$ | Z$^a$ |
| 88-85 | 89-85 | 90-85 | 91-85 | 92-85 | R$^a$ | R$^{1b}$ | R$^{4a}$ | R$^{5a}$ | G$^b$ | Z$^a$ |
| 88-86 | 89-86 | 90-86 | 91-86 | 92-86 | R$^b$ | R$^{1b}$ | R$^{4a}$ | R$^{5a}$ | G$^b$ | Z$^a$ |
| 88-87 | 89-87 | 90-87 | 91-87 | 92-87 | R$^c$ | R$^{1b}$ | R$^{4a}$ | R$^{5a}$ | G$^b$ | Z$^a$ |
| 88-88 | 89-88 | 90-88 | 91-88 | 92-88 | R$^a$ | R$^{1c}$ | R$^{4a}$ | R$^{5a}$ | G$^b$ | Z$^a$ |

-continued

| | | Formulae | | | R | R¹ | R⁴ | R⁵ | G | Z |
|---|---|---|---|---|---|---|---|---|---|---|
| 88-89 | 89-89 | 90-89 | 91-89 | 92-89 | $R^b$ | $R^{1c}$ | $R^{4a}$ | $R^{5a}$ | $G^b$ | $Z^a$ |
| 88-90 | 89-90 | 90-90 | 91-90 | 92-90 | $R^c$ | $R^{1c}$ | $R^{4a}$ | $R^{5a}$ | $G^b$ | $Z^a$ |
| 88-91 | 89-91 | 90-91 | 91-91 | 92-91 | $R^a$ | $R^{1a}$ | $R^{4b}$ | $R^{5a}$ | $G^b$ | $Z^a$ |
| 88-92 | 89-92 | 90-92 | 91-92 | 92-92 | $R^b$ | $R^{1a}$ | $R^{4b}$ | $R^{5a}$ | $G^b$ | $Z^a$ |
| 88-93 | 89-93 | 90-93 | 91-93 | 92-93 | $R^c$ | $R^{1a}$ | $R^{4b}$ | $R^{5a}$ | $G^b$ | $Z^a$ |
| 88-94 | 89-94 | 90-94 | 91-94 | 92-94 | $R^a$ | $R^{1b}$ | $R^{4b}$ | $R^{5a}$ | $G^b$ | $Z^a$ |
| 88-95 | 89-95 | 90-95 | 91-95 | 92-95 | $R^b$ | $R^{1b}$ | $R^{4b}$ | $R^{5a}$ | $G^b$ | $Z^a$ |
| 88-96 | 89-96 | 90-96 | 91-96 | 92-96 | $R^c$ | $R^{1b}$ | $R^{4b}$ | $R^{5a}$ | $G^b$ | $Z^a$ |
| 88-97 | 89-97 | 90-97 | 91-97 | 92-97 | $R^a$ | $R^{1c}$ | $R^{4b}$ | $R^{5a}$ | $G^b$ | $Z^a$ |
| 88-98 | 89-98 | 90-98 | 91-98 | 92-98 | $R^b$ | $R^{1c}$ | $R^{4b}$ | $R^{5a}$ | $G^b$ | $Z^a$ |
| 88-99 | 89-99 | 90-99 | 91-99 | 92-99 | $R^c$ | $R^{1c}$ | $R^{4b}$ | $R^{5a}$ | $G^b$ | $Z^a$ |
| 88-100 | 89-100 | 90-100 | 91-100 | 92-100 | $R^a$ | $R^{1a}$ | $R^{4c}$ | $R^{5a}$ | $G^b$ | $Z^a$ |
| 88-101 | 89-101 | 90-101 | 91-101 | 92-101 | $R^b$ | $R^{1a}$ | $R^{4c}$ | $R^{5a}$ | $G^b$ | $Z^a$ |
| 88-102 | 89-102 | 90-102 | 91-102 | 92-102 | $R^c$ | $R^{1a}$ | $R^{4c}$ | $R^{5a}$ | $G^b$ | $Z^a$ |
| 88-103 | 89-103 | 90-103 | 91-103 | 92-103 | $R^a$ | $R^{1b}$ | $R^{4c}$ | $R^{5a}$ | $G^b$ | $Z^a$ |
| 88-104 | 89-104 | 90-104 | 91-104 | 92-104 | $R^b$ | $R^{1b}$ | $R^{4c}$ | $R^{5a}$ | $G^b$ | $Z^a$ |
| 88-105 | 89-105 | 90-105 | 91-105 | 92-105 | $R^c$ | $R^{1b}$ | $R^{4c}$ | $R^{5a}$ | $G^b$ | $Z^a$ |
| 88-106 | 89-106 | 90-106 | 91-106 | 92-106 | $R^a$ | $R^{1c}$ | $R^{4c}$ | $R^{5a}$ | $G^b$ | $Z^a$ |
| 88-107 | 89-107 | 90-107 | 91-107 | 92-107 | $R^b$ | $R^{1c}$ | $R^{4c}$ | $R^{5a}$ | $G^b$ | $Z^a$ |
| 88-108 | 89-108 | 90-108 | 91-108 | 92-108 | $R^c$ | $R^{1c}$ | $R^{4c}$ | $R^{5a}$ | $G^b$ | $Z^a$ |
| 88-109 | 89-109 | 90-109 | 91-109 | 92-109 | $R^a$ | $R^{1a}$ | $R^{4a}$ | $R^{5b}$ | $G^b$ | $Z^a$ |
| 88-110 | 89-110 | 90-110 | 91-110 | 92-110 | $R^b$ | $R^{1a}$ | $R^{4a}$ | $R^{5b}$ | $G^b$ | $Z^a$ |
| 88-111 | 89-111 | 90-111 | 91-111 | 92-111 | $R^c$ | $R^{1a}$ | $R^{4a}$ | $R^{5b}$ | $G^b$ | $Z^a$ |
| 88-112 | 89-112 | 90-112 | 91-112 | 92-112 | $R^a$ | $R^{1b}$ | $R^{4a}$ | $R^{5b}$ | $G^b$ | $Z^a$ |
| 88-113 | 89-113 | 90-113 | 91-113 | 92-113 | $R^b$ | $R^{1b}$ | $R^{4a}$ | $R^{5b}$ | $G^b$ | $Z^a$ |
| 88-114 | 89-114 | 90-114 | 91-114 | 92-114 | $R^c$ | $R^{1b}$ | $R^{4a}$ | $R^{5b}$ | $G^b$ | $Z^a$ |
| 88-115 | 89-115 | 90-115 | 91-115 | 92-115 | $R^a$ | $R^{1c}$ | $R^{4a}$ | $R^{5b}$ | $G^b$ | $Z^a$ |
| 88-116 | 89-116 | 90-116 | 91-116 | 92-116 | $R^b$ | $R^{1c}$ | $R^{4a}$ | $R^{5b}$ | $G^b$ | $Z^a$ |
| 88-117 | 89-117 | 90-117 | 91-117 | 92-117 | $R^c$ | $R^{1c}$ | $R^{4a}$ | $R^{5b}$ | $G^b$ | $Z^a$ |
| 88-118 | 89-118 | 90-118 | 91-118 | 92-118 | $R^a$ | $R^{1a}$ | $R^{4b}$ | $R^{5b}$ | $G^b$ | $Z^a$ |
| 88-119 | 89-119 | 90-119 | 91-119 | 92-119 | $R^b$ | $R^{1a}$ | $R^{4b}$ | $R^{5b}$ | $G^b$ | $Z^a$ |
| 88-120 | 89-120 | 90-120 | 91-120 | 92-120 | $R^c$ | $R^{1a}$ | $R^{4b}$ | $R^{5b}$ | $G^b$ | $Z^a$ |
| 88-121 | 89-121 | 90-121 | 91-121 | 92-121 | $R^a$ | $R^{1b}$ | $R^{4b}$ | $R^{5b}$ | $G^b$ | $Z^a$ |
| 88-122 | 89-122 | 90-122 | 91-122 | 92-122 | $R^b$ | $R^{1b}$ | $R^{4b}$ | $R^{5b}$ | $G^b$ | $Z^a$ |
| 88-123 | 89-123 | 90-123 | 91-123 | 92-123 | $R^c$ | $R^{1b}$ | $R^{4b}$ | $R^{5b}$ | $G^b$ | $Z^a$ |
| 88-124 | 89-124 | 90-124 | 91-124 | 92-124 | $R^a$ | $R^{1c}$ | $R^{4b}$ | $R^{5b}$ | $G^b$ | $Z^a$ |
| 88-125 | 89-125 | 90-125 | 91-125 | 92-125 | $R^b$ | $R^{1c}$ | $R^{4b}$ | $R^{5b}$ | $G^b$ | $Z^a$ |
| 88-126 | 89-126 | 90-126 | 91-126 | 92-126 | $R^c$ | $R^{1c}$ | $R^{4b}$ | $R^{5b}$ | $G^b$ | $Z^a$ |
| 88-127 | 89-127 | 90-127 | 91-127 | 92-127 | $R^a$ | $R^{1a}$ | $R^{4c}$ | $R^{5b}$ | $G^b$ | $Z^a$ |
| 88-128 | 89-128 | 90-128 | 91-128 | 92-128 | $R^b$ | $R^{1a}$ | $R^{4c}$ | $R^{5b}$ | $G^b$ | $Z^a$ |
| 88-129 | 89-129 | 90-129 | 91-129 | 92-129 | $R^c$ | $R^{1a}$ | $R^{4c}$ | $R^{5b}$ | $G^b$ | $Z^a$ |
| 88-130 | 89-130 | 90-130 | 91-130 | 92-130 | $R^a$ | $R^{1b}$ | $R^{4c}$ | $R^{5b}$ | $G^b$ | $Z^a$ |
| 88-131 | 89-131 | 90-131 | 91-131 | 92-131 | $R^b$ | $R^{1b}$ | $R^{4c}$ | $R^{5b}$ | $G^b$ | $Z^a$ |
| 88-132 | 89-132 | 90-132 | 91-132 | 92-132 | $R^c$ | $R^{1b}$ | $R^{4c}$ | $R^{5b}$ | $G^b$ | $Z^a$ |
| 88-133 | 89-133 | 90-133 | 91-133 | 92-133 | $R^a$ | $R^{1c}$ | $R^{4c}$ | $R^{5b}$ | $G^b$ | $Z^a$ |
| 88-134 | 89-134 | 90-134 | 91-134 | 92-134 | $R^b$ | $R^{1c}$ | $R^{4c}$ | $R^{5b}$ | $G^b$ | $Z^a$ |
| 88-135 | 89-135 | 90-135 | 91-135 | 92-135 | $R^c$ | $R^{1c}$ | $R^{4c}$ | $R^{5b}$ | $G^b$ | $Z^a$ |
| 88-136 | 89-136 | 90-136 | 91-136 | 92-136 | $R^a$ | $R^{1a}$ | $R^{4a}$ | $R^{5c}$ | $G^b$ | $Z^a$ |
| 88-137 | 89-137 | 90-137 | 91-137 | 92-137 | $R^b$ | $R^{1a}$ | $R^{4a}$ | $R^{5c}$ | $G^b$ | $Z^a$ |
| 88-138 | 89-138 | 90-138 | 91-138 | 92-138 | $R^c$ | $R^{1a}$ | $R^{4a}$ | $R^{5c}$ | $G^b$ | $Z^a$ |
| 88-139 | 89-139 | 90-139 | 91-139 | 92-139 | $R^a$ | $R^{1b}$ | $R^{4a}$ | $R^{5c}$ | $G^b$ | $Z^a$ |
| 88-140 | 89-140 | 90-140 | 91-140 | 92-140 | $R^b$ | $R^{1b}$ | $R^{4a}$ | $R^{5c}$ | $G^b$ | $Z^a$ |
| 88-141 | 89-141 | 90-141 | 91-141 | 92-141 | $R^c$ | $R^{1b}$ | $R^{4a}$ | $R^{5c}$ | $G^b$ | $Z^a$ |
| 88-142 | 89-142 | 90-142 | 91-142 | 92-142 | $R^a$ | $R^{1c}$ | $R^{4a}$ | $R^{5c}$ | $G^b$ | $Z^a$ |
| 88-143 | 89-143 | 90-143 | 91-143 | 92-143 | $R^b$ | $R^{1c}$ | $R^{4a}$ | $R^{5c}$ | $G^b$ | $Z^a$ |
| 88-144 | 89-144 | 90-144 | 91-144 | 92-144 | $R^c$ | $R^{1c}$ | $R^{4a}$ | $R^{5c}$ | $G^b$ | $Z^a$ |
| 88-145 | 89-145 | 90-145 | 91-145 | 92-145 | $R^a$ | $R^{1a}$ | $R^{4b}$ | $R^{5c}$ | $G^b$ | $Z^a$ |
| 88-146 | 89-146 | 90-146 | 91-146 | 92-146 | $R^b$ | $R^{1a}$ | $R^{4b}$ | $R^{5c}$ | $G^b$ | $Z^a$ |
| 88-147 | 89-147 | 90-147 | 91-147 | 92-147 | $R^c$ | $R^{1a}$ | $R^{4b}$ | $R^{5c}$ | $G^b$ | $Z^a$ |
| 88-148 | 89-148 | 90-148 | 91-148 | 92-148 | $R^a$ | $R^{1b}$ | $R^{4b}$ | $R^{5c}$ | $G^b$ | $Z^a$ |
| 88-149 | 89-149 | 90-149 | 91-149 | 92-149 | $R^b$ | $R^{1b}$ | $R^{4b}$ | $R^{5c}$ | $G^b$ | $Z^a$ |
| 88-150 | 89-150 | 90-150 | 91-150 | 92-150 | $R^c$ | $R^{1b}$ | $R^{4b}$ | $R^{5c}$ | $G^b$ | $Z^a$ |
| 88-151 | 89-151 | 90-151 | 91-151 | 92-151 | $R^a$ | $R^{1c}$ | $R^{4b}$ | $R^{5c}$ | $G^b$ | $Z^a$ |
| 88-152 | 89-152 | 90-152 | 91-152 | 92-152 | $R^b$ | $R^{1c}$ | $R^{4b}$ | $R^{5c}$ | $G^b$ | $Z^a$ |
| 88-153 | 89-153 | 90-153 | 91-153 | 92-153 | $R^c$ | $R^{1c}$ | $R^{4b}$ | $R^{5c}$ | $G^b$ | $Z^a$ |
| 88-154 | 89-154 | 90-154 | 91-154 | 92-154 | $R^a$ | $R^{1a}$ | $R^{4c}$ | $R^{5c}$ | $G^b$ | $Z^a$ |
| 88-155 | 89-155 | 90-155 | 91-155 | 92-155 | $R^b$ | $R^{1a}$ | $R^{4c}$ | $R^{5c}$ | $G^b$ | $Z^a$ |
| 88-156 | 89-156 | 90-156 | 91-156 | 92-156 | $R^c$ | $R^{1a}$ | $R^{4c}$ | $R^{5c}$ | $G^b$ | $Z^a$ |
| 88-157 | 89-157 | 90-157 | 91-157 | 92-157 | $R^a$ | $R^{1b}$ | $R^{4c}$ | $R^{5c}$ | $G^b$ | $Z^a$ |
| 88-158 | 89-158 | 90-158 | 91-158 | 92-158 | $R^b$ | $R^{1b}$ | $R^{4c}$ | $R^{5c}$ | $G^b$ | $Z^a$ |
| 88-159 | 89-159 | 90-159 | 91-159 | 92-159 | $R^c$ | $R^{1b}$ | $R^{4c}$ | $R^{5c}$ | $G^b$ | $Z^a$ |
| 88-160 | 89-160 | 90-160 | 91-160 | 92-160 | $R^a$ | $R^{1c}$ | $R^{4c}$ | $R^{5c}$ | $G^b$ | $Z^a$ |
| 88-161 | 89-161 | 90-161 | 91-161 | 92-161 | $R^b$ | $R^{1c}$ | $R^{4c}$ | $R^{5c}$ | $G^b$ | $Z^a$ |
| 88-162 | 89-162 | 90-162 | 91-162 | 92-162 | $R^c$ | $R^{1c}$ | $R^{4c}$ | $R^{5c}$ | $G^b$ | $Z^a$ |
| 88-163 | 89-163 | 90-163 | 91-163 | 92-163 | $R^a$ | $R^{1a}$ | $R^{4a}$ | $R^{5a}$ | $G^c$ | $Z^a$ |
| 88-164 | 89-164 | 90-164 | 91-164 | 92-164 | $R^b$ | $R^{1a}$ | $R^{4a}$ | $R^{5a}$ | $G^c$ | $Z^a$ |
| 88-165 | 89-165 | 90-165 | 91-165 | 92-165 | $R^c$ | $R^{1a}$ | $R^{4a}$ | $R^{5a}$ | $G^c$ | $Z^a$ |

-continued

| | | Formulae | | | R | R$^1$ | R$^4$ | R$^5$ | G | Z |
|---|---|---|---|---|---|---|---|---|---|---|
| 88-166 | 89-166 | 90-166 | 91-166 | 92-166 | R$^a$ | R$^{1b}$ | R$^{4a}$ | R$^{5a}$ | G$^c$ | Z$^a$ |
| 88-167 | 89-167 | 90-167 | 91-167 | 92-167 | R$^b$ | R$^{1b}$ | R$^{4a}$ | R$^{5a}$ | G$^c$ | Z$^a$ |
| 88-168 | 89-168 | 90-168 | 91-168 | 92-168 | R$^c$ | R$^{1b}$ | R$^{4a}$ | R$^{5a}$ | G$^c$ | Z$^a$ |
| 88-169 | 89-169 | 90-169 | 91-169 | 92-169 | R$^a$ | R$^{1c}$ | R$^{4a}$ | R$^{5a}$ | G$^c$ | Z$^a$ |
| 88-170 | 89-170 | 90-170 | 91-170 | 92-170 | R$^b$ | R$^{1c}$ | R$^{4a}$ | R$^{5a}$ | G$^c$ | Z$^a$ |
| 88-171 | 89-171 | 90-171 | 91-171 | 92-171 | R$^c$ | R$^{1c}$ | R$^{4a}$ | R$^{5a}$ | G$^c$ | Z$^a$ |
| 88-172 | 89-172 | 90-172 | 91-172 | 92-172 | R$^a$ | R$^{1a}$ | R$^{4b}$ | R$^{5a}$ | G$^c$ | Z$^a$ |
| 88-173 | 89-173 | 90-173 | 91-173 | 92-173 | R$^b$ | R$^{1a}$ | R$^{4b}$ | R$^{5a}$ | G$^c$ | Z$^a$ |
| 88-174 | 89-174 | 90-174 | 91-174 | 92-174 | R$^c$ | R$^{1a}$ | R$^{4b}$ | R$^{5a}$ | G$^c$ | Z$^a$ |
| 88-175 | 89-175 | 90-175 | 91-175 | 92-175 | R$^a$ | R$^{1b}$ | R$^{4b}$ | R$^{5a}$ | G$^c$ | Z$^a$ |
| 88-176 | 89-176 | 90-176 | 91-176 | 92-176 | R$^b$ | R$^{1b}$ | R$^{4b}$ | R$^{5a}$ | G$^c$ | Z$^a$ |
| 88-177 | 89-177 | 90-177 | 91-177 | 92-177 | R$^c$ | R$^{1b}$ | R$^{4b}$ | R$^{5a}$ | G$^c$ | Z$^a$ |
| 88-178 | 89-178 | 90-178 | 91-178 | 92-178 | R$^a$ | R$^{1c}$ | R$^{4b}$ | R$^{5a}$ | G$^c$ | Z$^a$ |
| 88-179 | 89-179 | 90-179 | 91-179 | 92-179 | R$^b$ | R$^{1c}$ | R$^{4b}$ | R$^{5a}$ | G$^c$ | Z$^a$ |
| 88-180 | 89-180 | 90-180 | 91-180 | 92-180 | R$^c$ | R$^{1c}$ | R$^{4b}$ | R$^{5a}$ | G$^c$ | Z$^a$ |
| 88-181 | 89-181 | 90-181 | 91-181 | 92-181 | R$^a$ | R$^{1a}$ | R$^{4c}$ | R$^{5a}$ | G$^c$ | Z$^a$ |
| 88-182 | 89-182 | 90-182 | 91-182 | 92-182 | R$^b$ | R$^{1a}$ | R$^{4c}$ | R$^{5a}$ | G$^c$ | Z$^a$ |
| 88-183 | 89-183 | 90-183 | 91-183 | 92-183 | R$^c$ | R$^{1a}$ | R$^{4c}$ | R$^{5a}$ | G$^c$ | Z$^a$ |
| 88-184 | 89-184 | 90-184 | 91-184 | 92-184 | R$^a$ | R$^{1b}$ | R$^{4c}$ | R$^{5a}$ | G$^c$ | Z$^a$ |
| 88-185 | 89-185 | 90-185 | 91-185 | 92-185 | R$^b$ | R$^{1b}$ | R$^{4c}$ | R$^{5a}$ | G$^c$ | Z$^a$ |
| 88-186 | 89-186 | 90-186 | 91-186 | 92-186 | R$^c$ | R$^{1b}$ | R$^{4c}$ | R$^{5a}$ | G$^c$ | Z$^a$ |
| 88-187 | 89-187 | 90-187 | 91-187 | 92-187 | R$^a$ | R$^{1c}$ | R$^{4c}$ | R$^{5a}$ | G$^c$ | Z$^a$ |
| 88-188 | 89-188 | 90-188 | 91-188 | 92-188 | R$^b$ | R$^{1c}$ | R$^{4c}$ | R$^{5a}$ | G$^c$ | Z$^a$ |
| 88-189 | 89-189 | 90-189 | 91-189 | 92-189 | R$^c$ | R$^{1c}$ | R$^{4c}$ | R$^{5a}$ | G$^c$ | Z$^a$ |
| 88-190 | 89-190 | 90-190 | 91-190 | 92-190 | R$^a$ | R$^{1a}$ | R$^{4a}$ | R$^{5b}$ | G$^c$ | Z$^a$ |
| 88-191 | 89-191 | 90-191 | 91-191 | 92-191 | R$^b$ | R$^{1a}$ | R$^{4a}$ | R$^{5b}$ | G$^c$ | Z$^a$ |
| 88-192 | 89-192 | 90-192 | 91-192 | 92-192 | R$^c$ | R$^{1a}$ | R$^{4a}$ | R$^{5b}$ | G$^c$ | Z$^a$ |
| 88-193 | 89-193 | 90-193 | 91-193 | 92-193 | R$^a$ | R$^{1b}$ | R$^{4a}$ | R$^{5b}$ | G$^c$ | Z$^a$ |
| 88-194 | 89-194 | 90-194 | 91-194 | 92-194 | R$^b$ | R$^{1b}$ | R$^{4a}$ | R$^{5b}$ | G$^c$ | Z$^a$ |
| 88-195 | 89-195 | 90-195 | 91-195 | 92-195 | R$^c$ | R$^{1b}$ | R$^{4a}$ | R$^{5b}$ | G$^c$ | Z$^a$ |
| 88-196 | 89-196 | 90-196 | 91-196 | 92-196 | R$^a$ | R$^{1c}$ | R$^{4a}$ | R$^{5b}$ | G$^c$ | Z$^a$ |
| 88-197 | 89-197 | 90-197 | 91-197 | 92-197 | R$^b$ | R$^{1c}$ | R$^{4a}$ | R$^{5b}$ | G$^c$ | Z$^a$ |
| 88-198 | 89-198 | 90-198 | 91-198 | 92-198 | R$^c$ | R$^{1c}$ | R$^{4a}$ | R$^{5b}$ | G$^c$ | Z$^a$ |
| 88-199 | 89-199 | 90-199 | 91-199 | 92-199 | R$^a$ | R$^{1a}$ | R$^{4b}$ | R$^{5b}$ | G$^c$ | Z$^a$ |
| 88-200 | 89-200 | 90-200 | 91-200 | 92-200 | R$^b$ | R$^{1a}$ | R$^{4b}$ | R$^{5b}$ | G$^c$ | Z$^a$ |
| 88-201 | 89-201 | 90-201 | 91-201 | 92-201 | R$^c$ | R$^{1a}$ | R$^{4b}$ | R$^{5b}$ | G$^c$ | Z$^a$ |
| 88-202 | 89-202 | 90-202 | 91-202 | 92-202 | R$^a$ | R$^{1b}$ | R$^{4b}$ | R$^{5b}$ | G$^c$ | Z$^a$ |
| 88-203 | 89-203 | 90-203 | 91-203 | 92-203 | R$^b$ | R$^{1b}$ | R$^{4b}$ | R$^{5b}$ | G$^c$ | Z$^a$ |
| 88-204 | 89-204 | 90-204 | 91-204 | 92-204 | R$^c$ | R$^{1b}$ | R$^{4b}$ | R$^{5b}$ | G$^c$ | Z$^a$ |
| 88-205 | 89-205 | 90-205 | 91-205 | 92-205 | R$^a$ | R$^{1c}$ | R$^{4b}$ | R$^{5b}$ | G$^c$ | Z$^a$ |
| 88-206 | 89-206 | 90-206 | 91-206 | 92-206 | R$^b$ | R$^{1c}$ | R$^{4b}$ | R$^{5b}$ | G$^c$ | Z$^a$ |
| 88-207 | 89-207 | 90-207 | 91-207 | 92-207 | R$^c$ | R$^{1c}$ | R$^{4b}$ | R$^{5b}$ | G$^c$ | Z$^a$ |
| 88-208 | 89-208 | 90-208 | 91-208 | 92-208 | R$^a$ | R$^{1a}$ | R$^{4c}$ | R$^{5b}$ | G$^c$ | Z$^a$ |
| 88-209 | 89-209 | 90-209 | 91-209 | 92-209 | R$^b$ | R$^{1a}$ | R$^{4c}$ | R$^{5b}$ | G$^c$ | Z$^a$ |
| 88-210 | 89-210 | 90-210 | 91-210 | 92-210 | R$^c$ | R$^{1a}$ | R$^{4c}$ | R$^{5b}$ | G$^c$ | Z$^a$ |
| 88-211 | 89-211 | 90-211 | 91-211 | 92-211 | R$^a$ | R$^{1b}$ | R$^{4c}$ | R$^{5b}$ | G$^c$ | Z$^a$ |
| 88-212 | 89-212 | 90-212 | 91-212 | 92-212 | R$^b$ | R$^{1b}$ | R$^{4c}$ | R$^{5b}$ | G$^c$ | Z$^a$ |
| 88-213 | 89-213 | 90-213 | 91-213 | 92-213 | R$^c$ | R$^{1b}$ | R$^{4c}$ | R$^{5b}$ | G$^c$ | Z$^a$ |
| 88-214 | 89-214 | 90-214 | 91-214 | 92-214 | R$^a$ | R$^{1c}$ | R$^{4c}$ | R$^{5b}$ | G$^c$ | Z$^a$ |
| 88-215 | 89-215 | 90-215 | 91-215 | 92-215 | R$^b$ | R$^{1c}$ | R$^{4c}$ | R$^{5b}$ | G$^c$ | Z$^a$ |
| 88-216 | 89-216 | 90-216 | 91-216 | 92-216 | R$^c$ | R$^{1c}$ | R$^{4c}$ | R$^{5b}$ | G$^c$ | Z$^a$ |
| 88-217 | 89-217 | 90-217 | 91-217 | 92-217 | R$^a$ | R$^{1a}$ | R$^{4a}$ | R$^{5c}$ | G$^c$ | Z$^a$ |
| 88-218 | 89-218 | 90-218 | 91-218 | 92-218 | R$^b$ | R$^{1a}$ | R$^{4a}$ | R$^{5c}$ | G$^c$ | Z$^a$ |
| 88-219 | 89-219 | 90-219 | 91-219 | 92-219 | R$^c$ | R$^{1a}$ | R$^{4a}$ | R$^{5c}$ | G$^c$ | Z$^a$ |
| 88-220 | 89-220 | 90-220 | 91-220 | 92-220 | R$^a$ | R$^{1b}$ | R$^{4a}$ | R$^{5c}$ | G$^c$ | Z$^a$ |
| 88-221 | 89-221 | 90-221 | 91-221 | 92-221 | R$^b$ | R$^{1b}$ | R$^{4a}$ | R$^{5c}$ | G$^c$ | Z$^a$ |
| 88-222 | 89-222 | 90-222 | 91-222 | 92-222 | R$^c$ | R$^{1b}$ | R$^{4a}$ | R$^{5c}$ | G$^c$ | Z$^a$ |
| 88-223 | 89-223 | 90-223 | 91-223 | 92-223 | R$^a$ | R$^{1c}$ | R$^{4a}$ | R$^{5c}$ | G$^c$ | Z$^a$ |
| 88-224 | 89-224 | 90-224 | 91-224 | 92-224 | R$^b$ | R$^{1c}$ | R$^{4a}$ | R$^{5c}$ | G$^c$ | Z$^a$ |
| 88-225 | 89-225 | 90-225 | 91-225 | 92-225 | R$^c$ | R$^{1c}$ | R$^{4a}$ | R$^{5c}$ | G$^c$ | Z$^a$ |
| 88-226 | 89-226 | 90-226 | 91-226 | 92-226 | R$^a$ | R$^{1a}$ | R$^{4b}$ | R$^{5c}$ | G$^c$ | Z$^a$ |
| 88-227 | 89-227 | 90-227 | 91-227 | 92-227 | R$^b$ | R$^{1a}$ | R$^{4b}$ | R$^{5c}$ | G$^c$ | Z$^a$ |
| 88-228 | 89-228 | 90-228 | 91-228 | 92-228 | R$^c$ | R$^{1a}$ | R$^{4b}$ | R$^{5c}$ | G$^c$ | Z$^a$ |
| 88-229 | 89-229 | 90-229 | 91-229 | 92-229 | R$^a$ | R$^{1b}$ | R$^{4b}$ | R$^{5c}$ | G$^c$ | Z$^a$ |
| 88-230 | 89-230 | 90-230 | 91-230 | 92-230 | R$^b$ | R$^{1b}$ | R$^{4b}$ | R$^{5c}$ | G$^c$ | Z$^a$ |
| 88-231 | 89-231 | 90-231 | 91-231 | 92-231 | R$^c$ | R$^{1b}$ | R$^{4b}$ | R$^{5c}$ | G$^c$ | Z$^a$ |
| 88-232 | 89-232 | 90-232 | 91-232 | 92-232 | R$^a$ | R$^{1c}$ | R$^{4b}$ | R$^{5c}$ | G$^c$ | Z$^a$ |
| 88-233 | 89-233 | 90-233 | 91-233 | 92-233 | R$^b$ | R$^{1c}$ | R$^{4b}$ | R$^{5c}$ | G$^c$ | Z$^a$ |
| 88-234 | 89-234 | 90-234 | 91-234 | 92-234 | R$^c$ | R$^{1c}$ | R$^{4b}$ | R$^{5c}$ | G$^c$ | Z$^a$ |
| 88-235 | 89-235 | 90-235 | 91-235 | 92-235 | R$^a$ | R$^{1a}$ | R$^{4c}$ | R$^{5c}$ | G$^c$ | Z$^a$ |
| 88-236 | 89-236 | 90-236 | 91-236 | 92-236 | R$^b$ | R$^{1a}$ | R$^{4c}$ | R$^{5c}$ | G$^c$ | Z$^a$ |
| 88-237 | 89-237 | 90-237 | 91-237 | 92-237 | R$^c$ | R$^{1a}$ | R$^{4c}$ | R$^{5c}$ | G$^c$ | Z$^a$ |
| 88-238 | 89-238 | 90-238 | 91-238 | 92-238 | R$^a$ | R$^{1b}$ | R$^{4c}$ | R$^{5c}$ | G$^c$ | Z$^a$ |
| 88-239 | 89-239 | 90-239 | 91-239 | 92-239 | R$^b$ | R$^{1b}$ | R$^{4c}$ | R$^{5c}$ | G$^c$ | Z$^a$ |
| 88-240 | 89-240 | 90-240 | 91-240 | 92-240 | R$^c$ | R$^{1b}$ | R$^{4c}$ | R$^{5c}$ | G$^c$ | Z$^a$ |
| 88-241 | 89-241 | 90-241 | 91-241 | 92-241 | R$^a$ | R$^{1c}$ | R$^{4c}$ | R$^{5c}$ | G$^c$ | Z$^a$ |
| 88-242 | 89-242 | 90-242 | 91-242 | 92-242 | R$^b$ | R$^{1c}$ | R$^{4c}$ | R$^{5c}$ | G$^c$ | Z$^a$ |

-continued

| Formulae | | | | | R | R¹ | R⁴ | R⁵ | G | Z |
|---|---|---|---|---|---|---|---|---|---|---|
| 88-243 | 89-243 | 90-243 | 91-243 | 92-243 | Rᶜ | R¹ᶜ | R⁴ᶜ | R⁵ᶜ | Gᶜ | Zᵃ |
| 88-244 | 89-244 | 90-244 | 91-244 | 92-244 | Rᵃ | R¹ᵃ | R⁴ᵃ | R⁵ᵃ | Gᵃ | Zᵇ |
| 88-245 | 89-245 | 90-245 | 91-245 | 92-245 | Rᵇ | R¹ᵃ | R⁴ᵃ | R⁵ᵃ | Gᵃ | Zᵇ |
| 88-246 | 89-246 | 90-246 | 91-246 | 92-246 | Rᶜ | R¹ᵃ | R⁴ᵃ | R⁵ᵃ | Gᵃ | Zᵇ |
| 88-247 | 89-247 | 90-247 | 91-247 | 92-247 | Rᵃ | R¹ᵇ | R⁴ᵃ | R⁵ᵃ | Gᵃ | Zᵇ |
| 88-248 | 89-248 | 90-248 | 91-248 | 92-248 | Rᵇ | R¹ᵇ | R⁴ᵃ | R⁵ᵃ | Gᵃ | Zᵇ |
| 88-249 | 89-249 | 90-249 | 91-249 | 92-249 | Rᶜ | R¹ᵇ | R⁴ᵃ | R⁵ᵃ | Gᵃ | Zᵇ |
| 88-250 | 89-250 | 90-250 | 91-250 | 92-250 | Rᵃ | R¹ᶜ | R⁴ᵃ | R⁵ᵃ | Gᵃ | Zᵇ |
| 88-251 | 89-251 | 90-251 | 91-251 | 92-251 | Rᵇ | R¹ᶜ | R⁴ᵃ | R⁵ᵃ | Gᵃ | Zᵇ |
| 88-252 | 89-252 | 90-252 | 91-252 | 92-252 | Rᶜ | R¹ᶜ | R⁴ᵃ | R⁵ᵃ | Gᵃ | Zᵇ |
| 88-253 | 89-253 | 90-253 | 91-253 | 92-253 | Rᵃ | R¹ᵃ | R⁴ᵇ | R⁵ᵃ | Gᵃ | Zᵇ |
| 88-254 | 89-254 | 90-254 | 91-254 | 92-254 | Rᵇ | R¹ᵃ | R⁴ᵇ | R⁵ᵃ | Gᵃ | Zᵇ |
| 88-255 | 89-255 | 90-255 | 91-255 | 92-255 | Rᶜ | R¹ᵃ | R⁴ᵇ | R⁵ᵃ | Gᵃ | Zᵇ |
| 88-256 | 89-256 | 90-256 | 91-256 | 92-256 | Rᵃ | R¹ᵇ | R⁴ᵇ | R⁵ᵃ | Gᵃ | Zᵇ |
| 88-257 | 89-257 | 90-257 | 91-257 | 92-257 | Rᵇ | R¹ᵇ | R⁴ᵇ | R⁵ᵃ | Gᵃ | Zᵇ |
| 88-258 | 89-258 | 90-258 | 91-258 | 92-258 | Rᶜ | R¹ᵇ | R⁴ᵇ | R⁵ᵃ | Gᵃ | Zᵇ |
| 88-259 | 89-259 | 90-259 | 91-259 | 92-259 | Rᵃ | R¹ᶜ | R⁴ᵇ | R⁵ᵃ | Gᵃ | Zᵇ |
| 88-260 | 89-260 | 90-260 | 91-260 | 92-260 | Rᵇ | R¹ᶜ | R⁴ᵇ | R⁵ᵃ | Gᵃ | Zᵇ |
| 88-261 | 89-261 | 90-261 | 91-261 | 92-261 | Rᶜ | R¹ᶜ | R⁴ᵇ | R⁵ᵃ | Gᵃ | Zᵇ |
| 88-262 | 89-262 | 90-262 | 91-262 | 92-262 | Rᵃ | R¹ᵃ | R⁴ᶜ | R⁵ᵃ | Gᵃ | Zᵇ |
| 88-263 | 89-263 | 90-263 | 91-263 | 92-263 | Rᵇ | R¹ᵃ | R⁴ᶜ | R⁵ᵃ | Gᵃ | Zᵇ |
| 88-264 | 89-264 | 90-264 | 91-264 | 92-264 | Rᶜ | R¹ᵃ | R⁴ᶜ | R⁵ᵃ | Gᵃ | Zᵇ |
| 88-265 | 89-265 | 90-265 | 91-265 | 92-265 | Rᵃ | R¹ᵇ | R⁴ᶜ | R⁵ᵃ | Gᵃ | Zᵇ |
| 88-266 | 89-266 | 90-266 | 91-266 | 92-266 | Rᵇ | R¹ᵇ | R⁴ᶜ | R⁵ᵃ | Gᵃ | Zᵇ |
| 88-267 | 89-267 | 90-267 | 91-267 | 92-267 | Rᶜ | R¹ᵇ | R⁴ᶜ | R⁵ᵃ | Gᵃ | Zᵇ |
| 88-268 | 89-268 | 90-268 | 91-268 | 92-268 | Rᵃ | R¹ᶜ | R⁴ᶜ | R⁵ᵃ | Gᵃ | Zᵇ |
| 88-269 | 89-269 | 90-269 | 91-269 | 92-269 | Rᵇ | R¹ᶜ | R⁴ᶜ | R⁵ᵃ | Gᵃ | Zᵇ |
| 88-270 | 89-270 | 90-270 | 91-270 | 92-270 | Rᶜ | R¹ᶜ | R⁴ᶜ | R⁵ᵃ | Gᵃ | Zᵇ |
| 88-271 | 89-271 | 90-271 | 91-271 | 92-271 | Rᵃ | R¹ᵃ | R⁴ᵃ | R⁵ᵇ | Gᵃ | Zᵇ |
| 88-272 | 89-272 | 90-272 | 91-272 | 92-272 | Rᵇ | R¹ᵃ | R⁴ᵃ | R⁵ᵇ | Gᵃ | Zᵇ |
| 88-273 | 89-273 | 90-273 | 91-273 | 92-273 | Rᶜ | R¹ᵃ | R⁴ᵃ | R⁵ᵇ | Gᵃ | Zᵇ |
| 88-274 | 89-274 | 90-274 | 91-274 | 92-274 | Rᵃ | R¹ᵇ | R⁴ᵃ | R⁵ᵇ | Gᵃ | Zᵇ |
| 88-275 | 89-275 | 90-275 | 91-275 | 92-275 | Rᵇ | R¹ᵇ | R⁴ᵃ | R⁵ᵇ | Gᵃ | Zᵇ |
| 88-276 | 89-276 | 90-276 | 91-276 | 92-276 | Rᶜ | R¹ᵇ | R⁴ᵃ | R⁵ᵇ | Gᵃ | Zᵇ |
| 88-277 | 89-277 | 90-277 | 91-277 | 92-277 | Rᵃ | R¹ᶜ | R⁴ᵃ | R⁵ᵇ | Gᵃ | Zᵇ |
| 88-278 | 89-278 | 90-278 | 91-278 | 92-278 | Rᵇ | R¹ᶜ | R⁴ᵃ | R⁵ᵇ | Gᵃ | Zᵇ |
| 88-279 | 89-279 | 90-279 | 91-279 | 92-279 | Rᶜ | R¹ᶜ | R⁴ᵃ | R⁵ᵇ | Gᵃ | Zᵇ |
| 88-280 | 89-280 | 90-280 | 91-280 | 92-280 | Rᵃ | R¹ᵃ | R⁴ᵇ | R⁵ᵇ | Gᵃ | Zᵇ |
| 88-281 | 89-281 | 90-281 | 91-281 | 92-281 | Rᵇ | R¹ᵃ | R⁴ᵇ | R⁵ᵇ | Gᵃ | Zᵇ |
| 88-282 | 89-282 | 90-282 | 91-282 | 92-282 | Rᶜ | R¹ᵃ | R⁴ᵇ | R⁵ᵇ | Gᵃ | Zᵇ |
| 88-283 | 89-283 | 90-283 | 91-283 | 92-283 | Rᵃ | R¹ᵇ | R⁴ᵇ | R⁵ᵇ | Gᵃ | Zᵇ |
| 88-284 | 89-284 | 90-284 | 91-284 | 92-284 | Rᵇ | R¹ᵇ | R⁴ᵇ | R⁵ᵇ | Gᵃ | Zᵇ |
| 88-285 | 89-285 | 90-285 | 91-285 | 92-285 | Rᶜ | R¹ᵇ | R⁴ᵇ | R⁵ᵇ | Gᵃ | Zᵇ |
| 88-286 | 89-286 | 90-286 | 91-286 | 92-286 | Rᵃ | R¹ᶜ | R⁴ᵇ | R⁵ᵇ | Gᵃ | Zᵇ |
| 88-287 | 89-287 | 90-287 | 91-287 | 92-287 | Rᵇ | R¹ᶜ | R⁴ᵇ | R⁵ᵇ | Gᵃ | Zᵇ |
| 88-288 | 89-288 | 90-288 | 91-288 | 92-288 | Rᶜ | R¹ᶜ | R⁴ᵇ | R⁵ᵇ | Gᵃ | Zᵇ |
| 88-289 | 89-289 | 90-289 | 91-289 | 92-289 | Rᵃ | R¹ᵃ | R⁴ᶜ | R⁵ᵇ | Gᵃ | Zᵇ |
| 88-290 | 89-290 | 90-290 | 91-290 | 92-290 | Rᵇ | R¹ᵃ | R⁴ᶜ | R⁵ᵇ | Gᵃ | Zᵇ |
| 88-291 | 89-291 | 90-291 | 91-291 | 92-291 | Rᶜ | R¹ᵃ | R⁴ᶜ | R⁵ᵇ | Gᵃ | Zᵇ |
| 88-292 | 89-292 | 90-292 | 91-292 | 92-292 | Rᵃ | R¹ᵇ | R⁴ᶜ | R⁵ᵇ | Gᵃ | Zᵇ |
| 88-293 | 89-293 | 90-293 | 91-293 | 92-293 | Rᵇ | R¹ᵇ | R⁴ᶜ | R⁵ᵇ | Gᵃ | Zᵇ |
| 88-294 | 89-294 | 90-294 | 91-294 | 92-294 | Rᶜ | R¹ᵇ | R⁴ᶜ | R⁵ᵇ | Gᵃ | Zᵇ |
| 88-295 | 89-295 | 90-295 | 91-295 | 92-295 | Rᵃ | R¹ᶜ | R⁴ᶜ | R⁵ᵇ | Gᵃ | Zᵇ |
| 88-296 | 89-296 | 90-296 | 91-296 | 92-296 | Rᵇ | R¹ᶜ | R⁴ᶜ | R⁵ᵇ | Gᵃ | Zᵇ |
| 88-297 | 89-297 | 90-297 | 91-297 | 92-297 | Rᶜ | R¹ᶜ | R⁴ᶜ | R⁵ᵇ | Gᵃ | Zᵇ |
| 88-298 | 89-298 | 90-298 | 91-298 | 92-298 | Rᵃ | R¹ᵃ | R⁴ᵃ | R⁵ᶜ | Gᵃ | Zᵇ |
| 88-299 | 89-299 | 90-299 | 91-299 | 92-299 | Rᵇ | R¹ᵃ | R⁴ᵃ | R⁵ᶜ | Gᵃ | Zᵇ |
| 88-300 | 89-300 | 90-300 | 91-300 | 92-300 | Rᶜ | R¹ᵃ | R⁴ᵃ | R⁵ᶜ | Gᵃ | Zᵇ |
| 88-301 | 89-301 | 90-301 | 91-301 | 92-301 | Rᵃ | R¹ᵇ | R⁴ᵃ | R⁵ᶜ | Gᵃ | Zᵇ |
| 88-302 | 89-302 | 90-302 | 91-302 | 92-302 | Rᵇ | R¹ᵇ | R⁴ᵃ | R⁵ᶜ | Gᵃ | Zᵇ |
| 88-303 | 89-303 | 90-303 | 91-303 | 92-303 | Rᶜ | R¹ᵇ | R⁴ᵃ | R⁵ᶜ | Gᵃ | Zᵇ |
| 88-304 | 89-304 | 90-304 | 91-304 | 92-304 | Rᵃ | R¹ᶜ | R⁴ᵃ | R⁵ᶜ | Gᵃ | Zᵇ |
| 88-305 | 89-305 | 90-305 | 91-305 | 92-305 | Rᵇ | R¹ᶜ | R⁴ᵃ | R⁵ᶜ | Gᵃ | Zᵇ |
| 88-306 | 89-306 | 90-306 | 91-306 | 92-306 | Rᶜ | R¹ᶜ | R⁴ᵃ | R⁵ᶜ | Gᵃ | Zᵇ |
| 88-307 | 89-307 | 90-307 | 91-307 | 92-307 | Rᵃ | R¹ᵃ | R⁴ᵇ | R⁵ᶜ | Gᵃ | Zᵇ |
| 88-308 | 89-308 | 90-308 | 91-308 | 92-308 | Rᵇ | R¹ᵃ | R⁴ᵇ | R⁵ᶜ | Gᵃ | Zᵇ |
| 88-309 | 89-309 | 90-309 | 91-309 | 92-309 | Rᶜ | R¹ᵃ | R⁴ᵇ | R⁵ᶜ | Gᵃ | Zᵇ |
| 88-310 | 89-310 | 90-310 | 91-310 | 92-310 | Rᵃ | R¹ᵇ | R⁴ᵇ | R⁵ᶜ | Gᵃ | Zᵇ |
| 88-311 | 89-311 | 90-311 | 91-311 | 92-311 | Rᵇ | R¹ᵇ | R⁴ᵇ | R⁵ᶜ | Gᵃ | Zᵇ |
| 88-312 | 89-312 | 90-312 | 91-312 | 92-312 | Rᶜ | R¹ᵇ | R⁴ᵇ | R⁵ᶜ | Gᵃ | Zᵇ |
| 88-313 | 89-313 | 90-313 | 91-313 | 92-313 | Rᵃ | R¹ᶜ | R⁴ᵇ | R⁵ᶜ | Gᵃ | Zᵇ |
| 88-314 | 89-314 | 90-314 | 91-314 | 92-314 | Rᵇ | R¹ᶜ | R⁴ᵇ | R⁵ᶜ | Gᵃ | Zᵇ |
| 88-315 | 89-315 | 90-315 | 91-315 | 92-315 | Rᶜ | R¹ᶜ | R⁴ᵇ | R⁵ᶜ | Gᵃ | Zᵇ |
| 88-316 | 89-316 | 90-316 | 91-316 | 92-316 | Rᵃ | R¹ᵃ | R⁴ᶜ | R⁵ᶜ | Gᵃ | Zᵇ |
| 88-317 | 89-317 | 90-317 | 91-317 | 92-317 | Rᵇ | R¹ᵃ | R⁴ᶜ | R⁵ᶜ | Gᵃ | Zᵇ |
| 88-318 | 89-318 | 90-318 | 91-318 | 92-318 | Rᶜ | R¹ᵃ | R⁴ᶜ | R⁵ᶜ | Gᵃ | Zᵇ |
| 88-319 | 89-319 | 90-319 | 91-319 | 92-319 | Rᵃ | R¹ᵇ | R⁴ᶜ | R⁵ᶜ | Gᵃ | Zᵇ |

-continued

| | | Formulae | | | R | R¹ | R⁴ | R⁵ | G | Z |
|---|---|---|---|---|---|---|---|---|---|---|
| 88-320 | 89-320 | 90-320 | 91-320 | 92-320 | Rᵇ | R¹ᵇ | R⁴ᶜ | R⁵ᶜ | Gᵃ | Zᵇ |
| 88-321 | 89-321 | 90-321 | 91-321 | 92-321 | Rᶜ | R¹ᵇ | R⁴ᶜ | R⁵ᶜ | Gᵃ | Zᵇ |
| 88-322 | 89-322 | 90-322 | 91-322 | 92-322 | Rᵃ | R¹ᶜ | R⁴ᶜ | R⁵ᶜ | Gᵃ | Zᵇ |
| 88-323 | 89-323 | 90-323 | 91-323 | 92-323 | Rᵇ | R¹ᶜ | R⁴ᶜ | R⁵ᶜ | Gᵃ | Zᵇ |
| 88-324 | 89-324 | 90-324 | 91-324 | 92-324 | Rᶜ | R¹ᶜ | R⁴ᶜ | R⁵ᶜ | Gᵃ | Zᵇ |
| 88-325 | 89-325 | 90-325 | 91-325 | 92-325 | Rᵃ | R¹ᵃ | R⁴ᵃ | R⁵ᵃ | Gᵇ | Zᵇ |
| 88-326 | 89-326 | 90-326 | 91-326 | 92-326 | Rᵇ | R¹ᵃ | R⁴ᵃ | R⁵ᵃ | Gᵇ | Zᵇ |
| 88-327 | 89-327 | 90-327 | 91-327 | 92-327 | Rᶜ | R¹ᵃ | R⁴ᵃ | R⁵ᵃ | Gᵇ | Zᵇ |
| 88-328 | 89-328 | 90-328 | 91-328 | 92-328 | Rᵃ | R¹ᵇ | R⁴ᵃ | R⁵ᵃ | Gᵇ | Zᵇ |
| 88-329 | 89-329 | 90-329 | 91-329 | 92-329 | Rᵇ | R¹ᵇ | R⁴ᵃ | R⁵ᵃ | Gᵇ | Zᵇ |
| 88-330 | 89-330 | 90-330 | 91-330 | 92-330 | Rᶜ | R¹ᵇ | R⁴ᵃ | R⁵ᵃ | Gᵇ | Zᵇ |
| 88-331 | 89-331 | 90-331 | 91-331 | 92-331 | Rᵃ | R¹ᶜ | R⁴ᵃ | R⁵ᵃ | Gᵇ | Zᵇ |
| 88-332 | 89-332 | 90-332 | 91-332 | 92-332 | Rᵇ | R¹ᶜ | R⁴ᵃ | R⁵ᵃ | Gᵇ | Zᵇ |
| 88-333 | 89-333 | 90-333 | 91-333 | 92-333 | Rᶜ | R¹ᶜ | R⁴ᵃ | R⁵ᵃ | Gᵇ | Zᵇ |
| 88-334 | 89-334 | 90-334 | 91-334 | 92-334 | Rᵃ | R¹ᵃ | R⁴ᵇ | R⁵ᵃ | Gᵇ | Zᵇ |
| 88-335 | 89-335 | 90-335 | 91-335 | 92-335 | Rᵇ | R¹ᵃ | R⁴ᵇ | R⁵ᵃ | Gᵇ | Zᵇ |
| 88-336 | 89-336 | 90-336 | 91-336 | 92-336 | Rᶜ | R¹ᵃ | R⁴ᵇ | R⁵ᵃ | Gᵇ | Zᵇ |
| 88-337 | 89-337 | 90-337 | 91-337 | 92-337 | Rᵃ | R¹ᵇ | R⁴ᵇ | R⁵ᵃ | Gᵇ | Zᵇ |
| 88-338 | 89-338 | 90-338 | 91-338 | 92-338 | Rᵇ | R¹ᵇ | R⁴ᵇ | R⁵ᵃ | Gᵇ | Zᵇ |
| 88-339 | 89-339 | 90-339 | 91-339 | 92-339 | Rᶜ | R¹ᵇ | R⁴ᵇ | R⁵ᵃ | Gᵇ | Zᵇ |
| 88-340 | 89-340 | 90-340 | 91-340 | 92-340 | Rᵃ | R¹ᶜ | R⁴ᵇ | R⁵ᵃ | Gᵇ | Zᵇ |
| 88-341 | 89-341 | 90-341 | 91-341 | 92-341 | Rᵇ | R¹ᶜ | R⁴ᵇ | R⁵ᵃ | Gᵇ | Zᵇ |
| 88-342 | 89-342 | 90-342 | 91-342 | 92-342 | Rᶜ | R¹ᶜ | R⁴ᵇ | R⁵ᵃ | Gᵇ | Zᵇ |
| 88-343 | 89-343 | 90-343 | 91-343 | 92-343 | Rᵃ | R¹ᵃ | R⁴ᶜ | R⁵ᵃ | Gᵇ | Zᵇ |
| 88-344 | 89-344 | 90-344 | 91-344 | 92-344 | Rᵇ | R¹ᵃ | R⁴ᶜ | R⁵ᵃ | Gᵇ | Zᵇ |
| 88-345 | 89-345 | 90-345 | 91-345 | 92-345 | Rᶜ | R¹ᵃ | R⁴ᶜ | R⁵ᵃ | Gᵇ | Zᵇ |
| 88-346 | 89-346 | 90-346 | 91-346 | 92-346 | Rᵃ | R¹ᵇ | R⁴ᶜ | R⁵ᵃ | Gᵇ | Zᵇ |
| 88-347 | 89-347 | 90-347 | 91-347 | 92-347 | Rᵇ | R¹ᵇ | R⁴ᶜ | R⁵ᵃ | Gᵇ | Zᵇ |
| 88-348 | 89-348 | 90-348 | 91-348 | 92-348 | Rᶜ | R¹ᵇ | R⁴ᶜ | R⁵ᵃ | Gᵇ | Zᵇ |
| 88-349 | 89-349 | 90-349 | 91-349 | 92-349 | Rᵃ | R¹ᶜ | R⁴ᶜ | R⁵ᵃ | Gᵇ | Zᵇ |
| 88-350 | 89-350 | 90-350 | 91-350 | 92-350 | Rᵇ | R¹ᶜ | R⁴ᶜ | R⁵ᵃ | Gᵇ | Zᵇ |
| 88-351 | 89-351 | 90-351 | 91-351 | 92-351 | Rᶜ | R¹ᶜ | R⁴ᶜ | R⁵ᵃ | Gᵇ | Zᵇ |
| 88-352 | 89-352 | 90-352 | 91-352 | 92-352 | Rᵃ | R¹ᵃ | R⁴ᵃ | R⁵ᵇ | Gᵇ | Zᵇ |
| 88-353 | 89-353 | 90-353 | 91-353 | 92-353 | Rᵇ | R¹ᵃ | R⁴ᵃ | R⁵ᵇ | Gᵇ | Zᵇ |
| 88-354 | 89-354 | 90-354 | 91-354 | 92-354 | Rᶜ | R¹ᵃ | R⁴ᵃ | R⁵ᵇ | Gᵇ | Zᵇ |
| 88-355 | 89-355 | 90-355 | 91-355 | 92-355 | Rᵃ | R¹ᵇ | R⁴ᵃ | R⁵ᵇ | Gᵇ | Zᵇ |
| 88-356 | 89-356 | 90-356 | 91-356 | 92-356 | Rᵇ | R¹ᵇ | R⁴ᵃ | R⁵ᵇ | Gᵇ | Zᵇ |
| 88-357 | 89-357 | 90-357 | 91-357 | 92-357 | Rᶜ | R¹ᵇ | R⁴ᵃ | R⁵ᵇ | Gᵇ | Zᵇ |
| 88-358 | 89-358 | 90-358 | 91-358 | 92-358 | Rᵃ | R¹ᶜ | R⁴ᵃ | R⁵ᵇ | Gᵇ | Zᵇ |
| 88-359 | 89-359 | 90-359 | 91-359 | 92-359 | Rᵇ | R¹ᶜ | R⁴ᵃ | R⁵ᵇ | Gᵇ | Zᵇ |
| 88-360 | 89-360 | 90-360 | 91-360 | 92-360 | Rᶜ | R¹ᶜ | R⁴ᵃ | R⁵ᵇ | Gᵇ | Zᵇ |
| 88-361 | 89-361 | 90-361 | 91-361 | 92-361 | Rᵃ | R¹ᵃ | R⁴ᵇ | R⁵ᵇ | Gᵇ | Zᵇ |
| 88-362 | 89-362 | 90-362 | 91-362 | 92-362 | Rᵇ | R¹ᵃ | R⁴ᵇ | R⁵ᵇ | Gᵇ | Zᵇ |
| 88-363 | 89-363 | 90-363 | 91-363 | 92-363 | Rᶜ | R¹ᵃ | R⁴ᵇ | R⁵ᵇ | Gᵇ | Zᵇ |
| 88-364 | 89-364 | 90-364 | 91-364 | 92-364 | Rᵃ | R¹ᵇ | R⁴ᵇ | R⁵ᵇ | Gᵇ | Zᵇ |
| 88-365 | 89-365 | 90-365 | 91-365 | 92-365 | Rᵇ | R¹ᵇ | R⁴ᵇ | R⁵ᵇ | Gᵇ | Zᵇ |
| 88-366 | 89-366 | 90-366 | 91-366 | 92-366 | Rᶜ | R¹ᵇ | R⁴ᵇ | R⁵ᵇ | Gᵇ | Zᵇ |
| 88-367 | 89-367 | 90-367 | 91-367 | 92-367 | Rᵃ | R¹ᶜ | R⁴ᵇ | R⁵ᵇ | Gᵇ | Zᵇ |
| 88-368 | 89-368 | 90-368 | 91-368 | 92-368 | Rᵇ | R¹ᶜ | R⁴ᵇ | R⁵ᵇ | Gᵇ | Zᵇ |
| 88-369 | 89-369 | 90-369 | 91-369 | 92-369 | Rᶜ | R¹ᶜ | R⁴ᵇ | R⁵ᵇ | Gᵇ | Zᵇ |
| 88-370 | 89-370 | 90-370 | 91-370 | 92-370 | Rᵃ | R¹ᵃ | R⁴ᶜ | R⁵ᵇ | Gᵇ | Zᵇ |
| 88-371 | 89-371 | 90-371 | 91-371 | 92-371 | Rᵇ | R¹ᵃ | R⁴ᶜ | R⁵ᵇ | Gᵇ | Zᵇ |
| 88-372 | 89-372 | 90-372 | 91-372 | 92-372 | Rᶜ | R¹ᵃ | R⁴ᶜ | R⁵ᵇ | Gᵇ | Zᵇ |
| 88-373 | 89-373 | 90-373 | 91-373 | 92-373 | Rᵃ | R¹ᵇ | R⁴ᶜ | R⁵ᵇ | Gᵇ | Zᵇ |
| 88-374 | 89-374 | 90-374 | 91-374 | 92-374 | Rᵇ | R¹ᵇ | R⁴ᶜ | R⁵ᵇ | Gᵇ | Zᵇ |
| 88-375 | 89-375 | 90-375 | 91-375 | 92-375 | Rᶜ | R¹ᵇ | R⁴ᶜ | R⁵ᵇ | Gᵇ | Zᵇ |
| 88-376 | 89-376 | 90-376 | 91-376 | 92-376 | Rᵃ | R¹ᶜ | R⁴ᶜ | R⁵ᵇ | Gᵇ | Zᵇ |
| 88-377 | 89-377 | 90-377 | 91-377 | 92-377 | Rᵇ | R¹ᶜ | R⁴ᶜ | R⁵ᵇ | Gᵇ | Zᵇ |
| 88-378 | 89-378 | 90-378 | 91-378 | 92-378 | Rᶜ | R¹ᶜ | R⁴ᶜ | R⁵ᵇ | Gᵇ | Zᵇ |
| 88-379 | 89-379 | 90-379 | 91-379 | 92-379 | Rᵃ | R¹ᵃ | R⁴ᵃ | R⁵ᶜ | Gᵇ | Zᵇ |
| 88-380 | 89-380 | 90-380 | 91-380 | 92-380 | Rᵇ | R¹ᵃ | R⁴ᵃ | R⁵ᶜ | Gᵇ | Zᵇ |
| 88-381 | 89-381 | 90-381 | 91-381 | 92-381 | Rᶜ | R¹ᵃ | R⁴ᵃ | R⁵ᶜ | Gᵇ | Zᵇ |
| 88-382 | 89-382 | 90-382 | 91-382 | 92-382 | Rᵃ | R¹ᵇ | R⁴ᵃ | R⁵ᶜ | Gᵇ | Zᵇ |
| 88-383 | 89-383 | 90-383 | 91-383 | 92-383 | Rᵇ | R¹ᵇ | R⁴ᵃ | R⁵ᶜ | Gᵇ | Zᵇ |
| 88-384 | 89-384 | 90-384 | 91-384 | 92-384 | Rᶜ | R¹ᵇ | R⁴ᵃ | R⁵ᶜ | Gᵇ | Zᵇ |
| 88-385 | 89-385 | 90-385 | 91-385 | 92-385 | Rᵃ | R¹ᶜ | R⁴ᵃ | R⁵ᶜ | Gᵇ | Zᵇ |
| 88-386 | 89-386 | 90-386 | 91-386 | 92-386 | Rᵇ | R¹ᶜ | R⁴ᵃ | R⁵ᶜ | Gᵇ | Zᵇ |
| 88-387 | 89-387 | 90-387 | 91-387 | 92-387 | Rᶜ | R¹ᶜ | R⁴ᵃ | R⁵ᶜ | Gᵇ | Zᵇ |
| 88-388 | 89-388 | 90-388 | 91-388 | 92-388 | Rᵃ | R¹ᵃ | R⁴ᵇ | R⁵ᶜ | Gᵇ | Zᵇ |
| 88-389 | 89-389 | 90-389 | 91-389 | 92-389 | Rᵇ | R¹ᵃ | R⁴ᵇ | R⁵ᶜ | Gᵇ | Zᵇ |
| 88-390 | 89-390 | 90-390 | 91-390 | 92-390 | Rᶜ | R¹ᵃ | R⁴ᵇ | R⁵ᶜ | Gᵇ | Zᵇ |
| 88-391 | 89-391 | 90-391 | 91-391 | 92-391 | Rᵃ | R¹ᵇ | R⁴ᵇ | R⁵ᶜ | Gᵇ | Zᵇ |
| 88-392 | 89-392 | 90-392 | 91-392 | 92-392 | Rᵇ | R¹ᵇ | R⁴ᵇ | R⁵ᶜ | Gᵇ | Zᵇ |
| 88-393 | 89-393 | 90-393 | 91-393 | 92-393 | Rᶜ | R¹ᵇ | R⁴ᵇ | R⁵ᶜ | Gᵇ | Zᵇ |
| 88-394 | 89-394 | 90-394 | 91-394 | 92-394 | Rᵃ | R¹ᶜ | R⁴ᵇ | R⁵ᶜ | Gᵇ | Zᵇ |
| 88-395 | 89-395 | 90-395 | 91-395 | 92-395 | Rᵇ | R¹ᶜ | R⁴ᵇ | R⁵ᶜ | Gᵇ | Zᵇ |
| 88-396 | 89-396 | 90-396 | 91-396 | 92-396 | Rᶜ | R¹ᶜ | R⁴ᵇ | R⁵ᶜ | Gᵇ | Zᵇ |

-continued

| | | Formulae | | | R | R¹ | R⁴ | R⁵ | G | Z |
|---|---|---|---|---|---|---|---|---|---|---|
| 88-397 | 89-397 | 90-397 | 91-397 | 92-397 | Rᵃ | R¹ᵃ | R⁴ᶜ | R⁵ᶜ | Gᵇ | Zᵇ |
| 88-398 | 89-398 | 90-398 | 91-398 | 92-398 | Rᵇ | R¹ᵃ | R⁴ᶜ | R⁵ᶜ | Gᵇ | Zᵇ |
| 88-399 | 89-399 | 90-399 | 91-399 | 92-399 | Rᶜ | R¹ᵃ | R⁴ᶜ | R⁵ᶜ | Gᵇ | Zᵇ |
| 88-400 | 89-400 | 90-400 | 91-400 | 92-400 | Rᵃ | R¹ᵇ | R⁴ᶜ | R⁵ᶜ | Gᵇ | Zᵇ |
| 88-401 | 89-401 | 90-401 | 91-401 | 92-401 | Rᵇ | R¹ᵇ | R⁴ᶜ | R⁵ᶜ | Gᵇ | Zᵇ |
| 88-402 | 89-402 | 90-402 | 91-402 | 92-402 | Rᶜ | R¹ᵇ | R⁴ᶜ | R⁵ᶜ | Gᵇ | Zᵇ |
| 88-403 | 89-403 | 90-403 | 91-403 | 92-403 | Rᵃ | R¹ᶜ | R⁴ᶜ | R⁵ᶜ | Gᵇ | Zᵇ |
| 88-404 | 89-404 | 90-404 | 91-404 | 92-404 | Rᵇ | R¹ᶜ | R⁴ᶜ | R⁵ᶜ | Gᵇ | Zᵇ |
| 88-405 | 89-405 | 90-405 | 91-405 | 92-405 | Rᶜ | R¹ᶜ | R⁴ᶜ | R⁵ᶜ | Gᵇ | Zᵇ |
| 88-406 | 89-406 | 90-406 | 91-406 | 92-406 | Rᵃ | R¹ᵃ | R⁴ᵃ | R⁵ᵃ | Gᶜ | Zᵇ |
| 88-407 | 89-407 | 90-407 | 91-407 | 92-407 | Rᵇ | R¹ᵃ | R⁴ᵃ | R⁵ᵃ | Gᶜ | Zᵇ |
| 88-408 | 89-408 | 90-408 | 91-408 | 92-408 | Rᶜ | R¹ᵃ | R⁴ᵃ | R⁵ᵃ | Gᶜ | Zᵇ |
| 88-409 | 89-409 | 90-409 | 91-409 | 92-409 | Rᵃ | R¹ᵇ | R⁴ᵃ | R⁵ᵃ | Gᶜ | Zᵇ |
| 88-410 | 89-410 | 90-410 | 91-410 | 92-410 | Rᵇ | R¹ᵇ | R⁴ᵃ | R⁵ᵃ | Gᶜ | Zᵇ |
| 88-411 | 89-411 | 90-411 | 91-411 | 92-411 | Rᶜ | R¹ᵇ | R⁴ᵃ | R⁵ᵃ | Gᶜ | Zᵇ |
| 88-412 | 89-412 | 90-412 | 91-412 | 92-412 | Rᵃ | R¹ᶜ | R⁴ᵃ | R⁵ᵃ | Gᶜ | Zᵇ |
| 88-413 | 89-413 | 90-413 | 91-413 | 92-413 | Rᵇ | R¹ᶜ | R⁴ᵃ | R⁵ᵃ | Gᶜ | Zᵇ |
| 88-414 | 89-414 | 90-414 | 91-414 | 92-414 | Rᶜ | R¹ᶜ | R⁴ᵃ | R⁵ᵃ | Gᶜ | Zᵇ |
| 88-415 | 89-415 | 90-415 | 91-415 | 92-415 | Rᵃ | R¹ᵃ | R⁴ᵇ | R⁵ᵃ | Gᶜ | Zᵇ |
| 88-416 | 89-416 | 90-416 | 91-416 | 92-416 | Rᵇ | R¹ᵃ | R⁴ᵇ | R⁵ᵃ | Gᶜ | Zᵇ |
| 88-417 | 89-417 | 90-417 | 91-417 | 92-417 | Rᶜ | R¹ᵃ | R⁴ᵇ | R⁵ᵃ | Gᶜ | Zᵇ |
| 88-418 | 89-418 | 90-418 | 91-418 | 92-418 | Rᵃ | R¹ᵇ | R⁴ᵇ | R⁵ᵃ | Gᶜ | Zᵇ |
| 88-419 | 89-419 | 90-419 | 91-419 | 92-419 | Rᵇ | R¹ᵇ | R⁴ᵇ | R⁵ᵃ | Gᶜ | Zᵇ |
| 88-420 | 89-420 | 90-420 | 91-420 | 92-420 | Rᶜ | R¹ᵇ | R⁴ᵇ | R⁵ᵃ | Gᶜ | Zᵇ |
| 88-421 | 89-421 | 90-421 | 91-421 | 92-421 | Rᵃ | R¹ᶜ | R⁴ᵇ | R⁵ᵃ | Gᶜ | Zᵇ |
| 88-422 | 89-422 | 90-422 | 91-422 | 92-422 | Rᵇ | R¹ᶜ | R⁴ᵇ | R⁵ᵃ | Gᶜ | Zᵇ |
| 88-423 | 89-423 | 90-423 | 91-423 | 92-423 | Rᶜ | R¹ᶜ | R⁴ᵇ | R⁵ᵃ | Gᶜ | Zᵇ |
| 88-424 | 89-424 | 90-424 | 91-424 | 92-424 | Rᵃ | R¹ᵃ | R⁴ᶜ | R⁵ᵃ | Gᶜ | Zᵇ |
| 88-425 | 89-425 | 90-425 | 91-425 | 92-425 | Rᵇ | R¹ᵃ | R⁴ᶜ | R⁵ᵃ | Gᶜ | Zᵇ |
| 88-426 | 89-426 | 90-426 | 91-426 | 92-426 | Rᶜ | R¹ᵃ | R⁴ᶜ | R⁵ᵃ | Gᶜ | Zᵇ |
| 88-427 | 89-427 | 90-427 | 91-427 | 92-427 | Rᵃ | R¹ᵇ | R⁴ᶜ | R⁵ᵃ | Gᶜ | Zᵇ |
| 88-428 | 89-428 | 90-428 | 91-428 | 92-428 | Rᵇ | R¹ᵇ | R⁴ᶜ | R⁵ᵃ | Gᶜ | Zᵇ |
| 88-429 | 89-429 | 90-429 | 91-429 | 92-429 | Rᶜ | R¹ᵇ | R⁴ᶜ | R⁵ᵃ | Gᶜ | Zᵇ |
| 88-430 | 89-430 | 90-430 | 91-430 | 92-430 | Rᵃ | R¹ᶜ | R⁴ᶜ | R⁵ᵃ | Gᶜ | Zᵇ |
| 88-431 | 89-431 | 90-431 | 91-431 | 92-431 | Rᵇ | R¹ᶜ | R⁴ᶜ | R⁵ᵃ | Gᶜ | Zᵇ |
| 88-432 | 89-432 | 90-432 | 91-432 | 92-432 | Rᶜ | R¹ᶜ | R⁴ᶜ | R⁵ᵃ | Gᶜ | Zᵇ |
| 88-433 | 89-433 | 90-433 | 91-433 | 92-433 | Rᵃ | R¹ᵃ | R⁴ᵃ | R⁵ᵇ | Gᶜ | Zᵇ |
| 88-434 | 89-434 | 90-434 | 91-434 | 92-434 | Rᵇ | R¹ᵃ | R⁴ᵃ | R⁵ᵇ | Gᶜ | Zᵇ |
| 88-435 | 89-435 | 90-435 | 91-435 | 92-435 | Rᶜ | R¹ᵃ | R⁴ᵃ | R⁵ᵇ | Gᶜ | Zᵇ |
| 88-436 | 89-436 | 90-436 | 91-436 | 92-436 | Rᵃ | R¹ᵇ | R⁴ᵃ | R⁵ᵇ | Gᶜ | Zᵇ |
| 88-437 | 89-437 | 90-437 | 91-437 | 92-437 | Rᵇ | R¹ᵇ | R⁴ᵃ | R⁵ᵇ | Gᶜ | Zᵇ |
| 88-438 | 89-438 | 90-438 | 91-438 | 92-438 | Rᶜ | R¹ᵇ | R⁴ᵃ | R⁵ᵇ | Gᶜ | Zᵇ |
| 88-439 | 89-439 | 90-439 | 91-439 | 92-439 | Rᵃ | R¹ᶜ | R⁴ᵃ | R⁵ᵇ | Gᶜ | Zᵇ |
| 88-440 | 89-440 | 90-440 | 91-440 | 92-440 | Rᵇ | R¹ᶜ | R⁴ᵃ | R⁵ᵇ | Gᶜ | Zᵇ |
| 88-441 | 89-441 | 90-441 | 91-441 | 92-441 | Rᶜ | R¹ᶜ | R⁴ᵃ | R⁵ᵇ | Gᶜ | Zᵇ |
| 88-442 | 89-442 | 90-442 | 91-442 | 92-442 | Rᵃ | R¹ᵃ | R⁴ᵇ | R⁵ᵇ | Gᶜ | Zᵇ |
| 88-443 | 89-443 | 90-443 | 91-443 | 92-443 | Rᵇ | R¹ᵃ | R⁴ᵇ | R⁵ᵇ | Gᶜ | Zᵇ |
| 88-444 | 89-444 | 90-444 | 91-444 | 92-444 | Rᶜ | R¹ᵃ | R⁴ᵇ | R⁵ᵇ | Gᶜ | Zᵇ |
| 88-445 | 89-445 | 90-445 | 91-445 | 92-445 | Rᵃ | R¹ᵇ | R⁴ᵇ | R⁵ᵇ | Gᶜ | Zᵇ |
| 88-446 | 89-446 | 90-446 | 91-446 | 92-446 | Rᵇ | R¹ᵇ | R⁴ᵇ | R⁵ᵇ | Gᶜ | Zᵇ |
| 88-447 | 89-447 | 90-447 | 91-447 | 92-447 | Rᶜ | R¹ᵇ | R⁴ᵇ | R⁵ᵇ | Gᶜ | Zᵇ |
| 88-448 | 89-448 | 90-448 | 91-448 | 92-448 | Rᵃ | R¹ᶜ | R⁴ᵇ | R⁵ᵇ | Gᶜ | Zᵇ |
| 88-449 | 89-449 | 90-449 | 91-449 | 92-449 | Rᵇ | R¹ᶜ | R⁴ᵇ | R⁵ᵇ | Gᶜ | Zᵇ |
| 88-450 | 89-450 | 90-450 | 91-450 | 92-450 | Rᶜ | R¹ᶜ | R⁴ᵇ | R⁵ᵇ | Gᶜ | Zᵇ |
| 88-451 | 89-451 | 90-451 | 91-451 | 92-451 | Rᵃ | R¹ᵃ | R⁴ᶜ | R⁵ᵇ | Gᶜ | Zᵇ |
| 88-452 | 89-452 | 90-452 | 91-452 | 92-452 | Rᵇ | R¹ᵃ | R⁴ᶜ | R⁵ᵇ | Gᶜ | Zᵇ |
| 88-453 | 89-453 | 90-453 | 91-453 | 92-453 | Rᶜ | R¹ᵃ | R⁴ᶜ | R⁵ᵇ | Gᶜ | Zᵇ |
| 88-454 | 89-454 | 90-454 | 91-454 | 92-454 | Rᵃ | R¹ᵇ | R⁴ᶜ | R⁵ᵇ | Gᶜ | Zᵇ |
| 88-455 | 89-455 | 90-455 | 91-455 | 92-455 | Rᵇ | R¹ᵇ | R⁴ᶜ | R⁵ᵇ | Gᶜ | Zᵇ |
| 88-456 | 89-456 | 90-456 | 91-456 | 92-456 | Rᶜ | R¹ᵇ | R⁴ᶜ | R⁵ᵇ | Gᶜ | Zᵇ |
| 88-457 | 89-457 | 90-457 | 91-457 | 92-457 | Rᵃ | R¹ᶜ | R⁴ᶜ | R⁵ᵇ | Gᶜ | Zᵇ |
| 88-458 | 89-458 | 90-458 | 91-458 | 92-458 | Rᵇ | R¹ᶜ | R⁴ᶜ | R⁵ᵇ | Gᶜ | Zᵇ |
| 88-459 | 89-459 | 90-459 | 91-459 | 92-459 | Rᶜ | R¹ᶜ | R⁴ᶜ | R⁵ᵇ | Gᶜ | Zᵇ |
| 88-460 | 89-460 | 90-460 | 91-460 | 92-460 | Rᵃ | R¹ᵃ | R⁴ᵃ | R⁵ᶜ | Gᶜ | Zᵇ |
| 88-461 | 89-461 | 90-461 | 91-461 | 92-461 | Rᵇ | R¹ᵃ | R⁴ᵃ | R⁵ᶜ | Gᶜ | Zᵇ |
| 88-462 | 89-462 | 90-462 | 91-462 | 92-462 | Rᶜ | R¹ᵃ | R⁴ᵃ | R⁵ᶜ | Gᶜ | Zᵇ |
| 88-463 | 89-463 | 90-463 | 91-463 | 92-463 | Rᵃ | R¹ᵇ | R⁴ᵃ | R⁵ᶜ | Gᶜ | Zᵇ |
| 88-464 | 89-464 | 90-464 | 91-464 | 92-464 | Rᵇ | R¹ᵇ | R⁴ᵃ | R⁵ᶜ | Gᶜ | Zᵇ |
| 88-465 | 89-465 | 90-465 | 91-465 | 92-465 | Rᶜ | R¹ᵇ | R⁴ᵃ | R⁵ᶜ | Gᶜ | Zᵇ |
| 88-466 | 89-466 | 90-466 | 91-466 | 92-466 | Rᵃ | R¹ᶜ | R⁴ᵃ | R⁵ᶜ | Gᶜ | Zᵇ |
| 88-467 | 89-467 | 90-467 | 91-467 | 92-467 | Rᵇ | R¹ᶜ | R⁴ᵃ | R⁵ᶜ | Gᶜ | Zᵇ |
| 88-468 | 89-468 | 90-468 | 91-468 | 92-468 | Rᶜ | R¹ᶜ | R⁴ᵃ | R⁵ᶜ | Gᶜ | Zᵇ |
| 88-469 | 89-469 | 90-469 | 91-469 | 92-469 | Rᵃ | R¹ᵃ | R⁴ᵇ | R⁵ᶜ | Gᶜ | Zᵇ |
| 88-470 | 89-470 | 90-470 | 91-470 | 92-470 | Rᵇ | R¹ᵃ | R⁴ᵇ | R⁵ᶜ | Gᶜ | Zᵇ |
| 88-471 | 89-471 | 90-471 | 91-471 | 92-471 | Rᶜ | R¹ᵃ | R⁴ᵇ | R⁵ᶜ | Gᶜ | Zᵇ |
| 88-472 | 89-472 | 90-472 | 91-472 | 92-472 | Rᵃ | R¹ᵇ | R⁴ᵇ | R⁵ᶜ | Gᶜ | Zᵇ |
| 88-473 | 89-473 | 90-473 | 91-473 | 92-473 | Rᵇ | R¹ᵇ | R⁴ᵇ | R⁵ᶜ | Gᶜ | Zᵇ |

-continued

| Formulae | | | | | R | R$^1$ | R$^4$ | R$^5$ | G | Z |
|---|---|---|---|---|---|---|---|---|---|---|
| 88-474 | 89-474 | 90-474 | 91-474 | 92-474 | R$^c$ | R$^{1b}$ | R$^{4b}$ | R$^{5c}$ | G$^c$ | Z$^b$ |
| 88-475 | 89-475 | 90-475 | 91-475 | 92-475 | R$^a$ | R$^{1c}$ | R$^{4b}$ | R$^{5c}$ | G$^c$ | Z$^b$ |
| 88-476 | 89-476 | 90-476 | 91-476 | 92-476 | R$^b$ | R$^{1c}$ | R$^{4b}$ | R$^{5c}$ | G$^c$ | Z$^b$ |
| 88-477 | 89-477 | 90-477 | 91-477 | 92-477 | R$^c$ | R$^{1c}$ | R$^{4b}$ | R$^{5c}$ | G$^c$ | Z$^b$ |
| 88-478 | 89-478 | 90-478 | 91-478 | 92-478 | R$^a$ | R$^{1a}$ | R$^{4c}$ | R$^{5c}$ | G$^c$ | Z$^b$ |
| 88-479 | 89-479 | 90-479 | 91-479 | 92-479 | R$^b$ | R$^{1a}$ | R$^{4c}$ | R$^{5c}$ | G$^c$ | Z$^b$ |
| 88-480 | 89-480 | 90-480 | 91-480 | 92-480 | R$^c$ | R$^{1a}$ | R$^{4c}$ | R$^{5c}$ | G$^c$ | Z$^b$ |
| 88-481 | 89-481 | 90-481 | 91-481 | 92-481 | R$^a$ | R$^{1b}$ | R$^{4c}$ | R$^{5c}$ | G$^c$ | Z$^b$ |
| 88-482 | 89-482 | 90-482 | 91-482 | 92-482 | R$^b$ | R$^{1b}$ | R$^{4c}$ | R$^{5c}$ | G$^c$ | Z$^b$ |
| 88-483 | 89-483 | 90-483 | 91-483 | 92-483 | R$^c$ | R$^{1b}$ | R$^{4c}$ | R$^{5c}$ | G$^c$ | Z$^b$ |
| 88-484 | 89-484 | 90-484 | 91-484 | 92-484 | R$^a$ | R$^{1c}$ | R$^{4c}$ | R$^{5c}$ | G$^c$ | Z$^b$ |
| 88-485 | 89-485 | 90-485 | 91-485 | 92-485 | R$^b$ | R$^{1c}$ | R$^{4c}$ | R$^{5c}$ | G$^c$ | Z$^b$ |
| 88-486 | 89-486 | 90-486 | 91-486 | 92-486 | R$^c$ | R$^{1c}$ | R$^{4c}$ | R$^{5c}$ | G$^c$ | Z$^b$ |
| 88-487 | 89-487 | 90-487 | 91-487 | 92-487 | R$^a$ | R$^{1a}$ | R$^{4a}$ | R$^{5a}$ | G$^a$ | Z$^c$ |
| 88-488 | 89-488 | 90-488 | 91-488 | 92-488 | R$^b$ | R$^{1a}$ | R$^{4a}$ | R$^{5a}$ | G$^a$ | Z$^c$ |
| 88-489 | 89-489 | 90-489 | 91-489 | 92-489 | R$^c$ | R$^{1a}$ | R$^{4a}$ | R$^{5a}$ | G$^a$ | Z$^c$ |
| 88-490 | 89-490 | 90-490 | 91-490 | 92-490 | R$^a$ | R$^{1b}$ | R$^{4a}$ | R$^{5a}$ | G$^a$ | Z$^c$ |
| 88-491 | 89-491 | 90-491 | 91-491 | 92-491 | R$^b$ | R$^{1b}$ | R$^{4a}$ | R$^{5a}$ | G$^a$ | Z$^c$ |
| 88-492 | 89-492 | 90-492 | 91-492 | 92-492 | R$^c$ | R$^{1b}$ | R$^{4a}$ | R$^{5a}$ | G$^a$ | Z$^c$ |
| 88-493 | 89-493 | 90-493 | 91-493 | 92-493 | R$^a$ | R$^{1c}$ | R$^{4a}$ | R$^{5a}$ | G$^a$ | Z$^c$ |
| 88-494 | 89-494 | 90-494 | 91-494 | 92-494 | R$^b$ | R$^{1c}$ | R$^{4a}$ | R$^{5a}$ | G$^a$ | Z$^c$ |
| 88-495 | 89-495 | 90-495 | 91-495 | 92-495 | R$^c$ | R$^{1c}$ | R$^{4a}$ | R$^{5a}$ | G$^a$ | Z$^c$ |
| 88-496 | 89-496 | 90-496 | 91-496 | 92-496 | R$^a$ | R$^{1a}$ | R$^{4b}$ | R$^{5a}$ | G$^a$ | Z$^c$ |
| 88-497 | 89-497 | 90-497 | 91-497 | 92-497 | R$^b$ | R$^{1a}$ | R$^{4b}$ | R$^{5a}$ | G$^a$ | Z$^c$ |
| 88-498 | 89-498 | 90-498 | 91-498 | 92-498 | R$^c$ | R$^{1a}$ | R$^{4b}$ | R$^{5a}$ | G$^a$ | Z$^c$ |
| 88-499 | 89-499 | 90-499 | 91-499 | 92-499 | R$^a$ | R$^{1b}$ | R$^{4b}$ | R$^{5a}$ | G$^a$ | Z$^c$ |
| 88-500 | 89-500 | 90-500 | 91-500 | 92-500 | R$^b$ | R$^{1b}$ | R$^{4b}$ | R$^{5a}$ | G$^a$ | Z$^c$ |
| 88-501 | 89-501 | 90-501 | 91-501 | 92-501 | R$^c$ | R$^{1b}$ | R$^{4b}$ | R$^{5a}$ | G$^a$ | Z$^c$ |
| 88-502 | 89-502 | 90-502 | 91-502 | 92-502 | R$^a$ | R$^{1c}$ | R$^{4b}$ | R$^{5a}$ | G$^a$ | Z$^c$ |
| 88-503 | 89-503 | 90-503 | 91-503 | 92-503 | R$^b$ | R$^{1c}$ | R$^{4b}$ | R$^{5a}$ | G$^a$ | Z$^c$ |
| 88-504 | 89-504 | 90-504 | 91-504 | 92-504 | R$^c$ | R$^{1c}$ | R$^{4b}$ | R$^{5a}$ | G$^a$ | Z$^c$ |
| 88-505 | 89-505 | 90-505 | 91-505 | 92-505 | R$^a$ | R$^{1a}$ | R$^{4c}$ | R$^{5a}$ | G$^a$ | Z$^c$ |
| 88-506 | 89-506 | 90-506 | 91-506 | 92-506 | R$^b$ | R$^{1a}$ | R$^{4c}$ | R$^{5a}$ | G$^a$ | Z$^c$ |
| 88-507 | 89-507 | 90-507 | 91-507 | 92-507 | R$^c$ | R$^{1a}$ | R$^{4c}$ | R$^{5a}$ | G$^a$ | Z$^c$ |
| 88-508 | 89-508 | 90-508 | 91-508 | 92-508 | R$^a$ | R$^{1b}$ | R$^{4c}$ | R$^{5a}$ | G$^a$ | Z$^c$ |
| 88-509 | 89-509 | 90-509 | 91-509 | 92-509 | R$^b$ | R$^{1b}$ | R$^{4c}$ | R$^{5a}$ | G$^a$ | Z$^c$ |
| 88-510 | 89-510 | 90-510 | 91-510 | 92-510 | R$^c$ | R$^{1b}$ | R$^{4c}$ | R$^{5a}$ | G$^a$ | Z$^c$ |
| 88-511 | 89-511 | 90-511 | 91-511 | 92-511 | R$^a$ | R$^{1c}$ | R$^{4c}$ | R$^{5a}$ | G$^a$ | Z$^c$ |
| 88-512 | 89-512 | 90-512 | 91-512 | 92-512 | R$^b$ | R$^{1c}$ | R$^{4c}$ | R$^{5a}$ | G$^a$ | Z$^c$ |
| 88-513 | 89-513 | 90-513 | 91-513 | 92-513 | R$^c$ | R$^{1c}$ | R$^{4c}$ | R$^{5a}$ | G$^a$ | Z$^c$ |
| 88-514 | 89-514 | 90-514 | 91-514 | 92-514 | R$^a$ | R$^{1a}$ | R$^{4a}$ | R$^{5b}$ | G$^a$ | Z$^c$ |
| 88-515 | 89-515 | 90-515 | 91-515 | 92-515 | R$^b$ | R$^{1a}$ | R$^{4a}$ | R$^{5b}$ | G$^a$ | Z$^c$ |
| 88-516 | 89-516 | 90-516 | 91-516 | 92-516 | R$^c$ | R$^{1a}$ | R$^{4a}$ | R$^{5b}$ | G$^a$ | Z$^c$ |
| 88-517 | 89-517 | 90-517 | 91-517 | 92-517 | R$^a$ | R$^{1b}$ | R$^{4a}$ | R$^{5b}$ | G$^a$ | Z$^c$ |
| 88-518 | 89-518 | 90-518 | 91-518 | 92-518 | R$^b$ | R$^{1b}$ | R$^{4a}$ | R$^{5b}$ | G$^a$ | Z$^c$ |
| 88-519 | 89-519 | 90-519 | 91-519 | 92-519 | R$^c$ | R$^{1b}$ | R$^{4a}$ | R$^{5b}$ | G$^a$ | Z$^c$ |
| 88-520 | 89-520 | 90-520 | 91-520 | 92-520 | R$^a$ | R$^{1c}$ | R$^{4a}$ | R$^{5b}$ | G$^a$ | Z$^c$ |
| 88-521 | 89-521 | 90-521 | 91-521 | 92-521 | R$^b$ | R$^{1c}$ | R$^{4a}$ | R$^{5b}$ | G$^a$ | Z$^c$ |
| 88-522 | 89-522 | 90-522 | 91-522 | 92-522 | R$^c$ | R$^{1c}$ | R$^{4a}$ | R$^{5b}$ | G$^a$ | Z$^c$ |
| 88-523 | 89-523 | 90-523 | 91-523 | 92-523 | R$^a$ | R$^{1a}$ | R$^{4b}$ | R$^{5b}$ | G$^a$ | Z$^c$ |
| 88-524 | 89-524 | 90-524 | 91-524 | 92-524 | R$^b$ | R$^{1a}$ | R$^{4b}$ | R$^{5b}$ | G$^a$ | Z$^c$ |
| 88-525 | 89-525 | 90-525 | 91-525 | 92-525 | R$^c$ | R$^{1a}$ | R$^{4b}$ | R$^{5b}$ | G$^a$ | Z$^c$ |
| 88-526 | 89-526 | 90-526 | 91-526 | 92-526 | R$^a$ | R$^{1b}$ | R$^{4b}$ | R$^{5b}$ | G$^a$ | Z$^c$ |
| 88-527 | 89-527 | 90-527 | 91-527 | 92-527 | R$^b$ | R$^{1b}$ | R$^{4b}$ | R$^{5b}$ | G$^a$ | Z$^c$ |
| 88-528 | 89-528 | 90-528 | 91-528 | 92-528 | R$^c$ | R$^{1b}$ | R$^{4b}$ | R$^{5b}$ | G$^a$ | Z$^c$ |
| 88-529 | 89-529 | 90-529 | 91-529 | 92-529 | R$^a$ | R$^{1c}$ | R$^{4b}$ | R$^{5b}$ | G$^a$ | Z$^c$ |
| 88-530 | 89-530 | 90-530 | 91-530 | 92-530 | R$^b$ | R$^{1c}$ | R$^{4b}$ | R$^{5b}$ | G$^a$ | Z$^c$ |
| 88-531 | 89-531 | 90-531 | 91-531 | 92-531 | R$^c$ | R$^{1c}$ | R$^{4b}$ | R$^{5b}$ | G$^a$ | Z$^c$ |
| 88-532 | 89-532 | 90-532 | 91-532 | 92-532 | R$^a$ | R$^{1a}$ | R$^{4c}$ | R$^{5b}$ | G$^a$ | Z$^c$ |
| 88-533 | 89-533 | 90-533 | 91-533 | 92-533 | R$^b$ | R$^{1a}$ | R$^{4c}$ | R$^{5b}$ | G$^a$ | Z$^c$ |
| 88-534 | 89-534 | 90-534 | 91-534 | 92-534 | R$^c$ | R$^{1a}$ | R$^{4c}$ | R$^{5b}$ | G$^a$ | Z$^c$ |
| 88-535 | 89-535 | 90-535 | 91-535 | 92-535 | R$^a$ | R$^{1b}$ | R$^{4c}$ | R$^{5b}$ | G$^a$ | Z$^c$ |
| 88-536 | 89-536 | 90-536 | 91-536 | 92-536 | R$^b$ | R$^{1b}$ | R$^{4c}$ | R$^{5b}$ | G$^a$ | Z$^c$ |
| 88-537 | 89-537 | 90-537 | 91-537 | 92-537 | R$^c$ | R$^{1b}$ | R$^{4c}$ | R$^{5b}$ | G$^a$ | Z$^c$ |
| 88-538 | 89-538 | 90-538 | 91-538 | 92-538 | R$^a$ | R$^{1c}$ | R$^{4c}$ | R$^{5b}$ | G$^a$ | Z$^c$ |
| 88-539 | 89-539 | 90-539 | 91-539 | 92-539 | R$^b$ | R$^{1c}$ | R$^{4c}$ | R$^{5b}$ | G$^a$ | Z$^c$ |
| 88-540 | 89-540 | 90-540 | 91-540 | 92-540 | R$^c$ | R$^{1c}$ | R$^{4c}$ | R$^{5b}$ | G$^a$ | Z$^c$ |
| 88-541 | 89-541 | 90-541 | 91-541 | 92-541 | R$^a$ | R$^{1a}$ | R$^{4a}$ | R$^{5c}$ | G$^a$ | Z$^c$ |
| 88-542 | 89-542 | 90-542 | 91-542 | 92-542 | R$^b$ | R$^{1a}$ | R$^{4a}$ | R$^{5c}$ | G$^a$ | Z$^c$ |
| 88-543 | 89-543 | 90-543 | 91-543 | 92-543 | R$^c$ | R$^{1a}$ | R$^{4a}$ | R$^{5c}$ | G$^a$ | Z$^c$ |
| 88-544 | 89-544 | 90-544 | 91-544 | 92-544 | R$^a$ | R$^{1b}$ | R$^{4a}$ | R$^{5c}$ | G$^a$ | Z$^c$ |
| 88-545 | 89-545 | 90-545 | 91-545 | 92-545 | R$^b$ | R$^{1b}$ | R$^{4a}$ | R$^{5c}$ | G$^a$ | Z$^c$ |
| 88-546 | 89-546 | 90-546 | 91-546 | 92-546 | R$^c$ | R$^{1b}$ | R$^{4a}$ | R$^{5c}$ | G$^a$ | Z$^c$ |
| 88-547 | 89-547 | 90-547 | 91-547 | 92-547 | R$^a$ | R$^{1c}$ | R$^{4a}$ | R$^{5c}$ | G$^a$ | Z$^c$ |
| 88-548 | 89-548 | 90-548 | 91-548 | 92-548 | R$^b$ | R$^{1c}$ | R$^{4a}$ | R$^{5c}$ | G$^a$ | Z$^c$ |
| 88-549 | 89-549 | 90-549 | 91-549 | 92-549 | R$^c$ | R$^{1c}$ | R$^{4b}$ | R$^{5c}$ | G$^a$ | Z$^c$ |
| 88-550 | 89-550 | 90-550 | 91-550 | 92-550 | R$^a$ | R$^{1a}$ | R$^{4b}$ | R$^{5c}$ | G$^a$ | Z$^c$ |

-continued

| Formulae | | | | | R | R$^1$ | R$^4$ | R$^5$ | G | Z |
|---|---|---|---|---|---|---|---|---|---|---|
| 88-551 | 89-551 | 90-551 | 91-551 | 92-551 | R$^b$ | R$^{1a}$ | R$^{4b}$ | R$^{5c}$ | G$^a$ | Z$^c$ |
| 88-552 | 89-552 | 90-552 | 91-552 | 92-552 | R$^c$ | R$^{1a}$ | R$^{4b}$ | R$^{5c}$ | G$^a$ | Z$^c$ |
| 88-553 | 89-553 | 90-553 | 91-553 | 92-553 | R$^a$ | R$^{1b}$ | R$^{4b}$ | R$^{5c}$ | G$^a$ | Z$^c$ |
| 88-554 | 89-554 | 90-554 | 91-554 | 92-554 | R$^b$ | R$^{1b}$ | R$^{4b}$ | R$^{5c}$ | G$^a$ | Z$^c$ |
| 88-555 | 89-555 | 90-555 | 91-555 | 92-555 | R$^c$ | R$^{1b}$ | R$^{4b}$ | R$^{5c}$ | G$^a$ | Z$^c$ |
| 88-556 | 89-556 | 90-556 | 91-556 | 92-556 | R$^a$ | R$^{1c}$ | R$^{4b}$ | R$^{5c}$ | G$^a$ | Z$^c$ |
| 88-557 | 89-557 | 90-557 | 91-557 | 92-557 | R$^b$ | R$^{1c}$ | R$^{4b}$ | R$^{5c}$ | G$^a$ | Z$^c$ |
| 88-558 | 89-558 | 90-558 | 91-558 | 92-558 | R$^c$ | R$^{1c}$ | R$^{4b}$ | R$^{5c}$ | G$^a$ | Z$^c$ |
| 88-559 | 89-559 | 90-559 | 91-559 | 92-559 | R$^a$ | R$^{1a}$ | R$^{4c}$ | R$^{5c}$ | G$^a$ | Z$^c$ |
| 88-560 | 89-560 | 90-560 | 91-560 | 92-560 | R$^b$ | R$^{1a}$ | R$^{4c}$ | R$^{5c}$ | G$^a$ | Z$^c$ |
| 88-561 | 89-561 | 90-561 | 91-561 | 92-561 | R$^c$ | R$^{1a}$ | R$^{4c}$ | R$^{5c}$ | G$^a$ | Z$^c$ |
| 88-562 | 89-562 | 90-562 | 91-562 | 92-562 | R$^a$ | R$^{1b}$ | R$^{4c}$ | R$^{5c}$ | G$^a$ | Z$^c$ |
| 88-563 | 89-563 | 90-563 | 91-563 | 92-563 | R$^b$ | R$^{1b}$ | R$^{4c}$ | R$^{5c}$ | G$^a$ | Z$^c$ |
| 88-564 | 89-564 | 90-564 | 91-564 | 92-564 | R$^c$ | R$^{1b}$ | R$^{4c}$ | R$^{5c}$ | G$^a$ | Z$^c$ |
| 88-565 | 89-565 | 90-565 | 91-565 | 92-565 | R$^a$ | R$^{1c}$ | R$^{4c}$ | R$^{5c}$ | G$^a$ | Z$^c$ |
| 88-566 | 89-566 | 90-566 | 91-566 | 92-566 | R$^b$ | R$^{1c}$ | R$^{4c}$ | R$^{5c}$ | G$^a$ | Z$^c$ |
| 88-567 | 89-567 | 90-567 | 91-567 | 92-567 | R$^c$ | R$^{1c}$ | R$^{4c}$ | R$^{5c}$ | G$^a$ | Z$^c$ |
| 88-568 | 89-568 | 90-568 | 91-568 | 92-568 | R$^a$ | R$^{1a}$ | R$^{4a}$ | R$^{5a}$ | G$^b$ | Z$^c$ |
| 88-569 | 89-569 | 90-569 | 91-569 | 92-569 | R$^b$ | R$^{1a}$ | R$^{4a}$ | R$^{5a}$ | G$^b$ | Z$^c$ |
| 88-570 | 89-570 | 90-570 | 91-570 | 92-570 | R$^c$ | R$^{1a}$ | R$^{4a}$ | R$^{5a}$ | G$^b$ | Z$^c$ |
| 88-571 | 89-571 | 90-571 | 91-571 | 92-571 | R$^a$ | R$^{1b}$ | R$^{4a}$ | R$^{5a}$ | G$^b$ | Z$^c$ |
| 88-572 | 89-572 | 90-572 | 91-572 | 92-572 | R$^b$ | R$^{1b}$ | R$^{4a}$ | R$^{5a}$ | G$^b$ | Z$^c$ |
| 88-573 | 89-573 | 90-573 | 91-573 | 92-573 | R$^c$ | R$^{1b}$ | R$^{4a}$ | R$^{5a}$ | G$^b$ | Z$^c$ |
| 88-574 | 89-574 | 90-574 | 91-574 | 92-574 | R$^a$ | R$^{1c}$ | R$^{4a}$ | R$^{5a}$ | G$^b$ | Z$^c$ |
| 88-575 | 89-575 | 90-575 | 91-575 | 92-575 | R$^b$ | R$^{1c}$ | R$^{4a}$ | R$^{5a}$ | G$^b$ | Z$^c$ |
| 88-576 | 89-576 | 90-576 | 91-576 | 92-576 | R$^c$ | R$^{1c}$ | R$^{4a}$ | R$^{5a}$ | G$^b$ | Z$^c$ |
| 88-577 | 89-577 | 90-577 | 91-577 | 92-577 | R$^a$ | R$^{1a}$ | R$^{4b}$ | R$^{5a}$ | G$^b$ | Z$^c$ |
| 88-578 | 89-578 | 90-578 | 91-578 | 92-578 | R$^b$ | R$^{1a}$ | R$^{4b}$ | R$^{5a}$ | G$^b$ | Z$^c$ |
| 88-579 | 89-579 | 90-579 | 91-579 | 92-579 | R$^c$ | R$^{1a}$ | R$^{4b}$ | R$^{5a}$ | G$^b$ | Z$^c$ |
| 88-580 | 89-580 | 90-580 | 91-580 | 92-580 | R$^a$ | R$^{1b}$ | R$^{4b}$ | R$^{5a}$ | G$^b$ | Z$^c$ |
| 88-581 | 89-581 | 90-581 | 91-581 | 92-581 | R$^b$ | R$^{1b}$ | R$^{4b}$ | R$^{5a}$ | G$^b$ | Z$^c$ |
| 88-582 | 89-582 | 90-582 | 91-582 | 92-582 | R$^c$ | R$^{1b}$ | R$^{4b}$ | R$^{5a}$ | G$^b$ | Z$^c$ |
| 88-583 | 89-583 | 90-583 | 91-583 | 92-583 | R$^a$ | R$^{1c}$ | R$^{4b}$ | R$^{5a}$ | G$^b$ | Z$^c$ |
| 88-584 | 89-584 | 90-584 | 91-584 | 92-584 | R$^b$ | R$^{1c}$ | R$^{4b}$ | R$^{5a}$ | G$^b$ | Z$^c$ |
| 88-585 | 89-585 | 90-585 | 91-585 | 92-585 | R$^c$ | R$^{1c}$ | R$^{4b}$ | R$^{5a}$ | G$^b$ | Z$^c$ |
| 88-586 | 89-586 | 90-586 | 91-586 | 92-586 | R$^a$ | R$^{1a}$ | R$^{4c}$ | R$^{5a}$ | G$^b$ | Z$^c$ |
| 88-587 | 89-587 | 90-587 | 91-587 | 92-587 | R$^b$ | R$^{1a}$ | R$^{4c}$ | R$^{5a}$ | G$^b$ | Z$^c$ |
| 88-588 | 89-588 | 90-588 | 91-588 | 92-588 | R$^c$ | R$^{1a}$ | R$^{4c}$ | R$^{5a}$ | G$^b$ | Z$^c$ |
| 88-589 | 89-589 | 90-589 | 91-589 | 92-589 | R$^a$ | R$^{1b}$ | R$^{4c}$ | R$^{5a}$ | G$^b$ | Z$^c$ |
| 88-590 | 89-590 | 90-590 | 91-590 | 92-590 | R$^b$ | R$^{1b}$ | R$^{4c}$ | R$^{5a}$ | G$^b$ | Z$^c$ |
| 88-591 | 89-591 | 90-591 | 91-591 | 92-591 | R$^c$ | R$^{1b}$ | R$^{4c}$ | R$^{5a}$ | G$^b$ | Z$^c$ |
| 88-592 | 89-592 | 90-592 | 91-592 | 92-592 | R$^a$ | R$^{1c}$ | R$^{4c}$ | R$^{5a}$ | G$^b$ | Z$^c$ |
| 88-593 | 89-593 | 90-593 | 91-593 | 92-593 | R$^b$ | R$^{1c}$ | R$^{4c}$ | R$^{5a}$ | G$^b$ | Z$^c$ |
| 88-594 | 89-594 | 90-594 | 91-594 | 92-594 | R$^c$ | R$^{1c}$ | R$^{4c}$ | R$^{5a}$ | G$^b$ | Z$^c$ |
| 88-595 | 89-595 | 90-595 | 91-595 | 92-595 | R$^a$ | R$^{1a}$ | R$^{4a}$ | R$^{5b}$ | G$^b$ | Z$^c$ |
| 88-596 | 89-596 | 90-596 | 91-596 | 92-596 | R$^b$ | R$^{1a}$ | R$^{4a}$ | R$^{5b}$ | G$^b$ | Z$^c$ |
| 88-597 | 89-597 | 90-597 | 91-597 | 92-597 | R$^c$ | R$^{1a}$ | R$^{4a}$ | R$^{5b}$ | G$^b$ | Z$^c$ |
| 88-598 | 89-598 | 90-598 | 91-598 | 92-598 | R$^a$ | R$^{1b}$ | R$^{4a}$ | R$^{5b}$ | G$^b$ | Z$^c$ |
| 88-599 | 89-599 | 90-599 | 91-599 | 92-599 | R$^b$ | R$^{1b}$ | R$^{4a}$ | R$^{5b}$ | G$^b$ | Z$^c$ |
| 88-600 | 89-600 | 90-600 | 91-600 | 92-600 | R$^c$ | R$^{1b}$ | R$^{4a}$ | R$^{5b}$ | G$^b$ | Z$^c$ |
| 88-601 | 89-601 | 90-601 | 91-601 | 92-601 | R$^a$ | R$^{1c}$ | R$^{4a}$ | R$^{5b}$ | G$^b$ | Z$^c$ |
| 88-602 | 89-602 | 90-602 | 91-602 | 92-602 | R$^b$ | R$^{1c}$ | R$^{4a}$ | R$^{5b}$ | G$^b$ | Z$^c$ |
| 88-603 | 89-603 | 90-603 | 91-603 | 92-603 | R$^c$ | R$^{1c}$ | R$^{4a}$ | R$^{5b}$ | G$^b$ | Z$^c$ |
| 88-604 | 89-604 | 90-604 | 91-604 | 92-604 | R$^a$ | R$^{1a}$ | R$^{4b}$ | R$^{5b}$ | G$^b$ | Z$^c$ |
| 88-605 | 89-605 | 90-605 | 91-605 | 92-605 | R$^b$ | R$^{1a}$ | R$^{4b}$ | R$^{5b}$ | G$^b$ | Z$^c$ |
| 88-606 | 89-606 | 90-606 | 91-606 | 92-606 | R$^c$ | R$^{1a}$ | R$^{4b}$ | R$^{5b}$ | G$^b$ | Z$^c$ |
| 88-607 | 89-607 | 90-607 | 91-607 | 92-607 | R$^a$ | R$^{1b}$ | R$^{4b}$ | R$^{5b}$ | G$^b$ | Z$^c$ |
| 88-608 | 89-608 | 90-608 | 91-608 | 92-608 | R$^b$ | R$^{1b}$ | R$^{4b}$ | R$^{5b}$ | G$^b$ | Z$^c$ |
| 88-609 | 89-609 | 90-609 | 91-609 | 92-609 | R$^c$ | R$^{1b}$ | R$^{4b}$ | R$^{5b}$ | G$^b$ | Z$^c$ |
| 88-610 | 89-610 | 90-610 | 91-610 | 92-610 | R$^a$ | R$^{1c}$ | R$^{4b}$ | R$^{5b}$ | G$^b$ | Z$^c$ |
| 88-611 | 89-611 | 90-611 | 91-611 | 92-611 | R$^b$ | R$^{1c}$ | R$^{4b}$ | R$^{5b}$ | G$^b$ | Z$^c$ |
| 88-612 | 89-612 | 90-612 | 91-612 | 92-612 | R$^c$ | R$^{1c}$ | R$^{4b}$ | R$^{5b}$ | G$^b$ | Z$^c$ |
| 88-613 | 89-613 | 90-613 | 91-613 | 92-613 | R$^a$ | R$^{1a}$ | R$^{4c}$ | R$^{5b}$ | G$^b$ | Z$^c$ |
| 88-614 | 89-614 | 90-614 | 91-614 | 92-614 | R$^b$ | R$^{1a}$ | R$^{4c}$ | R$^{5b}$ | G$^b$ | Z$^c$ |
| 88-615 | 89-615 | 90-615 | 91-615 | 92-615 | R$^c$ | R$^{1a}$ | R$^{4c}$ | R$^{5b}$ | G$^b$ | Z$^c$ |
| 88-616 | 89-616 | 90-616 | 91-616 | 92-616 | R$^a$ | R$^{1b}$ | R$^{4c}$ | R$^{5b}$ | G$^b$ | Z$^c$ |
| 88-617 | 89-617 | 90-617 | 91-617 | 92-617 | R$^b$ | R$^{1b}$ | R$^{4c}$ | R$^{5b}$ | G$^b$ | Z$^c$ |
| 88-618 | 89-618 | 90-618 | 91-618 | 92-618 | R$^c$ | R$^{1b}$ | R$^{4c}$ | R$^{5b}$ | G$^b$ | Z$^c$ |
| 88-619 | 89-619 | 90-619 | 91-619 | 92-619 | R$^a$ | R$^{1c}$ | R$^{4c}$ | R$^{5b}$ | G$^b$ | Z$^c$ |
| 88-620 | 89-620 | 90-620 | 91-620 | 92-620 | R$^b$ | R$^{1c}$ | R$^{4c}$ | R$^{5b}$ | G$^b$ | Z$^c$ |
| 88-621 | 89-621 | 90-621 | 91-621 | 92-621 | R$^c$ | R$^{1c}$ | R$^{4c}$ | R$^{5b}$ | G$^b$ | Z$^c$ |
| 88-622 | 89-622 | 90-622 | 91-622 | 92-622 | R$^a$ | R$^{1a}$ | R$^{4a}$ | R$^{5c}$ | G$^b$ | Z$^c$ |
| 88-623 | 89-623 | 90-623 | 91-623 | 92-623 | R$^b$ | R$^{1a}$ | R$^{4a}$ | R$^{5c}$ | G$^b$ | Z$^c$ |
| 88-624 | 89-624 | 90-624 | 91-624 | 92-624 | R$^c$ | R$^{1a}$ | R$^{4a}$ | R$^{5c}$ | G$^b$ | Z$^c$ |
| 88-625 | 89-625 | 90-625 | 91-625 | 92-625 | R$^a$ | R$^{1b}$ | R$^{4a}$ | R$^{5c}$ | G$^b$ | Z$^c$ |
| 88-626 | 89-626 | 90-626 | 91-626 | 92-626 | R$^b$ | R$^{1b}$ | R$^{4a}$ | R$^{5c}$ | G$^b$ | Z$^c$ |
| 88-627 | 89-627 | 90-627 | 91-627 | 92-627 | R$^c$ | R$^{1b}$ | R$^{4a}$ | R$^{5c}$ | G$^b$ | Z$^c$ |

-continued

| Formulae | | | | | R | R¹ | R⁴ | R⁵ | G | Z |
|---|---|---|---|---|---|---|---|---|---|---|
| 88-628 | 89-628 | 90-628 | 91-628 | 92-628 | Rᵃ | R¹ᶜ | R⁴ᵃ | R⁵ᶜ | Gᵇ | Zᶜ |
| 88-629 | 89-629 | 90-629 | 91-629 | 92-629 | Rᵇ | R¹ᶜ | R⁴ᵃ | R⁵ᶜ | Gᵇ | Zᶜ |
| 88-630 | 89-630 | 90-630 | 91-630 | 92-630 | Rᶜ | R¹ᶜ | R⁴ᵃ | R⁵ᶜ | Gᵇ | Zᶜ |
| 88-631 | 89-631 | 90-631 | 91-631 | 92-631 | Rᵃ | R¹ᵃ | R⁴ᵇ | R⁵ᶜ | Gᵇ | Zᶜ |
| 88-632 | 89-632 | 90-632 | 91-632 | 92-632 | Rᵇ | R¹ᵃ | R⁴ᵇ | R⁵ᶜ | Gᵇ | Zᶜ |
| 88-633 | 89-633 | 90-633 | 91-633 | 92-633 | Rᶜ | R¹ᵃ | R⁴ᵇ | R⁵ᶜ | Gᵇ | Zᶜ |
| 88-634 | 89-634 | 90-634 | 91-634 | 92-634 | Rᵃ | R¹ᵇ | R⁴ᵇ | R⁵ᶜ | Gᵇ | Zᶜ |
| 88-635 | 89-635 | 90-635 | 91-635 | 92-635 | Rᵇ | R¹ᵇ | R⁴ᵇ | R⁵ᶜ | Gᵇ | Zᶜ |
| 88-636 | 89-636 | 90-636 | 91-636 | 92-636 | Rᶜ | R¹ᵇ | R⁴ᵇ | R⁵ᶜ | Gᵇ | Zᶜ |
| 88-637 | 89-637 | 90-637 | 91-637 | 92-637 | Rᵃ | R¹ᶜ | R⁴ᵇ | R⁵ᶜ | Gᵇ | Zᶜ |
| 88-638 | 89-638 | 90-638 | 91-638 | 92-638 | Rᵇ | R¹ᶜ | R⁴ᵇ | R⁵ᶜ | Gᵇ | Zᶜ |
| 88-639 | 89-639 | 90-639 | 91-639 | 92-639 | Rᶜ | R¹ᶜ | R⁴ᵇ | R⁵ᶜ | Gᵇ | Zᶜ |
| 88-640 | 89-640 | 90-640 | 91-640 | 92-640 | Rᵃ | R¹ᵃ | R⁴ᶜ | R⁵ᶜ | Gᵇ | Zᶜ |
| 88-641 | 89-641 | 90-641 | 91-641 | 92-641 | Rᵇ | R¹ᵃ | R⁴ᶜ | R⁵ᶜ | Gᵇ | Zᶜ |
| 88-642 | 89-642 | 90-642 | 91-642 | 92-642 | Rᶜ | R¹ᵃ | R⁴ᶜ | R⁵ᶜ | Gᵇ | Zᶜ |
| 88-643 | 89-643 | 90-643 | 91-643 | 92-643 | Rᵃ | R¹ᵇ | R⁴ᶜ | R⁵ᶜ | Gᵇ | Zᶜ |
| 88-644 | 89-644 | 90-644 | 91-644 | 92-644 | Rᵇ | R¹ᵇ | R⁴ᶜ | R⁵ᶜ | Gᵇ | Zᶜ |
| 88-645 | 89-645 | 90-645 | 91-645 | 92-645 | Rᶜ | R¹ᵇ | R⁴ᶜ | R⁵ᶜ | Gᵇ | Zᶜ |
| 88-646 | 89-646 | 90-646 | 91-646 | 92-646 | Rᵃ | R¹ᶜ | R⁴ᶜ | R⁵ᶜ | Gᵇ | Zᶜ |
| 88-647 | 89-647 | 90-647 | 91-647 | 92-647 | Rᵇ | R¹ᶜ | R⁴ᶜ | R⁵ᶜ | Gᵇ | Zᶜ |
| 88-648 | 89-648 | 90-648 | 91-648 | 92-648 | Rᶜ | R¹ᶜ | R⁴ᶜ | R⁵ᶜ | Gᵇ | Zᶜ |
| 88-649 | 89-649 | 90-649 | 91-649 | 92-649 | Rᵃ | R¹ᵃ | R⁴ᵃ | R⁵ᵃ | Gᶜ | Zᶜ |
| 88-650 | 89-650 | 90-650 | 91-650 | 92-650 | Rᵇ | R¹ᵃ | R⁴ᵃ | R⁵ᵃ | Gᶜ | Zᶜ |
| 88-651 | 89-651 | 90-651 | 91-651 | 92-651 | Rᶜ | R¹ᵃ | R⁴ᵃ | R⁵ᵃ | Gᶜ | Zᶜ |
| 88-652 | 89-652 | 90-652 | 91-652 | 92-652 | Rᵃ | R¹ᵇ | R⁴ᵃ | R⁵ᵃ | Gᶜ | Zᶜ |
| 88-653 | 89-653 | 90-653 | 91-653 | 92-653 | Rᵇ | R¹ᵇ | R⁴ᵃ | R⁵ᵃ | Gᶜ | Zᶜ |
| 88-654 | 89-654 | 90-654 | 91-654 | 92-654 | Rᶜ | R¹ᵇ | R⁴ᵃ | R⁵ᵃ | Gᶜ | Zᶜ |
| 88-655 | 89-655 | 90-655 | 91-655 | 92-655 | Rᵃ | R¹ᶜ | R⁴ᵃ | R⁵ᵃ | Gᶜ | Zᶜ |
| 88-656 | 89-656 | 90-656 | 91-656 | 92-656 | Rᵇ | R¹ᶜ | R⁴ᵃ | R⁵ᵃ | Gᶜ | Zᶜ |
| 88-657 | 89-657 | 90-657 | 91-657 | 92-657 | Rᶜ | R¹ᶜ | R⁴ᵃ | R⁵ᵃ | Gᶜ | Zᶜ |
| 88-658 | 89-658 | 90-658 | 91-658 | 92-658 | Rᵃ | R¹ᵃ | R⁴ᵇ | R⁵ᵃ | Gᶜ | Zᶜ |
| 88-659 | 89-659 | 90-659 | 91-659 | 92-659 | Rᵇ | R¹ᵃ | R⁴ᵇ | R⁵ᵃ | Gᶜ | Zᶜ |
| 88-660 | 89-660 | 90-660 | 91-660 | 92-660 | Rᶜ | R¹ᵃ | R⁴ᵇ | R⁵ᵃ | Gᶜ | Zᶜ |
| 88-661 | 89-661 | 90-661 | 91-661 | 92-661 | Rᵃ | R¹ᵇ | R⁴ᵇ | R⁵ᵃ | Gᶜ | Zᶜ |
| 88-662 | 89-662 | 90-662 | 91-662 | 92-662 | Rᵇ | R¹ᵇ | R⁴ᵇ | R⁵ᵃ | Gᶜ | Zᶜ |
| 88-663 | 89-663 | 90-663 | 91-663 | 92-663 | Rᶜ | R¹ᵇ | R⁴ᵇ | R⁵ᵃ | Gᶜ | Zᶜ |
| 88-664 | 89-664 | 90-664 | 91-664 | 92-664 | Rᵃ | R¹ᶜ | R⁴ᵇ | R⁵ᵃ | Gᶜ | Zᶜ |
| 88-665 | 89-665 | 90-665 | 91-665 | 92-665 | Rᵇ | R¹ᶜ | R⁴ᵇ | R⁵ᵃ | Gᶜ | Zᶜ |
| 88-666 | 89-666 | 90-666 | 91-666 | 92-666 | Rᶜ | R¹ᶜ | R⁴ᵇ | R⁵ᵃ | Gᶜ | Zᶜ |
| 88-667 | 89-667 | 90-667 | 91-667 | 92-667 | Rᵃ | R¹ᵃ | R⁴ᶜ | R⁵ᵃ | Gᶜ | Zᶜ |
| 88-668 | 89-668 | 90-668 | 91-668 | 92-668 | Rᵇ | R¹ᵃ | R⁴ᶜ | R⁵ᵃ | Gᶜ | Zᶜ |
| 88-669 | 89-669 | 90-669 | 91-669 | 92-669 | Rᶜ | R¹ᵃ | R⁴ᶜ | R⁵ᵃ | Gᶜ | Zᶜ |
| 88-670 | 89-670 | 90-670 | 91-670 | 92-670 | Rᵃ | R¹ᵇ | R⁴ᶜ | R⁵ᵃ | Gᶜ | Zᶜ |
| 88-671 | 89-671 | 90-671 | 91-671 | 92-671 | Rᵇ | R¹ᵇ | R⁴ᶜ | R⁵ᵃ | Gᶜ | Zᶜ |
| 88-672 | 89-672 | 90-672 | 91-672 | 92-672 | Rᶜ | R¹ᵇ | R⁴ᶜ | R⁵ᵃ | Gᶜ | Zᶜ |
| 88-673 | 89-673 | 90-673 | 91-673 | 92-673 | Rᵃ | R¹ᶜ | R⁴ᶜ | R⁵ᵃ | Gᶜ | Zᶜ |
| 88-674 | 89-674 | 90-674 | 91-674 | 92-674 | Rᵇ | R¹ᶜ | R⁴ᶜ | R⁵ᵃ | Gᶜ | Zᶜ |
| 88-675 | 89-675 | 90-675 | 91-675 | 92-675 | Rᶜ | R¹ᶜ | R⁴ᶜ | R⁵ᵃ | Gᶜ | Zᶜ |
| 88-676 | 89-676 | 90-676 | 91-676 | 92-676 | Rᵃ | R¹ᵃ | R⁴ᵃ | R⁵ᵇ | Gᶜ | Zᶜ |
| 88-677 | 89-677 | 90-677 | 91-677 | 92-677 | Rᵇ | R¹ᵃ | R⁴ᵃ | R⁵ᵇ | Gᶜ | Zᶜ |
| 88-678 | 89-678 | 90-678 | 91-678 | 92-678 | Rᶜ | R¹ᵃ | R⁴ᵃ | R⁵ᵇ | Gᶜ | Zᶜ |
| 88-679 | 89-679 | 90-679 | 91-679 | 92-679 | Rᵃ | R¹ᵇ | R⁴ᵃ | R⁵ᵇ | Gᶜ | Zᶜ |
| 88-680 | 89-680 | 90-680 | 91-680 | 92-680 | Rᵇ | R¹ᵇ | R⁴ᵃ | R⁵ᵇ | Gᶜ | Zᶜ |
| 88-681 | 89-681 | 90-681 | 91-681 | 92-681 | Rᶜ | R¹ᵇ | R⁴ᵃ | R⁵ᵇ | Gᶜ | Zᶜ |
| 88-682 | 89-682 | 90-682 | 91-682 | 92-682 | Rᵃ | R¹ᶜ | R⁴ᵃ | R⁵ᵇ | Gᶜ | Zᶜ |
| 88-683 | 89-683 | 90-683 | 91-683 | 92-683 | Rᵇ | R¹ᶜ | R⁴ᵃ | R⁵ᵇ | Gᶜ | Zᶜ |
| 88-684 | 89-684 | 90-684 | 91-684 | 92-684 | Rᶜ | R¹ᶜ | R⁴ᵃ | R⁵ᵇ | Gᶜ | Zᶜ |
| 88-685 | 89-685 | 90-685 | 91-685 | 92-685 | Rᵃ | R¹ᵃ | R⁴ᵇ | R⁵ᵇ | Gᶜ | Zᶜ |
| 88-686 | 89-686 | 90-686 | 91-686 | 92-686 | Rᵇ | R¹ᵃ | R⁴ᵇ | R⁵ᵇ | Gᶜ | Zᶜ |
| 88-687 | 89-687 | 90-687 | 91-687 | 92-687 | Rᶜ | R¹ᵃ | R⁴ᵇ | R⁵ᵇ | Gᶜ | Zᶜ |
| 88-688 | 89-688 | 90-688 | 91-688 | 92-688 | Rᵃ | R¹ᵇ | R⁴ᵇ | R⁵ᵇ | Gᶜ | Zᶜ |
| 88-689 | 89-689 | 90-689 | 91-689 | 92-689 | Rᵇ | R¹ᵇ | R⁴ᵇ | R⁵ᵇ | Gᶜ | Zᶜ |
| 88-690 | 89-690 | 90-690 | 91-690 | 92-690 | Rᶜ | R¹ᵇ | R⁴ᵇ | R⁵ᵇ | Gᶜ | Zᶜ |
| 88-691 | 89-691 | 90-691 | 91-691 | 92-691 | Rᵃ | R¹ᶜ | R⁴ᵇ | R⁵ᵇ | Gᶜ | Zᶜ |
| 88-692 | 89-692 | 90-692 | 91-692 | 92-692 | Rᵇ | R¹ᶜ | R⁴ᵇ | R⁵ᵇ | Gᶜ | Zᶜ |
| 88-693 | 89-693 | 90-693 | 91-693 | 92-693 | Rᶜ | R¹ᶜ | R⁴ᵇ | R⁵ᵇ | Gᶜ | Zᶜ |
| 88-694 | 89-694 | 90-694 | 91-694 | 92-694 | Rᵃ | R¹ᵃ | R⁴ᶜ | R⁵ᵇ | Gᶜ | Zᶜ |
| 88-695 | 89-695 | 90-695 | 91-695 | 92-695 | Rᵇ | R¹ᵃ | R⁴ᶜ | R⁵ᵇ | Gᶜ | Zᶜ |
| 88-696 | 89-696 | 90-696 | 91-696 | 92-696 | Rᶜ | R¹ᵃ | R⁴ᶜ | R⁵ᵇ | Gᶜ | Zᶜ |
| 88-697 | 89-697 | 90-697 | 91-697 | 92-697 | Rᵃ | R¹ᵇ | R⁴ᶜ | R⁵ᵇ | Gᶜ | Zᶜ |
| 88-698 | 89-698 | 90-698 | 91-698 | 92-698 | Rᵇ | R¹ᵇ | R⁴ᶜ | R⁵ᵇ | Gᶜ | Zᶜ |
| 88-699 | 89-699 | 90-699 | 91-699 | 92-699 | Rᶜ | R¹ᵇ | R⁴ᶜ | R⁵ᵇ | Gᶜ | Zᶜ |
| 88-700 | 89-700 | 90-700 | 91-700 | 92-700 | Rᵃ | R¹ᶜ | R⁴ᶜ | R⁵ᵇ | Gᶜ | Zᶜ |
| 88-701 | 89-701 | 90-701 | 91-701 | 92-701 | Rᵇ | R¹ᶜ | R⁴ᶜ | R⁵ᵇ | Gᶜ | Zᶜ |
| 88-702 | 89-702 | 90-702 | 91-702 | 92-702 | Rᶜ | R¹ᶜ | R⁴ᶜ | R⁵ᵇ | Gᶜ | Zᶜ |
| 88-703 | 89-703 | 90-703 | 91-703 | 92-703 | Rᵃ | R¹ᵃ | R⁴ᵃ | R⁵ᶜ | Gᶜ | Zᶜ |
| 88-704 | 89-704 | 90-704 | 91-704 | 92-704 | Rᵇ | R¹ᵃ | R⁴ᵃ | R⁵ᶜ | Gᶜ | Zᶜ |

-continued

| Formulae | | | | | R | $R^1$ | $R^4$ | $R^5$ | G | Z |
|---|---|---|---|---|---|---|---|---|---|---|
| 88-705 | 89-705 | 90-705 | 91-705 | 92-705 | $R^c$ | $R^{1a}$ | $R^{4a}$ | $R^{5c}$ | $G^e$ | $Z^c$ |
| 88-706 | 89-706 | 90-706 | 91-706 | 92-706 | $R^a$ | $R^{1b}$ | $R^{4a}$ | $R^{5c}$ | $G^e$ | $Z^c$ |
| 88-707 | 89-707 | 90-707 | 91-707 | 92-707 | $R^b$ | $R^{1b}$ | $R^{4a}$ | $R^{5c}$ | $G^e$ | $Z^c$ |
| 88-708 | 89-708 | 90-708 | 91-708 | 92-708 | $R^c$ | $R^{1b}$ | $R^{4a}$ | $R^{5c}$ | $G^e$ | $Z^c$ |
| 88-709 | 89-709 | 90-709 | 91-709 | 92-709 | $R^a$ | $R^{1c}$ | $R^{4a}$ | $R^{5c}$ | $G^e$ | $Z^c$ |
| 88-710 | 89-710 | 90-710 | 91-710 | 92-710 | $R^b$ | $R^{1c}$ | $R^{4a}$ | $R^{5c}$ | $G^e$ | $Z^c$ |
| 88-711 | 89-711 | 90-711 | 91-711 | 92-711 | $R^c$ | $R^{1c}$ | $R^{4a}$ | $R^{5c}$ | $G^e$ | $Z^c$ |
| 88-712 | 89-712 | 90-712 | 91-712 | 92-712 | $R^a$ | $R^{1a}$ | $R^{4b}$ | $R^{5c}$ | $G^e$ | $Z^c$ |
| 88-713 | 89-713 | 90-713 | 91-713 | 92-713 | $R^b$ | $R^{1a}$ | $R^{4b}$ | $R^{5c}$ | $G^e$ | $Z^c$ |
| 88-714 | 89-714 | 90-714 | 91-714 | 92-714 | $R^c$ | $R^{1a}$ | $R^{4b}$ | $R^{5c}$ | $G^e$ | $Z^c$ |
| 88-715 | 89-715 | 90-715 | 91-715 | 92-715 | $R^a$ | $R^{1b}$ | $R^{4b}$ | $R^{5c}$ | $G^e$ | $Z^c$ |
| 88-716 | 89-716 | 90-716 | 91-716 | 92-716 | $R^b$ | $R^{1b}$ | $R^{4b}$ | $R^{5c}$ | $G^e$ | $Z^c$ |
| 88-717 | 89-717 | 90-717 | 91-717 | 92-717 | $R^c$ | $R^{1b}$ | $R^{4b}$ | $R^{5c}$ | $G^e$ | $Z^c$ |
| 88-718 | 89-718 | 90-718 | 91-718 | 92-718 | $R^a$ | $R^{1c}$ | $R^{4b}$ | $R^{5c}$ | $G^e$ | $Z^c$ |
| 88-719 | 89-719 | 90-719 | 91-719 | 92-719 | $R^b$ | $R^{1c}$ | $R^{4b}$ | $R^{5c}$ | $G^e$ | $Z^c$ |
| 88-720 | 89-720 | 90-720 | 91-720 | 92-720 | $R^c$ | $R^{1c}$ | $R^{4b}$ | $R^{5c}$ | $G^e$ | $Z^c$ |
| 88-721 | 89-721 | 90-721 | 91-721 | 92-721 | $R^a$ | $R^{1a}$ | $R^{4c}$ | $R^{5c}$ | $G^e$ | $Z^c$ |
| 88-722 | 89-722 | 90-722 | 91-722 | 92-722 | $R^b$ | $R^{1a}$ | $R^{4c}$ | $R^{5c}$ | $G^e$ | $Z^c$ |
| 88-723 | 89-723 | 90-723 | 91-723 | 92-723 | $R^c$ | $R^{1a}$ | $R^{4c}$ | $R^{5c}$ | $G^e$ | $Z^c$ |
| 88-724 | 89-724 | 90-724 | 91-724 | 92-724 | $R^a$ | $R^{1b}$ | $R^{4c}$ | $R^{5c}$ | $G^e$ | $Z^c$ |
| 88-725 | 89-725 | 90-725 | 91-725 | 92-725 | $R^b$ | $R^{1b}$ | $R^{4c}$ | $R^{5c}$ | $G^e$ | $Z^c$ |
| 88-726 | 89-726 | 90-726 | 91-726 | 92-726 | $R^c$ | $R^{1b}$ | $R^{4c}$ | $R^{5c}$ | $G^e$ | $Z^c$ |
| 88-727 | 89-727 | 90-727 | 91-727 | 92-727 | $R^a$ | $R^{1c}$ | $R^{4c}$ | $R^{5c}$ | $G^e$ | $Z^c$ |
| 88-728 | 89-728 | 90-728 | 91-728 | 92-728 | $R^b$ | $R^{1c}$ | $R^{4c}$ | $R^{5c}$ | $G^e$ | $Z^c$ |
| 88-729 | 89-729 | 90-729 | 91-729 | 92-729 | $R^c$ | $R^{1c}$ | $R^{4c}$ | $R^{5c}$ | $G^e$ | $Z^c$ | where all symbols are as defined above.

In one aspect of any of formulae (88), (89), (90), (91), and (92) of the present invention, R is —H or $CH_3$, and all other symbols are as defined above in connection with formula (I).

In another aspect of any of formulae (88), (89), (90), (91), and (92) of the present invention, R is H or $CH_3$, $R^5$ is —H, and all other symbols are as defined above in connection with formula (I).

In another aspect of any of formulae (88), (89), (90), (91), and (92) of the present invention, R is —H or $CH_3$; $R^5$ is $CH_3$; and all other symbols are as defined above in connection with formula (I).

In still another aspect of any of formulae (88), (89), (90), (91), and (92) of the present invention, R is —H or $CH_3$; G is —$(CH_2)_s$—, where s is an integer from 0-5; and all other symbols are as defined above in connection with formula (I).

In a further aspect of any of formulae (88), (89), (90), (91), and (92) of the present invention, R is —H or —$CH_3$; $R^5$ is —H; G is —$(CH_2)_s$—, where s is an integer from 0-5; and all other symbols are as defined above in connection with formula (I).

In a further aspect of any of formulae (88), (89), (90), (91), and (92) of the present invention, R is —H or $CH_3$; $R^5$ is $CH_3$; G is —$(CH_2)_s$—, where s is an integer from 0-5; and all other symbols are as defined above in connection with formula (I).

In a further aspect of any of formulae (88), (89), (90), (91), and (92) of the present invention, R is —H or $CH_3$, Z is —NR; and all other symbols are as defined above in connection with formula (I).

In a further aspect of any of formulae (88), (89), (90), (91), and (92) of the present invention, R is —H or $CH_3$, $R^5$ is —H or $CH_3$; Z is —NR; and all other symbols are as defined above in connection with formula (I).

In a still further aspect of any of formulae (88), (89), (90), (91), and (92) of the present invention, R is —H or $CH_3$, G is —$(CH_2)_s$—, where s is an integer from 0-5; Z is —NR; and all other symbols are as defined above in connection with formula (I).

In a still further aspect of any of formulae (88), (89), (90), (91), and (92) of the present invention, R is —H or $CH_3$; $R^5$ is —H; G is —$(CH_2)_s$—, where s is an integer from 0-5; Z is —NR; and all other symbols are as defined above in connection with formula (I).

In a yet further aspect of any of formulae (88), (89), (90), (91), and (92) of the present invention, R is —H or $CH_3$, Z is O; and all other symbols are as defined above in connection with formula (I).

In a yet further aspect of any of formulae (88), (89), (90), (91), and (92) of the present invention, R is —H or $CH_3$; $R^5$ is $CH_3$; G is —$(CH_2)_s$—, where s is an integer from 0-5; Z is —NR; and all other symbols are as defined above in connection with formula (I).

In still another aspect of any of formulae (88), (89), (90), (91), and (92) of the present invention, R is —H or $CH_3$, $R^5$ is —H or $CH_3$, Z is O, and all other symbols are as defined above in connection with formula (I).

In still another aspect of any of formulae (88), (89), (90), (91), and (92) of the present invention, R is —H or $CH_3$; G is —$(CH_2)_s$—, where s is an integer from 0-5; Z is O; and all other symbols are as defined above in connection with formula (I).

In still another aspect of any of formulae (88), (89), (90), (91), and (92) of the present invention, R is —H or $CH_3$, G is —$(CH_2)_s$—, where s is an integer from 0-5; Z is O; and all other symbols are as defined above in connection with formula (I).

In still another aspect of any of formulae (88), (89), (90), (91), and (92) of the present invention, R is —H or $CH_3$; $R^5$ is —H; G is —$(CH_2)_s$—, where s is an integer from 0-5; Z is O; and all other symbols are as defined above in connection with formula (I).

In yet another aspect of any of formulae (88), (89), (90), (91), and (92) of the present invention, R is —H or $CH_3$; $R^5$ is $CH_3$; G is —$(CH_2)_s$—, where s is an integer from 0-5; Z is O; and all other symbols are as defined above in connection with formula (I).

In yet another aspect of any of formulae (88), (89), (90), (91), and (92) of the present invention, $R^4$ is a substituted or unsubstituted aryl group; and all other symbols are as defined above in connection with formula (I).

The present invention also encompasses various compounds of general formula (IV) having a formula:

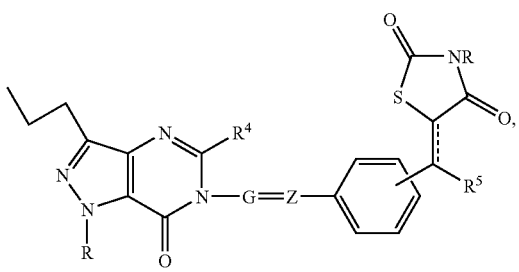

(93)

where all symbols are as defined above in connection with formula (I).

According to various aspects of the present invention, R, $R^4$, $R^5$, G, and Z of formula (93) are selected to produce compounds of formula (93-1) through (93-243) as follows:

| Formula | R | $R^4$ | $R^5$ | G | Z |
|---|---|---|---|---|---|
| 93-1 | $R^a$ | $R^{4a}$ | $R^{5a}$ | $G^a$ | $Z^a$ |
| 93-2 | $R^b$ | $R^{4a}$ | $R^{5a}$ | $G^a$ | $Z^a$ |
| 93-3 | $R^c$ | $R^{4a}$ | $R^{5a}$ | $G^a$ | $Z^a$ |
| 93-4 | $R^a$ | $R^{4b}$ | $R^{5a}$ | $G^a$ | $Z^a$ |
| 93-5 | $R^b$ | $R^{4b}$ | $R^{5a}$ | $G^a$ | $Z^a$ |
| 93-6 | $R^c$ | $R^{4b}$ | $R^{5a}$ | $G^a$ | $Z^a$ |
| 93-7 | $R^a$ | $R^{4c}$ | $R^{5a}$ | $G^a$ | $Z^a$ |
| 93-8 | $R^b$ | $R^{4c}$ | $R^{5a}$ | $G^a$ | $Z^a$ |
| 93-9 | $R^c$ | $R^{4c}$ | $R^{5a}$ | $G^a$ | $Z^a$ |
| 93-10 | $R^a$ | $R^{4a}$ | $R^{5b}$ | $G^a$ | $Z^a$ |
| 93-11 | $R^b$ | $R^{4a}$ | $R^{5b}$ | $G^a$ | $Z^a$ |
| 93-12 | $R^c$ | $R^{4a}$ | $R^{5b}$ | $G^a$ | $Z^a$ |
| 93-13 | $R^a$ | $R^{4b}$ | $R^{5b}$ | $G^a$ | $Z^a$ |
| 93-14 | $R^b$ | $R^{4b}$ | $R^{5b}$ | $G^a$ | $Z^a$ |
| 93-15 | $R^c$ | $R^{4b}$ | $R^{5b}$ | $G^a$ | $Z^a$ |
| 93-16 | $R^a$ | $R^{4c}$ | $R^{5b}$ | $G^a$ | $Z^a$ |
| 93-17 | $R^b$ | $R^{4c}$ | $R^{5b}$ | $G^a$ | $Z^a$ |
| 93-18 | $R^c$ | $R^{4c}$ | $R^{5b}$ | $G^a$ | $Z^a$ |
| 93-19 | $R^a$ | $R^{4a}$ | $R^{5c}$ | $G^a$ | $Z^a$ |
| 93-20 | $R^b$ | $R^{4a}$ | $R^{5c}$ | $G^a$ | $Z^a$ |
| 93-21 | $R^c$ | $R^{4a}$ | $R^{5c}$ | $G^a$ | $Z^a$ |
| 93-22 | $R^a$ | $R^{4b}$ | $R^{5c}$ | $G^a$ | $Z^a$ |
| 93-23 | $R^b$ | $R^{4b}$ | $R^{5c}$ | $G^a$ | $Z^a$ |
| 93-24 | $R^c$ | $R^{4b}$ | $R^{5c}$ | $G^a$ | $Z^a$ |
| 93-25 | $R^a$ | $R^{4c}$ | $R^{5c}$ | $G^a$ | $Z^a$ |
| 93-26 | $R^b$ | $R^{4c}$ | $R^{5c}$ | $G^a$ | $Z^a$ |
| 93-27 | $R^c$ | $R^{4c}$ | $R^{5c}$ | $G^a$ | $Z^a$ |
| 93-28 | $R^a$ | $R^{4a}$ | $R^{5a}$ | $G^b$ | $Z^a$ |
| 93-29 | $R^b$ | $R^{4a}$ | $R^{5a}$ | $G^b$ | $Z^a$ |
| 93-30 | $R^c$ | $R^{4a}$ | $R^{5a}$ | $G^b$ | $Z^a$ |
| 93-31 | $R^a$ | $R^{4b}$ | $R^{5a}$ | $G^b$ | $Z^a$ |
| 93-32 | $R^b$ | $R^{4b}$ | $R^{5a}$ | $G^b$ | $Z^a$ |
| 93-33 | $R^c$ | $R^{4b}$ | $R^{5a}$ | $G^b$ | $Z^a$ |
| 93-34 | $R^a$ | $R^{4c}$ | $R^{5a}$ | $G^b$ | $Z^a$ |
| 93-35 | $R^b$ | $R^{4c}$ | $R^{5a}$ | $G^b$ | $Z^a$ |
| 93-36 | $R^c$ | $R^{4c}$ | $R^{5a}$ | $G^b$ | $Z^a$ |
| 93-37 | $R^a$ | $R^{4a}$ | $R^{5b}$ | $G^b$ | $Z^a$ |
| 93-38 | $R^b$ | $R^{4a}$ | $R^{5b}$ | $G^b$ | $Z^a$ |
| 93-39 | $R^c$ | $R^{4a}$ | $R^{5b}$ | $G^b$ | $Z^a$ |
| 93-40 | $R^a$ | $R^{4b}$ | $R^{5b}$ | $G^b$ | $Z^a$ |
| 93-41 | $R^b$ | $R^{4b}$ | $R^{5b}$ | $G^b$ | $Z^a$ |
| 93-42 | $R^c$ | $R^{4b}$ | $R^{5b}$ | $G^b$ | $Z^a$ |
| 93-43 | $R^a$ | $R^{4c}$ | $R^{5b}$ | $G^b$ | $Z^a$ |
| 93-44 | $R^b$ | $R^{4c}$ | $R^{5b}$ | $G^b$ | $Z^a$ |
| 93-45 | $R^c$ | $R^{4c}$ | $R^{5b}$ | $G^b$ | $Z^a$ |
| 93-46 | $R^a$ | $R^{4a}$ | $R^{5c}$ | $G^b$ | $Z^a$ |
| 93-47 | $R^b$ | $R^{4a}$ | $R^{5c}$ | $G^b$ | $Z^a$ |
| 93-48 | $R^c$ | $R^{4a}$ | $R^{5c}$ | $G^b$ | $Z^a$ |
| 93-49 | $R^a$ | $R^{4b}$ | $R^{5c}$ | $G^b$ | $Z^a$ |
| 93-50 | $R^b$ | $R^{4b}$ | $R^{5c}$ | $G^b$ | $Z^a$ |
| 93-51 | $R^c$ | $R^{4b}$ | $R^{5c}$ | $G^b$ | $Z^a$ |
| 93-52 | $R^a$ | $R^{4c}$ | $R^{5c}$ | $G^b$ | $Z^a$ |
| 93-53 | $R^b$ | $R^{4c}$ | $R^{5c}$ | $G^b$ | $Z^a$ |
| 93-54 | $R^c$ | $R^{4c}$ | $R^{5c}$ | $G^b$ | $Z^a$ |
| 93-55 | $R^a$ | $R^{4a}$ | $R^{5a}$ | $G^c$ | $Z^a$ |
| 93-56 | $R^b$ | $R^{4a}$ | $R^{5a}$ | $G^c$ | $Z^a$ |
| 93-57 | $R^c$ | $R^{4a}$ | $R^{5a}$ | $G^c$ | $Z^a$ |
| 93-58 | $R^a$ | $R^{4b}$ | $R^{5a}$ | $G^c$ | $Z^a$ |
| 93-59 | $R^b$ | $R^{4b}$ | $R^{5a}$ | $G^c$ | $Z^a$ |
| 93-60 | $R^c$ | $R^{4b}$ | $R^{5a}$ | $G^c$ | $Z^a$ |
| 93-61 | $R^a$ | $R^{4c}$ | $R^{5a}$ | $G^c$ | $Z^a$ |
| 93-62 | $R^b$ | $R^{4c}$ | $R^{5a}$ | $G^c$ | $Z^a$ |
| 93-63 | $R^c$ | $R^{4c}$ | $R^{5a}$ | $G^c$ | $Z^a$ |
| 93-64 | $R^a$ | $R^{4a}$ | $R^{5b}$ | $G^c$ | $Z^a$ |
| 93-65 | $R^b$ | $R^{4a}$ | $R^{5b}$ | $G^c$ | $Z^a$ |
| 93-66 | $R^c$ | $R^{4a}$ | $R^{5b}$ | $G^c$ | $Z^a$ |
| 93-67 | $R^a$ | $R^{4b}$ | $R^{5b}$ | $G^c$ | $Z^a$ |
| 93-68 | $R^b$ | $R^{4b}$ | $R^{5b}$ | $G^c$ | $Z^a$ |
| 93-69 | $R^c$ | $R^{4b}$ | $R^{5b}$ | $G^c$ | $Z^a$ |
| 93-70 | $R^a$ | $R^{4c}$ | $R^{5b}$ | $G^c$ | $Z^a$ |
| 93-71 | $R^b$ | $R^{4c}$ | $R^{5b}$ | $G^c$ | $Z^a$ |
| 93-72 | $R^c$ | $R^{4c}$ | $R^{5b}$ | $G^c$ | $Z^a$ |
| 93-73 | $R^a$ | $R^{4a}$ | $R^{5c}$ | $G^c$ | $Z^a$ |
| 93-74 | $R^b$ | $R^{4a}$ | $R^{5c}$ | $G^c$ | $Z^a$ |
| 93-75 | $R^c$ | $R^{4a}$ | $R^{5c}$ | $G^c$ | $Z^a$ |
| 93-76 | $R^a$ | $R^{4b}$ | $R^{5c}$ | $G^c$ | $Z^a$ |
| 93-77 | $R^b$ | $R^{4b}$ | $R^{5c}$ | $G^c$ | $Z^a$ |
| 93-78 | $R^c$ | $R^{4b}$ | $R^{5c}$ | $G^c$ | $Z^a$ |
| 93-79 | $R^a$ | $R^{4c}$ | $R^{5c}$ | $G^c$ | $Z^a$ |
| 93-80 | $R^b$ | $R^{4c}$ | $R^{5c}$ | $G^c$ | $Z^a$ |
| 93-81 | $R^c$ | $R^{4c}$ | $R^{5c}$ | $G^c$ | $Z^a$ |
| 93-82 | $R^a$ | $R^{4a}$ | $R^{5a}$ | $G^a$ | $Z^b$ |
| 93-83 | $R^b$ | $R^{4a}$ | $R^{5a}$ | $G^a$ | $Z^b$ |
| 93-84 | $R^c$ | $R^{4a}$ | $R^{5a}$ | $G^a$ | $Z^b$ |
| 93-85 | $R^a$ | $R^{4b}$ | $R^{5a}$ | $G^a$ | $Z^b$ |
| 93-86 | $R^b$ | $R^{4b}$ | $R^{5a}$ | $G^a$ | $Z^b$ |
| 93-87 | $R^c$ | $R^{4b}$ | $R^{5a}$ | $G^a$ | $Z^b$ |
| 93-88 | $R^a$ | $R^{4c}$ | $R^{5a}$ | $G^a$ | $Z^b$ |
| 93-89 | $R^b$ | $R^{4c}$ | $R^{5a}$ | $G^a$ | $Z^b$ |
| 93-90 | $R^c$ | $R^{4c}$ | $R^{5a}$ | $G^a$ | $Z^b$ |
| 93-91 | $R^a$ | $R^{4a}$ | $R^{5b}$ | $G^a$ | $Z^b$ |
| 93-92 | $R^b$ | $R^{4a}$ | $R^{5b}$ | $G^a$ | $Z^b$ |
| 93-93 | $R^c$ | $R^{4a}$ | $R^{5b}$ | $G^a$ | $Z^b$ |
| 93-94 | $R^a$ | $R^{4b}$ | $R^{5b}$ | $G^a$ | $Z^b$ |
| 93-95 | $R^b$ | $R^{4b}$ | $R^{5b}$ | $G^a$ | $Z^b$ |
| 93-96 | $R^c$ | $R^{4b}$ | $R^{5b}$ | $G^a$ | $Z^b$ |
| 93-97 | $R^a$ | $R^{4c}$ | $R^{5b}$ | $G^a$ | $Z^b$ |
| 93-98 | $R^b$ | $R^{4c}$ | $R^{5b}$ | $G^a$ | $Z^b$ |
| 93-99 | $R^c$ | $R^{4c}$ | $R^{5b}$ | $G^a$ | $Z^b$ |
| 93-100 | $R^a$ | $R^{4a}$ | $R^{5c}$ | $G^a$ | $Z^b$ |
| 93-101 | $R^b$ | $R^{4a}$ | $R^{5c}$ | $G^a$ | $Z^b$ |
| 93-102 | $R^c$ | $R^{4a}$ | $R^{5c}$ | $G^a$ | $Z^b$ |
| 93-103 | $R^a$ | $R^{4b}$ | $R^{5c}$ | $G^a$ | $Z^b$ |
| 93-104 | $R^b$ | $R^{4b}$ | $R^{5c}$ | $G^a$ | $Z^b$ |
| 93-105 | $R^c$ | $R^{4b}$ | $R^{5c}$ | $G^a$ | $Z^b$ |
| 93-106 | $R^a$ | $R^{4c}$ | $R^{5c}$ | $G^a$ | $Z^b$ |
| 93-107 | $R^b$ | $R^{4c}$ | $R^{5c}$ | $G^a$ | $Z^b$ |
| 93-108 | $R^c$ | $R^{4c}$ | $R^{5c}$ | $G^a$ | $Z^b$ |
| 93-109 | $R^a$ | $R^{4a}$ | $R^{5a}$ | $G^b$ | $Z^b$ |
| 93-110 | $R^b$ | $R^{4a}$ | $R^{5a}$ | $G^b$ | $Z^b$ |
| 93-111 | $R^c$ | $R^{4a}$ | $R^{5a}$ | $G^b$ | $Z^b$ |
| 93-112 | $R^a$ | $R^{4b}$ | $R^{5a}$ | $G^b$ | $Z^b$ |
| 93-113 | $R^b$ | $R^{4b}$ | $R^{5a}$ | $G^b$ | $Z^b$ |
| 93-114 | $R^c$ | $R^{4b}$ | $R^{5a}$ | $G^b$ | $Z^b$ |
| 93-115 | $R^a$ | $R^{4c}$ | $R^{5a}$ | $G^b$ | $Z^b$ |
| 93-116 | $R^b$ | $R^{4c}$ | $R^{5a}$ | $G^b$ | $Z^b$ |
| 93-117 | $R^c$ | $R^{4c}$ | $R^{5a}$ | $G^b$ | $Z^b$ |
| 93-118 | $R^a$ | $R^{4a}$ | $R^{5b}$ | $G^b$ | $Z^b$ |
| 93-119 | $R^b$ | $R^{4a}$ | $R^{5b}$ | $G^b$ | $Z^b$ |
| 93-120 | $R^c$ | $R^{4a}$ | $R^{5b}$ | $G^b$ | $Z^b$ |
| 93-121 | $R^a$ | $R^{4b}$ | $R^{5b}$ | $G^b$ | $Z^b$ |
| 93-122 | $R^b$ | $R^{4b}$ | $R^{5b}$ | $G^b$ | $Z^b$ |
| 93-123 | $R^c$ | $R^{4b}$ | $R^{5b}$ | $G^b$ | $Z^b$ |
| 93-124 | $R^a$ | $R^{4c}$ | $R^{5b}$ | $G^b$ | $Z^b$ |
| 93-125 | $R^b$ | $R^{4c}$ | $R^{5b}$ | $G^b$ | $Z^b$ |
| 93-126 | $R^c$ | $R^{4c}$ | $R^{5b}$ | $G^b$ | $Z^b$ |

| Formula | R | $R^4$ | $R^5$ | G | Z |
|---|---|---|---|---|---|
| 93-127 | $R^a$ | $R^{4a}$ | $R^{5c}$ | $G^b$ | $Z^b$ |
| 93-128 | $R^b$ | $R^{4a}$ | $R^{5c}$ | $G^b$ | $Z^b$ |
| 93-129 | $R^c$ | $R^{4a}$ | $R^{5c}$ | $G^b$ | $Z^b$ |
| 93-130 | $R^a$ | $R^{4b}$ | $R^{5c}$ | $G^b$ | $Z^b$ |
| 93-131 | $R^b$ | $R^{4b}$ | $R^{5c}$ | $G^b$ | $Z^b$ |
| 93-132 | $R^c$ | $R^{4b}$ | $R^{5c}$ | $G^b$ | $Z^b$ |
| 93-133 | $R^a$ | $R^{4c}$ | $R^{5c}$ | $G^b$ | $Z^b$ |
| 93-134 | $R^b$ | $R^{4c}$ | $R^{5c}$ | $G^b$ | $Z^b$ |
| 93-135 | $R^c$ | $R^{4c}$ | $R^{5c}$ | $G^b$ | $Z^b$ |
| 93-136 | $R^a$ | $R^{4a}$ | $R^{5a}$ | $G^c$ | $Z^b$ |
| 93-137 | $R^b$ | $R^{4a}$ | $R^{5a}$ | $G^c$ | $Z^b$ |
| 93-138 | $R^c$ | $R^{4a}$ | $R^{5a}$ | $G^c$ | $Z^b$ |
| 93-139 | $R^a$ | $R^{4b}$ | $R^{5a}$ | $G^c$ | $Z^b$ |
| 93-140 | $R^b$ | $R^{4b}$ | $R^{5a}$ | $G^c$ | $Z^b$ |
| 93-141 | $R^c$ | $R^{4b}$ | $R^{5a}$ | $G^c$ | $Z^b$ |
| 93-142 | $R^a$ | $R^{4c}$ | $R^{5a}$ | $G^c$ | $Z^b$ |
| 93-143 | $R^b$ | $R^{4c}$ | $R^{5a}$ | $G^c$ | $Z^b$ |
| 93-144 | $R^c$ | $R^{4c}$ | $R^{5a}$ | $G^c$ | $Z^b$ |
| 93-145 | $R^a$ | $R^{4a}$ | $R^{5b}$ | $G^c$ | $Z^b$ |
| 93-146 | $R^b$ | $R^{4a}$ | $R^{5b}$ | $G^c$ | $Z^b$ |
| 93-147 | $R^c$ | $R^{4a}$ | $R^{5b}$ | $G^c$ | $Z^b$ |
| 93-148 | $R^a$ | $R^{4b}$ | $R^{5b}$ | $G^c$ | $Z^b$ |
| 93-149 | $R^b$ | $R^{4b}$ | $R^{5b}$ | $G^c$ | $Z^b$ |
| 93-150 | $R^c$ | $R^{4b}$ | $R^{5b}$ | $G^c$ | $Z^b$ |
| 93-151 | $R^a$ | $R^{4c}$ | $R^{5b}$ | $G^c$ | $Z^b$ |
| 93-152 | $R^b$ | $R^{4c}$ | $R^{5b}$ | $G^c$ | $Z^b$ |
| 93-153 | $R^c$ | $R^{4c}$ | $R^{5b}$ | $G^c$ | $Z^b$ |
| 93-154 | $R^a$ | $R^{4a}$ | $R^{5c}$ | $G^c$ | $Z^b$ |
| 93-155 | $R^b$ | $R^{4a}$ | $R^{5c}$ | $G^c$ | $Z^b$ |
| 93-156 | $R^c$ | $R^{4a}$ | $R^{5c}$ | $G^c$ | $Z^b$ |
| 93-157 | $R^a$ | $R^{4b}$ | $R^{5c}$ | $G^c$ | $Z^b$ |
| 93-158 | $R^b$ | $R^{4b}$ | $R^{5c}$ | $G^c$ | $Z^b$ |
| 93-159 | $R^c$ | $R^{4b}$ | $R^{5c}$ | $G^c$ | $Z^b$ |
| 93-160 | $R^a$ | $R^{4c}$ | $R^{5c}$ | $G^c$ | $Z^b$ |
| 93-161 | $R^b$ | $R^{4c}$ | $R^{5c}$ | $G^c$ | $Z^b$ |
| 93-162 | $R^c$ | $R^{4c}$ | $R^{5c}$ | $G^c$ | $Z^b$ |
| 93-163 | $R^a$ | $R^{4a}$ | $R^{5a}$ | $G^a$ | $Z^c$ |
| 93-164 | $R^b$ | $R^{4a}$ | $R^{5a}$ | $G^a$ | $Z^c$ |
| 93-165 | $R^c$ | $R^{4a}$ | $R^{5a}$ | $G^a$ | $Z^c$ |
| 93-166 | $R^a$ | $R^{4b}$ | $R^{5a}$ | $G^a$ | $Z^c$ |
| 93-167 | $R^b$ | $R^{4b}$ | $R^{5a}$ | $G^a$ | $Z^c$ |
| 93-168 | $R^c$ | $R^{4b}$ | $R^{5a}$ | $G^a$ | $Z^c$ |
| 93-169 | $R^a$ | $R^{4c}$ | $R^{5a}$ | $G^a$ | $Z^c$ |
| 93-170 | $R^b$ | $R^{4c}$ | $R^{5a}$ | $G^a$ | $Z^c$ |
| 93-171 | $R^c$ | $R^{4c}$ | $R^{5a}$ | $G^a$ | $Z^c$ |
| 93-172 | $R^a$ | $R^{4a}$ | $R^{5b}$ | $G^a$ | $Z^c$ |
| 93-173 | $R^b$ | $R^{4a}$ | $R^{5b}$ | $G^a$ | $Z^c$ |
| 93-174 | $R^c$ | $R^{4a}$ | $R^{5b}$ | $G^a$ | $Z^c$ |
| 93-175 | $R^a$ | $R^{4b}$ | $R^{5b}$ | $G^a$ | $Z^c$ |
| 93-176 | $R^b$ | $R^{4b}$ | $R^{5b}$ | $G^a$ | $Z^c$ |
| 93-177 | $R^c$ | $R^{4b}$ | $R^{5b}$ | $G^a$ | $Z^c$ |
| 93-178 | $R^a$ | $R^{4c}$ | $R^{5b}$ | $G^a$ | $Z^c$ |
| 93-179 | $R^b$ | $R^{4c}$ | $R^{5b}$ | $G^a$ | $Z^c$ |
| 93-180 | $R^c$ | $R^{4c}$ | $R^{5b}$ | $G^a$ | $Z^c$ |
| 93-181 | $R^a$ | $R^{4a}$ | $R^{5c}$ | $G^a$ | $Z^c$ |
| 93-182 | $R^b$ | $R^{4a}$ | $R^{5c}$ | $G^a$ | $Z^c$ |
| 93-183 | $R^c$ | $R^{4a}$ | $R^{5c}$ | $G^a$ | $Z^c$ |
| 93-184 | $R^a$ | $R^{4b}$ | $R^{5c}$ | $G^a$ | $Z^c$ |
| 93-185 | $R^b$ | $R^{4b}$ | $R^{5c}$ | $G^a$ | $Z^c$ |
| 93-186 | $R^c$ | $R^{4b}$ | $R^{5c}$ | $G^a$ | $Z^c$ |
| 93-187 | $R^a$ | $R^{4c}$ | $R^{5c}$ | $G^a$ | $Z^c$ |
| 93-188 | $R^b$ | $R^{4c}$ | $R^{5c}$ | $G^a$ | $Z^c$ |
| 93-189 | $R^c$ | $R^{4c}$ | $R^{5c}$ | $G^a$ | $Z^c$ |
| 93-190 | $R^a$ | $R^{4a}$ | $R^{5a}$ | $G^b$ | $Z^c$ |
| 93-191 | $R^b$ | $R^{4a}$ | $R^{5a}$ | $G^b$ | $Z^c$ |
| 93-192 | $R^c$ | $R^{4a}$ | $R^{5a}$ | $G^b$ | $Z^c$ |
| 93-193 | $R^a$ | $R^{4b}$ | $R^{5a}$ | $G^b$ | $Z^c$ |
| 93-194 | $R^b$ | $R^{4b}$ | $R^{5a}$ | $G^b$ | $Z^c$ |
| 93-195 | $R^c$ | $R^{4b}$ | $R^{5a}$ | $G^b$ | $Z^c$ |
| 93-196 | $R^a$ | $R^{4c}$ | $R^{5a}$ | $G^b$ | $Z^c$ |
| 93-197 | $R^b$ | $R^{4c}$ | $R^{5a}$ | $G^b$ | $Z^c$ |
| 93-198 | $R^c$ | $R^{4c}$ | $R^{5a}$ | $G^b$ | $Z^c$ |
| 93-199 | $R^a$ | $R^{4a}$ | $R^{5b}$ | $G^b$ | $Z^c$ |
| 93-200 | $R^b$ | $R^{4a}$ | $R^{5b}$ | $G^b$ | $Z^c$ |
| 93-201 | $R^c$ | $R^{4a}$ | $R^{5b}$ | $G^b$ | $Z^c$ |
| 93-202 | $R^a$ | $R^{4b}$ | $R^{5b}$ | $G^b$ | $Z^c$ |
| 93-203 | $R^b$ | $R^{4b}$ | $R^{5b}$ | $G^b$ | $Z^c$ |
| 93-204 | $R^c$ | $R^{4b}$ | $R^{5b}$ | $G^b$ | $Z^c$ |
| 93-205 | $R^a$ | $R^{4c}$ | $R^{5b}$ | $G^b$ | $Z^c$ |
| 93-206 | $R^b$ | $R^{4c}$ | $R^{5b}$ | $G^b$ | $Z^c$ |
| 93-207 | $R^c$ | $R^{4c}$ | $R^{5b}$ | $G^b$ | $Z^c$ |
| 93-208 | $R^a$ | $R^{4a}$ | $R^{5c}$ | $G^b$ | $Z^c$ |
| 93-209 | $R^b$ | $R^{4a}$ | $R^{5c}$ | $G^b$ | $Z^c$ |
| 93-210 | $R^c$ | $R^{4a}$ | $R^{5c}$ | $G^b$ | $Z^c$ |
| 93-211 | $R^a$ | $R^{4b}$ | $R^{5c}$ | $G^b$ | $Z^c$ |
| 93-212 | $R^b$ | $R^{4b}$ | $R^{5c}$ | $G^b$ | $Z^c$ |
| 93-213 | $R^c$ | $R^{4b}$ | $R^{5c}$ | $G^b$ | $Z^c$ |
| 93-214 | $R^a$ | $R^{4c}$ | $R^{5c}$ | $G^b$ | $Z^c$ |
| 93-215 | $R^b$ | $R^{4c}$ | $R^{5c}$ | $G^b$ | $Z^c$ |
| 93-216 | $R^c$ | $R^{4c}$ | $R^{5c}$ | $G^b$ | $Z^c$ |
| 93-217 | $R^a$ | $R^{4a}$ | $R^{5a}$ | $G^c$ | $Z^c$ |
| 93-218 | $R^b$ | $R^{4a}$ | $R^{5a}$ | $G^c$ | $Z^c$ |
| 93-219 | $R^c$ | $R^{4a}$ | $R^{5a}$ | $G^c$ | $Z^c$ |
| 93-220 | $R^a$ | $R^{4b}$ | $R^{5a}$ | $G^c$ | $Z^c$ |
| 93-221 | $R^b$ | $R^{4b}$ | $R^{5a}$ | $G^c$ | $Z^c$ |
| 93-222 | $R^c$ | $R^{4b}$ | $R^{5a}$ | $G^c$ | $Z^c$ |
| 93-223 | $R^a$ | $R^{4c}$ | $R^{5a}$ | $G^c$ | $Z^c$ |
| 93-224 | $R^b$ | $R^{4c}$ | $R^{5a}$ | $G^c$ | $Z^c$ |
| 93-225 | $R^c$ | $R^{4c}$ | $R^{5a}$ | $G^c$ | $Z^c$ |
| 93-226 | $R^a$ | $R^{4a}$ | $R^{5b}$ | $G^c$ | $Z^c$ |
| 93-227 | $R^b$ | $R^{4a}$ | $R^{5b}$ | $G^c$ | $Z^c$ |
| 93-228 | $R^c$ | $R^{4a}$ | $R^{5b}$ | $G^c$ | $Z^c$ |
| 93-229 | $R^a$ | $R^{4b}$ | $R^{5b}$ | $G^c$ | $Z^c$ |
| 93-230 | $R^b$ | $R^{4b}$ | $R^{5b}$ | $G^c$ | $Z^c$ |
| 93-231 | $R^c$ | $R^{4b}$ | $R^{5b}$ | $G^c$ | $Z^c$ |
| 93-232 | $R^a$ | $R^{4c}$ | $R^{5b}$ | $G^c$ | $Z^c$ |
| 93-233 | $R^b$ | $R^{4c}$ | $R^{5b}$ | $G^c$ | $Z^c$ |
| 93-234 | $R^c$ | $R^{4c}$ | $R^{5b}$ | $G^c$ | $Z^c$ |
| 93-235 | $R^a$ | $R^{4a}$ | $R^{5c}$ | $G^c$ | $Z^c$ |
| 93-236 | $R^b$ | $R^{4a}$ | $R^{5c}$ | $G^c$ | $Z^c$ |
| 93-237 | $R^c$ | $R^{4a}$ | $R^{5c}$ | $G^c$ | $Z^c$ |
| 93-238 | $R^a$ | $R^{4b}$ | $R^{5c}$ | $G^c$ | $Z^c$ |
| 93-239 | $R^b$ | $R^{4b}$ | $R^{5c}$ | $G^c$ | $Z^c$ |
| 93-240 | $R^c$ | $R^{4b}$ | $R^{5c}$ | $G^c$ | $Z^c$ |
| 93-241 | $R^a$ | $R^{4c}$ | $R^{5c}$ | $G^c$ | $Z^c$ |
| 93-242 | $R^b$ | $R^{4c}$ | $R^{5c}$ | $G^c$ | $Z^c$ |
| 93-243 | $R^c$ | $R^{4c}$ | $R^{5c}$ | $G^c$ | $Z^c$ | where all symbols are as defined above.

In one aspect of any of formula (93) of the present invention, R is —H or $CH_3$, and all other symbols are as defined above in connection with formula (I).

In another aspect of any of formula (93) of the present invention, $R^4$ is a substituted or unsubstituted aryl group; and all other symbols are as defined above in connection with formula (I).

In another aspect of any of formula (93) of the present invention, $R^5$ is —H or $CH_3$, and all other symbols are as defined above in connection with formula (I).

In yet another aspect of any of formula (93) of the present invention, G is —$(CH_2)_s$—, where s is an integer from 0-5; and all other symbols are as defined above in connection with formula (I).

In yet another aspect of formula (93) of the present invention, R is hydrogen, a hydroxy group, a halogen, a nitro group, an optionally substituted amino group, an alkyl group, an alkoxy group, an alkenyl group, or an alkoxyalkyl group; $R^4$ is an alkenyl group, a cycloalkenyl group, an alkoxyalkyl group, an alkenyloxy group, a cycloalkenyloxy group, an acyl group or an acyloxy group, an aryl group, an aryloxy group, an aroyl group, an aroyloxy group, an aralkyl group, an aralkenyl group, an aralkynyl group, an aralkoxy group, a heterocyclyl group, a heterocyclenyl group, a heteroaryl group, a heteroaralkyl group, a heteroaryloxy group, or a heteroaralkoxy group; $R^5$ is hydrogen, a hydroxy group, a halogen, a nitro group, an optionally substituted amino group, an alkyl group, an alkoxy group, an alkenyl group, or an alkoxyalkyl group; and all other symbols are as defined above in connection with formula (I).

In still another aspect of formula (93) of the present invention, R is hydrogen, a hydroxy group, a halogen, a nitro group, a carboxy group, a carbamoyl group, an optionally substituted amino group, or an alkyl group; $R^4$ is a cycloalkenyl group, a cycloalkenyloxy group, an acyl group or an acyloxy group, an aryl group, an aryloxy group, an aroyl group, an aroyloxy group, an aralkyl group, an aralkenyl group, an aralkynyl group, an aralkoxy group, a heterocyclyl group, a heterocyclenyl group, a heteroaryl group, a heteroaralkyl group, a heteroaryloxy group, or a heteroaralkoxy group; $R^5$ is hydrogen, a hydroxy group, a halogen, an alkyl group, or an alkoxy group; and all other symbols are as defined above in connection with formula (I).

In yet another aspect of formula (93) of the present invention, R is hydrogen or an alkyl group; $R^4$ is a substituted or unsubstituted aryl group; G is (—$CH_2$—)$_2$, (—$CH_2$—)$_3$, or (—$CH_2$—)$_4$; Z is O, S, or NH; and $R^5$ is hydrogen or an alkyl group.

In still another aspect of formula (93) of the present invention, R is —H or $CH_3$; $R^4$ is a substituted or unsubstituted aryl group; G is (—$CH_2$—)$_2$, (—$CH_2$—)$_3$, or (—$CH_2$—)$_4$; Z is O, S, or NH; and $R^5$ is —H or $CH_3$.

The present invention also encompasses various compounds of general formula (IV) as follows:

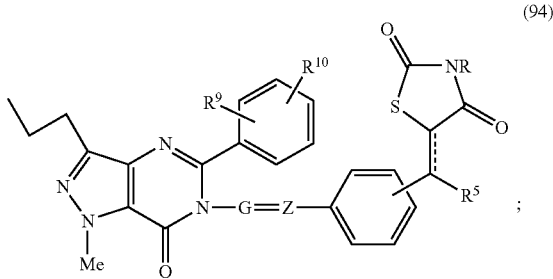

(94)

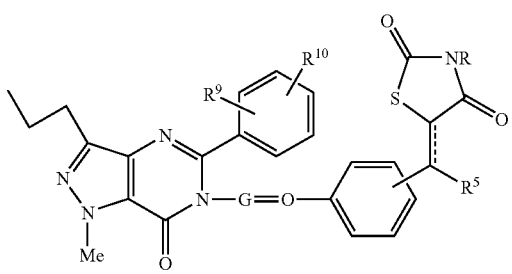

(95)

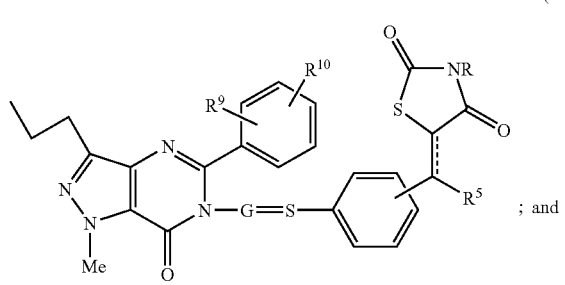

(96)

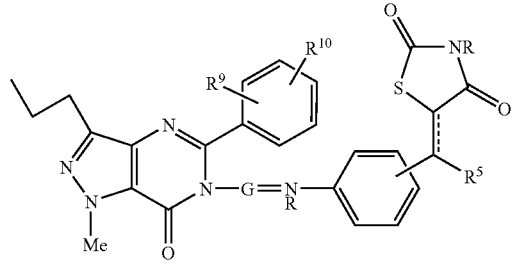

; and (97)

where $R^9$ and $R^{10}$ independently are hydrogen, a halogen, a nitro group, an amino group, a mono- or di-substituted amino group, a hydroxy group, an alkoxy group, a carboxy group, a cyano group, an oxo(O=) group, a thio(S=) group, an alkyl group, a cycloalkyl group, an alkoxy group, a haloalkoxy group, a cycloalkyl group, an aryl group, a benzyloxy group, an acyl group, an acyloxy group, an aroyl group, an alkoxycarbonyl group, an aryloxycarbonyl group, a heteroaryl group, a heterocyclyl group, an aralkyl group, an alkylsulfonyl group, an alkylsulfinyl group, an arylsulfonyl group, an arylsulfinyl group, an alkylthio group, an arylthio group, a heteroarylthio group, an aralkylthio group, or a heterocyclyl sulfonyl group, which is optionally substituted with a halogen, a hydroxyl group, a nitro group, an amino group, an alkyloxy group, or any combination thereof, and wherein the heterocycle group is optionally a substituted morpholinyl group, a thiomorpholinyl group, or a piperzinyl group, wherein the substituent on the heterocyclyl group is a halogen, a nitro group, an amino group, an alkyl group, an alkoxy group, or an aryl group; and all other symbols are as defined above in connection with formula (I).

According to various aspects of the present invention, R, $R^5$, G, Z, $R^9$, and $R^{10}$ of any of formulae (94), (95), (96), and (97) are selected to produce compounds of formulae (94-1), (95-1), (96-1), and (97-1) through formulae (94-729), (95-729), (96-729) as follows:

| Formulae | | | | R | $R^5$ | $R^9$ | $R^{10}$ | G | Z |
|---|---|---|---|---|---|---|---|---|---|
| 94-1 | 95-1 | 96-1 | 97-1 | $R^a$ | $R^{5a}$ | $R^{9a}$ | $R^{10a}$ | $G^a$ | $Z^a$ |
| 94-2 | 95-2 | 96-2 | 97-2 | $R^b$ | $R^{5a}$ | $R^{9a}$ | $R^{10a}$ | $G^a$ | $Z^a$ |
| 94-3 | 95-3 | 96-3 | 97-3 | $R^c$ | $R^{5a}$ | $R^{9a}$ | $R^{10a}$ | $G^a$ | $Z^a$ |
| 94-4 | 95-4 | 96-4 | 97-4 | $R^a$ | $R^{5b}$ | $R^{9a}$ | $R^{10a}$ | $G^a$ | $Z^a$ |
| 94-5 | 95-5 | 96-5 | 97-5 | $R^b$ | $R^{5b}$ | $R^{9a}$ | $R^{10a}$ | $G^a$ | $Z^a$ |
| 94-6 | 95-6 | 96-6 | 97-6 | $R^c$ | $R^{5b}$ | $R^{9a}$ | $R^{10a}$ | $G^a$ | $Z^a$ |
| 94-7 | 95-7 | 96-7 | 97-7 | $R^a$ | $R^{5c}$ | $R^{9a}$ | $R^{10a}$ | $G^a$ | $Z^a$ |
| 94-8 | 95-8 | 96-8 | 97-8 | $R^b$ | $R^{5c}$ | $R^{9a}$ | $R^{10a}$ | $G^a$ | $Z^a$ |
| 94-9 | 95-9 | 96-9 | 97-9 | $R^c$ | $R^{5c}$ | $R^{9a}$ | $R^{10a}$ | $G^a$ | $Z^a$ |
| 94-10 | 95-10 | 96-10 | 97-10 | $R^a$ | $R^{5a}$ | $R^{9b}$ | $R^{10a}$ | $G^a$ | $Z^a$ |
| 94-11 | 95-11 | 96-11 | 97-11 | $R^b$ | $R^{5a}$ | $R^{9b}$ | $R^{10a}$ | $G^a$ | $Z^a$ |
| 94-12 | 95-12 | 96-12 | 97-12 | $R^c$ | $R^{5a}$ | $R^{9b}$ | $R^{10a}$ | $G^a$ | $Z^a$ |
| 94-13 | 95-13 | 96-13 | 97-13 | $R^a$ | $R^{5b}$ | $R^{9b}$ | $R^{10a}$ | $G^a$ | $Z^a$ |
| 94-14 | 95-14 | 96-14 | 97-14 | $R^b$ | $R^{5b}$ | $R^{9b}$ | $R^{10a}$ | $G^a$ | $Z^a$ |
| 94-15 | 95-15 | 96-15 | 97-15 | $R^c$ | $R^{5b}$ | $R^{9b}$ | $R^{10a}$ | $G^a$ | $Z^a$ |
| 94-16 | 95-16 | 96-16 | 97-16 | $R^a$ | $R^{5c}$ | $R^{9b}$ | $R^{10a}$ | $G^a$ | $Z^a$ |
| 94-17 | 95-17 | 96-17 | 97-17 | $R^b$ | $R^{5c}$ | $R^{9b}$ | $R^{10a}$ | $G^a$ | $Z^a$ |
| 94-18 | 95-18 | 96-18 | 97-18 | $R^c$ | $R^{5c}$ | $R^{9b}$ | $R^{10a}$ | $G^a$ | $Z^a$ |
| 94-19 | 95-19 | 96-19 | 97-19 | $R^a$ | $R^{5a}$ | $R^{9c}$ | $R^{10a}$ | $G^a$ | $Z^a$ |
| 94-20 | 95-20 | 96-20 | 97-20 | $R^b$ | $R^{5a}$ | $R^{9c}$ | $R^{10a}$ | $G^a$ | $Z^a$ |
| 94-21 | 95-21 | 96-21 | 97-21 | $R^c$ | $R^{5a}$ | $R^{9c}$ | $R^{10a}$ | $G^a$ | $Z^a$ |
| 94-22 | 95-22 | 96-22 | 97-22 | $R^a$ | $R^{5b}$ | $R^{9c}$ | $R^{10a}$ | $G^a$ | $Z^a$ |
| 94-23 | 95-23 | 96-23 | 97-23 | $R^b$ | $R^{5b}$ | $R^{9c}$ | $R^{10a}$ | $G^a$ | $Z^a$ |
| 94-24 | 95-24 | 96-24 | 97-24 | $R^c$ | $R^{5b}$ | $R^{9c}$ | $R^{10a}$ | $G^a$ | $Z^a$ |
| 94-25 | 95-25 | 96-25 | 97-25 | $R^a$ | $R^{5c}$ | $R^{9c}$ | $R^{10a}$ | $G^a$ | $Z^a$ |
| 94-26 | 95-26 | 96-26 | 97-26 | $R^b$ | $R^{5c}$ | $R^{9c}$ | $R^{10a}$ | $G^a$ | $Z^a$ |

|  | Formulae |  |  | R | R⁵ | R⁹ | R¹⁰ | G | Z |
|---|---|---|---|---|---|---|---|---|---|
| 94-27 | 95-27 | 96-27 | 97-27 | Rᶜ | R⁵ᶜ | R⁹ᶜ | R¹⁰ᵃ | Gᵃ | Zᵃ |
| 94-28 | 95-28 | 96-28 | 97-28 | Rᵃ | R⁵ᵃ | R⁹ᵃ | R¹⁰ᵇ | Gᵃ | Zᵃ |
| 94-29 | 95-29 | 96-29 | 97-29 | Rᵇ | R⁵ᵃ | R⁹ᵃ | R¹⁰ᵇ | Gᵃ | Zᵃ |
| 94-30 | 95-30 | 96-30 | 97-30 | Rᶜ | R⁵ᵃ | R⁹ᵃ | R¹⁰ᵇ | Gᵃ | Zᵃ |
| 94-31 | 95-31 | 96-31 | 97-31 | Rᵃ | R⁵ᵇ | R⁹ᵃ | R¹⁰ᵇ | Gᵃ | Zᵃ |
| 94-32 | 95-32 | 96-32 | 97-32 | Rᵇ | R⁵ᵇ | R⁹ᵃ | R¹⁰ᵇ | Gᵃ | Zᵃ |
| 94-33 | 95-33 | 96-33 | 97-33 | Rᶜ | R⁵ᵇ | R⁹ᵃ | R¹⁰ᵇ | Gᵃ | Zᵃ |
| 94-34 | 95-34 | 96-34 | 97-34 | Rᵃ | R⁵ᶜ | R⁹ᵃ | R¹⁰ᵇ | Gᵃ | Zᵃ |
| 94-35 | 95-35 | 96-35 | 97-35 | Rᵇ | R⁵ᶜ | R⁹ᵃ | R¹⁰ᵇ | Gᵃ | Zᵃ |
| 94-36 | 95-36 | 96-36 | 97-36 | Rᶜ | R⁵ᶜ | R⁹ᵃ | R¹⁰ᵇ | Gᵃ | Zᵃ |
| 94-37 | 95-37 | 96-37 | 97-37 | Rᵃ | R⁵ᵃ | R⁹ᵇ | R¹⁰ᵇ | Gᵃ | Zᵃ |
| 94-38 | 95-38 | 96-38 | 97-38 | Rᵇ | R⁵ᵃ | R⁹ᵇ | R¹⁰ᵇ | Gᵃ | Zᵃ |
| 94-39 | 95-39 | 96-39 | 97-39 | Rᶜ | R⁵ᵃ | R⁹ᵇ | R¹⁰ᵇ | Gᵃ | Zᵃ |
| 94-40 | 95-40 | 96-40 | 97-40 | Rᵃ | R⁵ᵇ | R⁹ᵇ | R¹⁰ᵇ | Gᵃ | Zᵃ |
| 94-41 | 95-41 | 96-41 | 97-41 | Rᵇ | R⁵ᵇ | R⁹ᵇ | R¹⁰ᵇ | Gᵃ | Zᵃ |
| 94-42 | 95-42 | 96-42 | 97-42 | Rᶜ | R⁵ᵇ | R⁹ᵇ | R¹⁰ᵇ | Gᵃ | Zᵃ |
| 94-43 | 95-43 | 96-43 | 97-43 | Rᵃ | R⁵ᶜ | R⁹ᵇ | R¹⁰ᵇ | Gᵃ | Zᵃ |
| 94-44 | 95-44 | 96-44 | 97-44 | Rᵇ | R⁵ᶜ | R⁹ᵇ | R¹⁰ᵇ | Gᵃ | Zᵃ |
| 94-45 | 95-45 | 96-45 | 97-45 | Rᶜ | R⁵ᶜ | R⁹ᵇ | R¹⁰ᵇ | Gᵃ | Zᵃ |
| 94-46 | 95-46 | 96-46 | 97-46 | Rᵃ | R⁵ᵃ | R⁹ᶜ | R¹⁰ᵇ | Gᵃ | Zᵃ |
| 94-47 | 95-47 | 96-47 | 97-47 | Rᵇ | R⁵ᵃ | R⁹ᶜ | R¹⁰ᵇ | Gᵃ | Zᵃ |
| 94-48 | 95-48 | 96-48 | 97-48 | Rᶜ | R⁵ᵃ | R⁹ᶜ | R¹⁰ᵇ | Gᵃ | Zᵃ |
| 94-49 | 95-49 | 96-49 | 97-49 | Rᵃ | R⁵ᵇ | R⁹ᶜ | R¹⁰ᵇ | Gᵃ | Zᵃ |
| 94-50 | 95-50 | 96-50 | 97-50 | Rᵇ | R⁵ᵇ | R⁹ᶜ | R¹⁰ᵇ | Gᵃ | Zᵃ |
| 94-51 | 95-51 | 96-51 | 97-51 | Rᶜ | R⁵ᵇ | R⁹ᶜ | R¹⁰ᵇ | Gᵃ | Zᵃ |
| 94-52 | 95-52 | 96-52 | 97-52 | Rᵃ | R⁵ᶜ | R⁹ᶜ | R¹⁰ᵇ | Gᵃ | Zᵃ |
| 94-53 | 95-53 | 96-53 | 97-53 | Rᵇ | R⁵ᶜ | R⁹ᶜ | R¹⁰ᵇ | Gᵃ | Zᵃ |
| 94-54 | 95-54 | 96-54 | 97-54 | Rᶜ | R⁵ᶜ | R⁹ᶜ | R¹⁰ᵇ | Gᵃ | Zᵃ |
| 94-55 | 95-55 | 96-55 | 97-55 | Rᵃ | R⁵ᵃ | R⁹ᵃ | R¹⁰ᶜ | Gᵃ | Zᵃ |
| 94-56 | 95-56 | 96-56 | 97-56 | Rᵇ | R⁵ᵃ | R⁹ᵃ | R¹⁰ᶜ | Gᵃ | Zᵃ |
| 94-57 | 95-57 | 96-57 | 97-57 | Rᶜ | R⁵ᵃ | R⁹ᵃ | R¹⁰ᶜ | Gᵃ | Zᵃ |
| 94-58 | 95-58 | 96-58 | 97-58 | Rᵃ | R⁵ᵇ | R⁹ᵃ | R¹⁰ᶜ | Gᵃ | Zᵃ |
| 94-59 | 95-59 | 96-59 | 97-59 | Rᵇ | R⁵ᵇ | R⁹ᵃ | R¹⁰ᶜ | Gᵃ | Zᵃ |
| 94-60 | 95-60 | 96-60 | 97-60 | Rᶜ | R⁵ᵇ | R⁹ᵃ | R¹⁰ᶜ | Gᵃ | Zᵃ |
| 94-61 | 95-61 | 96-61 | 97-61 | Rᵃ | R⁵ᶜ | R⁹ᵃ | R¹⁰ᶜ | Gᵃ | Zᵃ |
| 94-62 | 95-62 | 96-62 | 97-62 | Rᵇ | R⁵ᶜ | R⁹ᵃ | R¹⁰ᶜ | Gᵃ | Zᵃ |
| 94-63 | 95-63 | 96-63 | 97-63 | Rᶜ | R⁵ᶜ | R⁹ᵃ | R¹⁰ᶜ | Gᵃ | Zᵃ |
| 94-64 | 95-64 | 96-64 | 97-64 | Rᵃ | R⁵ᵃ | R⁹ᵇ | R¹⁰ᶜ | Gᵃ | Zᵃ |
| 94-65 | 95-65 | 96-65 | 97-65 | Rᵇ | R⁵ᵃ | R⁹ᵇ | R¹⁰ᶜ | Gᵃ | Zᵃ |
| 94-66 | 95-66 | 96-66 | 97-66 | Rᶜ | R⁵ᵃ | R⁹ᵇ | R¹⁰ᶜ | Gᵃ | Zᵃ |
| 94-67 | 95-67 | 96-67 | 97-67 | Rᵃ | R⁵ᵇ | R⁹ᵇ | R¹⁰ᶜ | Gᵃ | Zᵃ |
| 94-68 | 95-68 | 96-68 | 97-68 | Rᵇ | R⁵ᵇ | R⁹ᵇ | R¹⁰ᶜ | Gᵃ | Zᵃ |
| 94-69 | 95-69 | 96-69 | 97-69 | Rᶜ | R⁵ᵇ | R⁹ᵇ | R¹⁰ᶜ | Gᵃ | Zᵃ |
| 94-70 | 95-70 | 96-70 | 97-70 | Rᵃ | R⁵ᶜ | R⁹ᵇ | R¹⁰ᶜ | Gᵃ | Zᵃ |
| 94-71 | 95-71 | 96-71 | 97-71 | Rᵇ | R⁵ᶜ | R⁹ᵇ | R¹⁰ᶜ | Gᵃ | Zᵃ |
| 94-72 | 95-72 | 96-72 | 97-72 | Rᶜ | R⁵ᶜ | R⁹ᵇ | R¹⁰ᶜ | Gᵃ | Zᵃ |
| 94-73 | 95-73 | 96-73 | 97-73 | Rᵃ | R⁵ᵃ | R⁹ᶜ | R¹⁰ᶜ | Gᵃ | Zᵃ |
| 94-74 | 95-74 | 96-74 | 97-74 | Rᵇ | R⁵ᵃ | R⁹ᶜ | R¹⁰ᶜ | Gᵃ | Zᵃ |
| 94-75 | 95-75 | 96-75 | 97-75 | Rᶜ | R⁵ᵃ | R⁹ᶜ | R¹⁰ᶜ | Gᵃ | Zᵃ |
| 94-76 | 95-76 | 96-76 | 97-76 | Rᵃ | R⁵ᵇ | R⁹ᶜ | R¹⁰ᶜ | Gᵃ | Zᵃ |
| 94-77 | 95-77 | 96-77 | 97-77 | Rᵇ | R⁵ᵇ | R⁹ᶜ | R¹⁰ᶜ | Gᵃ | Zᵃ |
| 94-78 | 95-78 | 96-78 | 97-78 | Rᶜ | R⁵ᵇ | R⁹ᶜ | R¹⁰ᶜ | Gᵃ | Zᵃ |
| 94-79 | 95-79 | 96-79 | 97-79 | Rᵃ | R⁵ᶜ | R⁹ᶜ | R¹⁰ᶜ | Gᵃ | Zᵃ |
| 94-80 | 95-80 | 96-80 | 97-80 | Rᵇ | R⁵ᶜ | R⁹ᶜ | R¹⁰ᶜ | Gᵃ | Zᵃ |
| 94-81 | 95-81 | 96-81 | 97-81 | Rᶜ | R⁵ᶜ | R⁹ᶜ | R¹⁰ᶜ | Gᵃ | Zᵃ |
| 94-82 | 95-82 | 96-82 | 97-82 | Rᵃ | R⁵ᵃ | R⁹ᵃ | R¹⁰ᶜ | Gᵇ | Zᵃ |
| 94-83 | 95-83 | 96-83 | 97-83 | Rᵇ | R⁵ᵃ | R⁹ᵃ | R¹⁰ᶜ | Gᵇ | Zᵃ |
| 94-84 | 95-84 | 96-84 | 97-84 | Rᶜ | R⁵ᵃ | R⁹ᵃ | R¹⁰ᶜ | Gᵇ | Zᵃ |
| 94-85 | 95-85 | 96-85 | 97-85 | Rᵃ | R⁵ᵇ | R⁹ᵃ | R¹⁰ᶜ | Gᵇ | Zᵃ |
| 94-86 | 95-86 | 96-86 | 97-86 | Rᵇ | R⁵ᵇ | R⁹ᵃ | R¹⁰ᶜ | Gᵇ | Zᵃ |
| 94-87 | 95-87 | 96-87 | 97-87 | Rᶜ | R⁵ᵇ | R⁹ᵃ | R¹⁰ᶜ | Gᵇ | Zᵃ |
| 94-88 | 95-88 | 96-88 | 97-88 | Rᵃ | R⁵ᶜ | R⁹ᵃ | R¹⁰ᶜ | Gᵇ | Zᵃ |
| 94-89 | 95-89 | 96-89 | 97-89 | Rᵇ | R⁵ᶜ | R⁹ᵃ | R¹⁰ᶜ | Gᵇ | Zᵃ |
| 94-90 | 95-90 | 96-90 | 97-90 | Rᶜ | R⁵ᶜ | R⁹ᵃ | R¹⁰ᶜ | Gᵇ | Zᵃ |
| 94-91 | 95-91 | 96-91 | 97-91 | Rᵃ | R⁵ᵃ | R⁹ᵇ | R¹⁰ᶜ | Gᵇ | Zᵃ |
| 94-92 | 95-92 | 96-92 | 97-92 | Rᵇ | R⁵ᵃ | R⁹ᵇ | R¹⁰ᶜ | Gᵇ | Zᵃ |
| 94-93 | 95-93 | 96-93 | 97-93 | Rᶜ | R⁵ᵃ | R⁹ᵇ | R¹⁰ᶜ | Gᵇ | Zᵃ |
| 94-94 | 95-94 | 96-94 | 97-94 | Rᵃ | R⁵ᵇ | R⁹ᵇ | R¹⁰ᶜ | Gᵇ | Zᵃ |
| 94-95 | 95-95 | 96-95 | 97-95 | Rᵇ | R⁵ᵇ | R⁹ᵇ | R¹⁰ᶜ | Gᵇ | Zᵃ |
| 94-96 | 95-96 | 96-96 | 97-96 | Rᶜ | R⁵ᵇ | R⁹ᵇ | R¹⁰ᶜ | Gᵇ | Zᵃ |
| 94-97 | 95-97 | 96-97 | 97-97 | Rᵃ | R⁵ᶜ | R⁹ᵇ | R¹⁰ᶜ | Gᵇ | Zᵃ |
| 94-98 | 95-98 | 96-98 | 97-98 | Rᵇ | R⁵ᶜ | R⁹ᵇ | R¹⁰ᶜ | Gᵇ | Zᵃ |
| 94-99 | 95-99 | 96-99 | 97-99 | Rᶜ | R⁵ᶜ | R⁹ᵇ | R¹⁰ᶜ | Gᵇ | Zᵃ |
| 94-100 | 95-100 | 96-100 | 97-100 | Rᵃ | R⁵ᵃ | R⁹ᶜ | R¹⁰ᶜ | Gᵇ | Zᵃ |
| 94-101 | 95-101 | 96-101 | 97-101 | Rᵇ | R⁵ᵃ | R⁹ᶜ | R¹⁰ᶜ | Gᵇ | Zᵃ |
| 94-102 | 95-102 | 96-102 | 97-102 | Rᶜ | R⁵ᵃ | R⁹ᶜ | R¹⁰ᶜ | Gᵇ | Zᵃ |
| 94-103 | 95-103 | 96-103 | 97-103 | Rᵃ | R⁵ᵇ | R⁹ᶜ | R¹⁰ᶜ | Gᵇ | Zᵃ |
| 94-104 | 95-104 | 96-104 | 97-104 | Rᵇ | R⁵ᵇ | R⁹ᶜ | R¹⁰ᶜ | Gᵇ | Zᵃ |
| 94-105 | 95-105 | 96-105 | 97-105 | Rᶜ | R⁵ᵇ | R⁹ᶜ | R¹⁰ᶜ | Gᵇ | Zᵃ |
| 94-106 | 95-106 | 96-106 | 97-106 | Rᵃ | R⁵ᶜ | R⁹ᶜ | R¹⁰ᶜ | Gᵇ | Zᵃ |
| 94-107 | 95-107 | 96-107 | 97-107 | Rᵇ | R⁵ᶜ | R⁹ᶜ | R¹⁰ᶜ | Gᵇ | Zᵃ |
| 94-108 | 95-108 | 96-108 | 97-108 | Rᶜ | R⁵ᶜ | R⁹ᶜ | R¹⁰ᶜ | Gᵇ | Zᵃ |
| 94-109 | 95-109 | 96-109 | 97-109 | Rᵃ | R⁵ᵃ | R⁹ᵃ | R¹⁰ᶜ | Gᵇ | Zᵃ |
| 94-110 | 95-110 | 96-110 | 97-110 | Rᵇ | R⁵ᵃ | R⁹ᵃ | R¹⁰ᶜ | Gᵇ | Zᵃ |
| 94-111 | 95-111 | 96-111 | 97-111 | Rᶜ | R⁵ᵃ | R⁹ᵃ | R¹⁰ᶜ | Gᵇ | Zᵃ |
| 94-112 | 95-112 | 96-112 | 97-112 | Rᵃ | R⁵ᵇ | R⁹ᵃ | R¹⁰ᶜ | Gᵇ | Zᵃ |
| 94-113 | 95-113 | 96-113 | 97-113 | Rᵇ | R⁵ᵇ | R⁹ᵃ | R¹⁰ᶜ | Gᵇ | Zᵃ |
| 94-114 | 95-114 | 96-114 | 97-114 | Rᶜ | R⁵ᵇ | R⁹ᵃ | R¹⁰ᶜ | Gᵇ | Zᵃ |
| 94-115 | 95-115 | 96-115 | 97-115 | Rᵃ | R⁵ᶜ | R⁹ᵃ | R¹⁰ᶜ | Gᵇ | Zᵃ |
| 94-116 | 95-116 | 96-116 | 97-116 | Rᵇ | R⁵ᶜ | R⁹ᵃ | R¹⁰ᶜ | Gᵇ | Zᵃ |
| 94-117 | 95-117 | 96-117 | 97-117 | Rᶜ | R⁵ᶜ | R⁹ᵃ | R¹⁰ᶜ | Gᵇ | Zᵃ |
| 94-118 | 95-118 | 96-118 | 97-118 | Rᵃ | R⁵ᵃ | R⁹ᵇ | R¹⁰ᶜ | Gᵇ | Zᵃ |
| 94-119 | 95-119 | 96-119 | 97-119 | Rᵇ | R⁵ᵃ | R⁹ᵇ | R¹⁰ᶜ | Gᵇ | Zᵃ |
| 94-120 | 95-120 | 96-120 | 97-120 | Rᶜ | R⁵ᵃ | R⁹ᵇ | R¹⁰ᶜ | Gᵇ | Zᵃ |
| 94-121 | 95-121 | 96-121 | 97-121 | Rᵃ | R⁵ᵇ | R⁹ᵇ | R¹⁰ᶜ | Gᵇ | Zᵃ |
| 94-122 | 95-122 | 96-122 | 97-122 | Rᵇ | R⁵ᵇ | R⁹ᵇ | R¹⁰ᶜ | Gᵇ | Zᵃ |
| 94-123 | 95-123 | 96-123 | 97-123 | Rᶜ | R⁵ᵇ | R⁹ᵇ | R¹⁰ᶜ | Gᵇ | Zᵃ |
| 94-124 | 95-124 | 96-124 | 97-124 | Rᵃ | R⁵ᶜ | R⁹ᵇ | R¹⁰ᶜ | Gᵇ | Zᵃ |
| 94-125 | 95-125 | 96-125 | 97-125 | Rᵇ | R⁵ᶜ | R⁹ᵇ | R¹⁰ᶜ | Gᵇ | Zᵃ |
| 94-126 | 95-126 | 96-126 | 97-126 | Rᶜ | R⁵ᶜ | R⁹ᵇ | R¹⁰ᶜ | Gᵇ | Zᵃ |
| 94-127 | 95-127 | 96-127 | 97-127 | Rᵃ | R⁵ᵃ | R⁹ᶜ | R¹⁰ᶜ | Gᵇ | Zᵃ |
| 94-128 | 95-128 | 96-128 | 97-128 | Rᵇ | R⁵ᵃ | R⁹ᶜ | R¹⁰ᶜ | Gᵇ | Zᵃ |
| 94-129 | 95-129 | 96-129 | 97-129 | Rᶜ | R⁵ᵃ | R⁹ᶜ | R¹⁰ᶜ | Gᵇ | Zᵃ |
| 94-130 | 95-130 | 96-130 | 97-130 | Rᵃ | R⁵ᵇ | R⁹ᶜ | R¹⁰ᶜ | Gᵇ | Zᵃ |
| 94-131 | 95-131 | 96-131 | 97-131 | Rᵇ | R⁵ᵇ | R⁹ᶜ | R¹⁰ᶜ | Gᵇ | Zᵃ |
| 94-132 | 95-132 | 96-132 | 97-132 | Rᶜ | R⁵ᵇ | R⁹ᶜ | R¹⁰ᶜ | Gᵇ | Zᵃ |
| 94-133 | 95-133 | 96-133 | 97-133 | Rᵃ | R⁵ᶜ | R⁹ᶜ | R¹⁰ᶜ | Gᵇ | Zᵃ |
| 94-134 | 95-134 | 96-134 | 97-134 | Rᵇ | R⁵ᶜ | R⁹ᶜ | R¹⁰ᶜ | Gᵇ | Zᵃ |
| 94-135 | 95-135 | 96-135 | 97-135 | Rᶜ | R⁵ᶜ | R⁹ᶜ | R¹⁰ᶜ | Gᵇ | Zᵃ |
| 94-136 | 95-136 | 96-136 | 97-136 | Rᵃ | R⁵ᵃ | R⁹ᵃ | R¹⁰ᶜ | Gᵇ | Zᵃ |
| 94-137 | 95-137 | 96-137 | 97-137 | Rᵇ | R⁵ᵃ | R⁹ᵃ | R¹⁰ᶜ | Gᵇ | Zᵃ |
| 94-138 | 95-138 | 96-138 | 97-138 | Rᶜ | R⁵ᵃ | R⁹ᵃ | R¹⁰ᶜ | Gᵇ | Zᵃ |
| 94-139 | 95-139 | 96-139 | 97-139 | Rᵃ | R⁵ᵇ | R⁹ᵃ | R¹⁰ᶜ | Gᵇ | Zᵃ |
| 94-140 | 95-140 | 96-140 | 97-140 | Rᵇ | R⁵ᵇ | R⁹ᵃ | R¹⁰ᶜ | Gᵇ | Zᵃ |
| 94-141 | 95-141 | 96-141 | 97-141 | Rᶜ | R⁵ᵇ | R⁹ᵃ | R¹⁰ᶜ | Gᵇ | Zᵃ |
| 94-142 | 95-142 | 96-142 | 97-142 | Rᵃ | R⁵ᶜ | R⁹ᵃ | R¹⁰ᶜ | Gᵇ | Zᵃ |
| 94-143 | 95-143 | 96-143 | 97-143 | Rᵇ | R⁵ᶜ | R⁹ᵃ | R¹⁰ᶜ | Gᵇ | Zᵃ |
| 94-144 | 95-144 | 96-144 | 97-144 | Rᶜ | R⁵ᶜ | R⁹ᵃ | R¹⁰ᶜ | Gᵇ | Zᵃ |
| 94-145 | 95-145 | 96-145 | 97-145 | Rᵃ | R⁵ᵃ | R⁹ᵇ | R¹⁰ᶜ | Gᵇ | Zᵃ |
| 94-146 | 95-146 | 96-146 | 97-146 | Rᵇ | R⁵ᵃ | R⁹ᵇ | R¹⁰ᶜ | Gᵇ | Zᵃ |
| 94-147 | 95-147 | 96-147 | 97-147 | Rᶜ | R⁵ᵃ | R⁹ᵇ | R¹⁰ᶜ | Gᵇ | Zᵃ |
| 94-148 | 95-148 | 96-148 | 97-148 | Rᵃ | R⁵ᵇ | R⁹ᵇ | R¹⁰ᶜ | Gᵇ | Zᵃ |
| 94-149 | 95-149 | 96-149 | 97-149 | Rᵇ | R⁵ᵇ | R⁹ᵇ | R¹⁰ᶜ | Gᵇ | Zᵃ |
| 94-150 | 95-150 | 96-150 | 97-150 | Rᶜ | R⁵ᵇ | R⁹ᵇ | R¹⁰ᶜ | Gᵇ | Zᵃ |
| 94-151 | 95-151 | 96-151 | 97-151 | Rᵃ | R⁵ᶜ | R⁹ᵇ | R¹⁰ᶜ | Gᵇ | Zᵃ |
| 94-152 | 95-152 | 96-152 | 97-152 | Rᵇ | R⁵ᶜ | R⁹ᵇ | R¹⁰ᶜ | Gᵇ | Zᵃ |
| 94-153 | 95-153 | 96-153 | 97-153 | Rᶜ | R⁵ᶜ | R⁹ᵇ | R¹⁰ᶜ | Gᵇ | Zᵃ |
| 94-154 | 95-154 | 96-154 | 97-154 | Rᵃ | R⁵ᵃ | R⁹ᶜ | R¹⁰ᶜ | Gᵇ | Zᵃ |
| 94-155 | 95-155 | 96-155 | 97-155 | Rᵇ | R⁵ᵃ | R⁹ᶜ | R¹⁰ᶜ | Gᵇ | Zᵃ |
| 94-156 | 95-156 | 96-156 | 97-156 | Rᶜ | R⁵ᵃ | R⁹ᶜ | R¹⁰ᶜ | Gᵇ | Zᵃ |
| 94-157 | 95-157 | 96-157 | 97-157 | Rᵃ | R⁵ᵇ | R⁹ᶜ | R¹⁰ᶜ | Gᵇ | Zᵃ |
| 94-158 | 95-158 | 96-158 | 97-158 | Rᵇ | R⁵ᵇ | R⁹ᶜ | R¹⁰ᶜ | Gᵇ | Zᵃ |
| 94-159 | 95-159 | 96-159 | 97-159 | Rᶜ | R⁵ᵇ | R⁹ᶜ | R¹⁰ᶜ | Gᵇ | Zᵃ |
| 94-160 | 95-160 | 96-160 | 97-160 | Rᵃ | R⁵ᶜ | R⁹ᶜ | R¹⁰ᶜ | Gᵇ | Zᵃ |
| 94-161 | 95-161 | 96-161 | 97-161 | Rᵇ | R⁵ᶜ | R⁹ᶜ | R¹⁰ᶜ | Gᵇ | Zᵃ |
| 94-162 | 95-162 | 96-162 | 97-162 | Rᶜ | R⁵ᶜ | R⁹ᶜ | R¹⁰ᶜ | Gᵇ | Zᵃ |
| 94-163 | 95-163 | 96-163 | 97-163 | Rᵃ | R⁵ᵃ | R⁹ᵃ | R¹⁰ᶜ | Gᶜ | Zᵃ |
| 94-164 | 95-164 | 96-164 | 97-164 | Rᵇ | R⁵ᵃ | R⁹ᵃ | R¹⁰ᶜ | Gᶜ | Zᵃ |
| 94-165 | 95-165 | 96-165 | 97-165 | Rᶜ | R⁵ᵃ | R⁹ᵃ | R¹⁰ᶜ | Gᶜ | Zᵃ |
| 94-166 | 95-166 | 96-166 | 97-166 | Rᵃ | R⁵ᵇ | R⁹ᵃ | R¹⁰ᶜ | Gᶜ | Zᵃ |
| 94-167 | 95-167 | 96-167 | 97-167 | Rᵇ | R⁵ᵇ | R⁹ᵃ | R¹⁰ᶜ | Gᶜ | Zᵃ |
| 94-168 | 95-168 | 96-168 | 97-168 | Rᶜ | R⁵ᵇ | R⁹ᵃ | R¹⁰ᶜ | Gᶜ | Zᵃ |
| 94-169 | 95-169 | 96-169 | 97-169 | Rᵃ | R⁵ᶜ | R⁹ᵃ | R¹⁰ᶜ | Gᶜ | Zᵃ |
| 94-170 | 95-170 | 96-170 | 97-170 | Rᵇ | R⁵ᶜ | R⁹ᵃ | R¹⁰ᶜ | Gᶜ | Zᵃ |
| 94-171 | 95-171 | 96-171 | 97-171 | Rᶜ | R⁵ᶜ | R⁹ᵃ | R¹⁰ᶜ | Gᶜ | Zᵃ |
| 94-172 | 95-172 | 96-172 | 97-172 | Rᵃ | R⁵ᵃ | R⁹ᵇ | R¹⁰ᶜ | Gᶜ | Zᵃ |
| 94-173 | 95-173 | 96-173 | 97-173 | Rᵇ | R⁵ᵃ | R⁹ᵇ | R¹⁰ᶜ | Gᶜ | Zᵃ |
| 94-174 | 95-174 | 96-174 | 97-174 | Rᶜ | R⁵ᵃ | R⁹ᵇ | R¹⁰ᶜ | Gᶜ | Zᵃ |
| 94-175 | 95-175 | 96-175 | 97-175 | Rᵃ | R⁵ᵇ | R⁹ᵇ | R¹⁰ᶜ | Gᶜ | Zᵃ |
| 94-176 | 95-176 | 96-176 | 97-176 | Rᵇ | R⁵ᵇ | R⁹ᵇ | R¹⁰ᶜ | Gᶜ | Zᵃ |
| 94-177 | 95-177 | 96-177 | 97-177 | Rᶜ | R⁵ᵇ | R⁹ᵇ | R¹⁰ᶜ | Gᶜ | Zᵃ |
| 94-178 | 95-178 | 96-178 | 97-178 | Rᵃ | R⁵ᶜ | R⁹ᵇ | R¹⁰ᶜ | Gᶜ | Zᵃ |
| 94-179 | 95-179 | 96-179 | 97-179 | Rᵇ | R⁵ᶜ | R⁹ᵇ | R¹⁰ᶜ | Gᶜ | Zᵃ |
| 94-180 | 95-180 | 96-180 | 97-180 | Rᶜ | R⁵ᶜ | R⁹ᵇ | R¹⁰ᶜ | Gᶜ | Zᵃ |

-continued

| Formulae | | | | R | R⁵ | R⁹ | R¹⁰ | G | Z |
|---|---|---|---|---|---|---|---|---|---|
| 94-181 | 95-181 | 96-181 | 97-181 | Rᵃ | R⁵ᵃ | R⁹ᶜ | R¹⁰ᶜ | Gᶜ | Zᵃ |
| 94-182 | 95-182 | 96-182 | 97-182 | Rᵇ | R⁵ᵃ | R⁹ᶜ | R¹⁰ᶜ | Gᶜ | Zᵃ |
| 94-183 | 95-183 | 96-183 | 97-183 | Rᶜ | R⁵ᵃ | R⁹ᶜ | R¹⁰ᶜ | Gᶜ | Zᵃ |
| 94-184 | 95-184 | 96-184 | 97-184 | Rᵃ | R⁵ᵇ | R⁹ᶜ | R¹⁰ᶜ | Gᶜ | Zᵃ |
| 94-185 | 95-185 | 96-185 | 97-185 | Rᵇ | R⁵ᵇ | R⁹ᶜ | R¹⁰ᶜ | Gᶜ | Zᵃ |
| 94-186 | 95-186 | 96-186 | 97-186 | Rᶜ | R⁵ᵇ | R⁹ᶜ | R¹⁰ᶜ | Gᶜ | Zᵃ |
| 94-187 | 95-187 | 96-187 | 97-187 | Rᵃ | R⁵ᶜ | R⁹ᶜ | R¹⁰ᶜ | Gᶜ | Zᵃ |
| 94-188 | 95-188 | 96-188 | 97-188 | Rᵇ | R⁵ᶜ | R⁹ᶜ | R¹⁰ᶜ | Gᶜ | Zᵃ |
| 94-189 | 95-189 | 96-189 | 97-189 | Rᶜ | R⁵ᶜ | R⁹ᶜ | R¹⁰ᶜ | Gᶜ | Zᵃ |
| 94-190 | 95-190 | 96-190 | 97-190 | Rᵃ | R⁵ᵃ | R⁹ᵃ | R¹⁰ᶜ | Gᶜ | Zᵃ |
| 94-191 | 95-191 | 96-191 | 97-191 | Rᵇ | R⁵ᵃ | R⁹ᵃ | R¹⁰ᶜ | Gᶜ | Zᵃ |
| 94-192 | 95-192 | 96-192 | 97-192 | Rᶜ | R⁵ᵃ | R⁹ᵃ | R¹⁰ᶜ | Gᶜ | Zᵃ |
| 94-193 | 95-193 | 96-193 | 97-193 | Rᵃ | R⁵ᵇ | R⁹ᵃ | R¹⁰ᶜ | Gᶜ | Zᵃ |
| 94-194 | 95-194 | 96-194 | 97-194 | Rᵇ | R⁵ᵇ | R⁹ᵃ | R¹⁰ᶜ | Gᶜ | Zᵃ |
| 94-195 | 95-195 | 96-195 | 97-195 | Rᶜ | R⁵ᵇ | R⁹ᵃ | R¹⁰ᶜ | Gᶜ | Zᵃ |
| 94-196 | 95-196 | 96-196 | 97-196 | Rᵃ | R⁵ᶜ | R⁹ᵃ | R¹⁰ᶜ | Gᶜ | Zᵃ |
| 94-197 | 95-197 | 96-197 | 97-197 | Rᵇ | R⁵ᶜ | R⁹ᵃ | R¹⁰ᶜ | Gᶜ | Zᵃ |
| 94-198 | 95-198 | 96-198 | 97-198 | Rᶜ | R⁵ᶜ | R⁹ᵃ | R¹⁰ᶜ | Gᶜ | Zᵃ |
| 94-199 | 95-199 | 96-199 | 97-199 | Rᵃ | R⁵ᵃ | R⁹ᵇ | R¹⁰ᶜ | Gᶜ | Zᵃ |
| 94-200 | 95-200 | 96-200 | 97-200 | Rᵇ | R⁵ᵃ | R⁹ᵇ | R¹⁰ᶜ | Gᶜ | Zᵃ |
| 94-201 | 95-201 | 96-201 | 97-201 | Rᶜ | R⁵ᵃ | R⁹ᵇ | R¹⁰ᶜ | Gᶜ | Zᵃ |
| 94-202 | 95-202 | 96-202 | 97-202 | Rᵃ | R⁵ᵇ | R⁹ᵇ | R¹⁰ᶜ | Gᶜ | Zᵃ |
| 94-203 | 95-203 | 96-203 | 97-203 | Rᵇ | R⁵ᵇ | R⁹ᵇ | R¹⁰ᶜ | Gᶜ | Zᵃ |
| 94-204 | 95-204 | 96-204 | 97-204 | Rᶜ | R⁵ᵇ | R⁹ᵇ | R¹⁰ᶜ | Gᶜ | Zᵃ |
| 94-205 | 95-205 | 96-205 | 97-205 | Rᵃ | R⁵ᶜ | R⁹ᵇ | R¹⁰ᶜ | Gᶜ | Zᵃ |
| 94-206 | 95-206 | 96-206 | 97-206 | Rᵇ | R⁵ᶜ | R⁹ᵇ | R¹⁰ᶜ | Gᶜ | Zᵃ |
| 94-207 | 95-207 | 96-207 | 97-207 | Rᶜ | R⁵ᶜ | R⁹ᵇ | R¹⁰ᶜ | Gᶜ | Zᵃ |
| 94-208 | 95-208 | 96-208 | 97-208 | Rᵃ | R⁵ᵃ | R⁹ᶜ | R¹⁰ᶜ | Gᶜ | Zᵃ |
| 94-209 | 95-209 | 96-209 | 97-209 | Rᵇ | R⁵ᵃ | R⁹ᶜ | R¹⁰ᶜ | Gᶜ | Zᵃ |
| 94-210 | 95-210 | 96-210 | 97-210 | Rᶜ | R⁵ᵃ | R⁹ᶜ | R¹⁰ᶜ | Gᶜ | Zᵃ |
| 94-211 | 95-211 | 96-211 | 97-211 | Rᵃ | R⁵ᵇ | R⁹ᶜ | R¹⁰ᶜ | Gᶜ | Zᵃ |
| 94-212 | 95-212 | 96-212 | 97-212 | Rᵇ | R⁵ᵇ | R⁹ᶜ | R¹⁰ᶜ | Gᶜ | Zᵃ |
| 94-213 | 95-213 | 96-213 | 97-213 | Rᶜ | R⁵ᵇ | R⁹ᶜ | R¹⁰ᶜ | Gᶜ | Zᵃ |
| 94-214 | 95-214 | 96-214 | 97-214 | Rᵃ | R⁵ᶜ | R⁹ᶜ | R¹⁰ᶜ | Gᶜ | Zᵃ |
| 94-215 | 95-215 | 96-215 | 97-215 | Rᵇ | R⁵ᶜ | R⁹ᶜ | R¹⁰ᶜ | Gᶜ | Zᵃ |
| 94-216 | 95-216 | 96-216 | 97-216 | Rᶜ | R⁵ᶜ | R⁹ᶜ | R¹⁰ᶜ | Gᶜ | Zᵃ |
| 94-217 | 95-217 | 96-217 | 97-217 | Rᵃ | R⁵ᵃ | R⁹ᵃ | R¹⁰ᶜ | Gᶜ | Zᵃ |
| 94-218 | 95-218 | 96-218 | 97-218 | Rᵇ | R⁵ᵃ | R⁹ᵃ | R¹⁰ᶜ | Gᶜ | Zᵃ |
| 94-219 | 95-219 | 96-219 | 97-219 | Rᶜ | R⁵ᵃ | R⁹ᵃ | R¹⁰ᶜ | Gᶜ | Zᵃ |
| 94-220 | 95-220 | 96-220 | 97-220 | Rᵃ | R⁵ᵇ | R⁹ᵃ | R¹⁰ᶜ | Gᶜ | Zᵃ |
| 94-221 | 95-221 | 96-221 | 97-221 | Rᵇ | R⁵ᵇ | R⁹ᵃ | R¹⁰ᶜ | Gᶜ | Zᵃ |
| 94-222 | 95-222 | 96-222 | 97-222 | Rᶜ | R⁵ᵇ | R⁹ᵃ | R¹⁰ᶜ | Gᶜ | Zᵃ |
| 94-223 | 95-223 | 96-223 | 97-223 | Rᵃ | R⁵ᶜ | R⁹ᵃ | R¹⁰ᶜ | Gᶜ | Zᵃ |
| 94-224 | 95-224 | 96-224 | 97-224 | Rᵇ | R⁵ᶜ | R⁹ᵃ | R¹⁰ᶜ | Gᶜ | Zᵃ |
| 94-225 | 95-225 | 96-225 | 97-225 | Rᶜ | R⁵ᶜ | R⁹ᵃ | R¹⁰ᶜ | Gᶜ | Zᵃ |
| 94-226 | 95-226 | 96-226 | 97-226 | Rᵃ | R⁵ᵃ | R⁹ᵇ | R¹⁰ᶜ | Gᶜ | Zᵃ |
| 94-227 | 95-227 | 96-227 | 97-227 | Rᵇ | R⁵ᵃ | R⁹ᵇ | R¹⁰ᶜ | Gᶜ | Zᵃ |
| 94-228 | 95-228 | 96-228 | 97-228 | Rᶜ | R⁵ᵃ | R⁹ᵇ | R¹⁰ᶜ | Gᶜ | Zᵃ |
| 94-229 | 95-229 | 96-229 | 97-229 | Rᵃ | R⁵ᵇ | R⁹ᵇ | R¹⁰ᶜ | Gᶜ | Zᵃ |
| 94-230 | 95-230 | 96-230 | 97-230 | Rᵇ | R⁵ᵇ | R⁹ᵇ | R¹⁰ᶜ | Gᶜ | Zᵃ |
| 94-231 | 95-231 | 96-231 | 97-231 | Rᶜ | R⁵ᵇ | R⁹ᵇ | R¹⁰ᶜ | Gᶜ | Zᵃ |
| 94-232 | 95-232 | 96-232 | 97-232 | Rᵃ | R⁵ᶜ | R⁹ᵇ | R¹⁰ᶜ | Gᶜ | Zᵃ |
| 94-233 | 95-233 | 96-233 | 97-233 | Rᵇ | R⁵ᶜ | R⁹ᵇ | R¹⁰ᶜ | Gᶜ | Zᵃ |
| 94-234 | 95-234 | 96-234 | 97-234 | Rᶜ | R⁵ᶜ | R⁹ᵇ | R¹⁰ᶜ | Gᶜ | Zᵃ |
| 94-235 | 95-235 | 96-235 | 97-235 | Rᵃ | R⁵ᵃ | R⁹ᶜ | R¹⁰ᶜ | Gᶜ | Zᵃ |
| 94-236 | 95-236 | 96-236 | 97-236 | Rᵇ | R⁵ᵃ | R⁹ᶜ | R¹⁰ᶜ | Gᶜ | Zᵃ |
| 94-237 | 95-237 | 96-237 | 97-237 | Rᶜ | R⁵ᵃ | R⁹ᶜ | R¹⁰ᶜ | Gᶜ | Zᵃ |
| 94-238 | 95-238 | 96-238 | 97-238 | Rᵃ | R⁵ᵇ | R⁹ᶜ | R¹⁰ᶜ | Gᶜ | Zᵃ |
| 94-239 | 95-239 | 96-239 | 97-239 | Rᵇ | R⁵ᵇ | R⁹ᶜ | R¹⁰ᶜ | Gᶜ | Zᵃ |
| 94-240 | 95-240 | 96-240 | 97-240 | Rᶜ | R⁵ᵇ | R⁹ᶜ | R¹⁰ᶜ | Gᶜ | Zᵃ |
| 94-241 | 95-241 | 96-241 | 97-241 | Rᵃ | R⁵ᶜ | R⁹ᶜ | R¹⁰ᶜ | Gᶜ | Zᵃ |
| 94-242 | 95-242 | 96-242 | 97-242 | Rᵇ | R⁵ᶜ | R⁹ᶜ | R¹⁰ᶜ | Gᶜ | Zᵃ |
| 94-243 | 95-243 | 96-243 | 97-243 | Rᶜ | R⁵ᶜ | R⁹ᶜ | R¹⁰ᶜ | Gᶜ | Zᵃ |
| 94-244 | 95-244 | 96-244 | 97-244 | Rᵃ | R⁵ᵃ | R⁹ᵃ | R¹⁰ᶜ | Gᵃ | Zᵇ |
| 94-245 | 95-245 | 96-245 | 97-245 | Rᵇ | R⁵ᵃ | R⁹ᵃ | R¹⁰ᶜ | Gᵃ | Zᵇ |
| 94-246 | 95-246 | 96-246 | 97-246 | Rᶜ | R⁵ᵃ | R⁹ᵃ | R¹⁰ᶜ | Gᵃ | Zᵇ |
| 94-247 | 95-247 | 96-247 | 97-247 | Rᵃ | R⁵ᵇ | R⁹ᵃ | R¹⁰ᶜ | Gᵃ | Zᵇ |
| 94-248 | 95-248 | 96-248 | 97-248 | Rᵇ | R⁵ᵇ | R⁹ᵃ | R¹⁰ᶜ | Gᵃ | Zᵇ |
| 94-249 | 95-249 | 96-249 | 97-249 | Rᶜ | R⁵ᵇ | R⁹ᵃ | R¹⁰ᶜ | Gᵃ | Zᵇ |
| 94-250 | 95-250 | 96-250 | 97-250 | Rᵃ | R⁵ᶜ | R⁹ᵃ | R¹⁰ᶜ | Gᵃ | Zᵇ |
| 94-251 | 95-251 | 96-251 | 97-251 | Rᵇ | R⁵ᶜ | R⁹ᵃ | R¹⁰ᶜ | Gᵃ | Zᵇ |
| 94-252 | 95-252 | 96-252 | 97-252 | Rᶜ | R⁵ᶜ | R⁹ᵃ | R¹⁰ᶜ | Gᵃ | Zᵇ |
| 94-253 | 95-253 | 96-253 | 97-253 | Rᵃ | R⁵ᵃ | R⁹ᵇ | R¹⁰ᶜ | Gᵃ | Zᵇ |
| 94-254 | 95-254 | 96-254 | 97-254 | Rᵇ | R⁵ᵃ | R⁹ᵇ | R¹⁰ᶜ | Gᵃ | Zᵇ |
| 94-255 | 95-255 | 96-255 | 97-255 | Rᶜ | R⁵ᵃ | R⁹ᵇ | R¹⁰ᶜ | Gᵃ | Zᵇ |
| 94-256 | 95-256 | 96-256 | 97-256 | Rᵃ | R⁵ᵇ | R⁹ᵇ | R¹⁰ᶜ | Gᵃ | Zᵇ |
| 94-257 | 95-257 | 96-257 | 97-257 | Rᵇ | R⁵ᵇ | R⁹ᵇ | R¹⁰ᶜ | Gᵃ | Zᵇ |
| 94-258 | 95-258 | 96-258 | 97-258 | Rᶜ | R⁵ᵇ | R⁹ᵇ | R¹⁰ᶜ | Gᵃ | Zᵇ |
| 94-259 | 95-259 | 96-259 | 97-259 | Rᵃ | R⁵ᶜ | R⁹ᵇ | R¹⁰ᶜ | Gᵃ | Zᵇ |
| 94-260 | 95-260 | 96-260 | 97-260 | Rᵇ | R⁵ᶜ | R⁹ᵇ | R¹⁰ᶜ | Gᵃ | Zᵇ |
| 94-261 | 95-261 | 96-261 | 97-261 | Rᶜ | R⁵ᶜ | R⁹ᵇ | R¹⁰ᶜ | Gᵃ | Zᵇ |
| 94-262 | 95-262 | 96-262 | 97-262 | Rᵃ | R⁵ᵃ | R⁹ᶜ | R¹⁰ᶜ | Gᵃ | Zᵇ |
| 94-263 | 95-263 | 96-263 | 97-263 | Rᵇ | R⁵ᵃ | R⁹ᶜ | R¹⁰ᶜ | Gᵃ | Zᵇ |
| 94-264 | 95-264 | 96-264 | 97-264 | Rᶜ | R⁵ᵃ | R⁹ᶜ | R¹⁰ᶜ | Gᵃ | Zᵇ |
| 94-265 | 95-265 | 96-265 | 97-265 | Rᵃ | R⁵ᵇ | R⁹ᶜ | R¹⁰ᶜ | Gᵃ | Zᵇ |
| 94-266 | 95-266 | 96-266 | 97-266 | Rᵇ | R⁵ᵇ | R⁹ᶜ | R¹⁰ᶜ | Gᵃ | Zᵇ |
| 94-267 | 95-267 | 96-267 | 97-267 | Rᶜ | R⁵ᵇ | R⁹ᶜ | R¹⁰ᶜ | Gᵃ | Zᵇ |
| 94-268 | 95-268 | 96-268 | 97-268 | Rᵃ | R⁵ᶜ | R⁹ᶜ | R¹⁰ᶜ | Gᵃ | Zᵇ |
| 94-269 | 95-269 | 96-269 | 97-269 | Rᵇ | R⁵ᶜ | R⁹ᶜ | R¹⁰ᶜ | Gᵃ | Zᵇ |
| 94-270 | 95-270 | 96-270 | 97-270 | Rᶜ | R⁵ᶜ | R⁹ᶜ | R¹⁰ᶜ | Gᵃ | Zᵇ |
| 94-271 | 95-271 | 96-271 | 97-271 | Rᵃ | R⁵ᵃ | R⁹ᵃ | R¹⁰ᶜ | Gᵃ | Zᵇ |
| 94-272 | 95-272 | 96-272 | 97-272 | Rᵇ | R⁵ᵃ | R⁹ᵃ | R¹⁰ᶜ | Gᵃ | Zᵇ |
| 94-273 | 95-273 | 96-273 | 97-273 | Rᶜ | R⁵ᵃ | R⁹ᵃ | R¹⁰ᶜ | Gᵃ | Zᵇ |
| 94-274 | 95-274 | 96-274 | 97-274 | Rᵃ | R⁵ᵇ | R⁹ᵃ | R¹⁰ᶜ | Gᵃ | Zᵇ |
| 94-275 | 95-275 | 96-275 | 97-275 | Rᵇ | R⁵ᵇ | R⁹ᵃ | R¹⁰ᶜ | Gᵃ | Zᵇ |
| 94-276 | 95-276 | 96-276 | 97-276 | Rᶜ | R⁵ᵇ | R⁹ᵃ | R¹⁰ᶜ | Gᵃ | Zᵇ |
| 94-277 | 95-277 | 96-277 | 97-277 | Rᵃ | R⁵ᶜ | R⁹ᵃ | R¹⁰ᶜ | Gᵃ | Zᵇ |
| 94-278 | 95-278 | 96-278 | 97-278 | Rᵇ | R⁵ᶜ | R⁹ᵃ | R¹⁰ᶜ | Gᵃ | Zᵇ |
| 94-279 | 95-279 | 96-279 | 97-279 | Rᶜ | R⁵ᶜ | R⁹ᵃ | R¹⁰ᶜ | Gᵃ | Zᵇ |
| 94-280 | 95-280 | 96-280 | 97-280 | Rᵃ | R⁵ᵃ | R⁹ᵇ | R¹⁰ᶜ | Gᵃ | Zᵇ |
| 94-281 | 95-281 | 96-281 | 97-281 | Rᵇ | R⁵ᵃ | R⁹ᵇ | R¹⁰ᶜ | Gᵃ | Zᵇ |
| 94-282 | 95-282 | 96-282 | 97-282 | Rᶜ | R⁵ᵃ | R⁹ᵇ | R¹⁰ᶜ | Gᵃ | Zᵇ |
| 94-283 | 95-283 | 96-283 | 97-283 | Rᵃ | R⁵ᵇ | R⁹ᵇ | R¹⁰ᶜ | Gᵃ | Zᵇ |
| 94-284 | 95-284 | 96-284 | 97-284 | Rᵇ | R⁵ᵇ | R⁹ᵇ | R¹⁰ᶜ | Gᵃ | Zᵇ |
| 94-285 | 95-285 | 96-285 | 97-285 | Rᶜ | R⁵ᵇ | R⁹ᵇ | R¹⁰ᶜ | Gᵃ | Zᵇ |
| 94-286 | 95-286 | 96-286 | 97-286 | Rᵃ | R⁵ᶜ | R⁹ᵇ | R¹⁰ᶜ | Gᵃ | Zᵇ |
| 94-287 | 95-287 | 96-287 | 97-287 | Rᵇ | R⁵ᶜ | R⁹ᵇ | R¹⁰ᶜ | Gᵃ | Zᵇ |
| 94-288 | 95-288 | 96-288 | 97-288 | Rᶜ | R⁵ᶜ | R⁹ᵇ | R¹⁰ᶜ | Gᵃ | Zᵇ |
| 94-289 | 95-289 | 96-289 | 97-289 | Rᵃ | R⁵ᵃ | R⁹ᶜ | R¹⁰ᶜ | Gᵃ | Zᵇ |
| 94-290 | 95-290 | 96-290 | 97-290 | Rᵇ | R⁵ᵃ | R⁹ᶜ | R¹⁰ᶜ | Gᵃ | Zᵇ |
| 94-291 | 95-291 | 96-291 | 97-291 | Rᶜ | R⁵ᵃ | R⁹ᶜ | R¹⁰ᶜ | Gᵃ | Zᵇ |
| 94-292 | 95-292 | 96-292 | 97-292 | Rᵃ | R⁵ᵇ | R⁹ᶜ | R¹⁰ᶜ | Gᵃ | Zᵇ |
| 94-293 | 95-293 | 96-293 | 97-293 | Rᵇ | R⁵ᵇ | R⁹ᶜ | R¹⁰ᶜ | Gᵃ | Zᵇ |
| 94-294 | 95-294 | 96-294 | 97-294 | Rᶜ | R⁵ᵇ | R⁹ᶜ | R¹⁰ᶜ | Gᵃ | Zᵇ |
| 94-295 | 95-295 | 96-295 | 97-295 | Rᵃ | R⁵ᶜ | R⁹ᶜ | R¹⁰ᶜ | Gᵃ | Zᵇ |
| 94-296 | 95-296 | 96-296 | 97-296 | Rᵇ | R⁵ᶜ | R⁹ᶜ | R¹⁰ᶜ | Gᵃ | Zᵇ |
| 94-297 | 95-297 | 96-297 | 97-297 | Rᶜ | R⁵ᶜ | R⁹ᶜ | R¹⁰ᶜ | Gᵃ | Zᵇ |
| 94-298 | 95-298 | 96-298 | 97-298 | Rᵃ | R⁵ᵃ | R⁹ᵃ | R¹⁰ᶜ | Gᵃ | Zᵇ |
| 94-299 | 95-299 | 96-299 | 97-299 | Rᵇ | R⁵ᵃ | R⁹ᵃ | R¹⁰ᶜ | Gᵃ | Zᵇ |
| 94-300 | 95-300 | 96-300 | 97-300 | Rᶜ | R⁵ᵃ | R⁹ᵃ | R¹⁰ᶜ | Gᵃ | Zᵇ |
| 94-301 | 95-301 | 96-301 | 97-301 | Rᵃ | R⁵ᵇ | R⁹ᵃ | R¹⁰ᶜ | Gᵃ | Zᵇ |
| 94-302 | 95-302 | 96-302 | 97-302 | Rᵇ | R⁵ᵇ | R⁹ᵃ | R¹⁰ᶜ | Gᵃ | Zᵇ |
| 94-303 | 95-303 | 96-303 | 97-303 | Rᶜ | R⁵ᵇ | R⁹ᵃ | R¹⁰ᶜ | Gᵃ | Zᵇ |
| 94-304 | 95-304 | 96-304 | 97-304 | Rᵃ | R⁵ᶜ | R⁹ᵃ | R¹⁰ᶜ | Gᵃ | Zᵇ |
| 94-305 | 95-305 | 96-305 | 97-305 | Rᵇ | R⁵ᶜ | R⁹ᵃ | R¹⁰ᶜ | Gᵃ | Zᵇ |
| 94-306 | 95-306 | 96-306 | 97-306 | Rᶜ | R⁵ᶜ | R⁹ᵃ | R¹⁰ᶜ | Gᵃ | Zᵇ |
| 94-307 | 95-307 | 96-307 | 97-307 | Rᵃ | R⁵ᵃ | R⁹ᵇ | R¹⁰ᶜ | Gᵃ | Zᵇ |
| 94-308 | 95-308 | 96-308 | 97-308 | Rᵇ | R⁵ᵃ | R⁹ᵇ | R¹⁰ᶜ | Gᵃ | Zᵇ |
| 94-309 | 95-309 | 96-309 | 97-309 | Rᶜ | R⁵ᵃ | R⁹ᵇ | R¹⁰ᶜ | Gᵃ | Zᵇ |
| 94-310 | 95-310 | 96-310 | 97-310 | Rᵃ | R⁵ᵇ | R⁹ᵇ | R¹⁰ᶜ | Gᵃ | Zᵇ |
| 94-311 | 95-311 | 96-311 | 97-311 | Rᵇ | R⁵ᵇ | R⁹ᵇ | R¹⁰ᶜ | Gᵃ | Zᵇ |
| 94-312 | 95-312 | 96-312 | 97-312 | Rᶜ | R⁵ᵇ | R⁹ᵇ | R¹⁰ᶜ | Gᵃ | Zᵇ |
| 94-313 | 95-313 | 96-313 | 97-313 | Rᵃ | R⁵ᶜ | R⁹ᵇ | R¹⁰ᶜ | Gᵃ | Zᵇ |
| 94-314 | 95-314 | 96-314 | 97-314 | Rᵇ | R⁵ᶜ | R⁹ᵇ | R¹⁰ᶜ | Gᵃ | Zᵇ |
| 94-315 | 95-315 | 96-315 | 97-315 | Rᶜ | R⁵ᶜ | R⁹ᵇ | R¹⁰ᶜ | Gᵃ | Zᵇ |
| 94-316 | 95-316 | 96-316 | 97-316 | Rᵃ | R⁵ᵃ | R⁹ᶜ | R¹⁰ᶜ | Gᵃ | Zᵇ |
| 94-317 | 95-317 | 96-317 | 97-317 | Rᵇ | R⁵ᵃ | R⁹ᶜ | R¹⁰ᶜ | Gᵃ | Zᵇ |
| 94-318 | 95-318 | 96-318 | 97-318 | Rᶜ | R⁵ᵃ | R⁹ᶜ | R¹⁰ᶜ | Gᵃ | Zᵇ |
| 94-319 | 95-319 | 96-319 | 97-319 | Rᵃ | R⁵ᵇ | R⁹ᶜ | R¹⁰ᶜ | Gᵃ | Zᵇ |
| 94-320 | 95-320 | 96-320 | 97-320 | Rᵇ | R⁵ᵇ | R⁹ᶜ | R¹⁰ᶜ | Gᵃ | Zᵇ |
| 94-321 | 95-321 | 96-321 | 97-321 | Rᶜ | R⁵ᵇ | R⁹ᶜ | R¹⁰ᶜ | Gᵃ | Zᵇ |
| 94-322 | 95-322 | 96-322 | 97-322 | Rᵃ | R⁵ᶜ | R⁹ᶜ | R¹⁰ᶜ | Gᵃ | Zᵇ |
| 94-323 | 95-323 | 96-323 | 97-323 | Rᵇ | R⁵ᶜ | R⁹ᶜ | R¹⁰ᶜ | Gᵃ | Zᵇ |
| 94-324 | 95-324 | 96-324 | 97-324 | Rᶜ | R⁵ᶜ | R⁹ᶜ | R¹⁰ᶜ | Gᵃ | Zᵇ |
| 94-325 | 95-325 | 96-325 | 97-325 | Rᵃ | R⁵ᵃ | R⁹ᵃ | R¹⁰ᶜ | Gᵇ | Zᵇ |
| 94-326 | 95-326 | 96-326 | 97-326 | Rᵇ | R⁵ᵃ | R⁹ᵃ | R¹⁰ᶜ | Gᵇ | Zᵇ |
| 94-327 | 95-327 | 96-327 | 97-327 | Rᶜ | R⁵ᵃ | R⁹ᵃ | R¹⁰ᶜ | Gᵇ | Zᵇ |
| 94-328 | 95-328 | 96-328 | 97-328 | Rᵃ | R⁵ᵇ | R⁹ᵃ | R¹⁰ᶜ | Gᵇ | Zᵇ |
| 94-329 | 95-329 | 96-329 | 97-329 | Rᵇ | R⁵ᵇ | R⁹ᵃ | R¹⁰ᶜ | Gᵇ | Zᵇ |
| 94-330 | 95-330 | 96-330 | 97-330 | Rᶜ | R⁵ᵇ | R⁹ᵃ | R¹⁰ᶜ | Gᵇ | Zᵇ |
| 94-331 | 95-331 | 96-331 | 97-331 | Rᵃ | R⁵ᶜ | R⁹ᵃ | R¹⁰ᶜ | Gᵇ | Zᵇ |
| 94-332 | 95-332 | 96-332 | 97-332 | Rᵇ | R⁵ᶜ | R⁹ᵃ | R¹⁰ᶜ | Gᵇ | Zᵇ |
| 94-333 | 95-333 | 96-333 | 97-333 | Rᶜ | R⁵ᶜ | R⁹ᵃ | R¹⁰ᶜ | Gᵇ | Zᵇ |
| 94-334 | 95-334 | 96-334 | 97-334 | Rᵃ | R⁵ᵃ | R⁹ᵇ | R¹⁰ᶜ | Gᵇ | Zᵇ |

-continued

| Formulae | | | | R | R⁵ | R⁹ | R¹⁰ | G | Z |
|---|---|---|---|---|---|---|---|---|---|
| 94-335 | 95-335 | 96-335 | 97-335 | Rᵇ | R⁵ᵃ | R⁹ᵇ | R¹⁰ᶜ | Gᵇ | Zᵇ |
| 94-336 | 95-336 | 96-336 | 97-336 | Rᶜ | R⁵ᵃ | R⁹ᵇ | R¹⁰ᶜ | Gᵇ | Zᵇ |
| 94-337 | 95-337 | 96-337 | 97-337 | Rᵃ | R⁵ᵇ | R⁹ᵇ | R¹⁰ᶜ | Gᵇ | Zᵇ |
| 94-338 | 95-338 | 96-338 | 97-338 | Rᵇ | R⁵ᵇ | R⁹ᵇ | R¹⁰ᶜ | Gᵇ | Zᵇ |
| 94-339 | 95-339 | 96-339 | 97-339 | Rᶜ | R⁵ᵇ | R⁹ᵇ | R¹⁰ᶜ | Gᵇ | Zᵇ |
| 94-340 | 95-340 | 96-340 | 97-340 | Rᵃ | R⁵ᶜ | R⁹ᵇ | R¹⁰ᶜ | Gᵇ | Zᵇ |
| 94-341 | 95-341 | 96-341 | 97-341 | Rᵇ | R⁵ᶜ | R⁹ᵇ | R¹⁰ᶜ | Gᵇ | Zᵇ |
| 94-342 | 95-342 | 96-342 | 97-342 | Rᶜ | R⁵ᶜ | R⁹ᵇ | R¹⁰ᶜ | Gᵇ | Zᵇ |
| 94-343 | 95-343 | 96-343 | 97-343 | Rᵃ | R⁵ᵃ | R⁹ᶜ | R¹⁰ᶜ | Gᵇ | Zᵇ |
| 94-344 | 95-344 | 96-344 | 97-344 | Rᵇ | R⁵ᵃ | R⁹ᶜ | R¹⁰ᶜ | Gᵇ | Zᵇ |
| 94-345 | 95-345 | 96-345 | 97-345 | Rᶜ | R⁵ᵃ | R⁹ᶜ | R¹⁰ᶜ | Gᵇ | Zᵇ |
| 94-346 | 95-346 | 96-346 | 97-346 | Rᵃ | R⁵ᵇ | R⁹ᶜ | R¹⁰ᶜ | Gᵇ | Zᵇ |
| 94-347 | 95-347 | 96-347 | 97-347 | Rᵇ | R⁵ᵇ | R⁹ᶜ | R¹⁰ᶜ | Gᵇ | Zᵇ |
| 94-348 | 95-348 | 96-348 | 97-348 | Rᶜ | R⁵ᵇ | R⁹ᶜ | R¹⁰ᶜ | Gᵇ | Zᵇ |
| 94-349 | 95-349 | 96-349 | 97-349 | Rᵃ | R⁵ᶜ | R⁹ᶜ | R¹⁰ᶜ | Gᵇ | Zᵇ |
| 94-350 | 95-350 | 96-350 | 97-350 | Rᵇ | R⁵ᶜ | R⁹ᶜ | R¹⁰ᶜ | Gᵇ | Zᵇ |
| 94-351 | 95-351 | 96-351 | 97-351 | Rᶜ | R⁵ᶜ | R⁹ᶜ | R¹⁰ᶜ | Gᵇ | Zᵇ |
| 94-352 | 95-352 | 96-352 | 97-352 | Rᵃ | R⁵ᵃ | R⁹ᵃ | R¹⁰ᶜ | Gᵇ | Zᵇ |
| 94-353 | 95-353 | 96-353 | 97-353 | Rᵇ | R⁵ᵃ | R⁹ᵃ | R¹⁰ᶜ | Gᵇ | Zᵇ |
| 94-354 | 95-354 | 96-354 | 97-354 | Rᶜ | R⁵ᵃ | R⁹ᵃ | R¹⁰ᶜ | Gᵇ | Zᵇ |
| 94-355 | 95-355 | 96-355 | 97-355 | Rᵃ | R⁵ᵇ | R⁹ᵃ | R¹⁰ᶜ | Gᵇ | Zᵇ |
| 94-356 | 95-356 | 96-356 | 97-356 | Rᵇ | R⁵ᵇ | R⁹ᵃ | R¹⁰ᶜ | Gᵇ | Zᵇ |
| 94-357 | 95-357 | 96-357 | 97-357 | Rᶜ | R⁵ᵇ | R⁹ᵃ | R¹⁰ᶜ | Gᵇ | Zᵇ |
| 94-358 | 95-358 | 96-358 | 97-358 | Rᵃ | R⁵ᶜ | R⁹ᵃ | R¹⁰ᶜ | Gᵇ | Zᵇ |
| 94-359 | 95-359 | 96-359 | 97-359 | Rᵇ | R⁵ᶜ | R⁹ᵃ | R¹⁰ᶜ | Gᵇ | Zᵇ |
| 94-360 | 95-360 | 96-360 | 97-360 | Rᶜ | R⁵ᶜ | R⁹ᵃ | R¹⁰ᶜ | Gᵇ | Zᵇ |
| 94-361 | 95-361 | 96-361 | 97-361 | Rᵃ | R⁵ᵃ | R⁹ᵇ | R¹⁰ᶜ | Gᵇ | Zᵇ |
| 94-362 | 95-362 | 96-362 | 97-362 | Rᵇ | R⁵ᵃ | R⁹ᵇ | R¹⁰ᶜ | Gᵇ | Zᵇ |
| 94-363 | 95-363 | 96-363 | 97-363 | Rᶜ | R⁵ᵃ | R⁹ᵇ | R¹⁰ᶜ | Gᵇ | Zᵇ |
| 94-364 | 95-364 | 96-364 | 97-364 | Rᵃ | R⁵ᵇ | R⁹ᵇ | R¹⁰ᶜ | Gᵇ | Zᵇ |
| 94-365 | 95-365 | 96-365 | 97-365 | Rᵇ | R⁵ᵇ | R⁹ᵇ | R¹⁰ᶜ | Gᵇ | Zᵇ |
| 94-366 | 95-366 | 96-366 | 97-366 | Rᶜ | R⁵ᵇ | R⁹ᵇ | R¹⁰ᶜ | Gᵇ | Zᵇ |
| 94-367 | 95-367 | 96-367 | 97-367 | Rᵃ | R⁵ᶜ | R⁹ᵇ | R¹⁰ᶜ | Gᵇ | Zᵇ |
| 94-368 | 95-368 | 96-368 | 97-368 | Rᵇ | R⁵ᶜ | R⁹ᵇ | R¹⁰ᶜ | Gᵇ | Zᵇ |
| 94-369 | 95-369 | 96-369 | 97-369 | Rᶜ | R⁵ᶜ | R⁹ᵇ | R¹⁰ᶜ | Gᵇ | Zᵇ |
| 94-370 | 95-370 | 96-370 | 97-370 | Rᵃ | R⁵ᵃ | R⁹ᶜ | R¹⁰ᶜ | Gᵇ | Zᵇ |
| 94-371 | 95-371 | 96-371 | 97-371 | Rᵇ | R⁵ᵃ | R⁹ᶜ | R¹⁰ᶜ | Gᵇ | Zᵇ |
| 94-372 | 95-372 | 96-372 | 97-372 | Rᶜ | R⁵ᵃ | R⁹ᶜ | R¹⁰ᶜ | Gᵇ | Zᵇ |
| 94-373 | 95-373 | 96-373 | 97-373 | Rᵃ | R⁵ᵇ | R⁹ᶜ | R¹⁰ᶜ | Gᵇ | Zᵇ |
| 94-374 | 95-374 | 96-374 | 97-374 | Rᵇ | R⁵ᵇ | R⁹ᶜ | R¹⁰ᶜ | Gᵇ | Zᵇ |
| 94-375 | 95-375 | 96-375 | 97-375 | Rᶜ | R⁵ᵇ | R⁹ᶜ | R¹⁰ᶜ | Gᵇ | Zᵇ |
| 94-376 | 95-376 | 96-376 | 97-376 | Rᵃ | R⁵ᶜ | R⁹ᶜ | R¹⁰ᶜ | Gᵇ | Zᵇ |
| 94-377 | 95-377 | 96-377 | 97-377 | Rᵇ | R⁵ᶜ | R⁹ᶜ | R¹⁰ᶜ | Gᵇ | Zᵇ |
| 94-378 | 95-378 | 96-378 | 97-378 | Rᶜ | R⁵ᶜ | R⁹ᶜ | R¹⁰ᶜ | Gᵇ | Zᵇ |
| 94-379 | 95-379 | 96-379 | 97-379 | Rᵃ | R⁵ᵃ | R⁹ᵃ | R¹⁰ᶜ | Gᵇ | Zᵇ |
| 94-380 | 95-380 | 96-380 | 97-380 | Rᵇ | R⁵ᵃ | R⁹ᵃ | R¹⁰ᶜ | Gᵇ | Zᵇ |
| 94-381 | 95-381 | 96-381 | 97-381 | Rᶜ | R⁵ᵃ | R⁹ᵃ | R¹⁰ᶜ | Gᵇ | Zᵇ |
| 94-382 | 95-382 | 96-382 | 97-382 | Rᵃ | R⁵ᵇ | R⁹ᵃ | R¹⁰ᶜ | Gᵇ | Zᵇ |
| 94-383 | 95-383 | 96-383 | 97-383 | Rᵇ | R⁵ᵇ | R⁹ᵃ | R¹⁰ᶜ | Gᵇ | Zᵇ |
| 94-384 | 95-384 | 96-384 | 97-384 | Rᶜ | R⁵ᵇ | R⁹ᵃ | R¹⁰ᶜ | Gᵇ | Zᵇ |
| 94-385 | 95-385 | 96-385 | 97-385 | Rᵃ | R⁵ᶜ | R⁹ᵃ | R¹⁰ᶜ | Gᵇ | Zᵇ |
| 94-386 | 95-386 | 96-386 | 97-386 | Rᵇ | R⁵ᶜ | R⁹ᵃ | R¹⁰ᶜ | Gᵇ | Zᵇ |
| 94-387 | 95-387 | 96-387 | 97-387 | Rᶜ | R⁵ᶜ | R⁹ᵃ | R¹⁰ᶜ | Gᵇ | Zᵇ |
| 94-388 | 95-388 | 96-388 | 97-388 | Rᵃ | R⁵ᵃ | R⁹ᵇ | R¹⁰ᶜ | Gᵇ | Zᵇ |
| 94-389 | 95-389 | 96-389 | 97-389 | Rᵇ | R⁵ᵃ | R⁹ᵇ | R¹⁰ᶜ | Gᵇ | Zᵇ |
| 94-390 | 95-390 | 96-390 | 97-390 | Rᶜ | R⁵ᵃ | R⁹ᵇ | R¹⁰ᶜ | Gᵇ | Zᵇ |
| 94-391 | 95-391 | 96-391 | 97-391 | Rᵃ | R⁵ᵇ | R⁹ᵇ | R¹⁰ᶜ | Gᵇ | Zᵇ |
| 94-392 | 95-392 | 96-392 | 97-392 | Rᵇ | R⁵ᵇ | R⁹ᵇ | R¹⁰ᶜ | Gᵇ | Zᵇ |
| 94-393 | 95-393 | 96-393 | 97-393 | Rᶜ | R⁵ᵇ | R⁹ᵇ | R¹⁰ᶜ | Gᵇ | Zᵇ |
| 94-394 | 95-394 | 96-394 | 97-394 | Rᵃ | R⁵ᶜ | R⁹ᵇ | R¹⁰ᶜ | Gᵇ | Zᵇ |
| 94-395 | 95-395 | 96-395 | 97-395 | Rᵇ | R⁵ᶜ | R⁹ᵇ | R¹⁰ᶜ | Gᵇ | Zᵇ |
| 94-396 | 95-396 | 96-396 | 97-396 | Rᶜ | R⁵ᶜ | R⁹ᵇ | R¹⁰ᶜ | Gᵇ | Zᵇ |
| 94-397 | 95-397 | 96-397 | 97-397 | Rᵃ | R⁵ᵃ | R⁹ᶜ | R¹⁰ᶜ | Gᵇ | Zᵇ |
| 94-398 | 95-398 | 96-398 | 97-398 | Rᵇ | R⁵ᵃ | R⁹ᶜ | R¹⁰ᶜ | Gᵇ | Zᵇ |
| 94-399 | 95-399 | 96-399 | 97-399 | Rᶜ | R⁵ᵃ | R⁹ᶜ | R¹⁰ᶜ | Gᵇ | Zᵇ |
| 94-400 | 95-400 | 96-400 | 97-400 | Rᵃ | R⁵ᵇ | R⁹ᶜ | R¹⁰ᶜ | Gᵇ | Zᵇ |
| 94-401 | 95-401 | 96-401 | 97-401 | Rᵇ | R⁵ᵇ | R⁹ᶜ | R¹⁰ᶜ | Gᵇ | Zᵇ |
| 94-402 | 95-402 | 96-402 | 97-402 | Rᶜ | R⁵ᵇ | R⁹ᶜ | R¹⁰ᶜ | Gᵇ | Zᵇ |
| 94-403 | 95-403 | 96-403 | 97-403 | Rᵃ | R⁵ᶜ | R⁹ᶜ | R¹⁰ᶜ | Gᵇ | Zᵇ |
| 94-404 | 95-404 | 96-404 | 97-404 | Rᵇ | R⁵ᶜ | R⁹ᶜ | R¹⁰ᶜ | Gᵇ | Zᵇ |
| 94-405 | 95-405 | 96-405 | 97-405 | Rᶜ | R⁵ᶜ | R⁹ᶜ | R¹⁰ᶜ | Gᵇ | Zᵇ |
| 94-406 | 95-406 | 96-406 | 97-406 | Rᵃ | R⁵ᵃ | R⁹ᵃ | R¹⁰ᶜ | Gᶜ | Zᵇ |
| 94-407 | 95-407 | 96-407 | 97-407 | Rᵇ | R⁵ᵃ | R⁹ᵃ | R¹⁰ᶜ | Gᶜ | Zᵇ |
| 94-408 | 95-408 | 96-408 | 97-408 | Rᶜ | R⁵ᵃ | R⁹ᵃ | R¹⁰ᶜ | Gᶜ | Zᵇ |
| 94-409 | 95-409 | 96-409 | 97-409 | Rᵃ | R⁵ᵇ | R⁹ᵃ | R¹⁰ᶜ | Gᶜ | Zᵇ |
| 94-410 | 95-410 | 96-410 | 97-410 | Rᵇ | R⁵ᵇ | R⁹ᵃ | R¹⁰ᶜ | Gᶜ | Zᵇ |
| 94-411 | 95-411 | 96-411 | 97-411 | Rᶜ | R⁵ᵇ | R⁹ᵃ | R¹⁰ᶜ | Gᶜ | Zᵇ |
| 94-412 | 95-412 | 96-412 | 97-412 | Rᵃ | R⁵ᶜ | R⁹ᵃ | R¹⁰ᶜ | Gᶜ | Zᵇ |
| 94-413 | 95-413 | 96-413 | 97-413 | Rᵇ | R⁵ᶜ | R⁹ᵃ | R¹⁰ᶜ | Gᶜ | Zᵇ |
| 94-414 | 95-414 | 96-414 | 97-414 | Rᶜ | R⁵ᶜ | R⁹ᵃ | R¹⁰ᶜ | Gᶜ | Zᵇ |
| 94-415 | 95-415 | 96-415 | 97-415 | Rᵃ | R⁵ᵃ | R⁹ᵇ | R¹⁰ᶜ | Gᶜ | Zᵇ |
| 94-416 | 95-416 | 96-416 | 97-416 | Rᵇ | R⁵ᵃ | R⁹ᵇ | R¹⁰ᶜ | Gᶜ | Zᵇ |
| 94-417 | 95-417 | 96-417 | 97-417 | Rᶜ | R⁵ᵃ | R⁹ᵇ | R¹⁰ᶜ | Gᶜ | Zᵇ |
| 94-418 | 95-418 | 96-418 | 97-418 | Rᵃ | R⁵ᵇ | R⁹ᵇ | R¹⁰ᶜ | Gᶜ | Zᵇ |
| 94-419 | 95-419 | 96-419 | 97-419 | Rᵇ | R⁵ᵇ | R⁹ᵇ | R¹⁰ᶜ | Gᶜ | Zᵇ |
| 94-420 | 95-420 | 96-420 | 97-420 | Rᶜ | R⁵ᵇ | R⁹ᵇ | R¹⁰ᶜ | Gᶜ | Zᵇ |
| 94-421 | 95-421 | 96-421 | 97-421 | Rᵃ | R⁵ᶜ | R⁹ᵇ | R¹⁰ᶜ | Gᶜ | Zᵇ |
| 94-422 | 95-422 | 96-422 | 97-422 | Rᵇ | R⁵ᶜ | R⁹ᵇ | R¹⁰ᶜ | Gᶜ | Zᵇ |
| 94-423 | 95-423 | 96-423 | 97-423 | Rᶜ | R⁵ᶜ | R⁹ᵇ | R¹⁰ᶜ | Gᶜ | Zᵇ |
| 94-424 | 95-424 | 96-424 | 97-424 | Rᵃ | R⁵ᵃ | R⁹ᶜ | R¹⁰ᶜ | Gᶜ | Zᵇ |
| 94-425 | 95-425 | 96-425 | 97-425 | Rᵇ | R⁵ᵃ | R⁹ᶜ | R¹⁰ᶜ | Gᶜ | Zᵇ |
| 94-426 | 95-426 | 96-426 | 97-426 | Rᶜ | R⁵ᵃ | R⁹ᶜ | R¹⁰ᶜ | Gᶜ | Zᵇ |
| 94-427 | 95-427 | 96-427 | 97-427 | Rᵃ | R⁵ᵇ | R⁹ᶜ | R¹⁰ᶜ | Gᶜ | Zᵇ |
| 94-428 | 95-428 | 96-428 | 97-428 | Rᵇ | R⁵ᵇ | R⁹ᶜ | R¹⁰ᶜ | Gᶜ | Zᵇ |
| 94-429 | 95-429 | 96-429 | 97-429 | Rᶜ | R⁵ᵇ | R⁹ᶜ | R¹⁰ᶜ | Gᶜ | Zᵇ |
| 94-430 | 95-430 | 96-430 | 97-430 | Rᵃ | R⁵ᶜ | R⁹ᶜ | R¹⁰ᶜ | Gᶜ | Zᵇ |
| 94-431 | 95-431 | 96-431 | 97-431 | Rᵇ | R⁵ᶜ | R⁹ᶜ | R¹⁰ᶜ | Gᶜ | Zᵇ |
| 94-432 | 95-432 | 96-432 | 97-432 | Rᶜ | R⁵ᶜ | R⁹ᶜ | R¹⁰ᶜ | Gᶜ | Zᵇ |
| 94-433 | 95-433 | 96-433 | 97-433 | Rᵃ | R⁵ᵃ | R⁹ᵃ | R¹⁰ᶜ | Gᶜ | Zᵇ |
| 94-434 | 95-434 | 96-434 | 97-434 | Rᵇ | R⁵ᵃ | R⁹ᵃ | R¹⁰ᶜ | Gᶜ | Zᵇ |
| 94-435 | 95-435 | 96-435 | 97-435 | Rᶜ | R⁵ᵃ | R⁹ᵃ | R¹⁰ᶜ | Gᶜ | Zᵇ |
| 94-436 | 95-436 | 96-436 | 97-436 | Rᵃ | R⁵ᵇ | R⁹ᵃ | R¹⁰ᶜ | Gᶜ | Zᵇ |
| 94-437 | 95-437 | 96-437 | 97-437 | Rᵇ | R⁵ᵇ | R⁹ᵃ | R¹⁰ᶜ | Gᶜ | Zᵇ |
| 94-438 | 95-438 | 96-438 | 97-438 | Rᶜ | R⁵ᵇ | R⁹ᵃ | R¹⁰ᶜ | Gᶜ | Zᵇ |
| 94-439 | 95-439 | 96-439 | 97-439 | Rᵃ | R⁵ᶜ | R⁹ᵃ | R¹⁰ᶜ | Gᶜ | Zᵇ |
| 94-440 | 95-440 | 96-440 | 97-440 | Rᵇ | R⁵ᶜ | R⁹ᵃ | R¹⁰ᶜ | Gᶜ | Zᵇ |
| 94-441 | 95-441 | 96-441 | 97-441 | Rᶜ | R⁵ᶜ | R⁹ᵃ | R¹⁰ᶜ | Gᶜ | Zᵇ |
| 94-442 | 95-442 | 96-442 | 97-442 | Rᵃ | R⁵ᵃ | R⁹ᵇ | R¹⁰ᶜ | Gᶜ | Zᵇ |
| 94-443 | 95-443 | 96-443 | 97-443 | Rᵇ | R⁵ᵃ | R⁹ᵇ | R¹⁰ᶜ | Gᶜ | Zᵇ |
| 94-444 | 95-444 | 96-444 | 97-444 | Rᶜ | R⁵ᵃ | R⁹ᵇ | R¹⁰ᶜ | Gᶜ | Zᵇ |
| 94-445 | 95-445 | 96-445 | 97-445 | Rᵃ | R⁵ᵇ | R⁹ᵇ | R¹⁰ᶜ | Gᶜ | Zᵇ |
| 94-446 | 95-446 | 96-446 | 97-446 | Rᵇ | R⁵ᵇ | R⁹ᵇ | R¹⁰ᶜ | Gᶜ | Zᵇ |
| 94-447 | 95-447 | 96-447 | 97-447 | Rᶜ | R⁵ᵇ | R⁹ᵇ | R¹⁰ᶜ | Gᶜ | Zᵇ |
| 94-448 | 95-448 | 96-448 | 97-448 | Rᵃ | R⁵ᶜ | R⁹ᵇ | R¹⁰ᶜ | Gᶜ | Zᵇ |
| 94-449 | 95-449 | 96-449 | 97-449 | Rᵇ | R⁵ᶜ | R⁹ᵇ | R¹⁰ᶜ | Gᶜ | Zᵇ |
| 94-450 | 95-450 | 96-450 | 97-450 | Rᶜ | R⁵ᶜ | R⁹ᵇ | R¹⁰ᶜ | Gᶜ | Zᵇ |
| 94-451 | 95-451 | 96-451 | 97-451 | Rᵃ | R⁵ᵃ | R⁹ᶜ | R¹⁰ᶜ | Gᶜ | Zᵇ |
| 94-452 | 95-452 | 96-452 | 97-452 | Rᵇ | R⁵ᵃ | R⁹ᶜ | R¹⁰ᶜ | Gᶜ | Zᵇ |
| 94-453 | 95-453 | 96-453 | 97-453 | Rᶜ | R⁵ᵃ | R⁹ᶜ | R¹⁰ᶜ | Gᶜ | Zᵇ |
| 94-454 | 95-454 | 96-454 | 97-454 | Rᵃ | R⁵ᵇ | R⁹ᶜ | R¹⁰ᶜ | Gᶜ | Zᵇ |
| 94-455 | 95-455 | 96-455 | 97-455 | Rᵇ | R⁵ᵇ | R⁹ᶜ | R¹⁰ᶜ | Gᶜ | Zᵇ |
| 94-456 | 95-456 | 96-456 | 97-456 | Rᶜ | R⁵ᵇ | R⁹ᶜ | R¹⁰ᶜ | Gᶜ | Zᵇ |
| 94-457 | 95-457 | 96-457 | 97-457 | Rᵃ | R⁵ᶜ | R⁹ᶜ | R¹⁰ᶜ | Gᶜ | Zᵇ |
| 94-458 | 95-458 | 96-458 | 97-458 | Rᵇ | R⁵ᶜ | R⁹ᶜ | R¹⁰ᶜ | Gᶜ | Zᵇ |
| 94-459 | 95-459 | 96-459 | 97-459 | Rᶜ | R⁵ᶜ | R⁹ᶜ | R¹⁰ᶜ | Gᶜ | Zᵇ |
| 94-460 | 95-460 | 96-460 | 97-460 | Rᵃ | R⁵ᵃ | R⁹ᵃ | R¹⁰ᶜ | Gᶜ | Zᵇ |
| 94-461 | 95-461 | 96-461 | 97-461 | Rᵇ | R⁵ᵃ | R⁹ᵃ | R¹⁰ᶜ | Gᶜ | Zᵇ |
| 94-462 | 95-462 | 96-462 | 97-462 | Rᶜ | R⁵ᵃ | R⁹ᵃ | R¹⁰ᶜ | Gᶜ | Zᵇ |
| 94-463 | 95-463 | 96-463 | 97-463 | Rᵃ | R⁵ᵇ | R⁹ᵃ | R¹⁰ᶜ | Gᶜ | Zᵇ |
| 94-464 | 95-464 | 96-464 | 97-464 | Rᵇ | R⁵ᵇ | R⁹ᵃ | R¹⁰ᶜ | Gᶜ | Zᵇ |
| 94-465 | 95-465 | 96-465 | 97-465 | Rᶜ | R⁵ᵇ | R⁹ᵃ | R¹⁰ᶜ | Gᶜ | Zᵇ |
| 94-466 | 95-466 | 96-466 | 97-466 | Rᵃ | R⁵ᶜ | R⁹ᵃ | R¹⁰ᶜ | Gᶜ | Zᵇ |
| 94-467 | 95-467 | 96-467 | 97-467 | Rᵇ | R⁵ᶜ | R⁹ᵃ | R¹⁰ᶜ | Gᶜ | Zᵇ |
| 94-468 | 95-468 | 96-468 | 97-468 | Rᶜ | R⁵ᶜ | R⁹ᵃ | R¹⁰ᶜ | Gᶜ | Zᵇ |
| 94-469 | 95-469 | 96-469 | 97-469 | Rᵃ | R⁵ᵃ | R⁹ᵇ | R¹⁰ᶜ | Gᶜ | Zᵇ |
| 94-470 | 95-470 | 96-470 | 97-470 | Rᵇ | R⁵ᵃ | R⁹ᵇ | R¹⁰ᶜ | Gᶜ | Zᵇ |
| 94-471 | 95-471 | 96-471 | 97-471 | Rᶜ | R⁵ᵃ | R⁹ᵇ | R¹⁰ᶜ | Gᶜ | Zᵇ |
| 94-472 | 95-472 | 96-472 | 97-472 | Rᵃ | R⁵ᵇ | R⁹ᵇ | R¹⁰ᶜ | Gᶜ | Zᵇ |
| 94-473 | 95-473 | 96-473 | 97-473 | Rᵇ | R⁵ᵇ | R⁹ᵇ | R¹⁰ᶜ | Gᶜ | Zᵇ |
| 94-474 | 95-474 | 96-474 | 97-474 | Rᶜ | R⁵ᵇ | R⁹ᵇ | R¹⁰ᶜ | Gᶜ | Zᵇ |
| 94-475 | 95-475 | 96-475 | 97-475 | Rᵃ | R⁵ᶜ | R⁹ᵇ | R¹⁰ᶜ | Gᶜ | Zᵇ |
| 94-476 | 95-476 | 96-476 | 97-476 | Rᵇ | R⁵ᶜ | R⁹ᵇ | R¹⁰ᶜ | Gᶜ | Zᵇ |
| 94-477 | 95-477 | 96-477 | 97-477 | Rᶜ | R⁵ᶜ | R⁹ᵇ | R¹⁰ᶜ | Gᶜ | Zᵇ |
| 94-478 | 95-478 | 96-478 | 97-478 | Rᵃ | R⁵ᵃ | R⁹ᶜ | R¹⁰ᶜ | Gᶜ | Zᵇ |
| 94-479 | 95-479 | 96-479 | 97-479 | Rᵇ | R⁵ᵃ | R⁹ᶜ | R¹⁰ᶜ | Gᶜ | Zᵇ |
| 94-480 | 95-480 | 96-480 | 97-480 | Rᶜ | R⁵ᵃ | R⁹ᶜ | R¹⁰ᶜ | Gᶜ | Zᵇ |
| 94-481 | 95-481 | 96-481 | 97-481 | Rᵃ | R⁵ᵇ | R⁹ᶜ | R¹⁰ᶜ | Gᶜ | Zᵇ |
| 94-482 | 95-482 | 96-482 | 97-482 | Rᵇ | R⁵ᵇ | R⁹ᶜ | R¹⁰ᶜ | Gᶜ | Zᵇ |
| 94-483 | 95-483 | 96-483 | 97-483 | Rᶜ | R⁵ᵇ | R⁹ᶜ | R¹⁰ᶜ | Gᶜ | Zᵇ |
| 94-484 | 95-484 | 96-484 | 97-484 | Rᵃ | R⁵ᶜ | R⁹ᶜ | R¹⁰ᶜ | Gᶜ | Zᵇ |
| 94-485 | 95-485 | 96-485 | 97-485 | Rᵇ | R⁵ᶜ | R⁹ᶜ | R¹⁰ᶜ | Gᶜ | Zᵇ |
| 94-486 | 95-486 | 96-486 | 97-486 | Rᶜ | R⁵ᶜ | R⁹ᶜ | R¹⁰ᶜ | Gᶜ | Zᵇ |
| 94-487 | 95-487 | 96-487 | 97-487 | Rᵃ | R⁵ᵃ | R⁹ᵃ | R¹⁰ᶜ | Gᵃ | Zᶜ |
| 94-488 | 95-488 | 96-488 | 97-488 | Rᵇ | R⁵ᵃ | R⁹ᵃ | R¹⁰ᶜ | Gᵃ | Zᶜ |

-continued

| Formulae | | | | R | R⁵ | R⁹ | R¹⁰ | G | Z |
|---|---|---|---|---|---|---|---|---|---|
| 94-489 | 95-489 | 96-489 | 97-489 | Rᶜ | R⁵ᵃ | R⁹ᵃ | R¹⁰ᶜ | Gᵃ | Zᶜ |
| 94-490 | 95-490 | 96-490 | 97-490 | Rᵃ | R⁵ᵇ | R⁹ᵃ | R¹⁰ᶜ | Gᵃ | Zᶜ |
| 94-491 | 95-491 | 96-491 | 97-491 | Rᵇ | R⁵ᵇ | R⁹ᵃ | R¹⁰ᶜ | Gᵃ | Zᶜ |
| 94-492 | 95-492 | 96-492 | 97-492 | Rᶜ | R⁵ᵇ | R⁹ᵃ | R¹⁰ᶜ | Gᵃ | Zᶜ |
| 94-493 | 95-493 | 96-493 | 97-493 | Rᵃ | R⁵ᶜ | R⁹ᵃ | R¹⁰ᶜ | Gᵃ | Zᶜ |
| 94-494 | 95-494 | 96-494 | 97-494 | Rᵇ | R⁵ᶜ | R⁹ᵃ | R¹⁰ᶜ | Gᵃ | Zᶜ |
| 94-495 | 95-495 | 96-495 | 97-495 | Rᶜ | R⁵ᶜ | R⁹ᵃ | R¹⁰ᶜ | Gᵃ | Zᶜ |
| 94-496 | 95-496 | 96-496 | 97-496 | Rᵃ | R⁵ᵃ | R⁹ᵇ | R¹⁰ᶜ | Gᵃ | Zᶜ |
| 94-497 | 95-497 | 96-497 | 97-497 | Rᵇ | R⁵ᵃ | R⁹ᵇ | R¹⁰ᶜ | Gᵃ | Zᶜ |
| 94-498 | 95-498 | 96-498 | 97-498 | Rᶜ | R⁵ᵃ | R⁹ᵇ | R¹⁰ᶜ | Gᵃ | Zᶜ |
| 94-499 | 95-499 | 96-499 | 97-499 | Rᵃ | R⁵ᵇ | R⁹ᵇ | R¹⁰ᶜ | Gᵃ | Zᶜ |
| 94-500 | 95-500 | 96-500 | 97-500 | Rᵇ | R⁵ᵇ | R⁹ᵇ | R¹⁰ᶜ | Gᵃ | Zᶜ |
| 94-501 | 95-501 | 96-501 | 97-501 | Rᶜ | R⁵ᵇ | R⁹ᵇ | R¹⁰ᶜ | Gᵃ | Zᶜ |
| 94-502 | 95-502 | 96-502 | 97-502 | Rᵃ | R⁵ᶜ | R⁹ᵇ | R¹⁰ᶜ | Gᵃ | Zᶜ |
| 94-503 | 95-503 | 96-503 | 97-503 | Rᵇ | R⁵ᶜ | R⁹ᵇ | R¹⁰ᶜ | Gᵃ | Zᶜ |
| 94-504 | 95-504 | 96-504 | 97-504 | Rᶜ | R⁵ᶜ | R⁹ᵇ | R¹⁰ᶜ | Gᵃ | Zᶜ |
| 94-505 | 95-505 | 96-505 | 97-505 | Rᵃ | R⁵ᵃ | R⁹ᶜ | R¹⁰ᶜ | Gᵃ | Zᶜ |
| 94-506 | 95-506 | 96-506 | 97-506 | Rᵇ | R⁵ᵃ | R⁹ᶜ | R¹⁰ᶜ | Gᵃ | Zᶜ |
| 94-507 | 95-507 | 96-507 | 97-507 | Rᶜ | R⁵ᵃ | R⁹ᶜ | R¹⁰ᶜ | Gᵃ | Zᶜ |
| 94-508 | 95-508 | 96-508 | 97-508 | Rᵃ | R⁵ᵇ | R⁹ᶜ | R¹⁰ᶜ | Gᵃ | Zᶜ |
| 94-509 | 95-509 | 96-509 | 97-509 | Rᵇ | R⁵ᵇ | R⁹ᶜ | R¹⁰ᶜ | Gᵃ | Zᶜ |
| 94-510 | 95-510 | 96-510 | 97-510 | Rᶜ | R⁵ᵇ | R⁹ᶜ | R¹⁰ᶜ | Gᵃ | Zᶜ |
| 94-511 | 95-511 | 96-511 | 97-511 | Rᵃ | R⁵ᶜ | R⁹ᶜ | R¹⁰ᶜ | Gᵃ | Zᶜ |
| 94-512 | 95-512 | 96-512 | 97-512 | Rᵇ | R⁵ᶜ | R⁹ᶜ | R¹⁰ᶜ | Gᵃ | Zᶜ |
| 94-513 | 95-513 | 96-513 | 97-513 | Rᶜ | R⁵ᶜ | R⁹ᶜ | R¹⁰ᶜ | Gᵃ | Zᶜ |
| 94-514 | 95-514 | 96-514 | 97-514 | Rᵃ | R⁵ᵃ | R⁹ᵃ | R¹⁰ᶜ | Gᵃ | Zᶜ |
| 94-515 | 95-515 | 96-515 | 97-515 | Rᵇ | R⁵ᵃ | R⁹ᵃ | R¹⁰ᶜ | Gᵃ | Zᶜ |
| 94-516 | 95-516 | 96-516 | 97-516 | Rᶜ | R⁵ᵃ | R⁹ᵃ | R¹⁰ᶜ | Gᵃ | Zᶜ |
| 94-517 | 95-517 | 96-517 | 97-517 | Rᵃ | R⁵ᵇ | R⁹ᵃ | R¹⁰ᶜ | Gᵃ | Zᶜ |
| 94-518 | 95-518 | 96-518 | 97-518 | Rᶜ | R⁵ᵇ | R⁹ᵃ | R¹⁰ᶜ | Gᵃ | Zᶜ |
| 94-519 | 95-519 | 96-519 | 97-519 | Rᶜ | R⁵ᵇ | R⁹ᵃ | R¹⁰ᶜ | Gᵃ | Zᶜ |
| 94-520 | 95-520 | 96-520 | 97-520 | Rᵃ | R⁵ᶜ | R⁹ᵃ | R¹⁰ᶜ | Gᵃ | Zᶜ |
| 94-521 | 95-521 | 96-521 | 97-521 | Rᵇ | R⁵ᶜ | R⁹ᵃ | R¹⁰ᶜ | Gᵃ | Zᶜ |
| 94-522 | 95-522 | 96-522 | 97-522 | Rᶜ | R⁵ᶜ | R⁹ᵃ | R¹⁰ᶜ | Gᵃ | Zᶜ |
| 94-523 | 95-523 | 96-523 | 97-523 | Rᵃ | R⁵ᵃ | R⁹ᵇ | R¹⁰ᶜ | Gᵃ | Zᶜ |
| 94-524 | 95-524 | 96-524 | 97-524 | Rᵇ | R⁵ᵃ | R⁹ᵇ | R¹⁰ᶜ | Gᵃ | Zᶜ |
| 94-525 | 95-525 | 96-525 | 97-525 | Rᶜ | R⁵ᵃ | R⁹ᵇ | R¹⁰ᶜ | Gᵃ | Zᶜ |
| 94-526 | 95-526 | 96-526 | 97-526 | Rᵃ | R⁵ᵇ | R⁹ᵇ | R¹⁰ᶜ | Gᵃ | Zᶜ |
| 94-527 | 95-527 | 96-527 | 97-527 | Rᵇ | R⁵ᵇ | R⁹ᵇ | R¹⁰ᶜ | Gᵃ | Zᶜ |
| 94-528 | 95-528 | 96-528 | 97-528 | Rᶜ | R⁵ᵇ | R⁹ᵇ | R¹⁰ᶜ | Gᵃ | Zᶜ |
| 94-529 | 95-529 | 96-529 | 97-529 | Rᵃ | R⁵ᶜ | R⁹ᵇ | R¹⁰ᶜ | Gᵃ | Zᶜ |
| 94-530 | 95-530 | 96-530 | 97-530 | Rᵇ | R⁵ᶜ | R⁹ᵇ | R¹⁰ᶜ | Gᵃ | Zᶜ |
| 94-531 | 95-531 | 96-531 | 97-531 | Rᶜ | R⁵ᶜ | R⁹ᵇ | R¹⁰ᶜ | Gᵃ | Zᶜ |
| 94-532 | 95-532 | 96-532 | 97-532 | Rᵃ | R⁵ᵃ | R⁹ᶜ | R¹⁰ᶜ | Gᵃ | Zᶜ |
| 94-533 | 95-533 | 96-533 | 97-533 | Rᵇ | R⁵ᵃ | R⁹ᶜ | R¹⁰ᶜ | Gᵃ | Zᶜ |
| 94-534 | 95-534 | 96-534 | 97-534 | Rᶜ | R⁵ᵃ | R⁹ᶜ | R¹⁰ᶜ | Gᵃ | Zᶜ |
| 94-535 | 95-535 | 96-535 | 97-535 | Rᵃ | R⁵ᵇ | R⁹ᶜ | R¹⁰ᶜ | Gᵃ | Zᶜ |
| 94-536 | 95-536 | 96-536 | 97-536 | Rᵇ | R⁵ᵇ | R⁹ᶜ | R¹⁰ᶜ | Gᵃ | Zᶜ |
| 94-537 | 95-537 | 96-537 | 97-537 | Rᶜ | R⁵ᵇ | R⁹ᶜ | R¹⁰ᶜ | Gᵃ | Zᶜ |
| 94-538 | 95-538 | 96-538 | 97-538 | Rᵃ | R⁵ᶜ | R⁹ᶜ | R¹⁰ᶜ | Gᵃ | Zᶜ |
| 94-539 | 95-539 | 96-539 | 97-539 | Rᵇ | R⁵ᶜ | R⁹ᶜ | R¹⁰ᶜ | Gᵃ | Zᶜ |
| 94-540 | 95-540 | 96-540 | 97-540 | Rᶜ | R⁵ᶜ | R⁹ᶜ | R¹⁰ᶜ | Gᵃ | Zᶜ |
| 94-541 | 95-541 | 96-541 | 97-541 | Rᵃ | R⁵ᵃ | R⁹ᵃ | R¹⁰ᶜ | Gᵃ | Zᶜ |
| 94-542 | 95-542 | 96-542 | 97-542 | Rᵇ | R⁵ᵃ | R⁹ᵃ | R¹⁰ᶜ | Gᵃ | Zᶜ |
| 94-543 | 95-543 | 96-543 | 97-543 | Rᶜ | R⁵ᵃ | R⁹ᵃ | R¹⁰ᶜ | Gᵃ | Zᶜ |
| 94-544 | 95-544 | 96-544 | 97-544 | Rᵃ | R⁵ᵇ | R⁹ᵃ | R¹⁰ᶜ | Gᵃ | Zᶜ |
| 94-545 | 95-545 | 96-545 | 97-545 | Rᵇ | R⁵ᵇ | R⁹ᵃ | R¹⁰ᶜ | Gᵃ | Zᶜ |
| 94-546 | 95-546 | 96-546 | 97-546 | Rᶜ | R⁵ᵇ | R⁹ᵃ | R¹⁰ᶜ | Gᵃ | Zᶜ |
| 94-547 | 95-547 | 96-547 | 97-547 | Rᵃ | R⁵ᶜ | R⁹ᵃ | R¹⁰ᶜ | Gᵃ | Zᶜ |
| 94-548 | 95-548 | 96-548 | 97-548 | Rᵇ | R⁵ᶜ | R⁹ᵃ | R¹⁰ᶜ | Gᵃ | Zᶜ |
| 94-549 | 95-549 | 96-549 | 97-549 | Rᶜ | R⁵ᶜ | R⁹ᵃ | R¹⁰ᶜ | Gᵃ | Zᶜ |
| 94-550 | 95-550 | 96-550 | 97-550 | Rᵃ | R⁵ᵃ | R⁹ᵇ | R¹⁰ᶜ | Gᵃ | Zᶜ |
| 94-551 | 95-551 | 96-551 | 97-551 | Rᵇ | R⁵ᵃ | R⁹ᵇ | R¹⁰ᶜ | Gᵃ | Zᶜ |
| 94-552 | 95-552 | 96-552 | 97-552 | Rᶜ | R⁵ᵃ | R⁹ᵇ | R¹⁰ᶜ | Gᵃ | Zᶜ |
| 94-553 | 95-553 | 96-553 | 97-553 | Rᵃ | R⁵ᵇ | R⁹ᵇ | R¹⁰ᶜ | Gᵃ | Zᶜ |
| 94-554 | 95-554 | 96-554 | 97-554 | Rᵇ | R⁵ᵇ | R⁹ᵇ | R¹⁰ᶜ | Gᵃ | Zᶜ |
| 94-555 | 95-555 | 96-555 | 97-555 | Rᶜ | R⁵ᵇ | R⁹ᵇ | R¹⁰ᶜ | Gᵃ | Zᶜ |
| 94-556 | 95-556 | 96-556 | 97-556 | Rᵃ | R⁵ᶜ | R⁹ᵇ | R¹⁰ᶜ | Gᵃ | Zᶜ |
| 94-557 | 95-557 | 96-557 | 97-557 | Rᵇ | R⁵ᶜ | R⁹ᵇ | R¹⁰ᶜ | Gᵃ | Zᶜ |
| 94-558 | 95-558 | 96-558 | 97-558 | Rᶜ | R⁵ᶜ | R⁹ᵇ | R¹⁰ᶜ | Gᵃ | Zᶜ |
| 94-559 | 95-559 | 96-559 | 97-559 | Rᵃ | R⁵ᵃ | R⁹ᶜ | R¹⁰ᶜ | Gᵃ | Zᶜ |
| 94-560 | 95-560 | 96-560 | 97-560 | Rᵇ | R⁵ᵃ | R⁹ᶜ | R¹⁰ᶜ | Gᵃ | Zᶜ |
| 94-561 | 95-561 | 96-561 | 97-561 | Rᶜ | R⁵ᵃ | R⁹ᶜ | R¹⁰ᶜ | Gᵃ | Zᶜ |
| 94-562 | 95-562 | 96-562 | 97-562 | Rᵃ | R⁵ᵇ | R⁹ᶜ | R¹⁰ᶜ | Gᵃ | Zᶜ |
| 94-563 | 95-563 | 96-563 | 97-563 | Rᵇ | R⁵ᵇ | R⁹ᶜ | R¹⁰ᶜ | Gᵃ | Zᶜ |
| 94-564 | 95-564 | 96-564 | 97-564 | Rᶜ | R⁵ᵇ | R⁹ᶜ | R¹⁰ᶜ | Gᵃ | Zᶜ |
| 94-565 | 95-565 | 96-565 | 97-565 | Rᵃ | R⁵ᶜ | R⁹ᶜ | R¹⁰ᶜ | Gᵃ | Zᶜ |
| 94-566 | 95-566 | 96-566 | 97-566 | Rᵇ | R⁵ᶜ | R⁹ᶜ | R¹⁰ᶜ | Gᵃ | Zᶜ |
| 94-567 | 95-567 | 96-567 | 97-567 | Rᶜ | R⁵ᶜ | R⁹ᶜ | R¹⁰ᶜ | Gᵃ | Zᶜ |
| 94-568 | 95-568 | 96-568 | 97-568 | Rᵃ | R⁵ᵃ | R⁹ᵃ | R¹⁰ᶜ | Gᵇ | Zᶜ |
| 94-569 | 95-569 | 96-569 | 97-569 | Rᵇ | R⁵ᵃ | R⁹ᵃ | R¹⁰ᶜ | Gᵇ | Zᶜ |
| 94-570 | 95-570 | 96-570 | 97-570 | Rᶜ | R⁵ᵃ | R⁹ᵃ | R¹⁰ᶜ | Gᵇ | Zᶜ |
| 94-571 | 95-571 | 96-571 | 97-571 | Rᵃ | R⁵ᵇ | R⁹ᵃ | R¹⁰ᶜ | Gᵇ | Zᶜ |
| 94-572 | 95-572 | 96-572 | 97-572 | Rᵇ | R⁵ᵇ | R⁹ᵃ | R¹⁰ᶜ | Gᵇ | Zᶜ |
| 94-573 | 95-573 | 96-573 | 97-573 | Rᶜ | R⁵ᵇ | R⁹ᵃ | R¹⁰ᶜ | Gᵇ | Zᶜ |
| 94-574 | 95-574 | 96-574 | 97-574 | Rᵃ | R⁵ᶜ | R⁹ᵃ | R¹⁰ᶜ | Gᵇ | Zᶜ |
| 94-575 | 95-575 | 96-575 | 97-575 | Rᵇ | R⁵ᶜ | R⁹ᵃ | R¹⁰ᶜ | Gᵇ | Zᶜ |
| 94-576 | 95-576 | 96-576 | 97-576 | Rᶜ | R⁵ᶜ | R⁹ᵃ | R¹⁰ᶜ | Gᵇ | Zᶜ |
| 94-577 | 95-577 | 96-577 | 97-577 | Rᵃ | R⁵ᵃ | R⁹ᵇ | R¹⁰ᶜ | Gᵇ | Zᶜ |
| 94-578 | 95-578 | 96-578 | 97-578 | Rᵇ | R⁵ᵃ | R⁹ᵇ | R¹⁰ᶜ | Gᵇ | Zᶜ |
| 94-579 | 95-579 | 96-579 | 97-579 | Rᶜ | R⁵ᵃ | R⁹ᵇ | R¹⁰ᶜ | Gᵇ | Zᶜ |
| 94-580 | 95-580 | 96-580 | 97-580 | Rᵃ | R⁵ᵇ | R⁹ᵇ | R¹⁰ᶜ | Gᵇ | Zᶜ |
| 94-581 | 95-581 | 96-581 | 97-581 | Rᵇ | R⁵ᵇ | R⁹ᵇ | R¹⁰ᶜ | Gᵇ | Zᶜ |
| 94-582 | 95-582 | 96-582 | 97-582 | Rᶜ | R⁵ᵇ | R⁹ᵇ | R¹⁰ᶜ | Gᵇ | Zᶜ |
| 94-583 | 95-583 | 96-583 | 97-583 | Rᵃ | R⁵ᶜ | R⁹ᵇ | R¹⁰ᶜ | Gᵇ | Zᶜ |
| 94-584 | 95-584 | 96-584 | 97-584 | Rᵇ | R⁵ᶜ | R⁹ᵇ | R¹⁰ᶜ | Gᵇ | Zᶜ |
| 94-585 | 95-585 | 96-585 | 97-585 | Rᶜ | R⁵ᶜ | R⁹ᵇ | R¹⁰ᶜ | Gᵇ | Zᶜ |
| 94-586 | 95-586 | 96-586 | 97-586 | Rᵃ | R⁵ᵃ | R⁹ᶜ | R¹⁰ᶜ | Gᵇ | Zᶜ |
| 94-587 | 95-587 | 96-587 | 97-587 | Rᵇ | R⁵ᵃ | R⁹ᶜ | R¹⁰ᶜ | Gᵇ | Zᶜ |
| 94-588 | 95-588 | 96-588 | 97-588 | Rᶜ | R⁵ᵃ | R⁹ᶜ | R¹⁰ᶜ | Gᵇ | Zᶜ |
| 94-589 | 95-589 | 96-589 | 97-589 | Rᵃ | R⁵ᵇ | R⁹ᶜ | R¹⁰ᶜ | Gᵇ | Zᶜ |
| 94-590 | 95-590 | 96-590 | 97-590 | Rᵇ | R⁵ᵇ | R⁹ᶜ | R¹⁰ᶜ | Gᵇ | Zᶜ |
| 94-591 | 95-591 | 96-591 | 97-591 | Rᶜ | R⁵ᵇ | R⁹ᶜ | R¹⁰ᶜ | Gᵇ | Zᶜ |
| 94-592 | 95-592 | 96-592 | 97-592 | Rᵃ | R⁵ᶜ | R⁹ᶜ | R¹⁰ᶜ | Gᵇ | Zᶜ |
| 94-593 | 95-593 | 96-593 | 97-593 | Rᵇ | R⁵ᶜ | R⁹ᶜ | R¹⁰ᶜ | Gᵇ | Zᶜ |
| 94-594 | 95-594 | 96-594 | 97-594 | Rᶜ | R⁵ᶜ | R⁹ᶜ | R¹⁰ᶜ | Gᵇ | Zᶜ |
| 94-595 | 95-595 | 96-595 | 97-595 | Rᵃ | R⁵ᵃ | R⁹ᵃ | R¹⁰ᶜ | Gᵇ | Zᶜ |
| 94-596 | 95-596 | 96-596 | 97-596 | Rᵇ | R⁵ᵃ | R⁹ᵃ | R¹⁰ᶜ | Gᵇ | Zᶜ |
| 94-597 | 95-597 | 96-597 | 97-597 | Rᶜ | R⁵ᵃ | R⁹ᵃ | R¹⁰ᶜ | Gᵇ | Zᶜ |
| 94-598 | 95-598 | 96-598 | 97-598 | Rᵃ | R⁵ᵇ | R⁹ᵃ | R¹⁰ᶜ | Gᵇ | Zᶜ |
| 94-599 | 95-599 | 96-599 | 97-599 | Rᵇ | R⁵ᵇ | R⁹ᵃ | R¹⁰ᶜ | Gᵇ | Zᶜ |
| 94-600 | 95-600 | 96-600 | 97-600 | Rᶜ | R⁵ᵇ | R⁹ᵃ | R¹⁰ᶜ | Gᵇ | Zᶜ |
| 94-601 | 95-601 | 96-601 | 97-601 | Rᵃ | R⁵ᶜ | R⁹ᵃ | R¹⁰ᶜ | Gᵇ | Zᶜ |
| 94-602 | 95-602 | 96-602 | 97-602 | Rᵇ | R⁵ᶜ | R⁹ᵃ | R¹⁰ᶜ | Gᵇ | Zᶜ |
| 94-603 | 95-603 | 96-603 | 97-603 | Rᶜ | R⁵ᶜ | R⁹ᵃ | R¹⁰ᶜ | Gᵇ | Zᶜ |
| 94-604 | 95-604 | 96-604 | 97-604 | Rᵃ | R⁵ᵃ | R⁹ᵇ | R¹⁰ᶜ | Gᵇ | Zᶜ |
| 94-605 | 95-605 | 96-605 | 97-605 | Rᵇ | R⁵ᵃ | R⁹ᵇ | R¹⁰ᶜ | Gᵇ | Zᶜ |
| 94-606 | 95-606 | 96-606 | 97-606 | Rᶜ | R⁵ᵃ | R⁹ᵇ | R¹⁰ᶜ | Gᵇ | Zᶜ |
| 94-607 | 95-607 | 96-607 | 97-607 | Rᵃ | R⁵ᵇ | R⁹ᵇ | R¹⁰ᶜ | Gᵇ | Zᶜ |
| 94-608 | 95-608 | 96-608 | 97-608 | Rᵇ | R⁵ᵇ | R⁹ᵇ | R¹⁰ᶜ | Gᵇ | Zᶜ |
| 94-609 | 95-609 | 96-609 | 97-609 | Rᶜ | R⁵ᵇ | R⁹ᵇ | R¹⁰ᶜ | Gᵇ | Zᶜ |
| 94-610 | 95-610 | 96-610 | 97-610 | Rᵃ | R⁵ᶜ | R⁹ᵇ | R¹⁰ᶜ | Gᵇ | Zᶜ |
| 94-611 | 95-611 | 96-611 | 97-611 | Rᵇ | R⁵ᶜ | R⁹ᵇ | R¹⁰ᶜ | Gᵇ | Zᶜ |
| 94-612 | 95-612 | 96-612 | 97-612 | Rᶜ | R⁵ᶜ | R⁹ᵇ | R¹⁰ᶜ | Gᵇ | Zᶜ |
| 94-613 | 95-613 | 96-613 | 97-613 | Rᵃ | R⁵ᵃ | R⁹ᶜ | R¹⁰ᶜ | Gᵇ | Zᶜ |
| 94-614 | 95-614 | 96-614 | 97-614 | Rᵇ | R⁵ᵃ | R⁹ᶜ | R¹⁰ᶜ | Gᵇ | Zᶜ |
| 94-615 | 95-615 | 96-615 | 97-615 | Rᶜ | R⁵ᵃ | R⁹ᶜ | R¹⁰ᶜ | Gᵇ | Zᶜ |
| 94-616 | 95-616 | 96-616 | 97-616 | Rᵃ | R⁵ᵇ | R⁹ᶜ | R¹⁰ᶜ | Gᵇ | Zᶜ |
| 94-617 | 95-617 | 96-617 | 97-617 | Rᵇ | R⁵ᵇ | R⁹ᶜ | R¹⁰ᶜ | Gᵇ | Zᶜ |
| 94-618 | 95-618 | 96-618 | 97-618 | Rᶜ | R⁵ᵇ | R⁹ᶜ | R¹⁰ᶜ | Gᵇ | Zᶜ |
| 94-619 | 95-619 | 96-619 | 97-619 | Rᵃ | R⁵ᶜ | R⁹ᶜ | R¹⁰ᶜ | Gᵇ | Zᶜ |
| 94-620 | 95-620 | 96-620 | 97-620 | Rᵇ | R⁵ᶜ | R⁹ᶜ | R¹⁰ᶜ | Gᵇ | Zᶜ |
| 94-621 | 95-621 | 96-621 | 97-621 | Rᶜ | R⁵ᶜ | R⁹ᶜ | R¹⁰ᶜ | Gᵇ | Zᶜ |
| 94-622 | 95-622 | 96-622 | 97-622 | Rᵃ | R⁵ᵃ | R⁹ᵃ | R¹⁰ᶜ | Gᵇ | Zᶜ |
| 94-623 | 95-623 | 96-623 | 97-623 | Rᵇ | R⁵ᵃ | R⁹ᵃ | R¹⁰ᶜ | Gᵇ | Zᶜ |
| 94-624 | 95-624 | 96-624 | 97-624 | Rᶜ | R⁵ᵃ | R⁹ᵃ | R¹⁰ᶜ | Gᵇ | Zᶜ |
| 94-625 | 95-625 | 96-625 | 97-625 | Rᵃ | R⁵ᵇ | R⁹ᵃ | R¹⁰ᶜ | Gᵇ | Zᶜ |
| 94-626 | 95-626 | 96-626 | 97-626 | Rᵇ | R⁵ᵇ | R⁹ᵃ | R¹⁰ᶜ | Gᵇ | Zᶜ |
| 94-627 | 95-627 | 96-627 | 97-627 | Rᶜ | R⁵ᵇ | R⁹ᵃ | R¹⁰ᶜ | Gᵇ | Zᶜ |
| 94-628 | 95-628 | 96-628 | 97-628 | Rᵃ | R⁵ᶜ | R⁹ᵃ | R¹⁰ᶜ | Gᵇ | Zᶜ |
| 94-629 | 95-629 | 96-629 | 97-629 | Rᵇ | R⁵ᶜ | R⁹ᵃ | R¹⁰ᶜ | Gᵇ | Zᶜ |
| 94-630 | 95-630 | 96-630 | 97-630 | Rᶜ | R⁵ᶜ | R⁹ᵃ | R¹⁰ᶜ | Gᵇ | Zᶜ |
| 94-631 | 95-631 | 96-631 | 97-631 | Rᵃ | R⁵ᵃ | R⁹ᵇ | R¹⁰ᶜ | Gᵇ | Zᶜ |
| 94-632 | 95-632 | 96-632 | 97-632 | Rᵇ | R⁵ᵃ | R⁹ᵇ | R¹⁰ᶜ | Gᵇ | Zᶜ |
| 94-633 | 95-633 | 96-633 | 97-633 | Rᶜ | R⁵ᵃ | R⁹ᵇ | R¹⁰ᶜ | Gᵇ | Zᶜ |
| 94-634 | 95-634 | 96-634 | 97-634 | Rᵃ | R⁵ᵇ | R⁹ᵇ | R¹⁰ᶜ | Gᵇ | Zᶜ |
| 94-635 | 95-635 | 96-635 | 97-635 | Rᵇ | R⁵ᵇ | R⁹ᵇ | R¹⁰ᶜ | Gᵇ | Zᶜ |
| 94-636 | 95-636 | 96-636 | 97-636 | Rᶜ | R⁵ᵇ | R⁹ᵇ | R¹⁰ᶜ | Gᵇ | Zᶜ |
| 94-637 | 95-637 | 96-637 | 97-637 | Rᵃ | R⁵ᶜ | R⁹ᵇ | R¹⁰ᶜ | Gᵇ | Zᶜ |
| 94-638 | 95-638 | 96-638 | 97-638 | Rᵇ | R⁵ᶜ | R⁹ᵇ | R¹⁰ᶜ | Gᵇ | Zᶜ |
| 94-639 | 95-639 | 96-639 | 97-639 | Rᶜ | R⁵ᶜ | R⁹ᵇ | R¹⁰ᶜ | Gᵇ | Zᶜ |
| 94-640 | 95-640 | 96-640 | 97-640 | Rᵃ | R⁵ᵃ | R⁹ᶜ | R¹⁰ᶜ | Gᵇ | Zᶜ |
| 94-641 | 95-641 | 96-641 | 97-641 | Rᵇ | R⁵ᵃ | R⁹ᶜ | R¹⁰ᶜ | Gᵇ | Zᶜ |
| 94-642 | 95-642 | 96-642 | 97-642 | Rᶜ | R⁵ᵃ | R⁹ᶜ | R¹⁰ᶜ | Gᵇ | Zᶜ |

-continued

| Formulae | | | | R | R⁵ | R⁹ | R¹⁰ | G | Z |
|---|---|---|---|---|---|---|---|---|---|
| 94-643 | 95-643 | 96-643 | 97-643 | Rᵃ | R⁵ᵇ | R⁹ᶜ | R¹⁰ᶜ | Gᵇ | Zᶜ |
| 94-644 | 95-644 | 96-644 | 97-644 | Rᵇ | R⁵ᵇ | R⁹ᶜ | R¹⁰ᶜ | Gᵇ | Zᶜ |
| 94-645 | 95-645 | 96-645 | 97-645 | Rᶜ | R⁵ᵇ | R⁹ᶜ | R¹⁰ᶜ | Gᵇ | Zᶜ |
| 94-646 | 95-646 | 96-646 | 97-646 | Rᵃ | R⁵ᶜ | R⁹ᶜ | R¹⁰ᶜ | Gᵇ | Zᶜ |
| 94-647 | 95-647 | 96-647 | 97-647 | Rᵇ | R⁵ᶜ | R⁹ᶜ | R¹⁰ᶜ | Gᵇ | Zᶜ |
| 94-648 | 95-648 | 96-648 | 97-648 | Rᶜ | R⁵ᶜ | R⁹ᶜ | R¹⁰ᶜ | Gᵇ | Zᶜ |
| 94-649 | 95-649 | 96-649 | 97-649 | Rᵃ | R⁵ᵃ | R⁹ᵃ | R¹⁰ᶜ | Gᶜ | Zᶜ |
| 94-650 | 95-650 | 96-650 | 97-650 | Rᵇ | R⁵ᵃ | R⁹ᵃ | R¹⁰ᶜ | Gᶜ | Zᶜ |
| 94-651 | 95-651 | 96-651 | 97-651 | Rᶜ | R⁵ᵃ | R⁹ᵃ | R¹⁰ᶜ | Gᶜ | Zᶜ |
| 94-652 | 95-652 | 96-652 | 97-652 | Rᵃ | R⁵ᵇ | R⁹ᵃ | R¹⁰ᶜ | Gᶜ | Zᶜ |
| 94-653 | 95-653 | 96-653 | 97-653 | Rᵇ | R⁵ᵇ | R⁹ᵃ | R¹⁰ᶜ | Gᶜ | Zᶜ |
| 94-654 | 95-654 | 96-654 | 97-654 | Rᶜ | R⁵ᵇ | R⁹ᵃ | R¹⁰ᶜ | Gᶜ | Zᶜ |
| 94-655 | 95-655 | 96-655 | 97-655 | Rᵃ | R⁵ᶜ | R⁹ᵃ | R¹⁰ᶜ | Gᶜ | Zᶜ |
| 94-656 | 95-656 | 96-656 | 97-656 | Rᵇ | R⁵ᶜ | R⁹ᵃ | R¹⁰ᶜ | Gᶜ | Zᶜ |
| 94-657 | 95-657 | 96-657 | 97-657 | Rᶜ | R⁵ᶜ | R⁹ᵃ | R¹⁰ᶜ | Gᶜ | Zᶜ |
| 94-658 | 95-658 | 96-658 | 97-658 | Rᵃ | R⁵ᵃ | R⁹ᵇ | R¹⁰ᶜ | Gᶜ | Zᶜ |
| 94-659 | 95-659 | 96-659 | 97-659 | Rᵇ | R⁵ᵃ | R⁹ᵇ | R¹⁰ᶜ | Gᶜ | Zᶜ |
| 94-660 | 95-660 | 96-660 | 97-660 | Rᶜ | R⁵ᵃ | R⁹ᵇ | R¹⁰ᶜ | Gᶜ | Zᶜ |
| 94-661 | 95-661 | 96-661 | 97-661 | Rᵃ | R⁵ᵇ | R⁹ᵇ | R¹⁰ᶜ | Gᶜ | Zᶜ |
| 94-662 | 95-662 | 96-662 | 97-662 | Rᵇ | R⁵ᵇ | R⁹ᵇ | R¹⁰ᶜ | Gᶜ | Zᶜ |
| 94-663 | 95-663 | 96-663 | 97-663 | Rᶜ | R⁵ᵇ | R⁹ᵇ | R¹⁰ᶜ | Gᶜ | Zᶜ |
| 94-664 | 95-664 | 96-664 | 97-664 | Rᵃ | R⁵ᶜ | R⁹ᵇ | R¹⁰ᶜ | Gᶜ | Zᶜ |
| 94-665 | 95-665 | 96-665 | 97-665 | Rᵇ | R⁵ᶜ | R⁹ᵇ | R¹⁰ᶜ | Gᶜ | Zᶜ |
| 94-666 | 95-666 | 96-666 | 97-666 | Rᶜ | R⁵ᶜ | R⁹ᵇ | R¹⁰ᶜ | Gᶜ | Zᶜ |
| 94-667 | 95-667 | 96-667 | 97-667 | Rᵃ | R⁵ᵃ | R⁹ᶜ | R¹⁰ᶜ | Gᶜ | Zᶜ |
| 94-668 | 95-668 | 96-668 | 97-668 | Rᵇ | R⁵ᵃ | R⁹ᶜ | R¹⁰ᶜ | Gᶜ | Zᶜ |
| 94-669 | 95-669 | 96-669 | 97-669 | Rᶜ | R⁵ᵃ | R⁹ᶜ | R¹⁰ᶜ | Gᶜ | Zᶜ |
| 94-670 | 95-670 | 96-670 | 97-670 | Rᵃ | R⁵ᵇ | R⁹ᶜ | R¹⁰ᶜ | Gᶜ | Zᶜ |
| 94-671 | 95-671 | 96-671 | 97-671 | Rᵇ | R⁵ᵇ | R⁹ᶜ | R¹⁰ᶜ | Gᶜ | Zᶜ |
| 94-672 | 95-672 | 96-672 | 97-672 | Rᶜ | R⁵ᵇ | R⁹ᶜ | R¹⁰ᶜ | Gᶜ | Zᶜ |
| 94-673 | 95-673 | 96-673 | 97-673 | Rᵃ | R⁵ᶜ | R⁹ᶜ | R¹⁰ᶜ | Gᶜ | Zᶜ |
| 94-674 | 95-674 | 96-674 | 97-674 | Rᵇ | R⁵ᶜ | R⁹ᶜ | R¹⁰ᶜ | Gᶜ | Zᶜ |
| 94-675 | 95-675 | 96-675 | 97-675 | Rᶜ | R⁵ᶜ | R⁹ᶜ | R¹⁰ᶜ | Gᶜ | Zᶜ |
| 94-676 | 95-676 | 96-676 | 97-676 | Rᵃ | R⁵ᵃ | R⁹ᵃ | R¹⁰ᶜ | Gᵉ | Zᶜ |
| 94-677 | 95-677 | 96-677 | 97-677 | Rᵇ | R⁵ᵃ | R⁹ᵃ | R¹⁰ᶜ | Gᵉ | Zᶜ |
| 94-678 | 95-678 | 96-678 | 97-678 | Rᶜ | R⁵ᵃ | R⁹ᵃ | R¹⁰ᶜ | Gᵉ | Zᶜ |
| 94-679 | 95-679 | 96-679 | 97-679 | Rᵃ | R⁵ᵇ | R⁹ᵃ | R¹⁰ᶜ | Gᵉ | Zᶜ |
| 94-680 | 95-680 | 96-680 | 97-680 | Rᵇ | R⁵ᵇ | R⁹ᵃ | R¹⁰ᶜ | Gᵉ | Zᶜ |
| 94-681 | 95-681 | 96-681 | 97-681 | Rᶜ | R⁵ᵇ | R⁹ᵃ | R¹⁰ᶜ | Gᵉ | Zᶜ |
| 94-682 | 95-682 | 96-682 | 97-682 | Rᵃ | R⁵ᶜ | R⁹ᵃ | R¹⁰ᶜ | Gᵉ | Zᶜ |
| 94-683 | 95-683 | 96-683 | 97-683 | Rᵇ | R⁵ᶜ | R⁹ᵃ | R¹⁰ᶜ | Gᵉ | Zᶜ |
| 94-684 | 95-684 | 96-684 | 97-684 | Rᶜ | R⁵ᶜ | R⁹ᵃ | R¹⁰ᶜ | Gᵉ | Zᶜ |
| 94-685 | 95-685 | 96-685 | 97-685 | Rᵃ | R⁵ᵃ | R⁹ᵇ | R¹⁰ᶜ | Gᵉ | Zᶜ |
| 94-686 | 95-686 | 96-686 | 97-686 | Rᵇ | R⁵ᵃ | R⁹ᵇ | R¹⁰ᶜ | Gᵉ | Zᶜ |
| 94-687 | 95-687 | 96-687 | 97-687 | Rᶜ | R⁵ᵃ | R⁹ᵇ | R¹⁰ᶜ | Gᵉ | Zᶜ |
| 94-688 | 95-688 | 96-688 | 97-688 | Rᵃ | R⁵ᵇ | R⁹ᵇ | R¹⁰ᶜ | Gᵉ | Zᶜ |
| 94-689 | 95-689 | 96-689 | 97-689 | Rᵇ | R⁵ᵇ | R⁹ᵇ | R¹⁰ᶜ | Gᵉ | Zᶜ |
| 94-690 | 95-690 | 96-690 | 97-690 | Rᶜ | R⁵ᵇ | R⁹ᵇ | R¹⁰ᶜ | Gᵉ | Zᶜ |
| 94-691 | 95-691 | 96-691 | 97-691 | Rᵃ | R⁵ᶜ | R⁹ᵇ | R¹⁰ᶜ | Gᵉ | Zᶜ |
| 94-692 | 95-692 | 96-692 | 97-692 | Rᵇ | R⁵ᶜ | R⁹ᵇ | R¹⁰ᶜ | Gᵉ | Zᶜ |
| 94-693 | 95-693 | 96-693 | 97-693 | Rᶜ | R⁵ᶜ | R⁹ᵇ | R¹⁰ᶜ | Gᵉ | Zᶜ |
| 94-694 | 95-694 | 96-694 | 97-694 | Rᵃ | R⁵ᵃ | R⁹ᶜ | R¹⁰ᶜ | Gᵉ | Zᶜ |
| 94-695 | 95-695 | 96-695 | 97-695 | Rᵇ | R⁵ᵃ | R⁹ᶜ | R¹⁰ᶜ | Gᵉ | Zᶜ |
| 94-696 | 95-696 | 96-696 | 97-696 | Rᶜ | R⁵ᵃ | R⁹ᶜ | R¹⁰ᶜ | Gᵉ | Zᶜ |
| 94-697 | 95-697 | 96-697 | 97-697 | Rᵃ | R⁵ᵇ | R⁹ᶜ | R¹⁰ᶜ | Gᵉ | Zᶜ |
| 94-698 | 95-698 | 96-698 | 97-698 | Rᵇ | R⁵ᵇ | R⁹ᶜ | R¹⁰ᶜ | Gᵉ | Zᶜ |
| 94-699 | 95-699 | 96-699 | 97-699 | Rᶜ | R⁵ᵇ | R⁹ᶜ | R¹⁰ᶜ | Gᵉ | Zᶜ |
| 94-700 | 95-700 | 96-700 | 97-700 | Rᵃ | R⁵ᶜ | R⁹ᶜ | R¹⁰ᶜ | Gᵉ | Zᶜ |
| 94-701 | 95-701 | 96-701 | 97-701 | Rᵇ | R⁵ᶜ | R⁹ᶜ | R¹⁰ᶜ | Gᵉ | Zᶜ |
| 94-702 | 95-702 | 96-702 | 97-702 | Rᶜ | R⁵ᶜ | R⁹ᶜ | R¹⁰ᶜ | Gᵉ | Zᶜ |
| 94-703 | 95-703 | 96-703 | 97-703 | Rᵃ | R⁵ᵃ | R⁹ᵃ | R¹⁰ᶜ | Gᵉ | Zᶜ |
| 94-704 | 95-704 | 96-704 | 97-704 | Rᵇ | R⁵ᵃ | R⁹ᵃ | R¹⁰ᶜ | Gᵉ | Zᶜ |
| 94-705 | 95-705 | 96-705 | 97-705 | Rᶜ | R⁵ᵃ | R⁹ᵃ | R¹⁰ᶜ | Gᵉ | Zᶜ |
| 94-706 | 95-706 | 96-706 | 97-706 | Rᵃ | R⁵ᵇ | R⁹ᵃ | R¹⁰ᶜ | Gᵉ | Zᶜ |
| 94-707 | 95-707 | 96-707 | 97-707 | Rᵇ | R⁵ᵇ | R⁹ᵃ | R¹⁰ᶜ | Gᵉ | Zᶜ |
| 94-708 | 95-708 | 96-708 | 97-708 | Rᶜ | R⁵ᵇ | R⁹ᵃ | R¹⁰ᶜ | Gᵉ | Zᶜ |
| 94-709 | 95-709 | 96-709 | 97-709 | Rᵃ | R⁵ᶜ | R⁹ᵃ | R¹⁰ᶜ | Gᵉ | Zᶜ |
| 94-710 | 95-710 | 96-710 | 97-710 | Rᵇ | R⁵ᶜ | R⁹ᵃ | R¹⁰ᶜ | Gᵉ | Zᶜ |
| 94-711 | 95-711 | 96-711 | 97-711 | Rᶜ | R⁵ᶜ | R⁹ᵃ | R¹⁰ᶜ | Gᵉ | Zᶜ |
| 94-712 | 95-712 | 96-712 | 97-712 | Rᵃ | R⁵ᵃ | R⁹ᵇ | R¹⁰ᶜ | Gᵉ | Zᶜ |
| 94-713 | 95-713 | 96-713 | 97-713 | Rᵇ | R⁵ᵃ | R⁹ᵇ | R¹⁰ᶜ | Gᵉ | Zᶜ |
| 94-714 | 95-714 | 96-714 | 97-714 | Rᶜ | R⁵ᵃ | R⁹ᵇ | R¹⁰ᶜ | Gᵉ | Zᶜ |
| 94-715 | 95-715 | 96-715 | 97-715 | Rᵃ | R⁵ᵇ | R⁹ᵇ | R¹⁰ᶜ | Gᵉ | Zᶜ |
| 94-716 | 95-716 | 96-716 | 97-716 | Rᵇ | R⁵ᵇ | R⁹ᵇ | R¹⁰ᶜ | Gᵉ | Zᶜ |
| 94-717 | 95-717 | 96-717 | 97-717 | Rᶜ | R⁵ᵇ | R⁹ᵇ | R¹⁰ᶜ | Gᵉ | Zᶜ |
| 94-718 | 95-718 | 96-718 | 97-718 | Rᵃ | R⁵ᶜ | R⁹ᵇ | R¹⁰ᶜ | Gᵉ | Zᶜ |
| 94-719 | 95-719 | 96-719 | 97-719 | Rᵇ | R⁵ᶜ | R⁹ᵇ | R¹⁰ᶜ | Gᵉ | Zᶜ |
| 94-720 | 95-720 | 96-720 | 97-720 | Rᶜ | R⁵ᶜ | R⁹ᵇ | R¹⁰ᶜ | Gᵉ | Zᶜ |
| 94-721 | 95-721 | 96-721 | 97-721 | Rᵃ | R⁵ᵃ | R⁹ᶜ | R¹⁰ᶜ | Gᵉ | Zᶜ |
| 94-722 | 95-722 | 96-722 | 97-722 | Rᵇ | R⁵ᵃ | R⁹ᶜ | R¹⁰ᶜ | Gᵉ | Zᶜ |
| 94-723 | 95-723 | 96-723 | 97-723 | Rᶜ | R⁵ᵃ | R⁹ᶜ | R¹⁰ᶜ | Gᵉ | Zᶜ |
| 94-724 | 95-724 | 96-724 | 97-724 | Rᵃ | R⁵ᵇ | R⁹ᶜ | R¹⁰ᶜ | Gᵉ | Zᶜ |
| 94-725 | 95-725 | 96-725 | 97-725 | Rᵇ | R⁵ᵇ | R⁹ᶜ | R¹⁰ᶜ | Gᵉ | Zᶜ |
| 94-726 | 95-726 | 96-726 | 97-726 | Rᶜ | R⁵ᵇ | R⁹ᶜ | R¹⁰ᶜ | Gᵉ | Zᶜ |
| 94-727 | 95-727 | 96-727 | 97-727 | Rᵃ | R⁵ᶜ | R⁹ᶜ | R¹⁰ᶜ | Gᵉ | Zᶜ |
| 94-728 | 95-728 | 96-728 | 97-728 | Rᵇ | R⁵ᶜ | R⁹ᶜ | R¹⁰ᶜ | Gᵉ | Zᶜ |
| 94-729 | 95-729 | 96-729 | 97-729 | Rᶜ | R⁵ᶜ | R⁹ᶜ | R¹⁰ᶜ | Gᵉ | Zᶜ | where all symbols are as defined above.

In one aspect of any of formulae (94), (95), (96), and (97) of the present invention, R is hydrogen, a hydroxy group, a halogen, a nitro group, an optionally substituted amino group, an alkyl group, an alkoxy group, an alkenyl group, or an alkoxyalkyl group; $R^5$ is hydrogen, a hydroxy group, a halogen, a nitro group, an optionally substituted amino group, an alkyl group, an alkoxy group, an alkenyl group, or an alkoxyalkyl group; $R^9$ and $R^{10}$ independently are hydrogen, a halogen, a nitro group, an amino group, a mono- or di-substituted amino group, a hydroxy group, an alkoxy group, a carboxy group, a cyano group, an oxo(O=) group, or a thio(S=) group; G is (—CH$_2$—)$_2$, (—CH$_2$—)$_3$, or (—CH$_2$—)$_4$; and all other symbols are as defined above in connection with formula (I).

In another aspect of any of formulae (94), (95), (96), and (97) of the present invention, R is hydrogen, a hydroxy group, a halogen, a nitro group, an optionally substituted amino group, an alkyl group, an alkoxy group, an alkenyl group, or an alkoxyalkyl group; $R^5$ is hydrogen, a hydroxy group, a halogen, a nitro group, an optionally substituted amino group, an alkyl group, an alkoxy group, an alkenyl group, or an alkoxyalkyl group; $R^9$ and $R^{10}$ independently are an alkyl group, a cycloalkyl group, an alkoxy group, a haloalkoxy group, a cycloalkyl group, an aryl group, a benzyloxy group, an acyl group, an acyloxy group, an aroyl group, an alkoxycarbonyl group, an aryloxycarbonyl group, a heteroaryl group, a heterocyclyl group, or an aralkyl group; and G is (—CH$_2$—)$_2$, (—CH$_2$—)$_3$, or (—CH$_2$—)$_4$; and all other symbols are as defined as above in connection with formula (I).

In yet another aspect of of formulae (94), (95), (96), and (97) the present invention, R is hydrogen, a hydroxy group, a halogen, a nitro group, an optionally substituted amino group, an alkyl group, an alkoxy group, an alkenyl group, or an alkoxyalkyl group; $R^5$ is hydrogen, a hydroxy group, a halogen, a nitro group, an optionally substituted amino group, an alkyl group, an alkoxy group, an alkenyl group, or an alkoxyalkyl group; $R^9$ and $R^{10}$ independently are an alkylsulfonyl group, an alkylsulfinyl group, an arylsulfonyl group, an arylsulfinyl group, an alkylthio group, an arylthio group, a heteroarylthio group, an aralkylthio group, or a heterocyclyl sulfonyl group, which is optionally substituted with a halogen, a hydroxyl group, a nitro group, an amino group, an alkyloxy group, or any combination thereof, and wherein the heterocycle group is optionally a substituted morpholinyl group, a thiomorpholinyl group, or a piperzinyl group, wherein the substituent on the heterocyclyl group is a halogen, a nitro group, an amino group, an alkyl group, an alkoxy group, or an aryl group; and G is (—CH$_2$—)$_2$, (—CH$_2$—)$_3$, or (—CH$_2$—)$_4$; and all other symbols are as defined as above in connection with formula (I).

In still another aspect of any of formulae (94), (95), (96), and (97) of the present invention, R is hydrogen or an alkyl group; $R^5$ is hydrogen or an alkyl group; $R^9$ is hydrogen, an alkoxy group, or

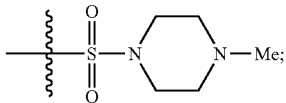

$R^{10}$ is hydrogen or an alkoxy group; and G is (—CH$_2$—)$_2$, (—CH$_2$—)$_3$, or (—CH$_2$—)$_4$.

In still another aspect of any of formulae (94), (95), (96), and (97) of the present invention, R is —H or Me; $R^5$ is —H or Me; $R^9$ is —H, —OMe, or

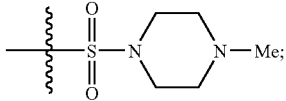

$R^{10}$ is —H, —OMe, or —OEt; and G is (—CH$_2$—)$_2$, (—CH$_2$—)$_3$, or (—CH$_2$—)$_4$.

The present invention further encompasses various compounds of general formula (IV) as follows:

(98)

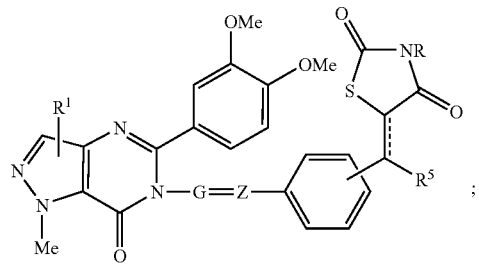

(99)

(100)

; and (101)

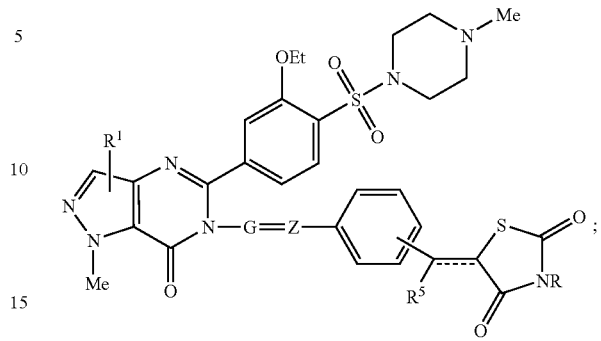

where all symbols are as defined above in connection with formula (I).

According to various aspects of the present invention, R, $R^1$, $R^5$, G, and Z of any of formulae (98), (99), (100), and (101) are selected to produce compounds of formulae (98-1), (99-1), (100-1), and (101-1) through formulae (98-243), (99-243), (100-243), and (101-243) as follows:

| Formulae | | | | R | $R^1$ | $R^5$ | G | Z |
|---|---|---|---|---|---|---|---|---|
| 98-1 | 99-1 | 100-1 | 101-1 | $R^a$ | $R^{1a}$ | $R^{5a}$ | $G^a$ | $Z^a$ |
| 98-2 | 99-2 | 100-2 | 101-2 | $R^b$ | $R^{1a}$ | $R^{5a}$ | $G^a$ | $Z^a$ |
| 98-3 | 99-3 | 100-3 | 101-3 | $R^c$ | $R^{1a}$ | $R^{5a}$ | $G^a$ | $Z^a$ |
| 98-4 | 99-4 | 100-4 | 101-4 | $R^a$ | $R^{1b}$ | $R^{5a}$ | $G^a$ | $Z^a$ |
| 98-5 | 99-5 | 100-5 | 101-5 | $R^b$ | $R^{1b}$ | $R^{5a}$ | $G^a$ | $Z^a$ |
| 98-6 | 99-6 | 100-6 | 101-6 | $R^c$ | $R^{1b}$ | $R^{5a}$ | $G^a$ | $Z^a$ |
| 98-7 | 99-7 | 100-7 | 101-7 | $R^a$ | $R^{1c}$ | $R^{5a}$ | $G^a$ | $Z^a$ |
| 98-8 | 99-8 | 100-8 | 101-8 | $R^b$ | $R^{1c}$ | $R^{5a}$ | $G^a$ | $Z^a$ |
| 98-9 | 99-9 | 100-9 | 101-9 | $R^c$ | $R^{1c}$ | $R^{5a}$ | $G^a$ | $Z^a$ |
| 98-10 | 99-10 | 100-10 | 101-10 | $R^a$ | $R^{1a}$ | $R^{5b}$ | $G^a$ | $Z^a$ |
| 98-11 | 99-11 | 100-11 | 101-11 | $R^b$ | $R^{1a}$ | $R^{5b}$ | $G^a$ | $Z^a$ |
| 98-12 | 99-12 | 100-12 | 101-12 | $R^c$ | $R^{1a}$ | $R^{5b}$ | $G^a$ | $Z^a$ |
| 98-13 | 99-13 | 100-13 | 101-13 | $R^a$ | $R^{1b}$ | $R^{5b}$ | $G^a$ | $Z^a$ |
| 98-14 | 99-14 | 100-14 | 101-14 | $R^b$ | $R^{1b}$ | $R^{5b}$ | $G^a$ | $Z^a$ |
| 98-15 | 99-15 | 100-15 | 101-15 | $R^c$ | $R^{1b}$ | $R^{5b}$ | $G^a$ | $Z^a$ |
| 98-16 | 99-16 | 100-16 | 101-16 | $R^a$ | $R^{1c}$ | $R^{5b}$ | $G^a$ | $Z^a$ |
| 98-17 | 99-17 | 100-17 | 101-17 | $R^b$ | $R^{1c}$ | $R^{5b}$ | $G^a$ | $Z^a$ |
| 98-18 | 99-18 | 100-18 | 101-18 | $R^c$ | $R^{1c}$ | $R^{5b}$ | $G^a$ | $Z^a$ |
| 98-19 | 99-19 | 100-19 | 101-19 | $R^a$ | $R^{1a}$ | $R^{5c}$ | $G^a$ | $Z^a$ |
| 98-20 | 99-20 | 100-20 | 101-20 | $R^b$ | $R^{1a}$ | $R^{5c}$ | $G^a$ | $Z^a$ |
| 98-21 | 99-21 | 100-21 | 101-21 | $R^c$ | $R^{1a}$ | $R^{5c}$ | $G^a$ | $Z^a$ |
| 98-22 | 99-22 | 100-22 | 101-22 | $R^a$ | $R^{1b}$ | $R^{5c}$ | $G^a$ | $Z^a$ |
| 98-23 | 99-23 | 100-23 | 101-23 | $R^b$ | $R^{1b}$ | $R^{5c}$ | $G^a$ | $Z^a$ |
| 98-24 | 99-24 | 100-24 | 101-24 | $R^c$ | $R^{1b}$ | $R^{5c}$ | $G^a$ | $Z^a$ |
| 98-25 | 99-25 | 100-25 | 101-25 | $R^a$ | $R^{1c}$ | $R^{5c}$ | $G^a$ | $Z^a$ |
| 98-26 | 99-26 | 100-26 | 101-26 | $R^b$ | $R^{1c}$ | $R^{5c}$ | $G^a$ | $Z^a$ |
| 98-27 | 99-27 | 100-27 | 101-27 | $R^c$ | $R^{1c}$ | $R^{5c}$ | $G^a$ | $Z^a$ |
| 98-28 | 99-28 | 100-28 | 101-28 | $R^a$ | $R^{1a}$ | $R^{5a}$ | $G^b$ | $Z^a$ |
| 98-29 | 99-29 | 100-29 | 101-29 | $R^b$ | $R^{1a}$ | $R^{5a}$ | $G^b$ | $Z^a$ |
| 98-30 | 99-30 | 100-30 | 101-30 | $R^c$ | $R^{1a}$ | $R^{5a}$ | $G^b$ | $Z^a$ |
| 98-31 | 99-31 | 100-31 | 101-31 | $R^a$ | $R^{1b}$ | $R^{5a}$ | $G^b$ | $Z^a$ |
| 98-32 | 99-32 | 100-32 | 101-32 | $R^b$ | $R^{1b}$ | $R^{5a}$ | $G^b$ | $Z^a$ |
| 98-33 | 99-33 | 100-33 | 101-33 | $R^c$ | $R^{1b}$ | $R^{5a}$ | $G^b$ | $Z^a$ |
| 98-34 | 99-34 | 100-34 | 101-34 | $R^a$ | $R^{1c}$ | $R^{5a}$ | $G^b$ | $Z^a$ |
| 98-35 | 99-35 | 100-35 | 101-35 | $R^b$ | $R^{1c}$ | $R^{5a}$ | $G^b$ | $Z^a$ |
| 98-36 | 99-36 | 100-36 | 101-36 | $R^c$ | $R^{1c}$ | $R^{5a}$ | $G^b$ | $Z^a$ |
| 98-37 | 99-37 | 100-37 | 101-37 | $R^a$ | $R^{1a}$ | $R^{5b}$ | $G^b$ | $Z^a$ |
| 98-38 | 99-38 | 100-38 | 101-38 | $R^b$ | $R^{1a}$ | $R^{5b}$ | $G^b$ | $Z^a$ |
| 98-39 | 99-39 | 100-39 | 101-39 | $R^c$ | $R^{1a}$ | $R^{5b}$ | $G^b$ | $Z^a$ |
| 98-40 | 99-40 | 100-40 | 101-40 | $R^a$ | $R^{1b}$ | $R^{5b}$ | $G^b$ | $Z^a$ |
| 98-41 | 99-41 | 100-41 | 101-41 | $R^b$ | $R^{1b}$ | $R^{5b}$ | $G^b$ | $Z^a$ |
| 98-42 | 99-42 | 100-42 | 101-42 | $R^c$ | $R^{1b}$ | $R^{5b}$ | $G^b$ | $Z^a$ |
| 98-43 | 99-43 | 100-43 | 101-43 | $R^a$ | $R^{1c}$ | $R^{5b}$ | $G^b$ | $Z^a$ |
| 98-44 | 99-44 | 100-44 | 101-44 | $R^b$ | $R^{1c}$ | $R^{5b}$ | $G^b$ | $Z^a$ |
| 98-45 | 99-45 | 100-45 | 101-45 | $R^c$ | $R^{1c}$ | $R^{5b}$ | $G^b$ | $Z^a$ |

-continued

| Formulae | | | | R | R¹ | R⁵ | G | Z |
|---|---|---|---|---|---|---|---|---|
| 98-46 | 99-46 | 100-46 | 101-46 | Rᵃ | R¹ᵃ | R⁵ᶜ | Gᵇ | Zᵃ |
| 98-47 | 99-47 | 100-47 | 101-47 | Rᵇ | R¹ᵃ | R⁵ᶜ | Gᵇ | Zᵃ |
| 98-48 | 99-48 | 100-48 | 101-48 | Rᶜ | R¹ᵃ | R⁵ᶜ | Gᵇ | Zᵃ |
| 98-49 | 99-49 | 100-49 | 101-49 | Rᵃ | R¹ᵇ | R⁵ᶜ | Gᵇ | Zᵃ |
| 98-50 | 99-50 | 100-50 | 101-50 | Rᵇ | R¹ᵇ | R⁵ᶜ | Gᵇ | Zᵃ |
| 98-51 | 99-51 | 100-51 | 101-51 | Rᶜ | R¹ᵇ | R⁵ᶜ | Gᵇ | Zᵃ |
| 98-52 | 99-52 | 100-52 | 101-52 | Rᵃ | R¹ᶜ | R⁵ᶜ | Gᵇ | Zᵃ |
| 98-53 | 99-53 | 100-53 | 101-53 | Rᵇ | R¹ᶜ | R⁵ᶜ | Gᵇ | Zᵃ |
| 98-54 | 99-54 | 100-54 | 101-54 | Rᶜ | R¹ᶜ | R⁵ᶜ | Gᵇ | Zᵃ |
| 98-55 | 99-55 | 100-55 | 101-55 | Rᵃ | R¹ᵃ | R⁵ᵃ | Gᶜ | Zᵃ |
| 98-56 | 99-56 | 100-56 | 101-56 | Rᵇ | R¹ᵃ | R⁵ᵃ | Gᶜ | Zᵃ |
| 98-57 | 99-57 | 100-57 | 101-57 | Rᶜ | R¹ᵃ | R⁵ᵃ | Gᶜ | Zᵃ |
| 98-58 | 99-58 | 100-58 | 101-58 | Rᵃ | R¹ᵇ | R⁵ᵃ | Gᶜ | Zᵃ |
| 98-59 | 99-59 | 100-59 | 101-59 | Rᵇ | R¹ᵇ | R⁵ᵃ | Gᶜ | Zᵃ |
| 98-60 | 99-60 | 100-60 | 101-60 | Rᶜ | R¹ᵇ | R⁵ᵃ | Gᶜ | Zᵃ |
| 98-61 | 99-61 | 100-61 | 101-61 | Rᵃ | R¹ᶜ | R⁵ᵃ | Gᶜ | Zᵃ |
| 98-62 | 99-62 | 100-62 | 101-62 | Rᵇ | R¹ᶜ | R⁵ᵃ | Gᶜ | Zᵃ |
| 98-63 | 99-63 | 100-63 | 101-63 | Rᶜ | R¹ᶜ | R⁵ᵃ | Gᶜ | Zᵃ |
| 98-64 | 99-64 | 100-64 | 101-64 | Rᵃ | R¹ᵃ | R⁵ᵇ | Gᶜ | Zᵃ |
| 98-65 | 99-65 | 100-65 | 101-65 | Rᵇ | R¹ᵃ | R⁵ᵇ | Gᶜ | Zᵃ |
| 98-66 | 99-66 | 100-66 | 101-66 | Rᶜ | R¹ᵃ | R⁵ᵇ | Gᶜ | Zᵃ |
| 98-67 | 99-67 | 100-67 | 101-67 | Rᵃ | R¹ᵇ | R⁵ᵇ | Gᶜ | Zᵃ |
| 98-68 | 99-68 | 100-68 | 101-68 | Rᵇ | R¹ᵇ | R⁵ᵇ | Gᶜ | Zᵃ |
| 98-69 | 99-69 | 100-69 | 101-69 | Rᶜ | R¹ᵇ | R⁵ᵇ | Gᶜ | Zᵃ |
| 98-70 | 99-70 | 100-70 | 101-70 | Rᵃ | R¹ᶜ | R⁵ᵇ | Gᶜ | Zᵃ |
| 98-71 | 99-71 | 100-71 | 101-71 | Rᵇ | R¹ᶜ | R⁵ᵇ | Gᶜ | Zᵃ |
| 98-72 | 99-72 | 100-72 | 101-72 | Rᶜ | R¹ᶜ | R⁵ᵇ | Gᶜ | Zᵃ |
| 98-73 | 99-73 | 100-73 | 101-73 | Rᵃ | R¹ᵃ | R⁵ᶜ | Gᶜ | Zᵃ |
| 98-74 | 99-74 | 100-74 | 101-74 | Rᵇ | R¹ᵃ | R⁵ᶜ | Gᶜ | Zᵃ |
| 98-75 | 99-75 | 100-75 | 101-75 | Rᶜ | R¹ᵃ | R⁵ᶜ | Gᶜ | Zᵃ |
| 98-76 | 99-76 | 100-76 | 101-76 | Rᵃ | R¹ᵇ | R⁵ᶜ | Gᶜ | Zᵃ |
| 98-77 | 99-77 | 100-77 | 101-77 | Rᵇ | R¹ᵇ | R⁵ᶜ | Gᶜ | Zᵃ |
| 98-78 | 99-78 | 100-78 | 101-78 | Rᶜ | R¹ᵇ | R⁵ᶜ | Gᶜ | Zᵃ |
| 98-79 | 99-79 | 100-79 | 101-79 | Rᵃ | R¹ᶜ | R⁵ᶜ | Gᶜ | Zᵃ |
| 98-80 | 99-80 | 100-80 | 101-80 | Rᵇ | R¹ᶜ | R⁵ᶜ | Gᶜ | Zᵃ |
| 98-81 | 99-81 | 100-81 | 101-81 | Rᶜ | R¹ᶜ | R⁵ᶜ | Gᶜ | Zᵃ |
| 98-82 | 99-82 | 100-82 | 101-82 | Rᵃ | R¹ᵃ | R⁵ᵃ | Gᵃ | Zᵇ |
| 98-83 | 99-83 | 100-83 | 101-83 | Rᵇ | R¹ᵃ | R⁵ᵃ | Gᵃ | Zᵇ |
| 98-84 | 99-84 | 100-84 | 101-84 | Rᶜ | R¹ᵃ | R⁵ᵃ | Gᵃ | Zᵇ |
| 98-85 | 99-85 | 100-85 | 101-85 | Rᵃ | R¹ᵇ | R⁵ᵃ | Gᵃ | Zᵇ |
| 98-86 | 99-86 | 100-86 | 101-86 | Rᵇ | R¹ᵇ | R⁵ᵃ | Gᵃ | Zᵇ |
| 98-87 | 99-87 | 100-87 | 101-87 | Rᶜ | R¹ᵇ | R⁵ᵃ | Gᵃ | Zᵇ |
| 98-88 | 99-88 | 100-88 | 101-88 | Rᵃ | R¹ᶜ | R⁵ᵃ | Gᵃ | Zᵇ |
| 98-89 | 99-89 | 100-89 | 101-89 | Rᵇ | R¹ᶜ | R⁵ᵃ | Gᵃ | Zᵇ |
| 98-90 | 99-90 | 100-90 | 101-90 | Rᶜ | R¹ᶜ | R⁵ᵃ | Gᵃ | Zᵇ |
| 98-91 | 99-91 | 100-91 | 101-91 | Rᵃ | R¹ᵃ | R⁵ᵇ | Gᵃ | Zᵇ |
| 98-92 | 99-92 | 100-92 | 101-92 | Rᵇ | R¹ᵃ | R⁵ᵇ | Gᵃ | Zᵇ |
| 98-93 | 99-93 | 100-93 | 101-93 | Rᶜ | R¹ᵃ | R⁵ᵇ | Gᵃ | Zᵇ |
| 98-94 | 99-94 | 100-94 | 101-94 | Rᵃ | R¹ᵇ | R⁵ᵇ | Gᵃ | Zᵇ |
| 98-95 | 99-95 | 100-95 | 101-95 | Rᵇ | R¹ᵇ | R⁵ᵇ | Gᵃ | Zᵇ |
| 98-96 | 99-96 | 100-96 | 101-96 | Rᶜ | R¹ᵇ | R⁵ᵇ | Gᵃ | Zᵇ |
| 98-97 | 99-97 | 100-97 | 101-97 | Rᵃ | R¹ᶜ | R⁵ᵇ | Gᵃ | Zᵇ |
| 98-98 | 99-98 | 100-98 | 101-98 | Rᵇ | R¹ᶜ | R⁵ᵇ | Gᵃ | Zᵇ |
| 98-99 | 99-99 | 100-99 | 101-99 | Rᶜ | R¹ᶜ | R⁵ᵇ | Gᵃ | Zᵇ |
| 98-100 | 99-100 | 100-100 | 101-100 | Rᵃ | R¹ᵃ | R⁵ᶜ | Gᵃ | Zᵇ |
| 98-101 | 99-101 | 100-101 | 101-101 | Rᵇ | R¹ᵃ | R⁵ᶜ | Gᵃ | Zᵇ |
| 98-102 | 99-102 | 100-102 | 101-102 | Rᶜ | R¹ᵃ | R⁵ᶜ | Gᵃ | Zᵇ |
| 98-103 | 99-103 | 100-103 | 101-103 | Rᵃ | R¹ᵇ | R⁵ᶜ | Gᵃ | Zᵇ |
| 98-104 | 99-104 | 100-104 | 101-104 | Rᵇ | R¹ᵇ | R⁵ᶜ | Gᵃ | Zᵇ |
| 98-105 | 99-105 | 100-105 | 101-105 | Rᶜ | R¹ᵇ | R⁵ᶜ | Gᵃ | Zᵇ |
| 98-106 | 99-106 | 100-106 | 101-106 | Rᵃ | R¹ᶜ | R⁵ᶜ | Gᵃ | Zᵇ |
| 98-107 | 99-107 | 100-107 | 101-107 | Rᵇ | R¹ᶜ | R⁵ᶜ | Gᵃ | Zᵇ |
| 98-108 | 99-108 | 100-108 | 101-108 | Rᶜ | R¹ᶜ | R⁵ᶜ | Gᵃ | Zᵇ |
| 98-109 | 99-109 | 100-109 | 101-109 | Rᵃ | R¹ᵃ | R⁵ᵃ | Gᵇ | Zᵇ |
| 98-110 | 99-110 | 100-110 | 101-110 | Rᵇ | R¹ᵃ | R⁵ᵃ | Gᵇ | Zᵇ |
| 98-111 | 99-111 | 100-111 | 101-111 | Rᶜ | R¹ᵃ | R⁵ᵃ | Gᵇ | Zᵇ |
| 98-112 | 99-112 | 100-112 | 101-112 | Rᵃ | R¹ᵇ | R⁵ᵃ | Gᵇ | Zᵇ |
| 98-113 | 99-113 | 100-113 | 101-113 | Rᵇ | R¹ᵇ | R⁵ᵃ | Gᵇ | Zᵇ |
| 98-114 | 99-114 | 100-114 | 101-114 | Rᶜ | R¹ᵇ | R⁵ᵃ | Gᵇ | Zᵇ |
| 98-115 | 99-115 | 100-115 | 101-115 | Rᵃ | R¹ᶜ | R⁵ᵃ | Gᵇ | Zᵇ |
| 98-116 | 99-116 | 100-116 | 101-116 | Rᵇ | R¹ᶜ | R⁵ᵃ | Gᵇ | Zᵇ |
| 98-117 | 99-117 | 100-117 | 101-117 | Rᶜ | R¹ᶜ | R⁵ᵃ | Gᵇ | Zᵇ |
| 98-118 | 99-118 | 100-118 | 101-118 | Rᵃ | R¹ᵃ | R⁵ᵇ | Gᵇ | Zᵇ |
| 98-119 | 99-119 | 100-119 | 101-119 | Rᵇ | R¹ᵃ | R⁵ᵇ | Gᵇ | Zᵇ |
| 98-120 | 99-120 | 100-120 | 101-120 | Rᶜ | R¹ᵃ | R⁵ᵇ | Gᵇ | Zᵇ |
| 98-121 | 99-121 | 100-121 | 101-121 | Rᵃ | R¹ᵇ | R⁵ᵇ | Gᵇ | Zᵇ |
| 98-122 | 99-122 | 100-122 | 101-122 | Rᵇ | R¹ᵇ | R⁵ᵇ | Gᵇ | Zᵇ |
| 98-123 | 99-123 | 100-123 | 101-123 | Rᶜ | R¹ᵇ | R⁵ᵇ | Gᵇ | Zᵇ |
| 98-124 | 99-124 | 100-124 | 101-124 | Rᵃ | R¹ᶜ | R⁵ᵇ | Gᵇ | Zᵇ |
| 98-125 | 99-125 | 100-125 | 101-125 | Rᵇ | R¹ᶜ | R⁵ᵇ | Gᵇ | Zᵇ |
| 98-126 | 99-126 | 100-126 | 101-126 | Rᶜ | R¹ᶜ | R⁵ᵇ | Gᵇ | Zᵇ |
| 98-127 | 99-127 | 100-127 | 101-127 | Rᵃ | R¹ᵃ | R⁵ᶜ | Gᵇ | Zᵇ |
| 98-128 | 99-128 | 100-128 | 101-128 | Rᵇ | R¹ᵃ | R⁵ᶜ | Gᵇ | Zᵇ |
| 98-129 | 99-129 | 100-129 | 101-129 | Rᶜ | R¹ᵃ | R⁵ᶜ | Gᵇ | Zᵇ |
| 98-130 | 99-130 | 100-130 | 101-130 | Rᵃ | R¹ᵇ | R⁵ᶜ | Gᵇ | Zᵇ |
| 98-131 | 99-131 | 100-131 | 101-131 | Rᵇ | R¹ᵇ | R⁵ᶜ | Gᵇ | Zᵇ |
| 98-132 | 99-132 | 100-132 | 101-132 | Rᶜ | R¹ᵇ | R⁵ᶜ | Gᵇ | Zᵇ |
| 98-133 | 99-133 | 100-133 | 101-133 | Rᵃ | R¹ᶜ | R⁵ᶜ | Gᵇ | Zᵇ |
| 98-134 | 99-134 | 100-134 | 101-134 | Rᵇ | R¹ᶜ | R⁵ᶜ | Gᵇ | Zᵇ |
| 98-135 | 99-135 | 100-135 | 101-135 | Rᶜ | R¹ᶜ | R⁵ᶜ | Gᵇ | Zᵇ |
| 98-136 | 99-136 | 100-136 | 101-136 | Rᵃ | R¹ᵃ | R⁵ᵃ | Gᶜ | Zᵇ |
| 98-137 | 99-137 | 100-137 | 101-137 | Rᵇ | R¹ᵃ | R⁵ᵃ | Gᶜ | Zᵇ |
| 98-138 | 99-138 | 100-138 | 101-138 | Rᶜ | R¹ᵃ | R⁵ᵃ | Gᶜ | Zᵇ |
| 98-139 | 99-139 | 100-139 | 101-139 | Rᵃ | R¹ᵇ | R⁵ᵃ | Gᶜ | Zᵇ |
| 98-140 | 99-140 | 100-140 | 101-140 | Rᵇ | R¹ᵇ | R⁵ᵃ | Gᶜ | Zᵇ |
| 98-141 | 99-141 | 100-141 | 101-141 | Rᶜ | R¹ᵇ | R⁵ᵃ | Gᶜ | Zᵇ |
| 98-142 | 99-142 | 100-142 | 101-142 | Rᵃ | R¹ᶜ | R⁵ᵃ | Gᶜ | Zᵇ |
| 98-143 | 99-143 | 100-143 | 101-143 | Rᵇ | R¹ᶜ | R⁵ᵃ | Gᶜ | Zᵇ |
| 98-144 | 99-144 | 100-144 | 101-144 | Rᶜ | R¹ᶜ | R⁵ᵃ | Gᶜ | Zᵇ |
| 98-145 | 99-145 | 100-145 | 101-145 | Rᵃ | R¹ᵃ | R⁵ᵇ | Gᶜ | Zᵇ |
| 98-146 | 99-146 | 100-146 | 101-146 | Rᵇ | R¹ᵃ | R⁵ᵇ | Gᶜ | Zᵇ |
| 98-147 | 99-147 | 100-147 | 101-147 | Rᶜ | R¹ᵃ | R⁵ᵇ | Gᶜ | Zᵇ |
| 98-148 | 99-148 | 100-148 | 101-148 | Rᵃ | R¹ᵇ | R⁵ᵇ | Gᶜ | Zᵇ |
| 98-149 | 99-149 | 100-149 | 101-149 | Rᵇ | R¹ᵇ | R⁵ᵇ | Gᶜ | Zᵇ |
| 98-150 | 99-150 | 100-150 | 101-150 | Rᶜ | R¹ᵇ | R⁵ᵇ | Gᶜ | Zᵇ |
| 98-151 | 99-151 | 100-151 | 101-151 | Rᵃ | R¹ᶜ | R⁵ᵇ | Gᶜ | Zᵇ |
| 98-152 | 99-152 | 100-152 | 101-152 | Rᵇ | R¹ᶜ | R⁵ᵇ | Gᶜ | Zᵇ |
| 98-153 | 99-153 | 100-153 | 101-153 | Rᶜ | R¹ᶜ | R⁵ᵇ | Gᶜ | Zᵇ |
| 98-154 | 99-154 | 100-154 | 101-154 | Rᵃ | R¹ᵃ | R⁵ᶜ | Gᶜ | Zᵇ |
| 98-155 | 99-155 | 100-155 | 101-155 | Rᵇ | R¹ᵃ | R⁵ᶜ | Gᶜ | Zᵇ |
| 98-156 | 99-156 | 100-156 | 101-156 | Rᶜ | R¹ᵃ | R⁵ᶜ | Gᶜ | Zᵇ |
| 98-157 | 99-157 | 100-157 | 101-157 | Rᵃ | R¹ᵇ | R⁵ᶜ | Gᶜ | Zᵇ |
| 98-158 | 99-158 | 100-158 | 101-158 | Rᵇ | R¹ᵇ | R⁵ᶜ | Gᶜ | Zᵇ |
| 98-159 | 99-159 | 100-159 | 101-159 | Rᶜ | R¹ᵇ | R⁵ᶜ | Gᶜ | Zᵇ |
| 98-160 | 99-160 | 100-160 | 101-160 | Rᵃ | R¹ᶜ | R⁵ᶜ | Gᶜ | Zᵇ |
| 98-161 | 99-161 | 100-161 | 101-161 | Rᵇ | R¹ᶜ | R⁵ᶜ | Gᶜ | Zᵇ |
| 98-162 | 99-162 | 100-162 | 101-162 | Rᶜ | R¹ᶜ | R⁵ᶜ | Gᶜ | Zᵇ |
| 98-163 | 99-163 | 100-163 | 101-163 | Rᵃ | R¹ᵃ | R⁵ᵃ | Gᵃ | Zᶜ |
| 98-164 | 99-164 | 100-164 | 101-164 | Rᵇ | R¹ᵃ | R⁵ᵃ | Gᵃ | Zᶜ |
| 98-165 | 99-165 | 100-165 | 101-165 | Rᶜ | R¹ᵃ | R⁵ᵃ | Gᵃ | Zᶜ |
| 98-166 | 99-166 | 100-166 | 101-166 | Rᵃ | R¹ᵇ | R⁵ᵃ | Gᵃ | Zᶜ |
| 98-167 | 99-167 | 100-167 | 101-167 | Rᵇ | R¹ᵇ | R⁵ᵃ | Gᵃ | Zᶜ |
| 98-168 | 99-168 | 100-168 | 101-168 | Rᶜ | R¹ᵇ | R⁵ᵃ | Gᵃ | Zᶜ |
| 98-169 | 99-169 | 100-169 | 101-169 | Rᵃ | R¹ᶜ | R⁵ᵃ | Gᵃ | Zᶜ |
| 98-170 | 99-170 | 100-170 | 101-170 | Rᵇ | R¹ᶜ | R⁵ᵃ | Gᵃ | Zᶜ |
| 98-171 | 99-171 | 100-171 | 101-171 | Rᶜ | R¹ᶜ | R⁵ᵃ | Gᵃ | Zᶜ |
| 98-172 | 99-172 | 100-172 | 101-172 | Rᵃ | R¹ᵃ | R⁵ᵇ | Gᵃ | Zᶜ |
| 98-173 | 99-173 | 100-173 | 101-173 | Rᵇ | R¹ᵃ | R⁵ᵇ | Gᵃ | Zᶜ |
| 98-174 | 99-174 | 100-174 | 101-174 | Rᶜ | R¹ᵃ | R⁵ᵇ | Gᵃ | Zᶜ |
| 98-175 | 99-175 | 100-175 | 101-175 | Rᵃ | R¹ᵇ | R⁵ᵇ | Gᵃ | Zᶜ |
| 98-176 | 99-176 | 100-176 | 101-176 | Rᵇ | R¹ᵇ | R⁵ᵇ | Gᵃ | Zᶜ |
| 98-177 | 99-177 | 100-177 | 101-177 | Rᶜ | R¹ᵇ | R⁵ᵇ | Gᵃ | Zᶜ |
| 98-178 | 99-178 | 100-178 | 101-178 | Rᵃ | R¹ᶜ | R⁵ᵇ | Gᵃ | Zᶜ |
| 98-179 | 99-179 | 100-179 | 101-179 | Rᵇ | R¹ᶜ | R⁵ᵇ | Gᵃ | Zᶜ |
| 98-180 | 99-180 | 100-180 | 101-180 | Rᶜ | R¹ᶜ | R⁵ᵇ | Gᵃ | Zᶜ |
| 98-181 | 99-181 | 100-181 | 101-181 | Rᵃ | R¹ᵃ | R⁵ᶜ | Gᵃ | Zᶜ |
| 98-182 | 99-182 | 100-182 | 101-182 | Rᵇ | R¹ᵃ | R⁵ᶜ | Gᵃ | Zᶜ |
| 98-183 | 99-183 | 100-183 | 101-183 | Rᶜ | R¹ᵃ | R⁵ᶜ | Gᵃ | Zᶜ |
| 98-184 | 99-184 | 100-184 | 101-184 | Rᵃ | R¹ᵇ | R⁵ᶜ | Gᵃ | Zᶜ |
| 98-185 | 99-185 | 100-185 | 101-185 | Rᵇ | R¹ᵇ | R⁵ᶜ | Gᵃ | Zᶜ |
| 98-186 | 99-186 | 100-186 | 101-186 | Rᶜ | R¹ᵇ | R⁵ᶜ | Gᵃ | Zᶜ |
| 98-187 | 99-187 | 100-187 | 101-187 | Rᵃ | R¹ᶜ | R⁵ᶜ | Gᵃ | Zᶜ |
| 98-188 | 99-188 | 100-188 | 101-188 | Rᵇ | R¹ᶜ | R⁵ᶜ | Gᵃ | Zᶜ |
| 98-189 | 99-189 | 100-189 | 101-189 | Rᶜ | R¹ᶜ | R⁵ᶜ | Gᵃ | Zᶜ |
| 98-190 | 99-190 | 100-190 | 101-190 | Rᵃ | R¹ᵃ | R⁵ᵃ | Gᵇ | Zᶜ |
| 98-191 | 99-191 | 100-191 | 101-191 | Rᵇ | R¹ᵃ | R⁵ᵃ | Gᵇ | Zᶜ |
| 98-192 | 99-192 | 100-192 | 101-192 | Rᶜ | R¹ᵃ | R⁵ᵃ | Gᵇ | Zᶜ |
| 98-193 | 99-193 | 100-193 | 101-193 | Rᵃ | R¹ᵇ | R⁵ᵃ | Gᵇ | Zᶜ |
| 98-194 | 99-194 | 100-194 | 101-194 | Rᵇ | R¹ᵇ | R⁵ᵃ | Gᵇ | Zᶜ |
| 98-195 | 99-195 | 100-195 | 101-195 | Rᵇ | R¹ᵇ | R⁵ᵃ | Gᵇ | Zᶜ |
| 98-196 | 99-196 | 100-196 | 101-196 | Rᵃ | R¹ᶜ | R⁵ᵃ | Gᵇ | Zᶜ |
| 98-197 | 99-197 | 100-197 | 101-197 | Rᵇ | R¹ᶜ | R⁵ᵃ | Gᵇ | Zᶜ |
| 98-198 | 99-198 | 100-198 | 101-198 | Rᶜ | R¹ᶜ | R⁵ᵃ | Gᵇ | Zᶜ |
| 98-199 | 99-199 | 100-199 | 101-199 | Rᵃ | R¹ᵃ | R⁵ᵇ | Gᵇ | Zᶜ |

-continued

| Formulae | | | | R | R$^1$ | R$^5$ | G | Z |
|---|---|---|---|---|---|---|---|---|
| 98-200 | 99-200 | 100-200 | 101-200 | R$^b$ | R$^{1a}$ | R$^{5b}$ | G$^b$ | Z$^c$ |
| 98-201 | 99-201 | 100-201 | 101-201 | R$^c$ | R$^{1a}$ | R$^{5b}$ | G$^b$ | Z$^c$ |
| 98-202 | 99-202 | 100-202 | 101-202 | R$^a$ | R$^{1b}$ | R$^{5b}$ | G$^b$ | Z$^c$ |
| 98-203 | 99-203 | 100-203 | 101-203 | R$^b$ | R$^{1b}$ | R$^{5b}$ | G$^b$ | Z$^c$ |
| 98-204 | 99-204 | 100-204 | 101-204 | R$^c$ | R$^{1b}$ | R$^{5b}$ | G$^b$ | Z$^c$ |
| 98-205 | 99-205 | 100-205 | 101-205 | R$^a$ | R$^{1c}$ | R$^{5b}$ | G$^b$ | Z$^c$ |
| 98-206 | 99-206 | 100-206 | 101-206 | R$^b$ | R$^{1c}$ | R$^{5b}$ | G$^b$ | Z$^c$ |
| 98-207 | 99-207 | 100-207 | 101-207 | R$^c$ | R$^{1c}$ | R$^{5b}$ | G$^b$ | Z$^c$ |
| 98-208 | 99-208 | 100-208 | 101-208 | R$^a$ | R$^{1a}$ | R$^{5c}$ | G$^b$ | Z$^c$ |
| 98-209 | 99-209 | 100-209 | 101-209 | R$^b$ | R$^{1a}$ | R$^{5c}$ | G$^b$ | Z$^c$ |
| 98-210 | 99-210 | 100-210 | 101-210 | R$^c$ | R$^{1a}$ | R$^{5c}$ | G$^b$ | Z$^c$ |
| 98-211 | 99-211 | 100-211 | 101-211 | R$^a$ | R$^{1b}$ | R$^{5c}$ | G$^b$ | Z$^c$ |
| 98-212 | 99-212 | 100-212 | 101-212 | R$^b$ | R$^{1b}$ | R$^{5c}$ | G$^b$ | Z$^c$ |
| 98-213 | 99-213 | 100-213 | 101-213 | R$^c$ | R$^{1b}$ | R$^{5c}$ | G$^b$ | Z$^c$ |
| 98-214 | 99-214 | 100-214 | 101-214 | R$^a$ | R$^{1c}$ | R$^{5c}$ | G$^b$ | Z$^c$ |
| 98-215 | 99-215 | 100-215 | 101-215 | R$^b$ | R$^{1c}$ | R$^{5c}$ | G$^b$ | Z$^c$ |
| 98-216 | 99-216 | 100-216 | 101-216 | R$^c$ | R$^{1c}$ | R$^{5c}$ | G$^b$ | Z$^c$ |
| 98-217 | 99-217 | 100-217 | 101-217 | R$^a$ | R$^{1a}$ | R$^{5a}$ | G$^c$ | Z$^c$ |
| 98-218 | 99-218 | 100-218 | 101-218 | R$^b$ | R$^{1a}$ | R$^{5a}$ | G$^c$ | Z$^c$ |
| 98-219 | 99-219 | 100-219 | 101-219 | R$^c$ | R$^{1a}$ | R$^{5a}$ | G$^c$ | Z$^c$ |
| 98-220 | 99-220 | 100-220 | 101-220 | R$^a$ | R$^{1b}$ | R$^{5a}$ | G$^c$ | Z$^c$ |
| 98-221 | 99-221 | 100-221 | 101-221 | R$^b$ | R$^{1b}$ | R$^{5a}$ | G$^c$ | Z$^c$ |
| 98-222 | 99-222 | 100-222 | 101-222 | R$^c$ | R$^{1b}$ | R$^{5a}$ | G$^c$ | Z$^c$ |
| 98-223 | 99-223 | 100-223 | 101-223 | R$^a$ | R$^{1c}$ | R$^{5a}$ | G$^c$ | Z$^c$ |
| 98-224 | 99-224 | 100-224 | 101-224 | R$^b$ | R$^{1c}$ | R$^{5a}$ | G$^c$ | Z$^c$ |
| 98-225 | 99-225 | 100-225 | 101-225 | R$^c$ | R$^{1c}$ | R$^{5a}$ | G$^c$ | Z$^c$ |
| 98-226 | 99-226 | 100-226 | 101-226 | R$^a$ | R$^{1a}$ | R$^{5b}$ | G$^c$ | Z$^c$ |
| 98-227 | 99-227 | 100-227 | 101-227 | R$^b$ | R$^{1a}$ | R$^{5b}$ | G$^c$ | Z$^c$ |
| 98-228 | 99-228 | 100-228 | 101-228 | R$^c$ | R$^{1a}$ | R$^{5b}$ | G$^c$ | Z$^c$ |
| 98-229 | 99-229 | 100-229 | 101-229 | R$^a$ | R$^{1b}$ | R$^{5b}$ | G$^c$ | Z$^c$ |
| 98-230 | 99-230 | 100-230 | 101-230 | R$^b$ | R$^{1b}$ | R$^{5b}$ | G$^c$ | Z$^c$ |
| 98-231 | 99-231 | 100-231 | 101-231 | R$^c$ | R$^{1b}$ | R$^{5b}$ | G$^c$ | Z$^c$ |
| 98-232 | 99-232 | 100-232 | 101-232 | R$^a$ | R$^{1c}$ | R$^{5b}$ | G$^c$ | Z$^c$ |
| 98-233 | 99-233 | 100-233 | 101-233 | R$^b$ | R$^{1c}$ | R$^{5b}$ | G$^c$ | Z$^c$ |
| 98-234 | 99-234 | 100-234 | 101-234 | R$^c$ | R$^{1c}$ | R$^{5b}$ | G$^c$ | Z$^c$ |
| 98-235 | 99-235 | 100-235 | 101-235 | R$^a$ | R$^{1a}$ | R$^{5c}$ | G$^c$ | Z$^c$ |
| 98-236 | 99-236 | 100-236 | 101-236 | R$^b$ | R$^{1a}$ | R$^{5c}$ | G$^c$ | Z$^c$ |
| 98-237 | 99-237 | 100-237 | 101-237 | R$^c$ | R$^{1a}$ | R$^{5c}$ | G$^c$ | Z$^c$ |
| 98-238 | 99-238 | 100-238 | 101-238 | R$^a$ | R$^{1b}$ | R$^{5c}$ | G$^c$ | Z$^c$ |
| 98-239 | 99-239 | 100-239 | 101-239 | R$^b$ | R$^{1b}$ | R$^{5c}$ | G$^c$ | Z$^c$ |
| 98-240 | 99-240 | 100-240 | 101-240 | R$^c$ | R$^{1b}$ | R$^{5c}$ | G$^c$ | Z$^c$ |
| 98-241 | 99-241 | 100-241 | 101-241 | R$^a$ | R$^{1c}$ | R$^{5c}$ | G$^c$ | Z$^c$ |
| 98-242 | 99-242 | 100-242 | 101-242 | R$^b$ | R$^{1c}$ | R$^{5c}$ | G$^c$ | Z$^c$ |
| 98-243 | 99-243 | 100-243 | 101-243 | R$^c$ | R$^{1c}$ | R$^{5c}$ | G$^c$ | Z$^c$ | where all symbols are as defined above.

In one aspect of any of formulae (98), (99), (100), and (101) of the present invention, R is hydrogen, a hydroxy group, a halogen, a nitro group, an optionally substituted amino group, an alkyl group, an alkoxy group, an alkenyl group, or an alkoxyalkyl group; R$^1$ is hydrogen, a hydroxy group, a halogen, a nitro group, a carboxy group, a carbamoyl group, or an optionally substituted amino group, an alkyl group, a cycloalkyl group, an alkoxy group, a cycloalkoxy group, an alkenyl group, a cycloalkenyl group, an alkoxyalkyl group, an alkenyloxy group, or a cycloalkenyloxy group; R$^5$ is is hydrogen, a hydroxy group, a halogen, a nitro group, a carboxy group, a carbamoyl group, or an optionally substituted amino group, an alkyl group, a alkoxy group, a cycloalkoxy group, an alkenyl group, a cycloalkenyl group, an alkoxyalkyl group, an alkenyloxy group, or a cycloalkenyloxy group; and all other symbols are as defined above in connection with formula (I).

In another aspect of any of formulae (98), (99), (100), and (101) of the present invention, G is —(CH$_2$)$_s$—, where s is an integer from 0-5; and all other symbols are as defined above in connection with formula (I).

In another aspect of any of formulae (98), (99), (100), and (101) of the present invention, G is —(CH$_2$)$_s$—CH=CH— (CH$_2$)$_s$—, where s is an integer from 0-5; and all other symbols are as defined above in connection with formula (I).

In another aspect of any of formulae (98), (99), (100), and (101) of the present invention, G is —(CH$_2$)$_s$—C≡C— (CH$_2$)$_s$—, where s is an integer from 0-5; and all other symbols are as defined above in connection with formula (I).

In another aspect of any of formulae (98), (99), (100), and (101) of the present invention, Z is O, and all other symbols are as defined above in connection with formula (I).

In another aspect of any of formulae (98), (99), (100), and (101) of the present invention, Z is NR, and all other symbols are as defined above in connection with formula (I).

In another aspect of any of formulae (98), (99), (100), and (I) of the present invention, Z is (—CH$_2$—)$_u$ or S(=O)$_u$, where u is an integer from 0-2; and all other symbols are as defined above in connection with formula (1).

In still another aspect of any of formulae (98), (99), (100), and (101) of the present invention, E is O, and all other symbols are as defined above in connection with formula (I).

In still another aspect of any of formulae (98), (99), (100), and (101) of the present invention, E is S, and all other symbols are as defined above in connection with formula (I).

In still another aspect of any of formulae (98), (99), (100), and (101) of the present invention, E is NR, and all other symbols are as defined above in connection with formula (I).

Examples of compounds having general formula (IV) include, but are not limited to:

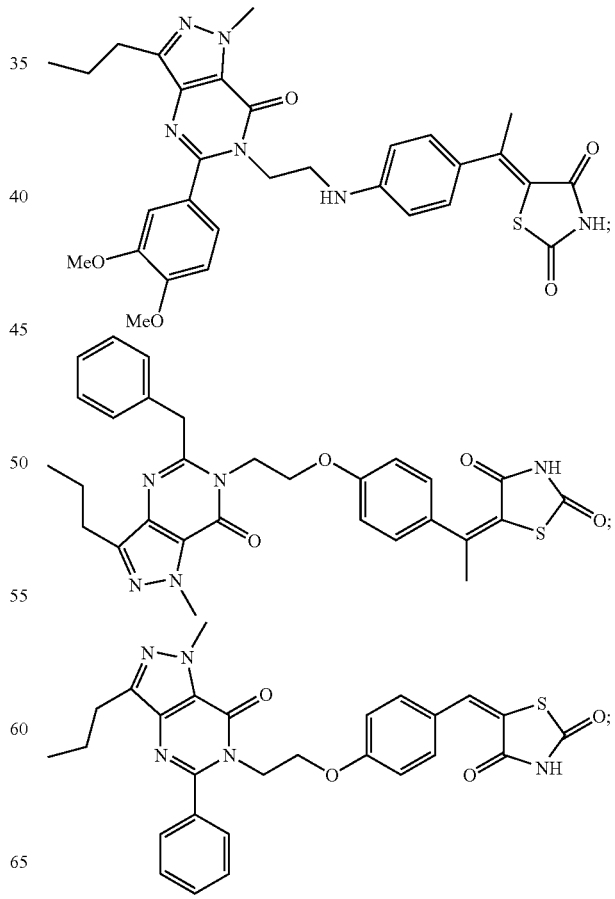

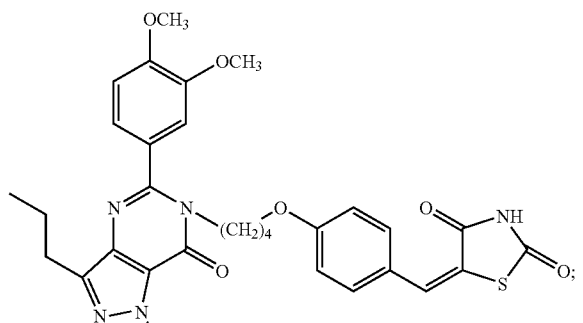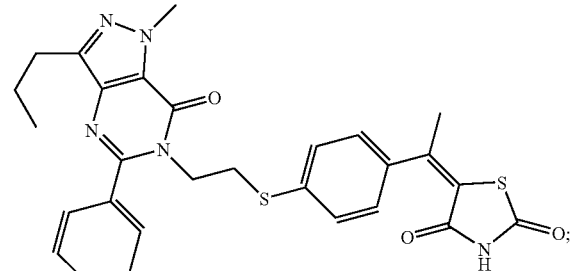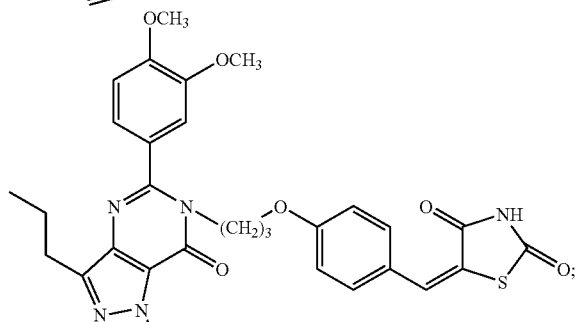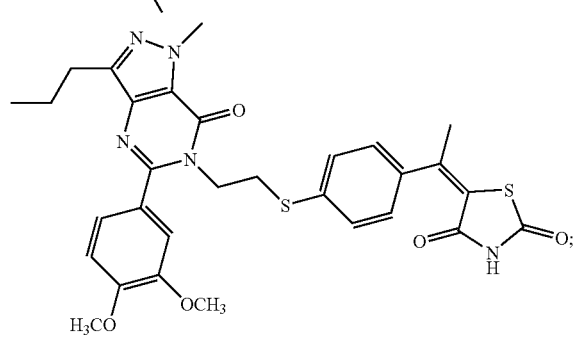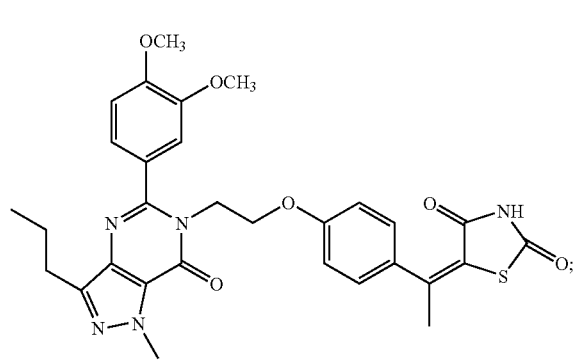

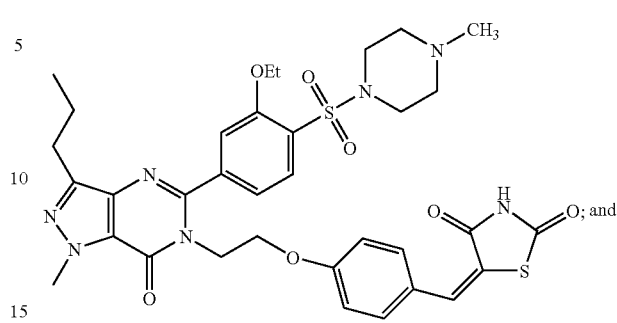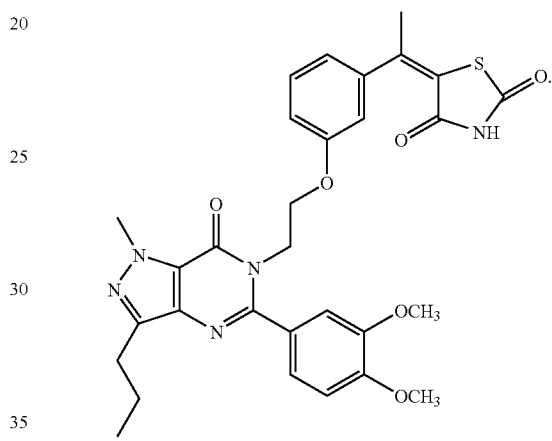

According to another aspect of the present invention, various compounds of general formula (I) having general formula (V)

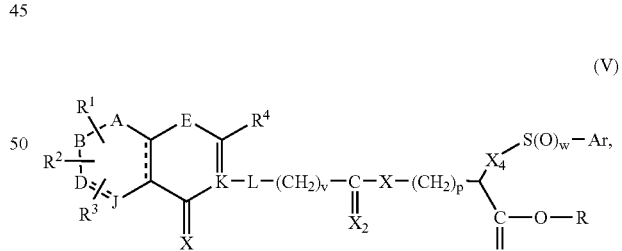

its tautomeric forms, its stereoisomers, its polymorphs, its pharmaceutically acceptable salts, and its pharmaceutically acceptable solvates are provided. Except as otherwise provided herein, all symbols are as defined above in connection with formula (I).

Examples of compounds having the general formula (V) contemplated by the present invention include, but are not limited to:

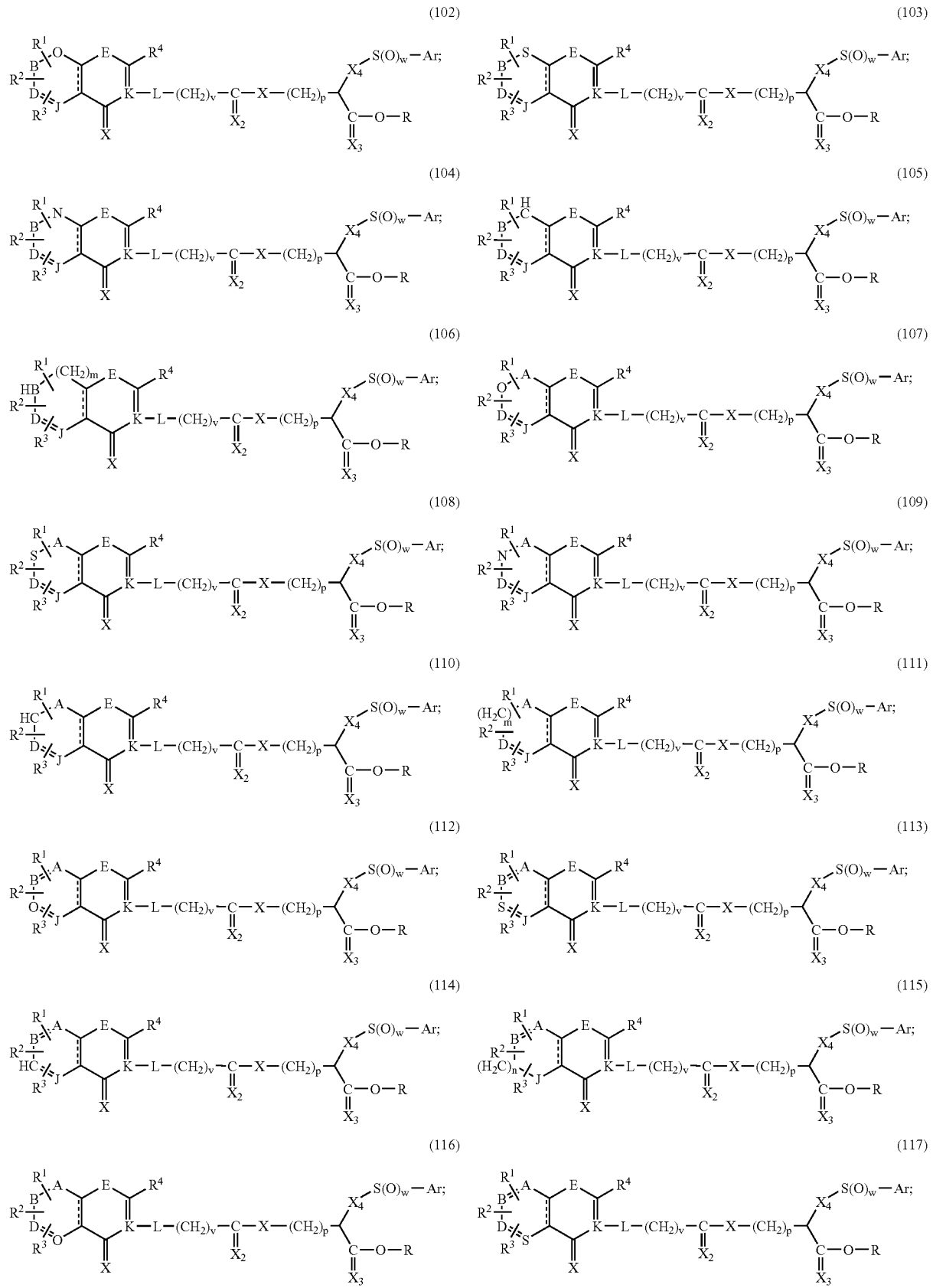

-continued
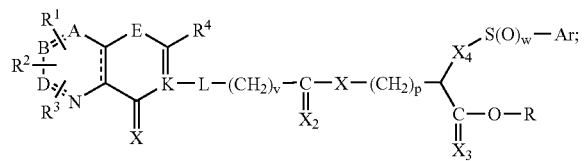 (118)
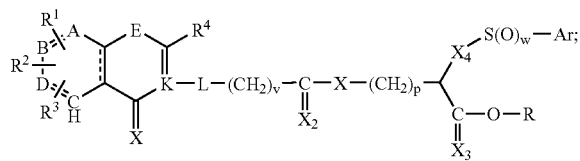 (119)
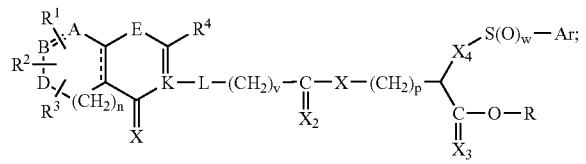 (120)
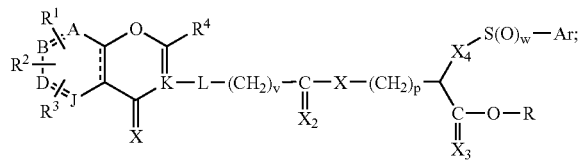 (121)
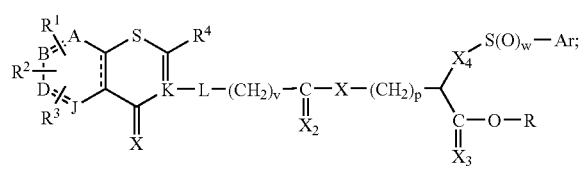 (122)
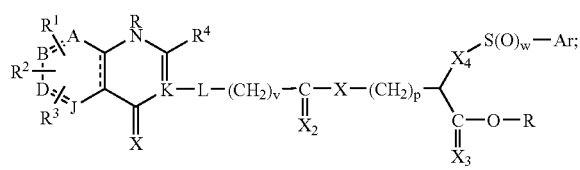 (123)
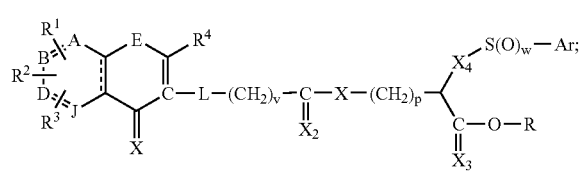 (125)
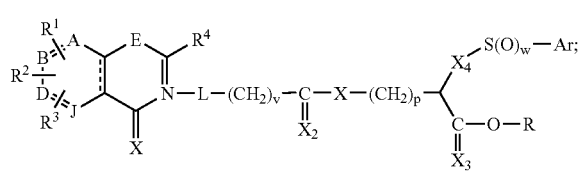 (124)
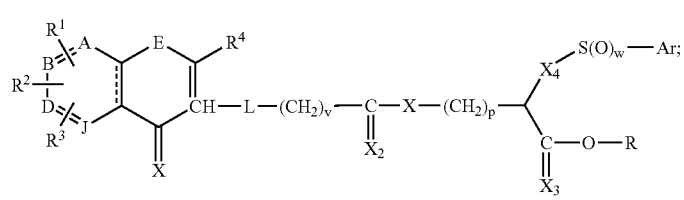 (126)
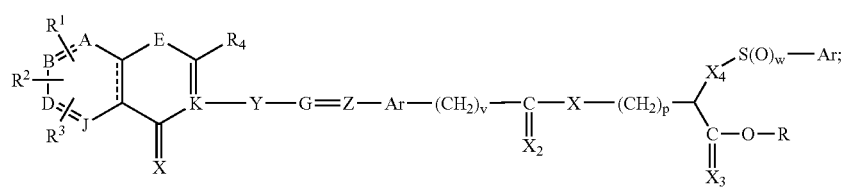 (127)
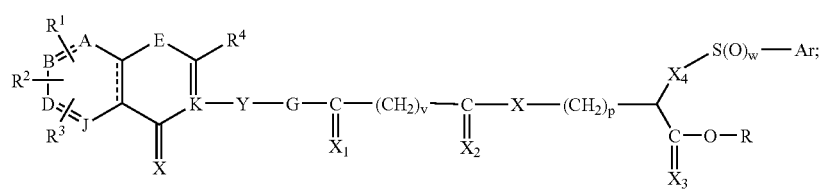 (128)
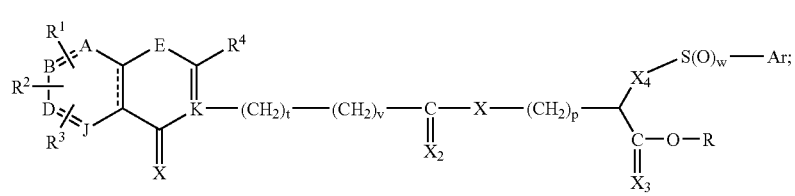 (129)

-continued
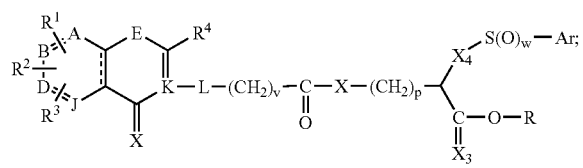 (130)
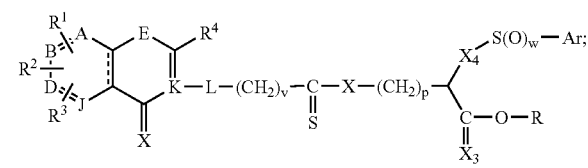 (131)
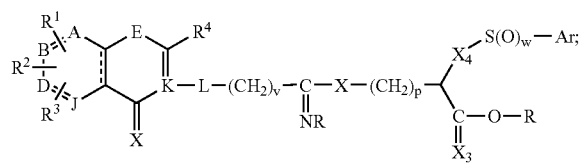 (132)
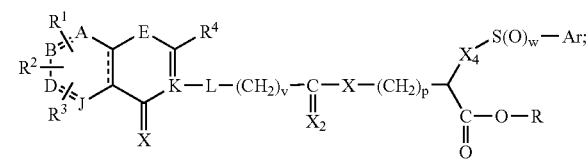 (133)
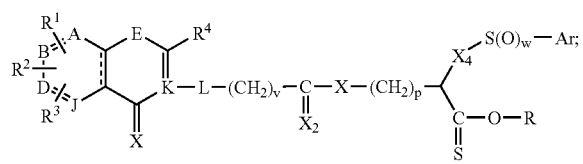 (134)
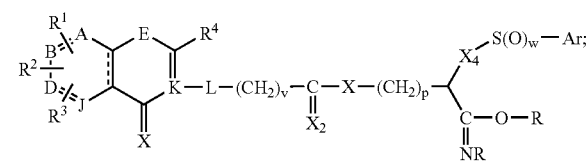 (135)
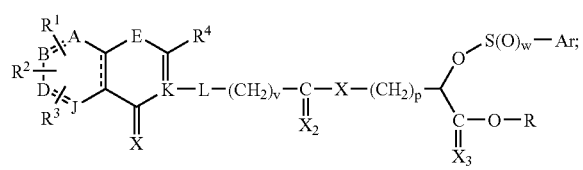 (136)
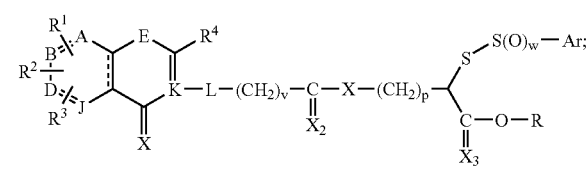 (137)
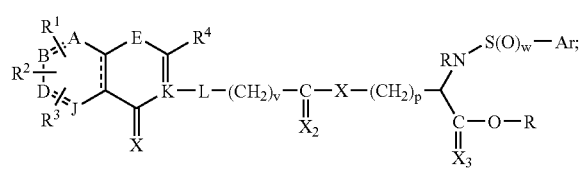 (138)
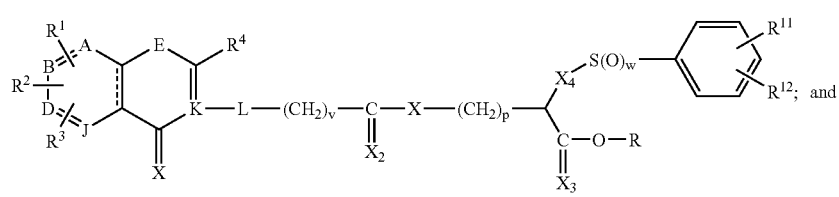 (139)
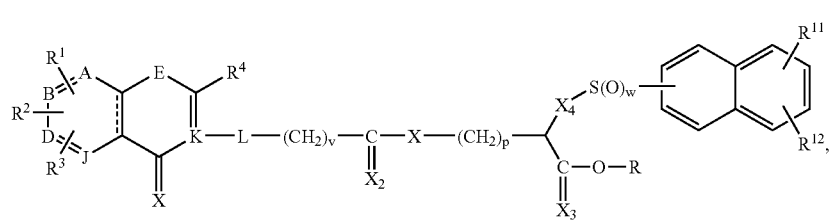 (140)
where all symbols are as defined above in connection with formula (I).
The present invention contemplates various compounds of general formula (V) having the formula:

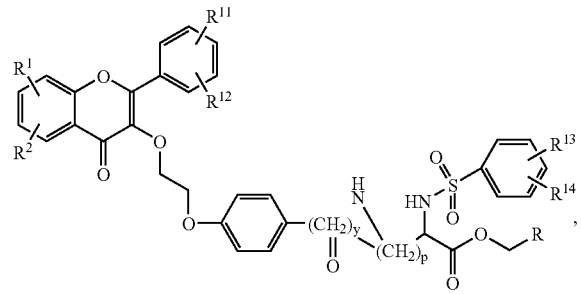

(141)

where $R^{11}$, $R^{12}$, $R^{13}$, and $R^{14}$ independently are hydrogen, a halogen, a nitro group, an amino group, a mono- or di-substituted amino group, a hydroxy group, an alkoxy group, a carboxy group, a cyano group, an oxo(O=) group, a thio (S=) group, an alkyl group, a cycloalkyl group, an alkoxy group, a haloalkoxy group, a cycloalkyl group, an aryl group, a benzyloxy group, an acyl group, an acyloxy group, an aroyl group, an alkoxycarbonyl group, an aryloxycarbonyl group, a heteroaryl group, a heterocyclyl group, an aralkyl group, an alkylsulfonyl group, an alkylsulfinyl group, an arylsulfonyl group, an arylsulfinyl group, an alkylthio group, an arylthio group, a heteroarylthio group, an aralkylthio group, or a heterocyclyl sulfonyl group, which is optionally substituted with a halogen, a hydroxyl group, a nitro group, an amino group, an alkyloxy group, or any combination thereof, and wherein the heterocycle group is optionally a substituted morpholinyl group, a thiomorpholinyl group, or a piperzinyl group, wherein the substituent on the heterocyclyl group is a halogen, a nitro group, an amino group, an alkyl group, an alkoxy group, or an aryl group; and all other symbols are defined as above in connection with formula (I).

In one aspect of formula (141) of the present invention, R is hydrogen, a hydroxy group, a halogen, a nitro group, or an optionally substituted amino group; and all other symbols are as defined in connection with formula (I).

In another aspect of formula (141) of the present invention, R is an alkyl group, an alkoxy group, an alkenyl group, or an alkoxyalkyl group; and all other symbols are as defined in connection with formula (I).

In another aspect of formula (141) of the present invention, $R^1$ is hydrogen, a hydroxy group, a halogen, a nitro group, a carboxy group, a carbamoyl group, or an optionally substituted amino group, an alkyl group, a cycloalkyl group, an alkoxy group, a cycloalkoxy group, an alkenyl group, a cycloalkenyl group, an alkoxyalkyl group, an alkenyloxy group, or a cycloalkenyloxy group; and all other symbols are as defined in connection with formula (I).

In another aspect of formula (141) of the present invention, $R^2$ is hydrogen, a hydroxy group, a halogen, a nitro group, a carboxy group, a carbamoyl group, or an optionally substituted amino group, an alkyl group, a cycloalkyl group, an alkoxy group, a cycloalkoxy group, an alkenyl group, a cycloalkenyl group, an alkoxyalkyl group, an alkenyloxy group, or a cycloalkenyloxy group; and all other symbols are as defined in connection with formula (I).

In yet another aspect of formula (141) of the present invention, $R^{11}$ is hydrogen, a halogen, a nitro group, an amino group, a mono- or di-substituted amino group, a hydroxy group, an alkoxy group, a carboxy group, a cyano group, an oxo(O=) group, or a thio(S=) group; and all other symbols are as defined in connection with formula (I).

In still another aspect of formula (141) of the present invention, $R^{11}$ is an alkylsulfonyl group, an alkylsulfinyl group, an arylsulfonyl group, an arylsulfinyl group, an alkylthio group, an arylthio group, a heteroarylthio group, an aralkylthio group, or a heterocyclyl sulfonyl group, which is optionally substituted with a halogen, a hydroxyl group, a nitro group, an amino group, an alkyloxy group, or any combination thereof, and wherein the heterocycle group is optionally a substituted morpholinyl group, a thiomorpholinyl group, or a piperzinyl group, wherein the substituent on the heterocyclyl group is a halogen, a nitro group, an amino group, an alkyl group, an alkoxy group, or an aryl group; and all other symbols are as defined in connection with formula (I).

In yet another aspect of formula (141) of the present invention, $R^{12}$ is hydrogen, a halogen, a nitro group, an amino group, a mono- or di-substituted amino group, a hydroxy group, an alkoxy group, a carboxy group, a cyano group, an oxo(O=) group, or a thio(S=) group; and all other symbols are as defined in connection with formula (I).

In still another aspect of formula (141) of the present invention, $R^{12}$ is an alkylsulfonyl group, an alkylsulfinyl group, an arylsulfonyl group, an arylsulfinyl group, an alkylthio group, an arylthio group, a heteroarylthio group, an aralkylthio group, or a heterocyclyl sulfonyl group, which is optionally substituted with a halogen, a hydroxyl group, a nitro group, an amino group, an alkyloxy group, or any combination thereof, and wherein the heterocycle group is optionally a substituted morpholinyl group, a thiomorpholinyl group, or a piperzinyl group, wherein the substituent on the heterocyclyl group is a halogen, a nitro group, an amino group, an alkyl group, an alkoxy group, or an aryl group; and all other symbols are as defined in connection with formula (I).

In a further aspect of formula (141) of the present invention, $R^{13}$ is hydrogen, a halogen, a nitro group, an amino group, a mono- or di-substituted amino group, a hydroxy group, an alkoxy group, a carboxy group, a cyano group, an oxo(O=) group, or a thio(S=) group; and all other symbols are as defined in connection with formula (I).

In another aspect of formula (141) of the present invention, $R^{13}$ is an alkylsulfonyl group, an alkylsulfinyl group, an arylsulfonyl group, an arylsulfinyl group, an alkylthio group, an arylthio group, a heteroarylthio group, an aralkylthio group, or a heterocyclyl sulfonyl group, which is optionally substituted with a halogen, a hydroxyl group, a nitro group, an amino group, an alkyloxy group, or any combination thereof, and wherein the heterocycle group is optionally a substituted morpholinyl group, a thiomorpholinyl group, or a piperzinyl group, wherein the substituent on the heterocyclyl group is a halogen, a nitro group, an amino group, an alkyl group, an alkoxy group, or an aryl group; and all other symbols are as defined in connection with formula (I).

In another aspect of formula (141) of the present invention, $R^{14}$ is hydrogen, a halogen, a nitro group, an amino group, a mono- or di-substituted amino group, a hydroxy group, an alkoxy group, a carboxy group, a cyano group, an oxo(O=) group, or a thio(S=) group; and all other symbols are as defined in connection with formula (I).

In yet another aspect of formula (141) of the present invention, $R^{14}$ is an alkylsulfonyl group, an alkylsulfinyl group, an arylsulfonyl group, an arylsulfinyl group, an alkylthio group, an arylthio group, a heteroarylthio group, an aralkylthio group, or a heterocyclyl sulfonyl group, which is optionally substituted with a halogen, a hydroxyl group, a nitro group, an amino group, an alkyloxy group, or any combination thereof, and wherein the heterocycle group is optionally a substituted morpholinyl group, a thiomorpholinyl group, or a piperzinyl group, wherein the substituent on the heterocyclyl group is a halogen, a nitro group, an amino group, an alkyl group, an alkoxy group, or an aryl group; and all other symbols are as defined in connection with formula (I).

In yet another aspect of formula (141) of the present invention, R is hydrogen or an alkyl group, and all other symbols are as defined in connection with formula (I).

In another aspect of formula (141) of the present invention, R is —H, $CH_3$, or $C_2H_5$, and all other symbols are as defined in connection with formula (I).

In still another aspect of formula (141) of the present invention, $R^1$ is hydrogen or an alkyl group, and all other symbols are as defined in connection with formula (I).

In yet another aspect of formula (141) of the present invention, $R^1$ is —H, $CH_3$, or $C_2H_5$, and all other symbols are as defined in connection with formula (I).

In another aspect of formula (141) of the present invention, $R^2$ is hydrogen or an alkyl group, and all other symbols are as defined in connection with formula (I).

In another aspect of formula (141) of the present invention, $R^2$ is —H, $CH_3$, or $C_2H_5$, and all other symbols are as defined in connection with formula (I).

In yet another aspect of formula (141) of the present invention, $R^{11}$ is hydrogen, a halogen, an alkoxy group, or an alkylthio group; and all other symbols are as defined in connection with formula (I).

In another aspect of formula (141) of the present invention, $R^{12}$ is —H, —Cl, —$OCH_3$, or —$SCH_3$, and all other symbols are as defined in connection with formula (I).

In a further aspect of formula (141) of the present invention, R is hydrogen, a halogen, an alkoxy group, or an alkylthio group; and all other symbols are as defined in connection with formula (I).

In a another aspect of formula (141) of the present invention, $R^{12}$ is H, Cl, —$OCH_3$, or —$SCH_3$, and all other symbols are as defined in connection with formula (I).

In a further aspect of formula (141) of the present invention, $R^{13}$ is hydrogen, a halogen, or an alkyl group, and all other symbols are as defined in connection with formula (I).

In a still further aspect of formula (141) of the present invention, $R^{13}$ is —H, —F, or $CH_3$, and all other symbols are as defined in connection with formula (I).

In yet another aspect of formula (141) of the present invention, $R^{14}$ is hydrogen, a halogen, or an alkyl group, and all other symbols are as defined in connection with formula (I).

In a further aspect of formula (141) of the present invention, $R^{14}$ is —H, —F, or —$CH_3$, and all other symbols are as defined in connection with formula (I).

In another aspect of formula (141) of the present invention, $R^1$ and $R^2$ independently are hydrogen, a hydroxy group, a halogen, a nitro group, a carboxy group, a carbamoyl group, an optionally substituted amino group, an alkyl group, a cycloalkyl group, an alkoxy group, a cycloalkoxy group, an alkenyl group, a cycloalkenyl group, an alkoxyalkyl group, an alkenyloxy group, or a cycloalkenyloxy group; $R^{11}$, $R^{12}$, $R^{13}$, and $R^{14}$ independently are hydrogen, a halogen, a nitro group, an amino group, a mono- or di-substituted amino group, a hydroxy group, an alkoxy group, a carboxy group, a cyano group, an oxo(O=) group, or a thio(S=) group, an alkyl group, or a cycloalkyl group, an alkoxy group; and all other symbols are as defined as above in connection with formula (I).

In another aspect of formula (141) of the present invention, $R^1$ and $R^2$ independently are hydrogen, a hydroxy group, a halogen, an alkoxy group; $R^{11}$, $R^{12}$, $R^{13}$, and $R^{14}$ independently are hydrogen, a halogen, a hydroxy group, an alkoxy group; and all other symbols are as defined as above in connection with formula (I).

In yet another aspect of formula (141) of the present invention, $R^1$ and $R^2$ independently are —H or —$OCH_3$; $R^{11}$ is —Cl, —$OCH_3$, or —$SCH_3$; $R^{12}$ is —Cl, —$OCH_3$, or —H; R is —H, $CH_3$, or $C_2H_5$; $R^{13}$ is F or $CH_3$; $R^{14}$ is F or $CH_3$; v is 0 or 1; and all other symbols a defined as above in connection with formula (I).

The present invention also contemplates various compounds of general formula (V) as follows:

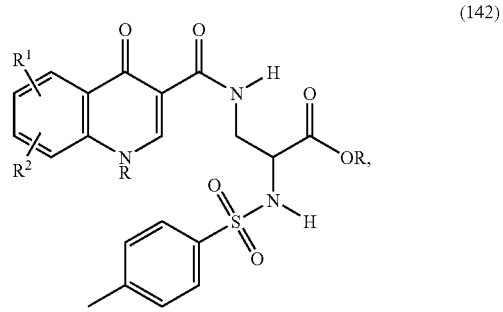

(142)

where all symbols are as defined above in connection with formula (I).

According to various aspects of the present invention, R, R1, and R2 of formula (142) are selected to produce various compounds of formula (142-1) through formula (142-27) as follows:

| Formula | R | $R^1$ | $R^2$ |
|---|---|---|---|
| 142-1 | $R^a$ | $R^{1a}$ | $R^{2a}$ |
| 142-2 | $R^b$ | $R^{1a}$ | $R^{2a}$ |
| 142-3 | $R^c$ | $R^{1a}$ | $R^{2a}$ |
| 142-4 | $R^a$ | $R^{1b}$ | $R^{2a}$ |
| 142-5 | $R^b$ | $R^{1b}$ | $R^{2a}$ |
| 142-6 | $R^c$ | $R^{1b}$ | $R^{2a}$ |
| 142-7 | $R^a$ | $R^{1c}$ | $R^{2a}$ |
| 142-8 | $R^b$ | $R^{1c}$ | $R^{2a}$ |
| 142-9 | $R^c$ | $R^{1c}$ | $R^{2a}$ |
| 142-10 | $R^a$ | $R^{1a}$ | $R^{2b}$ |
| 142-11 | $R^b$ | $R^{1a}$ | $R^{2b}$ |
| 142-12 | $R^c$ | $R^{1a}$ | $R^{2b}$ |
| 142-13 | $R^a$ | $R^{1b}$ | $R^{2b}$ |
| 142-14 | $R^b$ | $R^{1b}$ | $R^{2b}$ |
| 142-15 | $R^c$ | $R^{1b}$ | $R^{2b}$ |
| 142-16 | $R^a$ | $R^{1c}$ | $R^{2b}$ |
| 142-17 | $R^b$ | $R^{1c}$ | $R^{2b}$ |
| 142-18 | $R^c$ | $R^{1c}$ | $R^{2b}$ |
| 142-19 | $R^a$ | $R^{1a}$ | $R^{2c}$ |
| 142-20 | $R^b$ | $R^{1a}$ | $R^{2c}$ |
| 142-21 | $R^c$ | $R^{1a}$ | $R^{2c}$ |
| 142-22 | $R^a$ | $R^{1b}$ | $R^{2c}$ |
| 142-23 | $R^b$ | $R^{1b}$ | $R^{2c}$ |
| 142-24 | $R^c$ | $R^{1b}$ | $R^{2c}$ |
| 142-25 | $R^a$ | $R1^c$ | $R^{2c}$ |
| 142-26 | $R^b$ | $R^{1c}$ | $R^{2c}$ |
| 142-27 | $R^c$ | $R^{1c}$ | $R^{2c}$ | where all symbols are as defined above.

In one aspect of formula (142) of the present invention, R is hydrogen, a hydroxy group, a halogen, a nitro group, an optionally substituted amino group, alkyl group, an alkoxy group, an alkenyl group, or an alkoxyalkyl group; and $R^1$ and $R^2$ independently are hydrogen, a hydroxy group, a halogen, a nitro group, a carboxy group, a carbamoyl group, an optionally substituted amino group, an alkyl group, a cycloalkyl group, an alkoxy group, a cycloalkoxy group, an alkenyl group, a cycloalkenyl group, an alkoxyalkyl group, an alkenyloxy group, or a cycloalkenyloxy group.

In another aspect of formula (142) of the present invention, $R^1$ and $R^2$ are independently a halogen or an alkyl group; and R is hydrogen, an alkyl group,

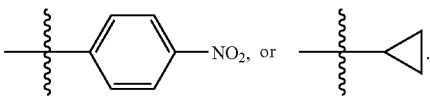

In still another aspect of formula (142) of the present invention, $R^1$ is —$OCH_3$ or —F; $R^2$ is —$OCH_3$ or —Cl; R is —H or $C_2H_5$,

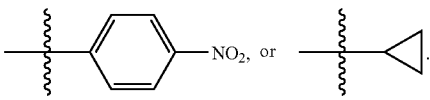

The present invention also contemplates various compounds of general formula (V) as follows:

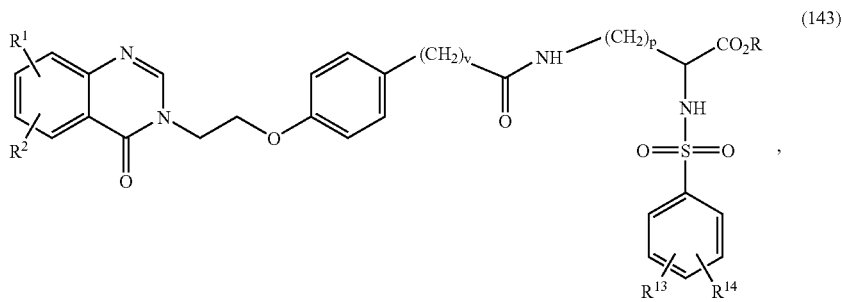

(143)

where all symbols are as defined above in connection with formula (I).

In one aspect of formula (143) of the present invention, $R^1$ and $R^2$ independently are hydrogen, a hydroxy group, a halogen, a nitro group, a carboxy group, a carbamoyl group, an optionally substituted amino group, an alkyl group, a cycloalkyl group, an alkoxy group, a cycloalkoxy group, an alkenyl group, a cycloalkenyl group, an alkoxyalkyl group, an alkenyloxy group, or a cycloalkenyloxy group; $R^{13}$ and $R^{14}$ independently are hydrogen, a halogen, a nitro group, an amino group, a mono- or di-substituted amino group, a hydroxy group, an alkoxy group, a carboxy group, a cyano group, an oxo(O=) group, a thio(S=) group, an alkyl group, a cycloalkyl group, an alkoxy group, a haloalkoxy group, a cycloalkyl group, an aryl group, a benzyloxy group, an acyl group, an acyloxy group, an aroyl group, an alkoxycarbonyl group, an aryloxycarbonyl group, a heteroaryl group, or a heterocyclyl group, an aralkyl group; and all other symbols are as defined in connection with formula (I).

In another aspect of formula (143) of the present invention, $R^1$ and $R^2$ independently are an acyl group, an acyloxy group, an aryl group, an aryloxy group, an aroyl group, an aroyloxy group, an aralkyl group, an aralkoxy group; a heterocyclyl group, a heteroaryl group, a heteroaralkyl group, a heteroaryloxy group, a heteroaralkoxy group, an alkoxycarbonyl group, an aryloxycarbonyl group, or a heteroarylcarbonyl group; $R^{13}$ and $R^{14}$ independently are hydrogen, a halogen, a nitro group, an amino group, a mono- or di-substituted amino group, a hydroxy group, an alkoxy group, a carboxy group, a cyano group, an oxo(O=) group, a thio(S=) group, an alkyl group, a cycloalkyl group, an alkoxy group, a haloalkoxy group, a cycloalkyl group, an aryl group, a benzyloxy group, an acyl group, an acyloxy group, an aroyl group, an alkoxycarbonyl group, an aryloxycarbonyl group, a heteroaryl group, or a heterocyclyl group, an aralkyl group; and all other symbols are as defined in connection with formula (I).

In another aspect of formula (143) of the present invention, $R^1$ and $R^2$ independently are hydrogen, an alkyl group, or an alkoxy group; $R^{13}$ and $R^{14}$ independently are hydrogen, a halogen, an alkyl group, or an alkoxy group; and all other symbols are as defined in connection with formula (I).

In yet another aspect of formula (143) of the present invention, $R^1$ and $R^2$ are —H or —$OCH_3$; $R^{13}$ is $CH_3$ or —F; $R^{14}$ is —H or —F; and all other symbols are as defined in connection with formula (I).

The present invention also contemplates various compounds of general formula (V) having the formula:

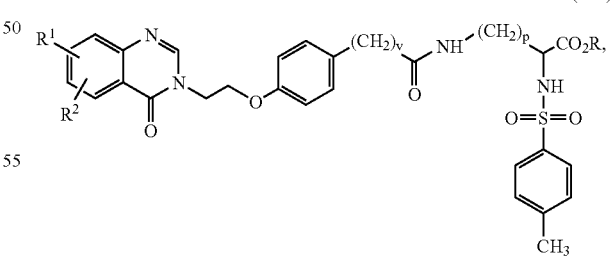

(144)

where all symbols are as defined above in connection with formula (I).

According to various aspects of the present invention, R, $R^1$, $R^2$, v, and p of formula (144) are selected to produce various compounds of formula (144-1) through (144-243) as follows:

| Formula | R | R$^1$ | R$^2$ | v | p |
|---|---|---|---|---|---|
| 144-1 | R$^a$ | R$^{1a}$ | R$^{2a}$ | v$^a$ | p$^a$ |
| 144-2 | R$^b$ | R$^{1a}$ | R$^{2a}$ | v$^a$ | p$^a$ |
| 144-3 | R$^c$ | R$^{1a}$ | R$^{2a}$ | v$^a$ | p$^a$ |
| 144-4 | R$^a$ | R$^{1b}$ | R$^{2a}$ | v$^a$ | p$^a$ |
| 144-5 | R$^b$ | R$^{1b}$ | R$^{2a}$ | v$^a$ | p$^a$ |
| 144-6 | R$^c$ | R$^{1b}$ | R$^{2a}$ | v$^a$ | p$^a$ |
| 144-7 | R$^a$ | R$^{1c}$ | R$^{2a}$ | v$^a$ | p$^a$ |
| 144-8 | R$^b$ | R$^{1c}$ | R$^{2a}$ | v$^a$ | p$^a$ |
| 144-9 | R$^c$ | R$^{1c}$ | R$^{2a}$ | v$^a$ | p$^a$ |
| 144-10 | R$^a$ | R$^{1a}$ | R$^{2b}$ | v$^a$ | p$^a$ |
| 144-11 | R$^b$ | R$^{1a}$ | R$^{2b}$ | v$^a$ | p$^a$ |
| 144-12 | R$^c$ | R$^{1a}$ | R$^{2b}$ | v$^a$ | p$^a$ |
| 144-13 | R$^a$ | R$^{1b}$ | R$^{2b}$ | v$^a$ | p$^a$ |
| 144-14 | R$^b$ | R$^{1b}$ | R$^{2b}$ | v$^a$ | p$^a$ |
| 144-15 | R$^c$ | R$^{1b}$ | R$^{2b}$ | v$^a$ | p$^a$ |
| 144-16 | R$^a$ | R$^{1c}$ | R$^{2b}$ | v$^a$ | p$^a$ |
| 144-17 | R$^b$ | R$^{1c}$ | R$^{2b}$ | v$^a$ | p$^a$ |
| 144-18 | R$^c$ | R$^{1c}$ | R$^{2b}$ | v$^a$ | p$^a$ |
| 144-19 | R$^a$ | R$^{1a}$ | R$^{2c}$ | v$^a$ | p$^a$ |
| 144-20 | R$^b$ | R$^{1a}$ | R$^{2c}$ | v$^a$ | p$^a$ |
| 144-21 | R$^c$ | R$^{1a}$ | R$^{2c}$ | v$^a$ | p$^a$ |
| 144-22 | R$^a$ | R$^{1b}$ | R$^{2c}$ | v$^a$ | p$^a$ |
| 144-23 | R$^b$ | R$^{1b}$ | R$^{2c}$ | v$^a$ | p$^a$ |
| 144-24 | R$^c$ | R$^{1b}$ | R$^{2c}$ | v$^a$ | p$^a$ |
| 144-25 | R$^a$ | R$^{1c}$ | R$^{2c}$ | v$^a$ | p$^a$ |
| 144-26 | R$^b$ | R$^{1c}$ | R$^{2c}$ | v$^a$ | p$^a$ |
| 144-27 | R$^c$ | R$^{1c}$ | R$^{2c}$ | v$^a$ | p$^a$ |
| 144-28 | R$^a$ | R$^{1a}$ | R$^{2a}$ | v$^b$ | p$^a$ |
| 144-29 | R$^b$ | R$^{1a}$ | R$^{2a}$ | v$^b$ | p$^a$ |
| 144-30 | R$^c$ | R$^{1a}$ | R$^{2a}$ | v$^b$ | p$^a$ |
| 144-31 | R$^a$ | R$^{1b}$ | R$^{2a}$ | v$^b$ | p$^a$ |
| 144-32 | R$^b$ | R$^{1b}$ | R$^{2a}$ | v$^b$ | p$^a$ |
| 144-33 | R$^c$ | R$^{1b}$ | R$^{2a}$ | v$^b$ | p$^a$ |
| 144-34 | R$^a$ | R$^{1c}$ | R$^{2a}$ | v$^b$ | p$^a$ |
| 144-35 | R$^b$ | R$^{1c}$ | R$^{2a}$ | v$^b$ | p$^a$ |
| 144-36 | R$^c$ | R$^{1c}$ | R$^{2a}$ | v$^b$ | p$^a$ |
| 144-37 | R$^a$ | R$^{1a}$ | R$^{2b}$ | v$^b$ | p$^a$ |
| 144-38 | R$^b$ | R$^{1a}$ | R$^{2b}$ | v$^b$ | p$^a$ |
| 144-39 | R$^c$ | R$^{1a}$ | R$^{2b}$ | v$^b$ | p$^a$ |
| 144-40 | R$^a$ | R$^{1b}$ | R$^{2b}$ | v$^b$ | p$^a$ |
| 144-41 | R$^b$ | R$^{1b}$ | R$^{2b}$ | v$^b$ | p$^a$ |
| 144-42 | R$^c$ | R$^{1b}$ | R$^{2b}$ | v$^b$ | p$^a$ |
| 144-43 | R$^a$ | R$^{1c}$ | R$^{2b}$ | v$^b$ | p$^a$ |
| 144-44 | R$^b$ | R$^{1c}$ | R$^{2b}$ | v$^b$ | p$^a$ |
| 144-45 | R$^c$ | R$^{1c}$ | R$^{2b}$ | v$^b$ | p$^a$ |
| 144-46 | R$^a$ | R$^{1a}$ | R$^{2c}$ | v$^b$ | p$^a$ |
| 144-47 | R$^b$ | R$^{1a}$ | R$^{2c}$ | v$^b$ | p$^a$ |
| 144-48 | R$^c$ | R$^{1a}$ | R$^{2c}$ | v$^b$ | p$^a$ |
| 144-49 | R$^a$ | R$^{1b}$ | R$^{2c}$ | v$^b$ | p$^a$ |
| 144-50 | R$^b$ | R$^{1b}$ | R$^{2c}$ | v$^b$ | p$^a$ |
| 144-51 | R$^c$ | R$^{1b}$ | R$^{2c}$ | v$^b$ | p$^a$ |
| 144-52 | R$^a$ | R$^{1c}$ | R$^{2c}$ | v$^b$ | p$^a$ |
| 144-53 | R$^b$ | R$^{1c}$ | R$^{2c}$ | v$^b$ | p$^a$ |
| 144-54 | R$^c$ | R$^{1c}$ | R$^{2c}$ | v$^b$ | p$^a$ |
| 144-55 | R$^a$ | R$^{1a}$ | R$^{2a}$ | v$^c$ | p$^a$ |
| 144-56 | R$^b$ | R$^{1a}$ | R$^{2a}$ | v$^c$ | p$^a$ |
| 144-57 | R$^c$ | R$^{1a}$ | R$^{2a}$ | v$^c$ | p$^a$ |
| 144-58 | R$^a$ | R$^{1b}$ | R$^{2a}$ | v$^c$ | p$^a$ |
| 144-59 | R$^b$ | R$^{1b}$ | R$^{2a}$ | v$^c$ | p$^a$ |
| 144-60 | R$^c$ | R$^{1b}$ | R$^{2a}$ | v$^c$ | p$^a$ |
| 144-61 | R$^a$ | R$^{1c}$ | R$^{2a}$ | v$^c$ | p$^a$ |
| 144-62 | R$^b$ | R$^{1c}$ | R$^{2a}$ | v$^c$ | p$^a$ |
| 144-63 | R$^c$ | R$^{1c}$ | R$^{2a}$ | v$^c$ | p$^a$ |
| 144-64 | R$^a$ | R$^{1a}$ | R$^{2b}$ | v$^c$ | p$^a$ |
| 144-65 | R$^b$ | R$^{1a}$ | R$^{2b}$ | v$^c$ | p$^a$ |
| 144-66 | R$^c$ | R$^{1a}$ | R$^{2b}$ | v$^c$ | p$^a$ |
| 144-67 | R$^a$ | R$^{1b}$ | R$^{2b}$ | v$^c$ | p$^a$ |
| 144-68 | R$^b$ | R$^{1b}$ | R$^{2b}$ | v$^c$ | p$^a$ |
| 144-69 | R$^c$ | R$^{1b}$ | R$^{2b}$ | v$^c$ | p$^a$ |
| 144-70 | R$^a$ | R$^{1c}$ | R$^{2b}$ | v$^c$ | p$^a$ |
| 144-71 | R$^b$ | R$^{1c}$ | R$^{2b}$ | v$^c$ | p$^a$ |
| 144-72 | R$^c$ | R$^{1c}$ | R$^{2b}$ | v$^c$ | p$^a$ |
| 144-73 | R$^a$ | R$^{1a}$ | R$^{2c}$ | v$^c$ | p$^a$ |
| 144-74 | R$^b$ | R$^{1a}$ | R$^{2c}$ | v$^c$ | p$^a$ |
| 144-75 | R$^c$ | R$^{1a}$ | R$^{2c}$ | v$^c$ | p$^a$ |
| 144-76 | R$^a$ | R$^{1b}$ | R$^{2c}$ | v$^c$ | p$^a$ |
| 144-77 | R$^b$ | R$^{1b}$ | R$^{2c}$ | v$^c$ | p$^a$ |
| 144-78 | R$^c$ | R$^{1b}$ | R$^{2c}$ | v$^c$ | p$^a$ |
| 144-79 | R$^a$ | R$^{1c}$ | R$^{2c}$ | v$^c$ | p$^a$ |
| 144-80 | R$^b$ | R$^{1c}$ | R$^{2c}$ | v$^c$ | p$^a$ |
| 144-81 | R$^c$ | R$^{1c}$ | R$^{2c}$ | v$^c$ | p$^a$ |
| 144-82 | R$^a$ | R$^{1a}$ | R$^{2a}$ | v$^a$ | p$^b$ |
| 144-83 | R$^b$ | R$^{1a}$ | R$^{2a}$ | v$^a$ | p$^b$ |
| 144-84 | R$^c$ | R$^{1a}$ | R$^{2a}$ | v$^a$ | p$^b$ |
| 144-85 | R$^a$ | R$^{1b}$ | R$^{2a}$ | v$^a$ | p$^b$ |
| 144-86 | R$^b$ | R$^{1b}$ | R$^{2a}$ | v$^a$ | p$^b$ |
| 144-87 | R$^c$ | R$^{1b}$ | R$^{2a}$ | v$^a$ | p$^b$ |
| 144-88 | R$^a$ | R$^{1c}$ | R$^{2a}$ | v$^a$ | p$^b$ |
| 144-89 | R$^b$ | R$^{1c}$ | R$^{2a}$ | v$^a$ | p$^b$ |
| 144-90 | R$^c$ | R$^{1c}$ | R$^{2a}$ | v$^a$ | p$^b$ |
| 144-91 | R$^a$ | R$^{1a}$ | R$^{2b}$ | v$^a$ | p$^b$ |
| 144-92 | R$^b$ | R$^{1a}$ | R$^{2b}$ | v$^a$ | p$^b$ |
| 144-93 | R$^c$ | R$^{1a}$ | R$^{2b}$ | v$^a$ | p$^b$ |
| 144-94 | R$^a$ | R$^{1b}$ | R$^{2b}$ | v$^a$ | p$^b$ |
| 144-95 | R$^b$ | R$^{1b}$ | R$^{2b}$ | v$^a$ | p$^b$ |
| 144-96 | R$^c$ | R$^{1b}$ | R$^{2b}$ | v$^a$ | p$^b$ |
| 144-97 | R$^a$ | R$^{1c}$ | R$^{2b}$ | v$^a$ | p$^b$ |
| 144-98 | R$^b$ | R$^{1c}$ | R$^{2b}$ | v$^a$ | p$^b$ |
| 144-99 | R$^c$ | R$^{1c}$ | R$^{2b}$ | v$^a$ | p$^b$ |
| 144-100 | R$^a$ | R$^{1a}$ | R$^{2c}$ | v$^a$ | p$^b$ |
| 144-101 | R$^b$ | R$^{1a}$ | R$^{2c}$ | v$^a$ | p$^b$ |
| 144-102 | R$^c$ | R$^{1a}$ | R$^{2c}$ | v$^a$ | p$^b$ |
| 144-103 | R$^a$ | R$^{1b}$ | R$^{2c}$ | v$^a$ | p$^b$ |
| 144-104 | R$^b$ | R$^{1b}$ | R$^{2c}$ | v$^a$ | p$^b$ |
| 144-105 | R$^c$ | R$^{1b}$ | R$^{2c}$ | v$^a$ | p$^b$ |
| 144-106 | R$^a$ | R$^{1c}$ | R$^{2c}$ | v$^a$ | p$^b$ |
| 144-107 | R$^b$ | R$^{1c}$ | R$^{2c}$ | v$^a$ | p$^b$ |
| 144-108 | R$^c$ | R$^{1c}$ | R$^{2c}$ | v$^a$ | p$^b$ |
| 144-109 | R$^a$ | R$^{1a}$ | R$^{2a}$ | v$^b$ | p$^b$ |
| 144-110 | R$^b$ | R$^{1a}$ | R$^{2a}$ | v$^b$ | p$^b$ |
| 144-111 | R$^c$ | R$^{1a}$ | R$^{2a}$ | v$^b$ | p$^b$ |
| 144-112 | R$^a$ | R$^{1b}$ | R$^{2a}$ | v$^b$ | p$^b$ |
| 144-113 | R$^b$ | R$^{1b}$ | R$^{2a}$ | v$^b$ | p$^b$ |
| 144-114 | R$^c$ | R$^{1b}$ | R$^{2a}$ | v$^b$ | p$^b$ |
| 144-115 | R$^a$ | R$^{1c}$ | R$^{2a}$ | v$^b$ | p$^b$ |
| 144-116 | R$^b$ | R$^{1c}$ | R$^{2a}$ | v$^b$ | p$^b$ |
| 144-117 | R$^c$ | R$^{1c}$ | R$^{2a}$ | v$^b$ | p$^b$ |
| 144-118 | R$^a$ | R$^{1a}$ | R$^{2b}$ | v$^b$ | p$^b$ |
| 144-119 | R$^b$ | R$^{1a}$ | R$^{2b}$ | v$^b$ | p$^b$ |
| 144-120 | R$^c$ | R$^{1a}$ | R$^{2b}$ | v$^b$ | p$^b$ |
| 144-121 | R$^a$ | R$^{1b}$ | R$^{2b}$ | v$^b$ | p$^b$ |
| 144-122 | R$^b$ | R$^{1b}$ | R$^{2b}$ | v$^b$ | p$^b$ |
| 144-123 | R$^c$ | R$^{1b}$ | R$^{2b}$ | v$^b$ | p$^b$ |
| 144-124 | R$^a$ | R$^{1c}$ | R$^{2b}$ | v$^b$ | p$^b$ |
| 144-125 | R$^b$ | R$^{1c}$ | R$^{2b}$ | v$^b$ | p$^b$ |
| 144-126 | R$^c$ | R$^{1c}$ | R$^{2b}$ | v$^b$ | p$^b$ |
| 144-127 | R$^a$ | R$^{1a}$ | R$^{2c}$ | v$^b$ | p$^b$ |
| 144-128 | R$^b$ | R$^{1a}$ | R$^{2c}$ | v$^b$ | p$^b$ |
| 144-129 | R$^c$ | R$^{1a}$ | R$^{2c}$ | v$^b$ | p$^b$ |
| 144-130 | R$^a$ | R$^{1b}$ | R$^{2c}$ | v$^b$ | p$^b$ |
| 144-131 | R$^b$ | R$^{1b}$ | R$^{2c}$ | v$^b$ | p$^b$ |
| 144-132 | R$^c$ | R$^{1b}$ | R$^{2c}$ | v$^b$ | p$^b$ |
| 144-133 | R$^a$ | R$^{1c}$ | R$^{2c}$ | v$^b$ | p$^b$ |
| 144-134 | R$^b$ | R$^{1c}$ | R$^{2c}$ | v$^b$ | p$^b$ |
| 144-135 | R$^c$ | R$^{1c}$ | R$^{2c}$ | v$^b$ | p$^b$ |
| 144-136 | R$^a$ | R$^{1a}$ | R$^{2a}$ | v$^c$ | p$^b$ |
| 144-137 | R$^b$ | R$^{1a}$ | R$^{2a}$ | v$^c$ | p$^b$ |
| 144-138 | R$^c$ | R$^{1a}$ | R$^{2a}$ | v$^c$ | p$^b$ |
| 144-139 | R$^a$ | R$^{1b}$ | R$^{2a}$ | v$^c$ | p$^b$ |
| 144-140 | R$^b$ | R$^{1b}$ | R$^{2a}$ | v$^c$ | p$^b$ |
| 144-141 | R$^c$ | R$^{1b}$ | R$^{2a}$ | v$^c$ | p$^b$ |
| 144-142 | R$^a$ | R$^{1c}$ | R$^{2a}$ | v$^c$ | p$^b$ |
| 144-143 | R$^b$ | R$^{1c}$ | R$^{2a}$ | v$^c$ | p$^b$ |
| 144-144 | R$^c$ | R$^{1c}$ | R$^{2a}$ | v$^c$ | p$^b$ |
| 144-145 | R$^a$ | R$^{1a}$ | R$^{2b}$ | v$^c$ | p$^b$ |
| 144-146 | R$^b$ | R$^{1a}$ | R$^{2b}$ | v$^c$ | p$^b$ |
| 144-147 | R$^c$ | R$^{1a}$ | R$^{2b}$ | v$^c$ | p$^b$ |
| 144-148 | R$^a$ | R$^{1b}$ | R$^{2b}$ | v$^c$ | p$^b$ |
| 144-149 | R$^b$ | R$^{1b}$ | R$^{2b}$ | v$^c$ | p$^b$ |
| 144-150 | R$^c$ | R$^{1b}$ | R$^{2b}$ | v$^c$ | p$^b$ |
| 144-151 | R$^a$ | R$^{1c}$ | R$^{2b}$ | v$^c$ | p$^b$ |
| 144-152 | R$^b$ | R$^{1c}$ | R$^{2b}$ | v$^c$ | p$^b$ |
| 144-153 | R$^c$ | R$^{1c}$ | R$^{2b}$ | v$^c$ | p$^b$ |
| 144-154 | R$^a$ | R$^{1a}$ | R$^{2c}$ | v$^c$ | p$^b$ |

-continued

| Formula | R | R¹ | R² | v | p |
|---|---|---|---|---|---|
| 144-155 | $R^b$ | $R^{1a}$ | $R^{2c}$ | $v^c$ | $p^b$ |
| 144-156 | $R^c$ | $R^{1a}$ | $R^{2c}$ | $v^c$ | $p^b$ |
| 144-157 | $R^a$ | $R^{1b}$ | $R^{2c}$ | $v^c$ | $p^b$ |
| 144-158 | $R^b$ | $R^{1b}$ | $R^{2c}$ | $v^c$ | $p^b$ |
| 144-159 | $R^c$ | $R^{1b}$ | $R^{2c}$ | $v^c$ | $p^b$ |
| 144-160 | $R^a$ | $R^{1c}$ | $R^{2c}$ | $v^c$ | $p^b$ |
| 144-161 | $R^b$ | $R^{1c}$ | $R^{2c}$ | $v^c$ | $p^b$ |
| 144-162 | $R^c$ | $R^{1c}$ | $R^{2c}$ | $v^c$ | $p^b$ |
| 144-163 | $R^a$ | $R^{1a}$ | $R^{2a}$ | $v^a$ | $p^c$ |
| 144-164 | $R^b$ | $R^{1a}$ | $R^{2a}$ | $v^a$ | $p^c$ |
| 144-165 | $R^c$ | $R^{1a}$ | $R^{2a}$ | $v^a$ | $p^c$ |
| 144-166 | $R^a$ | $R^{1b}$ | $R^{2a}$ | $v^a$ | $p^c$ |
| 144-167 | $R^b$ | $R^{1b}$ | $R^{2a}$ | $v^a$ | $p^c$ |
| 144-168 | $R^c$ | $R^{1b}$ | $R^{2a}$ | $v^a$ | $p^c$ |
| 144-169 | $R^a$ | $R^{1c}$ | $R^{2a}$ | $v^a$ | $p^c$ |
| 144-170 | $R^b$ | $R^{1c}$ | $R^{2a}$ | $v^a$ | $p^c$ |
| 144-171 | $R^c$ | $R^{1c}$ | $R^{2a}$ | $v^a$ | $p^c$ |
| 144-172 | $R^a$ | $R^{1a}$ | $R^{2b}$ | $v^a$ | $p^c$ |
| 144-173 | $R^b$ | $R^{1a}$ | $R^{2b}$ | $v^a$ | $p^c$ |
| 144-174 | $R^c$ | $R^{1a}$ | $R^{2b}$ | $v^a$ | $p^c$ |
| 144-175 | $R^a$ | $R^{1b}$ | $R^{2b}$ | $v^a$ | $p^c$ |
| 144-176 | $R^b$ | $R^{1b}$ | $R^{2b}$ | $v^a$ | $p^c$ |
| 144-177 | $R^c$ | $R^{1b}$ | $R^{2b}$ | $v^a$ | $p^c$ |
| 144-178 | $R^a$ | $R^{1c}$ | $R^{2b}$ | $v^a$ | $p^c$ |
| 144-179 | $R^b$ | $R^{1c}$ | $R^{2b}$ | $v^a$ | $p^c$ |
| 144-180 | $R^c$ | $R^{1c}$ | $R^{2b}$ | $v^a$ | $p^c$ |
| 144-181 | $R^a$ | $R^{1a}$ | $R^{2c}$ | $v^a$ | $p^c$ |
| 144-182 | $R^b$ | $R^{1a}$ | $R^{2c}$ | $v^a$ | $p^c$ |
| 144-183 | $R^c$ | $R^{1a}$ | $R^{2c}$ | $v^a$ | $p^c$ |
| 144-184 | $R^a$ | $R^{1b}$ | $R^{2c}$ | $v^a$ | $p^c$ |
| 144-185 | $R^b$ | $R^{1b}$ | $R^{2c}$ | $v^a$ | $p^c$ |
| 144-186 | $R^c$ | $R^{1b}$ | $R^{2c}$ | $v^a$ | $p^c$ |
| 144-187 | $R^a$ | $R^{1c}$ | $R^{2c}$ | $v^a$ | $p^c$ |
| 144-188 | $R^b$ | $R^{1c}$ | $R^{2c}$ | $v^a$ | $p^c$ |
| 144-189 | $R^c$ | $R^{1c}$ | $R^{2c}$ | $v^a$ | $p^c$ |
| 144-190 | $R^a$ | $R^{1a}$ | $R^{2a}$ | $v^b$ | $p^c$ |
| 144-191 | $R^b$ | $R^{1a}$ | $R^{2a}$ | $v^b$ | $p^c$ |
| 144-192 | $R^c$ | $R^{1a}$ | $R^{2a}$ | $v^b$ | $p^c$ |
| 144-193 | $R^a$ | $R^{1b}$ | $R^{2a}$ | $v^b$ | $p^c$ |
| 144-194 | $R^b$ | $R^{1b}$ | $R^{2a}$ | $v^b$ | $p^c$ |
| 144-195 | $R^c$ | $R^{1b}$ | $R^{2a}$ | $v^b$ | $p^c$ |
| 144-196 | $R^a$ | $R^{1c}$ | $R^{2a}$ | $v^b$ | $p^c$ |
| 144-197 | $R^b$ | $R^{1c}$ | $R^{2a}$ | $v^b$ | $p^c$ |
| 144-198 | $R^c$ | $R^{1c}$ | $R^{2a}$ | $v^b$ | $p^c$ |
| 144-199 | $R^a$ | $R^{1a}$ | $R^{2b}$ | $v^b$ | $p^c$ |
| 144-200 | $R^b$ | $R^{1a}$ | $R^{2b}$ | $v^b$ | $p^c$ |
| 144-201 | $R^c$ | $R^{1a}$ | $R^{2b}$ | $v^b$ | $p^c$ |
| 144-202 | $R^a$ | $R^{1b}$ | $R^{2b}$ | $v^b$ | $p^c$ |
| 144-203 | $R^b$ | $R^{1b}$ | $R^{2b}$ | $v^b$ | $p^c$ |
| 144-204 | $R^c$ | $R^{1b}$ | $R^{2b}$ | $v^b$ | $p^c$ |
| 144-205 | $R^a$ | $R^{1c}$ | $R^{2b}$ | $v^b$ | $p^c$ |
| 144-206 | $R^b$ | $R^{1c}$ | $R^{2b}$ | $v^b$ | $p^c$ |
| 144-207 | $R^c$ | $R^{1c}$ | $R^{2b}$ | $v^b$ | $p^c$ |
| 144-208 | $R^a$ | $R^{1a}$ | $R^{2c}$ | $v^b$ | $p^c$ |
| 144-209 | $R^b$ | $R^{1a}$ | $R^{2c}$ | $v^b$ | $p^c$ |
| 144-210 | $R^c$ | $R^{1a}$ | $R^{2c}$ | $v^b$ | $p^c$ |
| 144-211 | $R^a$ | $R^{1b}$ | $R^{2c}$ | $v^b$ | $p^c$ |
| 144-212 | $R^b$ | $R^{1b}$ | $R^{2c}$ | $v^b$ | $p^c$ |
| 144-213 | $R^c$ | $R^{1b}$ | $R^{2c}$ | $v^b$ | $p^c$ |
| 144-214 | $R^a$ | $R^{1c}$ | $R^{2c}$ | $v^b$ | $p^c$ |
| 144-215 | $R^b$ | $R^{1c}$ | $R^{2c}$ | $v^b$ | $p^c$ |
| 144-216 | $R^c$ | $R^{1c}$ | $R^{2c}$ | $v^b$ | $p^c$ |
| 144-217 | $R^a$ | $R^{1a}$ | $R^{2a}$ | $v^c$ | $p^c$ |
| 144-218 | $R^b$ | $R^{1a}$ | $R^{2a}$ | $v^c$ | $p^c$ |
| 144-219 | $R^c$ | $R^{1a}$ | $R^{2a}$ | $v^c$ | $p^c$ |
| 144-220 | $R^a$ | $R^{1b}$ | $R^{2a}$ | $v^c$ | $p^c$ |
| 144-221 | $R^b$ | $R^{1b}$ | $R^{2a}$ | $v^c$ | $p^c$ |
| 144-222 | $R^c$ | $R^{1b}$ | $R^{2a}$ | $v^c$ | $p^c$ |
| 144-223 | $R^a$ | $R^{1c}$ | $R^{2a}$ | $v^c$ | $p^c$ |
| 144-224 | $R^b$ | $R^{1c}$ | $R^{2a}$ | $v^c$ | $p^c$ |
| 144-225 | $R^c$ | $R^{1c}$ | $R^{2a}$ | $v^c$ | $p^c$ |
| 144-226 | $R^a$ | $R^{1a}$ | $R^{2b}$ | $v^c$ | $p^c$ |
| 144-227 | $R^b$ | $R^{1a}$ | $R^{2b}$ | $v^c$ | $p^c$ |
| 144-228 | $R^c$ | $R^{1a}$ | $R^{2b}$ | $v^c$ | $p^c$ |
| 144-229 | $R^a$ | $R^{1b}$ | $R^{2b}$ | $v^c$ | $p^c$ |
| 144-230 | $R^b$ | $R^{1b}$ | $R^{2b}$ | $v^c$ | $p^c$ |
| 144-231 | $R^c$ | $R^{1b}$ | $R^{2b}$ | $v^c$ | $p^c$ |
| 144-232 | $R^a$ | $R^{1c}$ | $R^{2b}$ | $v^c$ | $p^c$ |
| 144-233 | $R^b$ | $R^{1c}$ | $R^{2b}$ | $v^c$ | $p^c$ |
| 144-234 | $R^c$ | $R^{1c}$ | $R^{2b}$ | $v^c$ | $p^c$ |
| 144-235 | $R^a$ | $R^{1a}$ | $R^{2c}$ | $v^c$ | $p^c$ |
| 144-236 | $R^b$ | $R^{1a}$ | $R^{2c}$ | $v^c$ | $p^c$ |
| 144-237 | $R^c$ | $R^{1a}$ | $R^{2c}$ | $v^c$ | $p^c$ |
| 144-238 | $R^a$ | $R^{1b}$ | $R^{2c}$ | $v^c$ | $p^c$ |
| 144-239 | $R^b$ | $R^{1b}$ | $R^{2c}$ | $v^c$ | $p^c$ |
| 144-240 | $R^c$ | $R^{1b}$ | $R^{2c}$ | $v^c$ | $p^c$ |
| 144-241 | $R^a$ | $R^{1c}$ | $R^{2c}$ | $v^c$ | $p^c$ |
| 144-242 | $R^b$ | $R^{1c}$ | $R^{2c}$ | $v^c$ | $p^c$ |
| 144-243 | $R^c$ | $R^{1c}$ | $R^{2c}$ | $v^c$ | $p^c$ | where all symbols are as defined above.

In one aspect of formula (144) of the present invention, R is hydrogen, a hydroxy group, a halogen, a nitro group, an optionally substituted amino group, an alkyl group, an s alkoxy group, an alkenyl group, or an alkoxyalkyl group; $R^1$ and $R^2$ independently are hydrogen, a hydroxy group, a halogen, a nitro group, a carboxy group, a carbamoyl group, an optionally substituted amino group, an alkyl group, a cycloalkyl group, an alkoxy group, a cycloalkoxy group, an alkenyl group, a cycloalkenyl group, an alkoxyalkyl group, an alkenyloxy group, or a cycloalkenyloxy group; and all other symbols are as defined in connection with formula (I).

In another aspect of formula (144) of the present invention, $R^1$ and $R^2$ are independently hydrogen, an alkyl group, or an alkoxy group; and all other symbols are as defined in connection with formula (I).

In yet another aspect of formula (144) of the present invention, $R^1$ and $R^2$ are —OCH$_3$; and all other symbols are as defined in connection with formula (I).

The present invention further contemplates various compounds of general formula (V) having the formula:

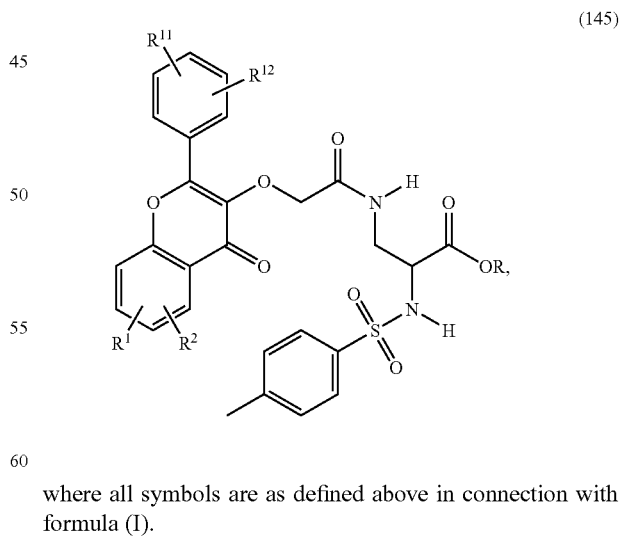

(145)

where all symbols are as defined above in connection with formula (I).

According to various aspects of the present invention, R, $R^1$, $R^2$, $R^{11}$, and $R^{12}$ of formula (145) are selected to provide various compounds of formula (145-1) through formula (145-243) as follows:

| Formula | R | $R^1$ | $R^2$ | $R^{11}$ | $R^{12}$ |
|---|---|---|---|---|---|
| 145-1 | $R^a$ | $R^{1a}$ | $R^{2a}$ | $R^{11a}$ | $R^{12a}$ |
| 145-2 | $R^b$ | $R^{1a}$ | $R^{2a}$ | $R^{11a}$ | $R^{12a}$ |
| 145-3 | $R^c$ | $R^{1a}$ | $R^{2a}$ | $R^{11a}$ | $R^{12a}$ |
| 145-4 | $R^a$ | $R^{1b}$ | $R^{2a}$ | $R^{11a}$ | $R^{12a}$ |
| 145-5 | $R^b$ | $R^{1b}$ | $R^{2a}$ | $R^{11a}$ | $R^{12a}$ |
| 145-6 | $R^c$ | $R^{1b}$ | $R^{2a}$ | $R^{11a}$ | $R^{12a}$ |
| 145-7 | $R^a$ | $R^{1c}$ | $R^{2a}$ | $R^{11a}$ | $R^{12a}$ |
| 145-8 | $R^b$ | $R^{1c}$ | $R^{2a}$ | $R^{11a}$ | $R^{12a}$ |
| 145-9 | $R^c$ | $R^{1c}$ | $R^{2a}$ | $R^{11a}$ | $R^{12a}$ |
| 145-10 | $R^a$ | $R^{1a}$ | $R^{2b}$ | $R^{11a}$ | $R^{12a}$ |
| 145-11 | $R^b$ | $R^{1a}$ | $R^{2b}$ | $R^{11a}$ | $R^{12a}$ |
| 145-12 | $R^c$ | $R^{1a}$ | $R^{2b}$ | $R^{11a}$ | $R^{12a}$ |
| 145-13 | $R^a$ | $R^{1b}$ | $R^{2b}$ | $R^{11a}$ | $R^{12a}$ |
| 145-14 | $R^b$ | $R^{1b}$ | $R^{2b}$ | $R^{11a}$ | $R^{12a}$ |
| 145-15 | $R^c$ | $R^{1b}$ | $R^{2b}$ | $R^{11a}$ | $R^{12a}$ |
| 145-16 | $R^a$ | $R^{1c}$ | $R^{2b}$ | $R^{11a}$ | $R^{12a}$ |
| 145-17 | $R^b$ | $R^{1c}$ | $R^{2b}$ | $R^{11a}$ | $R^{12a}$ |
| 145-18 | $R^c$ | $R^{1c}$ | $R^{2b}$ | $R^{11a}$ | $R^{12a}$ |
| 145-19 | $R^a$ | $R^{1a}$ | $R^{2c}$ | $R^{11a}$ | $R^{12a}$ |
| 145-20 | $R^b$ | $R^{1a}$ | $R^{2c}$ | $R^{11a}$ | $R^{12a}$ |
| 145-21 | $R^c$ | $R^{1a}$ | $R^{2c}$ | $R^{11a}$ | $R^{12a}$ |
| 145-22 | $R^a$ | $R^{1b}$ | $R^{2c}$ | $R^{11a}$ | $R^{12a}$ |
| 145-23 | $R^b$ | $R^{1b}$ | $R^{2c}$ | $R^{11a}$ | $R^{12a}$ |
| 145-24 | $R^c$ | $R^{1b}$ | $R^{2c}$ | $R^{11a}$ | $R^{12a}$ |
| 145-25 | $R^a$ | $R^{1c}$ | $R^{2c}$ | $R^{11a}$ | $R^{12a}$ |
| 145-26 | $R^b$ | $R^{1c}$ | $R^{2c}$ | $R^{11a}$ | $R^{12a}$ |
| 145-27 | $R^c$ | $R^{1c}$ | $R^{2c}$ | $R^{11a}$ | $R^{12a}$ |
| 145-28 | $R^a$ | $R^{1a}$ | $R^{2a}$ | $R^{11b}$ | $R^{12a}$ |
| 145-29 | $R^b$ | $R^{1a}$ | $R^{2a}$ | $R^{11b}$ | $R^{12a}$ |
| 145-30 | $R^c$ | $R^{1a}$ | $R^{2a}$ | $R^{11b}$ | $R^{12a}$ |
| 145-31 | $R^a$ | $R^{1b}$ | $R^{2a}$ | $R^{11b}$ | $R^{12a}$ |
| 145-32 | $R^b$ | $R^{1b}$ | $R^{2a}$ | $R^{11b}$ | $R^{12a}$ |
| 145-33 | $R^c$ | $R^{1b}$ | $R^{2a}$ | $R^{11b}$ | $R^{12a}$ |
| 145-34 | $R^a$ | $R^{1c}$ | $R^{2a}$ | $R^{11b}$ | $R^{12a}$ |
| 145-35 | $R^b$ | $R^{1c}$ | $R^{2a}$ | $R^{11b}$ | $R^{12a}$ |
| 145-36 | $R^c$ | $R^{1c}$ | $R^{2a}$ | $R^{11b}$ | $R^{12a}$ |
| 145-37 | $R^a$ | $R^{1a}$ | $R^{2b}$ | $R^{11b}$ | $R^{12a}$ |
| 145-38 | $R^b$ | $R^{1a}$ | $R^{2b}$ | $R^{11b}$ | $R^{12a}$ |
| 145-39 | $R^c$ | $R^{1a}$ | $R^{2b}$ | $R^{11b}$ | $R^{12a}$ |
| 145-40 | $R^a$ | $R^{1b}$ | $R^{2b}$ | $R^{11b}$ | $R^{12a}$ |
| 145-41 | $R^b$ | $R^{1b}$ | $R^{2b}$ | $R^{11b}$ | $R^{12a}$ |
| 145-42 | $R^c$ | $R^{1b}$ | $R^{2b}$ | $R^{11b}$ | $R^{12a}$ |
| 145-43 | $R^a$ | $R^{1c}$ | $R^{2b}$ | $R^{11b}$ | $R^{12a}$ |
| 145-44 | $R^b$ | $R^{1c}$ | $R^{2b}$ | $R^{11b}$ | $R^{12a}$ |
| 145-45 | $R^c$ | $R^{1c}$ | $R^{2b}$ | $R^{11b}$ | $R^{12a}$ |
| 145-46 | $R^a$ | $R^{1a}$ | $R^{2c}$ | $R^{11b}$ | $R^{12a}$ |
| 145-47 | $R^b$ | $R^{1a}$ | $R^{2c}$ | $R^{11b}$ | $R^{12a}$ |
| 145-48 | $R^c$ | $R^{1a}$ | $R^{2c}$ | $R^{11b}$ | $R^{12a}$ |
| 145-49 | $R^a$ | $R^{1b}$ | $R^{2c}$ | $R^{11b}$ | $R^{12a}$ |
| 145-50 | $R^b$ | $R^{1b}$ | $R^{2c}$ | $R^{11b}$ | $R^{12a}$ |
| 145-51 | $R^c$ | $R^{1b}$ | $R^{2c}$ | $R^{11b}$ | $R^{12a}$ |
| 145-52 | $R^a$ | $R^{1c}$ | $R^{2c}$ | $R^{11b}$ | $R^{12a}$ |
| 145-53 | $R^b$ | $R^{1c}$ | $R^{2c}$ | $R^{11b}$ | $R^{12a}$ |
| 145-54 | $R^c$ | $R^{1c}$ | $R^{2c}$ | $R^{11b}$ | $R^{12a}$ |
| 145-55 | $R^a$ | $R^{1a}$ | $R^{2a}$ | $R^{11c}$ | $R^{12a}$ |
| 145-56 | $R^b$ | $R^{1a}$ | $R^{2a}$ | $R^{11c}$ | $R^{12a}$ |
| 145-57 | $R^c$ | $R^{1a}$ | $R^{2a}$ | $R^{11c}$ | $R^{12a}$ |
| 145-58 | $R^a$ | $R^{1b}$ | $R^{2a}$ | $R^{11c}$ | $R^{12a}$ |
| 145-59 | $R^b$ | $R^{1b}$ | $R^{2a}$ | $R^{11c}$ | $R^{12a}$ |
| 145-60 | $R^c$ | $R^{1b}$ | $R^{2a}$ | $R^{11c}$ | $R^{12a}$ |
| 145-61 | $R^a$ | $R^{1c}$ | $R^{2a}$ | $R^{11c}$ | $R^{12a}$ |
| 145-62 | $R^b$ | $R^{1c}$ | $R^{2a}$ | $R^{11c}$ | $R^{12a}$ |
| 145-63 | $R^c$ | $R^{1c}$ | $R^{2a}$ | $R^{11c}$ | $R^{12a}$ |
| 145-64 | $R^a$ | $R^{1a}$ | $R^{2b}$ | $R^{11c}$ | $R^{12a}$ |
| 145-65 | $R^b$ | $R^{1a}$ | $R^{2b}$ | $R^{11c}$ | $R^{12a}$ |
| 145-66 | $R^c$ | $R^{1a}$ | $R^{2b}$ | $R^{11c}$ | $R^{12a}$ |
| 145-67 | $R^a$ | $R^{1b}$ | $R^{2b}$ | $R^{11c}$ | $R^{12a}$ |
| 145-68 | $R^b$ | $R^{1b}$ | $R^{2b}$ | $R^{11c}$ | $R^{12a}$ |
| 145-69 | $R^c$ | $R^{1b}$ | $R^{2b}$ | $R^{11c}$ | $R^{12a}$ |
| 145-70 | $R^a$ | $R^{1c}$ | $R^{2b}$ | $R^{11c}$ | $R^{12a}$ |
| 145-71 | $R^b$ | $R^{1c}$ | $R^{2b}$ | $R^{11c}$ | $R^{12a}$ |
| 145-72 | $R^c$ | $R^{1c}$ | $R^{2b}$ | $R^{11c}$ | $R^{12a}$ |
| 145-73 | $R^a$ | $R^{1a}$ | $R^{2c}$ | $R^{11c}$ | $R^{12a}$ |
| 145-74 | $R^b$ | $R^{1a}$ | $R^{2c}$ | $R^{11c}$ | $R^{12a}$ |
| 145-75 | $R^c$ | $R^{1a}$ | $R^{2c}$ | $R^{11c}$ | $R^{12a}$ |
| 145-76 | $R^a$ | $R^{1b}$ | $R^{2c}$ | $R^{11c}$ | $R^{12a}$ |
| 145-77 | $R^b$ | $R^{1b}$ | $R^{2c}$ | $R^{11c}$ | $R^{12a}$ |
| 145-78 | $R^c$ | $R^{1b}$ | $R^{2c}$ | $R^{11c}$ | $R^{12a}$ |
| 145-79 | $R^a$ | $R^{1c}$ | $R^{2c}$ | $R^{11c}$ | $R^{12a}$ |
| 145-80 | $R^b$ | $R^{1c}$ | $R^{2c}$ | $R^{11c}$ | $R^{12a}$ |
| 145-81 | $R^c$ | $R^{1c}$ | $R^{2c}$ | $R^{11c}$ | $R^{12a}$ |
| 145-82 | $R^a$ | $R^{1a}$ | $R^{2a}$ | $R^{11a}$ | $R^{12b}$ |
| 145-83 | $R^b$ | $R^{1a}$ | $R^{2a}$ | $R^{11a}$ | $R^{12b}$ |
| 145-84 | $R^c$ | $R^{1a}$ | $R^{2a}$ | $R^{11a}$ | $R^{12b}$ |
| 145-85 | $R^a$ | $R^{1b}$ | $R^{2a}$ | $R^{11a}$ | $R^{12b}$ |
| 145-86 | $R^b$ | $R^{1b}$ | $R^{2a}$ | $R^{11a}$ | $R^{12b}$ |
| 145-87 | $R^c$ | $R^{1b}$ | $R^{2a}$ | $R^{11a}$ | $R^{12b}$ |
| 145-88 | $R^a$ | $R^{1c}$ | $R^{2a}$ | $R^{11a}$ | $R^{12b}$ |
| 145-89 | $R^b$ | $R^{1c}$ | $R^{2a}$ | $R^{11a}$ | $R^{12b}$ |
| 145-90 | $R^c$ | $R^{1c}$ | $R^{2a}$ | $R^{11a}$ | $R^{12b}$ |
| 145-91 | $R^a$ | $R^{1a}$ | $R^{2b}$ | $R^{11a}$ | $R^{12b}$ |
| 145-92 | $R^b$ | $R^{1a}$ | $R^{2b}$ | $R^{11a}$ | $R^{12b}$ |
| 145-93 | $R^c$ | $R^{1a}$ | $R^{2b}$ | $R^{11a}$ | $R^{12b}$ |
| 145-94 | $R^a$ | $R^{1b}$ | $R^{2b}$ | $R^{11a}$ | $R^{12b}$ |
| 145-95 | $R^b$ | $R^{1b}$ | $R^{2b}$ | $R^{11a}$ | $R^{12b}$ |
| 145-96 | $R^c$ | $R^{1b}$ | $R^{2b}$ | $R^{11a}$ | $R^{12b}$ |
| 145-97 | $R^a$ | $R^{1c}$ | $R^{2b}$ | $R^{11a}$ | $R^{12b}$ |
| 145-98 | $R^b$ | $R^{1c}$ | $R^{2b}$ | $R^{11a}$ | $R^{12b}$ |
| 145-99 | $R^c$ | $R^{1c}$ | $R^{2b}$ | $R^{11a}$ | $R^{12b}$ |
| 145-100 | $R^a$ | $R^{1a}$ | $R^{2c}$ | $R^{11a}$ | $R^{12b}$ |
| 145-101 | $R^b$ | $R^{1a}$ | $R^{2c}$ | $R^{11a}$ | $R^{12b}$ |
| 145-102 | $R^c$ | $R^{1a}$ | $R^{2c}$ | $R^{11a}$ | $R^{12b}$ |
| 145-103 | $R^a$ | $R^{1b}$ | $R^{2c}$ | $R^{11a}$ | $R^{12b}$ |
| 145-104 | $R^b$ | $R^{1b}$ | $R^{2c}$ | $R^{11a}$ | $R^{12b}$ |
| 145-105 | $R^c$ | $R^{1b}$ | $R^{2c}$ | $R^{11a}$ | $R^{12b}$ |
| 145-106 | $R^a$ | $R^{1c}$ | $R^{2c}$ | $R^{11a}$ | $R^{12b}$ |
| 145-107 | $R^b$ | $R^{1c}$ | $R^{2c}$ | $R^{11a}$ | $R^{12b}$ |
| 145-108 | $R^c$ | $R^{1c}$ | $R^{2c}$ | $R^{11a}$ | $R^{12b}$ |
| 145-109 | $R^a$ | $R^{1a}$ | $R^{2a}$ | $R^{11b}$ | $R^{12b}$ |
| 145-110 | $R^b$ | $R^{1a}$ | $R^{2a}$ | $R^{11b}$ | $R^{12b}$ |
| 145-111 | $R^c$ | $R^{1a}$ | $R^{2a}$ | $R^{11b}$ | $R^{12b}$ |
| 145-112 | $R^a$ | $R^{1b}$ | $R^{2a}$ | $R^{11b}$ | $R^{12b}$ |
| 145-113 | $R^b$ | $R^{1b}$ | $R^{2a}$ | $R^{11b}$ | $R^{12b}$ |
| 145-114 | $R^c$ | $R^{1b}$ | $R^{2a}$ | $R^{11b}$ | $R^{12b}$ |
| 145-115 | $R^a$ | $R^{1c}$ | $R^{2a}$ | $R^{11b}$ | $R^{12b}$ |
| 145-116 | $R^b$ | $R^{1c}$ | $R^{2a}$ | $R^{11b}$ | $R^{12b}$ |
| 145-117 | $R^c$ | $R^{1c}$ | $R^{2a}$ | $R^{11b}$ | $R^{12b}$ |
| 145-118 | $R^a$ | $R^{1a}$ | $R^{2b}$ | $R^{11b}$ | $R^{12b}$ |
| 145-119 | $R^b$ | $R^{1a}$ | $R^{2b}$ | $R^{11b}$ | $R^{12b}$ |
| 145-120 | $R^c$ | $R^{1a}$ | $R^{2b}$ | $R^{11b}$ | $R^{12b}$ |
| 145-121 | $R^a$ | $R^{1b}$ | $R^{2b}$ | $R^{11b}$ | $R^{12b}$ |
| 145-122 | $R^b$ | $R^{1b}$ | $R^{2b}$ | $R^{11b}$ | $R^{12b}$ |
| 145-123 | $R^c$ | $R^{1b}$ | $R^{2b}$ | $R^{11b}$ | $R^{12b}$ |
| 145-124 | $R^a$ | $R^{1c}$ | $R^{2b}$ | $R^{11b}$ | $R^{12b}$ |
| 145-125 | $R^b$ | $R^{1c}$ | $R^{2b}$ | $R^{11b}$ | $R^{12b}$ |
| 145-126 | $R^c$ | $R^{1c}$ | $R^{2b}$ | $R^{11b}$ | $R^{12b}$ |
| 145-127 | $R^a$ | $R^{1a}$ | $R^{2c}$ | $R^{11b}$ | $R^{12b}$ |
| 145-128 | $R^b$ | $R^{1a}$ | $R^{2c}$ | $R^{11b}$ | $R^{12b}$ |
| 145-129 | $R^c$ | $R^{1a}$ | $R^{2c}$ | $R^{11b}$ | $R^{12b}$ |
| 145-130 | $R^a$ | $R^{1b}$ | $R^{2c}$ | $R^{11b}$ | $R^{12b}$ |
| 145-131 | $R^b$ | $R^{1b}$ | $R^{2c}$ | $R^{11b}$ | $R^{12b}$ |
| 145-132 | $R^c$ | $R^{1b}$ | $R^{2c}$ | $R^{11b}$ | $R^{12b}$ |
| 145-133 | $R^a$ | $R^{1c}$ | $R^{2c}$ | $R^{11b}$ | $R^{12b}$ |
| 145-134 | $R^b$ | $R^{1c}$ | $R^{2c}$ | $R^{11b}$ | $R^{12b}$ |
| 145-135 | $R^c$ | $R^{1c}$ | $R^{2c}$ | $R^{11b}$ | $R^{12b}$ |
| 145-136 | $R^a$ | $R^{1a}$ | $R^{2a}$ | $R^{11c}$ | $R^{12b}$ |
| 145-137 | $R^b$ | $R^{1a}$ | $R^{2a}$ | $R^{11c}$ | $R^{12b}$ |
| 145-138 | $R^c$ | $R^{1a}$ | $R^{2a}$ | $R^{11c}$ | $R^{12b}$ |
| 145-139 | $R^a$ | $R^{1b}$ | $R^{2a}$ | $R^{11c}$ | $R^{12b}$ |
| 145-140 | $R^b$ | $R^{1b}$ | $R^{2a}$ | $R^{11c}$ | $R^{12b}$ |
| 145-141 | $R^c$ | $R^{1b}$ | $R^{2a}$ | $R^{11c}$ | $R^{12b}$ |
| 145-142 | $R^a$ | $R^{1c}$ | $R^{2a}$ | $R^{11c}$ | $R^{12b}$ |
| 145-143 | $R^b$ | $R^{1c}$ | $R^{2a}$ | $R^{11c}$ | $R^{12b}$ |
| 145-144 | $R^c$ | $R^{1c}$ | $R^{2a}$ | $R^{11c}$ | $R^{12b}$ |
| 145-145 | $R^a$ | $R^{1a}$ | $R^{2b}$ | $R^{11c}$ | $R^{12b}$ |
| 145-146 | $R^b$ | $R^{1a}$ | $R^{2b}$ | $R^{11c}$ | $R^{12b}$ |
| 145-147 | $R^c$ | $R^{1a}$ | $R^{2b}$ | $R^{11c}$ | $R^{12b}$ |
| 145-148 | $R^a$ | $R^{1b}$ | $R^{2b}$ | $R^{11c}$ | $R^{12b}$ |
| 145-149 | $R^b$ | $R^{1b}$ | $R^{2b}$ | $R^{11c}$ | $R^{12b}$ |
| 145-150 | $R^c$ | $R^{1b}$ | $R^{2b}$ | $R^{11c}$ | $R^{12b}$ |
| 145-151 | $R^a$ | $R^{1c}$ | $R^{2b}$ | $R^{11c}$ | $R^{12b}$ |
| 145-152 | $R^b$ | $R^{1c}$ | $R^{2b}$ | $R^{11c}$ | $R^{12b}$ |
| 145-153 | $R^c$ | $R^{1c}$ | $R^{2b}$ | $R^{11c}$ | $R^{12b}$ |
| 145-154 | $R^a$ | $R^{1a}$ | $R^{2c}$ | $R^{11c}$ | $R^{12b}$ |

-continued

| Formula | R | R¹ | R² | R¹¹ | R¹² |
|---------|---|-----|-----|------|------|
| 145-155 | $R^b$ | $R^{1a}$ | $R^{2c}$ | $R^{11c}$ | $R^{12b}$ |
| 145-156 | $R^c$ | $R^{1a}$ | $R^{2c}$ | $R^{11c}$ | $R^{12b}$ |
| 145-157 | $R^a$ | $R^{1b}$ | $R^{2c}$ | $R^{11c}$ | $R^{12b}$ |
| 145-158 | $R^b$ | $R^{1b}$ | $R^{2c}$ | $R^{11c}$ | $R^{12b}$ |
| 145-159 | $R^c$ | $R^{1b}$ | $R^{2c}$ | $R^{11c}$ | $R^{12b}$ |
| 145-160 | $R^a$ | $R^{1c}$ | $R^{2c}$ | $R^{11c}$ | $R^{12b}$ |
| 145-161 | $R^b$ | $R^{1c}$ | $R^{2c}$ | $R^{11c}$ | $R^{12b}$ |
| 145-162 | $R^c$ | $R^{1c}$ | $R^{2c}$ | $R^{11c}$ | $R^{12b}$ |
| 145-163 | $R^a$ | $R^{1a}$ | $R^{2a}$ | $R^{11a}$ | $R^{12c}$ |
| 145-164 | $R^b$ | $R^{1a}$ | $R^{2a}$ | $R^{11a}$ | $R^{12c}$ |
| 145-165 | $R^c$ | $R^{1a}$ | $R^{2a}$ | $R^{11a}$ | $R^{12c}$ |
| 145-166 | $R^a$ | $R^{1b}$ | $R^{2a}$ | $R^{11a}$ | $R^{12c}$ |
| 145-167 | $R^b$ | $R^{1b}$ | $R^{2a}$ | $R^{11a}$ | $R^{12c}$ |
| 145-168 | $R^c$ | $R^{1b}$ | $R^{2a}$ | $R^{11a}$ | $R^{12c}$ |
| 145-169 | $R^a$ | $R^{1c}$ | $R^{2a}$ | $R^{11a}$ | $R^{12c}$ |
| 145-170 | $R^b$ | $R^{1c}$ | $R^{2a}$ | $R^{11a}$ | $R^{12c}$ |
| 145-171 | $R^c$ | $R^{1c}$ | $R^{2a}$ | $R^{11a}$ | $R^{12c}$ |
| 145-172 | $R^a$ | $R^{1a}$ | $R^{2b}$ | $R^{11a}$ | $R^{12c}$ |
| 145-173 | $R^b$ | $R^{1a}$ | $R^{2b}$ | $R^{11a}$ | $R^{12c}$ |
| 145-174 | $R^c$ | $R^{1a}$ | $R^{2b}$ | $R^{11a}$ | $R^{12c}$ |
| 145-175 | $R^a$ | $R^{1b}$ | $R^{2b}$ | $R^{11a}$ | $R^{12c}$ |
| 145-176 | $R^b$ | $R^{1b}$ | $R^{2b}$ | $R^{11a}$ | $R^{12c}$ |
| 145-177 | $R^c$ | $R^{1b}$ | $R^{2b}$ | $R^{11a}$ | $R^{12c}$ |
| 145-178 | $R^a$ | $R^{1c}$ | $R^{2b}$ | $R^{11a}$ | $R^{12c}$ |
| 145-179 | $R^b$ | $R^{1c}$ | $R^{2b}$ | $R^{11a}$ | $R^{12c}$ |
| 145-180 | $R^c$ | $R^{1c}$ | $R^{2b}$ | $R^{11a}$ | $R^{12c}$ |
| 145-181 | $R^a$ | $R^{1a}$ | $R^{2c}$ | $R^{11a}$ | $R^{12c}$ |
| 145-182 | $R^b$ | $R^{1a}$ | $R^{2c}$ | $R^{11a}$ | $R^{12c}$ |
| 145-183 | $R^c$ | $R^{1a}$ | $R^{2c}$ | $R^{11a}$ | $R^{12c}$ |
| 145-184 | $R^a$ | $R^{1b}$ | $R^{2c}$ | $R^{11a}$ | $R^{12c}$ |
| 145-185 | $R^b$ | $R^{1b}$ | $R^{2c}$ | $R^{11a}$ | $R^{12c}$ |
| 145-186 | $R^c$ | $R^{1b}$ | $R^{2c}$ | $R^{11a}$ | $R^{12c}$ |
| 145-187 | $R^a$ | $R^{1c}$ | $R^{2c}$ | $R^{11a}$ | $R^{12c}$ |
| 145-188 | $R^b$ | $R^{1c}$ | $R^{2c}$ | $R^{11a}$ | $R^{12c}$ |
| 145-189 | $R^c$ | $R^{1c}$ | $R^{2c}$ | $R^{11a}$ | $R^{12c}$ |
| 145-190 | $R^a$ | $R^{1a}$ | $R^{2a}$ | $R^{11b}$ | $R^{12c}$ |
| 145-191 | $R^b$ | $R^{1a}$ | $R^{2a}$ | $R^{11b}$ | $R^{12c}$ |
| 145-192 | $R^c$ | $R^{1a}$ | $R^{2a}$ | $R^{11b}$ | $R^{12c}$ |
| 145-193 | $R^a$ | $R^{1b}$ | $R^{2a}$ | $R^{11b}$ | $R^{12c}$ |
| 145-194 | $R^b$ | $R^{1b}$ | $R^{2a}$ | $R^{11b}$ | $R^{12c}$ |
| 145-195 | $R^c$ | $R^{1b}$ | $R^{2a}$ | $R^{11b}$ | $R^{12c}$ |
| 145-196 | $R^a$ | $R^{1c}$ | $R^{2a}$ | $R^{11b}$ | $R^{12c}$ |
| 145-197 | $R^b$ | $R^{1c}$ | $R^{2a}$ | $R^{11b}$ | $R^{12c}$ |
| 145-198 | $R^c$ | $R^{1c}$ | $R^{2a}$ | $R^{11b}$ | $R^{12c}$ |
| 145-199 | $R^a$ | $R^{1a}$ | $R^{2b}$ | $R^{11b}$ | $R^{12c}$ |
| 145-200 | $R^b$ | $R^{1a}$ | $R^{2b}$ | $R^{11b}$ | $R^{12c}$ |
| 145-201 | $R^c$ | $R^{1a}$ | $R^{2b}$ | $R^{11b}$ | $R^{12c}$ |
| 145-202 | $R^a$ | $R^{1b}$ | $R^{2b}$ | $R^{11b}$ | $R^{12c}$ |
| 145-203 | $R^b$ | $R^{1b}$ | $R^{2b}$ | $R^{11b}$ | $R^{12c}$ |
| 145-204 | $R^c$ | $R^{1b}$ | $R^{2b}$ | $R^{11b}$ | $R^{12c}$ |
| 145-205 | $R^a$ | $R^{1c}$ | $R^{2b}$ | $R^{11b}$ | $R^{12c}$ |
| 145-206 | $R^b$ | $R^{1c}$ | $R^{2b}$ | $R^{11b}$ | $R^{12c}$ |
| 145-207 | $R^c$ | $R^{1c}$ | $R^{2b}$ | $R^{11b}$ | $R^{12c}$ |
| 145-208 | $R^a$ | $R^{1a}$ | $R^{2c}$ | $R^{11b}$ | $R^{12c}$ |
| 145-209 | $R^b$ | $R^{1a}$ | $R^{2c}$ | $R^{11b}$ | $R^{12c}$ |
| 145-210 | $R^c$ | $R^{1a}$ | $R^{2c}$ | $R^{11b}$ | $R^{12c}$ |
| 145-211 | $R^a$ | $R^{1b}$ | $R^{2c}$ | $R^{11b}$ | $R^{12c}$ |
| 145-212 | $R^b$ | $R^{1b}$ | $R^{2c}$ | $R^{11b}$ | $R^{12c}$ |
| 145-213 | $R^c$ | $R^{1b}$ | $R^{2c}$ | $R^{11b}$ | $R^{12c}$ |
| 145-214 | $R^a$ | $R^{1c}$ | $R^{2c}$ | $R^{11b}$ | $R^{12c}$ |
| 145-215 | $R^b$ | $R^{1c}$ | $R^{2c}$ | $R^{11b}$ | $R^{12c}$ |
| 145-216 | $R^c$ | $R^{1c}$ | $R^{2c}$ | $R^{11b}$ | $R^{12c}$ |
| 145-217 | $R^a$ | $R^{1a}$ | $R^{2a}$ | $R^{11c}$ | $R^{12c}$ |
| 145-218 | $R^b$ | $R^{1a}$ | $R^{2a}$ | $R^{11c}$ | $R^{12c}$ |
| 145-219 | $R^c$ | $R^{1a}$ | $R^{2a}$ | $R^{11c}$ | $R^{12c}$ |
| 145-220 | $R^a$ | $R^{1b}$ | $R^{2a}$ | $R^{11c}$ | $R^{12c}$ |
| 145-221 | $R^b$ | $R^{1b}$ | $R^{2a}$ | $R^{11c}$ | $R^{12c}$ |
| 145-222 | $R^c$ | $R^{1b}$ | $R^{2a}$ | $R^{11c}$ | $R^{12c}$ |
| 145-223 | $R^a$ | $R^{1c}$ | $R^{2a}$ | $R^{11c}$ | $R^{12c}$ |
| 145-224 | $R^b$ | $R^{1c}$ | $R^{2a}$ | $R^{11c}$ | $R^{12c}$ |
| 145-225 | $R^c$ | $R^{1c}$ | $R^{2a}$ | $R^{11c}$ | $R^{12c}$ |
| 145-226 | $R^a$ | $R^{1a}$ | $R^{2b}$ | $R^{11c}$ | $R^{12c}$ |
| 145-227 | $R^b$ | $R^{1a}$ | $R^{2b}$ | $R^{11c}$ | $R^{12c}$ |
| 145-228 | $R^c$ | $R^{1a}$ | $R^{2b}$ | $R^{11c}$ | $R^{12c}$ |
| 145-229 | $R^a$ | $R^{1b}$ | $R^{2b}$ | $R^{11c}$ | $R^{12c}$ |
| 145-230 | $R^b$ | $R^{1b}$ | $R^{2b}$ | $R^{11c}$ | $R^{12c}$ |
| 145-231 | $R^c$ | $R^{1b}$ | $R^{2b}$ | $R^{11c}$ | $R^{12c}$ |
| 145-232 | $R^a$ | $R^{1c}$ | $R^{2b}$ | $R^{11c}$ | $R^{12c}$ |
| 145-233 | $R^b$ | $R^{1c}$ | $R^{2b}$ | $R^{11c}$ | $R^{12c}$ |
| 145-234 | $R^c$ | $R^{1c}$ | $R^{2b}$ | $R^{11c}$ | $R^{12c}$ |
| 145-235 | $R^a$ | $R^{1a}$ | $R^{2c}$ | $R^{11c}$ | $R^{12c}$ |
| 145-236 | $R^b$ | $R^{1a}$ | $R^{2c}$ | $R^{11c}$ | $R^{12c}$ |
| 145-237 | $R^c$ | $R^{1a}$ | $R^{2c}$ | $R^{11c}$ | $R^{12c}$ |
| 145-238 | $R^a$ | $R^{1b}$ | $R^{2c}$ | $R^{11c}$ | $R^{12c}$ |
| 145-239 | $R^b$ | $R^{1b}$ | $R^{2c}$ | $R^{11c}$ | $R^{12c}$ |
| 145-240 | $R^c$ | $R^{1b}$ | $R^{2c}$ | $R^{11c}$ | $R^{12c}$ |
| 145-241 | $R^a$ | $R^{1c}$ | $R^{2c}$ | $R^{11c}$ | $R^{12c}$ |
| 145-242 | $R^b$ | $R^{1c}$ | $R^{2c}$ | $R^{11c}$ | $R^{12c}$ |
| 145-243 | $R^c$ | $R^{1c}$ | $R^{2c}$ | $R^{11c}$ | $R^{12c}$ | where all symbols are as defined above.

In one aspect of formula (145) of the present invention, R is hydrogen, a hydroxy group, a halogen, a nitro group, an optionally substituted amino group, an alkyl group, an alkoxy group, an alkenyl group, or an alkoxyalkyl group; $R^1$ and $R^2$ independently are hydrogen, a hydroxy group, a halogen, a nitro group, a carboxy group, a carbamoyl group, an optionally substituted amino group, an alkyl group, a cycloalkyl group, an alkoxy group, a cycloalkoxy group, an alkenyl group, a cycloalkenyl group, an alkoxyalkyl group, an alkenyloxy group, or a cycloalkenyloxy group; and $R^{11}$ and $R^{12}$ independently are hydrogen, a halogen, a nitro group, an amino group, a mono- or di-substituted amino group, a hydroxy group, an alkoxy group, a carboxy group, a cyano group, an oxo(O=) group, or a thio(S=) group, an alkyl group, or a cycloalkyl group, an alkoxy group.

In another aspect of formula (145) of the present invention, R is hydrogen or an alkyl group; $R^1$ and $R^2$ independently are hydrogen, a hydroxy group, a halogen, an alkoxy group; and $R^{11}$ and $R^{12}$ independently are hydrogen, a halogen, a hydroxy group, or an alkoxy group.

In yet another aspect of formula (145) of the present invention, R is —H or $C_2H_5$; $R^1$ and $R^2$ are —$OCH_3$; and $R^{11}$ and $R^{12}$ independently are —H, —F, or $CH_3$.

The present invention still further contemplates various compounds of general formula (V) having the formula:

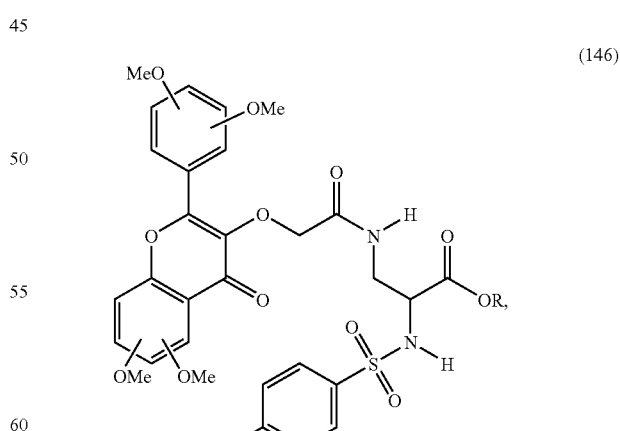

(146)

where R is as defined above in connection with formula (I).

In one aspect of formula (146) of the present invention, R is hydrogen, a hydroxy group, a halogen, a nitro group, or an optionally substituted amino group.

In another aspect of formula (146) of the present invention, R is an alkyl group, an alkoxy group, an alkenyl group, or an alkoxyalkyl group.

In yet another aspect of formula (146) of the present invention, R is a cycloalkenyloxy group, an acyl group, an aryl group, an aralkyl group, a heterocyclyl group, or a heteroaryl group.

In still another aspect of formula (146) of the present invention, R is —H or an alkyl group.

In still another aspect of formula (146) of the present invention, R is —H or $C_2H_5$.

Additional examples of compounds having general formula (V) include, but are not limited to:

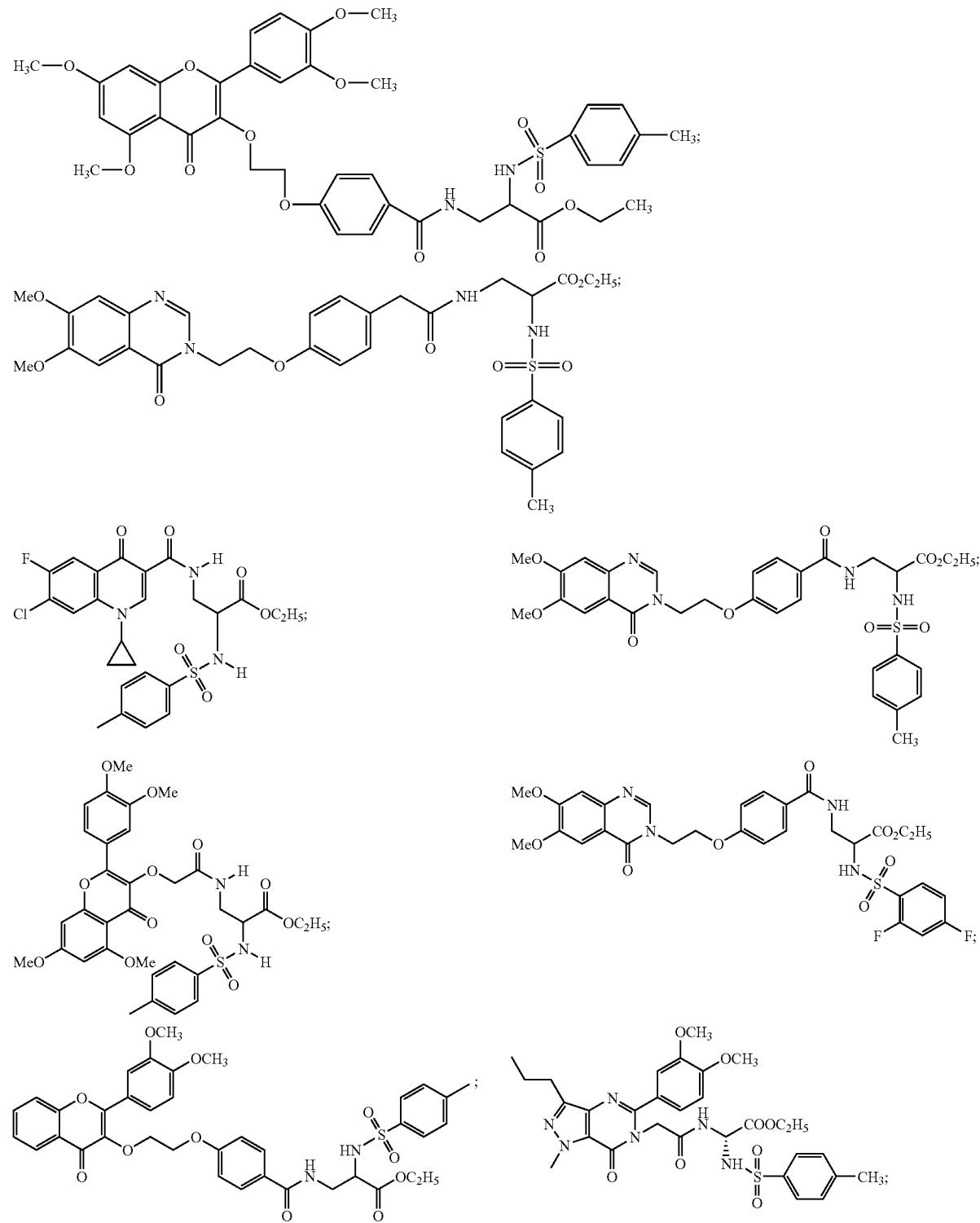

-continued
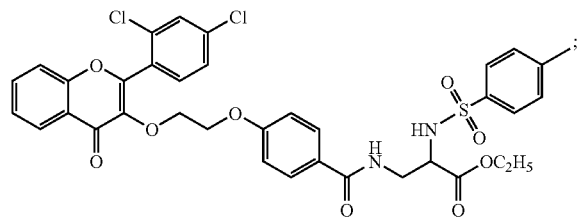;
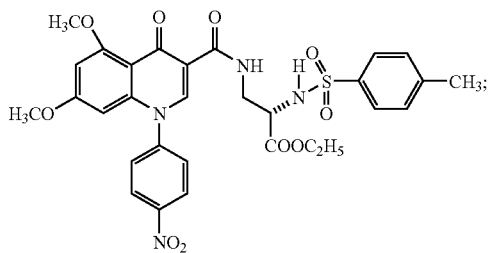;
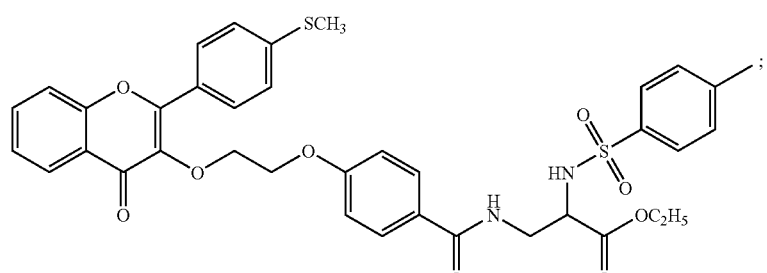;
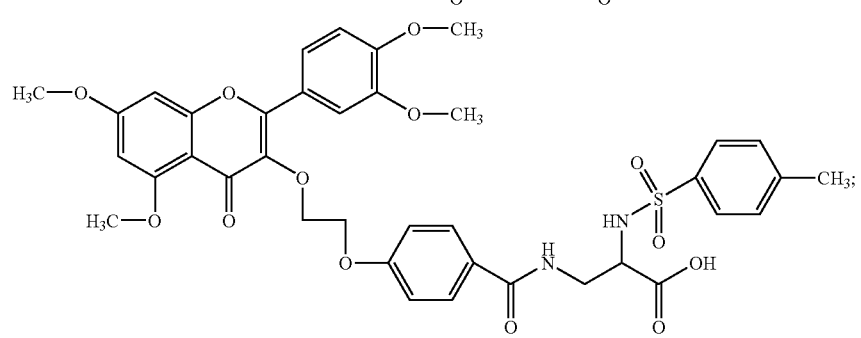;
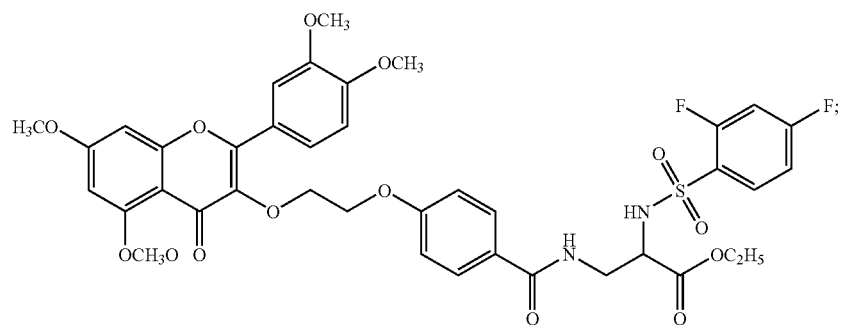;
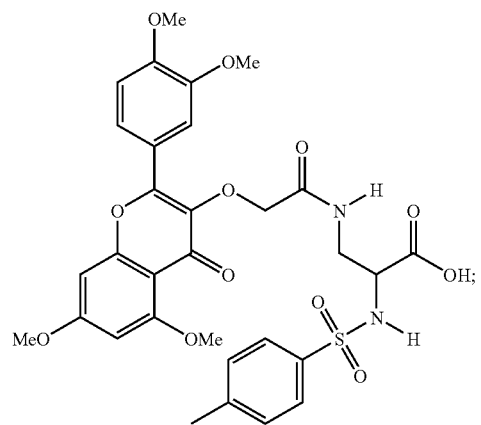;

-continued

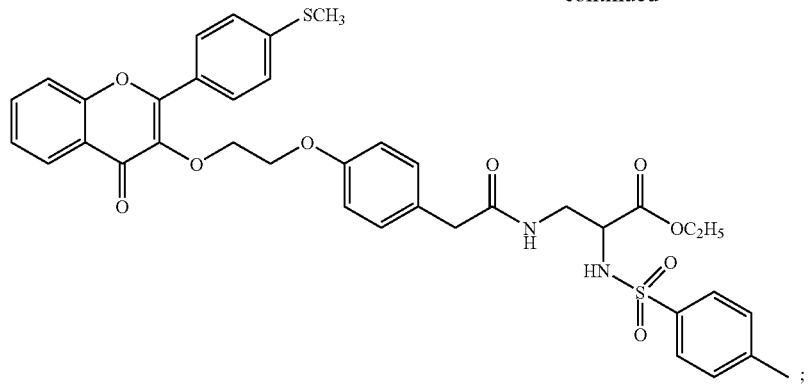

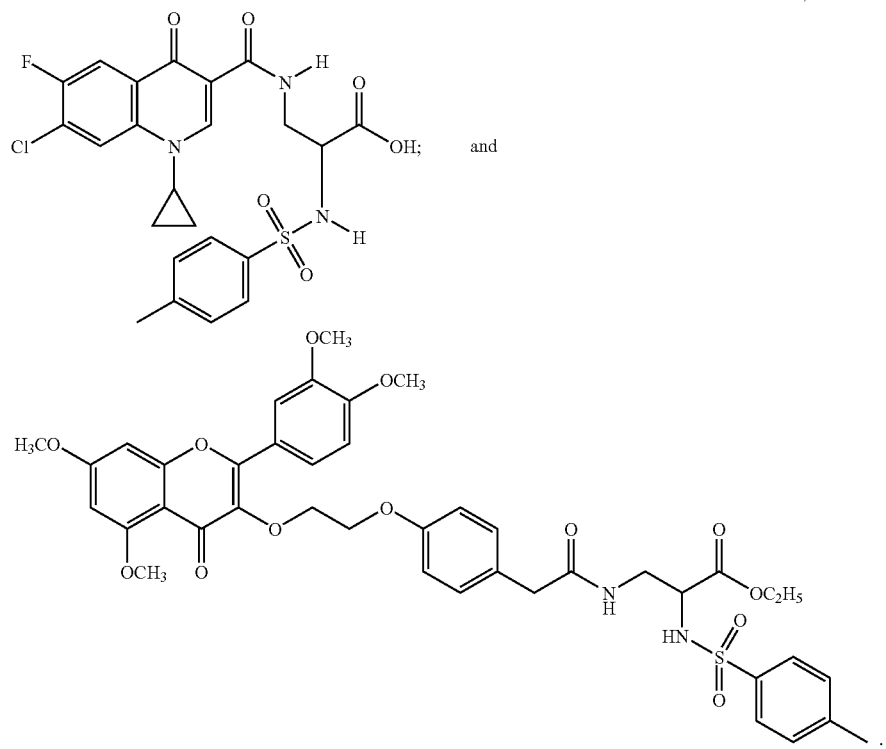

It is contemplated that any compound shown or described herein, including compounds of the various formulae shown or described above, may be provided as a pharmaceutically acceptable salt. Pharmaceutically acceptable salts forming part of this invention include salts derived from inorganic bases such as Li, Na, K, Ca, Mg, Fe, Cu, Zn, Mn; salts of organic bases such as N,N'-diacetylethylenediamine, betaine, caffeine, 2-diethylaminoethanol, 2-dimethylaminoethanol, N-ethylmorpholine, N-ethylpiperidine, glucamine, glucosamine, hydrabamine, isopropylamine, methylglucamine, morpholine, piperazine, piperidine, procaine, purines, theobromine, triethylamine, trimethylamine, tripropylamine, tromethamine, diethanolamine, meglumine, ethylenediamine, N,N'-diphenylethylenediamine, N,N'-dibenzylethylenediamine, N-benzyl phenylethylamine, choline, choline hydroxide, dicyclohexylamine, metformin, benzylamine, phenylethylamine, dialkylamine, trialkylamine, thiamine, aminopyrimidine, aminopyridine, purine, or spermidine; chiral bases like alkylphenylamine, glycinol, or phenyl glycinol; salts of natural amino acids such as glycine, alanine, valine, leucine, isoleucine, norleucine, tyrosine, cystine, cysteine, methionine, proline, hydroxy proline, histidine, ornithine, lysine, arginine, serine, threonine, phenylalanine; unnatural amino acids such as D-isomers or substituted amino acids; guanidine, substituted guanidine wherein the substituents are selected from nitro, amino, alkyl, alkenyl, or alkynyl; ammonium or substituted ammonium salts and aluminum salts. Salts may include acid addition salts where appropriate which are, sulphates, nitrates, phosphates, perchlorates, borates, hydrohalides, acetates, tartrates, maleates, citrates, succinates, palmoates, methanesulphonates, benzoates, salicylates, hydroxynaphthoates, benzenesulfonates, ascorbates, glycerophosphates, ketoglutarates. Pharmaceutically acceptable solvates may be hydrates or may comprise other solvents of crystallization such as alcohols.

Processes for Preparing the Compounds

The compounds of the present invention can be prepared according to the following processes. However, it should be understood that other processes having other process conditions may be used to form the compounds of the present invention.

Process 1

According to one aspect of the present invention, a process for preparing a compound of general formula (II)

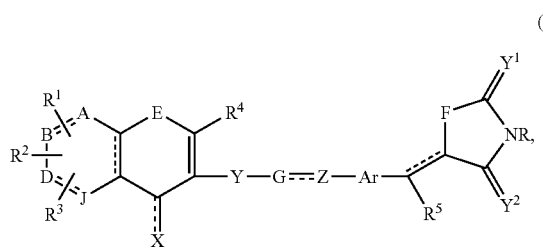
(II)

where $R^1$ is attached to B; $R^2$ is attached to J; $R^3$ is —H; A, B, D and J independently are —CH; $R^1$ and $R^2$ independently are an alkoxy group or an aralkoxy group; $R^4$ is a phenyl group optionally substituted with an alkoxy group or an aralkoxy group at the third position and/or fourth position respectively; X and E are each O, G is —$(CH_2)_s$—, —$(CH_2)_s$—CH=CH—$(CH_2)_s$—, or —$(CH_2)_s$—CH=CH—$(CH_2)_s$—, where s is an integer from 0-5; F is O, S or —NR; Y and Z independently are O, —NR, —$(CH_2)_n$—, or $S(=O)_n$, where n is an integer from 0-2; $Y^1$ and $Y^2$ independently are O or S; R and $R^5$ independently are hydrogen, a hydroxy group, a halogen, a nitro group, an optionally substituted amino group, an alkyl group, an alkoxy group, an alkenyl group, an alkoxyalkyl group, a cycloalkenyloxy group, an acyl group, an aryl group, an aralkyl group, a heterocyclyl group or a heteroaryl group; and 'Ar' is an optionally substituted phenyl group or an optionally substituted naphthyl group is provided.

The process comprises first alkylating the Rutin hydrate of formula (IIa)

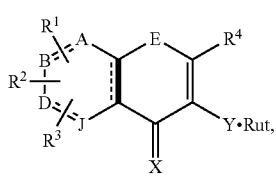
(IIa)

where 'Rut' is rutinose; $R^1$ is attached to B; $R^2$ is attached to J; $R^3$ is H; A, B, D and J independently are —CH, $R^1$ and $R^2$ independently are a hydroxy group; $R^4$ is a phenyl group optionally substituted with a hydroxy group at the third and/or fourth positions; X, Y, and E are O; and ' - - - ' is an optional chemical bond;

to a compound of formula (IIa), where $R^1$ is attached to B; $R^2$ is attached to J; $R^3$ is H; A, B, D and J independently are —CH; $R^1$ and $R^2$ independently are an alkoxy group or an aryloxy group; $R^4$ is a phenyl group optionally substituted with an alkoxy group or an aralkoxy group at the third and fourth positions; X, Y, and E are O; and all other symbols are as defined above.

The alkylation is carried out using an alkyl halide alkylating or aralkylating agent. Examples of agents that may be suitable include MeI, EtI, EtBr, n-PrI, n-PrBr, i-PrBr, i-PrI, n-BuCl, or s-BuBr; a dialkylsulphate such as dimethylsulphate or diethylsulphate; or an aralkyl halide such as benzyl halide. The reaction may be carried out in the presence of an alkali, for example, sodiumhydride (NaH), potassiumhydride (KH), potassium tertiary butoxide (t-BuOK), potassium acetate (KOAc), sodium acetate (NaOAc), n-butyl lithium (n-BuLi), sec-butyl lithium (s-BuLi), tert butyl lithium (t-BuLi), lithium diisopropyl amide (LDA), sodium carbonate ($Na_2CO_3$), potassium carbonate ($K_2CO_3$), sodium bicarbonate ($NaHCO_3$), potaasium bicarbonate ($KHCO_3$), sodium hydroxide (NaOH), potassium hydroxide (KOH), or any mixture thereof. The solvent used is, for example, dimethylformamide (DMF), dimethylsulfoxide (DMSO), hexametaphosphoric acid (HMPA), 1,4-dioxane, acetone, dimethyl ether, diethyl ether, tetrahydrofuran (THF), or any mixture thereof.

According to one aspect of the invention, the reaction temperature may be from about –30° C. to about 250° C., for example, from about 30° C. to about 100° C. The duration of the reaction may be from about 0.5 hours to about 100 hours, for example, from about 20 hours to about 80 hours. The reaction may be carried out under an inert atmosphere of, for example, nitrogen ($N_2$), argon (Ar), or helium (He).

Next, the compound of formula (IIa) is hydrolysed to a compound of formula (IIb)

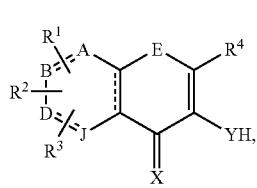
(IIb)

where $R^1$ is attached to B; $R^2$ is attached to J; $R^3$ is H; A, B, D and J independently are —CH; $R^1$ and $R^2$ independently are an alkoxy group or an aralkoxy group; $R^4$ is a phenyl group optionally substituted with an alkoxy group or an aralkoxy group at the third and fourth positions; X, Y, and E are O; and all other symbols are as defined above.

The hydrolysis is optionally carried out using an inorganic acid, such as hydrochloric acid (HCl), sulfuric acid ($H_2SO_4$), or a mixture thereof with water. The reaction temperature may be maintained at from about –30° C. to about 250° C., for example, from about 50° C. to about 150° C. The duration of the reaction may be from about 0.5 hours to about 100 hours, for example, from about 1 hour to about 50 hours.

Next, the compound of formula (IIb) is reacted with a compound of formula (IIc),

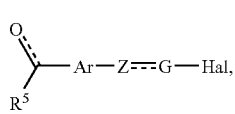
(IIc)

where 'Hal' is a halogen; 'Ar', G, Z and $R^5$ are as defined above; and ' - - - ' is an optional chemical bond, to obtain a compound of formula (IId)

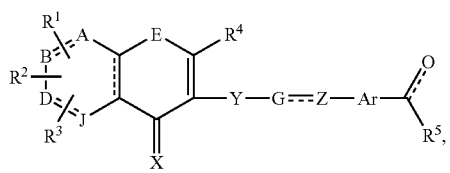

(IId)

where R is attached to B; $R^2$ is attached to J; $R^3$ is H; A, B, D, and J independently are —CH; $R^1$ and $R^2$ independently are an alkoxy group or an aralkoxy group; $R^4$ is a phenyl group optionally substituted with an alkoxy group or an aralkoxy group at the third and fourth positions; and all other symbols are as defined above.

This reaction is carried out in the presence of a base, for example, NaH, KH, KOtBu, KOAc, NaOAc, NaOEt, KOEt, n-BuLi, s-BuLi, t-BuLi, LDA, $Na_2CO_3$, $K_2CO_3$, $NaHCO_3$, $KHCO_3$, NaOH, or KOH. The reaction is optionally carried out in the presence of a solvent, for example, DMF, DMSO, HMPA, 1,4-dioxane, acetone, dimethyl ether, diethyl ether, THF, or any mixture thereof. The reaction temperature may be maintained at from about −30° C. to 150° C., for example, from about 30° C. to about 100° C. The duration of the reaction may be from about 1 hour to about 50 hours, for example, from about 2 hours to about 25 hours. The reaction may be carried out under an inert atmosphere of $N_2$, Ar, or He.

Lastly, the compound of formula (IId) is condensed with a compound of formula (IIe),

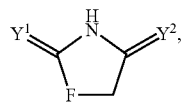

(IIe)

where F, $Y^1$, and $Y^2$ are as defined above, to obtain a compound of formula (II)

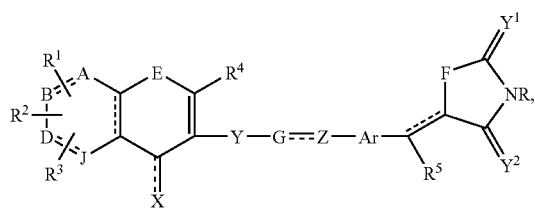

(II)

where all symbols are as defined above.

The condensation may be carried out using a base, for example, $Et_3N$, diethylamine, diisopropylethyl amine, diisopropyl amine, DBU, piperidine, or any mixture thereof. The reaction may be carried out in the presence of an acid, for example, benzoic acid, formic acid, acetic acid, or any mixture thereof. The reaction may be carried out in the presence of a solvent, for example, benzene, toluene, xylene, ethanol, i-propanol, bytanol, DMF, DMSO, 1,4-dioxane, or any mixture thereof. The reaction may be maintained at a temperature of from about 30° C. to about 300° C., for example, from about 50° C. to about 200° C. The duration of the reaction may be from about 10 hours to about 150 hours, for example, from about 20 hours to about 80 hours. The reaction may be carried out under an inert atmosphere of $N_2$, Ar, or He.

Process 2

According to another aspect of the present invention, a process for preparing a compound of formula (II) is provided. All symbols are as defined above, except that X and E are O.

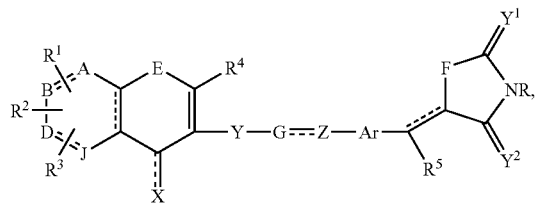

(II)

First, a compound of formula (IIf)

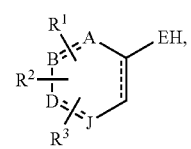

(IIf)

where X and E are O; and all other symbols are as defined above, is acylated to a compound of formula (IIg)

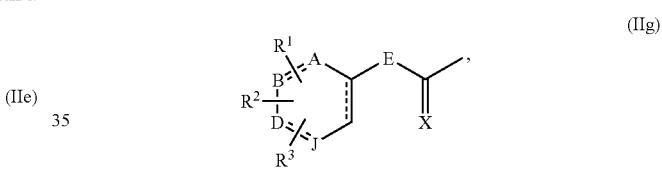

(IIg)

The acylation may be carried out by using an acylating agent such as, for example, acetic anhydride. The reaction is optionally carried out in the presence of a base such as, for example, $Na_2CO_3$, $K_2CO_3$, $NaHCO_3$, $KHCO_3$, NaOH, KOH, or any mixture thereof. The reaction may be maintained at a temperature of from about −30° C. to about 150° C., for example, from about 10° C. to about 50° C. The duration of the reaction may be from about 10 minutes to about 5 hours, for example, from about 20 minutes to about 2 hours.

The compound of formula (IIg) is then rearranged to a compound of formula (IIh)

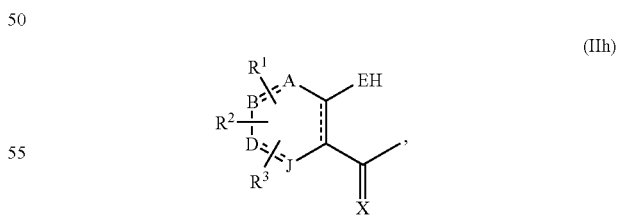

(IIh)

where X and E are O; and all other symbols are as defined above. This reaction is optionally carried out in the presence of a solvent, for example, DCM, $CHCl_3$, 1,2-dichloroethane, carbon tetrachloride, carbon disulfide, nitrobenzene, 1,2-dichlorobenzene, or any mixture thereof. The reaction may be carried out in the presence of a Lewis acid, such as aluminium chloride ($AlCl_3$), zinc chloride ($ZnCl_2$), or tin chloride ($SnCl_4$), or in the presence of UV light. The reaction temperature may be maintained at from about 50° C. to about 300° C., for example, from about 80° C. to about 200° C. The duration of the reaction may be from about 10 minutes to about 50 hours, for example, from about 20 minutes to about 10 hours. The reaction may be carried out under anhydrous reaction conditions.

The compound of formula (IIh) is then condensed to a compound of formula (IIi)

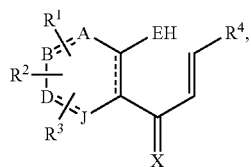
(IIi)

where X and E represent O and all other symbols are as defined above. The reaction is carried out in the presence of a base, for example, $Na_2CO_3$, $K_2CO_3$, $NaHCO_3$, $KHCO_3$, NaOH, KOH, or any mixture thereof. The reaction temperature may be maintained at from about −30° C. to about 50° C., for example, from about 0° C. to about 20° C. The duration of the reaction may be from about 2 hours to about 50 hours, for example, from about 5 hours to about 20 hours.

The compound of formula (IIi) then undergoes a cyclization reaction to form a compound of formula (IIb)

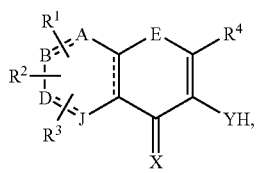
(IIb)

where all symbols are as defined above. This reaction is carried out using a base, for example, $Na_2CO_3$, $K_2CO_3$, $NaHCO_3$, $KHCO_3$, NaOH, KOH, or any mixture thereof. The reaction temperature may be maintained at from about −30° C. to about 50° C., for example, from about −5° C. to about 30° C. The duration of the reaction may be from about 0.5 hours to about 10 hours, for example, from about 0.2 hours to about 5 hours.

The compound of formula (IIb) is then reacted with a compound of formula (IIc)

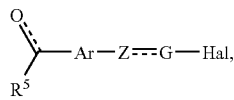
(IIc)

where 'Hal' is a halogen; and all other symbols are as defined above, to obtain a compound of formula (IId)

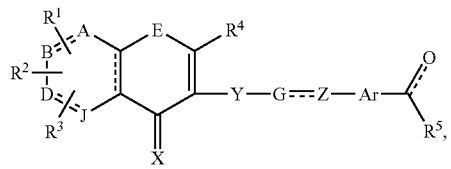
(IId)

where all symbols are as defined above.

The compound of formula (IId) is then reacted with a compound of formula (IIe)

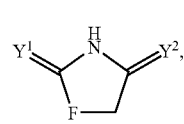
(IIe)

where F is O, S, or —NR; $Y^1$ and $Y^2$ independently are O or S, to obtain a compound of formula (II)

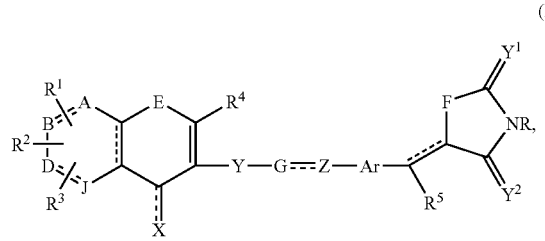
(II)

where E and X are O; and all other symbols are as defined above.

The conversion of compound of formula (IIb) to compound of formula (II) is carried out as provided in Process 1.

Process 3

According to another aspect of the present invention, a process for preparing a compound of formula (II) is provided,

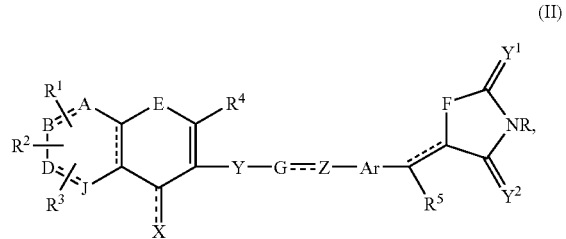
(II)

where X is O, E is —NR, and all other symbols are as defined above.

First a compound of formula (IIj)

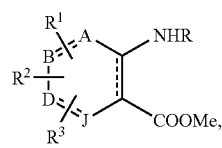
(IIj)

where all symbols are as defined above, is converted to a compound of formula (IIk),

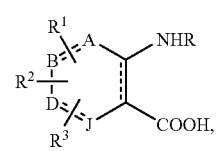
(IIk)

where all symbols are as defined above. This reaction may be carried out using a base, for example, $Na_2CO_3$, $K_2CO_3$, NaHCO$_3$, KHCO$_3$, NaOH, KOH, or any mixture thereof. The reaction may be carried out in the presence of a solvent, for example, benzene, toluene, xylene, methanol, ethanol, i-propanol, butanol, DMF, DMSO, 1,4-dioxane, or any mixture thereof. The reaction temperature may be maintained at from about −30° C. to about 150° C., for example, from about 20° C. to about 80° C. The duration of the reaction may be from about 0.5 hours to about 20 hours, for example, from about 2 hours to about 10 hours.

The compound of formula (IIk) is then reacted with a compound of formula (IIm)

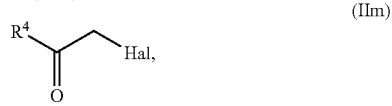

(IIm)

where 'Hal' is a halogen, and R$^4$ is as defined above, to obtain a compound of formula (IIn)

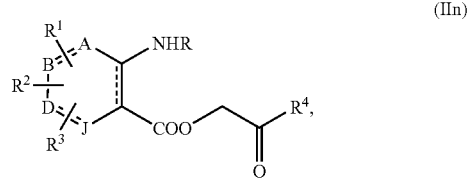

(IIn)

where all symbols are as defined above.

This reaction may occur in the presence of a brominating agent, for example, bromine, bromine water, N-bromosuccinamide, copper bromide, or any mixture thereof. The solvent is acetic acid, propanoic acid, butanoic acid, pentanoic acid, hexanoic acid, dichloromethane (DCM), chloroform (CHCl$_3$), 1,2-dichloroethane, carbon tetrachloride, methanol, ethanol, propanol, butanol, or any mixture thereof. The reaction may be carried out in the presence of catalytic amount of hydrobromic acid. The reaction temperature may be from about −10° C. to about 150° C., for example, from about 0° C. to about 40° C. The duration of the reaction may be from about 1 hour to about 72 hours, for example, from about 1 hour to about 20 hours.

Alternatively, the reaction may be carried out in the presence of a solvent, for example, acetonitrile, DMF, DMSO, DCM, CHCl$_3$, 1,2-dichloroethane, carbon tetrachloride, methanol, ethanol, propanol, butanol, HMPA, 1,4-dioxane, acetone, dimethyl ether, diethyl ether, THF, water, or any mixture thereof. The reaction may be carried out in the presence of a base, for example, NaH, KH, KO$^t$Bu, KOAc, NaOAc, n-BuLi, s-BuLi, t-BuLi, LDA, Na$_2$CO$_3$, K$_2$CO$_3$, NaHCO$_3$, KHCO$_3$, NaOH, KOH, an amine base such as Et$_3$N, diethyl amine, diisopropylethyl amine, diisopropyl amine, DBU, or any mixture thereof. The reaction temperature may be from about −78° C. to about 150° C., for example, from about −30° C. to 40° C. The duration of the reaction may vary from about 10 minutes to about 72 hours, for example, from about 30 minutes to about 15 hours. The reaction may be carried out under an inert atmosphere maintained by N$_2$, Ar, or He.

The compound of formula (IIn) is then converted to a compound of formula (IIb)

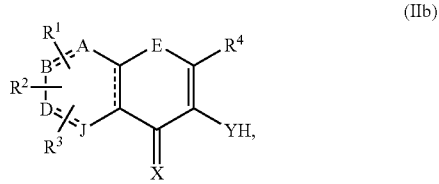

(IIb)

where X is O, E is —NR, and all other symbols are as defined above. This reaction may be carried out using polyphosphoric acid. Optionally, the reaction may be carried out in the presence of a solvent, for example, acetonitrile, DMSO, 1,4-dioxane, THF, water, or any mixture thereof. The reaction temperature may be from about 0° C. to 300° C., for example, from about 50° C. to about 180° C. The duration of the reaction may be from about 10 minutes to about 72 hours, for example, from about 2 to 15 hours. The reaction may be carried out under an inert atmosphere maintained by N$_2$, Ar, or He.

The compound of formula (IIb) is then reacted with a compound of formula (IIc)

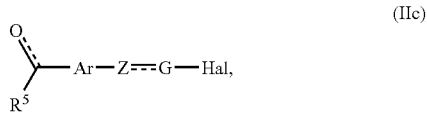

(IIc)

where all symbols are as defined above, to obtain a compound of formula (IId)

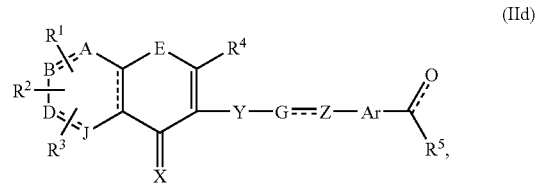

(IId)

where E is —NR, and all other symbols are as defined above.

The compound of formula (IId) is then reacted with a compound of formula (IIe)

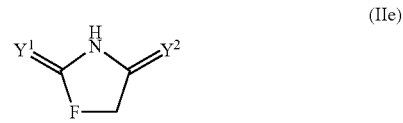

(IIe)

where all symbols are as defined above, to obtain a compound of formula (II)

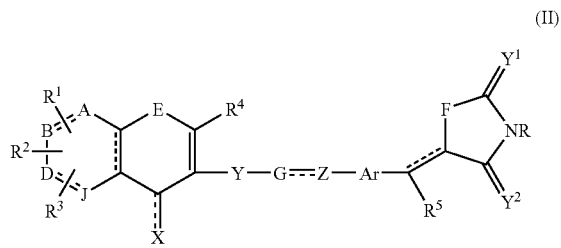

(II)

where X is O, E is —NR, and all other symbols are as defined above.

Process 4

According to another aspect of the present invention, a process for preparing a compound of formula (IV) is provided. The process comprises the following:

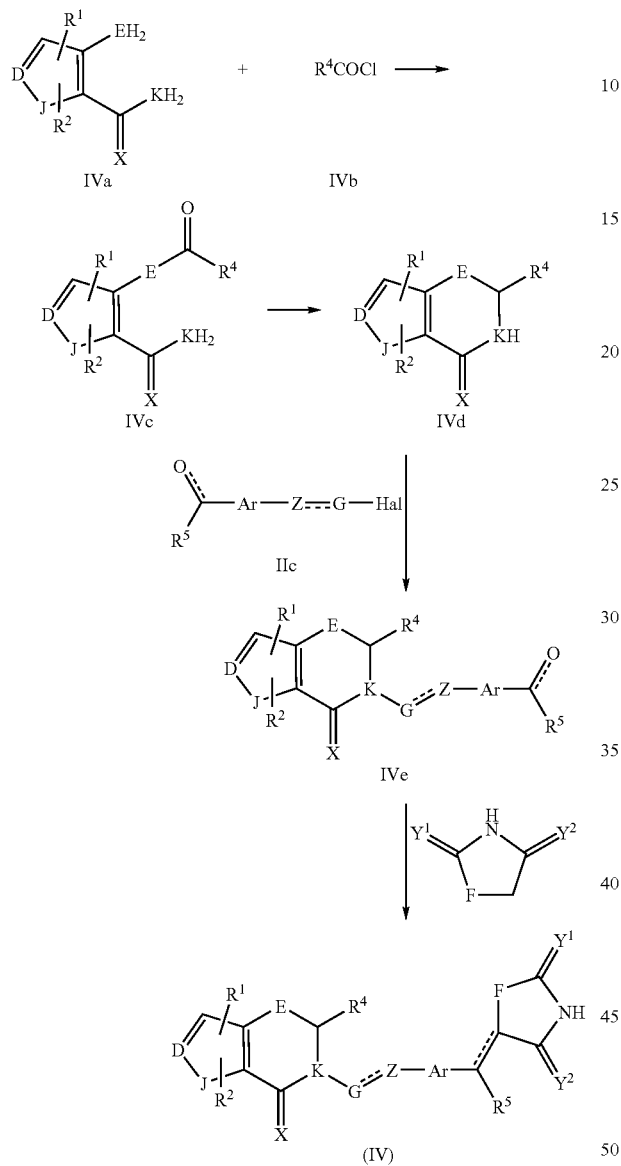

where all symbols are as defined above.

The conversion of a compound of formula (IVa) to a compound of formula of (IVc) may be carried out using an appropriate acylchloride of formula IVb in the presence of a base, for example, $Na_2CO_3$, $K_2CO_3$, $NaHCO_3$, $KHCO_3$, NaOH, KOH, triethyl amine, diisopropylethylamine, or any mixture thereof. The reaction may be carried out in a solvent, for example, benzene, toluene, xylene, DMF, DMSO, 1,4-dioxane, dichloromethane, $CHCl_3$, 1,2-dichloroethane, carbon tetrachloride, or any mixture thereof. The reaction temperature may be maintained at from about $-30°$ C. to about $150°$ C., for example, from about $20°$ C. to about $80°$ C. The duration of the reaction may be from about 6 hours to about 72 hours, for example, from about 2 hours to about 24 hours. The reaction may be carried out under an inert atmosphere of $N_2$, Ar, or He.

The conversion of a compound of formula (IVc) to a compound of (IVd) may be carried out using a base, for example, NaH, KH, KOtBu, KOAc, NaOAc, NaOEt, KOEt, n-BULi, s-BULi, t-BULi, LDA, $Na_2CO_3$, $K_2CO_3$, $NaHCO_3$, $KHCO_3$, NaOH, KOH, or any mixture thereof. The reaction may be carried out in a solvent, for example, benzene, toluene, xylene, methanol, ethanol, i-propanol, t-butanol, or any mixture thereof. The reaction temperature may be maintained at from about $-70°$ C. to about $250°$ C., for example, from about $-10°$ C. to about $150°$ C. The duration of reaction may be from about 5 hours to about 150 hours, for example, from about 20 to about 100 hours. The reaction may be carried out under an inert atmosphere of $N_2$, Ar, or He.

The conversion of compound of formula (IVd) to a compound of formula (IV) may be carried out as provided in Process 1.

Process 5

According to another aspect of the present invention, a process for preparing a compound of formula (Va) is provided. The process comprises:

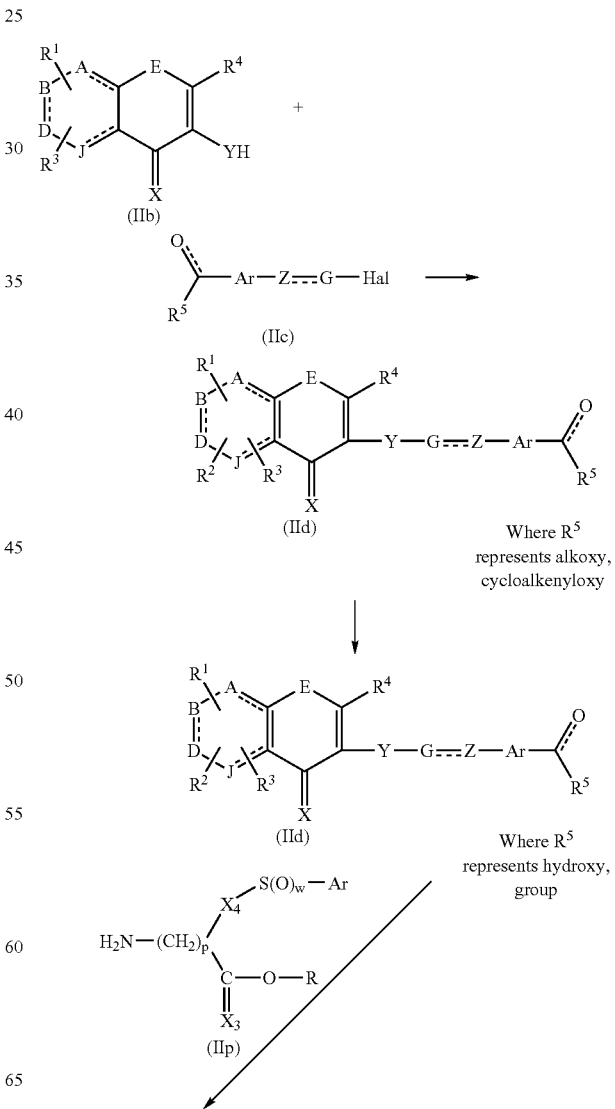

Where $R^5$ represents alkoxy, cycloalkenyloxy

Where $R^5$ represents hydroxy, group

-continued

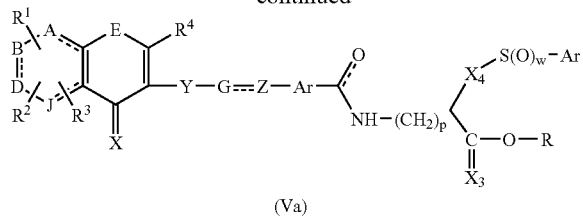

(Va)

The conversion of a compound of formula (IIb) to a compound of formula (IId) may be carried out as provided in Process 1. The conversion of the compound of formula (IId) to a compound of formula (Va) may be carried out by reacting the compound of formula (IId) with compound of formula (IIp) in the presence of a reagent, for example, EDCI or CDI, and a solvent, for example, DMF, chloroform, dichloromethane, dimethylacetamide, tetrahydrofuran, dioxane, ether, or any mixture thereof. The temperature of the reaction may be maintained at from about 10° C. to about 60° C., for example, from about 20° C. to about 35° C. The duration of the reaction may be from about 5 hours to about 12 hours, for example, from about 10 hours to about 12 hours. The reaction may be carried out in a nitrogen atmosphere.

Process 6

According to another aspect of the present invention, a process for preparing a compound of formula (Vb) is provided.

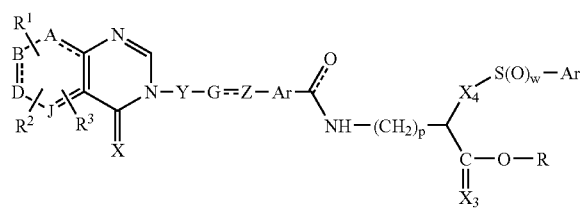

(Vb)

The process comprises:

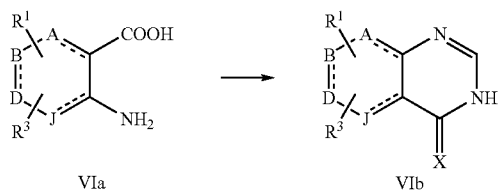

VIa            VIb

The conversion of a compound of formula (VIa) to a compound of formula (VIb) is carried out in the presence of formamide in a nitrogen atmosphere. The temperature of the reaction may be maintained at from about 10° C. to about 70° C., for example, 25° C. to about 45° C. The duration of the reaction may be from about 1 hour to about 9 hours, for example, from about 2 to about 4 hours.

The conversion of the compound of formula (VIb) to a compound of formula (Vb) is carried out as provided in Process 5.

It should be understood that in any of the reactions presented herein, any reactive group on the substrate molecule may be protected according to conventional chemical practice. Suitable protecting groups include, for example, tertiarybutyldimethylsilyl, methoxymethyl, triphenyl methyl, benzyloxycarbonyl, or tetrahydropyran (THP) to protect a hydroxyl or phenolic hydroxy group; N-tert-butoxycarbonyl (N-Boc), N-benzyloxycarbonyl (N—Cbz), N-9-fluorenyl methoxy carbonyl (—N—FMOC), benzophenoneimine, or propargyloxy carbonyl (POC) to protect an amino or anilino group; acetal protection for an aldehyde; and ketal protection for a ketone. The methods of formation and removal of such protecting groups are those conventional methods appropriate to the molecule being protected.

The enantiomers of compound of formula (II) may be prepared by using reactants in their single enantiomeric form in the process wherever applicable or by conducting the reaction in the presence of reagents or catalysts in their single enantiomeric form. The single enantiomers also may be prepared by resolving the racemic mixture by conventional methods.

The stereoisomers of the compounds of the present invention may be prepared by using reactants in their single enantiomeric form in the process, by conducting the reaction in the presence of reagents or catalysts in their single enantiomer form, or by resolving the mixture of stereoisomers by conventional methods. Some of the methods include using microbial resolution, resolving the diastereomeric salts formed with chiral acids such as mandelic acid, camphorsulfonic acid, tartaric acid, or lactic acid, wherever applicable, or chiral bases such as brucine, cinchona alkaloids and their derivatives. Commonly used methods are compiled by JAQUES, ENANTIOMERS, RACEMATES AND RESOLUTION (1981). Where appropriate, the compounds of formula (I) may be resolved by: treating with chiral amines, aminoacids, aminoalcohols derived from aminoacids; employing conventional reaction conditions to convert the acid into an amide; separating the diastereomers by fractional crystallization or chromatography; and preparing the stereoisomers of compound of formula (I) by hydrolyzing the pure diastereomeric amide.

The stereoisomers of the present invention also may include E and Z isomers or their mixtures in various rations.

Formulations and Pharmaceutical Compositions

The present invention provides compounds of general formula (I), pharmaceutical compositions comprising one or more compound of general formula (I), their salts, or their pharmaceutically acceptable compositions, in combination with pharmaceutically acceptable carriers and diluents.

The pharmaceutical compositions of the present invention may be used for the treatment of bacterial infections. They also may be used for the treatment of bacterial infections associated with multi-drug resistance. The pharmaceutical compositions of the present invention also may be used to modulate inflammatory responses, particularly those resulting from AGE and glycated protein accumulation. The pharmaceutical compositions of the present invention also may be used to modulate smooth muscle cell proliferation and the diseases or conditions related thereto. The compositions provided herein also may be used to treat vascular occlusive conditions, such as stenosis, restenosis and atherosclerosis; diseases mediated by inflammation, such as autoimmune diseases; and hyperproliferative diseases, such as cancer.

A. Pharmaceutically Acceptable Salts

The compositions of the present invention optionally include one or more salts of the compounds of the present invention contained therein. Such salts are commonly referred to as non-toxic, "pharmaceutically acceptable salts".

Other salts, however, may be useful in the preparation of the compounds of the present invention or of their pharmaceutically acceptable salts. Suitable pharmaceutically acceptable salts of the compounds of the present invention include acid addition salts that may, for example, be formed by mixing a solution of the compound with a solution of a pharmaceutically acceptable acid, for example, hydrochloric acid, sulfuric acid, fumaric acid, maleic acid, succinic acid, acetic acid, benzoic acid, citric acid, tartaric acid, carbonic acid, phosphoric acid, or any mixture thereof. Furthermore, where the compounds of the invention carry an acidic moiety, suitable pharmaceutically acceptable salts thereof may include alkali metal salts, for example, sodium or potassium salts; alkaline earth salts, for example, calcium or magnesium salts; salts formed with suitable organic ligands, for example, quaternary ammonium salts; or any mixture thereof.

Examples of pharmaceutically acceptable salts include, but are not limited to, acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide, and valerate.

B. Alternative Forms of the Compounds

Where the compounds of the present invention have at least one chiral center, they may accordingly exist as enantiomers. Where the compounds possess two or more chiral centers, they additionally may exist as diastereomers. Where compounds of the present invention have geometrical isomers, it is to be understood that all such isomers and mixtures thereof are encompassed within the scope of the present invention. Furthermore, some of the crystalline forms for the compounds may exist as polymorphs and are contemplated hereby. In addition, some of the compounds may form solvates with water (i.e., hydrates) or common organic solvents, and such solvates are also intended to be encompassed hereby. Where the processes for the preparation of the compounds according to the invention give rise to mixture of stereoisomers, these isomers may be separated by conventional techniques such as preparative chromatography.

Moreover, the compounds of the present invention may be prepared in racemic form. Alternatively, individual enantiomers may be prepared either by enantiospecific synthesis or by resolution. The compounds may be resolved into their component enantiomers by standard techniques, such as the formation of diastereomeric pairs by salt formation with an optically active acid, for example, (+)di-p-toluoyl-d-tartaric acid and/or (+)-di-p-toluoyl-l-tartaric acid, followed by fractional crystallization and regeneration of the free base. The compounds also may be resolved by formation of diastereomeric esters or amides, followed by chromatographic separation and removal of the chiral auxiliary. Alternatively, the compounds may be resolved using a chiral HPLC column.

The compounds of the present invention optionally are formulated and administered as a prodrug. In general, prodrugs comprise functional derivatives of the claimed compounds that are capable of being enzymatically activated or converted into the more active parent form. Thus, in the treatment methods of the present invention, the term "administering" encompasses the treatment of the various disorders described with the compound specifically disclosed or with a compound that may not be specifically disclosed, but that converts to the specified compound in vivo after administration to the patient. Conventional procedures for the selection and preparation of suitable prodrug derivatives are described, for example, in DESIGN OF PRODRUGS (1985); Wihnan, 14 BIOCHEM. SOC. TRANS. 375-82 (1986); STELLA ET AL., Prodrugs: A Chemical Approach to Targeted Drug Delivery in DIRECTED DRUG DELIVERY 247-67 (1985), each of which is incorporated by reference herein in its entirety.

The prodrugs of present invention include, but are not limited to, phosphate-containing prodrugs, thiophosphate-containing prodrugs, sulfate-containing prodrugs, peptide-containing prodrugs, D-amino acid-modified prodrugs, glycosylated prodrugs, β-lactam-containing prodrugs, optionally substituted phenoxyacetamide-containing prodrugs or optionally substituted phenylacetamide-containing prodrugs, 5-fluorocytosine, and other 5-fluorouridine prodrugs that may be converted into the more active drug.

Enzymes that may be used in the methods and compositions of the present invention include, but are not limited to, alkaline phosphatase for converting phosphate-containing prodrugs into free drugs; arylsulfatase for converting sulfate containing prodrugs into free drugs; cytosine deaminase for converting non-toxic 5-fluorocytosine into the anti-cancer drug, 5-fluorouracil; proteases, such as serratia protease, thermolysin, subtilisin, carboxypeptidases, and cathepsins, such as cathepsins B and L, for converting peptide-containing prodrugs into free drugs; D-alanylcarboxypeptidases for converting prodrugs that contain D-amino acid substituents; carbohydrate cleaving enzymes such as β-galactosidase and neuraminidase for converting glycosylated prodrugs into free drugs; β-lactamase for converting drugs derivatized with β-lactams into free drugs; and penicillin amidases, such as penicillin V amidase or penicillin G amidase, for converting drugs derivatized at their amine nitrogens with phenoxyacetyl or phenylacetyl groups, respectively, into free drugs.

Alternatively, antibodies with enzymatic activity, also known in the art as "abzymes", may be used to convert the prodrugs of the present invention into free active drugs. See for example, Massey, 328 NATURE 457-48 (1987).

C. Pharmaceutical Auxiliaries

In addition to the compounds contemplated hereby, the pharmaceutical compositions of the present invention optionally comprise at least one suitable auxiliary or carrier such as, but not limited to, a diluent, binder, stabilizer, buffer, salt, lipophilic solvent, preservative, adjuvant, or any combination thereof. Pharmaceutically acceptable auxiliaries typically are used. Examples and methods of preparing such sterile solutions are described in, for example, REMINGTON'S PHARMACEUTICAL SCIENCES (Gennaro, Ed., 18th Edition, Mack Publishing Co. (1990)), incorporated by reference herein in its entirety. Pharmaceutically acceptable carriers routinely are selected to be suitable for the mode of administration, solubility, and/or stability of the compound.

Pharmaceutical excipients and additives useful in the present invention include, but are not limited to, proteins, peptides, amino acids, lipids, and carbohydrates (for example, sugars, including monosaccharides, di-, tri-, tetra-, and oligosaccharides; derivatized sugars such as alditols, aldonic acids, esterified sugars; and polysaccharides), which can be present singly or in combination, comprising alone or in combination 1-99.99% by weight or volume. Exemplary protein excipients include serum albumin, such as human serum albumin (HSA), recombinant human albumin (rHA), gelatin, casein, or any combination thereof. Representative amino acid components, which also can function in a buffering capacity, include alanine, glycine, arginine, betaine, histidine, glutamic acid, aspartic acid, cysteine, lysine, leucine, isoleucine, valine, methionine, phenylalanine, and aspartame.

Carbohydrate excipients suitable for use in the present invention include, for example, monosaccharides such as fructose, maltose, galactose, glucose, D-mannose, sorbose; disaccharides, such as lactose, sucrose, trehalose, cellobiose; polysaccharides, such as raffinose, melezitose, maltodextrins, dextrans, starches; and alditols, such as mannitol, xylitol, maltitol, lactitol, xylitol sorbitol (glucitol), myoinositol.

The pharmaceutical compositions comprising the compounds of the present invention also can include a buffer or a pH adjusting agent. Typically, the buffer is a salt prepared from an organic acid or base. Exemplary buffers include organic acid salts, such as salts of citric acid, ascorbic acid, gluconic acid, carbonic acid, tartaric acid, succinic acid, acetic acid, or phthalic acid; Tris; tromethamine hydrochloride; phosphate buffers; or any combination thereof.

Additionally, pharmaceutical compositions of the invention optionally include polymeric excipients/additives, such as polyvinylpyrrolidones, ficolls (a polymeric sugar), dextrates (for example, cyclodextrins, such as 2-hydroxypropyl-β-cyclodextrin), polyethylene glycols, flavoring agents, antimicrobial agents, sweeteners, antioxidants, anti-static agents, surfactants (for example, polysorbates such as "TWEEN 20" and "TWEEN 80"), lipids (for example, phospholipids, fatty acids), steroids (for example, cholesterol), chelating agents (for example, EDTA), and any combination thereof. Exemplary pharmaceutical excipients and/or additives are described in REMINGTON: THE SCIENCE & PRACTICE OF PHARMACY (19$^{th}$ ed., Williams & Williams (1995)) and PHYSICIAN'S DESK REFERENCE (52$^{nd}$ ed., Medical Economics (1998)), each of which is incorporated herein by reference in its entirety.

1. Pharmaceutical Compositions for Oral Administration

For oral administration in the form of a tablet or capsule, a compound may be combined with an oral, non-toxic pharmaceutically acceptable inert carrier such as ethanol, glycerol, water, or any mixture thereof. Moreover, suitable binders, lubricants, disintegrating agents, and coloring agents also may be incorporated into the mixture. Suitable binders include, without limitation, starch; gelatin; natural sugars such as glucose or beta-lactose; corn sweeteners; natural and synthetic gums such as acacia, tragacanth, or sodium alginate, carboxymethylcellulose; polyethylene glycol; waxes; or any combination thereof. Lubricants used in these dosage forms include, without limitation, sodium oleate, sodium stearate, magnesium stearate, sodium benzoate, sodium acetate, sodium chloride, or any combination thereof. Disintegrators include, without limitation, starch, methyl cellulose, agar, bentonite, xanthan gum, or any combination thereof.

Formulations of the present invention suitable for oral administration may be presented as discrete units such as capsules, cachets, or tablets, each containing a predetermined amount of the active ingredient; as a powder or granules; as a solution or a suspension in an aqueous liquid or a non-aqueous liquid; or as an oil-in-water liquid emulsion or a water-in-oil emulsion and as a bolus.

A tablet may be made by compression or molding, optionally with one or more auxiliary ingredients. Compressed tablets typically are prepared by compressing, in a suitable machine, the active ingredient in a free-flowing form such as a powder or granules optionally mixed with a binder, lubricant, inert diluent, preservative, surface active or dispersing agent. Molded tablets typically are made by molding, in a suitable machine, a mixture of the powdered compound moistened with an inert liquid diluent. The tablets optionally are coated or scored and may be formulated to provide a slow or controlled release of the active ingredient therein.

The compositions of the present invention optionally are incorporated into a biodegradable polymer, thereby allowing for sustained release of the compound. The polymer is implanted in the vicinity of where drug delivery is desired, for example, at the site of restenosis. Such biodegradable polymers are described, for example, in Brem et al., 74 J. NEUROSURG. 441-46 (1991). Suitable examples of sustained-release compositions include semipermeable matrices of solid hydrophobic polymers containing a compound of the present invention, which matrices are formed into shaped articles, for example, films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919, incorporated by reference herein in its entirety), copolymers of L-glutamic acid and y ethyl-L-glutamate, non-degradable ethylene-vinyl acetate, degradable lactic acid-glycolic acid copolymers such as the LUPRON DEPOT® (Tap Pharmaceuticals, Inc., Chicago, Ill.) (injectable microspheres composed of lactic acid glycolic acid copolymer and leuprolide acetate), and poly-D-(−)-3-hydroxybutyric acid.

2. Pharmaceutical Compositions for Parenteral Administration

As used herein, "parenteral" includes subcutaneous injections, intravenous, intramuscular, intraperitoneal injections, or infusion techniques. Formulations suitable for parenteral administration include aqueous and non-aqueous sterile injection solutions that may contain anti-oxidants, buffers, bacteriostats, and solutes that render the formulation isotonic with the blood of the intended recipient, and aqueous and non-aqueous sterile suspensions that optionally include suspending agents and thickening agents. The formulations may be presented in unit-dose or multi-dose containers, for example, sealed ampules and vials, and may be stored in a freeze-dried (lyophilized) condition requiring only the addition of the sterile liquid carrier, for example, water for injections, immediately prior to use. Extemporaneous injection solutions and suspensions may be prepared from sterile powders, granules, and tablets, such as those described above.

For parenteral administration, sterile suspensions and solutions are desired. Isotonic preparations which generally contain suitable preservatives are employed when intravenous administration is desired. The pharmaceutical compositions may be administered parenterally via injection of a formulation consisting of the active ingredient dissolved in an inert liquid carrier. Acceptable liquid carriers include, for example, vegetable oils such as peanut oil, cotton seed oil, sesame oil, and organic solvents such as solketal and glycerol formal. The formulations may be prepared by dissolving or suspending the active ingredient in the liquid carrier such that the final formulation contains from about 0.005% to 30% by weight of the active ingredient, for example, a compound of the present invention.

3. Pharmaceutical Compositions for Other Routes of Administration

Formulations suitable for topical administration in the mouth include lozenges comprising the ingredients in a flavored basis or medium, usually sucrose and acacia or tragacanth; pastilles comprising the active ingredient in an inert basis or medium such as gelatin and glycerin, or sucrose and acacia; and mouthwashes comprising the compound to be administered in a suitable liquid carrier. The liquid forms may include suitably flavored suspending or dispersing agents, such as the synthetic and natural gums, for example, tragacanth, acacia, and methyl-cellulose.

Formulations for rectal administration may be presented as a suppository with a suitable base comprising, for example, cocoa butter or a salicylate.

Formulations suitable for vaginal administration may be presented as pessaries, tamports, creams, gels, pastes, foams, or spray formulations comprising the active ingredient and an appropriate carrier.

The compounds also may be entrapped in microcapsules prepared, for example, by coacervation techniques or by interfacial polymerization, for example, hydroxymethylcellulose or gelatin-microcapsules and poly(methylmethacylate) microcapsules, respectively, in colloidal drug delivery systems (for example, liposomes, albumin microspheres, microemulsions, nano-particles and nanocapsules) or in macroemulsions. REMINGTON'S PHARMACEUTICAL SCIENCES (A. Osol ed., 16th ed. (1980)), incorporated by reference herein in its entirety.

The compounds contemplated hereby optionally are formulated as liposomes. Liposomes may be prepared by any suitable method, such as those described in U.S. Pat. Nos. 5,013,556; 4,485,045; 4,544,545; WO 97/38731; Epstein et al., 82 PROC. NATL. ACAD. SCI. USA 3688 (1985); and Hwang et al., 77 PROC. NATL. ACAD. SCI. USA 4030 (1980), each of which is incorporated by reference herein in its entirety. The compounds of the present invention also can be administered in the form of liposome delivery systems, such as small unilamellar vesicles, large unilamellar vesicles, and multilamellar vesicles. Liposomes can be formed from a variety of phospholipids, such as cholesterol, stearylamine, or phophatidylcholines.

Compounds of the present invention also may be delivered by the use of monoclonal antibodies as individual carriers to which the compound molecules are coupled. The compounds of the present invention also may be coupled with soluble polymers as targetable drug carriers. Such polymers can include polyvinylpyrrolidone, pyran copolymer, polyhydroxypropylmethacrylamidephenol, polyhydroxyethylaspartamidephenol, or polyethyl-eneoxidepolylysine optionally substituted with palmitoyl residue.

D. Pharmaceutically Acceptable Preservatives

The present invention provides stable formulations, preserved solutions and formulations containing a preservative, and multi-use preserved formulations suitable for pharmaceutical or veterinary use, comprising at least one compound contemplated hereby in a pharmaceutically acceptable formulation. Preserved formulations contain at least one known preservative comprising at least one of phenol, m-cresol, p-cresol, o-cresol, chlorocresol, benzyl alcohol, phenylmercuric nitrite, phenoxyethanol, formaldehyde, chlorobutanol, magnesium chloride (for example, hexahydrate), alkylparaben (methyl, ethyl, propyl, butyl), benzalkonium chloride, benzethonium chloride, sodium dehydroacetate and thimerosal, or any mixture thereof, in an aqueous diluent. Any suitable concentration or mixture can be used, such as 0.001-5%, or any range or value therein including, but not limited to, 0.001, 0.003, 0.005, 0.009, 0.01, 0.02, 0.03, 0.05, 0.09, 0.1, 0.2, 0.3, 0.4., 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.3, 4.5, 4.6, 4.7, 4.8, 4.9. Non-limiting examples include, no preservative, 0.1-2% m-cresol (for example, 0.1, 0.2, 0.3, 0.4, 0.5, 0.9, 1.0%), 0.1-3% benzyl alcohol (for example, 0.5, 0.9, 1.1., 1.5, 1.9, 2.0, 2.5%), 0.001-0.5% thimerosal (for example, 0.005, 0.01), 0.001-2.0% phenol (for example, 0.05, 0.25, 0.28, 0.5, 0.9, 1.0%), and 0.0005-1.0% alkylparaben(s) (for example, 0.00075, 0.0009, 0.001, 0.002, 0.005, 0.0075, 0.009, 0.01, 0.02, 0.05, 0.075, 0.09, 0.1, 0.2, 0.3, 0.5, 0.75, 0.9, 1.0%).

Other excipients, for example, isotonicity agents, buffers, antioxidants, preservative enhancers, optionally are added to the diluent. An isotonicity agent, such as glycerin, is commonly used at known concentrations. A physiologically tolerated buffer is typically added to provide improved pH control. The formulations can cover a wide range of pHs, such as from about pH 4 to about pH 10, specifically, a range from about pH 5 to about pH 9, more specifically, a range of about 6.0 to about 8.0. According to one aspect of the present invention, the formulations of the present invention have pH between about 6.8 and about 7.8. Suitable buffers include phosphate buffers, for example, sodium phosphate and phosphate buffered saline (PBS).

Other additives, such as a pharmaceutically acceptable solubilizers like Tween 20 (polyoxyethylene (20)sorbitan monolaurate), Tween 40 (polyoxyethylene (20)sorbitan monopalmitate), Tween 80 (polyoxyethylene (20)sorbitan monooleate), Pluronic F68 (polyoxyethylene polyoxypropylene block copolymers), and PEG (polyethylene glycol) or non-ionic surfactants such as polysorbate 20 or 80 or poloxamer 184 or 188, Pluronic® polyls, other block co-polymers, and chelators such as EDTA and EGTA is optionally added to the pharmaceutical compositions to reduce aggregation. These additives are particularly useful if a pump or plastic container is used to administer the pharmaceutical composition. The presence of pharmaceutically acceptable surfactant mitigates the propensity for the composition to aggregate.

During any of the processes of preparing of the compounds of the present invention, it may be necessary and/or desirable to protect sensitive or reactive groups on any of the molecules concerned. This may be achieved by means of conventional protecting groups, such as those described in PROTECTIVE GROUPS IN ORGANIC CHEMISTRY (1973); and GREENE AND WUTS, PROTECTIVE GROUPS IN ORGANIC SYNTHESIS (1991), each of which is incorporated by reference herein in its entirety. The protecting groups may be removed at a convenient subsequent stage using methods known from the art.

E. Combination Therapy

In addition, co-administration or sequential administration of the compounds of the present invention and other therapeutic agents may be desirable, such as chemotherapeutic agents, immunosuppressive agents, cytokines, cytotoxic agents, nucleolytic compounds, radioactive isotopes, receptors, and pro-drug activating enzymes, which may be naturally occurring or produced by recombinant methods. The combined administration includes co-administration, using separate formulations or a single pharmaceutical formulation, and consecutive administration in either order, where there is a time period while both (or all) active therapeutic agents simultaneously exert their biological activities.

The compounds of this invention optionally are administered in combination with an antirheumatic (for example, methotrexate, auranofin, aurothioglucose, azathioprine, etanercept, gold sodium thiomalate, hydroxychloroquine sulfate, leflunomide, sulfasalzine), a muscle relaxant, a narcotic, a non-steroid anti-inflammatory drug (NSAID), an analgesic, an anesthetic, a sedative, a local anesthetic, a neuromuscular blocker, an anti-cancer, an antimicrobial (for example, aminoglycoside, an antifungal, an antiparasitic, an antiviral, a carbapenem, cephalosporin, a flurorquinolone, a macrolide, a penicillin, a sulfonamide, a tetracycline, another antimicrobial), an anti-psoriatic, a corticosteriod, an anabolic steroid, a diabetes-related agent, a mineral, a nutritional, a thyroid agent, a vitamin, a calcium-related hormone, an antidiarrheal, an anti-tussive, an anti-emetic, an anti-ulcer, a laxative, an anticoagulant, an erythropieitin (for example, epoetin alpha), a filgrastim (for example, G-CSF, Neupogen), a sargramostim (GM-CSF, Leukine), an immunization, an immunoglobulin, an immunosuppressive (for example, basiliximab, cyclosporine, daclizumab), a growth hormone, a hormone replacement drug, an estrogen receptor modulator, a mydriatic, a cycloplegic, an alkylating agent, an anti-metabolite, a mitotic inhibitor, a radiopharmaceutical, an anti-depressant, anti-manic agent, an anti-psychotic, an anxiolytic, a hypnotic, a sympathomimetic, a stimulant, donepezil, tacrine, an asthma medication, a beta agonist, an inhaled steroid, a leukotriene inhibitor, a methylxanthine, a cromolyn, an epinephrine or analog thereof, dornase alpha (Pulmozyme), a cytokine, or any combination thereof.

Such anti-cancer or antimicrobial compounds also can include toxin molecules that are associated, bound, co-formulated, co-administered, or sequentially administered, in either order, with at least one of the compounds of the present invention. The term "toxin" includes both endotoxins and exotoxins produced by any naturally occurring, mutant, or recombinant bacteria or viruses that may cause any pathological condition in humans and other mammals, including toxin shock, which can result in death. The toxin optionally can act to kill selectively the pathologic cell or tissue. The pathologic cell can be a cancer or other cell. Such toxins can be, but are not limited to, purified or recombinant toxin or toxin fragment comprising at least one functional cytotoxic domain of toxin, for example, selected from at least one of ricin, diphtheria toxin, a venom toxin, or a bacterial toxin. Such toxins may include, but are not limited to, enterotoxigenic *E. coli* heat-labile enterotoxin (LT), heat-stable enterotoxin (ST), *Shigella* cytotoxin, *Aeromonas* enterotoxins, toxic shock syndrome toxin-1 (TSST-1), *Staphylococcal* enterotoxin A (SEA), B (SEB), or C (SEC), *Streptococcal* enterotoxins. Such bacteria include, but are not limited to, strains of a species of enterotoxigenic *E. coli* (ETEC), enterohemorrhagic *E. coli* (for example, strains of serotype 0157: H7), *Staphylococcus* species (for example, *Staphylococcus aureus, Staphylococcus pyogenes*), *Shigella* species (for example, *Shigella dysenteriae, Shigella flexneri, Shigella boydii,* and *Shigella sonnei*), *Salmonella* species (for example, *Salmonella typhi, Salmonella cholera-suis, Salmonella enteritidis*), *Clostridium* species (for example, *Clostridium perfringens, Clostridium dificile, Clostridium botulinum*), *Camphlobacter* species (for example, *Camphlobacter jejuni, Camphlobacter fetus*), *Heliobacter* species, (for example, *Heliobacter pylori*), *Aeromonas* species (for example, *Aeromonas sobria, Aeromonas hydrophila, Aeromonas caviae*), *Pleisomonas shigelloides, Yersina enterocolitica, Vibrios* species (for example, *Vibrios cholerae, Vibrios parahemolyticus*), *Klebsiella* species, *Pseudomonas aeruginosa,* and *Streptococci.* See, for example, Stein, ed., INTERNAL MEDICINE 1-13 (3rd ed. Little, Brown and Co., Boston) (1990); EVANS ET AL., BACTERIAL INFECTIONS OF HUMANS: EPIDEMIOLOGY AND CONTROL 239-254 (2d. ed. Plenum Medical Book Co., New York) (1991); MANDELL ET AL., PRINCIPLES AND PRACTICE OF INFECTIOUS DISEASES (3d. ed. Churchill Livingstone) (1990); BERKOW ET AL., THE MERCK MANUAL (16th ed. Merck and Co.) (1992); Wood et al., 76 FEMS MICROBIOLOGY IMMUNOLOGY 121-134 (1991); Marrack et al., 248 SCIENCE 705-711 (1990), each of which is incorporated by reference in its entirety.

The compound of the present invention is optionally administered in combination with at least one immunosuppressive agent for use in, for example, treating or preventing a vascular occlusive condition, such as transplant vasculopathy. Suitable immunosuppressive agents include, but are not limited to, CellCept (Roche Labs.), Gengraf (Abbott Labs., Inc.), Micrhogam (Ortho-Clinical), Neoral (Novartis), Orthoclone OKT3 (Ortho-Biotech), Prograf (Fujisawa), Rapamune (Wyeth-Ayerst), Sandimmune (Novartis), Thymoglobulin (SangStat), Zenapax (Roche), or any combination thereof.

The therapeutic agent may be administered simultaneously or sequentially, in either order and at various times with a compound of the present invention that comprises a chemotherapeutic agent. A "chemotherapeutic agent" is a compound useful in the treatment of cancer. Examples of chemotherapeutic agents include alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; nitrogen mustards such as chlorambucil, chlomaphazine, cholophosphamide, estramustine, ifosfamide, mechlorethamine, mechlorethamine oxide hydrochloride, melphalan, novembiehin, phenesterine, prednimustine, trofosfamide, uracil mustard; nitroureas such as cannustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, chromoinycins, dactinomycin, daunorubicin, detorubicin, 6-diazo-5-oxo-L-norleucine, doxorubicin, epirubicin, esorubicin, idambicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elfomithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK®; razoxane; sizofrran; spirogermanium; tenuazonic acid; triaziquone; 2,2',2''-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxoids, for example, paclitaxel (TAXOL®, Bristol-Myers Squibb Oncology, Princeton, N.J.) and doxetaxel (TAXOTERE®, Rhone-Poulenc Rorer, Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS 2000; difluoromethylomithine (DMFO); retinoic acid; esperamicins; capecitabine; and pharmaceutically acceptable salts, acids, or derivatives of any of the above. Also included in this definition are anti-hormonal agents that act to regulate or inhibit hormone action on tumors such as anti-estrogens including for example tamoxifen, raloxifene, aromatase inhibiting 4(5)-imidazoles, 4 hydroxytamoxifen, trioxifene, keoxifene, onapristone, and toremifene (Fareston); and antiandrogens such as flutamide, nilutamide, bicalutamide, leuprolide, and goserelin; and pharmaceutically acceptable salts, acids or derivatives of any of the above.

The therapeutic agent may comprise a cytokine. The term "cytokine" is a generic term for proteins released by one cell population which act on another cell as intercellular mediators. As used herein, the term "cytokine" includes proteins from natural sources or from recombinant cell culture and biologically active equivalents of the native sequence cytokines. Examples of such cytokines are lymphokines, monokines, and traditional polypeptide hormones. Included among the cytokines are growth hormones such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-a and -β; mullerian-inhibiting substance; mouse gonadotropin-associated peptide; inhibin; activin; vascular endothelial growth factor; integrin; thrombopoietin (TPO); nerve growth factors such as NGF-β; platelet growth factor; transforming growth factors (TGFs) such as TGF-a and TGF-β; insulin-like growth factor-I and -II; erythropoietin (EPO); osteoinductive factors; interferons such as interferon-a, -β and -?; colony stimulating factors (CSFs) such as macrophage-CSF (M-CSF); granulocyte-macrophage-CSF (GM-CSF); and granulocyte-CSF (GCSF); interleukins (ILs) such as IL-1, IL-1a, IL-2, IL-3, IL-4, IL-5, IL-6, IL-7, IL-8, IL-9, IL-11, IL-12, IL-15; a tumor necrosis factor such as TNF-a or TNF-β; and other polypeptide factors including LIF and kit ligand (KL).

The compounds of the present invention may be administered in combination with an anti-inflammatory agent including, but not limited to, adrenocortical steroids (cortisol, cortisone, fludrocortisone, prednisone, prednisolone, 6a-methylprednisolone, triamcinolone, betamethasone, and dexamethasone), non-steroidal agents (salicylic acid derivatives, i.e., aspirin; para-aminophenol derivatives, i.e., acetominophen; indole and indene acetic acids (indomethacin, sulindac, and etodalac), heteroaryl acetic acids (tolmetin, diclofenac, and ketorolac), arylpropionic acids (ibuprofen and derivatives), anthranilic acids (mefenamic acid, and meclofenamic acid), enolic acids (piroxicam, tenoxicam, phenylbutazone, and oxyphenthatrazone), nabumetone, gold compounds (auranofin, aurothioglucose, gold sodium thiomalate). Commercially available nonsteroidal anti-inflammatory drugs include, but are not limited to, Anaprox (Roche Labs.), Arthrotec (Searle), Cataflam (Novartis), Celebrex (Pfizer), Clinoril (Merck), Dolobid (Merck), Feldene (Pfizer), Indocin (Merck), Lodine (Wyeth-Ayerst), Mobic (Boehringer Ingelheim), Motrin (McNeil Consumer), Naprosyn (Roche Labs.), Orudis (Wyeth-Ayerst), Oruvail (Wyeth-Ayerst), Ponstel (First Horizon), Relafen (GlaxoSmithKline), Tolectin (Ortho-McNeil), Toradol (Roche Labs., Inc.), Vioxx (Merck), Voltaren (Novartis), Advair (GlaxoSmithKline), Flovent (GlaxoSmithKline), Pulmicort (AstranZeneca), and Vanceril (Schering), Asacol (Procter & Gamble), Colazal (Salix), Dipentum (Pharmacia & Upjohn), and Rowasa (Solvay).

The compounds of the present invention may be administered in combination with an antirheumatic agent. Commercially available antirheumatic agents include, but are not limited to, Anaprox (Roche Labs.), Arava (Aventic), Arthrotec (Searle), Azulfidine (Pharmacia & Upjohn), Cataflam (Novartis), Celebrex (Pfizer), Celestone (Schering), Cuprimine (Merck), Enbrel (Immunex), Feldene (Pfizer), Gengraf (Abbott), Indocin (Merck), Lodine (Wyeth-Ayerst), Naprosyn (Roche Labs.), Neoral (Novartis), Pediapred (Celltech), Prednisone (Roxanne), Remicade (Centocor), Solu-Medrol (Pharmacia & Upjohn), Triliate (Purdue Frederick), and Voltaren (Novartis).

Moreover, the compounds of the present invention may be used in combination with any cardiovascular agent including, but not limited to, adrenergic blockers such as Cardura (Pfizer), Dibenzyline (WellSpring), Hytrin (Abbott), Minipress (Pfizer), and Minizide (Pfizer); adrenergic stimulants such as Aldoclor (Merck), Aldomet (Merck), Aldoril (Merck), Catapres (Boehringer Ingelheim), Clorpres (Bertek), and Tenex (Robins); alpha/beta adrenergic blockers such as Coreg (GlaxoSmithKline), and Normodyne (Schering); angiotensin converting enzyme inhibitors, such as Accupril (Parke-Davis), Aceon (Solvay), Altace (Monarch), Captopril (Mylan), Enalaprilat (Baxter Anesthesia), Lotensin (Novartis), Mavik (Abbott), Monopril (Bristol-Myers Squibb), Prinivil (Merck), Univasc (Schwarz), Vaotec (Merck), and Zestril (AstraZeneca); angiotenisin converting enzyme inhibitors such as Lexxel (AstraZeneca), Lotrel (Novartis), Tarka (Abbott), Accuretic (Parke-Davis), Lotensin (Novartis), Prinzide (Merck), Uniretic (Schwarz), Vaeretic (Merck), and Zestoretic (AstraZeneca); angiotensin II receptor antagonists such as Atacand (AstraZeneca), Avapro (Briston-Myers Squibb), Cozaar (Merck), Diovan (Novartis), Micardis (Boehringer Ingelheim), and Teveten (Unimed); antiarrhythmics (Groups I-IV), antilipemic agents such as bile acid sequestrants, fibric acid derivatives, HMG-CoA reductase inhibitors, and nicotinic acid; Beta adrenergic blocking agents; calcium channel blockers; inotropic agents; vasodilators including coronoary vasodilators, natriuretic peptides, and peripheral vasodilators; and vasopressors.

According to one aspect of the present invention, the therapeutic agent comprises a small molecule toxin, including maytansine, calicheamicin, trichothene, and CC 1065. According to another aspect of the present invention, the therapeutic agent comprises one more calicheamicin molecules. Members of the calicheamicin family of antibiotics are capable of producing double-stranded DNA breaks at sub-picomolar concentrations. Structured analogues of calicheamicin are also known. See Hinman et al., 53 CANCER RESEARCH 3336-42 (1993); Lode et al., 58 CANCER RESEARCH 2925-28 (1998), incorporated herein by reference in its entirety.

The therapeutic agent may comprise one or more enzymatically active toxins and fragments thereof. Examples of such toxins include nonbinding active fragments of diphtheria toxin, diphtheria A chain, exotoxin A chain (from Pseudomonas aeruginosa), ricin A chain, abrin A chain, modeccin A chain, alpha-sarcin, dianthin proteins, Phytolaca americana proteins (PAPI, PAPAII, and PAP-S), momordica charantia inhibitor, curcin, crotin sapaonaria officinalis inhibitor, gelonin, mitogellin, restrictoein, phenomvcin, enomycin and the tricothecenes. See, for example, WO 93/21232, incorporated herein by reference in its entirety.

The present invention further contemplates therapeutic agents that have nucleolytic activity such as a ribonuclease and a deoxyribonuclease. In addition, a variety of radioactive isotopes are available for the production of radioconjugated binding partners. Examples include $Y^{90}$, $At^{222}$, $Ret^{86}$, $Re^{186}$, $Sm^{153}$, $Bi^{212}$, $P^{32}$ and radioactive isotopes of Lu.

The compound of the present invention may be conjugated to a receptor, such as streptavidin, for utilization in tumor pretargeting. Briefly, the compound-receptor conjugate is administered to the patient and unbound conjugate is removed from circulation with a clearing agent. A ligand, such as biotin, which is conjugated to a cytotoxic agent, is then administered.

1. Timing of Administration

According to one aspect of the present invention, a compound described herein is administered before a second therapeutic agent. The administration of a compound may occur anytime from several minutes to several hours before the administration of the second therapeutic agent. The compound may alternatively be administered anytime from several hours to several days, possibly several weeks, and up to several months before the second therapeutic agent.

More specifically, a compound of the present invention may be administered at least about 1 minute, at least about minutes, at least about minutes, at least about minutes, at least about minutes, at least about 2 minutes, at least about 3 minutes, at least about 4 minutes, at least about 5 minutes, at least about 6 minutes, at least about 7 minutes, at least about 8 minutes, at least about 9 minutes, at least about 10 minutes, at least about 11 minutes, at least about 12 minutes, at least about 13 minutes, at least about 14 minutes, at least about 15 minutes, at least about 16 minutes, at least about 17 minutes, at least about 18 minutes, at least about 19 minutes, at least about 20 minutes, at least about 21 minutes, at least about 22 minutes, at least about 23 minutes, at least about 24 minutes, at least about 25 minutes, at least about 26 minutes, at least about 27 minutes, at least about 28 minutes, at least about 29 minutes, at least about 30 minutes, at least about 31 minutes, at least about 32 minutes, at least about 33 minutes, at least about 34 minutes, at least about 35 minutes, at least about 36 minutes, at least about 37 minutes, at least about 38 minutes, at least about 39 minutes, at least about 40 minutes, at least about 41 minutes, at least about 42 minutes, at least about 43 minutes, at least about 44 minutes, at least about 45 minutes, at least about 46 minutes, at least about 47 minutes, at least about 48 minutes, at least about 49 minutes, at least about 50 minutes, at least about 51 minutes, at least about 52 minutes, at least about 53 minutes, at least about 54 minutes, at least about 55 minutes, at least about 56 minutes, at least about 57 minutes, at least about 58 minutes, at least about 59 minutes, or at least about 60 minutes before the second therapeutic agent.

Furthermore, a compound of the present invention may be administered at least about 1 hour, at least about 2 hours, at least about 3 hours, at least about 4 hours, at least about 5 hours, at least about 6 hours, at least about 7 hours, at least about 8 hours, at least about 9 hours, at least about 10 hours, at least about 11 hours, at least about 12 hours, at least about 13 hours, at least about 14 hours, at least about 15 hours, at least about 16 hours, at least about 17 hours, at least about 18 hours, at least about 19 hours, at least about 20 hours, at least about 21 hours, at least about 22 hours, at least about 23 hours, or at least about 24 hours before the second therapeutic agent.

Moreover, a compound of the present invention may be administered at least about 1 day, at least about 2 days, at least about 3 days, at least about 4 days, at least about 5 days, at least about 6 days, at least about 7 days, at least about 8 days, at least about 9 days, at least about 10 days, at least about 11 days, at least about 12 days, at least about 13 days, at least about 14 days, at least about 15 days, at least about 16 days, at least about 17 days, at least about 18 days, at least about 19 days, at least about 20 days, at least about 21 days, at least about 22 days, at least about 23 days, at least about 24 days, at least about 25 days, at least about 26 days, at least about 27 days, at least about 28 days, at least about 29 days, at least about 30 days or at least about 31 days before the administration of the second therapeutic agent.

A compound of the present invention may be administered at least about 1 week, at least about 2 weeks, at least about 3 weeks, at least about 4 weeks, at least about 5 weeks, at least about 6 weeks, at least about 7 weeks, at least about 8 weeks, at least about 9 weeks, at least about 10 weeks, at least about 11 weeks, at least about 12 weeks, at least about 13 weeks, at least about 14 weeks, at least about 15 weeks, at least about 16 weeks, at least about 17 weeks, at least about 18 weeks, at least about 19 weeks, or at least about 20 weeks before the second therapeutic agent.

Further, a compound of the present invention may be administered at least about one month, at least about two months, at least about three months, at least about four months, at least about five months, at least about six months, at least about seven months, at least about eight months, at least about nine months, at least about ten months, at least about eleven months, or at least about twelve months before the second therapeutic agent.

According to another aspect of the present invention, a compound of the present invention is administered after the therapeutic agent. The administration of a compound may occur anytime from several minutes to several hours after the administration of the therapeutic agent. A compound may alternatively be administered anytime from several hours to several days, possibly several weeks, and even up to several months after the second therapeutic agent.

More specifically, a compound of the present invention may be administered at least about 1 minute, at least about minutes, at least about minutes, at least about minutes, at least about minutes, at least about 2 minutes, at least about 3 minutes, at least about 4 minutes, at least about 5 minutes, at least about 6 minutes, at least about 7 minutes, at least about 8 minutes, at least about 9 minutes, at least about 10 minutes, at least about 11 minutes, at least about 12 minutes, at least about 13 minutes, at least about 14 minutes, at least about 15 minutes, at least about 16 minutes, at least about 17 minutes, at least about 18 minutes, at least about 19 minutes, at least about 20 minutes, at least about 21 minutes, at least about 22 minutes, at least about 23 minutes, at least about 24 minutes, at least about 25 minutes, at least about 26 minutes, at least about 27 minutes, at least about 28 minutes, at least about 29 minutes, at least about 30 minutes, at least about 31 minutes, at least about 32 minutes, at least about 33 minutes, at least about 34 minutes, at least about 35 minutes, at least about 36 minutes, at least about 37 minutes, at least about 38 minutes, at least about 39 minutes, at least about 40 minutes, at least about 41 minutes, at least about 42 minutes, at least about 43 minutes, at least about 44 minutes, at least about 45 minutes, at least about 46 minutes, at least about 47 minutes, at least about 48 minutes, at least about 49 minutes, at least about 50 minutes, at least about 51 minutes, at least about 52 minutes, at least about 53 minutes, at least about 54 minutes, at least about 55 minutes, at least about 56 minutes, at least about 57 minutes, at least about 58 minutes, at least about 59 minutes, or at least about 60 minutes after the second therapeutic agent.

More specifically, a compound of the present invention may be administered at least about 1 hour, at least about 2 hours, at least about 3 hours, at least about 4 hours, at least about 5 hours, at least about 6 hours, at least about 7 hours, at least about 8 hours, at least about 9 hours, at least about 10 hours, at least about 11 hours, at least about 12 hours, at least about 13 hours, at least about 14 hours, at least about 15 hours, at least about 16 hours, at least about 17 hours, at least about 18 hours, at least about 19 hours, at least about 20 hours, at least about 21 hours, at least about 22 hours, at least about 23 hours, or at least about 24 hours after the second therapeutic agent.

Moreover, a compound of the present invention may be administered at least about 1 day, at least about 2 days, at least about 3 days, at least about 4 days, at least about 5 days, at least about 6 days, at least about 7 days, at least about 8 days, at least about 9 days, at least about 10 days, at least about 11 days, at least about 12 days, at least about 13 days, at least about 14 days, at least about 15 days, at least about 16 days, at least about 17 days, at least about 18 days, at least about 19 days, at least about 20 days, at least about 21 days, at least about 22 days, at least about 23 days, at least about 24 days, at least about 25 days, at least about 26 days, at least about 27 days, at least about 28 days, at least about 29 days, at least about 30 days or at least about 31 days after the administration of the second therapeutic agent.

A compound of the present invention may be administered at least about 1 week, at least about 2 weeks, at least about 3 weeks, at least about 4 weeks, at least about 5 weeks, at least about 6 weeks, at least about 7 weeks, at least about 8 weeks, at least about 9 weeks, at least about 10 weeks, at least about 11 weeks, at least about 12 weeks, at least about 13 weeks, at least about 14 weeks, at least about 15 weeks, at least about 16 weeks, at least about 17 weeks, at least about 18 weeks, at least about 19 weeks, or at least about 20 weeks after the second therapeutic agent.

Further, a compound of the present invention may be administered at least about one month, at least about two months, at least about three months, at least about four months, at least about five months, at least about six months, at least about seven months, at least about eight months, at least about nine months, at least about ten months, at least about eleven months, or at least about twelve months after the second therapeutic agent.

The compound of formula (I) also may be administered in conjunction with other medications used in the treatments of cardiovascular diseases, including platelets aggregation inhibitors such as aspirin, antithrombotic agents such as coumadin, calcium channel blockers such as dilteazem and nefidipine, angiotension converting enzyme (ACE) inhibitors such as captopril and enalopril and β blockers such as propanalol. The compound also can be administered in combination with non steroid antiinflamatory agents such as ibuprofen, indomethacin, sulindac, or COX II inhibitors such as rofecoxib or celecoxib. A therapeutic amount of the compound of formula (I) also can be administered with a carticosteroid. They also can be administered in combination with a TNF-a modulating agent for example etanercept or infliximab. A therapeutic amount of the compound of formula (I) also can be administered also can be administered with HMGCoA reductose inhibitors, PPAR-? agonists, HDL elevators or retinoids.

Methods of Administration

The compounds of the present invention may be administered by any suitable means, including, but not limited to, parenteral, subcutaneous, intramuscular, intravenous, intrarticular, intrabronchial, intraabdominal, intracapsular, intracartilaginous, intracavitary, intracelial, intracelebellar, intracerebroventricular, intracolic, intracervical, intragastric, intrahepatic, intramyocardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, bolus, vaginal, rectal, buccal, sublingual, intranasal, or transdermal means.

A. Pulmonary/Nasal Administration

There are a several desirable features of an inhalation device for administering a compound of the present invention. For example, delivery by the inhalation device is advantageously reliable, reproducible, and accurate. For pulmonary administration, at least one pharmaceutical composition is delivered in a particle size effective for reaching the lower airways of the lung or sinuses. The inhalation device optionally delivers small dry particles, typically less than about 10 µm, for example, about 1-5 µm, for good respirability.

The pharmaceutical composition of the present invention can be delivered by any suitable inhalation or nasal device. Devices capable of depositing aerosolized formulations in the sinus cavity or alveoli of a patient include, but are not limited to, metered dose inhalers, nebulizers, dry powder generators, and sprayers. Other devices suitable for directing pulmonary or nasal administration are also known in the art.

All such devices may be used for the administration of a pharmaceutical composition in an aerosol. Such aerosols may comprise either solutions (both aqueous and non aqueous) or solid particles. Metered dose inhalers like the Ventolin® metered dose inhaler, typically use a propellant gas and require actuation during inspiration. See, for example, WO 98/35888; WO 94/16970. Dry powder inhalers like Turbuhaler® (Astra), Rotahaler® (Glaxo), Diskus® (Glaxo), Spiros® inhaler (Dura), devices marketed by Inhale Therapeutics, and the Spinhaler® powder inhaler (Fisons), use breath-actuation of a mixed powder. See U.S. Pat. Nos. 5,458,135; 4,668,218; WO 97/25086; WO 94/08552; WO 94/06498; and EP 0 237 507, each of which is incorporated by reference herein in its entirety. Nebulizers, for example, AERx®, Aradigm, the Ultravent® nebulizer (Mallinckrodt), and the Acorn II® nebulizer (Marquest Medical Products) produce aerosols from solutions, while metered dose inhalers, and dry powder inhalers generate small particle aerosols. These specific examples of commercially available inhalation devices are intended to be a representative of specific devices suitable for the practice of the invention, and are not intended as limiting the scope of the invention.

Where the carrier is a solid, formulations suitable for nasal administration include a coarse powder having a particle size, for example, from about 20 to 500 microns that is administered in the manner in which snuff is administered, i.e., by rapid inhalation through the nasal passage from a container of the powder held close up to the nose. Where the carrier is a liquid, suitable formulations for administration as, for example, a nasal spray or as nasal drops, include aqueous or oily solutions of the active ingredient.

1. Administration as a Spray

A spray comprising a pharmaceutical composition of the present invention can be produced by forcing a suspension or solution of a compound contemplated hereby through a nozzle under pressure. The nozzle size and configuration, the applied pressure, and the liquid feed rate are chosen to achieve the desired output and particle size. An electrospray can be produced, for example, by an electric field in connection with a capillary or nozzle feed. Typically, particles of at least one compound delivered by a sprayer have a particle size less than about 20 µm, less than about 19 µm, less than about 18 µm, less than about 17 µm, less than about 16 µm, less than about 15 µm, less than about 14 µm, less than about 13 µm, less than about 12 µm, less than about 11 µm, less than about 10 µm, less than about 9 µm, less than about 8 µm, less than about 7 µm, less than about 6 µm, less than about 5 µm, less than about 4 µm, less than about 3 µm, less than about 2 µm, less than about 1 µm.

Pharmaceutical compositions according to the present invention suitable for use with a sprayer typically include a compound contemplated hereby in an aqueous solution at a concentration of about 0.1 mg to about 100 mg of a compound contemplated hereby per mL of solution or mg/gm, or any range or value therein including, but not limited to, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 45, 50, 60, 70, 80, 90 or 100 mg/mL or mg/gm. The pharmaceutical composition can include agents such as an excipient, a buffer, an isotonicity agent, a preservative, a surfactant, and, for example, zinc. The pharmaceutical composition also can include an excipient or agent for stabilization of the compound, such as a buffer, a reducing agent, a bulk protein, or a carbohydrate. Bulk proteins useful in pharmaceutical compositions suitable for use in a sprayer include albumin, protamine, or the like. Typical carbohydrates useful in pharmaceutical compositions include sucrose, mannitol, lactose, trehalose, glucose, or the like. The pharmaceutical composition also can include a surfactant, which can reduce or prevent surface-induced aggregation of the pharmaceutical composition caused by atomization of the solution in forming an aerosol. Various conventional surfactants can be employed such as polyoxyethylene fatty acid esters and alcohols, and polyoxyethylene sorbitol fatty acid esters. Amounts will generally range between 0.001 and 10% by weight of the formulation. Suitable surfactants include, but are not limited to, polyoxyethylene sorbitan monooleate, polysorbate 80, polysorbate 20, or the like. Additional agents known in the art also can be included in the pharmaceutical composition.

2. Administration by a Nebulizer

A pharmaceutical composition of the present invention can be administered by a nebulizer such as a jet nebulizer or an ultrasonic nebulizer. Typically, in a jet nebulizer, a compressed air source is used to create a high-velocity air jet through an orifice. As the gas expands beyond the nozzle, a low-pressure region is created, which draws a solution of composition protein through a capillary tube connected to a liquid reservoir. The liquid stream from the capillary tube is sheared into unstable filaments and droplets as it exits the tube, creating the aerosol. A range of configurations, flow rates, and baffle types can be employed to achieve the desired performance characteristics from a given jet nebulizer. In an ultrasonic nebulizer, high-frequency electrical energy is used to create vibrational, mechanical energy, typically employing a piezoelectric transducer. This energy is transmitted to the formulation of composition protein either directly or through a coupling fluid, creating an aerosol including the composition protein. Advantageously, particles of the pharmaceutical composition delivered by a nebulizer have a particle size less than about 20 μm, less than about 19 μm, less than about 18 μm, less than about 17 μm, less than about 16 μm, less than about 15 μm, less than about 14 μm, less than about 13 μm, less than about 12 μm, less than about 11 μm, less than about 10 μm, less than about 9 μm, less than about 8 μm, less than about 7 μm, less than about 6 μm, less than about 5 μm, less than about 4 μm, less than about 3 μm, less than about 2 μm, less than about 1 μm.

Pharmaceutical compositions comprising a compound of the present invention suitable for use with a nebulizer, either jet or ultrasonic, typically include a concentration of about 0.1 mg to about 100 mg of a compound contemplated hereby per mL of solution or mg/gm, or any range or value therein including, but not limited to, 0.1, 0.2., 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 45, 50, 60, 70, 80, 90 or 100 mg/mL or mg/gm. The pharmaceutical composition can include agents such as an excipient, a buffer, an isotonicity agent, a preservative, a surfactant, and, for example, zinc. The pharmaceutical composition also can include an excipient or agent for stabilization of the compound such as a buffer, a reducing agent, a bulk protein, or a carbohydrate. Bulk proteins useful in pharmaceutical compositions suitable for use in a sprayer include albumin, protamine, or the like. Typical carbohydrates useful in pharmaceutical compositions include sucrose, mannitol, lactose, trehalose, glucose, or any combination thereof. The pharmaceutical composition also can include a surfactant, which can reduce or prevent surface-induced aggregation of the pharmaceutical composition caused by atomization of the solution in forming an aerosol. Various conventional surfactants can be employed such as polyoxyethylene fatty acid esters and alcohols, and polyoxyethylene sorbitol fatty acid esters. Amounts will generally range between 0.001 and 10% by weight of the formulation. Suitable surfactants for purposes of this invention are polyoxyethylene sorbitan monooleate, polysorbate 80, polysorbate 20, or the like. Additional agents known in the art also can be included in the pharmaceutical composition.

3. Administration by a Metered Dose Inhaler

In a metered dose inhaler (MDI), a propellant, a compound of the present invention, and any excipients or other additives are contained in a cannister as a mixture including a liquefied, compressed gas. Actuation of the metering valve releases the mixture as an aerosol, typically containing particles in the size range of less than about 20 μm, less than about 19 μm, less than about 18 μm, less than about 17 μm, less than about 16 μm, less than about 15 μm, less than about 14 μm, less than about 13 μm, less than about 12 μm, less than about 11 μm, less than about 10 μm, less than about 9 μm, less than about 8 μm, less than about 7 μm, less than about 6 μm, less than about 5 μm, less than about 4 μm, less than about 3 μm, less than about 2 μm, less than about 1 μm.

The desired aerosol particle size can be obtained by employing a formulation of a compound of the present invention produced by various methods known to those of skill in the art including, but not limited to, jet-milling, spray drying, critical point condensation. Suitable metered dose inhalers include those manufactured by 3M or Glaxo and employing a hydrofluorocarbon propellant.

Pharmaceutical compositions for use with a metered-dose inhaler device will generally include a finely divided powder containing a compound contemplated hereby as a suspension in a non-aqueous medium, for example, suspended in a propellant with the aid of a surfactant. The propellant can be any conventional material employed for this purpose such as chlorofluorocarbon, a hydrochlorofluorocarbon, a hydrofluorocarbon, or a hydrocarbon including trichlorofluoromethane, dichlorodifluoromethane, dichlorotetrafluoroethanol and 1,1,1,2-tetrafluoroethane, HFA-134a (hydrofluroalkane-134a), HFA-227 (hydrofluroalkane-227), or the like. The surfactant can be chosen to stabilize the compound of the present invention as a suspension in the propellant, to protect the active agent against chemical degradation. Suitable surfactants include sorbitan trioleate, soya lecithin, oleic acid, or the like. In some cases solution aerosols are formed using solvents such as ethanol. One of ordinary skill in the art will recognize that the methods of the present invention can be achieved by pulmonary administration of a compound contemplated hereby via devices not described herein.

B. Mucosal Administration

For absorption through mucosal surfaces, the compositions and methods of the present invention for administering a compound contemplated hereby include an emulsion comprising a plurality of submicron particles, a mucoadhesive macromolecule, a bioactive peptide, and an aqueous continuous phase, which promotes absorption through mucosal surfaces by achieving mucoadhesion of the emulsion particles. See, for example, U.S. Pat. No. 5,514,670. Mucous surfaces suitable for application of the compositions of the present invention can include corneal, conjunctival, buccal, sublingual, nasal, vaginal, pulmonary, abdominal, intestinal, and rectal routes of administration. Pharmaceutical compositions for vaginal or rectal administration, such as suppositories, can contain as excipients, for example, polyalkyleneglycols, vaseline, cocoa butter. Pharmaceutical compositions for intranasal administration can be solid and contain excipients, for example, lactose or can be aqueous or oily solutions of nasal drops. For buccal administration, excipients include sugars, calcium stearate, magnesium stearate, pregelinatined starch. See, for example, U.S. Pat. No. 5,849,695.

C. Transdermal Administration

The pharmaceutical compositions of the present invention may be administered via transdermal routes using forms of transdermal skin patches. For transdermal administration, a compound of the present invention is encapsulated in a delivery device such as a liposome or polymeric nanoparticle, microparticle, microcapsule, or microsphere (referred to collectively as "microparticles" unless otherwise stated). Any suitable delivery device may be used, for example, microparticles made of synthetic polymers, such as polyhydroxy acids, for example, polylactic acid, polyglycolic acid and copolymers thereof, polyorthoesters, polyanhydrides, and polyphosphazenes, and natural polymers such as collagen, polyamino acids, albumin and other proteins, alginate and other polysaccharides, and any combination thereof. See, for example, U.S. Pat. No. 5,814,599, incorporated by reference herein in its entirety. To be administered in the form of a transdermal delivery system, the dosage administration may be continuous rather than intermittent throughout the dosage regimen.

Formulations suitable for topical administration to the skin may be presented as ointments, creams, gels, and pastes comprising the ingredient to be administered in a pharmaceutical acceptable carrier. According to one aspect of the present invention, a transdermal patch is used as a topical delivery system.

Topical compositions may be admixed with a variety of carrier materials including, for example, alcohols, aloe vera gel, allantoin, glycerine, vitamin A and E oils, mineral oil, PPG2 myristyl propionate, or any mixture thereof, to form, for example, alcoholic solutions, topical cleansers, cleansing creams, skin gels, skin lotions, and shampoos in cream or gel formulations. Examples of such carriers and methods of formulation may be found in Remington's Pharmaceutical Sciences (1990), incorporated by reference herein in its entirety. Pharmaceutical formulations may contain from about 0.005% to about 10% by weight of the active ingredient, for example, from about 0.01% to 5% by weight of the active ingredient.

D. Prolonged Administration

It may be desirable to deliver the compounds of the present invention to the subject over prolonged periods of time, for example, for periods of one week to one year for a single administration. Certain medical devices may be employed to provide a continuous intermittent or on demand dosing of a patient. The devices may include a pump or diffusion apparatus, or any other device containing a reservoir of drug and optionally diagnostic or monitoring components to regulate the delivery of the drug. Various slow-release, depot, or implant dosage forms can be utilized. For example, a dosage form can contain a pharmaceutically acceptable non-toxic salt of compound contemplated hereby that has a low degree of solubility in body fluids, for example, (a) an acid addition salt with a polybasic acid such as phosphoric acid, sulfuric acid, citric acid, tartaric acid, tannic acid, pamoic acid, alginic acid, polyglutamic acid, naphthalene mono- or di-sulfonic acids, polygalacturonic acid, or any mixture thereof; (b) a salt with a polyvalent metal cation such as zinc, calcium, bismuth, barium, magnesium, aluminum, copper, cobalt, nickel, cadmium, or any mixture thereof, or with an organic cation formed from for example, N,N'-dibenzyl-ethylenediamine or ethylenediamine; or (c) combinations of (a) and (b), for example, a zinc tannate salt. Additionally, the compounds of the present invention or a relatively insoluble salt, such as those just described, can be formulated in a gel, for example, an aluminum monostearate gel with, for example, sesame oil, suitable for injection. Exemplary salts include, but are not limited to, zinc salts, zinc tannate salts, pamoate salts, and any mixture thereof. Another type of slow-release depot formulation for injection may contain the compound or salt dispersed or encapsulated in a slow degrading, non-toxic, non-antigenic polymer such as a polylactic acid/polyglycolic acid polymer, for example, as described in U.S. Pat. No. 3,773,919. The compounds or relatively insoluble salts thereof also can be formulated in cholesterol matrix silastic pellets, particularly for use in animals. Additional slow-release, depot, or implant formulations, for example, gas or liquid liposomes are described in, for example, U.S. Pat. No. 5,770,222; Sustained and Controlled Release Drug Delivery Systems (1978), incorporated by reference herein in its entirety.

Dosage Determination

In general, the compounds contemplated hereby may be used alone or in concert with other therapeutic agents at appropriate dosages to obtain optimal efficacy while minimizing any potential toxicity. The dosage regimen utilizing a compound of the present invention may be selected in accordance with a variety of factors including type, species, age, weight, sex, medical condition of the patient; the severity of the condition to be treated; the route of administration; the renal and hepatic function of the patient; and the particular compound employed. A physician or veterinarian of ordinary skill can readily determine and prescribe the effective amount of the drug required to prevent, counter, or arrest the progress of the condition.

Optimal precision in achieving concentrations of drug within the range that yields maximum efficacy with minimal toxicity may require a regimen based on the kinetics of the compound's availability to a target site(s). Distribution, equilibrium, and elimination of a drug may be considered when determining the optimal concentration for a treatment regimen. The dosages of a compound contemplated hereby may be adjusted when combined to achieve desired effects. On the other hand, dosages of these various therapeutic agents may be independently optimized and combined to achieve a synergistic result wherein the pathology is reduced more than it would be if either agent were used alone.

In particular, toxicity and therapeutic efficacy of a compound contemplated hereby may be determined by standard pharmaceutical procedures in cell cultures or experimental animals, for example, for determining the $LD_{50}$ (the dose lethal to 50% of the population) and the $ED_{50}$ (the dose therapeutically effective in 50% of the population). The dose ratio between toxic and therapeutic effect is the therapeutic index and it may be expressed as the ratio $LD_{50}/ED_{50}$. Compounds exhibiting large therapeutic indices typically are used. Although compounds that exhibit toxic side effects may be used, care should be taken to design a delivery system that targets such compounds to the site of affected tissue in order to minimize potential damage to uninfected cells and, thereby, reduce side effects. Generally, the compounds of the present invention may be administered in a manner that maximizes efficacy and minimizes toxicity.

Data obtained from cell culture assays and animal studies may be used in formulating a range of dosages for use in humans. The dosages of such compounds are generally within a range of circulating concentrations that include the $ED_{50}$ with little or no toxicity. The dosage may vary within this range depending upon the dosage form employed and the route of administration utilized. For any compound used in the methods of the invention, the therapeutically effective dose may be estimated initially from cell culture assays. A dose may be formulated in animal models to achieve a circulating plasma concentration range that includes the $IC_{50}$ (the concentration of the test compound that achieves a half-maximal inhibition of symptoms) as determined in cell culture. Such information may be used to determine accurately useful doses in humans. Levels in plasma may be measured, for example, by high performance liquid chromatography.

Moreover, the dosage administration of the pharmaceutical compositions of the present invention may be optimized using a pharmacokinetic/pharmacodynamic modeling system. For example, one or more dosage regimens may be chosen and a pharmacokinetic/pharmacodynamic model may be used to determine the pharmacokinetic/pharmacodynamic profile of one or more dosage regimens. Next, one of the dosage regimens for administration may be selected which achieves the desired pharmacokinetic/pharmacodynamic response based on the particular pharmacokinetic/pharmacodynamic profile. See WO 00/67776, incorporated herein by reference in its entirety.

Methods are known in the art for determining effective doses for therapeutic and prophylactic purposes for the disclosed pharmaceutical compositions or the disclosed drug combinations, whether or not formulated in the same composition. For therapeutic purposes, the term "jointly effective amount", as used herein, means that amount of each active compound or pharmaceutical agent, alone or in combination, that elicits the biological or medicinal response in a tissue system, animal or human that is being sought by a researcher, veterinarian, medical doctor, or other clinician, which includes alleviation of the symptoms of the disease or disorder being treated. For prophylactic purposes (i.e., inhibiting the onset or progression of a disorder), the term "jointly effective amount" refers to that amount of each active compound or pharmaceutical agent, alone or in combination, that inhibits in a subject the onset or progression of a disorder as being sought by a researcher, veterinarian, medical doctor or other clinician. Thus, the present invention provides combinations of two or more therapeutic agents wherein, for example, (a) each therapeutic agent is administered in an independently therapeutically or prophylactically effective amount; (b) at least one therapeutic agent in the combination is administered in an amount that is sub-therapeutic or sub-prophylactic if administered alone, but is therapeutic or prophylactic when administered in combination with the second or additional therapeutic agents according to the invention; or (c) both therapeutic agents are administered in an amount that is subtherapeutic or sub-prophylactic if administered alone, but are therapeutic or prophylactic when administered together. Combinations of three or more therapeutic agents are analogously possible. Methods of combination therapy include coadministration of a single formulation containing all active agents; essentially contemporaneous administration of more than one formulation; and administration of two or more active agents separately formulated.

Dosages

The pharmaceutical compositions of the present invention may be administered in a single daily dose, or the total daily dosage may be administered in divided doses of two, three, or four times daily. In the case of oral administration, the daily dosage of the compositions may be varied over a wide range from about 0.0001 to about 1,000 mg per patient, per day. The range may more particularly be from about 0.001 mg/kg to 10 mg/kg of body weight per day, about 0.1-100 mg, about 1.0-50 mg or about 1.0-20 mg per day for adults (at about 60 kg).

For oral administration, the pharmaceutical compositions may be provided in a form of scored or unscored tablets containing about 0.01, 0.05, 0.1, 0.5, 1.0, 2.5, 5.0, 10.0, 15.0, 25.0, 50.0, 100, 150, 200, 250, 300, 350, 400, 450, 500, 550, 600, 650, or 700 mg of the active ingredient for the symptomatic adjustment of the dosage for the patient to be treated.

In the case of injections, it is usually convenient to give by an intravenous route in an amount of about 0.01-30 mg, about 0.1-20 mg or about 0.1-10 mg per day to adults (at about 60 kg). In the case of other animals, the dose calculated for 60 kg may be administered as well.

The daily dosage of the pharmaceutical compositions may be varied over a wide range from about 5 to about 1000 mg per adult human per day. For oral administration, the pharmaceutical compositions optionally are provided in the form of tablets containing, 5.0, 10.0, 15.0, 100, 150, 200, 250, 300, 350, 400, 450, 500, 550, 600, 650, or 700 milligrams of the active ingredient for the symptomatic adjustment of the dosage to the patient to be treated. An effective amount of the drug typically is provided at a dosage level of from about 0.1 mg/kg to about 20 mg/kg of body weight per day. According to one aspect of the present invention, the dosage level is from about 0.2 mg/kg to about 10 mg/kg of body weight per day. According to another aspect of the present invention, the dosage level is from about 0.5 mg/kg to about 10 mg/kg of body weight per day. The compounds may be administered on a regimen of about 1 to about 10 times per day.

Doses of a compound of the present invention optionally can include 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 and/or 100-500 mg/kg/administration or any range, value or fraction thereof, or to achieve a serum concentration of 0.1, 0.5, 0.9, 1.0, 1.1, 1.2, 1.5, 1.9, 2.0, 2.5, 2.9, 3.0, 3.5, 3.9, 4.0, 4.5, 4.9, 5.0, 5.5, 5.9, 6.0, 6.5, 6.9, 7.0, 7.5, 7.9, 8.0, 8.5, 8.9, 9.0, 9.5, 9.9, 10, 10.5, 10.9, 11, 11.5, 11.9, 20, 12.5, 12.9, 13.0, 13.5, 13.9, 14.0, 14.5, 4.9, 5.0, 5.5., 5.9, 6.0, 6.5, 6.9, 7.0, 7.5, 7.9, 8.0, 8.5, 8.9, 9.0, 9.5, 9.9, 10, 10.5, 10.9, 11, 11.5, 11.9, 12, 12.5, 12.9, 13.0, 13.5, 13.9, 14, 14.5, 15, 15.5, 15.9, 16, 16.5, 16.9, 17, 17.5, 17.9, 18, 18.5, 18.9, 19, 19.5, 19.9, 20, 20.5, 20.9, 21, 22, 23, 24, 25, 26, 27, 28, 29, 30, 35, 40, 45, 50, 55, 60, 65, 70, 75, 80, 85, 90, 96, 100, 200, 300, 400, 500, 600, 700, 800, 900, 1000, 1500, 2000, 2500, 3000, 3500, 4000, 4500, and/or 5000 µg/mL serum concentration per single or multiple administration or any range, value or fraction thereof.

As a non-limiting example, treatment of humans or animals can be provided as a one-time or periodic dosage of a compound of the present invention 0.1 to 100 mg/kg such as 0.5, 0.9, 1.0, 1.1, 1.5, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 45, 50, 60, 70, 80, 90 or 100 mg/kg, per day, on at least one of day 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40, or alternatively or additionally, at least one of week 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, or 52, or alternatively or additionally, at least one of 1, 2, 3, 4, 5, 6, 7, 8, 9, 10, 11, 12, 13, 14, 15, 16, 17, 18, 19, or 20 years, or any combination thereof, using single, infusion or repeated doses.

Specifically, the pharmaceutical compositions of the present invention may be administered at least once a week over the course of several weeks. According to one aspect of the present invention, the pharmaceutical compositions are administered at least once a week over several weeks to several months. According to another aspect of the present invention, the pharmaceutical compositions are administered once a week over four to eight weeks. According to yet another aspect of the present invention, the pharmaceutical compositions are administered once a week over four weeks.

More specifically, the pharmaceutical compositions may be administered at least once a day for about 2 days, at least once a day for about 3 days, at least once a day for about 4 days, at least once a day for about 5 days, at least once a day for about 6 days, at least once a day for about 7 days, at least once a day for about 8 days, at least once a day for about 9 days, at least once a day for about 10 days, at least once a day for about 11 days, at least once a day for about 12 days, at least once a day for about 13 days, at least once a day for about 14 days, at least once a day for about 15 days, at least once a day for about 16 days, at least once a day for about 17 days, at least once a day for about 18 days, at least once a day for about 19 days, at least once a day for about 20 days, at least once a day for about 21 days, at least once a day for about 22 days, at least once a day for about 23 days, at least once a day for about 24 days, at least once a day for about 25 days, at least once a day for about 26 days, at least once a day for about 27 days, at least once a day for about 28 days, at least once a day for about 29 days, at least once a day for about 30 days, or at least once a day for about 31 days.

Alternatively, the pharmaceutical compositions may be administered about once every day, about once every 2 days, about once every 3 days, about once every 4 days, about once every 5 days, about once every 6 days, about once every 7 days, about once every 8 days, about once every 9 days, about once every 10 days, about once every 11 days, about once every 12 days, about once every 13 days, about once every 14 days, about once every 15 days, about once every 16 days, about once every 17 days, about once every 18 days, about once every 19 days, about once every 20 days, about once every 21 days, about once every 22 days, about once every 23 days, about once every 24 days, about once every 25 days, about once every 26 days, about once every 27 days, about once every 28 days, about once every 29 days, about once every 30 days, or about once every 31 days.

The pharmaceutical compositions of the present invention may alternatively be administered about once every week, about once every 2 weeks, about once every 3 weeks, about once every 4 weeks, about once every 5 weeks, about once every 6 weeks, about once every 7 weeks, about once every 8 weeks, about once every 9 weeks, about once every 10 weeks, about once every 11 weeks, about once every 12 weeks, about once every 13 weeks, about once every 14 weeks, about once every 15 weeks, about once every 16 weeks, about once every 17 weeks, about once every 18 weeks, about once every 19 weeks, about once every 20 weeks.

Alternatively, the pharmaceutical compositions of the present invention may be administered about once every month, about once every 2 months, about once every 3 months, about once every 4 months, about once every 5 months, about once every 6 months, about once every 7 months, about once every 8 months, about once every 9 months, about once every 10 months, about once every 11 months, or about once every 12 months.

Alternatively, the pharmaceutical compositions may be administered at least once a week for about 2 weeks, at least once a week for about 3 weeks, at least once a week for about 4 weeks, at least once a week for about 5 weeks, at least once a week for about 6 weeks, at least once a week for about 7 weeks, at least once a week for about 8 weeks, at least once a week for about 9 weeks, at least once a week for about 10 weeks, at least once a week for about 11 weeks, at least once a week for about 12 weeks, at least once a week for about 13 weeks, at least once a week for about 14 weeks, at least once a week for about 15 weeks, at least once a week for about 16 weeks, at least once a week for about 17 weeks, at least once a week for about 18 weeks, at least once a week for about 19 weeks, or at least once a week for about 20 weeks.

Alternatively the pharmaceutical compositions may be administered at least once a week for about 1 month, at least once a week for about 2 months, at least once a week for about 3 months, at least once a week for about 4 months, at least once a week for about 5 months, at least once a week for about 6 months, at least once a week for about 7 months, at least once a week for about 8 months, at least once a week for about 9 months, at least once a week for about 10 months, at least once a week for about 11 months, or at least once a week for about 12 months.

Methods of Using the Compounds

A. Heparan Sulfate Proteoglycan Modulation

The present invention comprises methods and compositions comprising the identification of compounds for the treatment and prevention of vascular, particularly cardiovascular diseases. More specifically, the present invention relates to methods and compositions for the treatment and prevention of smooth muscle cell proliferation, such as "anti-proliferative" compounds that effect synthesis of proteoglycans. Methods for screening for compounds or molecules that induce HSPG synthesis comprise the addition of such compounds to assays and measuring HSPG synthesis including, but not limited to, the production of Syndecan, Glypican, and Perlecan. Methods for measuring the induction of Perlecan synthesis are also contemplated hereby. Although some aspects of the present invention are described with respect to Perlecan, it is important to note that the compositions, methods, and assays described herein are equally applicable in the context of other HSPGs including Syndecan and Glypican. HSPG production is important in regulating SMC proliferation and the methods and compositions described herein provide for high throughput screening of molecules that induce HSPG production and regulate SMC proliferation.

Additionally, the present invention comprises methods and compositions for gene therapy, comprising administering compositions comprising nucleic acids that effect the synthesis or expression of HSPG, particularly Perlecan. For example, vectors comprising nucleic acids coding for Perlecan or active fragments of Perlecan are provided to cells, for example, circulatory tissue cells such as, for example, endothelial cells. Such vectors are known to those skilled in the art and can be administered in formulations that enhance the uptake of the vector by the cells.

The present invention also comprises methods and compositions for inducing the synthesis or expression of HSPGs, including, but not limited to HSPGs such as Syndecan, Glypican and Perlecan, and also comprises induction and synthesis of active fragments of HSPGs, for example, active fragments of Perlecan. As used herein, when an HSPG is referred to, the entire molecule or fragments are included therein. For example, Perlecan refers to the entire Perlecan molecule or fragments thereof. Fragments of Perlecan may have the same or different effects on cells. All of these fragments and activities are contemplated in the present invention.

A major extracellular HSPG in the blood vessel matrix is Perlecan, a protein originally identified in basement membrane. It interacts with extracellular matrix proteins, growth factors and receptors. Perlecan also is present in basement membranes other than blood vessels and in other extracellular matrix structures. It consists of a core protein of Mr.~450,000 kDa to which three HS chains of Mr~70 kDa are attached to one end of the molecule. Perlecan core protein has a complex functional organization consisting of five consecutive domains with homologies to molecules involved in control of cell proliferation, lipoprotein binding and cell adhesion. The N-terminal domain I (aa~1-195) contains attachment sites for HS chains. Domain II comprises four repeats homologous to the ligand-binding portion of the LDL receptor. Domain III has homology to domains IVa and IVb of laminin and is thought to mediate cell attachment.

SMC hyperplasia is a major event in the development of atherosclerosis and also is responsible for the significant number of failure rates following vascular procedures such as angioplasty and coronary artery bypass surgery, particularly due to restenosis. Proliferation of arterial wall SMC in response to local injury is a major feature of many vascular proliferative disorders. While not wishing to be bound by theory, it is generally thought that the endothelium regulates the growth of the underlying SMC. In the normal vessel, SMC are quiescent, but they proliferate when damage to the endothelium occurs. Naturally occurring growth modulators, many of which are derived from the endothelium, tightly control SMC proliferation in vivo.

Though not wishing to be bound by any particular mechanism, it is believed that extracellular HSPGs mediate quiescence in SMCs. In serum-starved quiescent SMC, Perlecan synthesis is induced. For example, Perlecan inhibits DNA synthesis and SMC proliferation, and blocking Perlecan results in stimulation of DNA synthesis even in the absence of serum and growth factors. Induction of Perlecan and other HSPGs is an important event for the inhibition of SMC growth. Known antiproliferative agents fail to inhibit SMC proliferation when the effects of Perlecan are blocked. Thus, the present invention comprises methods and compositions for mediating Perlecan and other HSPG synthesis, expression and amounts are taught for the maintenance of SMC in a quiescent state. Such methods and compositions of the present invention also comprise treatment and prevention of vascular diseases, more specifically, pathologies related to SMC proliferation. In particular, such pathologies include atherosclerosis and restenosis.

The present invention also comprises methods and compositions for the treatment and prevention of vascular occlusive conditions including, but not limited to, neointimal hyperplasia, restenosis, transplant vasculopathy, cardiac allograft vasculopathy, atherosclerosis, and arteriosclerosis. Such methods and compositions comprise methods for inhibition of smooth muscle cell (SMC) growth and proliferation, and for induction of quiescence in smooth muscle cells. The present invention further comprise methods and compositions for inducing HSPG synthesis and expression including, but not limited to, the induction of HSPGs such as Syndecan, Glypican and Perlecan, for example, Perlecan synthesis and gene expression.

Neointimal hyperplasia is commonly seen after various forms of vascular injury and a major component of the vein graft's response to harvest and surgical implantation into high-pressure arterial circulation. In neointimal hyperplasia, smooth muscle cells in the middle layer of the vessel wall become activated, divide, proliferate, and migrate into the inner layer. The resulting abnormal neointimal cells express pro-inflammatory molecules, including cytokines, chemokines, and adhesion molecules that further trigger a cascade of events that lead to occlusive neointimal disease and eventually graft failure.

Proliferation of SMC in response to local injury is a major feature of vascular proliferative disorders such as atherosclerosis and restenosis after angioplasty. Though not wishing to be bound to any particular theory, it is generally believed that the endothelium regulates the growth of the underlying SMC. In normal vessels, SMC are quiescent, but they proliferate when damage to the endothelium occurs. The endothelium, in addition to producing a variety of growth factors, also generates key growth inhibitors. HSPGs are components of vascular cell membranes and extracellular matrix that are believed to control a variety of vascular functions including functioning as a barrier against cationic molecules and macromolecules, protecting the main structural component of the basement membrane, type IV collagen, from proteolytic attack, binding cytokines and growth factors including, but not limited to, basic fibroblast growth factor (bFGF), vascular endothelial growth factor (VEGF), hepatocyte growth factor (HGF), keratinocyte growth factor (KGF), and transforming growth factor $\beta$ (TGF-$\beta$), functioning as storage for these cytokines, regulating mesodermal cell fate, positioning of the heart, acting in vasculogenesis and angiogenesis after ischemic injury, effecting interactions of cells with adhesive proteins and blood vessels, inducing proliferation of smooth muscle cells during atherogenesis, acting to increase cell spreading, inhibiting chemotaxis, and effecting the metabolism of lipoproteins and nonthrombogenic characteristics of endothelial cells. Additionally, it is believed that the HSPGs have different functions in different locations. For example, while cell surface HSPGs function as co-receptors for growth factors and support cell growth, extracellular HSPG can inhibit cell growth.

Although it is currently believed that endothelial HSPGs inhibit SMC proliferation, it is not known whether SMC synthesize antiproliferative HSPGs that act as autocrine inhibitors. Not wishing to be bound by any particular mechanism, it is currently believed that HSPGs inhibit DNA synthesis and SMC proliferation, and blocking HSPGs results in stimulation of DNA synthesis even in the absence of serum and growth factors. Indeed, known antiproliferative agents fail to inhibit SMC proliferation when the effects of HSPGs are blocked.

Examples of HSPGs include Syndecan, Glypican, and Perlecan, which are generated within the cardiovascular system. Vascular SMCs express Syndecans 1, 2 and 4, Glypican-1 and Perlecan. The regulation of HSPG expression in these cells, however, is not known. Cell growth stimulators such as platelet derived growth factor (PDGF), thrombin, serum, oxidized low density lipoproteins (LDL) and lysolecithin have been shown to decrease HSPG, and in particular, to decrease Perlecan. In contrast, cellular antiproliferative agents, TGF-$\beta$, apolipoprotein E and heparin stimulate HSPGs.

The present invention comprises methods and compositions for the treatment and prevention of smooth muscle cell proliferation, including vascular occlusive pathologies. Such methods comprise administering compositions comprising therapeutic agents capable of inhibiting SMC proliferation. Administration of such therapeutic agents that are effective in inhibiting SMC proliferation, such as the aforementioned thizolidinedione compositions, are administered to humans and animals suspected of having or who have, for example, vasculopathy or who have undergone angioplasty or other procedures damaging to the endothelium. Effective amounts are administered to such humans and animals in dosages that are safe and effective. Routes of administration include, but are not limited to, intravenous, subcutaneous, transdermal, nasal, and inhalation therapies. Such therapeutic agents may be used in conjunction with other therapeutic agents or altered patient activities, such as changes in exercise or diet.

The compounds of the present invention are also useful in the treatment or prophylaxis of at least one cardiovascular disease in a cell, tissue, organ, animal, or patient including, but not limited to, cardiac stun syndrome, myocardial infarction, congestive heart failure, stroke, ischemic stroke, hemorrhage, arteriosclerosis, atherosclerosis, restenosis, diabetic ateriosclerotic disease, hypertension, arterial hypertension, renovascular hypertension, syncope, shock, syphilis of the cardiovascular system, heart failure, cor pulmonale, primary pulmonary hypertension, cardiac arrhythmias, atrial ectopic beats, atrial flutter, atrial fibrillation (sustained or paroxysmal), post perfusion syndrome, cardiopulmonary bypass inflammation response, chaotic or multifocal atrial tachycardia, regular narrow QRS tachycardia, specific arrythmias, ventricular fibrillation, His bundle arrythmias, atrioventricular block, bundle branch block, myocardial ischemic disorders, coronary artery disease, angina pectoris, myocardial infarction, cardiomyopathy, dilated congestive cardiomyopathy, restrictive cardiomyopathy, valvular heart diseases, endocarditis, pericardial disease, cardiac tumors, aordic and peripheral aneuryisms, aortic dissection, inflammation of the aorta, occulsion of the abdominal aorta and its branches, peripheral vascular disorders, occulsive arterial disorders, peripheral atherlosclerotic disease, thromboangitis obliterans, functional peripheral arterial disorders, Raynaud's phenomenon and disease, acrocyanosis, erythromelalgia, venous diseases, venous thrombosis, varicose veins, arteriovenous fistula, lymphederma, lipedema, unstable angina, reperfusion injury, post pump syndrome, ischemia-reperfusion injury, and dyslipidemia. Such a method optionally comprises administering an effective amount of a composition or pharmaceutical composition comprising at least one compound to a cell, tissue, organ, animal, or patient in need of such modulation, treatment, or therapy.

1. Assessing HSPG Activity

The present invention comprises methods and compositions for determining therapeutic agents that are capable of effecting SMC proliferation. Such assays are taught herein and can be used as assays to determine agents that affect the amount or activity of HSPGs, for example, Perlecan, in such assays. For example, in one assay, Perlecan is induced in cells by certain inducers, and the response is measured. Potential therapeutic agents are then added to a replicate assay and the effect on Perlecan induction is determined. Using such methods and compositions, therapeutic agents are determined that can either inhibit Perlecan, elevate induction of Perlecan, or that have no effect at all. Such therapeutic agents can then be used in animals with SMC proliferation pathologies.

The present invention also comprises compositions comprising the compounds identified by the methods as having a desired activity. The compositions have utility in treatment of cells, tissues, or whole organisms. Such compositions are formulated for use in methods of administration in an effective amount for treatment of conditions such as biological conditions including, but not limited to, vascular occlusive lesions including atherosclerosis, transplant vasculopathy, cardiac allograft vasculopathy, restenosis, and graft atherosclerosis after coronary transplantation. The compositions may comprise other compounds including compounds with activities and pharmaceutical adjuncts that are needed for administration of the compound or compounds with the desired activity. The compositions may additionally be administered exclusively or in conjunction with other pharmaceutical compositions and surgical methods for treating smooth muscle cell proliferation and vascular occlusive diseases, including, but not limited to, before, during and after PTCA procedures.

In the assays of the present invention, the compound initially has unknown activity, effect, or effects. The activity of the compound is unknown, in that the compound's effects in the assays of the present invention are not yet determined. The compound may have many other known activities, and may be a compound that has other therapeutic uses. Any agent that causes the cells or components of the assay to respond in a measurable manner is contemplated by the present invention.

The present invention comprises methods and compositions for measuring the activity of unknown compounds. Such methods comprise assays for specific activity of biological components involved in a known cellular response. The assays provide a measurable response in which the activity of the unknown compounds is determined. This response can be measured by methods known to those skilled in the art, for example, in an ELISA. One aspect of the present invention comprises measurement of the effects of compounds on SMC proliferation in response to an HSPG-inducing agent.

According to one aspect of the present invention, a compound suspected of effecting HSPG synthesis is added to cells in an assay. The response of the cells can be measured by determining levels of HSPG synthesis measured by methods known to those skilled in the art and compared to the amount of HSPG synthesis in untreated cells. The compound may have a stimulating effect, an inhibitory effect, a stabilizing effect, or no effect at all.

According to another aspect of the present invention, a composition suspected of effecting SMC proliferation is added to smooth muscle cells in growth medium or serum-free medium. The change in cell proliferation can be measured by methods known to those skilled in the art and compared to the proliferation of cells which are not treated with the compound. The composition may have a stimulating effect, an inhibitory effect, a stabilizing effect, or no effect at all.

Compositions with HSPG stimulating effects, particularly Perlecan stimulating effects, are useful as anti-proliferative therapeutics, specifically, inhibiting SMC proliferation and thus, treating vascular occlusive conditions. These selective activators of, for example, Perlecan include small organic molecules, peptides, peptoids, or polynucleotides that act directly upon Perlecan to modulate the biological activity or to increase the biological stability of the protein. In addition, the selective activators of Perlecan can increase the biosynthesis of Perlecan by increasing the transcription of the Perlecan gene, increasing the biological stability of the Perlecan mRNA or increasing the translation of Perlecan mRNA into protein. Furthermore, the selective activators of Perlecan can block or decrease the effects of agents or proteins that inhibit the activity of Perlecan.

The present invention also comprises methods and compositions for assays that may be used to identify such selective activators or inhibitors of Perlecan. These assays readily determine the activators that up-regulate and the inhibitors that down-regulate the amount of Perlecan and its biological activity. In general, such assays include, but are not limited to, promoter-based assays to identify compounds that affect Perlecan and assays for Perlecan biological activity in recombinant, partially purified protein, or lysates from cells expressing Perlecan in the presence or absence of compounds of interest. Measurements of Perlecan include biological activity assays and quantitation of Perlecan protein, using ELISA or Western blot determinations, or quantitation of Perlecan RNA using RT-PCR, or Northern blots.

Both indirect and direct methods of measurement of changes in Perlecan are contemplated by the present invention. The assay methods contemplated hereby rely on indirect measurement of Perlecan through measurement of determinants of Perlecan activity or expression.

Additionally, direct determination of the change in the amount of Perlecan protein can be done using other immunological methods, such as Western blots, densitometric measurements or ELISA methods. Alternatively, the direct determination of the change in the amount of Perlecan mRNA can be accomplished using RT-PCR or Northern analysis methods which are known to one skilled in the art. Measurements are also directly made using lysates of cells, and purified or partially purified Perlecan protein that is either a recombinant or natural form of the protein. The means for the measurement of biological activity are known to those skilled in the art.

Another method of identifying and determining compounds that affect Perlecan comprises identifying compounds that interact with the promoter regions of the Perlecan gene, or interact and effect proteins that interact with the promoter region, and are important in the transcriptional regulation of Perlecan expression. In general, the method comprises a vector comprising regulatory sequences of the Perlecan gene and an indicator region controlled by the regulatory sequences, such as an enzyme, in a promoter-reporter construct. The protein product of the indicator region is referred to herein as a reporter enzyme or reporter protein. The regulatory region of the sequence of Perlecan comprises a range of nucleotides from approximately −4000 to +2000, where the transcription initiation site is +1, for example, from −2500 to +1200, for example, from −1500 to +800 relative to the transcription initiation site.

Cells are transfected with the vector and then treated with compounds of interest. For example, the transfected cells are treated with a compound suspected of effecting the transcription of Perlecan and the level of activity of the Perlecan regulatory sequences are compared to the level of activity in cells that were not treated with the compound. The level of activity of the Perlecan regulatory sequences are determined by measuring the amount of the reporter protein or determining the activity of the reporter enzyme controlled by the regulatory sequences. An increase in the amount of the reporter protein or the reporter enzyme activity shows a stimulatory effect on Perlecan, by positively affecting the promoter, whereas a decrease in the amount or the reporter protein or the reporter enzyme activity shows a negative effect on the promoter and thus, on Perlecan.

Additionally, the present invention comprises methods and compositions for identifying selective inhibitors of Perlecan protein or biological activity. These selective inhibitors of Perlecan are small organic molecules, peptides, peptoids, or polynucleotides that act directly upon Perlecan or the promoter region of Perlecan to modulate expression or to decrease the biological stability of the protein. In addition, the selective inhibitors of Perlecan can decrease the biosynthesis of Perlecan by decreasing the transcription of the Perlecan gene, decreasing the biological stability of the Perlecan mRNA or decreasing the translation of Perlecan mRNA into protein. Furthermore, the selective inhibitors of Perlecan can block or decrease the effects of agents or proteins that increase the activity of Perlecan.

Table 1 presents exemplary that have been shown to induce HSPG.

TABLE 1

| S. No | Compound | Fold induced at 10 μM |
|---|---|---|
| 1 | | 2.9 |
| 2 | | 2.8 |

TABLE 1-continued

| S. No | Compound | Fold induced at 10 μM |
|---|---|---|
| 3 | 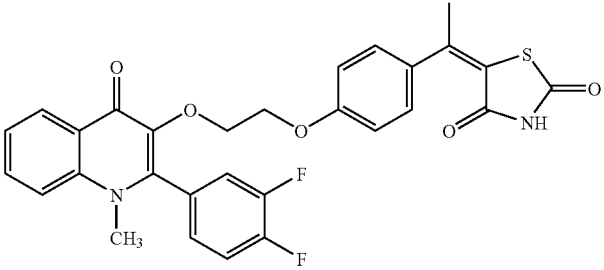 | 1.181 |
| 4 | 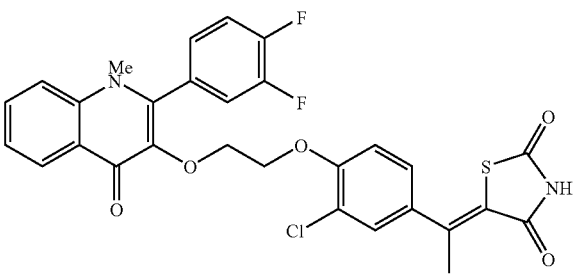 | 1.66 |
| 5 | 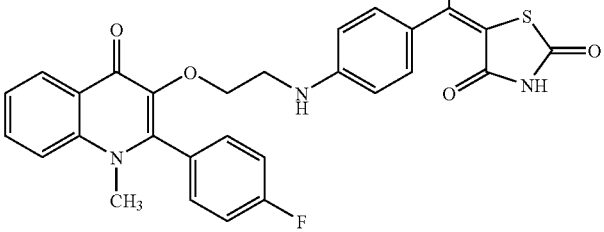 | 2.6 |

B. Heparanase Modulation

HSPGs are important components of the subendothelial extracellular matrix and the basement membrane of blood vessels. Rosenberg et al., 99 J. CLIN. INVEST. 2062-70 (1997). Basement membranes are continuous sheets of extracellular matrix composed of collagenous and noncollagenous proteins and proteoglycans that separate parenchymal cells from underlying interstitial connective tissue. They have characteristic permeabilities and play a role in maintaining tissue architecture.

In addition to HSPGs, the basal lamina consists predominantly of a complex network of adhesion proteins, fibronectin, laminin, collagen and vitronectin. Wight et al., 6 CURR. OPIN. LIPIDOL. 326-334 (1995). Heparan sulfate (HS) is an important structural component of the basal lamina. Each of the adhesion proteins interacts with HS side chains of HSPGs within the matrix. Thus, HSPGs function as a barrier to the extravasation of metastatic and inflammatory cells. Cleavage of HS by the endoglycosidase Heparanase produced by metastatic tumor cells and inflammatory cells destroys the filtering properties of the lamina. In addition, the degradation of the HS may assist in the disassembly of the extracellular matrix and thereby facilitate cell migration by allowing blood borne cells to escape into the bloodstream. Vlodavsky et al., 12 INVASION METASTASIS 112-127 (1992).

Heparanase activity has been described in a number of tissues and cell types including liver, placenta, platelets, fibroblasts, neutrophils, activated T and β-lymphocytes, monocytes, and endothelial cells (7-16). Nakajima et al., (31) CANCER LETT. 277-283 (1986); Nakajima et al., 36 J. CELL. BIOCHEM. 157-167 (1988); Ricoveri et al., 46 CANCER RES. 3855-3861 (1986); Gallagher et al., 250 BIOCHEM. J. 719-726 (1988); Dempsey et al., 10 GLYCOBIOLOGY 467 (2000); Goshen et al., 2 MOL. HUM. REPROD. 679 (1996); Parish et al., 76 IMMUNOL CELL BIOL. 104-113 (1998); Gilat et al., 181 J. EXP. MED. 1929-1934 (1995); Graham, et al., 39 BIOCHEM. MOL. BIOL. INT. 56371 (1996); Pillarisetti et al., 270 J.BIOL.CHEM. 29760-29765 (1995).

There is increasing interest in heparan sulfate compounds and their related enzymes due to a possible relationship between changes in normal activity and tumor invasiveness and tumor metastatic activity. An important process in tissue invasion by blood-borne tumor cells and white cells involves their passage through the vascular endothelial cell layer and subsequent degradation of the underlying basal lamina or basement membranes and extracellular matrix with a battery of secreted proteases and glycosidases. Nakajinia et al., 220 SCIENCE 611-613 (1983); Vlodavsky et al.,12 INVASION METASTASIS 112-127 (1992).

Heparanase activity was shown to correlate with the metastatic potential of animal and human tumor cell lines. Nakajima et al., 31 CANCER LETT. 277-283 (1986); Nakajima et al., 212 PROG CLIN BIOL RES. 113-122 (1986); Freeman et al., 325 BIOCHEM. J. 229-237 (1997); Vlodavsky et al., 5 NAT. MED. 793-802 (1999); Hulett et al., 5 NAT MED. 803-809 (1999). It also is known to regulate growth factor activity. Many growth factors remain bound to heparan sulfate in storage form and are disassociated by Heparanase during angiogenesis, improving the survival rate of cancer cells.

Serum Heparanase levels in rats were higher by more than an order of magnitude after injection of the rats with highly metastatic mammary adenocarcinoma cells. In addition, Heparanase activity in the sera of rats bearing MTLn3 tumors correlated well with the extent of the metastases. Moreover, serum/urine Heparanase activity in cancer patients was shown to be 2-4 fold increased in particular where tissue metastases were present. Because the cleavage of HS appears to be essential for the passage of metastatic tumor cells and leukocytes through basement membranes, studies of Heparanase inhibitors provides the potential of developing a novel and highly selective class of anti-metastatic and anti-inflammatory drugs.

Thus, the present invention further relates to compounds that modulate Heparanase activity. Such compounds are useful in treating and/or preventing cancer including, but not limited to, malignant and non-malignant cell growth, leukemia, acute leukemia, acute lymphoblastic leukemia (ALL), B-cell, T-cell or FAB ALL, acute myeloid leukemia (AML), chromic myelocytic leukemia (CML), chronic lymphocytic leukemia (CLL), hairy cell leukemia, myelodyplastic syndrome (MDS), a lymphoma, Hodgkin's disease, a malignamt lymphoma, non-hodgkin's lymphoma, Burkitt's lymphoma, multiple myeloma, Kaposi's sarcoma, colorectal carcinoma, pancreatic carcinoma, nasopharyngeal carcinoma, malignant histiocytosis, paraneoplastic syndrome/hypercalcemia of malignancy, solid tumors, adenocarcinomas, sarcomas, malignant melanoma, hemangioma, metastatic disease, cancer related bone resorption, cancer related bone pain.

According to another aspect of the present invention, the compounds contemplated hereby are useful in modulating heparanase activity as a means for treating and preventing autoimmune diseases.

By way of background, in the normal course of resolution of a disease in an infected tissue, local resting immune effector cells in the body become activated after recognizing antigens of the infecting organism as foreign. Upon activation these effector cells in the body synthesize and secrete signaling molecules (chemokines, lymphokines and cytokines), which attract additional immune effector cells to the site of infection, where they are also activated. Once activated, these immune effector cells become capable of exiting the vasculature and entering the infected tissue where they begin to attract and destroy the infectious agent and the infected tissue. This process continues until the infection is eradicated.

Occasionally, however, the immune system malfunctions or overreacts to the initial insult, which can lead to the initiation of debilitating and life threatening chronic and acute diseases. This can occur when (1) the immune system mistakenly identifies a cell surface molecule on normal tissue as a foreign molecule, (2) the synthesis and secretion of chemokines, cytokines, and lymphokines is not shut down after the eradication of the disease, or (3) the immune system overreacts to the apparent infection and destroys vast quantities of surrounding normal tissue.

In normal activity, the activated effector cells attract other effector cells to the blood vessels near the infection. To be "effective" these activated cells must leave the blood vessels and enter the infected tissue. The process of exiting the circulation and entering the inflamed tissue involves two distinct steps. First, the immune effector cells must bind to the luminal/apical surface of the blood vessel walls. This is accomplished through the interaction of adhesion molecules on the immune effector cells with their locally upregulated cognate receptors on the endothelial cells lining the vasculature near the site of infection.

Second, after binding to the apical surface and before entering the inflamed tissue, the immune effector cells must breach the basement membrane (BM) and extracellular matrix (ECM) that surround the basal portion of the blood vessels and give the vessels their shape and strength. The BM and ECM consists of structural proteins embedded in a fiber meshwork consisting mainly of complex carbohydrate containing structures (glycosaminoglycans), of which the main constituent is heparin sulfate proteoglycan (HSPG). In order to breach this barrier the immune effector cell must weaken or destroy it, which is accomplished through the local secretion of proteases and heparanase(s).

Thus, the inhibition of heparanase using the compounds of the present invention finds utitlity in treating arthritis and other autoimmune diseases. More specifically, the compounds of the present invention are useful in the treatment or prophylaxis of at least one autoimmune-related disease in a cell, tissue, organ, animal, or patient including, but not limited to, rheumatoid arthritis, juvenile rheumatoid arthritis, systemic onset juvenile rheumatoid arthritis, psoriatic arthritis, ankylosing spondilitis, gastric ulcer, seronegative arthropathies, osteoarthritis, inflammatory bowel disease, ulcerative colitis, systemic lupus erythematosis, antiphospholipid syndrome, iridocyclitis/uveitis/optic neuritis, idiopathic pulmonary fibrosis, systemic vasculitis/wegener's granulomatosis, sarcoidosis, orchitis/vasectomy reversal procedures, allergic/atopic diseases, asthma, allergic rhinitis, eczema, allergic contact dermatitis, allergic conjunctivitis, hypersensitivity pneumonitis, transplants, organ transplant rejection, graft-versus-host disease, systemic inflammatory response syndrome, sepsis syndrome, gram positive sepsis, gram negative sepsis, culture negative sepsis, fungal sepsis, neutropenic fever, urosepsis, meningococcemia, trauma/hemorrhage, burns, ionizing radiation exposure, acute pancreatitis, adult respiratory distress syndrome, rheumatoid arthritis, alcohol-induced hepatitis, chronic inflammatory pathologies, Crohn's pathology, sickle cell anemia, diabetes, nephrosis, atopic diseases, hypersensitivity reactions, allergic rhinitis, hay fever, perennial rhinitis, conjunctivitis, endometriosis, asthma, urticaria, systemic anaphalaxis, dermatitis, pernicious anemia, hemolytic disesease, thrombocytopenia, graft rejection of any organ or tissue, kidney transplant rejection, heart transplant rejection, liver transplant rejection, pancreas transplant rejection, lung transplant rejection, bone marrow transplant (BMT) rejection, skin allograft rejection, cartilage transplant rejection, bone graft rejection, small bowel transplant rejection, fetal thymus implant rejection, parathyroid transplant rejection, xenograft rejection of any organ or tissue, allograft rejection, anti-receptor hypersensitivity reactions, Graves disease, Raynoud's disease, type B insulin-resistant diabetes, asthma, myasthenia gravis, -meditated cytotoxicity, type III hypersensitivity reactions, POEMS syndrome (polyneuropathy, organomegaly, endocrinopathy, monoclonal gammopathy, and skin changes syndrome), polyneuropathy, organomegaly, endocrinopathy, monoclonal gammopathy, skin changes syndrome, anti-phospholipid syndrome, pemphigus, scleroderma, mixed connective tissue disease, idiopathic Addison's disease, diabetes mellitus, chronic active hepatitis, vitiligo, vasculitis, post-MI cardiotomy syndrome, type IV hypersensitivity, contact dermatitis, hypersensitivity pneumonitis, allograft rejection, granulomas due to intracellular organisms, drug sensitivity, metabolic/idiopathic, Wilson's disease, hemachromatosis, alpha-1-antitrypsin deficiency, diabetic retinopathy, hashimoto's thyroiditis, osteoporosis, hypothalamic-pituitary-adrenal axis evaluation, primary biliary cirrhosis, thyroiditis, encephalomyelitis, cachexia, cystic fibrosis, neonatal chronic lung disease, chronic obstructive pulmonary disease (COPD), familial hematophagocytic lymphohistiocytosis, dermatologic conditions, psoriasis, alopecia, nephrotic syndrome, nephritis, glomerular nephritis, acute renal failure, hemodialysis, uremia, toxicity, preeclampsia, ankylosing spondylitis, Behcet's disease, bullous pemphigoid, cardiomyopathy, celiac sprue-dermatitis, chronic fatigue immune dysfunction syndrome (CFIDS), chronic inflammatory demyelinating polyneuropathy, Churg-Strauss syndrome, cicatricial pemphigoid, CREST syndrome, cold agglutinin disease, discoid lupus, essential mixed cryoglobulinemia, fibromyalgia-fibromyositis, Graves' disease, Guillain-Barre, Hashimoto's thyroiditis, idiopathic thrombocytopenia purpura (ITP), IgA nephropathy, insulin dependent diabetes, juvenile arthritis, lichen planus, meniere's disease, multiple sclerosis, pemphigus vulgaris, polyarteritis nodosa, Cogan's syndrome, polychondritis, polyglandular syndromes, polymyalgia rheumatica, polymyositis and dermatomyositis, primary agammaglobulinemia, Raynaud's phenomenon, Reiter's syndrome, rheumatic fever, Sjögren's syndrome, stiffman syndrome, Takayasu arteritis, temporal arteritis/giant cell arteritis, Wegener's granulomatosis; okt3 therapy, anti-cd3 therapy, cytokine therapy, chemotherapy, radiation therapy (for example, including but not limited toasthenia, anemia, cachexia), chronic salicylate intoxication.

1. Heparanase Assays

The present invention further relates to methods for assaying Heparanase activity. In this regard, the effect of the compounds of the present invention may be evaluated using such assays. Future candidate compounds also useful in the treatment methods of the present invention also may be evaluated using the assays discussed herein. Furthermore, the present invention also contemplates compositions and methods for assays measuring any glycosidase activity including, but not limited to, any enzymes with glycosaminoglycan-degrading activity, chondroitinase, heparan sulfate endoglycosidase, heparan sulfate exoglycosidase, polysaccharide lyases, keratanase, hyaluronidase, glucanase, amylase, and other glycosidases and enzymes.

Thus, in one aspect, the present invention comprises compositions and methods for the measurement of cellular and enzymatic activities. Such assays can be used to measure such activities, both qualitatively and quantitatively. Moreover, the assays described herein for determining the presence of such activities may be used in methods for diagnosing metastases, metastatic potential and inflammatory states. In addition, the assays of the present invention also can be used to screen for compounds that alter, either stimulate or inhibit, such cellular and enzymatic activities.

Existing Heparanase assays require preparation of the radiolabeled substrate and separation of degraded products from the uncleaved substrate. See Goshen et al., 2 MOL. HUM. REPROD. 679-84 (1996); Nakajima et al., 31 CANCER LETT. 277-83 (1986). Other Heparanase assays require the biosynthetic radiolabeling of matrix-associated HSPG and the detection of HS chain degradation by gel-filtration analysis of radiolabeled material released from the matrix. Vlodasky et al., 12 INVASION METASTASIS 112-27 (1992).

Solid-phase Heparanase assays have also been developed where chemically and biosynthetically radiolabeled heparin and HS chains were attached to a solid support, with release of radiolabel from the solid support being a measure of enzyme activity. Assays using such procedures are taught in U.S. Pat. No. 4,859,581, which is entirely expressly herein incorporated by reference.

Previous studies have also radiolabeled both heparin and HS by iodination at naturally occurring glucosamine residues or by N-acetylation of the partially de-N-sulfated substrate. Such procedures require the use of radioactive iodine, which is a powerful ? emitter and therefore extremely hazardous. For example, one sensitive radioactive assay for Heparanase requires affinity chromatography of the Heparanase-cleaved products on columns of histidine-rich glycoprotein Sepharose. Freeman and Parish, 325 BIOCHEM. J. 229-37 (1997).

There are also some non-radioactive assays available for Heparanase. One assay for Heparanase involves measuring the optical density (at 230 nm) of unsaturated uronic acids formed during degradation of heparin. A color-based assay for measuring Heparanase activity utilizes heparin's ability to interfere with color development during the interaction of protein with the dye Coomassie brilliant blue. Kahn and Newman, 196 ANAL. BIOCHEM. 373-76 (1991).

In another Heparanase assay, a composition comprising biotin-HS is mixed with a biological sample such as a tumor sample, bodily fluid, or other fluid suspected of having Heparanase activity, to form a reaction mixture. This sample may be pretreated to remove contaminating or reactive substances such as endogenous biotin. After incubation, an aliquot or portion of the reaction mixture is removed and placed in a biotin-binding plate. After washing with buffers, a Streptavidin-enzyme conjugate is added to the biotin-binding plate. Reagents for the enzyme are added to form a detectable color product. For example, a decrease in color formation, from a known standard, indicates there was Heparanase activity in the sample. The biotin-binding plate comprises any means for binding biotin, for example, to a solid surface. See WO 02/23197, which is entirely expressly incorporated herein by reference.

In general, a method for measuring Heparanase activity comprises attaching one of a binding partner to a substrate for the enzyme to be measured. Incubation with a sample comprising the enzyme to be measured allows for activity by the enzyme to be measured in a reaction mixture. A portion or the whole reaction mixture, depending on the amount needed, is then mixed with the complementary binding partner, so that the binding partners are bound together. This is the first binding reaction. After incubating to allow for binding, washings are performed. A complementary binding partner, complementary to the first binding partner attached to the substrate, is added. This complementary binding partner may or may not be the same as the first complementary binding partner. This is the second binding reaction. The complementary binding partner in the second binding reaction is labeled in a manner that is detectable. For example, the complementary binding partner is labeled with an enzyme that causes a detectable color change when the appropriate reaction conditions exist.

Some methods comprise the use of binding partners including, but not limited to, biotin and Streptavidin. Other ways of binding one of the binding partners such as biotin, can be used at either biotin-binding step, either binding biotin to the plate or in detection of the available biotins. The number of biotins, or other binding partner, that are available for the second binding is the quantitative result of the assay. "Complementary binding partner" means one of the pair of the binding partners, such as biotin and Streptavidin or an antibody and its antigen. The biotin is the complementary binding partner of Streptavidin; Streptavidin is the complementary binding partner of biotin. An antibody that specifically binds biotin also is a complementary binding partner of biotin.

In the above method, the labeled binding partner, i.e., the enzyme labeled-streptavidin, can be labeled with any detectable marker including but not limited to, enzymes, dyes, chemiluminescence, and other methods known in the art. One such method comprises labeling with an enzyme that produces a color change in its substrate that is detectable. This method is safe, easy, and effective and can be used in both qualitative and quantitative methods.

Using the above methods, the amount of enzyme activity in a sample can be determined. Also, the above methods can be used to determine compounds that can inhibit enzyme activity. For example, a composition comprising the candidate compound is added to a known amount of Heparanase either before or during the incubation of the Heparanase and its substrate-binding partner. If the compound alters the activity of the Heparanase, the assay methods of the present invention will show a change in the amount of detectable label. Such assays are used for high throughput determination of the activity of candidate compounds. See WO 02/23197, which is entirely expressly incorporated herein by reference.

C. Inflammation Modulation

The present invention is directed to methods and compositions comprising compounds or molecules that have specific biological effects and are useful as therapeutic agents. In particular, the present invention is directed to methods and compositions comprising compounds or molecules that are effective in effecting inflammation. More particularly, the present invention is directed to methods and compositions comprising compounds or molecules that are effective in inhibiting inflammation caused by the accumulation or presence of glycated proteins or AGE. The present invention also provides compositions for and methods of treatment of biological conditions including, but not limited to, vascular complications of type I and type II diabetic-induced vasculopathies, other vasculopathies, microangiopathies, renal insufficiency, Alzheimer's syndrome, and inflammation-induced diseases such as atherosclerosis.

The present invention has utility in inhibiting inflammation or cell activation by glycated proteins or AGE. Pharmacological inhibition of AGE-induced cell activation provides the basis for therapeutic intervention in many diseases, most notably in diabetic complications and Alzheimer's disease. Therapeutic approaches for inhibition of AGE-induced inflammation include, but are not limited to, blocking the glycation of proteins, blocking AGE interactions with receptors and blocking AGE-induced signaling or signaling-associated inflammatory responses.

For example, a method of the present invention is to block AGE effects by inhibiting AGE induced signaling. The sequence of these signaling events leading to inflammation is not clear, but inhibition of these signaling events leads to reduced or no inflammatory results. Compounds that block AGE-induced up-regulation of inflammatory molecules were determined using screening assays. The present invention comprises methods and compositions comprising compounds or molecules such as the thizolidinedione compounds provided herein.

Other aspects of the present invention comprise methods and compositions comprising compounds that block glycated protein-induced inflammation. Further aspects of the present invention comprise thizolidinedione compounds that are capable of inhibiting AGE effects. Still further aspects of the present invention employ compositions comprising the compounds of the formulae contemplated hereby that block glycated protein-induced inflammation.

Enhanced formation and accumulation of glycated proteins and AGE are thought to play a major role in the pathogenesis of diabetic complications, and atherosclerosis, leading to the development of a range of diabetic complications including nephropathy, retinopathy, and neuropathy. There is ample in vivo evidence that suggests that diabetes-related complications can be reduced by 1) preventing glycation of proteins, 2) by breaking the cross-links in glycated proteins, or 3) by blocking glycated protein interaction with receptors. Despite the importance of AGE in the pathogenesis of diabetic microangiopathies, there are no currently available medications known to block AGE formation.

Aminoguanidine, which prevents AGE formation, is actively pursued as a therapy for diabetic vasculopathy. However it is not clear whether this drug would affect normal glucose metabolism or glycosylation of proteins. Moreover, some studies show that although aminoguanidine reduces AGE formation, it did not inhibit glomerular basement thickness in diabetic rats nor improved endothelial function. See, for example, Birrell et al., 43 DIABETOLOGIA 110-16 (2000); Wada et al., 42 DIABETOLOGIA 743-47 (1999); Soulis et al., 50 KIDNEY INT. 627-34 (1996).

In addition to the AGE formation inhibitors, AGE crosslink breakers are also actively pursued as a therapy for vasculopathy. N-Phenacylthiazolium bromide (PTB) is a prototype AGE cross-link breaker that reacts with and cleaves covalent AGE-derived protein cross-links. Although PTB reduced AGE accumulation, it did not prevent vascular permeability. Cooper et al., 43 DIABETOLOGIA 660-64 (2000); Oturai et al., 49(8) METABOLISM 996-1000 (2000).

Inhibition of reactions with receptors of AGE is an alternative approach to treatment of related pathologies. RAGE, a known receptor for AGE, is a possible therapeutic target. Blocking RAGE also inhibited AGE-induced inflammation. However, because of the multiple functions of RAGE and possible long term side effects of accumulated AGE in plasma, this method is not currently pursued in humans. Using the methods and compositions of the present invention, more specific inhibitory compounds can be used for treatments.

Endothelium is the target organ of damage in diabetes. See Laight et al., 15 DIABETES METAB. RES. REV. 274-82 (1999); Stehouwer et al., 34 CARDIOVASC. 55-68 (1997). Up-regulation of molecules involved in endothelial inflammation, such as IL-6 and monocyte chemoattractant protein-1 (MCP-1) leads to endothelial dysfunction and vasculopathy. See Stehouwer et al., 34 CARDIOVASC. 55-68 (1997); Libby, 247 J. INTERN. MED. 349-58 (2000); Van Lente, 293 CLINICA. CHIMICA. ACTA. 31-52 (2000).

An overall approach to the understanding and treatment of diabetes and its complications is to interfere in the regulation of genes, such as those leading to the production of cytokines, and to inhibit AGE-induced inflammation.

The effectiveness of the compounds of the present invention in inhibiting glycated protein- and AGE-induced inflammation can be determined using the assays described herein and in U.S. Provisional Patent Application Ser. No. 60/259, 306, which is incorporated by reference in herein its entirety. Such assays comprise measurement of the specific activity of biological components involved in a known cellular response. The assays provide a measurable response in which the activity of the compounds is determined. One aspect of the present invention comprises measurement of the effects of compounds on an inflammatory response by cells to the presence of a stimulating agent. Yet another aspect of the present invention includes an assay comprising endothelial cells that are stimulated by the addition of a glycated protein, the stimulating agent. The endothelial cells respond by producing specific cytokines. The amount of cytokines produced is determined by measurement protocols known to those skilled in the art. The compounds of the present invention are then added to the assay and the production of cytokines is measured. From the comparison of the assay without the compound with the assay with the compound, the biological effect of the compound can be determined. The compound may have an inhibitory effect, a stimulatory effect, or no effect at all. Compounds for treatment of inflammation include those that have an inhibitory effect.

Assays comprise endothelial cells that are stimulated in an inflammatory response by the presence of the glycated protein, glycated human serum albumin. Such endothelial cells produce cytokines. A method in accordance with the present invention comprises measurement of the amount of the cytokine IL-6, and another aspect of the present invention comprises measurement of the amount of the cytokine MCP-1. Preferably, although not required, the amount of cytokine produced is determined using immunological methods, such as ELISA assays. The methods of the present invention are not limited by the type of assay used to measure the amount of cytokine produced, and any methods known to those skilled in the art and later developed can be used to measure the amount of cytokines produced in response to the stimulating agent and to the compound having unknown activity.

IL-6 is a pro-inflammatory cytokine that is known to play a key role in the pathogenesis of diabetes and atherosclerosis. See Horii et al., 39 KIDNEY INT. SUPPL. 71-5 (1993); Huber et al., 19 ARTERIOSCLER THROMB. VASC. BIOL. 2364-67 (1999); Shikano et al., 85 NEPHRON 81-5 (2000); Pickup et al., 8(67) LIFE SCI. 291-300 (2000). IL-6 also promotes the growth of renal mesangial cells thus contributing to nephropathy. See Kado et al., 36 ACTA. DIABETOL. 67-72 (1999). The serum IL-6 level in diabetic subjects was significantly higher than in normal healthy controls (3.48+/−3.29 pg/mL vs 0.784+/−0.90 pg/mL, mean+/−SD). In addition the urinary IL-6 level is a good indicator of diabetic nephropathy. Serum IL-6 is useful in the evaluation of atherosclerosis and nephropathy.

MCP-1, another pro-inflammatory cytokine is found highly expressed in human atherosclerotic lesions and postulated to play a central in monocyte recruitment into the arterial wall and developing lesions. See Libby, 247 J. INTERN. MED. 349-58 (2000). Recent results show that MCP-1 also is a key pathogenic molecule in diabetic nephropathy. See Eitner et al., 51 KIDNEY INT. 69-78 (1997); Banba et al. 58 KIDNEY INT. 684-90 (2000).

Glycated albumin stimulates endothelial production of IL-6 and MCP-1. The effects of glycated albumin on IL-6 production are comparable to that of TNFα, a known inducer of IL-6. Because of the well established role of these cytokines in vascular diseases, screening for compounds that block AGE-induction of these cytokines provides a novel approach for identifying therapeutic agents that block AGE-induced inflammation in vivo.

Once the baseline response to the stimulating agent for the production of cytokines by the endothelial cells is established, thus comprising the control levels for the screening assay, the methods comprise addition of compounds having unknown activities. The effect of the compound on the baseline response is determined by comparing the amount of cytokine produced in the presence of the stimulating agent and the amount of cytokine produced in the presence of the stimulating agent and the compound of the present invention. In one method, compounds that have inhibitory effects on the inflammation of the cells in the presence of glycated albumin are then used as therapeutic agents. One or more compounds may be added to the screening assay. Combinations or mixtures of compounds can be added. Different amounts and formulations of the compounds are added to determine the effects on the screening assay. The screening assay also may be used to determine stimulatory compounds or compounds that have no effects in the assay.

Table 2 presents examples that have inhibited Proinflammatory cytokines IL-6 and MCP-1.

TABLE 2

| S. No | Compound | Proinflammatory cytokine | % of inhibition | Concentration in μM |
|---|---|---|---|---|
| 1 | | IL-6 | 50 | 4.64 |
| 2 | | MCP-1 | 50 | 7.9 |

TABLE 2-continued

| S. No | Compound | Proinflammatory cytokine | % of inhibition | Concentration in μM |
|---|---|---|---|---|
| 3 | | IL-6 | 49 | 5 |
| 4 | | MCP-1 | 44 | 5 |
| 5 | | MCP-1 | 50 | 4.4 |
| 6 | | MCP-1 | 61 | 5 |
| 7 | | MCP-1 | 50 | 6.5 |

TABLE 2-continued

| S. No | Compound | Proinflammatory cytokine | % of inhibition | Concentration in µM |
|---|---|---|---|---|
| 8 | 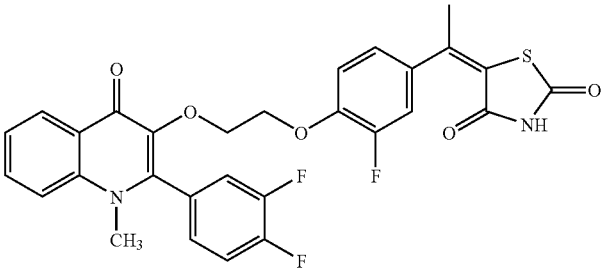 | MCP-1 | 50 | 7 |

The present invention also comprises compositions comprising the compounds identified by the methods as having a desired activity. The compositions have utility in treatment of cells, tissues, or whole organisms. Such compositions are formulated for administration in an effective amount for treatment of conditions such as biological conditions including, but not limited to, vascular complications of type I and type II diabetic induced vasculopathies, other vasculopathies, microangiopathies, renal insufficiency, Alzheimer's syndrome, and inflammation-induced diseases such as atherosclerosis. The compositions may comprise pharmacutical adjuncts that are needed for administration of the compound or compounds with the desired activity.

Moreover, the compounds of the present invention are useful in the treatment or prophylaxis of at least one autoimmune-related disease in a cell, tissue, organ, animal, or patient including, but not limited to, rheumatoid arthritis, juvenile rheumatoid arthritis, systemic onset juvenile rheumatoid arthritis, psoriatic arthritis, ankylosing spondilitis, gastric ulcer, seronegative arthropathies, osteoarthritis, inflammatory bowel disease, ulcerative colitis, systemic lupus erythematosis, antiphospholipid syndrome, iridocyclitis/uveitis/optic neuritis, idiopathic pulmonary fibrosis, systemic vasculitis/wegener's granulomatosis, sarcoidosis, orchitis/vasectomy reversal procedures, allergic/atopic diseases, asthma, allergic rhinitis, eczema, allergic contact dermatitis, allergic conjunctivitis, hypersensitivity pneumonitis, transplants, organ transplant rejection, graft-versus-host disease, systemic inflammatory response syndrome, sepsis syndrome, gram positive sepsis, gram negative sepsis, culture negative sepsis, fungal sepsis, neutropenic fever, urosepsis, meningococcemia, trauma/hemorrhage, burns, ionizing radiation exposure, acute pancreatitis, adult respiratory distress syndrome, rheumatoid arthritis, alcohol-induced hepatitis, chronic inflammatory pathologies, Crohn's pathology, sickle cell anemia, diabetes, nephrosis, atopic diseases, hypersensitity reactions, allergic rhinitis, hay fever, perennial rhinitis, conjunctivitis, endometriosis, asthma, urticaria, systemic anaphalaxis, dermatitis, pernicious anemia, hemolytic disesease, thrombocytopenia, graft rejection of any organ or tissue, kidney transplant rejection, heart transplant rejection, liver transplant rejection, pancreas transplant rejection, lung transplant rejection, bone marrow transplant (BMT) rejection, skin allograft rejection, cartilage transplant rejection, bone graft rejection, small bowel transplant rejection, fetal thymus implant rejection, parathyroid transplant rejection, xenograft rejection of any organ or tissue, allograft rejection, anti-receptor hypersensitivity reactions, Graves disease, Raynoud's disease, type B insulin-resistant diabetes, asthma, myasthenia gravis, -meditated cytotoxicity, type III hypersensitivity reactions, POEMS syndrome (polyneuropathy, organomegaly, endocrinopathy, monoclonal gammopathy, and skin changes syndrome), polyneuropathy, organomegaly, endocrinopathy, monoclonal gammopathy, skin changes syndrome, anti-phospholipid syndrome, pemphigus, scleroderma, mixed connective tissue disease, idiopathic Addison's disease, diabetes mellitus, chronic active hepatitis, vitiligo, vasculitis, post-MI cardiotomy syndrome, type IV hypersensitivity , contact dermatitis, hypersensitivity pneumonitis, allograft rejection, granulomas due to intracellular organisms, drug sensitivity, metabolic/idiopathic, Wilson's disease, hemachromatosis, alpha-1-antitrypsin deficiency, diabetic retinopathy, hashimoto's thyroiditis, osteoporosis, hypothalamic-pituitary-adrenal axis evaluation, primary biliary cirrhosis, thyroiditis, encephalomyelitis, cachexia, cystic fibrosis, neonatal chronic lung disease, chronic obstructive pulmonary disease (COPD), familial hematophagocytic lymphohistiocytosis, dermatologic conditions, psoriasis, alopecia, nephrotic syndrome, nephritis, glomerular nephritis, acute renal failure, hemodialysis, uremia, toxicity, preeclampsia, ankylosing spondylitis, Behcet's disease, bullous pemphigoid, cardiomyopathy, celiac sprue-dermatitis, chronic fatigue immune dysfunction syndrome (CFIDS), chronic inflammatory demyelinating polyneuropathy, Churg-Strauss syndrome, cicatricial pemphigoid, CREST syndrome, cold agglutinin disease, discoid lupus, essential mixed cryoglobulinemia, fibromyalgia-fibromyositis, Graves' disease, Guillain-Barré, Hashimoto's thyroiditis, idiopathic thrombocytopenia purpura (ITP), IgA nephropathy, insulin dependent diabetes, juvenile arthritis, lichen planus, ménière's disease, multiple sclerosis, pemphigus vulgaris, polyarteritis nodosa, Cogan's syndrome, polychondritis, polyglandular syndromes, polymyalgia rheumatica, polymyositis and dermatomyositis, primary agammaglobulinemia, Raynaud's phenomenon, Reiter's syndrome, rheumatic fever, Sjögren's syndrome, stiff-man syndrome, Takayasu arteritis, temporal arteritis/giant cell arteritis, Wegener's granulomatosis; okt3 therapy, anti-cd3 therapy, cytokine therapy, chemotherapy, radiation therapy (for example, including but not limited toasthenia, anemia, cachexia), chronic salicylate intoxication,. See, for example, The Merck Manual, 12th-17th Editions, Merck & Company, Rahway, N.J. (1972, 1977, 1982, 1987, 1992, 1999); Pharmacotherapy Handbook, Wells et al., eds., Second Edition, Appleton and Lange, Stamford, Conn. (1998, 2000).

D. Hyperproliferative Diseases

Several of the compounds of the present invention have cytotoxic activity and, thus, are also useful in the treatment or prophylaxis of at least one hyperproliferative disease in a cell, tissue, organ, animal, or patient including, but not limited to, malignant and non-malignant cell growth, leukemia, acute leukemia, acute lymphoblastic leukemia (ALL), B-cell, T-cell or FAB ALL, acute myeloid leukemia (AML), chromic myelocytic leukemia (CML), chronic lymphocytic leukemia (CLL), hairy cell leukemia, myelodyplastic syndrome (MDS), a lymphoma, Hodgkin's disease, a malignamt lymphoma, non-hodgkin's lymphoma, Burkitt's lymphoma, multiple myeloma, Kaposi's sarcoma, colorectal carcinoma, pancreatic carcinoma, nasopharyngeal carcinoma, malignant histiocytosis, paraneoplastic syndrome/hypercalcemia of malignancy, solid tumors, adenocarcinomas, sarcomas, malignant melanoma, hemangioma, metastatic disease, cancer related bone resorption, cancer related bone pain, or any combination thereof.

Drug-Coated Medical Devices

The compounds of the present invention may be used alone or in combination with other agents along with delivery devices to effectively prevent and treat vascular disease, and in particular, vascular disease caused by injury and/or by transplantation. Various medical treatment devices utilized in the treatment of vascular disease may ultimately induce further complications. For example, balloon angioplasty is a procedure utilized to increase blood flow through an artery and is the predominant treatment for coronary vessel stenosis. As stated above, however, the procedure typically causes a certain degree of damage to the vessel wall, thereby potentially exacerbating the problem at a point later in time. Although other procedures and diseases may cause similar injury, exemplary compounds of the present invention will be described with respect to the treatment of restenosis and related complications following percutaneous transluminal coronary angioplasty and other similar arterial/venous procedures, including the joining of arteries, veins and other fluid carrying conduits in other organs or sites of the body, such as the liver, lung, bladder, kidney, brain, prostate, neck and legs.

The local delivery of a compound of the present invention and, optionally, other therapeutic agents, from a stent prevents vessel recoil and remodeling through the scaffolding action of the stent. In addition, drug-coated stents can prevent multiple components of neointimal hyperplasia or restenosis as well as a reduce inflammation and thrombosis. Local administration of a compound of the present invention and other therapeutic agents to stented coronary arteries also may have additional therapeutic benefit. For example, higher tissue concentrations of the compounds of the present invention and other therapeutic agents may be achieved utilizing local delivery rather than systemic administration. In addition, reduced systemic toxicity may be achieved utilizing local delivery rather than systemic administration while maintaining higher tissue concentrations. In utilizing local delivery from a stent rather than systemic administration, a single procedure may suffice with better patient compliance. An additional benefit of combination therapeutic agent and/or compound therapy may be to reduce the dose of each of the therapeutic agents, thereby limiting their toxicity, while still achieving a reduction in restenosis, inflammation and thrombosis. Local stent-based therapy is therefore a means of improving the therapeutic ratio (efficacy/toxicity) of anti-restenosis, anti-inflammatory, and anti-thrombotic therapeutic agents.

Although exemplary compounds of the present invention are described herein with respect to the treatment of restenosis and other related complications, it is important to note that the local delivery of a compound of the present invention, alone or as part of a therapeutic agent combination, may be utilized to treat a wide variety of conditions utilizing any number of medical devices, or to enhance the function and/or life of the device. For example, intraocular lenses, placed to restore vision after cataract surgery is often compromised by the formation of a secondary cataract. The latter is often a result of cellular overgrowth on the lens surface and can be potentially minimized by combining a drug or drugs with the device. Other medical devices that often fail due to tissue in-growth or accumulation of proteinaceous material in, on and around the device, such as shunts for hydrocephalus, dialysis grafts, colostomy bag attachment devices, ear drainage tubes, leads for pace makers and implantable defibrillators also can benefit from the device-drug/drug combination approach. Other surgical devices, sutures, staples, anastornosis devices, vertebral disks, bone pins, suture anchors, hemostatic barriers, clamps, screws, plates, clips, vascular implants, tissue adhesives and sealants, tissue scaffolds, various types of dressings, bone substitutes, intraluminal devices, and vascular supports could also provide enhanced patient benefit using this drug-device combination approach. Any type of medical device may be coated in some fashion with a compound of the present invention, alone or as part of a therapeutic agent combination that enhances treatment over the singular use of the device or therapeutic agent.

In addition to various medical devices, the coatings may be used to deliver a compound of the present invention in combination with other therapeutic agents including antiproliferative/antimitotic agents including natural products such as vinca alkaloids (for example, vinblastine, vincristine, and vinorelbine), paclitaxel, epidipodophyllotoxins (for example, etoposide, teniposide), antibiotics (dactinomycin (actinomycin D) daunorubicin, doxorubicin and idarubicin), anthracyclines, mitoxantrone, bleomycins, plicamycin (mithramycin) and mitomycin, enzymes (L-asparaginase which systemically metabolizes L-asparagine and deprives cells which do not have the capacity to synthesize their own asparagine); antiplatelet agents such as G(GP) IIb/IIIa inhibitors and vitronectin receptor antagonists; antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nirtosoureas (carmustine (BCNU) and analogs, streptozocin), trazenes-dacarbazinine (DTIC); antiproliferative/antimitotic antimetabolites such as folic acid analogs (methotrexate), pyrimidine analogs (fluorouracil, floxuridine, and cytarabine), purine analogs and related inhibitors (mercaptopurine, thioguanine, pentostatin and 2-chlorodeoxyadenosine (cladribine)); platinum coordination complexes (cisplatin, carboplatin), procarbazine, hydroxyurea, mitotane, aminoglutethimide; hormones (e.g. estrogen); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory; antisecretory (breveldin); anti-inflammatory agents such as adrenocortical steroids (cortisol, cortisone, fludrocortisone, prednisone, prednisolone, 6a-methylprednisolone, triamcinolone, betamethasone, and dexamethasone), non-steroidal agents (salicylic acid derivatives, i.e., aspirin; para-aminophenol derivatives, i.e., acetominophen; indole and indene acetic acids (indomethacin, sulindac, and etodalac), heteroaryl acetic acids (tolmetin, diclofenac, and ketorolac), arylpropionic acids (ibuprofen and derivatives), anthranilic acids (mefenamic acid, and meclofenamic acid), enolic acids (piroxicam, tenoxicam, phenylbutazone, and oxyphenthatrazone), nabumetone, gold compounds (auranofin, aurothioglucose, gold sodium thiomalate); immunosuppressives (Cyclosporine, tacrolimus (FK-506), sirolimus (rapamycin), azathioprine, mycophenolate mofetil); angiogenic agents: vascular endothelial growth factor (VEGF), fibroblast growth factor (FGF); angiotensin receptor blockers; nitric oxide donors; anti-sense oligionucleotides and combinations thereof; cell cycle inhibitors, mTOR inhibitors, and growth factor signal transduction kinase inhibitors.

Although any number of stents may be utilized in accordance with the present invention, for simplicity, a limited number of stents will be described herein. The skilled artisan will recognize that any number of stents may be utilized in connection with the present invention. In addition, as stated above, other medical devices may be utilized.

A stent is commonly used as a tubular structure left inside the lumen of a duct to relieve an obstruction. Typically, stents are inserted into the lumen in a non-expanded form and are then expanded autonomously, or with the aid of a second device in situ. A common method of expansion occurs through the use of a catheter-mounted, angioplasty balloon that is inflated within the stenosed vessel or body passageway in order to shear and disrupt the obstructions associated with the wall components of the vessel and to obtain an enlarged lumen.

A stent may resemble an expandable cylinder and may comprise a fenestrated structure for placement in a blood vessel, duct or lumen to hold the vessel, duct or lumen open, more particularly for protecting a segment of artery from restenosis after angioplasty. The stent may be expanded circumferentially and maintained in an expanded configuration that is circumferentially or radially rigid. The stent may be axially flexible and when flexed at a band, for example, the stent avoids any externally protruding component parts.

The stent may be fabricated utilizing any number of methods. For example, the stent may be fabricated from a hollow or formed stainless steel tube that may be machined using lasers, electric discharge milling, chemical etching or other means. The stent is inserted into the body and placed at the desired site in an unexpanded form. Expansion may be effected in a blood vessel by a balloon catheter, where the final diameter of the stent is a function of the diameter of the balloon catheter used. It should be appreciated that a stent in accordance with the present invention may be embodied in a shape-memory material including, for example, an appropriate alloy of nickel and titanium or stainless steel.

Structures formed from stainless steel may be made self-expanding by configuring the stainless steel in a predetermined manner, for example, by twisting it into a braided configuration. After the stent has been formed it may be compressed to occupy a space sufficiently small as to permit its insertion in a blood vessel or other tissue by insertion means, wherein the insertion means include a suitable catheter, or flexible rod. Upon emerging from the catheter, the stent may be configured to expand into the desired configuration where the expansion is automatic or triggered by a change in pressure, temperature, or electrical stimulation.

Furthermore, a stent may be modified to comprise one or more reservoirs. Each of the reservoirs may be opened or closed as desired. These reservoirs may be specifically designed to hold the therapeutic agent/therapeutic agent combination to be delivered.

Regardless of the design of the stent, it is preferable to have the therapeutic agent/therapeutic agent combination dosage applied with enough specificity and a sufficient concentration to provide an effective dosage in the affected area. In this regard, the reservoir size in the bands is sized to apply adequately the therapeutic agent/therapeutic agent combination dosage at the desired location and in the desired amount.

Alternatively, the entire inner and outer surface of the stent may be coated with therapeutic agent/therapeutic agent combination in therapeutic dosage amounts. The coating techniques may vary depending on the therapeutic agent/therapeutic agent combination. Also, the coating techniques may vary depending on the material comprising the stent or other intraluminal medical device.

One or more compounds of the present invention and, in some instances, other therapeutic agents as a combination, may be incorporated onto or affixed to the stent in a number of ways. For example, the compound may be directly incorporated into a polymeric matrix and sprayed onto the outer surface of the stent. The compound elutes from the polymeric matrix over time and enters the surrounding tissue. The compound typically remains on the stent for at least three days up to approximately six months, for example, between seven and thirty days.

Any number of non-erodible polymers may be utilized in conjunction with the compound. According to one aspect of the present invention, the polymeric matrix comprises two layers. The base layer comprises a solution of poly(ethylene-covinylacetate) and polybutylmethacrylate. The compound is incorporated into this base layer. The outer layer comprises only polybutylmethacrylate and acts as a diffusion barrier to prevent the compound from eluting too quickly. The thickness of the outer layer or topcoat determines the rate at which the compound elutes from the matrix. Essentially, the compound elutes from the matrix by diffusion through the polymer matrix. Polymers are permeable, thereby allowing solids, liquids and gases to escape therefrom. The total thickness of the polymeric matrix is from about one micron to about twenty microns or greater. It is important to note that primer layers and metal surface treatments may be utilized before the polymeric matrix is affixed to the medical device. For example, acid cleaning, alkaline (base) cleaning, salinization and parylene deposition may be used as part of the overall process described above.

The poly(ethylene-co-vinylacetate), polybutylmethacrylate and compound solution may be incorporated into or onto the stent in a number of ways. For example, the solution may be sprayed onto the stent or the stent may be dipped into the solution. The solution may be sprayed onto the stent and then allowed to dry. The solution may be electrically charged to one polarity and the stent electrically charged to the opposite polarity. In this manner, the solution and stent will be attracted to one another. In using this type of spraying process, waste may be reduced and more precise control over the thickness of the coat may be achieved. Other methods include spin coating and plasma polymerization.

Drug-coated stents are manufactured by a number of companies including Johnson & Johnson, Inc. (New Brunswick, N.J.), Guidant Corp. (Santa Clara, Calif.), Medtronic, Inc. (Minneapolis, Minn.), Cook Group Incorporated (Bloomington, Ind.), Abbott Labs., Inc. (Abbott Park, Ill.), and Boston Scientific Corp. (Natick, Mass.). See for example, U.S. Pat. No. 6,273,913; U.S. patent application Ser. No. 20020051730; WO 02/26271; and WO 02/26139, each expressly entirely incorporated herein by reference.

Expression Profiles and Microarray Methods of Use

The present invention contemplates a variety of microarrays that may be used to study and monitor gene expression in response to treatment with the compounds of the present invention. For example, the microarrays of the present invention may be derived from, or representative of, for example, a specific organism or cell type, including human microarrays, vascular microarrays, inflammation microarrays, cancer microarrays, apoptosis microarrays, oncogene and tumor suppressor microarrays, cell-cell interaction microarrays, cytokine and cytokine receptor microarrays, blood microarrays, cell cycle microarrays, neuroarrays, mouse microarrays, and rat microarrays, or combinations thereof. The microarrays may represent diseases including cardiovascular diseases, vasculopathic conditions, inflammatory diseases, autoimmune diseases, neurological diseases, immunological diseases, various cancers, infectious diseases, endocrine disorders, and genetic diseases.

Alternatively, the microarrays useful in assessing the efficacy of the compounds of the present invention may represent a particular tissue type including, but not limited to, heart, liver, prostate, lung, nerve, muscle, or connective tissue; for example, coronary artery endothelium, umbilical artery endothelium, umbilical vein endothelium, aortic endothelium, dermal microvascular endothelium, pulmonary artery endothelium, myometrium microvascular endothelium, keratinocyte epithelium, bronchial epithelium, mammary epithelium, prostate epithelium, renal cortical epithelium, renal proximal tubule epithelium, small airway epithelium, renal epithelium, umbilical artery smooth muscle, neonatal dermal fibroblast, pulmonary artery smooth muscle, dermal fibroblast, neural progenitor cells, skeletal muscle, astrocytes, aortic smooth muscle, mesangial cells, coronary artery smooth muscle, bronchial smooth muscle, uterine smooth muscle, lung fibroblast, osteoblasts, prostate stromal cells, or combinations thereof.

The present invention further contemplates microarrays comprising a gene expression profile comprising one or more polynucleotide sequences including complementary and homologous sequences, wherein said gene expression profile is generated from a cell type treated with a compound of the present invention and is selected from the group comprising coronary artery endothelium, umbilical artery endothelium, umbilical vein endothelium, aortic endothelium, dermal microvascular endothelium, pulmonary artery endothelium, myometrium microvascular endothelium, keratinocyte epithelium, bronchial epithelium, mammary epithelium, prostate epithelium, renal cortical epithelium, renal proximal tubule epithelium, small airway epithelium, renal epithelium, umbilical artery smooth muscle, neonatal dermal fibroblast, pulmonary artery smooth muscle, dermal fibroblast, neural progenitor cells, skeletal muscle, astrocytes, aortic smooth muscle, mesangial cells, coronary artery smooth muscle, bronchial smooth muscle, uterine smooth muscle, lung fibroblast, osteoblasts, and prostate stromal cells.

The present invention contemplates microarrays comprising one or more protein-binding agents, wherein a protein expression profile is generated from a cell type treated with a compound of the present invention and is selected from the group comprising coronary artery endothelium, umbilical artery endothelium, umbilical vein endothelium, aortic endothelium, dermal microvascular endothelium, pulmonary artery endothelium, myometrium microvascular endothelium, keratinocyte epithelium, bronchial epithelium, mammary epithelium, prostate epithelium, renal cortical epithelium, renal proximal tubule epithelium, small airway epithelium, renal epithelium, umbilical artery smooth muscle, neonatal dermal fibroblast, pulmonary artery smooth muscle, dermal fibroblast, neural progenitor cells, skeletal muscle, astrocytes, aortic smooth muscle, mesangial cells, coronary artery smooth muscle, bronchial smooth muscle, uterine smooth muscle, lung fibroblast, osteoblasts, and prostate stromal cells.

More specifically, the present invention contemplates methods for the reproducible measurement and assessment of the expression of specific mRNAs or proteins in, for example, a specific set of cells. One method combines and utilizes the techniques of laser capture microdissection, T7-based RNA amplification, production of cDNA from amplified RNA, and DNA microarrays containing immobilized DNA molecules for a wide variety of specific genes, including HSPGs such as Perlecan, to produce a profile of gene expression analysis for very small numbers of specific cells. The desired cells are individually identified and attached to a substrate by the laser capture technique, and the captured cells are then separated from the remaining cells. RNA is then extracted from the captured cells and amplified about one million-fold using the T7-based amplification technique, and cDNA may be prepared from the amplified RNA. A wide variety of specific DNA molecules are prepared that hybridize with specific polynucleotides of the microarray, and the DNA molecules are immobilized on a suitable substrate. The cDNA made from the captured cells is applied to the microarray under conditions that allow hybridization of the cDNA to the immobilized DNA on the microarray. The expression profile of the captured cells is obtained from the analysis of the hybridization results using the amplified RNA or cDNA made from the amplified RNA of the captured cells, and the specific immobilized DNA molecules on the microarray. The hybridization results demonstrate, for example, which genes of those represented on the microarray as probes are hybridized to cDNA from the captured cells, and/or the amount of specific gene expression. The hybridization results represent the gene expression profile of the captured cells. The gene expression profile of the captured cells can be used to compare the gene expression profile of a different set of captured cells. For example, gene expression profiles may be generated from cells treated (and not treated) with a compound of the present invention. The similarities and differences provide useful information for determining the differences between the same cell type under different conditions, more specifically, the change in gene expression in response to treatment with a compound of the present invention.

The techniques used for gene expression analysis are likewise applicable in the context of protein expression profiles. Total protein may be isolated from a cell sample and hybridized to a microarray comprising a plurality of protein-binding agents, which may include antibodies, receptor proteins, small molecules,. Using any of several assays known in the art, hybridization may be detected and analyzed as described above. In the case of fluorescent detection, algorithms may be used to extract a protein expression profile representative of the particular cell type. In this regard, the change in protein expression in response to treatment of cells with a compound of the present invention may be evaluated.

Thus, in one aspect, the present invention relates to at least one microarray corresponding to a population of genes isolated from a particular tissue or cell type is used to detect changes in gene transcription levels that result from exposing the selected tissue or cells to a candidate drug such as a compound of the present invention. A biological sample derived from an organism, or an established cell line, may be exposed to the candidate drug in vivo or ex vivo. Thereafter, the gene transcripts, primarily mRNA, of the tissue or cells are isolated by methods well-known in the art. SAMBROOK ET AL., MOLECULAR CLONING: A LAB. MANUAL (2001). The isolated transcripts are then contacted with a microarray under conditions where the transcripts hybridize with a corresponding probe to form hybridization pairs. Thus, the microarray provides a model of the transcriptional responsiveness following exposure to a particular drug candidate. A hybridization signal may then be detected at each hybridization pair to obtain a gene expression profile.

Gene and/or protein expression profiles and microarrays also may be used to identify activating or non-activating compounds of a particular gene such as Perlecan or other HSPG. Compounds that increase transcription rates or stimulate, maintain, or stabilize the activity of a protein are considered activating, and compounds that decrease rates or inhibit the activity of a protein are non-activating. Moreover, the biological effects of a compound may be reflected in the biological state of a cell. This state is characterized by the cellular constituents. One aspect of the biological state of a cell is its transcriptional state. The transcriptional state of a cell includes the identities and amounts of the constituent RNA species, especially mRNAs, in the cell under a given set of conditions. Thus, the gene expression profiles, microarrays, and algorithms discussed herein may be used to analyze and characterize the transcriptional state of a given cell or tissue following exposure to an activating or non-activating compound, specifically, a compound of the present invention.

Microarray techniques and methods for analyzing results are well known in the art. See U.S. Pat. Nos. 6,263,287; 6,239,209; 6,218,122; 6,197,599; 6,156,501; 5,874,219; 5,837,832; 5,700,637; 5,445,934; U.S. patent application Ser. Nos. 2001/0014461 A1; 2001/0039016 A1; 2001/0034023 A1; WO 01/94946; and WO 01/77668. See also, Haab et al., 2 GENOME BIOLOGY 1-12 (2001); Brown et al., 97 PROC. NATL. ACAD. SCI. USA 262-7 (2000); Getz et al., 97 PROC. NATL. ACAD. SCI. USA 12079-84 (2000); Harrington et al., 3 CURRENT OPINION MICROBIOL 285-91 (2000); Holter et al., 97 PROC. NATL. ACAD. SCI. USA 8409-14 (2000); MacBeath et al., 289 SCIENCE 1760-63 (2000); Duggan et al., 21 NATURE GENET 10-14 (1999); Lipshutz et al., 21 NATURE GENET 5-9 (1999); Eisen et al., 95 PROC. NATL. ACAD. SCI. USA 14863-68 (1998); Ermolaeva et al., 20 NATURE GENET. 19-23 (1998); Hacia et al., 26 NUCLEIC ACIDS RES. 3865-66 (1998); Lockhart et al., NUCLEIC ACIDS SYMP. SER. 11-12 (1998); Schena et al., 16 TRENDS BIOTECHNOL. 301-6 (1998); Shalon, 46 PATHOL. BIOL. 107-9 (1998); Welford et al., 26 NUCLEIC ACID RES. 3059-65 (1998); Blanchard et al., 11 BIOSENSORS BIOELECTRONICS 687-90 (1996); Lockhart et al., 14 NATURE BIOTECHNOL. 1675-80 (1996); Schena et al., 93 PROC. NATL. ACAD. SCI. USA 10614-19 (1996); Tomayo et al., 96 PROC. NATL. ACAD. SCI. USA 2907-12 (1996); Schena et al., 270 SCIENCE 467-70 (1995).

Database Creation, Database Access and Associated Methods of Use

The present invention comprises a variety of methods including methods for providing diagnostics and predictors relating to biomolecules including HSPGS, particularly, Perlecan. The present invention further comprises methods of providing diagnostics and predictors relating to the efficacy of the compounds of the present invention. The present invention still further contemplates methods of providing expression profile databases, and methods for producing such databases, for normal and diseased tissues.

The expression profile database may be an internal database designed to include annotation information about the expression profiles generated to assess the effect of the compounds of the present invention and through other sources and methods. Such information may include, for example, the databases in which a given biomolecule was found, patient information associated with the expression profile, including age, cancer or tumor type or progression, information related to a compound of the present invention such as dosage and administration information, descriptive information about related cDNAs associated with the sequence, tissue or cell source, sequence data obtained from external sources, expression profiles for a given gene and the related disease state or course of disease, for example whether the expression profile relates to or signifies a particular disease state, and preparation methods. The expression profiles may be based on protein and/or polynucleotide microarray data obtained from publicly available or proprietary sources. The database may be divided into two sections: one for storing the sequences and related expression profiles and the other for storing the associated information. This database may be maintained as a private database with a firewall within the central computer facility. However, this invention is not so limited and the expression profile database may be made available to the public.

The database may be a network system connecting the network server with clients. The network may be any one of a number of conventional network systems, including a local area network (LAN) or a wide area network (WAN), as is known in the art (for example, Ethernet). The server may include software to access database information for processing user requests, and to provide an interface for serving information to client machines. The server may support the World Wide Web and maintain a website and Web browser for client use. Client/server environments, database servers, and networks are well documented in the technical, trade, and patent literature.

Through the Web browser, clients may construct search requests for retrieving data from, for example, a microarray database and an expression profile database. For example, the user may "point and click" to user interface elements such as buttons, pull down menus, and scroll bars. The client requests may be transmitted to a Web application that formats them to produce a query that may be used to gather information from the system database, based, for example, on microarray or expression data obtained by the client, and/or other phenotypic or genotypic information. Specifically, the client may submit expression data based on microarray expression profiles obtained from a patient treated with a compound of the present invention and use the system to obtain a diagnosis based on that information based on a comparison by the system of the client expression data with the expression data contained in the database. By way of example, the system compares the expression profiles submitted by the client with expression profiles contained in the database and then provides the client with diagnostic information based on the best match of the client expression profiles with the database profiles. Thus, in one aspect, the comparison of expression profiles aids the clinician in determining the effectiveness of treatment with a compound of the present invention. Based on such a comparison, the clinician may alter or adjust the treatment regimen.

In addition, the website may provide hypertext links to public databases such as GenBank and associated databases maintained by the National Center for Biotechnology Information (NCBI), part of the National Library of Medicine as well as, any links providing relevant information for gene expression analysis, genetic disorders, and scientific literature. Information including, but not limited to, identifiers, identifier types, biomolecular sequences, common cluster identifiers (GenBank, Unigene, Incyte template identifiers, and so forth) and species names associated with each gene, is contemplated.

The present invention also provides a system for accessing and comparing bioinformation, specifically expression profiles and other information which is useful in the context of the compositions and methods of the present invention. The computer system may comprise a computer processor, suitable memory that is operatively coupled to the computer processor, and a computer process stored in the memory that executes in the computer processor and which comprises a means for matching an expression profile of a biomolecular sequence from a patient with expression profile and sequence identification information of biomolecular sequences in a database. More specifically, the computer system is used to match an expression profile generated from a biological sample treated with a compound of the present invention with expression profile and other information in a database.

Furthermore, the system for accessing and comparing information contained in biomolecular databases comprises a computer program comprising computer code providing an algorithm for matching an expression profile generated from a patient, for example, treated with a compound of the present invention, with expression profile and sequence identification information of biomolecular sequences in a biomolecular database.

The present invention contemplates, for example, the use of a Graphical User Interface ("GUI") for the access of expression profile information stored in a biomolecular database. The GUI may be composed of two frames. A first frame may contain a selectable list of biomolecular databases accessible by the user. When a biomolecular database is selected in the first frame, a second frame may display information resulting from the pair-wise comparison of the expression profile database with the client-supplied expression profile as described above, along with any other phenotypic or genotypic information.

The second frame of the GUI may contain a listing of biomolecular sequence expression information and profiles contained in the selected database. Furthermore, the second frame may allow the user to select a subset, including all of the biomolecular sequences, and to perform an operation on the list of biomolecular sequences. The user may select the subset of biomolecular sequences by selecting a selection box associated with each biomolecular sequence. The operations that may be performed include, but are not limited to, downloading all listed biomolecular sequences to a database spreadsheet with classification information, saving the selected subset of biomolecular sequences to a user file, downloading all listed biomolecular sequences to a database spreadsheet without classification information, and displaying classification information on a selected subset of biomolecular sequences.

If the user chooses to display classification information on a selected subset of biomolecular sequences, a second GUI may be presented to the user. The second GUI may contain a listing of one or more external databases used to create the expression profile databases as described above. Furthermore, for each external database, the GUI may display a list of one or more fields associated with each external database. The GUI may allow the user to select or deselect each of the one or more fields displayed in the second GUI. The GUI also may allow the user to select or deselect each of the one or more external databases.

The methods of the present application further relate to the commercial and other uses of the compositions and methodologies of the present invention. In one aspect, the methods include the marketing, sale, or licensing of the compositions and methodologies of the present invention in the context of providing consumers, i.e., patients, medical practitioners, medical service providers, researchers, and pharmaceutical distributors and manufacturers, with expression profile databases including, in particular, databases produced in accordance with the use of the compounds of the present invention.

The methods of the present invention include establishing a distribution system for distributing the pharmaceutical compositions of the present invention for sale, and may optionally include establishing a sales group for marketing the pharmaceutical composition.

The present invention provides a method of conducting target discovery comprising identifying, by one or more of the above drug discovery methods, a test compound, as described above, which modulates the level of expression of a gene or the activity of a gene product such as Perlecan; conducting therapeutic profiling of agents identified, or further analogs thereof, for efficacy and toxicity in animals; and optionally formulating a pharmaceutical composition including one or more of the agents identified as having an acceptable therapeutic profile; and optionally licensing or selling, the rights for further drug development of said identified agents.

The present invention is further illustrated by the following preparations and examples, which are not to be construed in any way as imposing limitations upon the scope thereof. It will be clear to one of skill in the art that various other modifications, embodiments, and equivalents thereof exist that do not depart from the spirit of the present invention and/or the scope of the appended claims.

PREPARATION 1

1-[4-(2-Bromo ethoxy)phenyl]-1-ethanone

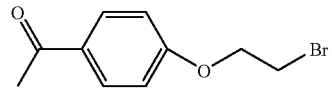

A mixture of 4-hydroxyacetophenone (20 g, 147 mmol) and potassium carbonate (81 g, 588 mmol) was placed into 2 L round bottomed flask and acetone (1 L) was added. To this reaction mixture dibromoethane (38 mL) was added in one portion, and then the reaction mixture was allowed to reflux for 36 hours, under nitrogen atmosphere. The reaction mixture was cooled to room temp, and filtered off, residue was washed with acetone (2×100 mL), and the filtrates were combined and concentrated under reduced pressure. The crude was chromatographed over silica gel by using 10-15% ethyl acetate/pet. ether (2 L), affording the title compound 7 g (20%) as a white solid. Mp. 58-61° C.

IR: $?_{max}$ (KBr, cm$^{-1}$): 1678, 1603; $^1$H NMR (200 MHz, CDCl$_3$): d 7.93 (d, J=8.87 Hz, 2H), 6.93 (d, J=8.87 Hz, 2H), 4.35 (t, J=6.18 Hz, 2H), 3.67 (t, J=6.28 Hz, 2H), 2.55 (s, 3H); Mass (CI method, I-butane): 245 (MH$^+$, 100), 243 (M$^+$, 100).

PREPARATION 2

2-(3,4-Dimethoxyphenyl)-3-hydroxy-5,7-dimethoxy-4H-4-chromenone

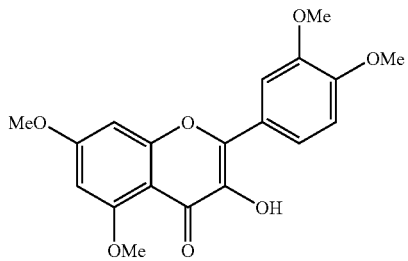

Step (i)

3-[(6-O-(deoxy-a-L-manopyranosyl)-β-glucopyranosyl)oxy]-2-(3,4-dimethoxyphenyl)-5,7-dimethoxy-4H-1-benzopyran-4-one

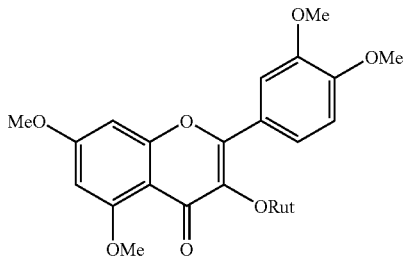

A mixture of Rutin hydrate (1) (80 g, 120.5 mmol) and potassium carbonate (320 g, 2319 mmol) was placed into a 2 L three neck round bottom flask, fitted with a reflux condenser with nitrogen atmosphere and dropping funnel and acetone (1.5 L) was added. To this reaction mixture dimethyl sulfate (160 mL) was added dropwise. The reaction mixture was refluxed at 60° C. for 68 hours. Then the reaction mixture was cooled to 25° C. and the solid separated was filtered. The residue was washed with acetone (1 L) followed by methanol (500 mL), filtrates were combined and concentrated under reduced pressure affording the title compound (80 g, 91%), as a yellow gummy solid.

Step (ii)

2-(3,4-dimethoxyphenyl)-3-hydroxy-5,7-dimethoxy-4H-4-chromenone

The compound obtained in step (i) (80 g, 110 mmol) was placed in a 2 L single neck round bottom flask and hydrochloric acid (20%, 1 L) was added at 25° C. The reaction mixture was allowed to reflux at 100° C. for 2 hours and then cooled to 25° C. The solid that separated was filtered, washed with isopropanol (200 mL) and dried under vacuum to affording the title compound (27.5 g, 70%) as a pale yellow solid. Mp. 192-194° C.

IR: $?_{max}$ (KBr, cm$^{-1}$): 3279, 2925, 1609, 1516; $^1$H NMR (200 MHz, CDCl$_3$): d 7.83-7.79 (m, 2H), 7.00 (d, J=9.14 Hz, 1H), 6.56 (d, J=1.88 Hz, 1H), 6.36 (s, 1H), 3.99 (s, 6H), 3.96 (s, 3H), 3.93 (s, 3H); Mass (CI method, I-butane): 359 (M$^+$, 100).

PREPARATION 3

1-(4-{2-[2-(3,4-Dimethoxyphenyl)-5,7-dimethoxy-4-oxo-4H-3-chromenyloxy]ethoxy}phenyl)-1-ethanone

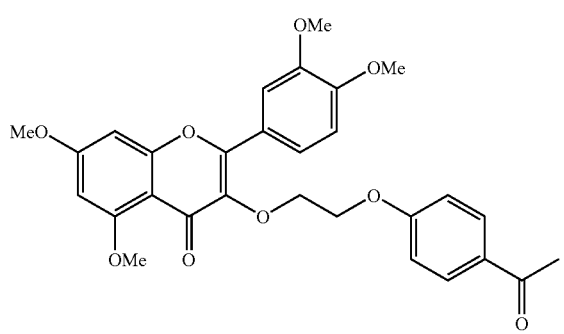

A mixture of compound obtained in Preparation 2 (25 g, 69.6 mmol), a compound obtained in Preparation 1 (21.5 g, 88.4 mmol) and potassium carbonate (77 g, 557 mmol) was placed in a 1 L round bottomed flask and DMF (400 mL) was added to the reaction mixture. The reaction mixture was heated to 80° C. with stirring for 3 hours under a nitrogen atmosphere. The reaction mixture was cooled to 25° C. and poured slowly into ice-cold water (1 L). The separated solid was filtered and washed with water (2×500 mL). It was triturated with methanol and filtered to afford the title compound (31.5 g, 87%), as a pale brown solid, after drying under vacuum. Mp. 143-144° C.

IR: $?_{max}$ (KBr, cm$^{-1}$): 1668, 1624, 1600; $^1$H NMR (200 MHz, CDCl$_3$): d 7.87 (d, J=8.79 Hz, 2H), 7.71-7.67 (m, 2H), 6.87-6.76 (m, 3H), 6.51 (s, 1H), 6.36 (s, 1H), 4.47 (d, J=4.40 Hz, 2H), 4.29 (t, J=4.40 Hz, 2H), 3.97 (s, 3H), 3.90 (s, 9H), 2.54 (s, 3H); Mass (CI method, I-butane): 521 MH$^+$, 30), 385 (100).

PREPARATION 4

4-Fluorophenylacetate

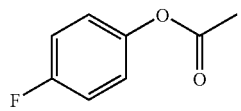

4-Fluorophenol (20 g, 178.5 mmol) was placed into single neck 1 L round bottomed flask to which sodium hydroxide solution (12 g in 100 mL water) was added. The reaction mixture was stirred for 5-10 min at 25° C. and crushed ice (50 g) was added to it followed by acetic anhydride (30 mL). The reaction mixture was stirred for 15 min at the same temperature and water (300 mL) followed by hydrochloric acid (6 N, 60 mL) was added to it. The mixture was extracted with chloroform (3×100 mL), combined extracts were dried over sodium sulphate and concentrated under reduced pressure to afford the title compound (26 g, 95%) as a white solid.

IR: $?_{max}$ (KBr, cm$^{-1}$): 1764; $^1$H NMR (200 MHz, CDCl$_3$): 7.05 (s, 2H), 7.01 (s, 2H), 2.27 (s, 3H); Mass (CI method, I-butane): 155(M$^{+1}$, 100).

PREPARATION 5

(2-Hydroxy-4-fluoro phenyl)-1-ethanone

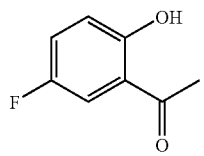

A mixture of 4-fluorophenylacetate obtained in Preparation 4 (25 g, 223 mmol), aluminium chloride (89 g, 670 mmol), was placed into 1 L single neck round bottom flask, fitted with an air condenser and calcium chloride guard tube. The reaction mixture was slowly heated to 120-125° C. over 30 minutes, and then to 165° C. (generation of HCl gas was observed). The mixture was stirred at the same temperature for 30 min and then cooled to room temp. Water (500 mL) was added to it followed by 6 N HCl (150 mL). The mixture was extracted with chloroform (3×200 mL), combined organic layers were dried over sodium sulfate and concentrated under reduced pressure to afford the title compound (21 g, 84%) as a white solid.

IR: ?$_{max}$ (KBr, cm$^1$): 3442, 1650; $^1$H NMR (200 MHz, CDCl$_3$): 11.98 (s, H, D$_2$O exchangeable), 7.43-7.37 (m, 1H), 7.27-7.17 (m, 1H), 6.98-6.91 (m, 1H), 2.62 (s, 3H); Mass (CI method, I-butane): 155 (M+1, 47).

PREPARATION 6

1-(5-Fluoro-2-hydroxyphenyl)-3-(4-methoxyphenyl)-2-propen-1-one

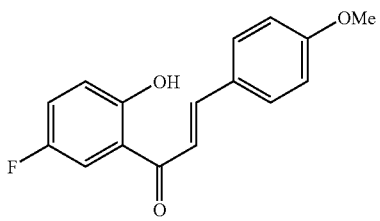

To a mixture of (2-hydroxy-4-fluoro phenyl)-1-ethanone (3 g, 19.7 mmol) obtained in Preparation 5, and 4-fluorobenzaldehyde (4.37 g, 19.7 mmol) in methanol was slowly added sodium hydroxide solution at 0° C., under N$_2$ atm. The reaction mixture was allowed to stir for 10 hours at 0-10° C. Water (100 mL) was added to it followed by 6 N HCl (15 mL). Solid separated was filtered off and dried under vacuum to afford 3 g (41%) of the title compound as a yellow solid.

IR: ?$_{max}$ (KBr, cm$^{-1}$): 3500, 1642; $^1$H NMR (200 MHz, CDCl$_3$): 12.6 (s, 1H, D$_2$O exchangeable), 7.92 (d, J=15.3 Hz, 2H), 7.76-7.55 (m, 3H), 7.41 (d, J=15.3 Hz, 2H), 7.0-6.94 (m, 2H), 3.87 (s, 3H); Mass (CI method, I-butane): 272 (M+, 100%).

PREPARATION 7

6-Fluoro-2-(4-methoxy phenyl)-3-hydroxy-4H-4-chromenone

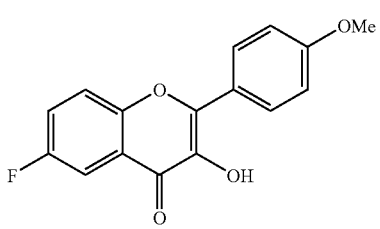

The chalcon product (3.0 g, 11 mmol), obtained in Preparation 6, was dissolved in methanol (30 mL) and cooled to 0° C. To this mixture was added sodium hydroxide solution (20 mL, 20%) and then the reaction mixture was stirred at the same temperature for 5-10 min. Hydrogen peroxide was added to this mixture and stirring continued at 0-10° C. for 1 hours. Water (100 mL) was added to it followed by 6 N HCl (30 mL). Separated solid was filtered off and dried under vacuum to afford 1.0 g (32%) of the title compound as a yellow solid.

IR: ?$_{max}$ (KBr, cm$^{-1}$): 3261, 1602, 1559; $^1$H NMR (200 MHz, CDCl$_3$): δ8.23 (d, J=9.13 Hz, 2H), 7.90-7.85 (m, 1H), 7.63-7.56 (m, 1H), 7.48-7.38 (m, 1H), 7.06 (d, J=9.13 Hz, 2H), 3,91 (s, 3H); Mass (CI method, I-butane): 287(M+1, 100%).

PREPARATION 8

1-(4-{2-[6-Fluoro-2-(4-methoxyphenyl)-4-oxo-4H-3-chromenyloxy}phenyl)-1

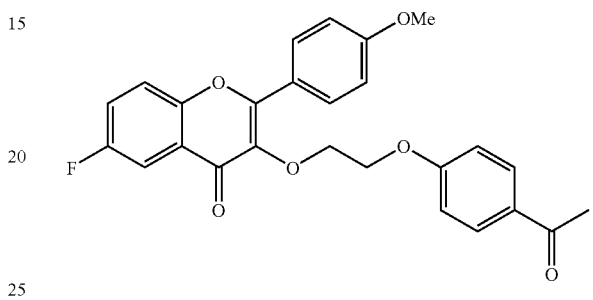

A mixture of the product obtained in Preparation 7 (0.3 g, 1.04 mmol), a compound obtained in Preparation 1 (0.25 g, 1.04 mmol) and potassium carbonate (0.86 g, 6.2 mmol) was placed in 1 L round bottomed flask and DMF (15 mL) was added to the mixture. The mixture was heated to 80° C. with stirring for 3 hours under a nitrogen atmosphere. The reaction mixture was cooled to 25° C. and poured slowly into ice-cold water (1 L). The solid that separated was filtered and washed with water (2×500 mL). It was triturated with methanol and filtered to afford the title compound (0.4 g, 85%), as a pale brown solid, after drying under vacuum.

PREPARATION 9

N-Methyl anthranilic acid

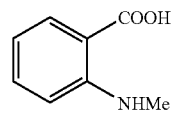

To a solution of methyl-N-methyl anthranilate (20 g, 121 mmol) in methanol (100 mL), placed in a 250 mL single neck round bottomed flask, was added a solution of NaOH (9.69 g, 242 mmol) in 25 mL of water at 0-10° C. The reaction mixture was heated to 50° C. for 6 hours and then cooled to room temperature. Methanol was removed completely from the reaction mixture and water (100 mL) was added to it. The mixture was washed with ether (3×50 mL) and the aqueous layer was acidified (pH ~5-6) with ice cold 2 N HCl. The solid that separated was filtered, washed with water (2×50 mL) and dried under vacuum to afford the title compound 17.0 g (93%) as a white color solid. mp-178-180° C.

$^1$H NMR (200 MHz, CDCl$_3$): δ7.99 (dd, 1H, J=1.34 Hz), 7.46-7.25 (m, 1H), 6.70-6.58 (m, 2H), 2.93 (s, 3H); Mass (CI method): 152 (M+1, 100%).

PREPARATION 10

2-Bromo-1-(4-methylphenyl)-1-ethanone

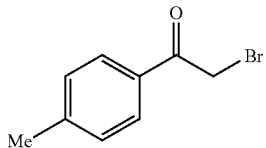

To a stirring solution of 20 g (150 mmol) of 4-methylacetophenone in 100 mL of glacial acetic acid was added catalytic amount of HBr (0.5 mL) followed by 21.40 g (134 mmol) of bromine dissolved in acetic acid (30 mL) dropwise at 10-15° C. The reaction mixture was stirred at 25-35° C. for 5 hrs, then poured into water (100 mL). The solid that separated was filtered to give the required product (20 g, 65%).

$^1$H NMR (200 MHz, CDCl$_3$): δ7.88(d, J=8.3 Hz, 2H), 7.29(d, 8 Hz, 2H), 4.42(s, 2H), 2.41(s, 3H).

PREPARATION 11

2-(4-Methyl phenyl)-2-oxo ethyl-2-methylaminobenzoate

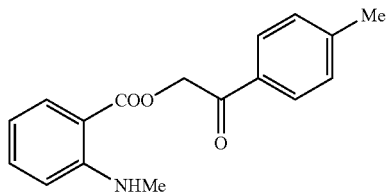

To a solution of N-methyl anthranilic acid (10.0 g, 66 mmol), obtained in Preparation 9, in 100 mL of dimethyl formamide, placed in a 250 mL single neck round bottomed flask was added a solution of KOH (3.89 g, 69 mmol) in 10 mL of water and the mixture was stirred for 45 min at 25-35° C. The mixture was cooled to 10° C., and the bromoketone (16.9 g, 79 mmol), obtained in Preparation 10, was added to it. The reaction mixture was stirred for 10 hours at room temperature and then poured in ice water (500 mL). The solid that separated out was filtered, washed with water (2×100 mL) and dried under vacuum to afford the title compound (11.0 g, 58%) as a white color solid. Mp: 96-98° C.

IR (KBr, cm$^{-1}$): 3382, 1684, 1674; $^1$H NMR (200 MHz, DMSO-d$_6$): δ 7.91-7.87 (m, 3H), 7.47-7.34 (m, 3H), 6.75-6.57 (m, 2H), 5.62 (s, 2H), 3.32 (s, NH), 2.83 (d, J=4.3 Hz, 3H), 2.38 (s, 3H); Mass (CI method): 284 (M+1, 100%).

PREPARATION 12

3-Hydroxy-1-methyl-2-(4-methylphenyl)-1,4-dihydro-4-quinolinone

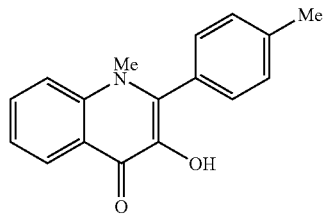

Polyphosphoric acid (PPA, 80 g) was heated to 140° C. under nitrogen atmosphere in a 250 mL single neck round bottom flask. 2-(4-Methyl phenyl)-2-oxo ethyl-2-methylaminobenzoate (10 g, 35 mmol) obtained in Preparation 11 was added in small portions and the mixture was stirred at 140° C. for 6 hours. The mixture was cooled to 25-35° C. and ice cooled water was added to the mixture and stirred for 30 min. Solids that separated were filtered, washed with water and dried under vacuum to afford the title compound (6.0 g, 73%) as brown solid. Mp. 216-218° C.

IR (KBr, cm$^{-1}$): 3433, 1598; $^1$H NMR (200 MHz, DMSO-d$_6$): δ 8.44 (d, J=8.3 Hz, 1H), 8.06-7.91 (m, 2H), 7.75-7.61 (m, 1H), 7.48-7.35 (m, 4H), 5.21 (bs, OH), 3.70 (s, 3H), 2.43 (s, 3H); Mass (CI method): 266 (M+1, 100%).

PREPARATION 13

4-(2-Bromoethoxy)benzaldehyde

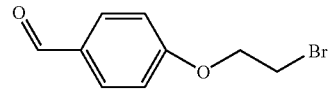

A mixture of 4-hydroxybenzaldehyde (10.0 g, 82 mmol) and potassium carbonate (46 g, 326 mmol) was placed into 2 L round bottom flask, and DMF (150 mL) was added. The mixture was stirred for 45 min. and dibromoethane (46 g) was added in one portion, then the reaction mixture was allowed to stir at 25-35° C. for 96 hrs under a nitrogen atmosphere. The reaction mixture was cooled to 25-35° C. and then poured into water (500 mL). The mixture was extracted with EtOAc (3×100 mL), combined organic layers were dried over anhydrous Na$_2$SO$_4$ and concentrated under reduced pressure. The crude product was purified by column chromatography over silicagel by using 10-15% ethyl acetate/pet. ether to afford the title compound (8.50 g, 45%) as a white solid.

IR(KBr, cm1): 3439, 1682, 1602,1577; $^1$H NMR (200 MHz, CDCl$_3$):δ9.88(s, 1H), 7.86(d, J=8.8 Hz ,2H), 7.03(d, J=8.8 Hz, 2H), 4.40(t, 2H, J=6.2 Hz), 3.69(t, J=5.9 Hz, 2H); Mass(CI method): 231 (M$^{+2}$, 231, 100%).

PREPARATION 14

1-(3-{2-[1-Methyl-2-(4-methylphenyl)-4-oxo-1,4-dihydro-3-quinoliniloxy]ethoxy}phenyl)-1-ethanone

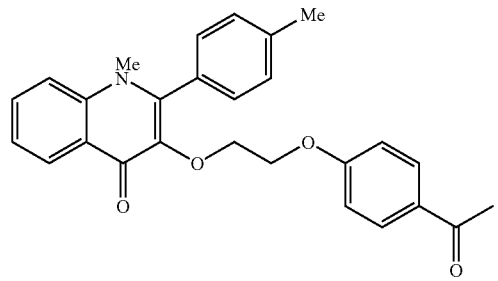

A mixture of hydroxy compound obtained in Preparation 12 (3.0 g, 11 mmol), bromoketo compound obtained in Preparation 1 (2.43 g, 10 mmol) and potassium carbonate (6.24 g, 45 mmol) was placed in a 1 L round bottomed flask and DMF (30 mL) was added. The mixture was heated to 80° C. with stirring and held at this temperature for 12 hours under a nitrogen atmosphere. The mixture was cooled to 25° C. and poured slowly into ice-cold water (1 L). The solid that separated was filtered and washed with water (2×500 mL). It was triturated with methanol and filtered to afford the title compound (2.8 g, 64%), as a pale brown solid, after drying under vacuum.

$^1$H NMR (200 MHz, CDCl$_3$): δ 8.60 (d, J=7.8 Hz, 1H), 7.74-7.21 (m, 10H), 6.93 (d, J=8.3 Hz, 1H), 4.37 (t, J=4.4 Hz,2H), 4.02 (t, J=4.9 Hz, 2H), 3.52 (s, 3H), 2.56 (s, 3H), 2.37 (s, 3H). Mass (CI method): 428 (M+1, 428, 100%).

PREPARATION 15

4-(2-Bromo-ethoxy)-benzoic Acid Ethyl Ester

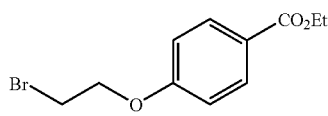

Step (i)

To a solution of 4-hydroxybenzoic acid (15 g, 108.6 mmol) in ethanol (200 mL) was added SOCl$_2$ (16 mL, 217.4 mmol) at 0° C. under anhydrous condition. The mixture was heated to reflux for 7 hours with stirring. After completion of the reaction, the mixture was concentrated under vacuum and the residue was neutralized by using aqueous NaHCO$_3$ solution until the pH reached 7.0. The solid separated was filtered, washed with water (2×50 mL), and dried under vacuum to afford the desired compound in 89% yield (16 g).

Step (ii)

A mixture of 4-hydroxybenzoic ester (5 g, 30.12 mmol) and anhydrous K$_2$CO$_3$ (4.62 g, 33.51 mmol) in acetone (50 mL) was stirred at 50° C. for 30 min. under Nitrogen atmosphere. 1,2-Dibromoethane (34 g, 180.7 mmol) was added to the mixture at the same temperature, and stirring continued for 6 hrs. The mixture was filtered and the residue was washed with acetone (2×25 mL). The filtrates were collected, combined and concentrated. The residue was purified by crystallization from hexane to give the desired product in 96% yield (6.0 g).

PREPARATION 16

4-{2-[2-(3,4-Dimethoxy-phenyl)-5,7-dimethoxy-4-oxo-4H-chromen-3-yloxy]-ethoxy}-benzoic Acid Ethyl Ester

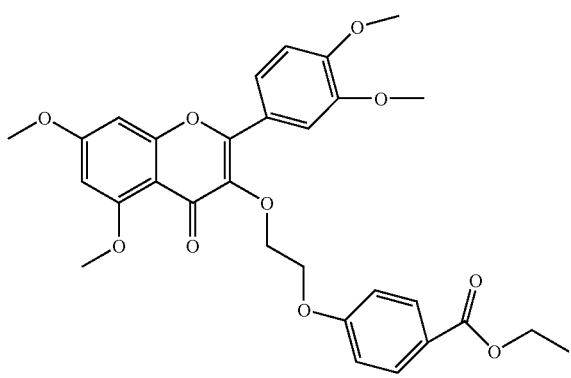

A mixture of 2-(3,4-dimethoxyphenyl)-3-hydroxy-5,7-dimethoxy-4H-4-chromenone (4 g, 11.17 mmol) obtained in Preparation 2,4-(2-Bromo-ethoxy)-benzoic acid ethyl ester (3.66 g, 13.40 mmol) obtained in Preparation 15 and K$_2$CO$_3$ (4.62 g, 33.51 mmol) in DMF (20 mL) was stirred at 80° C. for 9 hrs under Nitrogen atmosphere. The mixture was poured into water (60 mL) and stirred for 30 min. The separated solid was filtered, washed with water (2×20 mL) and dried under vacuum to give the desired product in 68% yield (4.2 g).

PREPARATION 17

4-{2-[2-(3,4-Dimethoxy-phenyl)-5,7-dimethoxy-4-oxo-4H-chromen-3-yloxy]-ethoxy}-benzoic Acid

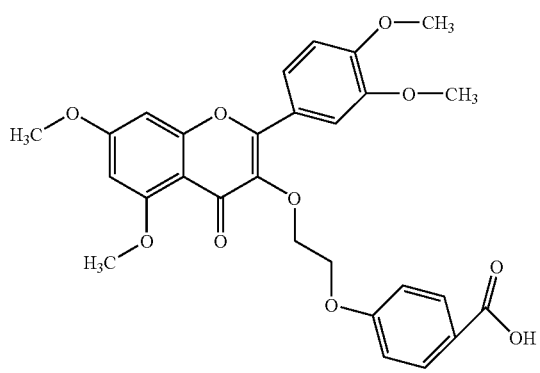

To a solution of 4-{2-[2-(3,4-Dimethoxy-phenyl)-5,7-dimethoxy-4-oxo-4H-chromen-3-yloxy]-ethoxy}-benzoic acid ethyl ester (4 g, 7.27 mmol) obtained in Preparation 16, in a mixture of methanol (40 mL) and dioxane (40 mL) was added a solution of KOH (2.0 g, is 36.36 mmol) in water (10 mL) at 25-35° C. and the mixture was stirred at 60° C. for 6 hrs. Then solvent was removed from the mixture under vacuum and the residue was acidified with cold HCl. The solid separated was filtered, washed with cold water (2×3 mL) and dried under vacuum. The crude product was purified further by crystallization from ethanol to give the desired acid in 84% yield (3.2 g).

PREPARATION 18

2-(Toluene-4-sulfonylamino)-succinamic Acid

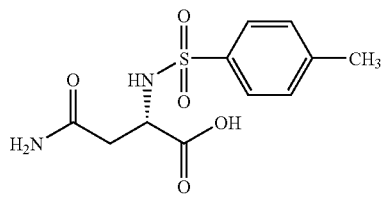

To a stirred solution of L-Aspergine (15 g, 100 mmol), NaOH (4.4 g, 110 mmol) in a mixture of water (75 mL) and dioxane (75 mL) was added p-toluenesulfonyl chloride (20.9 g, 110 mmol) at 0° C. After stirring for 1 min. additional quantity of NaOH (4.4 g, 110 mmol) in water (75 mL) was added to the reaction mixture at the same temperature. Stirring continued for 1 hr. and then dioxane was removed from the mixture under low vacuum. The residue was washed with ethylacetate (2×30 mL), aqueous layers collected, combined, and acidified with conc. HCl very slowly with stirring at 0° C. The solid separated was filtered and washed with cold water (2×30 mL) to afford the desired product in 59% yield (17 g). mp: 198-200° C.

PREPARATION 19

3-Amino-2-(toluene-4-sulfonylamino)propionic Acid Ethyl Ester

Step (i)

3-Amino-2-(toluene-4-sulfonylamino)-propionic Acid

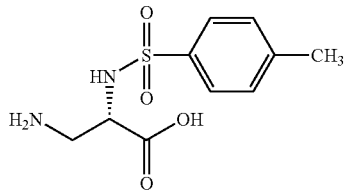

To a cold (0° C.) and stirring solution of NaOH (1.95 g, 48.95 mmol) in water (8.7 mL) was added bromine (0.36 mL, 6.99 mmol) slowly and drop wise. After 5 min. a cold solution of Preparation 18 (2.0 g, 6.99 mmol) and NaOH (0.55 g) in water (6.4 mL) was added in one portion. The solution was stirred for 20 min. at 0° C. and then for 30 min. at 90° C. The mixture was cooled to 0° C. and the pH was adjusted to 7.0 by slow addition of conc. HCl. The solid separated was filtered, washed with cold EtOAc (2×25 mL) and dried under vacuum to afford the desired compound in 61% yield (1.1 g). mp 225-226° C.

Step (ii)

3-Amino-2-(toluene-4-sulfonylamino)-propionic Acid Ethyl Ester

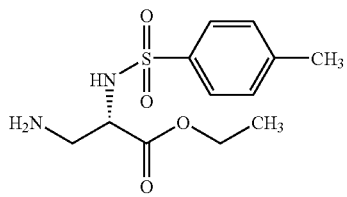

To a cold (0° C.) and stirring solution of the compound (2 g, 7.75 mmol), obtained in step (i), in ethanol (20 mL) was added SOCl$_2$ (1.25 mL, 17.05 mmol) under anhydrous condition. The mixture was heated to reflux for 12 hrs with stirring. After completion of the reaction, the mixture was concentrated under vacuum to afford the hydrochloride salt of title compound in 90% yield (2.0 g). This was used for the next step without further purification.

PREPARATION 20

4-(3,4-Dimethoxyphenylcarboxamido)-1-methyl-3-propyl-1H-5-pyrazolecarboxamide

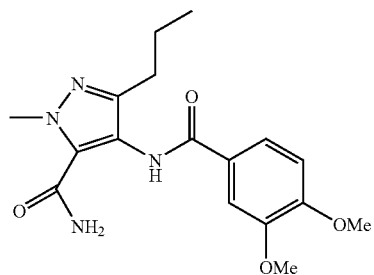

A mixture of 4-amino-1-methyl-3-propyl-1H-5-pyrazolecarboxmide (19.57 g, 107.5 mmol) and triethylamine (54.4 g, 134.38 mmol) in dichloromethane (300 mL) were taken in a 1 liter 3 neck round bottom flask fitted with a nitrogen balloon, pressure equalizing addition funnel and a septum. To the mixture was added a solution of 3,4-dimethoxy-1-benzenecarbonylchloride (21.5 g, 107.5 mmol) in dichloromethane (100 mL) at 0° C. through a pressure equalizing addition funnel over a period of 0.5 hours under nitrogen atmosphere. The reaction temperature was raised to 25° C. after addition and the contents were stirred for another 12 hours. Dichloromethane was removed from the reaction mixture under reduced pressure and the solid obtained was washed with cold water (2×150 mL), filtered and dried under vacuum to get the title compound 33 g, (89%) as a white solid. Mp: 176-178° C.

IR: $v_{max}$ (KBr, cm$^{-1}$): 3370, 3243, 2960, 1682, 1631; $^1$H NMR (200 MHz, CDCl$_3$): δ 7.81 (s, 1H), 7.49 (d, J=6.45 Hz, 2H), 6.94 (d, J=8.86 Hz, 1H), 3.99-3.96 (m, 9H), 2.53 (t, J=7.22 Hz, 2H), 1.68-1.57 (m, 2H J=7.51 Hz, 3H); Mass (CI method, I-butane): 347(MH$^+$, 100).

PREPARATION 21

5-(3,4-Dimethoxyphenyl)-1-methyl-3-propyl-6,7-dihydro-1H-pyrazolo[4,3-d]pyrimidin-7-one

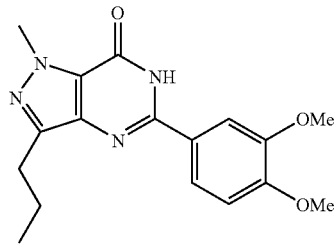

4-(3,4-dimethoxyphenylcarboxamido)-1-methyl-3-propyl-1H-5-pyrazolecarboxamide, obtained in Preparation 20 (17 g, 49.13 mmol) in tert-butanol (350 mL) was taken in a one liter single neck round bottom flask fitted with a reflux condenser and to it potassium tertiary butoxide (16.55 g, 147.38 mmol) was added carefully and the contents were refluxed for 63 hours under nitrogen atmosphere. The reaction mixture was cooled to 25-35° C. and tert-butanol was completely removed under vacuum. To the residue cold water (200 mL) was added followed by addition of dilute hydrochloric acid (3N) under stirring until the pH was constant at 7. The solid formed was filtered off and dried under vacuum to afford the title compound 13 g (81%) as a white solid. Mp: 210-212° C.

IR: $\nu_{max}$: (KBr, cm$^{-1}$): 3438, 3204, 1670; $^1$H NMR (200 MHz, DMSO-d$_6$): δ 12.3 (bs, D$_2$O exchangeable, 1H), 7.73 (m, 2H), 7.08 (d, J=8.32 Hz, 1H), 4.15 (s, 3H), 3.86 (s, 3H), 3.83 (s, 3H), 2.81 (t, J=7.25 Hz, 2H), 1.83-1.72 (m, 2H), 0.96 (t, J=7.24 Hz, 3H); Mass (CI method, i-butane): 329(M$^{+1}$, 100).

PREPARATION 22

1-[4-(2-Bromoethylamino)phenyl]-1-ethanone

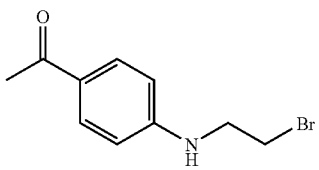

To a suspension of 60% NaH (5.93 g, 247.08 mmol) in DMF (80 mL) taken in a one liter 2 neck round bottom flask fitted with a pressure equalizing addition funnel and a septum was added a solution of p-aminoacetophenone (20 g, 148.1 mmol) in DMF (60 mL) in drops through the pressure equalizing addition funnel under nitrogen atmosphere at 0° C. and the contents were stirred for 2 hours at 25° C. Then to the stirred solution was added 1,2-dibromoethane (97.48 g, 518.5 mmol) in drops and the contents were further stirred for another 18 hours at 90° C. The reaction mixture was cooled to 25-35° C. and was carefully added to cold water (650 mL) while stirring. The organics were extracted with ethylacetate (3×200 mL) and combined organics were washed with water (2×100 mL) followed by a brine wash. The separated organics were dried over Na$_2$SO$_4$ and concentrated under reduced pressure. The crude was chromatographed over silicagel by using 15-20% ethyl acetate/pet. ether (3 Lit), affording the title compound 5.1 g (14%) as a pale yellow solid. Mp: 92-94° C.

IR: $\nu_{max}$: (KBr, cm$^{-1}$): 3360, 2927, 1650; $^1$H NMR (200 MHz, CDCl$_3$): δ 7.84 (d, J=8.89 Hz, 2H), 7.48 (d, J=8.58 Hz, 2H), 3.68-3.52 (m, 4H), 2.51 (s, 3H); Mass (CI method, I-butane): 244(M+2, 10), 162 (100).

PREPARATION 23

1-(4-{2-[5-(3,4-Dimethoxyphenyl)-1-methyl-7-oxo-3-propyl-6,7-dihydro-1H-pyrazolo[4,3-d]pyrimidin-6-yl]ethylamino}phenyl)-1-ethanone

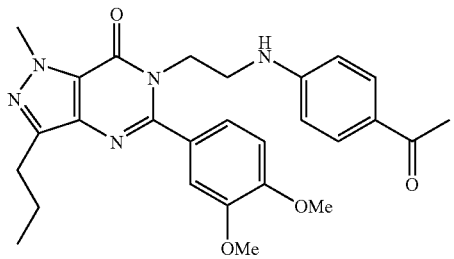

A mixture of 5-(3,4-dimethoxyphenyl)-1-methyl-3-propyl-6,7-dihydro-1H-pyrazolo[4,3-d]pyrimidin-7-one obtained in Preparation 21 (2 g, 6.09 mmol), 1-[4-(2-bromoethylamino)phenyl]-1-ethanone obtained in Preparation 22 (1.55 g, 6.405 mmol) and potassium carbonate (4.213 g, 3.5 mmol) were taken in 100 mL round bottom flask and DMF (20 mL) was added to this. The reaction mixture was stirred at 25° C. for 16 hours under nitrogen atmosphere. The reaction mixture was slowly poured into ice-cold water (100 mL). The solid separated was filtered, washed with water (2×5 mL) and dried under vacuum to afford the title compound 2.6 g (87%), as a pale yellow solid. Mp: 182-184° C.

IR: $\nu_{max}$ (KBr, cm$^{-1}$): 3381, 2927, 1660, 1599; $^1$H NMR (200 MHz, DMSO-d$_6$): δ 7.93 (d, J=5.68 Hz, 2H), 7.71 (d, J=8.31 Hz, 2H), 7.03 (d, J=8.79 Hz, 1H), 6.91 (s, 1H), 6.69 (d, J=8.79 Hz, 2H), 4.84 (m, 2H), 4.10 (s, 3H), 3.84 (s, 3H), 3.83 (s, 3H), 3.72 (t, J=4.5 Hz, 2H), 2.91 (t, J=7.33 Hz, 2H), 2.40 (s, 3H), 1.89-1.78 (m, 2H), 0.93 (t, J=7.32 Hz, 3H); Mass (CI method, I-butane): 490 (M$^{+1}$, 100).

PREPARATION 24

6,7-Dimethoxyquinazolin-4(3H)-one

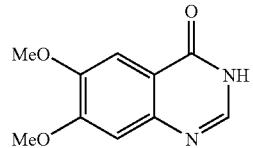

A mixture of 2-amino-4,5-dimethoxybenzoic acid (29.6 g, 0.15 mol) and formamide (0.6 mol, 24 mL) was stirred vigorously under nitrogen atmosphere. The mixture was heated to 145° C. for 4 hours. After completion the reaction mixture was cooled and water (120 mL) was added. The solid was filtered, washed with cold water (2×20 mL) followed by hexane (2×20 mL) to give 12.5 g of the desired product in 40% yield. Mp. 295-296° C. (lit 296-297° C).

$^1$H NMR (DMSO-d6, 200 MHz) 12.0 (bs, D20 exchangeable, 1H), 7.97 (s, 1H), 7.44 (s, 1H), 7.10 (s, 1H), 3.88 (s, 3H), 3.86 (s, 3H).

Reference: LeMahieu, R. A.; Carson, M.; Nason, W. C.; Parrish, D. R.; Welton, A. F.; Baruth, H. W.; Yaremko, B. *J Med. Chem.* 1983, 26, 420.

EXAMPLE 1

5-[-1-(4-{2-[2-(3,4-Dimethoxy phenyl)-5,7-dimethoxy-4-oxo-4h-3-chromenyloxy]ethoxy}phenyl)ethylidene]-1,3-thiazolane-2,4-dione

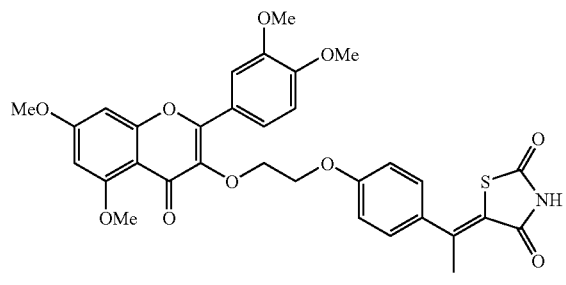

A mixture of compound (31 g, 59.6 mmol), obtained in Preparation 3, thiazolidene-1,3-dione (40 g, 341 mmol), benzoic acid (14.5 g, 118.8 mmol) and piperidine (10.1 g, 118.8 mmol) were placed into 1 L single neck round bottomed flask, to this toluene (600 mL) was added. The round bottomed flask was fitted with dean stark apparatus, which was connected to a reflux condenser. The reaction mixture was heated to reflux for 48 hours under nitrogen atmosphere. The reaction mixture was cooled to 25° C. and was allowed to pass through a silica gel column. The product was eluted by using 0.5-1% MeOH/CHCl$_3$ (5 L) to afford the title compound, 22 g (60%) as off white solid. Mp: 205-206° C.

IR: ?$_{max}$ (KBr, cm$^{-1}$): 3220, 1735, 1698, 1627, 1604; $^1$H NMR (200 MHz, CDCl$_3$): d 9.07 (bs, 1H, exchangeable with D$_2$O), 7.76-7.69 (m, 2H), 7.26 (d, J=8.30 Hz, 2H), 6.90 (d, J=8.79 Hz, 1H), 6.81 (d, J=8.79 Hz, 2H), 6.52 (s, 1H), 6.37 (s, 1H), 4.47 (t, J=4.40 Hz, 2H), 4.29 (t, J=4.40 Hz, 2H), 3.97 (s, 3H), 3.93 (s, 3H), 3.91 (s, 6H), 2.69 (s, 3H); Mass (ES method): 619 (M$^+$, 100).

EXAMPLE 2

Example 2 was prepared according to the methodology provided in Example 1.

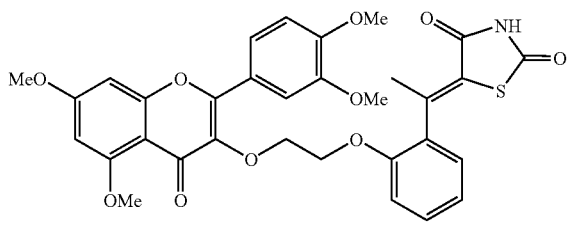

$^1$H NMR (200 MHz, CDCl$_3$): d 12 (s, D$_2$O exchangable), 7.68-7.44 (m, 4H), 7.10-6.84 (m, 4H), 6.51 (s, 1H), 4.37-4.33 (m, 4H), 3.90 (s, 3H), 3.85 (s, 3H), 3.76 (s, 3H), 2.50 (s, 3H). Mp: 120-124° C.

EXAMPLE 3

Example 3 was prepared according to the methodology provided in Example 1.

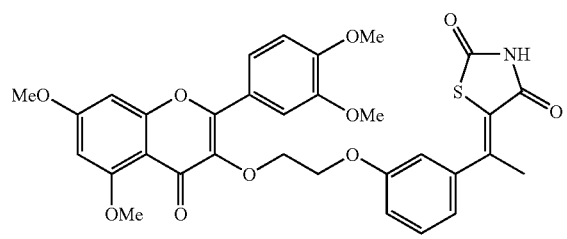

$^1$H NMR (200 MHz, CDCl$_3$): d 8.65 (s, D$_2$O exchangeable), 7.75-7.71 (m, 2H), 7.28-7.23 (m, 2H), 6.90-6.79 (m, 2H), 6.70 (s, 1H), 6.53 (s, 1H), 6.37 (s, 1H), 4.49 (s, 2H), 4.25 (s, 2H), 3.97 (s, 3H), 3.91 (s, 9H), 2.68 (s, 3H). Mp: 210-214° C.

EXAMPLE 4

Example 4 was prepared according to the methodology provided in Example 1.

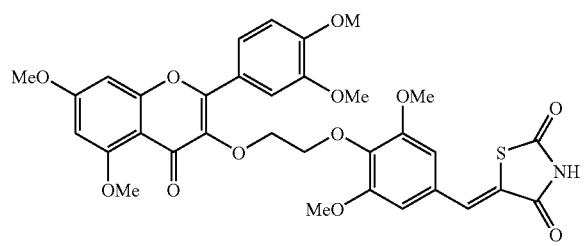

$^1$H NMR (200 MHz, CDCl$_3$): d 9.18 (s, D$_2$O exchangeable, 1H), 7.92 (s, 1H), 7.91-7.81 (m, 1H), 7.69 (s, 1H), 6.95 (d, J=8.79 Hz, 1H), 6.65 (s, 2H), 6.54 (s, 1H), 6.34 (s, 1H), 4.42 (s, 4H), 3.95 (s, 6H), 3.93 (s, 3H), 3.91 (s, 3H), 3.80 (s, 6H). Mp: 207-210° C.

EXAMPLE 5

Example 5 was prepared according to the methodology provided in Example 1.

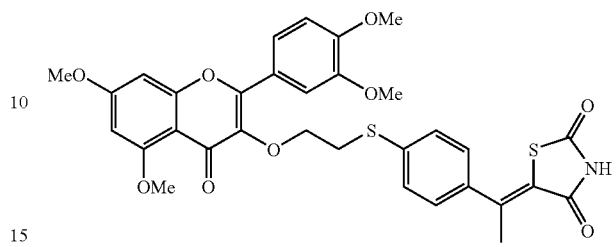

$^1$H NMR (200 MHz, CDCl$_3$): d 7.79 (d, J=8.36 Hz, 2H), 7.66 (s, 2H), 7.27 (d, J=9.7 Hz, 2H), 6.94 (d, J=8.9 Hz, 1H), 6.5 (s, 1H), 6.36 (s, 1H), 4.22 (t, J=6.74 Hz, 2H), 3.96 (s, 3H), 3.95 (s, 3H), 3.93 (s, 3H), 3.90 (s, 3H), 3.39 (t, J=6.74 Hz, 2H), 2.54 (s, 3H). Mp: 138-142° C.

EXAMPLE 6

Example 6 was prepared according to the methodology provided in Example 1.

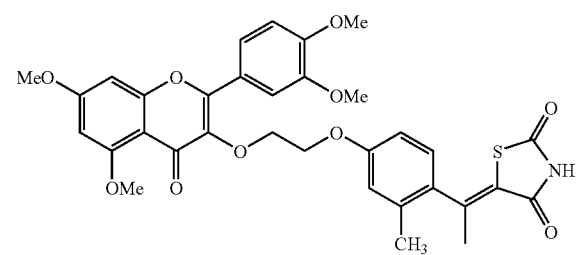

$^1$H NMR (200 MHz, CDCl$_3$): d 7.72-7.67 (d, J=10.78, 3H), 6.86 (d, J=8.36 Hz, 1H), 6.64-6.52 (m, 3H), 6.37 (s, 1H), 4.47 (s, 2H), 4.27 (s, 2H), 3.98 (s, 3H), 3.91 (s, 9H), 2.53 (s, 3H), 2.51 (s, 3H). Mp: 126-130° C.

EXAMPLE 7

Example 7 was prepared according to the methodology provided in Example 1.

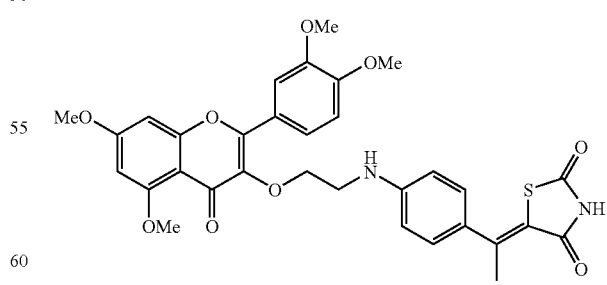

$^1$H NMR (200 MHz, CDCl$_3$): d 8.31 (s, D$_2$O exchangeable, 1H), 7.73 (d, J=8.3 Hz, 1H), 7.64 (s, 1H), 7.36 (d, J=10.2 Hz, 2H), 7.28 (m, 2H), 7.01 (d, J=8.79 Hz, 1H), 6.58 (s, 1H), 6.43 (s, 1H), 4.2 (s, 2H), 4.0 (s, 3H), 3.97 (s, 3H), 3.95 (s, 3H), 3.93 (s, 3H), 3.56 (s, 2H, 2.7 (s, 3H). Mp: 192-195° C.

EXAMPLE 8

Example 8 was prepared according to the methodology provided in Example 1.

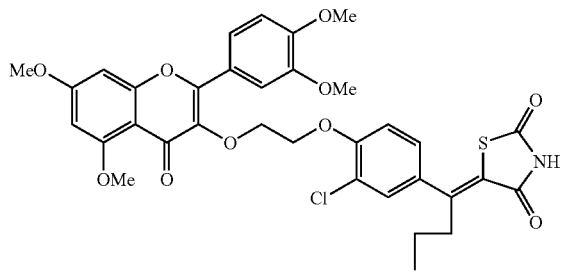

$^1$H NMR (200 MHz, CDCl$_3$): d 8.17 (s, D$_2$O exchangeable, 1H), 7.76 (d, J=8.3 Hz, 1H), 7.68 (s, 1H), 7.28 (s, 1H), 7.11 (m, 1H), 6.98-6.89 (m, 2H), 6.52 (s, 1H), 6.37 (s, 1H), 4.48 (bs, 2H), 4.41 (bs, 2H), 3.97 (s, 3H), 3.91 (s, 9H), 3.13 (t, J=7.3 Hz, 2H), 1.6-1.4 (m, 2H), 0.92 (t, J=7.3 Hz, 3H). Mp: 204-208° C.

EXAMPLE 9

Example 9 was prepared according to the methodology provided in Example 1.

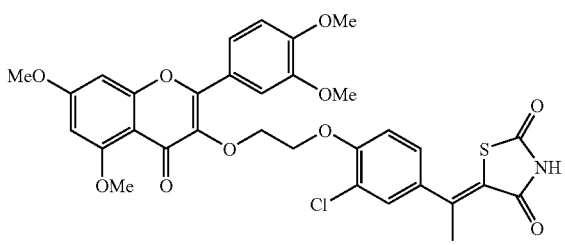

$^1$H NMR (200 MHz, CDCl$_3$): d 8.27 (s, D$_2$O exchangeable, 1H), 7.76 (d, J=8.53 Hz, 1H), 7.67 (s, 1H), 7.34 (s, 1H), 7.17 (m, 1H), 6.97-6.89 (m, 2H), 6.53 (s, 1H), 6.37 (s, 1H), 4.5 (s, 2H), 4.4 (s, 2H), 3.98 (s, 3H), 3.92 (s, 9H), 2.68 (s, 3H). Mp: 230-233° C.

EXAMPLE 10

Example 10 was prepared according to the methodology provided in Example 1.

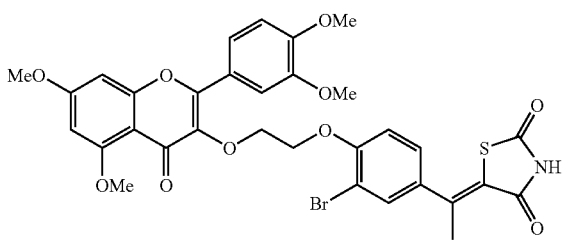

$^1$H NMR (200 MHz, CDCl$_3$): d 8.25 (s, D$_2$O exchangeable, 1H), 7.75 (d, J=6.74 Hz, 1H), 7.66 (s, 1H), 7.51 (s, 1H), 7.21 (s, 1H), 6.90 (d, J=8.4 Hz, 2H), 6.52 (s, 1H), 6.37 (s, 1H), 4.5 (bs, 2H), 4.39 (bs, 2H), 3.98 (s, 3H), 3.91 (s, 6H), 3.90 (s 3H), 2.69 (s, 3H). Mp: 235-236° C.

EXAMPLE 11

Example 11 was prepared according to the methodology provided in Example 1.

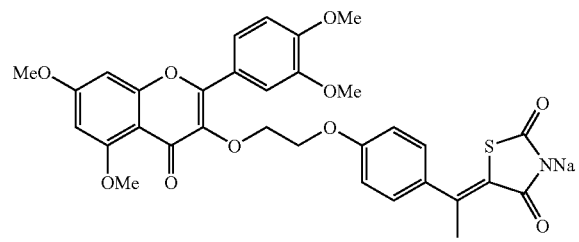

$^1$H NMR (200 MHz, CDCl$_3$): d 7.74 (d, J=8.3 Hz, 1H), 7.69 (s, 1H), 7.24 (d, J=7.9 Hz, 2H), 7.00 (d, J=8.0 Hz, 1H), 6.83 (d, J=6.10 Hz, 2 H), 6.76 (s, 1H), 6.5 (s, 1H), 4.33 (s, 2H), 4.2 (s, 2H), 3.90 (s, 3H), 3.85 (s, 3H), 3.81 (s, 3H), 3.77 (s, 3H), 2.53 (s, 3H). Mp: 225-228° C.

EXAMPLE 12

Example 12 was prepared according to the methodology provided in Example 1.

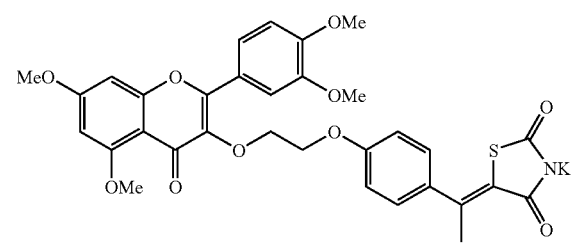

$^1$H NMR (200 MHz, CDCl$_3$): d 7.76-7.69 (m, 2H), 7.3 (d, J=8.3 Hz, 2H), 7.00 (d, J=8.3 Hz, 1H), 6.87-6.84 (m, 3H), 6.50 (s, 1H), 4.33 (s, 2H), 4.22 (s, 2H), 3.90 (s, 3H), 3.85 (s, 3H), 3.81 (s, 3H), 3.77 (s, 3H), 2.51 (s, 3H). Mp: 195-198° C.

EXAMPLE 13

5-[-1-(4-{2-[6-Fluoro-2-(4-methoxyphenyl)-4-oxo-4H-3-chromenyloxy]ethoxy}ethylidene]-1,3-thiazolane-2,4-dione

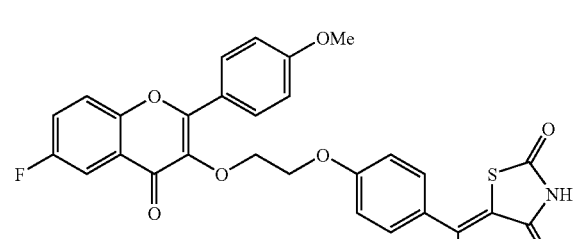

A mixture of compound obtained in Preparation 8 (0.35 g, 0.72 mmol), thiazolidene-1,3-dione (0.54 g, 4.68 mmol), benzoic acid (0.19 g, 1.56 mmol) and piperidine (0.13 g, 1.56 mol) were placed into a 50 mL single neck round bottomed flask, to this toluene (15 mL) was added. The round bottomed flask was fitted with Dean-Stark apparatus, which was connected to a reflux condenser. The reaction mixture was heated to reflux for 48 hours under nitrogen atmosphere. The reaction mixture was cooled to 25° C. and was allowed to pass through a silica gel column. The product was eluted by using 0.5-1% MeOH/CHCl$_3$ (5 L) to afford the title compound, 0.32 g (75%) as off white solid. Mp: 210-212° C.

$^1$H NMR (200 MHz, CDCl$_3$): d 12.2 (s, D$_2$O exchangeable, H), 8.14 (d, J=8.87 Hz, 2H), 7.91-7.77 (m, 1H), 7.71 (d, J=8.6 Hz, 2H), 7.36 (d, J=8.59 Hz, 2H), 7.02 (d, J=9.14 Hz, 2H), 6.92 (d, J=8.59 Hz, 2H), 4.44 (s, 2H), 4.24 (s, 2H), 3.81 (s, 3H), 2.5 (s, 3H).

EXAMPLE 14

This compound was prepared according to the procedure provided in Example 13.

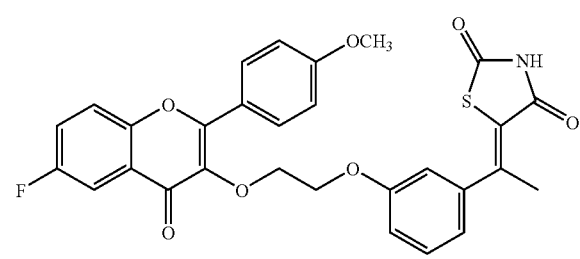

$^1$H NMR (200 MHz, CDCl$_3$): d 12.2 (s, D$_2$O exchangeable, 1H), 8.14 (d, J=8.87 Hz, 2H), 7.91-7.784 (m, 1H), 7.75 (d, J=8.6 Hz, 2H), 7.38-7.34 (d, J=8.59 Hz, 2H), 7.02 (d, J=9.14 Hz, 2H), 6.92 (d, J=8.59 Hz, 2H), 4.44 (s, 2H), 4.24 (s, 2H), 3.81 (s, 3H), 2.5 (s, 3H). Mp: 227-230° C.

EXAMPLE 15

This compound was prepared according to the procedure provided in Example 13.

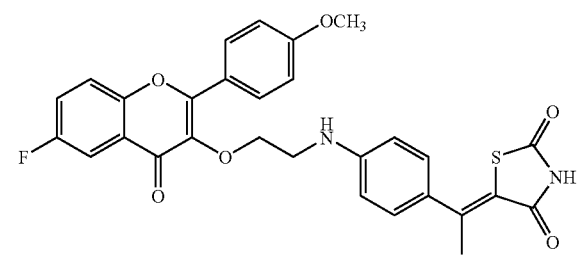

$^1$H NMR (200 MHz, CDCl$_3$): d 12.21 (s, D$_2$O exchangeable, 1H), 8.1 (m, 2H), 7.85-7.74 (m, 3H), 7.23 (m, 2H), 7.02 (d, J=7.79 Hz, 2H), 6.62 (d, J=8.06 Hz, 2H), 6.44 (s, D$_2$O exchangeable, 1H), 4.14 (s, 2H), 3.82 (s, 3H), 3.35 (s, 2H), 2.5 (s, 3H). Mp: 182-185° C.

EXAMPLE 16

This compound was prepared according to the procedure provided in Example 13.

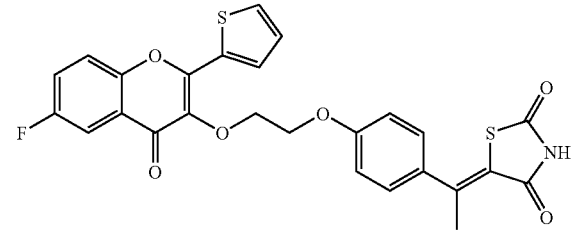

$^1$H NMR (200 MHz, CDCl$_3$): d 12.2 (s, D$_2$O exchangeable, 1H), 8.13 (d, J=3.23 Hz, 1H), 7.99 (d, J=5.1 Hz 1H), 7.71 (m, 1H), 7.73-7.69 (d, J=8.05 Hz, 2H), 7.38 (d, J=8.6 Hz, 2H), 7.31 (m, 1H), 7.00 (d, J=8.85 Hz, 2H), 4.62 (s, 2H), 4.43 (s, 2H), 2.5 (s, 3H). Mp: 238-240° C.

EXAMPLE 17

This compound was prepared according to the procedure provided in Example 13.

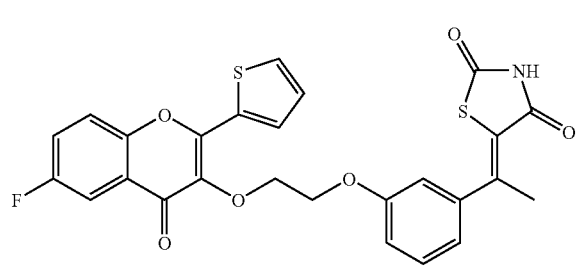

$^1$H NMR (200 MHz, CDCl$_3$): d 12.31 (s, D$_2$O exchangeable, 1H), 8.13 (d, J=3.8 Hz, 1H), 7.96 (d, J=5.1 Hz, 1H), 7.85-7.77 (m, 1H), 7.71 (d, J=8.33 Hz, 2H), 7.4-7.3 (m, 2H), 6.96 (d, J=8.87 Hz, 2H), 6.93-6.92 (m, 1H), 4.62 (s, 2H), 4.4 (s, 2H), 2.5 (s, 3H). Mp: 218-220° C.

EXAMPLE 18

This compound was prepared according to the procedure provided in Example 13.

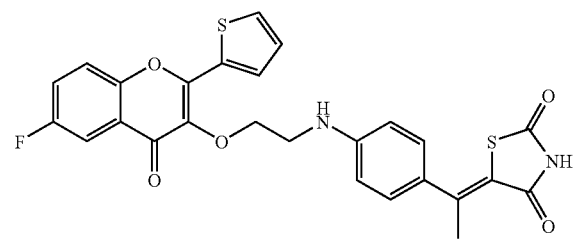

$^1$H NMR (200 MHz, CDCl$_3$): d 12.1 (s, D$_2$O exchangeable, 1H), 8.08 (d, J=2.95 Hz, 1H), 7.99 (d, J=4.83 Hz 2H), 7.91-7.78 (m, 1H), 7.72 (d, J=8.06 Hz, 2H), 7.3-7.23 (d, J=8.59 Hz, 2H), 6.56 (m, D$_2$O exchangeable, 1H), 4.33 (t, J=5.36 Hz, 2H), 3.59 (t, J=5.64 Hz, 2H), 2.62 (s, 3H). Mp: 218-219° C.

EXAMPLE 19

This compound was prepared according to the procedure provided in Example 13.

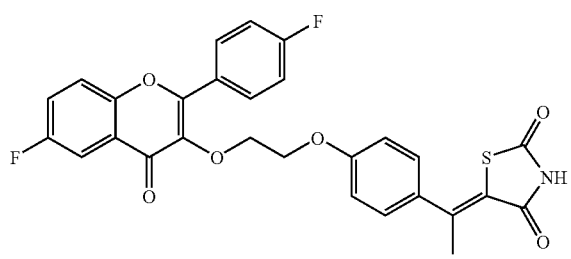

$^1$H NMR (200 MHz, CDCl$_3$): d 8.21-8.14 (m, 1H), 7.87-7.85 (m, 1H), 7.77 (d, J=8.3 Hz, 2H), 7.36-7.26 (m, 4H), 6.88 (d, J=8.8 Hz, 3H), 4.46 (s, 2H), 4.21 (s, 2H), 2.5 (s, 3H). Mp: 262-265° C.

EXAMPLE 20

This compound was prepared according to the procedure provided in Example 13.

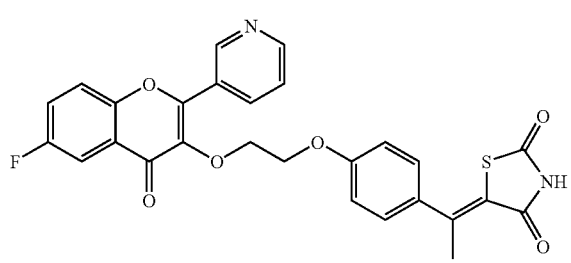

$^1$H NMR (200 MHz, CDCl$_3$): d 12.27 (s, D$_2$O exchangeable, 1H), 9.35 (s, 1H), 8.67 (d, J=4.57 Hz, 1H), 8.48 (d, J=8.33 Hz, 1H), 7.97-7.91 (m, 1H), 7.80 (d, J=8.3 Hz, 2H), 7.56-7.50 (m, 1H), 7.35 (d, J=8.3 Hz, 2H), 6.89 (d, J=8.6 Hz 2H), 4.53 (s, 2H), 4.23 (s, 2H), 2.5 (s, 3H). Mp: 251-254° C.

EXAMPLE 21

This compound was prepared according to the procedure provided in Example 13.

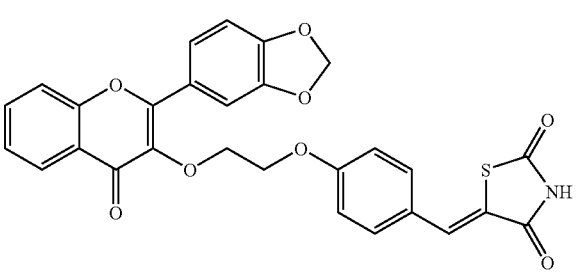

$^1$H NMR (200 MHz, CDCl$_3$): d 10.4 (bs, D$_2$O exchangeable, 1H), 8.06-8.00 (m, 1H), 7.78-7.65 (m, 4H), 7.48-7.40 (m, 2H), 7.14 (d, J=7.79 Hz, 2H), 7.01 (d, J=8.86 Hz, 1H), 6.84 (d, J=8.06 Hz, 2H), 6.04 (s, 2H), 4.44 (s, 2H), 4.18 (s, 2H). Mp: 198-200° C.

EXAMPLE 22

This compound was prepared according to the procedure provided in Example 13.

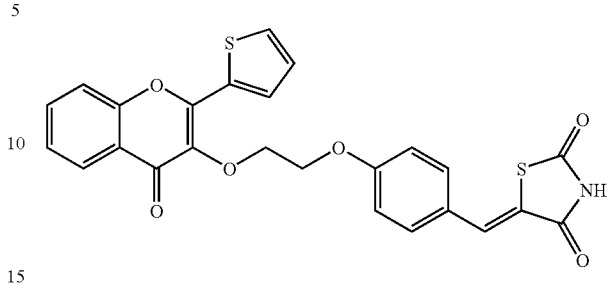

$^1$H NMR (200 MHz, CDCl$_3$): d 10.43 (bs, D$_2$O exchangeable, 1H), 8.15-8.07 (m, 2H), 7.96 (d, J=4.88 Hz, 1H) 7.84-7.73 (m, 2H), 7.53-7.46 (m, 1H), 7.32-7.28 (m, 1H) 7.19-7.15 (d, J=8.3 Hz, 2H), 6.92 (d, J=8.79 Hz, 2H), 4.62 (m, 2H), 4.32 (m, 2H). Mp: 166-168° C.

EXAMPLE 23

This compound was prepared according to the procedure provided in Example 13.

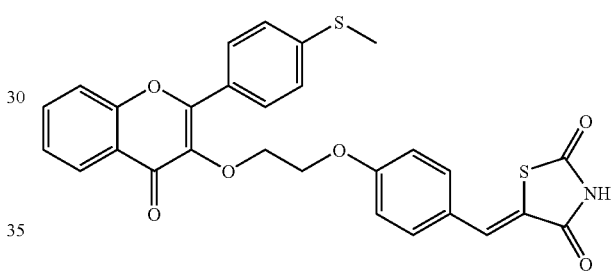

$^1$H NMR (200 MHz, CDCl$_3$): d 8.12 (bs, D$_2$O exch), 8.08-8.04 (m, 3H), 7.83-7.74 (m, 3H), 7.51 (d, J=8.3 Hz, 2H), 7.29 (d, J=8.3 Hz, 2H), 6.97 (d, J=8.89 Hz, 2H), 4.46 (m, 2H), 4.24 (m, 2H), 2.48 (s, 3H). Mp: 220-222° C.

EXAMPLE 24

5-[1-(4-{2-[1-Methyl-4-oxo-2-(4-methylphenyl)-1,4-dihydro-3-quinolinyloxy]ethoxy phenyl}methylidene]-1,3-thiazolane-2,4-dione

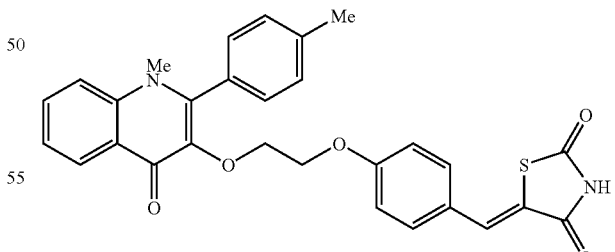

A mixture of compound obtained in Preparation 14 (150 mg, 0.36 mmol), thiazolidene-1,3-dione (64 mg, 0.54 mmol), benzoic acid (88 mg, 0.72 mmol) and piperidine (61 mg, 0.72 mmol) were placed into 1 L single neck round bottomed flask, to this toluene (600 mL) was added. The round bottomed flask was fitted with dean stark apparatus, which was connected to a reflux condenser. The reaction mixture was heated to reflux for 48 hours under nitrogen atmosphere. The reaction mixture was cooled to 25° C. and was allowed to pass through a silica gel column. The product was eluted by using 0.5-1% MeOH/CHCl₃ (5 L) to afford the title compound, 100 mg (54%) as brown solid. Mp: 250-252° C.

¹H NMR (200 MHz, CDCl₃): d 12.5 (s, NH), 8.33 (d, 1H, J=8.2 Hz), 7.78 (m, 2H), 7.52-7.22 (m, 8H), 6.88 (d, 2H, J=8.3 Hz), 4.23 (s, 2H), 3.99 (s, 2H), 3.47 (s, 3H), 2.34 (s, 3H).

EXAMPLE 25

This compound was prepared according to the procedure provided in Example 24.

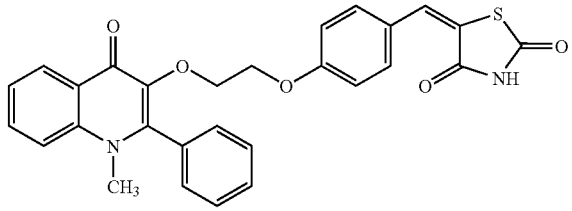

¹H NMR (200 MHz, CDCl₃): d 12.5 (s, NH), 8.34 (d, 1H, J=7.8 Hz), 7.78-7.47 (m, 11H), 6.90 (d, 2H, J=8.4 Hz), 4.23 (s, 2H), 3.99 (s, 2H), 3.47 (s, 3H). Mp: 250-252° C.

EXAMPLE 26

This compound was prepared according to the procedure provided in Example 24.

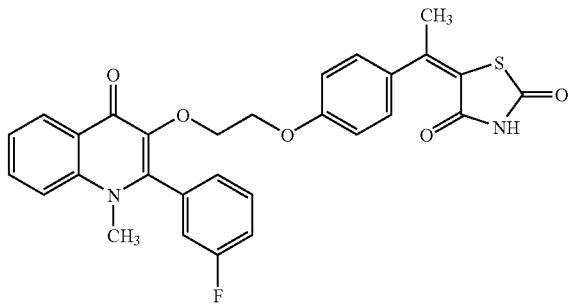

¹H NMR (200 MHz, CDCl₃): d 12.22 (s, NH), 8.34 (d, 2H, J=8.1 Hz), 7.8 (s, 2H), 7.53-7.26 (m, 6H), 6.82 (d, 2H, J=8.3 Hz), 4.25 (s, 2H), 3.97 (s, 2H), 3.48 (s, 3H), 2.63 (s, 3H). Mp: 196-198° C.

EXAMPLE 27

This compound was prepared according to the procedure provided in Example 24.

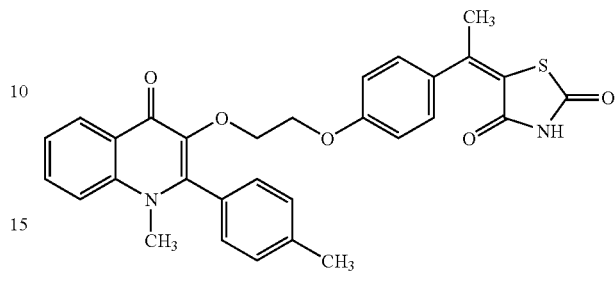

¹H NMR (200 MHz, CDCl₃): d 12.25 (bs, NH), 8.34 (d, 1H, J=7.8 Hz), 7.78 (d, 2H, J=2.9 Hz), 7.45-7.28 (m, 7H), 6.80 (d, 2H, J=8.8 Hz), 4.23 (s, 2H), 3.94 (s, 2H), 3.48 (s, 3H), 2.64 (s, 3H), 2.35 (s, 3H). Mp: 228-232° C.

EXAMPLE 28

This compound was prepared according to the procedure provided in Example 24.

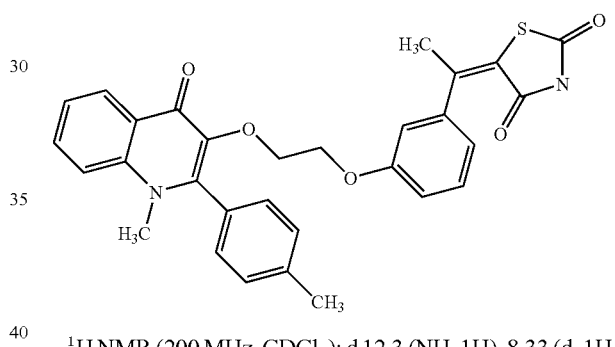

¹H NMR (200 MHz, CDCl₃): d 12.3 (NH, 1H), 8.33 (d, 1H, J=8.2 Hz), 7.77 (d, 2H, J=3.2 Hz), 7.46-7.27 (m, 6H), 6.95 (d, 1H, J=7.5 Hz), 6.78 (d, 2H, J=8.8 Hz), 4.22 (s, 2H), 3.92 (s, 2H), 3.46 (s, 3H), 2.62 (s, 3H), 2.33 (s, 3H). Mp: 210-212° C.

EXAMPLE 29

3-(4-{2-[2-(3,4-Dimethoxy-phenyl)-5,7-dimethoxy-4-oxo-4H-chromen-3-yloxy]-ethoxy}-benzoylamino)-2-(toluene-4-sulfonylamino)-propionic Acid Ethyl Ester

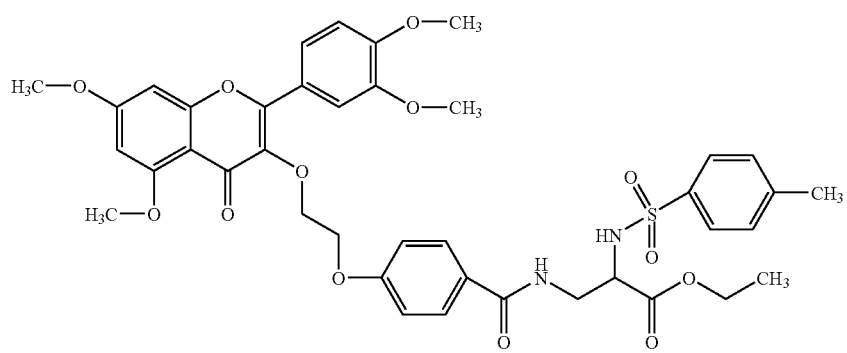

To a solution of 4-{2-[2-(3,4-Dimethoxy-phenyl)-5,7-dimethoxy-4-oxo-4H-chromen-3-yloxy]-ethoxy}-benzoic acid obtained in Preparation 17 (3 g, 5.74 mmol), 3-Amino-2-(toluene-4-sulfonylamino)-propionic acid ethyl ester obtained in Preparation 19 (2.22 g, 6.89 mmol) in DMF (20 mL) was added EDCI (1.64 g, 8.61 mmol), HOBt (1 g, 7.46 mmol) and N-methyl morpholine (2.0 g, 20.09 mmol) at 25-35° C. under Nitrogen atmosphere. The mixture was stirred at the same temperature for 12 hrs. After completion of the reaction the mixture was poured into water (60 mL) and stirred for 30 min. The separated solid was filtered, washed with water (2×20 mL) and dried under vacuum. The crude product was purified further by crystallization from ethanol to give the desired product in 51% yield (2.3 g).

$^1$H NMR (CDCl$_3$, 200 MHz) 7.73-7.65 (m, 5H), 7.25 (d, J=8.8 Hz, 2H), 6.88-6.73 (m, 4H), 6.52(d, J=2 Hz, 1H), 6.36 (d, J=2 Hz, 1H), 5.91 (d, J=7.8 Hz, D$_2$O exchangeable, 1H), 4.47 (m, 2H), 4.23 (m, 2H), 4.10-3.91 (m, 16H), 3.8 (m, 1H), 2.37 (s, 3H), 1.14 (t, J=7.3 Hz, 3H).

EXAMPLE 30

This compound was prepared according to the procedure provided in Example 29.

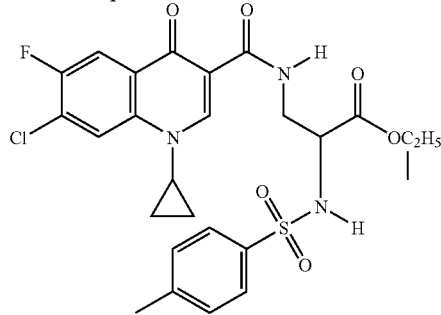

H$^1$ NMR (CDCl$_3$, 200 MHz) 10.06 (m, D$_2$O exchangeable, 1H), 8.82(s, 1H), 8.17-8.0 (m, 2H), 7.74 (d, J=8.3 Hz, 2H), 7.27-7.19 (m, 3H), 6.24 (d, J=7.8 Hz, D$_2$O exchangeable, 1H), 4.15-4.01 (m, 3H), 3.84-3.70 (m, 2H), 3.77-3.51 (m, 1H), 2.31 (s, 3H), 1.41 (d, J=6.3 Hz, 1H), 1.25-1.13 (m, 5H).

EXAMPLE 31

This compound was prepared according to the procedure provided in Example 29.

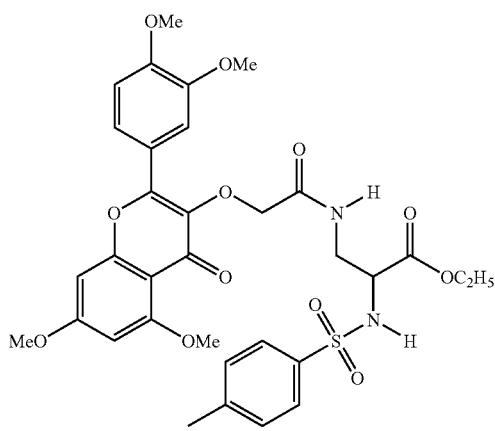

H$^1$ NMR (CDCl$_3$, 200 MHz) 9.30 (bs, D$_2$O exchangeable, 1H), 7.76 (d, J=8.1 Hz, 2H), 7.60 (d, J=6 Hz, 1H), 7.47 (s, 1H), 7.21 (d, J=8.1 Hz, 2H), 6.99 (d, J=7.5 Hz, 1H), 6.76(d, J=9.0 Hz, D$_2$O exchangeable, 1H), 6.53 (s, 1H), 6.41 (s, 1H), 4.17 (m, 2H), 4.02-3.86 (m, 15H), 3.46-3.39 (m, 2H), 2.35 (s, 3H), 1.06 (t, J=7.0 Hz, 3H).

EXAMPLE 32

This compound was prepared according to the procedure provided in Example 29.

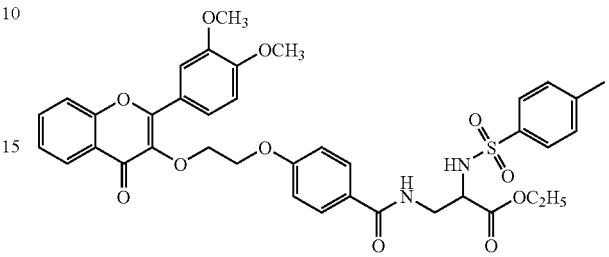

H$^1$ NMR (DMSO-d$_6$, 200 MHz), 8.32 (d, J=8.8 Hz, 2H), 8.10 (d, J=8.0 Hz, 1H), 7.80-7.5 (m, 7H), 7.28 (d, J=7.8 Hz, 2H), 7.03 (d, J=8.60 Hz, 1H), 6.85 (d, J=8.3 Hz, 2H), 4.43 (m, 2H), 4.37-4.26 (m, 2H), 4.07-4.03 (m, 2H), 3.79 (m, 8H), 3.47(m, 1H), 2.30(s, 3H), 0.95 (t, J=7.3 Hz, 3H).

EXAMPLE 33

This compound was prepared according to the procedure provided in Example 29.

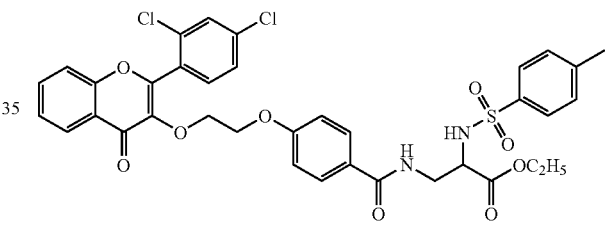

H$^1$ NMR (DMSO-d$_6$, 200 MHz), 8.32 (d, J=8.0 Hz, 2H), 8.17 (d, J=8.0 Hz, 1H), 7.83 (d, J=7.0 Hz, 1H), 7.69-7.47 (m, 7H), 7.28 (d, J=8.0 Hz, 2H), 6.73 (d, J=8.9 Hz, 2H), 4.39 (bs, 2H), 4.07 (bs, 2H), 3.82-3.75 (m, 2H), 3.34 (m, 3H), 2.30 (s, 3H), 0.95 (t, J=7.0 Hz, 3H).

EXAMPLE 34

This compound was prepared according to the procedure provided in Example 29.

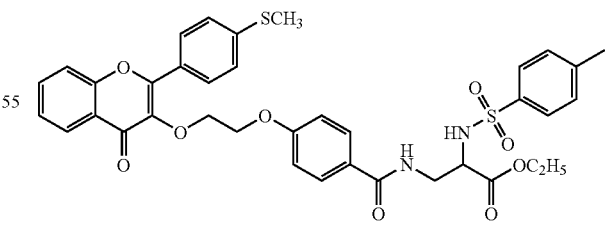

H$^1$ NMR (CDCl$_3$, 200 MHz), 8.25 (d, J=8.0 Hz, 1H), 8.05 (d, J=8.6 Hz, 2H), 7.73 -7.65(m, 5H), 7.52 (d, J=7.9 Hz, 1H), 7.40 (t, J=7.0 Hz, 1H), 7.24-7.18 (m, 4H), 6.74 (d, J=8.6 Hz, 2H), 6.64 (m, D$_2$O exchangeable, 1H), 5.69 (d, J=7.3 Hz, D$_2$O exchangeable, 1H), 4.52 (m, 2H), 4.22 (m, 2H), 4.10-3.99 (m, 3H), 3.95-3.85 (m, 1H), 3.69-3.59 (m, 2H), 2.48 (s, 3H), 2.37 (s, 3H), 1.13 (t, J=7.0 Hz, 3H).

EXAMPLE 35

This compound was prepared according to the procedure provided in Example 29.

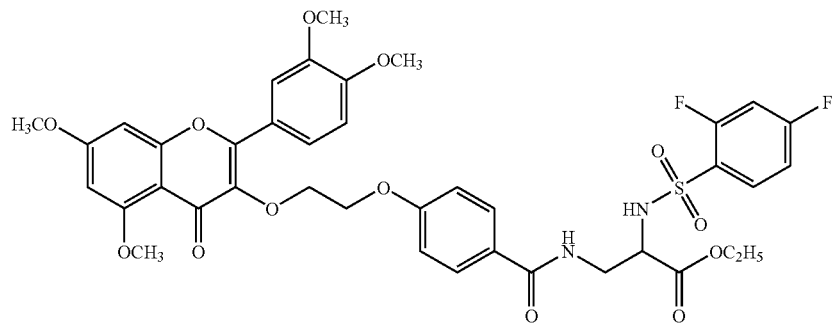

H¹ NMR (CDCl₃, 200 MHz), 7.87-7.84 (m, 1H), 7.70-7.64 (m, 3H), 6.93-6.72 (m, 5H), 6.53 (d, J=3.0 Hz, 1H), 6.37-6.29 (m, 2H), 4.46 (m, 2H), 4.23 (m, 2H), 4.17-4.06 (m, 2H), 3.96-3.74 (m, 15 H), 1.18 (t, J=7.0 Hz, 3H).

2H), 6.77 (d, J=8.3 Hz, 2H), 6.01 (m, 1H, D20 exchangeable), 5.65 (d, J=8.4 Hz, 1H, D₂O exchangeable), 4.52-4.51 (m, 2H), 4.21 (m, 2H), 4.02-3.92 (m, 3H), 3.59-3.40 (m, 4H), 2.51 (s, 3H), 2.40 (s, 3H), 1.06 (t, J=7.3 Hz, 3H).

EXAMPLE 36

This compound was prepared according to the procedure provided in Example 29.

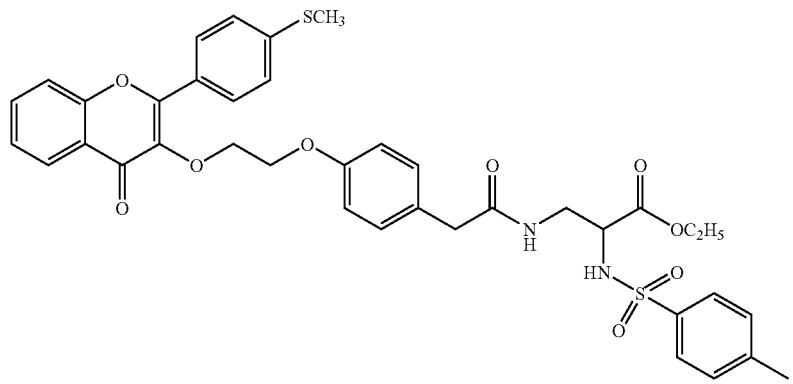

H¹ NMR (CDCl₃, 200 MHz), 8.25 (d, J=7.81 Hz, 1H), 8.13 (d, J=8.8 Hz, 2H), 7.70-7.67(m, 3H), 7.54 (d, J=8.3 Hz, 1H), 7.41 (t, J=7.3 Hz, 1H), 7.29-7.24 (m, 4H), 7.15 (d, J=8.3 Hz,

EXAMPLE 37

This compound was prepared according to the procedure provided in Example 29.

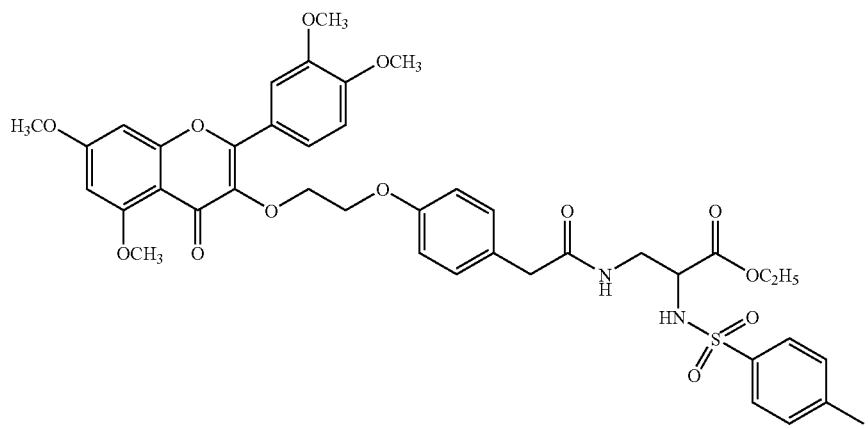

H¹ NMR (CDCl₃, 200 MHz) 7.75-7.66 (m, 3H), 7.29 (m, 2H), 7.09 (d, J=8.3 Hz, 2H), 6.91 (d, J=9.3 Hz, 2H), 6.72 (d, J=8.3 Hz, 2H), 6.52 (s, 1H), 6.36 (s, 1H), 5.99 (m, D₂O exchangeable, 1H), 5.62 (d, J=7.7 Hz, D₂O exchangeable, 1H), 4.46 (m, 2H), 4.20 (m, 2H), 4.14-3.87 (m, 16H), 3.49 (m, 3H), 2.40 (s, 3H), 1.10 (t, J=7.3 Hz, 3H).

EXAMPLE 38

This compound was prepared according to the procedure provided in Example 29.

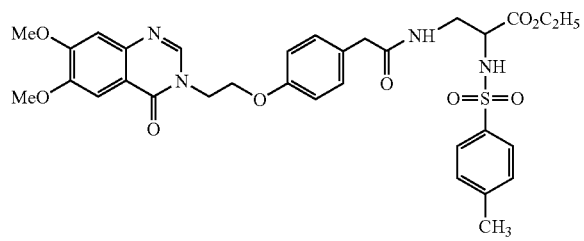

H¹ NMR (CDCl₃, 200 MHz) 7.67-7.59 (m, 3H), 7.26-7.23 (m, 3H), 7.15-7.10 (m, 3H), 6.84 (d, J=8.6 Hz, 2H), 6.01 (bs, D₂O exchangeable, 1H), 5.78 (bs, D₂O exchangeable, 1H), 4.39-4.30 (m, 4H), 3.98-3.88 (m, 10H), 3.60-3.36 (m, 3H), 2.38 (s, 3H), 1.06 (t, J=7.0 Hz, 3H).

EXAMPLE 39

This compound was prepared according to the procedure provided in Example 29.

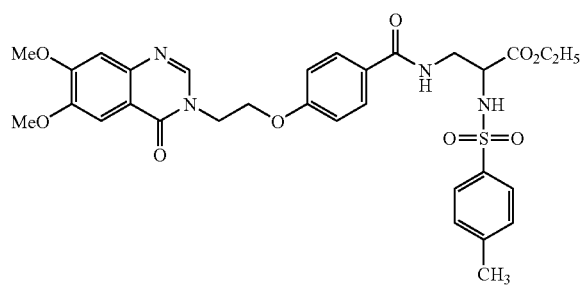

H¹ NMR (CDCl₃, 200 MHz) 8.30 (s, D₂O exchangeable, 1H), 8.26 (s, 1H), 7.69-7.57 (m, 4H), 7.47 (s, 1H), 7.26 (d, J=8.0 Hz, 2H), 7.14 (s, 1H), 6.98 (d, J=8.6 Hz, 2H), 4.36 (bs, 4H), 4.02 (m, 1H), 3.92-3.87 (m, 9H), 3.33 (m, 1H), 2.27 (s, 3H), 0.93 (t, J=7.3 Hz, 3H).

EXAMPLE 40

This compound was prepared according to the procedure provided in Example 29.

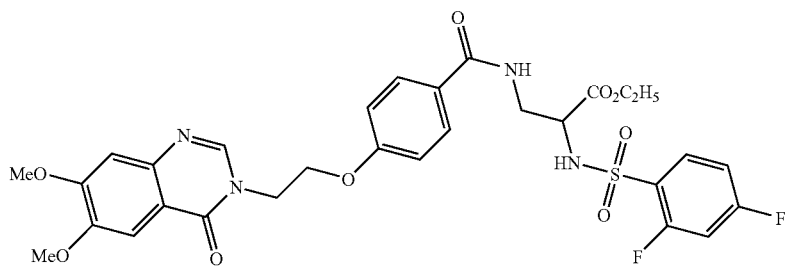

H¹ NMR (CDCl₃, 200 MHz) 8.13 (s, 1H), 7.89-7.78 (m, 1H), 7.69 (d, J=8.0 Hz, 2H). 7.60 (s, 1H), 7.12 (s, 1H), 6.96-6.74 (m, 4H), 6.35 (d, J=8.1 Hz, 1H), 4.41-4.31 (m, 4H), 4.21-4.17 (m, 1H), 4.13-4.02 (m, 2H), 3.99 (s, 6H), 3.86-3.84 (m, 1H), 3.78-3.68 (m, 1H), 1.15 (t, J=7.3 Hz, 3H).

EXAMPLE 41

This compound was prepared according to the procedure provided in Example 29.

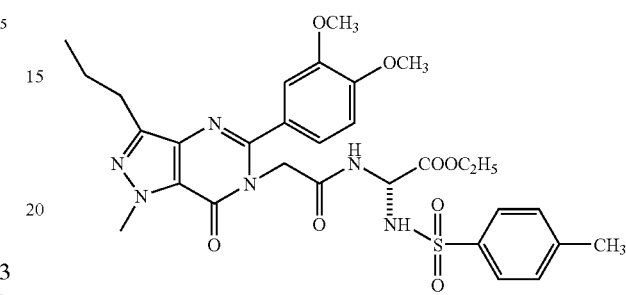

H¹ NMR NMR (CDCl3, 200 MHz): d 8.09(d, 2H, J=8.8 Hz), 7.58(d, 2H, J=8.3 Hz), 7.26(m, 3H), 6.98(d, 2H, J=8.3 Hz), 5.18(s, 2H), 4.77(s, 2H), 4.30(s, 3H), 4.03(s, 3H), 3.95 (s, 3), 3.55-3.40(m, 1H), 3.07-2.95(q, 2H, J=7.3 Hz),2.37(s, 3H), 1.98-1.87(q, 2H,J=7.8 Hz), 1.13-1.03(m, 6H).

EXAMPLE 42

This compound was prepared according to the procedure provided in Example 29.

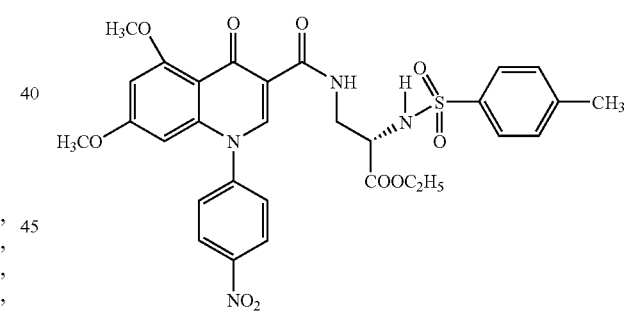

H¹ NMR (CDCl3, 200 MHz):d 12.0(bs, 1H), 8.43(m, 3H), 7.9(m, 1H), 7.75(m, 2H), 7.55-7.10(m, 5H), 6.05(s, 1H), 5.39(s, 1H), 4.2(m, 2H), 4.0-3.6(m, 8H), 2.4(s, 3H), 1.3-0.9 (m, 3H).

EXAMPLE 43

3-(4-{2-[2-(3,4-Dimethoxy-phenyl)-5,7-dimethoxy-4-oxo-4H-chromen-3-yloxy]-ethoxy}benzoylamino)-2-(toluene-4-sulfonylamino)-propionic Acid

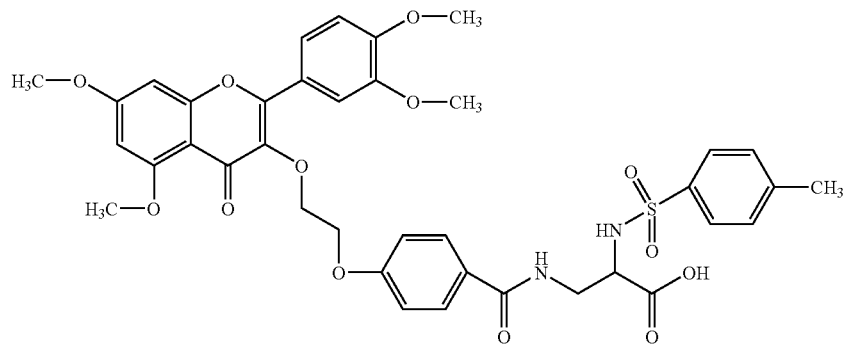

To a solution of ethyl ester of 3-(4-{2-[2-(3,4-Dimethoxy-phenyl)-5,7-dimethoxy4-oxo-4H-chromen-3-yloxy]-ethoxy}-benzoylamino)-2-(toluene-4-sulfonylamino)-propionic acid (500 mg, 0.73 mmol) obtained in example 29 in a mixture of ethanol (10 mL) and dioxane (10 mL) was added a solution of $K_2CO_3$ (300 mg, 2.19 mmol) in water (5 mL) at 25-35° C. and the mixture was stirred at the same temperature for 24 hrs. Then solvent was removed from the mixture under vacuum and the residue was acidified with cold HCl. The solid separated was filtered, washed with cold water (2×5 mL) and dried under vacuum to give the desired acid in 52% yield (250 mg).

$^1$HNMR (DMSO-$d_6$, 200 MHz) 12.9 (bs, $D_2O$ exchangeable, 1H), 8.32 (s, $D_2O$ exchangeable, 1H), 8.13 (d, J=8.3 Hz, 1H), 7.72-7.63 (m, 4H), 7.32 (d, J=7.3 Hz, 2H), 7.14 (d, J=8 Hz, 1H), 6.86 (s, 1H), 6.52 (s, 1H), 4.26 (s, 2H), 3.90-3.82 (m, 15H), 2.33 (s, 3H).

EXAMPLE 44

This compound was prepared according to the procedure provided in Example 43.

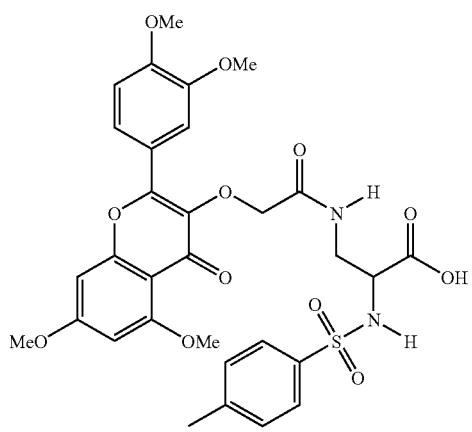

$H^1$ NMR (DMSO-$d_6$, 200 MHz) d 12.9 (bs, $D_2O$ exchangeable, 1H), 8.32 (s, $D_2O$ exchangeable, 1H), 8.13 (d, J=8.3 Hz, 1H), 7.72-7.63 (m, 4H), 7.32 (d, J=7.3 Hz, 2H), 7.14 (d, J=8 Hz, 1H), 6.86 (s, 1H), 6.52 (s, 1H), 4.26 (s, 2H), 3.90-3.82 (m, 15H), 2.33 (s, 3H).

EXAMPLE 45

This compound was prepared according to the procedure provided in Example 43.

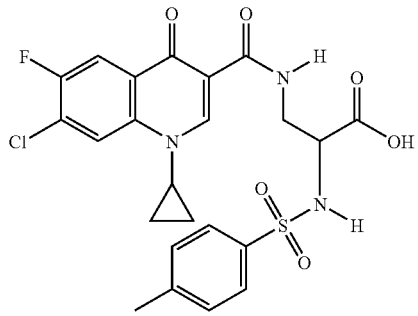

$H^1$ NMR (DMSO-$d_6$, 200 MHz): d 9.72 (bs, $D_2O$ exchangeable, 1H), 8.59 (s, 1H), 8.37(d, J=6.2 Hz, 1H), 8.14 (d, J=9.4 Hz, 1H), 7.60 (d, J=8 Hz, 2H), 7.19 (d, J=8.0 Hz, 2H), 3.76-3.43 (m, 4H), 2.49 (s, 3H), 1.31 (d, J=6.0 Hz, 2H), 1.11 (s, 2H).

EXAMPLE 46

5-[(E,Z)-1-(4-{2-[5-(3,4-Dimethoxyphenyl)-1-methyl-7-oxo-3-propyl-6,7-dihydro-1H-pyrazolo[4,3-d]pyrimidin-6-yl]ethylamino}phenyl)ethylidene]1,3-thiazolane-2,4-dione A mixture of 1-(4-{2-[5-(3,4-dimethoxyphenyl)-1-methyl-7-oxo-3-propyl-6,7-dihydro-1H-pyrazolo[4,3-d]pyrimidin-6-yl]ethylamino}phenyl)-1-ethanone obtained in Preparation 23 (2.4 g, 4.91 mmol), thiazolidene-2,4-dione (2.87 g, 24.54 mmol), benzoic acid (1.20 g, 9.81 mmol) and piperidine (0.84 g, 9.81 mmol) was taken into 100 mL single neck round bottom flask, to this toluene (60 mL) was added. The round bottomed flask (RBF) was fitted with dean stark, which was connected to a reflux condenser. The reaction mixture was heated to reflux for 35 hrs under nitrogen atmosphere. The reaction mixture was cooled to 25° C. and stirred for an hour. The solid product formed was filtered off. The pure product was obtained by triturating the solid with isopropanol (5 mL), filtered off and dried under vacuum to afford the title compound as a pale green solid (1.51 g, 2.56 mmol). Mp: 215-218° C.

IR: $\nu_{max}$ (KBr, cm$^{-1}$): 3380, 2956, 1679; $^1$H NMR (200 MHz, DMSO-d$_6$): δ 12.1(bs, D$_2$O exchangeable, 1H), 7.95 (d, J=6.98 Hz, 2H), 7.22 (d, J=8.6 Hz, 2H), 7.03 (d, J=7.86 Hz, 1H), 6.70 (d, J=8.59 Hz, 2H), 6.53 (bs, D$_2$O exchangeable, 1H), 4.82 (m, 2H), 4.07 (s, 3H), 3.84 (s, 3H), 3.81 (s, 3H), 3.67 (m, 2H), 2.90 (t, J=7.25 Hz, 2H), 2.59 (s, 3H), 1.88-1.77 (m, 2H), 0.95 (t, J=7.25 Hz, 3H); Mass (ESMS): 589 (MH$^+$, 100), Purity=94.5%.

EXAMPLE 47

This compound was prepared according to the procedure provided in Example 43.

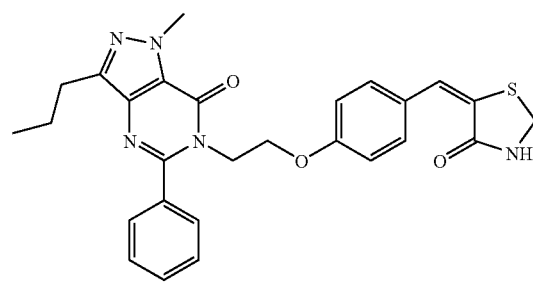

H$^1$ NMR: d 12.5(bs, D$_2$O exchangeable, 1H), 8.40-8.42 (m, 2H), 7.75 (s, 1H), 7.59-7.50 (m, 5H), 7.19 (d, J=8.3 Hz, 2H), 5.07 (m, 2H), 4.62 (m, 2H), 4.10 (s, 3H), 2.95 (t, J=7.32 Hz, 2H), 1.86-1.83 (m, 2H), 0.97 (t, J=7.32 Hz, 3H)

EXAMPLE 48

This compound was prepared according to the procedure provided in Example 46.

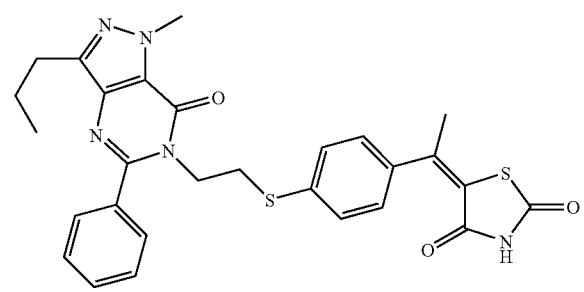

H$^1$ NMR: d 12.4 (bs, D$_2$O exchangeable, 1H), 8.36 (m, 2H), 7.48-7.31 (m, 7H), 4.94 (m, 2H), 4.05 (s, 3H), 3.64 (m, 2H), 2.91 (m, 2H), 2.60 (s, 3H), 1.85-1.82 (m, 2H), 0.98 (t, J=6.84 Hz, 3H)

EXAMPLE 49

This compound was prepared according to the procedure provided in Example 46.

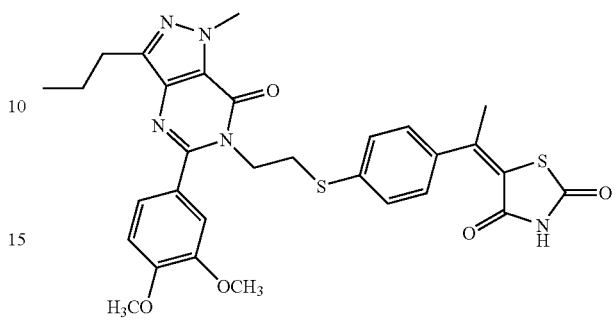

H$^1$ NMR: d 12.28 (bs, D$_2$O exchangeable, 1H), 7.93 (m, 2H), 7.49-7.29 (m, 4H), 7.04 (d, J=8.86 Hz, 1H), 4.93 (m, 2H), 4.04 (s, 3H), 3.83 (s, 3H), 3.82 (s, 3H), 3.64 (m, 2H), 2.90 (t, J=7.52 Hz, 2H), 2.59 (s, 3H), 1.89-1.78 (m, 2H), 0.96 (t, J=7.25 Hz, 3H).

EXAMPLE 50

This compound was prepared according to the procedure provided in Example 46.

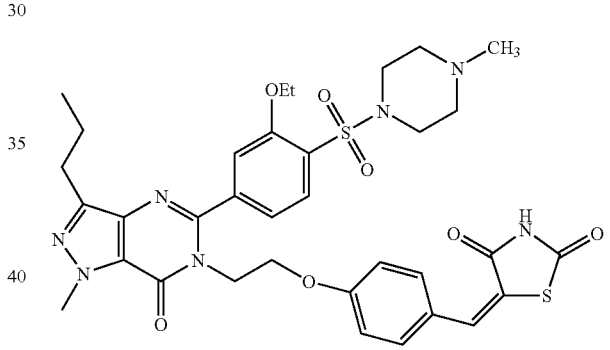

H$^1$ NMR: d 7.95-7.90 (m, 2H), 7.67 (s, 1H), 7.44-7.33 (m, 3H), 6.95 (d, J=8.63 Hz, 2H), 4.65-4.59 (m, 2H), 4.33-4.21 (m, 7H), 3.03 (m, 4H), 2.80 (t, J=7.25 Hz, 2H), 2.53-2.34 (m, 4H), 2.23 (s, 3H), 1.79-1.69 (m, 2H), 1.30 (t, J=6.99 Hz, 3H), 0.95 (t, J=7.25 Hz, 3H).

EXAMPLE 51

This compound was prepared according to the procedure provided in Example 46.

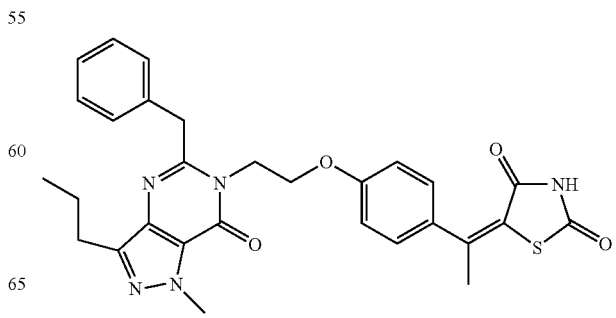

H¹ NMR: d 7.34-7.16 (m, 7H), 6.97-6.88 (m, 2H), 4.42 (s, 2H), 4.37-4.22 (m, 4H), 4.18 (s, 3H), 2.84 (t, J=7.33 Hz, 2H), 2.63 (s, 3H), 1.83-1.72 (m, 2H), 0.93 (t, J=7.32 Hz, 3H).

EXAMPLE 52

This compound was prepared according to the procedure provided in Example 46.

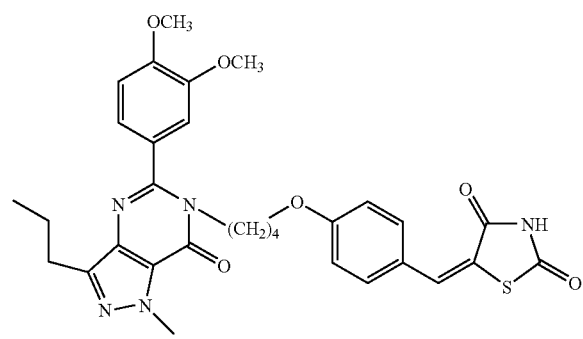

H¹ NMR: d 12.5 (bs, D₂O exchangeable, 1H) 7.98 (d, J=7.53 Hz, 2H), 7.72 (s, 1H), 7.51 (d, J=8.59 Hz, 2H), 7.08-7.01 (m, 3H), 4.76 (m, 2H), 4.18 (m, 2H), 4.1 (s, 3H), 3.85 (s, 3H), 3.81 (s, 3H), 2.91 (t, J=6.99 Hz, 2H), 2.08-2.04 (m, 4H), 1.89-1.78 (m, 2H), 0.97 (t, J=7.25 Hz, 3H).

EXAMPLE 53

This compound was prepared according to the procedure provided in Example 46.

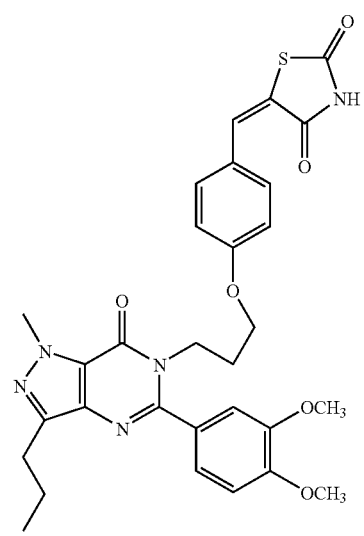

H¹ NMR: d 12.52 (bs, D₂O exchangeable, 1H), 8.01-7.96 (m, 2H), 7.72 (s, 1H), 7.3 (d, J=8.64 Hz, 2H), 7.12-7.02 (m, 3H), 4.85-4.8 (m, 2H), 4.4-4.32 (m, 2H), 4.13 (s, 3H), 3.85 (s, 3H), 3.82 (s, 3H), 2.91 (t, J=7.25 Hz, 2H), 2.5-2.39 (m, 2H), 1.86-1.82 (m, 2H), 0.97 (t, J=7.26 Hz, 3H).

EXAMPLE 54

This compound was prepared according to the procedure provided in Example 46.

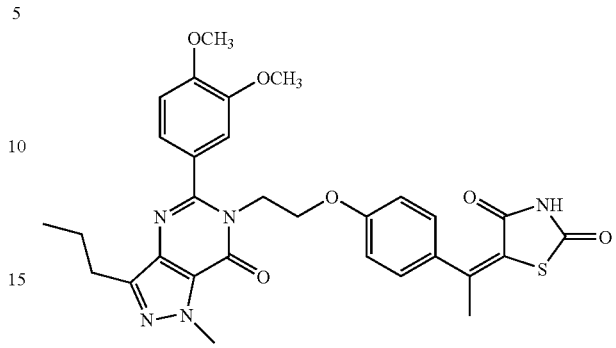

H¹ NMR: d 12.25 (bs, D₂O exchangeable, 1H), 8.01-7.96 (m, 2H), 7.42-6.97 (m, 5H), 5.02 (m, 2H), 4.56 (m, 2H), 4.07 (s, 3H), 3.86 (s, 3H), 3.83 (s, 3H), 2.91 (t, J=7.25, 2H), 3.36 (s, 3H), 1.89-1.78 (m, 2H), 0.97 (t, J=7.25 Hz, 3H).

EXAMPLE 55

This compound was prepared according to the procedure provided in Example 46.

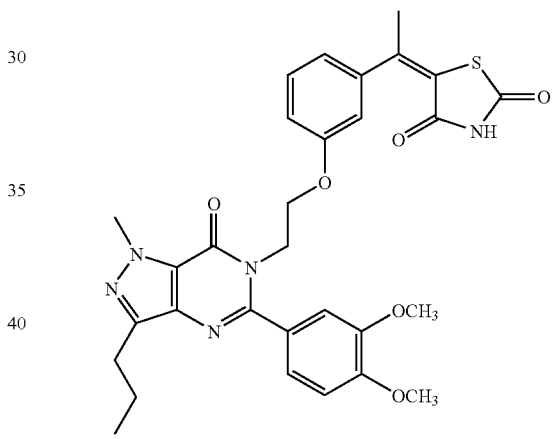

H¹ NMR: d 8.52 (bs, D₂O exchangeable, 1H), 8.07 (d, J=6.72 Hz, 2H), 7.41-7.33 (m, 2H), 6.97-6.92 (m, 3H), 5.07 (m, 2H), 4.49-4.48 (m, 2H), 4.19 (s, 3H), 4.02 (s, 3H), 3.96 (s, 3H), 3.03 (t, J=7.52 Hz, 2H), 2.69 (s, 3H), 1.98-1.86 (m, 2H), 1.04 (t, J=7.25 Hz, 3H).

EXAMPLE 56

5-[1-(3-Fluoro-4-{2-[2-(4-fluoro-phenyl)-1-methyl-4-oxo-1,4-dihydro-quinolin-3-yloxy]-ethoxy}-phenyl)-ethylidene]-thiazolidine-2,4-dione

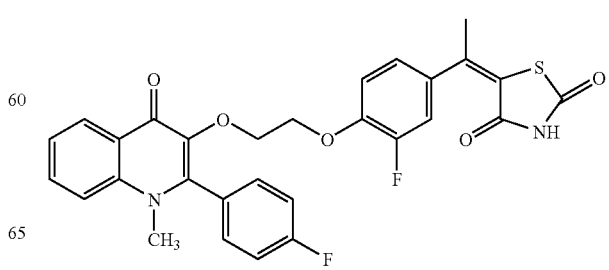

A mixture of compound 3-[2-(4-Acetyl-2-fluoro-phenoxy)-ethoxy]-2-(4-fluoro-phenyl)-1-methyl-1H-quinolin-4-one (0.45 g, 1.0 mmol), 2,4-thiazolidenedione (0.703 g, 6.01 mmol), benzoic acid (225 mg, 1.84 mmol), and piperidine (150 mg, 1.76 mmol) was taken into a single neck round bottom flask, to this toluene (50 mL) was added. The RBF was fitted with dean stark, which is connected to reflux condenser. The reaction mixture was heated to reflux for 72 hrs under nitrogen atmosphere. The reaction mixture was cooled to 25° C. and concentrated. The residue was purified by column chromatography using 1% MeOH—CHCl₃ to afford the title compound 209 mg (38%) as white solid.

¹H NMR (200 MHz, DMSO-d₆): d 12.31 (bs, D₂O exchangeable, NH), 8.32 (d, J=8.0 Hz, 1H), 7.79 (d, J=3.2 Hz, 2H), 7.50-6.99 (m, 8H), 4.27 (s, 2H), 4.06 (s, 2H), 3.47 (s, 3H), 2.64 (s, 3H).

Mp: 220-222° C.

EXAMPLE 57

5-[1-(3-Chloro-4-{2-[2-(2-fluoro-phenyl)-1-methyl-4-oxo-1,4-dihydro-quinolin-3-yloxy]-ethoxy}-phenyl)-ethylidene]-thiazolidine-2,4-dione

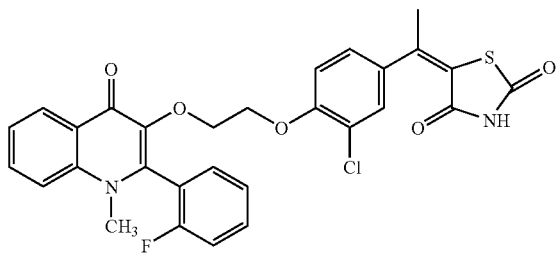

A mixture of compound 3-[2-(4-Acetyl-2-chloro-phenoxy)-ethoxy]-2-(2-fluoro-phenyl)-1-methyl-1H-quinolin-4-one (400 mg, 0.86 mmol), 2,4-thiazolidenedione (504 mg, 4.3 mmol), benzoic acid (250 mg, 2.04 mmol), and piperidine (160 mg, 1.88 mmol) was taken into 50 mL single neck round bottom flask, to this toluene (50 mL) was added. The RBF was fitted with dean stark, which is connected to reflux condenser. The reaction mixture was heated to reflux for 48 hrs under nitrogen atmosphere. The reaction mixture was cooled to 25° C. and concentrated under vacuum. The residue was purified by column chromatography followed by washing with ether to afford the title compound 200 mg (41%) as off white solid.

¹H NMR (200 MHz, DMSO-d₆): d12.39 (s, NH}, 8.43 (d, J=8.0 Hz, 1H), 7.89 (d, J=3.0 Hz, 2H), 7.54 (s, 4H), 7.41-7.27 (m, 3H), 7.12 (d, J=8.6 Hz, 1H), 4.41 (s, 2H), 4.16 (s, 2H), 3.59 (s, 3H), 2.71 (s, 3H).

Mp: 220-222° C.

EXAMPLE 58

5-[1-(4-{2-[2-(4-Fluoro-phenyl)-1-methyl-4-oxo-1,4-dihydro-quinolin-3-yloxy]-ethoxy}-phenyl)-ethylidene]-thiazolidine-2,4-dione

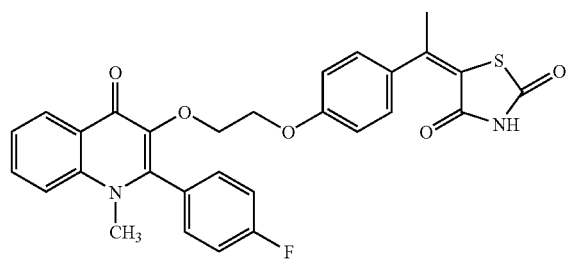

A mixture of compound 3-[2-(4-Acetyl-phenoxy)-ethoxy]-2-(4-fluoro-phenyl) 1-methyl-1H-quinolin-4-one (39 g, 9 mmol), 2,4-thiazolidenedione (63.5 g, 54 mmol), benzoic acid (22.2 g, 18.1 mmol), and piperidine (16 g, 18.79 mmol) was taken into a single neck round bottom flask, to this toluene (500 mL) was added. The RBF was fitted with dean stark, which is connected to reflux condenser. The reaction mixture was heated to reflux for 48 hrs under nitrogen atmosphere. The reaction mixture was cooled to 25° C. and concentrated under vacuum. The residue was purified by column chromatography using 0-1% MeOH—CHCl₃ to afford the title compound 24 g (50%) as light brown solid.

¹H NMR (200 MHz, DMSO-d₆): d12.09 (bs, D₂O exchangeable, 1H), 8.34 (d, J=7.8 Hz, 1H), 7.80 (d, J=3.4 Hz, 2H), 7.53-7.22 (m, 7H), 6.82(d, J=8.2 Hz, 2H), 4.23(s, 2H), 3.96(s, 2H), 3.48(s, 3H), 2.64 (s, 3H).

Mp: 228-230° C.

EXAMPLE 59

5-[1-(3-{2-[2-(3,4-Dimethoxy-phenyl)-6-fluoro-4-oxo-4H-chromen-3-yloxy]-ethoxy}-phenyl)-ethylidene]-thiazolidine-2,4-dione

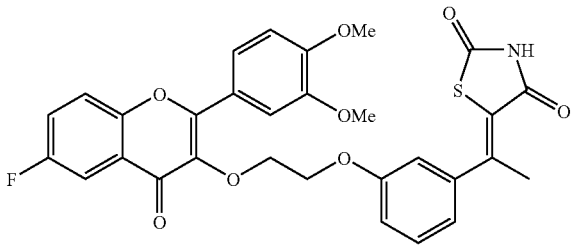

A mixture of compound 3-[2-(3-Acetyl-phenoxy)-ethoxy]-2-(3,4-dimethoxy-phenyl)-6-fluoro-chromen-4-one (0.5 g, 1.04 mmol), 2,4-thiazolidenedione (0.79 g, 6.6 mmol), benzoic acid (0.27 g, 2.2 mmol), and piperidine (0.19 g, 2.23 mmol) was taken into a single neck round bottom flask, to this toluene (35 mL) was added. The RBF was fitted with dean stark, which is connected to reflux condenser. The reaction mixture was heated to reflux for 48 hrs under nitrogen atmosphere. The reaction mixture was cooled to 25° C., stirred for 6 h at room temperature and filtered. The solid was triturated with i-PrOH (20 mL) and filtered to afford the title compound 0.38 g (63%) as off white solid.

¹H NMR (200 MHz, DMSO-d₆): d 12.88 (bs, D₂O exchangeable, 1H), 7.89-7.71 (m, 5H), 7.28 (s, 1H), 7.06 (d, J=8.6 Hz, 1H), 6.96 (d, J=7.5 Hz, 1H), 6.87 (d, J=8.32 Hz, 1H), 6.75 (s, 1H), 4.43 (s, 2H), 4.20 (s, 2H), 3.76 (s, 3H), 2.6 (s, 3H).

Mp: 228-230° C.

EXAMPLE 60

5-[1-(4-{2-[2-(4-Chloro-phenyl)-1-methyl-4-oxo-1,4-dihydro-quinolin-3-yloxy]-ethoxy}-phenyl)-ethylidene]-thiazolidine-2,4-dione

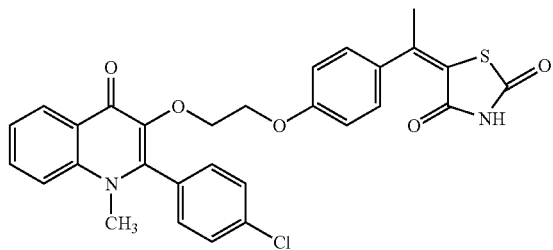

A mixture of compound 3-[2-(4-Acetyl-phenoxy)-ethoxy]-2-(4-chloro-phenyl)-1-methyl-1H-quinolin-4-one (1.19 g, 2.45 mmol), 2,4-thiazolidenedione (1.72 g, 14.70 mmol), benzoic acid (0.59 g, 4.83 mmol), and piperidine (0.415 g, 4.82 mmol) was taken into a single neck round bottom flask, to this toluene (100 mL) was added. The RBF was fitted with dean stark, which is connected to reflux condenser. The reaction mixture was heated to reflux for 72 hrs under a nitrogen atmosphere. The reaction mixture was cooled to 25° C. and concentrated under vacuum. The residue was purified by column chromatography using 6% MeOH—CHCl₃ to afford the title compound 0.73 g (30%) as light brown solid.

¹H NMR (200 MHz, DMSO-d₆): 8.32 (d, J=7.5 Hz, 1H), 7.79 (s, 2H), 7.97-7.32 (m, 7H), 6.79 (d, J=8.5 Hz, 2H), 4.24 (s, 2H), 3.96 (s, 2H), 3.47 (s, 3H), 2.69 (s, 3H).

Mp: 238-240° C.

EXAMPLE 61

5-[1-(3-{2-[2-(3,4-Difluoro-phenyl)-1-methyl-4-oxo-1,4-dihydro-quinolin-3-yloxy]-ethoxy}-phenyl)-ethylidene]-thiazolidine-2,4-dione

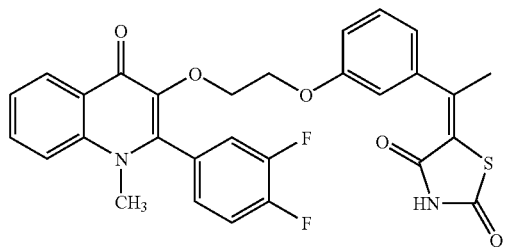

A mixture of compound 3-[2-(3-Acetyl-phenoxy)-ethoxy]-2-(3,4-difluoro-phenyl)-1-methyl-1H-quinolin-4-one (1.0 g, 2.22 mmol), 2,4-thiazolidenedione (1.56 g, 13.36 mmol), benzoic acid (325 mg, 2.67 mmol), and piperidine (325 mg, 3.82 mmol) was taken into a single neck round bottom flask, to this toluene (30 mL) was added. The RBF was fitted with dean stark, which is connected to reflux condenser. The reaction mixture was heated to reflux for 72 hrs under nitrogen atmosphere. The reaction mixture was cooled to 25° C. and concentrated. The residue was purified by column chromatography to afford the title compound 488 mg (40%) as light brown solid.

¹H NMR (200 MHz, DMSO-d6): d 12.31 (NH, 1H), 8.32 (d, 1H, J=7.8 Hz), 7.81 (s, 2H), 7.62-7.30 (m, 5H), 6.95 (d, 1H, J=7.8 Hz), 6.77 (d, 2H, J=9.7 Hz), 4.26 (s, 2H), 3.95 (s, 2H), 3.49 (s, 3H), 2.64 (s, 3H).

Mp: 236-240° C.

EXAMPLE 62

5-[1-(4-{2-[1-Ethyl-2-(4-fluoro-phenyl)-4-oxo-1,4-dihydro-quinolin-3-yloxy]-ethoxy}-phenyl)-ethylidene]-thiazolidine-2,4-dione

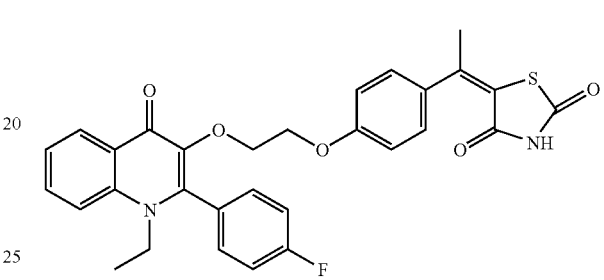

A mixture of compound 3-[2-(4-Acetyl-phenoxy)-ethoxy]-1-ethyl-2-(4-fluoro-phenyl)-1H-quinolin-4-one (0.6 g, 1.35 mmol), 2,4-thiazolidenedione (0.946 g, 8.08 mmol), benzoic acid (200 mg, 1.64 mmol), and piperidine (200 mg, 2.35 mmol) was taken into a single neck round bottom flask, to this toluene (30 mL) was added. The RBF was fitted with dean stark, which is connected to reflux condenser. The reaction mixture was heated to reflux for 72 hrs under nitrogen atmosphere. The reaction mixture was cooled to 25° C. and concentrated. The residue was purified by column chromatography using MeOH—CHCl₃ to afford the title compound 333 mg (45%) as light brown solid.

¹H NMR (200 MHz, DMSO-d6): d 12.09((bs, 1H, d20 exchangeable), 8.35(d, J=7.8 Hz, 1H), 7.87-7.77 (m, 2H), 7.55-7.23 (m, 7H), 6.83 (d, J=8.7 Hz, 2H), 4.23(s, 2H), 4.02-3.98(m, 4H), 2.64(s, 3H), 1.16(t, J=6.8 Hz, 3H).

Mp: 214-216° C.

EXAMPLE 63

5-[1-(4-{2-[2-(3,4-Difluoro-phenyl)-1-methyl-4-oxo-1,4-dihydro-quinolin-3-yloxy]-ethoxy}-phenyl)-ethylidene]-thiazolidine-2,4-dione

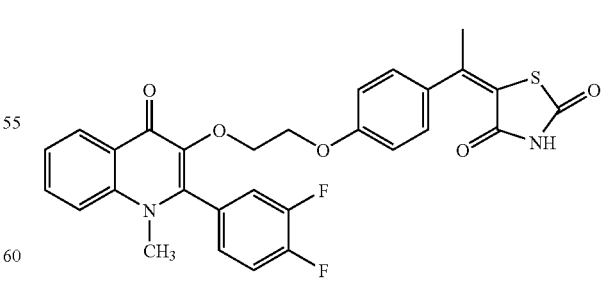

A mixture of compound 3-[2-(4-Acetyl-phenoxy)-ethoxy]-2-(3,4-difluoro-phenyl)-1-methyl-1H-quinolin-4-one (1.75 g, 3.89 mmol), 2,4-thiazolidenedione (2.74 g, 23.38 mmol), benzoic acid (475 mg, 3.89 mmol), and piperidine (331 mg, 3.89 mmol) was taken into a single neck round bottom flask, to this toluene (30 mL) was added. The RBF was fitted with dean stark, which is connected to reflux condenser. The reaction mixture was heated to reflux for 72 hrs under nitrogen atmosphere. The reaction mixture was cooled to 25° C. and concentrated. The residue was purified by column chromatography using MeOH—CHCl$_3$ to afford the title compound 830 mg (39%) as light brown solid.

$^1$H NMR (200 MHz, DMSO-d6): d 12.24 (bs, NH, D$_2$O exchangeable), 8.32 (d, J=8.0 Hz, 1H), 7.81 (s, 2H), 7.66-7.32 (m, 6H), 6.80 (d, J=8.6 Hz, 2H), 4.25 (s, 2H), 3.97 (s, 2H), 3.49 (s, 3H), 2.64 (s, 3H).

Mp: 248-250° C.

EXAMPLE 64

5-[1-(4-{2-[7-Chloro-2-(4-fluoro-phenyl)-1-methyl-4-oxo-1,4-dihydro-quinolin-3-yloxy]-ethoxy}-phenyl)-ethylidene]-thiazolidine-2,4-dione

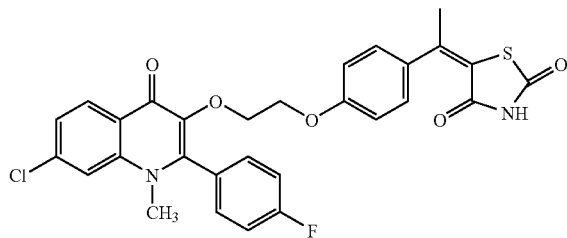

A mixture of compound 3-[2-(4-Acetyl-phenoxy)-ethoxy]-7-chloro-2-(4-fluoro-phenyl)-1-methyl-1H-quinolin-4-one (0.4 g, 0.85 mmol), 2,4-thiazolidenedione (0.502 g, 4.29 mmol), benzoic acid (190 mg, 1.55 mmol), and piperidine (145 mg, 1.70 mmol) was taken into a single neck round bottom flask, to this toluene (50 mL) was added. The RBF was fitted with dean stark, which is connected to reflux condenser. The reaction mixture was heated to reflux for 48 hrs under nitrogen atmosphere. The reaction mixture was cooled to 25° C. and filtered. The solid was treated with i-PrOH under reflux for 2 hours and then filtered. The solid was washed with hexane and purified by column chromatography to afford the title compound 200 mg (41%) as white solid.

$^1$H NMR (200 MHz, DMSO-d6): d 12.10 (bs, D$_2$O exchangeable, 1H), 8.32 (d, J=7.5 Hz, 1H), 7.89 (s, 1H), 7.48-7.27 (m, 7H), 6.82 (d, J=8.0 Hz, 2H), 4.23 (s, 2H), 3.95 (s, 2H), 3.45 (s, 3H), 2.63 (s, 3H).

Mp: 292-296° C.

EXAMPLE 65

5-[1-(4-{2-[2-(4-Fluoro-phenyl)-1-methyl-4-oxo-1,4-dihydro-quinolin-3-yloxy]-ethylamino}-phenyl)-ethylidene]-thiazolidine-2,4-dione

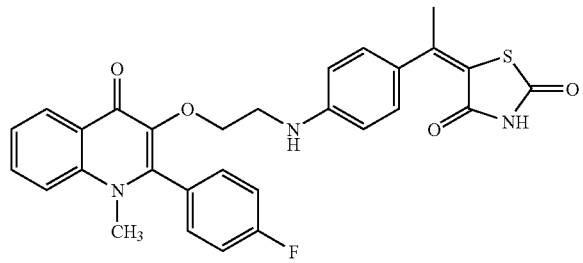

A mixture of compound 3-[2-(4-Acetyl-phenylamino)-ethoxy]-2-(4-fluoro-phenyl)-1-methyl-1H-quinolin-4-one (0.4 g, 0.93 mmol), 2,4-thiazolidenedione (0.65 g, 5.6 mmol), benzoic acid (225 mg, 1.84 mmol), and piperidine (180 mg, 2.11 mmol) was taken into a single neck round bottom flask, to this toluene (100 mL) was added. The RBF was fitted with dean stark, which is connected to reflux condenser. The reaction mixture was heated to reflux for 48 hrs under nitrogen atmosphere. The reaction mixture was cooled to 25° C. and concentrated. The residue was purified by column chromatography using 0-2% MeOH—CHCl$_3$ to afford the title compound 200 mg (41%) as yellow solid.

$^1$H NMR (200 MHz, DMSO-d6): d 8.61 (d, J=8.3 Hz, 2H), 7.77 (t, J=8.2 Hz, 2H), 7.56-7.19 (m, 6H), 6.56 (d, J=8.3 Hz, 2H), 5.99 (bs, NH), 3.94-3.92 (m, 2H), 3.53-3.41 (m, 4H), 3.18 (s, 2H), 2.68 (s, 3H).

Mp: 130-132° C.

EXAMPLE 66

5-(4-{2-[2-(4-Fluoro-phenyl)-1-methyl-4-oxo-1,4-dihydro-quinolin-3-yloxy]-ethoxy}-benzylidene)-thiazolidine-2,4-dione

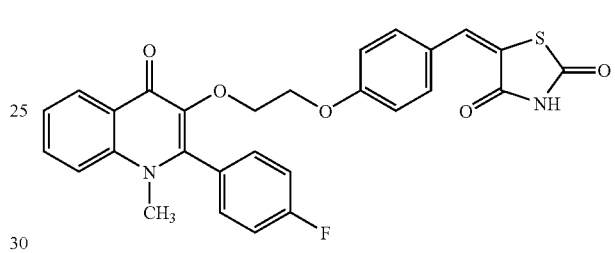

A mixture of compound 4-{2-[2-(4-Fluoro-phenyl)-1-methyl-4-oxo-1,4-dihydro-quinolin-3-yloxy]-ethoxy}-benzaldehyde (0.3 g, 0.719 mmol), 2,4-thiazolidenedione (0.168 g, 1.43 mmol), benzoic acid (30 mg, 0.24 mmol), and piperidine (30 mg, 0.35 mmol) was taken into a single neck round bottom flask, to this toluene (50 mL) was added. The RBF was fitted with dean stark, which is connected to reflux condenser. The reaction mixture was heated to reflux for 12 hrs under nitrogen atmosphere. The reaction mixture was cooled to 50° C. and filtered. The residue was washed with hot MeOH and dried under vacuum to afford the title compound 200 mg (54%) as brown solid.

$^1$H NMR (200 MHz, DMSO-d6): d 12.5 (s, NH, D$_2$O exchangeable), 8.35 (d, J=8.1 Hz, 1H), 7.81 (d, J=3.2 Hz, 2H), 7.72 (s, 1H), 7.51-7.47 (m, 5H), 7.29-7.25 (m, 2 H), 6.88 (d, J=8.6 Hz, 2H), 4.20 (s, 2H), 3.99 (s, 2H), 3.50 (s, 3H).

Mp: 225-228° C.

EXAMPLE 67

5-(4-{2-[2-(4-Bromo-phenyl)-1-methyl-4-oxo-1,4-dihydro-quinolin-3-yloxy]-ethoxy}-benzylidene)-thiazolidine-2,4-dione

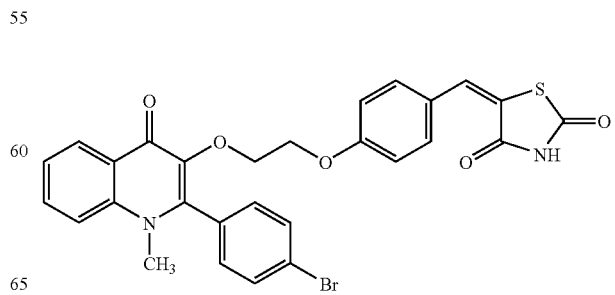

A mixture of compound 4-{2-[2-(4-Bromo-phenyl)-1-methyl-4-oxo-1,4-dihydro-quinolin-3-yloxy]-ethoxy}-benzaldehyde (0.125 g, 0.25 mmol), 2,4-thiazolidenedione (0.178 g, 1.5 mmol), benzoic acid (63 mg, 0.51 mmol), and piperidine (45 mg, 0.52 mmol) was taken into a single neck round bottom flask, to this toluene (50 mL) was added. The RBF was fitted with dean stark, which is connected to reflux condenser. The reaction mixture was heated to reflux for 12 hrs under nitrogen atmosphere. The reaction mixture was cooled to 25° C. and concentrated. The solid separated was filtered, washed with diethyl ether and dried under vacuum to afford the title compound 80 mg (53%) as light brown solid.

$^1$H NMR (200 MHz, DMSO-d6): d 8.35 (d, J=8.8 Hz, 1H), 7.87-7.39 (m, 11H), 6.89 (d, J=8.7 Hz, 2H), 4.24 (bs, 2H), 4.01(bs, 4H), 1.16 (t, J=6.8 Hz, 3H).

Mp: 151-154° C.

EXAMPLE 68

5-[1-(4-{2-[2-(5-Fluoro-2-methyl-phenyl)-1-methyl-4-oxo-1,4-dihydro-quinolin-3-yloxy]-ethoxy}-phenyl)-ethylidene]-thiazolidine-2,4-dione

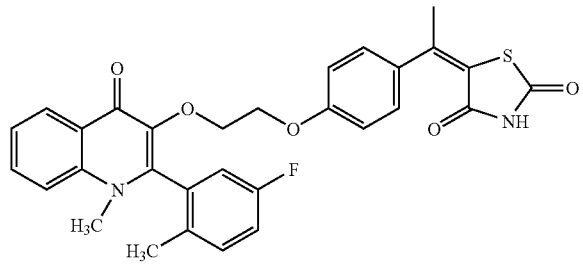

A mixture of compound 3-[2-(4-Acetyl-phenoxy)-ethoxy]-2-(5-fluoro-2-methyl-phenyl)-1-methyl-1H-quinolin-4-one (0.25 g, 0.56 mmol), 2,4-thiazolidenedione (0.394 g, 3.37 mmol), benzoic acid (142 mg, 1.16 mmol), and piperidine (100 mg, 1.17 mmol) was taken into a single neck round bottom flask, to this toluene (50 mL) was added. The RBF was fitted with dean stark, which is connected to reflux condenser. The reaction mixture was heated to reflux for 48 hrs under nitrogen atmosphere. The reaction mixture was cooled to 25° C. and concentrated. The residue was purified by column chromatography using 3-20% EtOAc—CHCl$_3$ to afford the title compound 80 mg (26%) as brown solid.

$^1$H NMR (200 MHz, DMSO-d6): d 12.30 (s, D$_2$O exchangeable, 1H), 8.35 (d, J=7.8 Hz, 1H), 7.80 (s, 2H), 7.47-7.16 (m, 5H), 6.96 (d, J=7.8 Hz, 1H), 6.79 (d, J=9.1 Hz, 2H), 4.31-4.26 (m, 2H), 3.95 (m, 2H), 3.52 (s, 3H), 2.62 (s, 3H), 2.21 (s, 3H).

Mp: 192-196° C.

EXAMPLE 69

5-[1-(3-{2-[2-(4-Fluoro-2-methyl-phenyl)-1-methyl-4-oxo-1,4-dihydro-quinolin-3yloxy]-ethoxy}-phenyl)-ethylidene]-thiazolidine-2,4-dione

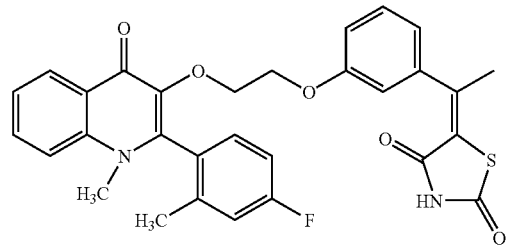

A mixture of compound 3-[2-(3-Acetyl-phenoxy)-ethoxy]-2-(4-fluoro-2-methyl-phenyl)-1-methyl-1H-quinolin-4-one (0.25 g, 0.56 mmol), 2,4-thiazolidenedione (0.394 g, 3.37 mmol), benzoic acid (150 mg, 1.22 mmol), and piperidine (100 mg, 1.17 mmol) was taken into a single neck round bottom flask, to this toluene (50 mL) was added. The RBF was fitted with dean stark, which is connected to reflux condenser. The reaction mixture was heated to reflux for 48 hrs under nitrogen atmosphere. The reaction mixture was cooled to 25° C. and concentrated. The residue was purified by column chromatography using 3-20% EtOAc—CHCl$_3$ to afford the title compound 120 mg (39%) as brown solid.

$^1$H NMR (200 MHz, DMSO-d6): d 11.22 (bs, 1H), 8.59 (d, J=7.2 Hz, 1H), 7.76-6.63 (m, 10OH), 4.45-4.26 (m, 2H), 4.0-3.98 (m, 2H), 3.58 (s, 3H), 2.67 (s, 3H), 2.15 (s, 3H).

Mp: 225-226° C.

EXAMPLE 70

5-[1-(4-{3-[2-(4-Fluoro-phenyl)-1-methyl-4-oxo-1,4-dihydro-quinolin-3-yloxy]-propoxy}-phenyl)-ethylidene]-thiazolidine-2,4-dione

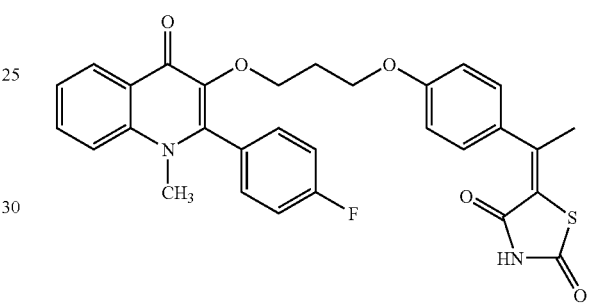

A mixture of compound 3-[3-(4-Acetyl-phenoxy)-propoxy]-2-(4-fluoro-phenyl)-1-methyl-1H-quinolin-4-one (0.40 g, 0.898 mmol), 2,4-thiazolidenedione (0.631 g, 5.39 mmol), benzoic acid (225 mg, 1.82 mmol), and piperidine (175 mg, 2.05 mmol) was taken into a single neck round bottom flask, to this toluene (30 mL) was added. The RBF was fitted with dean stark, which is connected to reflux condenser. The reaction mixture was heated to reflux for 72 hrs under nitrogen atmosphere. The reaction mixture was cooled to 25° C. and concentrated. The residue was purified by column chromatography using 1% MeOH—CHCl$_3$ to afford the title compound 130 mg (27%) as white solid.

$^1$H NMR (200 MHz, DMSO-d6): d 12.27 (bs, NH, D$_2$O exchangeable), 8.30 (d, J=7.8 Hz, 1H), 7.81 (s, 2H), 7.55-7.3 (m, 7H), 6.88 (d, J=7.8 Hz, 2H), 4.01 (s, 2H), 3.62 (s, 2H), 3.49 (s, 3H), 2.68 (s, 3H), 1.82 (s, 2H).

Mp: 262-264° C.

EXAMPLE 71

5-[1-(3-{3-[2-(4-Fluro-phenyl)-1-methyl-4-oxo-1,4-dihydro-quinolin-3-yloxy]-propoxy}-phenyl)-ethylidene]-thiazolidine-2,4-dione

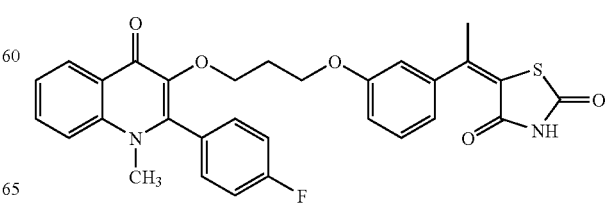

A mixture of compound 3-[3-(3-Acetyl-phenoxy)-propoxy]-2-(4-fluoro-phenyl)-1-methyl-1H-quinolin-4-one (0.45 g, 1.011 mmol), 2,4-thiazolidenedione (0.710 g, 6.06 mmol), benzoic acid (300 mg, 2.46 mmol), and piperidine (300 mg, 3.52 mmol) was taken into a single neck round bottom flask, to this toluene (50 mL) was added. The RBF was fitted with dean stark, which is connected to reflux condenser. The reaction mixture was heated to reflux for 72 hrs under nitrogen atmosphere. The reaction mixture was cooled to 25° C. and concentrated. The residue was purified by column chromatography using 0.3% MeOH—CHCl$_3$ to afford the title compound 187 mg (34%) as light brown solid.

$^1$H NMR (200 MHz, DMSO-d6): d 12.29 (NH, 1H), 8.31 (d, 1H, J=7.8 Hz), 7.78 (s, 2H), 7.56-7.22 (m, 6H), 6.97 (d, 1H, J=7.5 Hz), 6.80 (d, 2H, J=6.7 Hz), 3.99 (s, 2H), 3.58-3.55 (m, 2H), 3.46 (s, 3H), 2.66 (s, 3H), 1.79 (s, 2H).

Mp: 168-170° C.

EXAMPLE 72

5-[1-(3-Chloro-4-{3-[2-(4-fluoro-phenyl)-1-methyl-4-oxo-1,4-dihydro-quinolin-3-yloxy]-propoxy}-phenyl)-ethylidene]-thiazolidine-2,4-dione

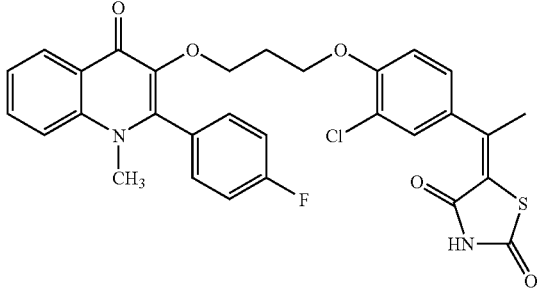

A mixture of compound 3-[3-(4-Acetyl-2-chloro-phenoxy)-propoxy]-2-(4-fluoro-phenyl)-1-methyl-1H-quinolin-4-one (0.60 g, 0.86 mmol), 2,4-thiazolidenedione (0.603 g, 5.16 mmol), benzoic acid (150 mg, 1.23 mmol), and piperidine (300 mg, 3.52 mmol) was taken into a single neck round bottom flask, to this toluene (50 mL) was added. The RBF was fitted with dean stark, which is connected to reflux condenser. The reaction mixture was heated to reflux for 72 hrs under nitrogen atmosphere. The reaction mixture was cooled to 25° C. and concentrated. The residue was purified by column chromatography using 2% MeOH—CHCl$_3$ to afford the title compound 140 mg (30%) as light brown solid.

$^1$H NMR (200 MHz, DMSO-d6): d 12.31 (NH, 1H), 8.32 (d, 1H, J=7.8 Hz), 7.80 (d, 2H, J=2.9 Hz), 7.48-7.13 (m, 7H), 7.02 (d, 1H, J=8.3 Hz), 4.29 (s, 2H), 4.07 (s, 2H), 3.47 (s, 3H), 2.64 (s, 3H), 1.82 (s, 2H).

Mp: 232-234° C.

EXAMPLE 73

5-[1-(4-{2-[7-Fluoro-2-(4-fluoro-phenyl)-1-methyl-4-oxo-1,4-dihydro-quinolin-3-yloxy]-ethoxy}-phenyl)-ethylidene]-thiazolidine-2,4-dione

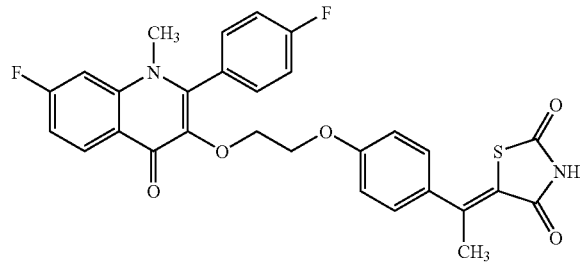

A mixture of compound 3-[2-(4-Acetyl-phenoxy)-ethoxy]-7-fluoro-2-(4-fluoro-phenyl)-1-methyl-1H-quinolin4-one (0.40 g, 0.89 mmol), 2,4-thiazolidenedione (0.521 g, 4.45 mmol), benzoic acid (200 mg, 1.63 mmol), and piperidine (150 mg, 1.76 mmol) was taken into a single neck round bottom flask, to this toluene (50 mL) was added. The RBF was fitted with dean stark, which is connected to reflux condenser. The reaction mixture was heated to reflux for 48 hrs under nitrogen atmosphere. The reaction mixture was cooled to 25° C. and concentrated. The residue was purified by column chromatography using 0.5-1% MeOH—CHCl$_3$ to afford the title compound 100 mg (21%) as brown solid.

$^1$H NMR (200 MHz, DMSO-d6): d 12.24 (bs, 1H), 8.39 (t, J=7.30 Hz, 1H), 7.67 (d, J=11.8 Hz, 1H), 7.52 (t, J=8.30 Hz, 2H), 7.36 (t, J=8.80 Hz, 5H), 6.82 (d, J=8.8 Hz, 2H), 4.22 (s, 2H), 3.95 (s, 2H), 3.33 (s, 3H), 2.63 (s, 3H).

Mp: 276-278° C.

EXAMPLE 74

5-[1-(4-{2-[2-(3,4-Difluoro-phenyl)-7-fluoro-1-methyl-4-oxo-1,4-dihydro-quinolin-3-yloxy]-ethoxy}-phenyl)-ethylidene]-thiazolidine-2,4-dione

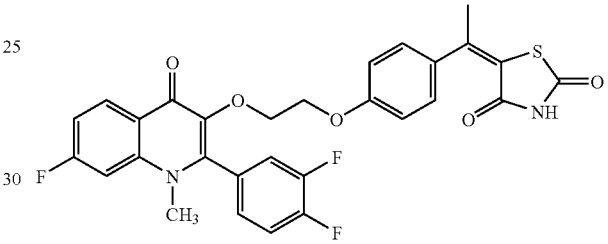

A mixture of compound 3-[2-(4-Acetyl-phenoxy)-ethoxy]-2-(3,4-difluoro-phenyl)-7-fluoro-1-methyl-1H-quinolin-4-one (0.40 g, 0.85 mmol), 2,4-thiazolidenedione (0.50 g, 4.28 mmol), benzoic acid (190 mg, 1.55 mmol), and piperidine (145 mg, 1.70 mmol) was taken into a single neck round bottom flask, to this toluene (50 mL) was added. The RBF was fitted with dean stark, which is connected to reflux condenser. The reaction mixture was heated to reflux for 48 hrs under nitrogen atmosphere. The reaction mixture was cooled to 50° C., filtered and washed with hot toluene. The solid was treated with toluene under reflux for 10 hours, filtered, washed with hot MeOH and dried to afford the title compound 125 mg (26%) as white solid.

$^1$H NMR (200 MHz, DMSO-d6): d 12.23 (s, 1H), 8.39 (t, J=8.6 Hz, 1H), 7.68-7.32 (m, 7H), 6.81 (d, J=8.6 Hz, 2H), 4.25 (s, 2H), 3.97 (s, 2H), 3.43 (s, 3H), 2.64 (s, 3H).

Mp: 270-272° C.

EXAMPLE 75

5-[1-(4-{2-[2-(3,4-Difluoro-phenyl)-1-methyl-4-oxo-1,4-dihydro-quinolin-3-yloxy]-ethoxy}-3-fluoro-phenyl)-ethylidene]-thiazolidine-2,4-dione

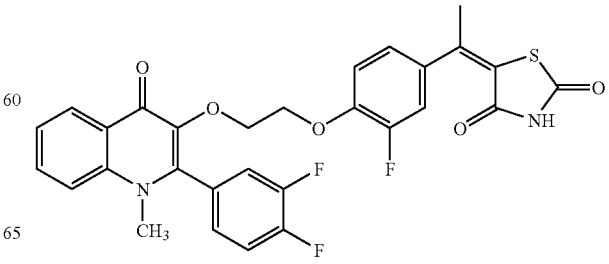

A mixture of compound 3-[2-(4-Acetyl-2-fluoro-phenoxy)-ethoxy]-2-(3,4-difluoro-phenyl)-1-methyl-1H-quinolin-4-one (0.40 g, 0.856 mmol), 2,4-thiazolidenedione (0.701 g, 5.99 mmol), benzoic acid (200 mg, 1.64 mmol), and piperidine (200 mg, 2.35 mmol) was taken into a single neck round bottom flask, to this toluene (30 mL) was added. The RBF was fitted with dean stark, which is connected to reflux condenser. The reaction mixture was heated to reflux for 72 hrs under nitrogen atmosphere. The reaction mixture was cooled to 25° C. and concentrated. The residue was purified by column chromatography using 1-2% MeOH—CHCl₃ to afford the title compound 170 mg (35%) as light brown solid.
$^1$H NMR (200 MHz, DMSO-d6): d 12.29 (NH, 1H), 8.32 (d, 1H, J=7.8 Hz), 7.80 (d, 2H, J=2.9 Hz), 7.62-6.99 (m, 7H), 4.28 (s, 2H), 4.07 (s, 2H), 3.48 (s, 3H), 2.64 (s, 3H).
Mp: 204-206° C.

EXAMPLE 76

5-[1-(4-{2-[7-Chloro-2-(3,4-difluoro-phenyl)-1-methyl-4-oxo-1,4-dihydro-quinolin-3-yloxy]-ethoxy}-phenyl)-ethylidene]-thiazolidine-2,4-dione

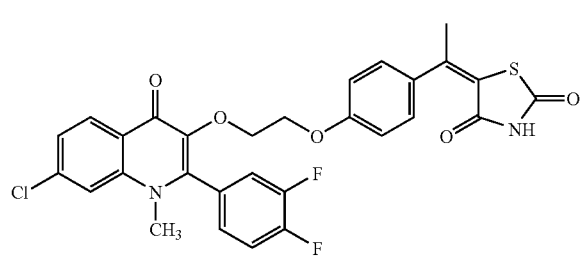

A mixture of compound 3-[2-(4-Acetyl-phenoxy)-ethoxy]-7-chloro-2-(3,4-difluoro-phenyl)-1-methyl-1H-quinolin-4-one (0.60 g, 1.2 mmol), 2,4-thiazolidenedione (0.872 g, 7.0 mmol), benzoic acid (151 mg, 1.2 mmol), and piperidine (105 mg, 1.2 mmol) was taken into a single neck round bottom flask, to this toluene (20 mL) was added. The RBF was fitted with dean stark, which is connected to reflux condenser. The reaction mixture was heated to reflux for 48 hrs under nitrogen atmosphere. The reaction mixture was cooled to 25° C. and concentrated. The residue was purified by column chromatography using MeOH—CHCl₃ to afford the title compound 150 mg (21%) as white solid.
$^1$H NMR (200 MHz, DMSO-d6): d 12.21 (bs, D₂O exchangeable, NH), 8.30 (d, J=8.8 Hz, 1H), 7.89 (s, 1H), 7.62-7.30 (m, 6H), 6.79 (d, J=8.8 Hz, 2H), 4.24 (s, 2H), 3.94 (s, 2H), 3.45 (s, 3H), 2.62 (s, 3H).
Mp: 296-298° C.

EXAMPLE 77

5-[1-(3-Chloro-4-{2-[7-chloro-2-(3,4-difluoro-phenyl)-1-methyl-4-oxo-1,4-dihydro-quinolin-3-yloxy]-ethoxy}-phenyl)-ethylidene]-thiazolidine-2,4-dione

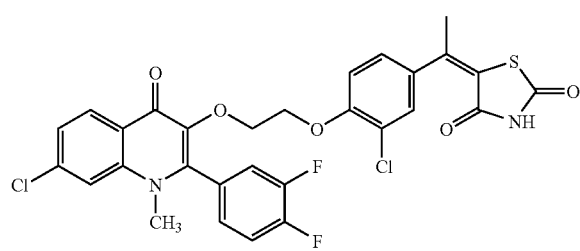

A mixture of compound 3-[2-(4-Acetyl-2-chloro-phenoxy)-ethoxy]-7-chloro-2-(3,4-difluoro-phenyl)-1-methyl-1H-quinolin-4-one (0.50 g, 0.96 mmol), 2,4-thiazolidenedione (0.677 g, 5.0 mmol), benzoic acid (117 mg, 0.96 mmol), and piperidine (95 mg, 0.96 mmol) was taken into a single neck round bottom flask, to this toluene (20 mL) was added. The RBF was fitted with dean stark, which is connected to reflux condenser. The reaction mixture was heated to reflux for 48 hrs under nitrogen atmosphere. The reaction mixture was cooled to 25° C. and concentrated. The residue was purified by column chromatography using MeOH—CHCl₃ to afford the title compound 120 mg (20%) as white solid.
$^1$H NMR (200 MHz, DMSO-d6): d 12.25 (bs, D₂O exchangeable, NH), 8.26 (d, J=8.3 Hz, 1H), 7.86 (s, 1H), 7.46-7.19 (m, 6H), 6.99 (d, J=8.8 Hz, 1H), 4.20 (s, 2H), 4.02 (s, 2H), 3.39 (s, 3H), 2.57 (s, 3H).
Mp: 140-142° C.

EXAMPLE 78

5-[1-(4-{2-[6-Fluoro-2-(4-fluoro-phenyl)-1-methyl-4-oxo-1,4-dihydro-quinolin-3-yloxy]-ethoxy}-phenyl)-ethylidene]-thiazolidine-2,4-dione

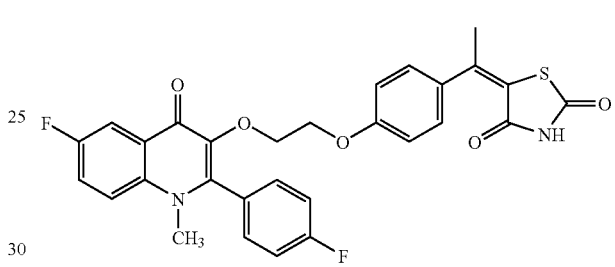

A mixture of compound 3-[2-(4-Acetyl-phenoxy)-ethoxy]-6-fluoro-2-(4-fluoro-phenyl)-1-methyl-1H-quinolin-4-one (0.4 g, 0.82 mmol), 2,4-thiazolidenedione (0.581 g, 4.96 mmol), benzoic acid (650 mg, 5.32 mmol), and piperidine (500 mg, 5.87 mmol) was taken into a single neck round bottom flask, to this toluene (30 mL) was added. The RBF was fitted with dean stark, which is connected to reflux condenser. The reaction mixture was heated to reflux for 72 hrs under nitrogen atmosphere. The reaction mixture was cooled to 25° C. and concentrated. The residue was purified by column chromatography using 0.5-1% MeOH—CHCl₃ to afford the title compound 80 mg (16%) as light brown solid.
$^1$H NMR (400 MHz, DMSO-d₆): d12.27 (bs, D₂O exchangeable, NH), 8.35 (dd, J=8.9, 7.0 Hz, 1H), 7.64 (d, J=12 Hz, 1H), 7.55-7.47 (m, 3H), 7.39-7.23 (m, 3H), 7.04 (d, J=8.6 Hz, 1H), 4.28-4.26 (m, 2H), 4.07-4.06 (m, 2H), 3.42 (s, 3H), 2.63 (s, 3H).
Mp: 245-248° C.

EXAMPLE 79

5-[1-(3-Chloro-4-{2-[2-(3,4-difluoro-phenyl)-6-fluoro-1-methyl-4-oxo-1,4-dihydro-quinolin-3-yloxy]-ethoxy}-phenyl)-ethylidene]-thiazolidine-2,4-dione

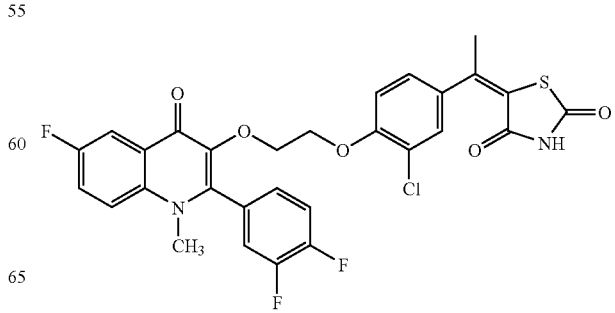

A mixture of compound 3-[2-(4-Acetyl-2-chloro-phenoxy)-ethoxy]-2-(3,4-difluoro-phenyl)-6-fluoro-1-methyl-1H-quinolin-4-one (1.4 g, 2.70 mmol), 2,4-thiazolidenedione (1.96 g, 16.7 mmol), benzoic acid (600 mg, 4.91 mmol), and piperidine (470 mg, 5.51 mmol) was taken into a single neck round bottom flask, to this toluene (30 mL) was added. The RBF was fitted with dean stark, which is connected to reflux condenser. The reaction mixture was heated to reflux for 72 hrs under nitrogen atmosphere. The reaction mixture was cooled to 25° C. and concentrated. The residue was purified by column chromatography using 0.5-1% MeOH—CHCl$_3$ to afford the title compound 40 mg (8%) as light brown solid.

$^1$H NMR (400 MHz, DMSO): d12.27 (bs, D$_2$O exchangeable, NH), 8.40-8.33 (m, 1H), 7.64 (d, J=12.0 Hz, 1H), 7.55-7.47 (m, 3H), 7.39-7.23 (m, 3H), 7.04 (d, J=8.6 Hz, 1H), 4.30 (m, 2H), 4.08 (m, 2H), 3.42 (s, 3H), 2.63 (s, 3H).

Mp: 215-218° C.

EXAMPLE 80

5-[1-(3-Chloro-4-{2-[2-(3,4-difluoro-phenyl)-1-methyl-4-oxo-1,4-dihydro-quinolin-3-yloxy]-ethoxy}-phenyl)-ethylidene]-thiazolidine-2,4-dione

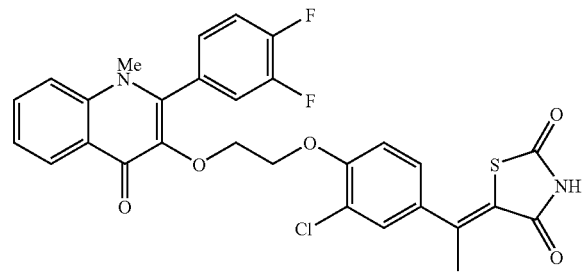

A mixture of compound 3-[2-(4-Acetyl-2-chloro-phenoxy)-ethoxy]-2-(3,4-difluoro-phenyl)-1-methyl-1H-quinolin-4-one (97 g, 200 mmol), thiazolidine-2,4-dione (141 g, 1200 mmol), benzoic acid (44 g, 361 mmol) and piperidine (35 g, 411.7 mmol) were taken a single neck round bottomed flask, to this toluene (1000 mL) was added. The round-bottomed flask 20 was fitted with dean stark apparatus, which was connected to a reflux condenser. The reaction mixture was heated to reflux for 48 hours under a nitrogen atmosphere. The reaction mixture was cooled to 25° C. and was allowed to pass through a silica gel column. The product was eluted by using 0.3-0.9% MeOH/CHCl$_3$ to afford the title compound, 37 g (32%) as off white solid.

$^1$H NMR (200 MHz, CDCl$_3$) δ12.30 (s, 1H), 8.32 (m, 1H), 7.77 (m, 2H), 7.52 (ddd, J=8.0, 2.0, 0.8 Hz, 1H), 7.48 (d, J=2.0 Hz, 1H), 7.45 (m, 1H), 7.25 (m, 1H), 7.35 (dd, J=10.0, 2.4 Hz, 1H), 7.31 (dd, J=8.4, 2.4 Hz, 1H), 7.04 (d, J=8.4 Hz, 1H), 4.31 (dd, J=3.4, 6.8 Hz, 2H), 4.09 (dd, J=3.4, 6.8 Hz, 2H), 3.47 (s, 3H), 2.63 (s, 3H)

Mp: 212-214° C.

EXAMPLE 81

5-[1-(4-{3-[2-(3,4-Dimethoxy-phenyl)-5,7-dimethoxy-4-oxo-4H-chromen-3-yloxy]-propoxy}-phenyl)-ethylidene]-thiazolidine-2,4-dione

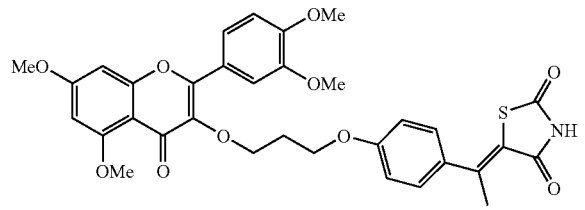

A mixture of compound 3-[3-(4-Acetyl-phenoxy)-propoxy]-2-(3,4-dimethoxy-phenyl)-7-ethyl-5-methoxy-chromen-4-one (0.30 g, 0.562 mmol), 2,4-thiazolidenedione (330 mg, 2.82 mmol), benzoic acid (132 mg, 1.08 mmol), and piperidine (96 mg, 1.13 mmol) was taken into 50 mL single neck round bottom flask, to this toluene (15 mL) was added. The RBF was fitted with dean stark, which is connected to reflux condenser. The reaction mixture was heated to reflux for 48 hrs under a nitrogen atmosphere. The reaction mixture was cooled to 25° C. and was filtered. The solid was dried to afford the title compound 189 mg (34%) as white solid.

$^1$H NMR (200 MHz, CDCl$_3$): d 8.38 (s, 1H), 7.68-7.65 (m, 2H), 7.3-7.25 (m, 2H), 6.91-6.85 (m, 3H), 6.51 (s, 1H), 6.37 (s, 1H), 4.25-4.13 (m, 4H), 3.97-3.91 (m, 12H), 2.7 (s, 1H), 2.25-2.19 (m, 2H)

Mp: 198-200° C.

EXAMPLES 82-91

The following compounds are readily prepared by one of skill in the art using the processes set forth above:

| Example | Compound |
|---------|----------|
| 82 | 5-[1-(3-Chloro-4-{2-[2-(3,4-difluoro-phenyl)-4-oxo-4H-chromen-3-yloxy]-ethoxy}-phenyl)-ethylidene]-thiazolidine-2,4-dione |
| 83 | 5-[1-(3-Chloro-4-{3-[2-(3,4-difluoro-phenyl)-4-oxo-4H-chromen-3-yl]-propoxy}-phenyl)-ethylidene]-thiazolidine-2,4-dione |
| 84 | 5-[1-(3-Chloro-4-{3-[2-(3,4-difluoro-phenyl)-4-oxo-4H-chromen-3-yloxy]-propyl}-phenyl)-ethylidene]-thiazolidine-2,4-dione |
| 85 | 5-[1-(3-Chloro-4-{3-[2-(3,4-difluoro-phenyl)-1-methyl-4-oxo-1,4-dihydro-quinolin-3-yl]-propoxy}-phenyl)-ethylidene]-thiazolidine-2,4-dione |
| 86 | 5-[1-(3-Chloro-4-{3-[2-(3,4-difluoro-phenyl)-1-methyl-4-oxo-1,4-dihydro-quinolin-3-yloxy]-propyl}-phenyl)-ethylidene]-thiazolidine-2,4-dione |
| 87 | 5-[1-(3-Chloro-4-{2-[5-(3,4-difluoro-phenyl)-1,3-dimethyl-7-oxo-1,7-dihydro-pyrazolo[4,3-d]pyrimidin-6-yl]-ethoxy}-phenyl)-ethylidene]-thiazolidine-2,4-dione |
| 88 | 5-[1-(3-Chloro-4-{3-[5-(3,4-difluoro-phenyl)-1,3-dimethyl-7-oxo-1,7-dihydro-pyrazolo[4,3-d]pyrimidin-6-yl]-propoxy}-phenyl)-ethylidene]-thiazolidine-2,4-dione |
| 89 | 3-[2-(3-Chloro-4-{2-[2-(3,4-difluoro-phenyl)-4-oxo-4H-chromen-3-yloxy]-ethoxy}-phenyl)-acetylamino]-2-(toluene-4-sulfonylamino)-propionic acid ethyl ester |
| 90 | 3-[2-(3-Chloro-4-{2-[2-(3,4-difluoro-phenyl)-1-methyl-4-oxo-1,4-dihydro-quinolin-3-yloxy]-ethoxy}-phenyl)-acetylamino]-2-(toluene-4-sulfonylamino)-propionic acid ethyl ester |
| 91 | 3-(4-{2-[2-(3,4-Difluoro-phenyl)-1-methyl-4-oxo-1,4-dihydro-quinolin-3-yloxy]-ethoxy}-benzoylamino)-2-(toluene-4-sulfonylamino)-propionic acid ethyl ester |

Similarly, other starting materials and intermediates are prepared by the application or adaptation of known methods, for example methods as described in the reference examples or their previous chemical equivalents (Ref: (i) J. HET. CHEM., 1999(36)141; (ii) For preparation of bromoketone see (a) J. MED. CHEM. 1996(39), 2939-2952; (b) J. HET. CHEM., 1972(9) 887; (b) INDIAN J. CHEM. SECT., 1990(29) 77; (c) TETRAHEDRON LETT., 1997(38)3581; (d) CHEM. PHARM. BULL. 1992(40)1170).

The pharmaceutically acceptable salts are prepared by reacting the compounds of formula (I) wherever applicable with 1 to 4 equivalents of a base, for example, sodium hydroxide, sodium methoxide, sodium hydride, potassium t-butoxide, calcium hydroxide, magnesium hydroxide, or any mixture thereof, in the presence of a solvent, for example, ether, THF, methanol, t-butanol, dioxane, isopropanol, ethanol, or any mixture thereof. Organic bases, for example, lysine, arginine, diethanolamine, choline, tromethamine, guanidine, or any derivative or mixture thereof, also may be used. Alternatively, acid addition salts wherever applicable are prepared by treatment with acids, for example, hydrochloric acid, hydrobromic acid, nitric acid, sulfuric acid, phosphoric acid, p-toluenesulphonic acid, methanesulfonic acid, acetic acid, citric acid, maleic acid salicylic acid, hydroxynaphthoic acid, ascorbic acid, palmitic acid, succinic acid, benzoic acid, benzenesulfonic acid, tartaric acid, or any mixture thereof, in the presence of a solvent, for example, ethyl acetate, ether, alcohols, acetone, THF, dioxane, or any mixture thereof. The salts of amino acid groups and other groups may be prepared by reacting the compounds of formula (I) with the respective groups in the presence of a solvent, for example, alcohols and ketones, or any mixture thereof.

Various polymorphs of a compound of general formula (I) according to the present invention may be prepared by crystallization of compound of formula (I) under different conditions, for example, by using different solvents or their mixtures for recrystallization; by performing crystallizations at different temperatures; or by using various modes of cooling, ranging from very fast to very slow cooling during crystallizations. Heating or melting the compound followed by gradual or fast cooling also may obtain polymorphs. The presence of polymorphs may be determined by solid probe NMR spectroscopy, IR spectroscopy, differential scanning calorimetry, powder X-ray diffraction or such other techniques.

Pharmaceutically acceptable solvates of compound of formula (I) forming part of this invention may be prepared by conventional methods such as dissolving the compounds of formula (I) in the presence of a solvent, for example, water, methanol, ethanol etc., for example, water and recrystallizing by using different crystallization techniques.

The regioisomers of a compound of formula (I) may be prepared by modifying the reaction conditions, for example, by using reagents, for example, acid to base or base to acid, or by reaction with free base hydrazine instead of its salt with diketone. The molar proportion also can change the regioisomer formation.

What is claimed is:

1. A compound of general formula (III)

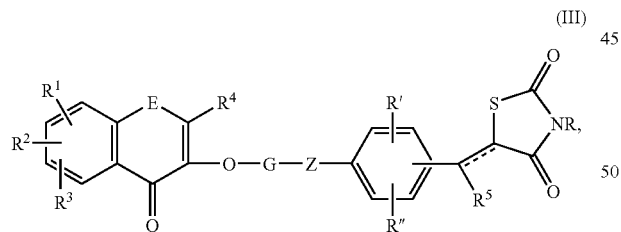

(III)

its tautomeric forms, its stereoisomers, or its pharmaceutically acceptable salts, wherein $R^1$, $R^2$, and $R^3$ independently are hydrogen, a hydroxy group, a halogen, a nitro group, a carboxy group, a carbamoyl group, an optionally substituted amino group, an alkyl group, a cycloalkyl group, an alkoxy group, a cycloalkoxy group, an alkenyl group, a cycloalkenyl group, an alkoxyalkyl group, an alkenyloxy group, a cycloalkenyloxy group, an acyl group, an acyloxy group, an aryl group, an aryloxy group, an aroyl group, an aroyloxy group, an aralkyl group, an aralkoxy group, a heterocyclyl group, a heteroaryl group, a heteroaralkyl group, a heteroaryloxy group, a heteroaralkoxy group, an alkoxycarbonyl group, an aryloxycarbonyl group, a heteroarylcarbonyl group, an alkylsulfonyl group, an arylsulfonyl group, an aralkylsulfinyl group, an alkylsulfinyl group, an arylsulfinyl group, a heteroarylsulfinyl group, an aralkylsulfinyl group, an alkylthio group, an arylthio group, a heteroarylthio group, an aralkylthio group, an aryloxyalkyl group, carboxylic acid or a derivative thereof, or sulfonic acid or a derivative thereof;

wherein $R^4$ is hydrogen, a hydroxy group, a halogen, a nitro group, a carboxy group, a carbamoyl group, an optionally substituted amino group, an alkyl group, a cycloalkyl group, an alkoxy group, a cycloalkoxy group, an alkenyl group, a cycloalkenyl group, an alkoxyalkyl group, an alkenyloxy group, a cycloalkenyloxy group, an acyl group, an acyloxy group, an aryl group, an aryloxy group, an aroyl group, an aroyloxy group, an aralkyl group, an aralkenyl group, an aralkynyl group, an aralkoxy group, a heterocyclyl group, a heterocyclenyl group, a heteroaryl group, a heteroaralkyl group, a heteroaryloxy group, a heteroaralkoxy group, an alkoxycarbonyl group, an aryloxycarbonyl group, an aralkoxycarbonyl group, a heteroarylcarbonyl group, an alkylsulfonyl group, an arylsulfonyl group, a heteroarylsulfonyl group, an alkylsulfinyl group, an arylsulfinyl group, an aralkylsulfinyl group, a heteroarylsulfinyl group, an aralkylsulfinyl group, an alkylthio group, an arylthio group, a heteroarylthio group, an aralkylthio group, an aryloxyalkyl group, an aralkoxyalkyl group, a fused heteroarylcycloalkenyl group, a fused heteroarylheterocyclenyl group, carboxylic acid or a derivative thereof;, or sulfonic acid or a derivative thereof;

wherein '_____' is an optional chemical bond;

wherein E is —NR;

wherein Z is O, —NR, (—CH$_2$—)$_u$, or S($=$O)$_u$;

wherein G is —(CH$_2$)$_s$—, —(CH$_2$)$_s$—CH=CH—(CH$_2$)$_s$—, or —(CH$_2$)$_s$—C≡C—(CH$_2$)$_s$—;

wherein u is an integer from 0-2;

wherein s is an integer from 0-5;

wherein R and $R^5$ independently are hydrogen, potassium, sodium, a hydroxy group, a halogen, a nitro group, an optionally substituted amino group, an alkyl group, an alkoxy group, an alkenyl group, an alkoxyalkyl group, a cycloalkenyloxy group, an acyl group, an aryl group, an aralkyl group, a heterocyclyl group, or a heteroaryl group; and wherein R' and R" independently are hydrogen, a halogen, a nitro group, an amino group, a mono- or di-substituted amino group, a hydroxyl group, an alkoxy group, a carboxy group, a cyano group, an oxo(O=) group, a thio (S=) group, an alkyl group, a cycloalkyl group, an alkoxy group, a haloalkoxy group, a cycloalkyl group, an aryl group, a benzyloxy group, an acyl group, an acyloxy group, an aroyl group, an alkoxycarbonyl group, an aryloxycarbonyl group, a heteroaryl group, a heterocyclyl group, an aralkyl group, an alkylsulfonyl group, an alkylsulfinyl group, an arylsulfonyl group, an arylsulfinyl group, an alkylthio group, an arylthio group, an aralkylthio group, or a heterocyclyl sulfonyl group.

2. A compound of general formula (II)

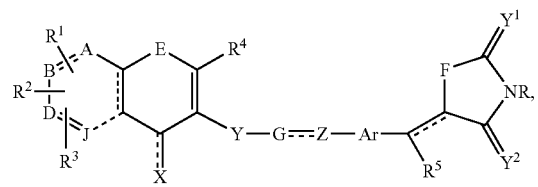

(II)

its tautomeric forms, its stereoisomers, or its pharmaceutically acceptable salts, wherein $R^1$, $R^2$, and $R^3$ independently are hydrogen, a hydroxy group, a halogen, a nitro group, a carboxy group, a carbamoyl group, an optionally substituted amino group, an alkyl group, a cycloalkyl group, an alkoxy group, a cycloalkoxy group, an alkenyl group, a cycloalkenyl group, an alkoxyalkyl group, an alkenyloxy group, a cycloalkenyloxy group, an acyl group, an acyloxy group, an aryl group, an aryloxy group, an aroyl group, an aroyloxy group, an aralkyl group, an aralkoxy group, a heterocyclyl group, a heteroaryl group, a heteroaralkyl group, a heteroaryloxy group, a heteroaralkoxy group, an alkoxycarbonyl group, an aryloxycarbonyl group, a heteroarylcarbonyl group, an alkylsulfonyl group, an arylsulfonyl group, a heteroarylsulfonyl group, an aralkylsulfinyl group, an alkylsulfinyl group, an arylsulfinyl group, a heteroarylsulfinyl group, an aralkylsulfinyl group, an alkylthio group, an arylthio group, a heteroarylthio group, an aralkylthio group, an aryloxyalkyl group, carboxylic acid or a derivative thereof, or sulfonic acid or a derivative thereof, wherein any two of $R^1$, $R^2$, and $R^3$ in combination optionally form a 5-member or 6-member saturated cyclic ring having from 1 to 3 heteroatoms, wherein the heteroatoms are O, S, or N;

wherein $R^4$ is hydrogen, a hydroxy group, a halogen, a nitro group, a carboxy group, a carbamoyl group, an optionally substituted amino group, an alkyl group, a cycloalkyl group, an alkoxy group, a cycloalkoxy group, an alkenyl group, a cycloalkenyl group, an alkoxyalkyl group, an alkenyloxy group, a cycloalkenyloxy group, an acyl group, an acyloxy group, an aryl group, an aryloxy group, an aroyl group, an aroyloxy group, an aralkyl group, an aralkenyl group, an aralalkynyl group, an aralkoxy group, a heterocyclyl group, a heterocyclenyl group, a heteroaryl group, a heteroaralkyl group, a heteroaryloxy group, a heteroaralkoxy group, an alkoxycarbonyl group, an aryloxycarbonyl group, an aralkoxycarbonyl group, a heteroarylcarbonyl group, an alkylsulfonyl group, an arylsulfonyl group, a heteroarylsulfonyl group, an alkylsulfinyl group, an arylsulfinyl group, an aralkylsulfinyl group, a heteroarylsulfinyl group, an aralkylsulfinyl group, an alkylthio group, an arylthio group, a heteroarylthio group, an aralkylthio group, an aryloxyalkyl group, an aralkoxyalkyl group, a fused heteroarylcycloalkyl group, a fused heteroarylcycloalkenyl group, a fused heteroarylheterocyclenyl group, carboxylic acid or a derivative thereof, or sulfonic acid or a derivative thereof;

wherein A, B, D, and J independently are $(-CH_2-)_n$;

wherein '_____' is an optional chemical bond;

wherein E is $-NR$;

wherein Z is independently O, $-NR$, $(-CH_2-)U$, or $S(=O)_u$;

wherein G is $-(CH_2)_s-$, $-(CH_2)_s-CH=CH-(CH_2)_s-$, or $-(CH_2)_s-C\equiv C-(CH_2)_s-$;

wherein X is O;

wherein F is S; wherein Y is O;

wherein $Y^1$ and $Y^2$ independently are O or S;

wherein n is 1, and u is an integer from 0-2;

wherein R and $R^5$ independently are hydrogen, potassium, sodium, a hydroxy group, a halogen, a nitro group, an optionally substituted amino group, an alkyl group, an alkoxy group, an alkenyl group, an alkoxyalkyl group, a cycloalkenyloxy group, an acyl group, an aryl group, an aralkyl group, a heterocyclyl group, or a heteroaryl group; and wherein 'Ar' is a substituted or unsubstituted phenyl.

3. The compound of claim 1, wherein any of $R^1$, $R^2$, $R^3$ and $R^4$ independently are substituted with hydrogen, a halogen, a nitro group, an amino group, a mono- or di-substituted amino group, a hydroxy group, an alkoxy group, a carboxy group, a cyano group, an oxo(O=) group, a thio(S=) group, an alkyl group, a cycloalkyl group, an alkoxy group, a haloalkoxy group, a cycloalkyl group, an aryl group, a benzyloxy group, an acyl group, an acyloxy group, an aroyl group, an alkoxycarbonyl group, an aryloxycarbonyl group, a heteroaryl group, a heterocyclyl group, an aralkyl group, an alkylsulfonyl group, an alkylsulfinyl group, an arylsulfonyl group, an arylsulfinyl group, an alkylthio group, an arylthio group, a heteroarylthio group, an aralkylthio group, or a heterocyclyl sulfonyl group, which is optionally substituted with a halogen, a hydroxyl group, a nitro group, an amino group, an alkyloxy group, or any combination thereof, and wherein the heterocycle group is optionally a substituted morpholinyl group, a thiomorpholinyl group, or a piperzinyl group, wherein the substituent on the heterocyclyl group is a halogen, a nitro group, an amino group, an alkyl group, an alkoxy group, or an aryl group.

4. The compound of claim 2, wherein any of $R^1$, $R^2$, $R^3$, and $R^4$ independently are substituted with hydrogen, a halogen, a nitro group, an amino group, a mono- or di-substituted amino group, a hydroxy group, an alkoxy group, a carboxy group, a cyano group, an oxo(O=) group, a thio(S=) group, an alkyl group, a cycloalkyl group, an alkoxy group, a haloalkoxy group, a cycloalkyl group, an aryl group, a benzyloxy group, an acyl group, an acyloxy group, an aroyl group, an alkoxycarbonyl group, an aryloxycarbonyl group, a heteroaryl group, a heterocyclyl group, an aralkyl group, an alkylsulfonyl group, an alkylsulfinyl group, an arylsulfonyl group, an arylsulfinyl group, an alkylthio group, an arylthio group, a heteroarylthio group, an aralkylthio group, or a heterocyclyl sulfonyl group, which is optionally substituted with a halogen, a hydroxyl group, a nitro group, an amino group, an alkyloxy group, or any combination thereof, and wherein the heterocycle group is optionally a substituted morpholinyl group, a thiomorpholinyl group, or a piperzinyl group, wherein the substituent on the heterocyclyl group is a halogen, a nitro group, an amino group, an alkyl group, an alkoxy group, or an aryl group.

5. The compound of claim 1, wherein any of $R^1$, $R^2$, $R^3$, and $R^4$ independently are substituted with hydrogen, a halogen, a nitro group, an amino group, a mono- or di-subsituted amino group, a hydroxyl group, an alkoxy group, a carboxy group, a cyano group, an oxo(O=) group, a thio(S=) group, an alkyl group, a cycloalkyl group, an alkoxy group, a haloalkoxy group, a cycloalkyl group, an aryl group, a benzyloxy group, an acyl group, an acyloxy group, an aroyl group, an alkoxycarbonyl group, an aryloxycarbonyl group, a heteroaryl group, a heterocyclyl group, an aralkyl group, an alkylsulfonyl group, an alkylsulfinyl group, an arylsulfonyl group, an arylsulfinyl group, an alkylthio group, an arylthio group, a heteroarylthio group, an aralkylthio group, or a heterocyclyl sulfonyl group, which is optionally substituted with a halogen, a hydroxyl group, a nitro group, an aminio group, an alkyloxy group, or any combination thereof, and wherein the heterocyclyl group is optionally a substituted morpholinyl group, a thiomorpholinyl group, or a piperzinyl group, wherein the substituent on the heterocyclyl group is a halogen, a nitro group, an amino group, an alkyl group, an alkoxy group, or an aryl group.

6. The compound of claim 1, wherein one or both of R' and R" independently are substituted with a halogen, a hydroxyl group, a nitro group, an amino group, or an alkyloxy group.

7. The compound of claim 1, wherein one or both of R' or R" independently are substituted with a heterocyclyl group comprising a morphonyl group, a thiomorphoine, or a piperzine.

8. The compound of formula (III) as claimed in claim 1, wherein the compound is:

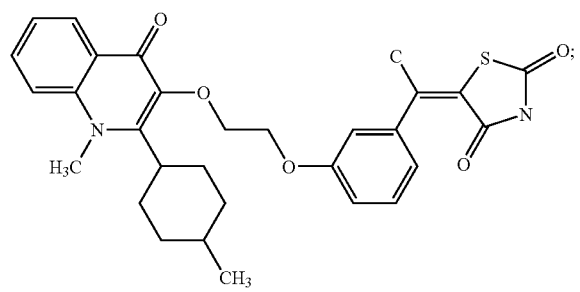

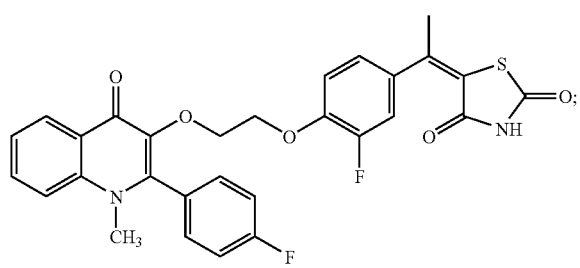

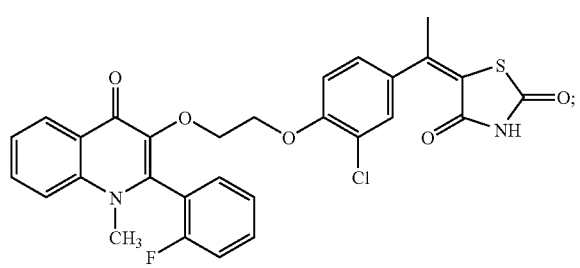

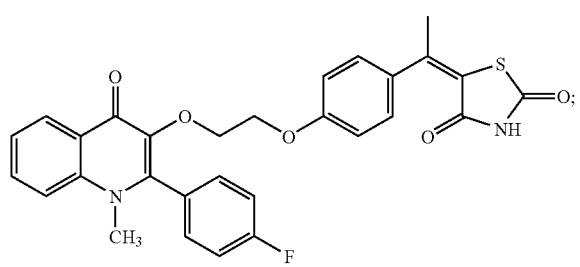

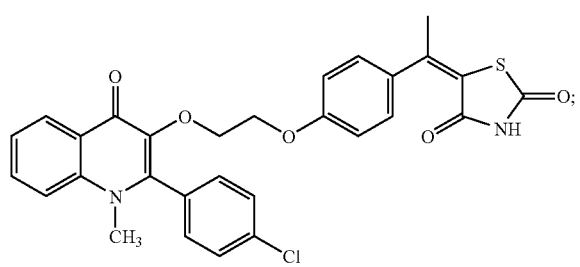

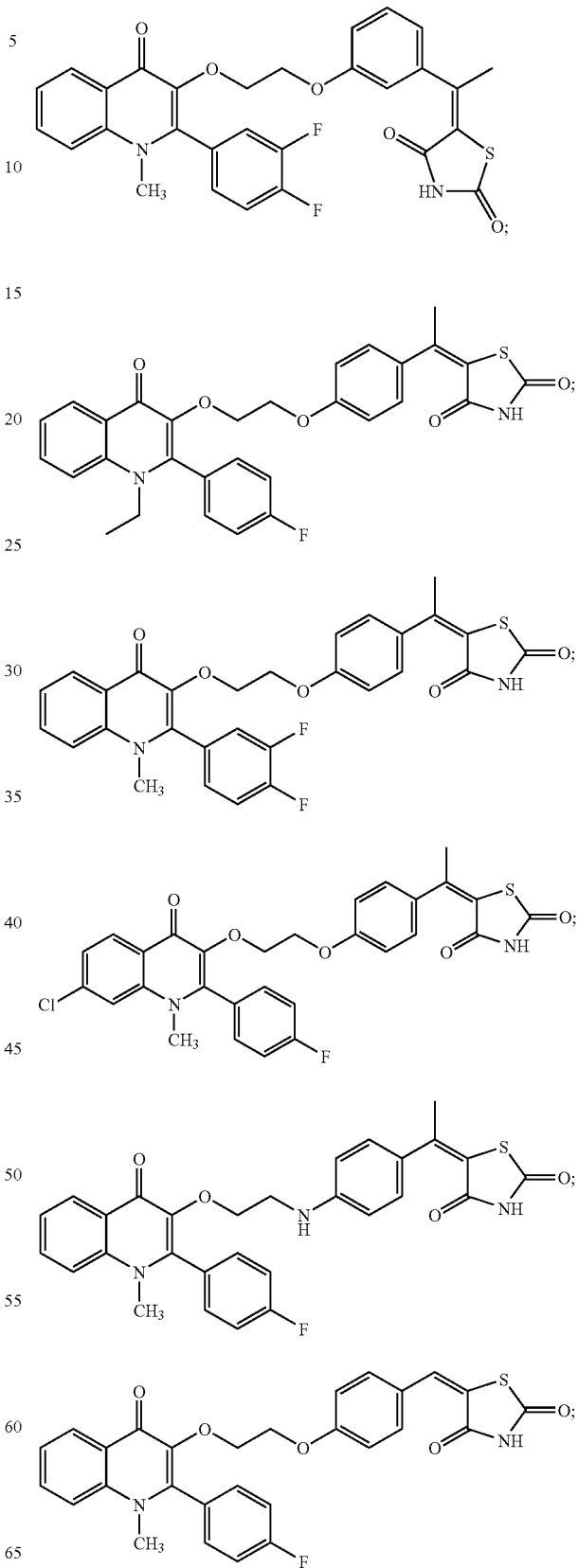

273
-continued
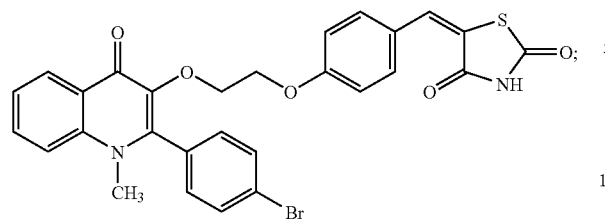
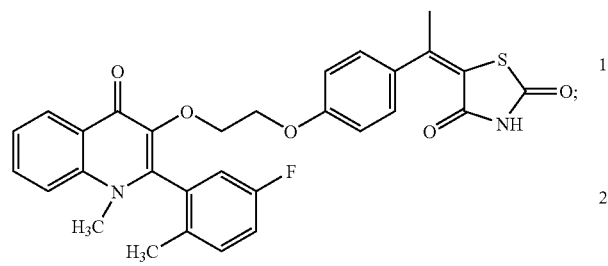
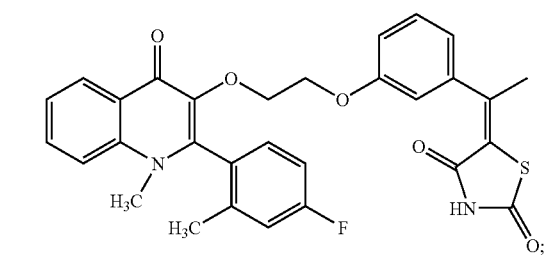
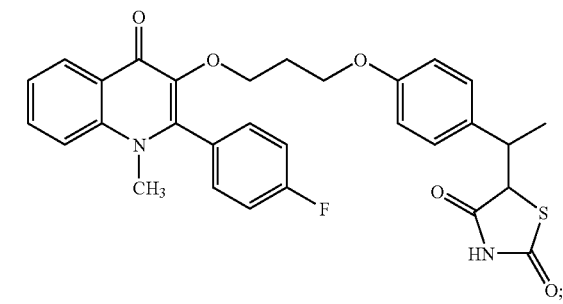
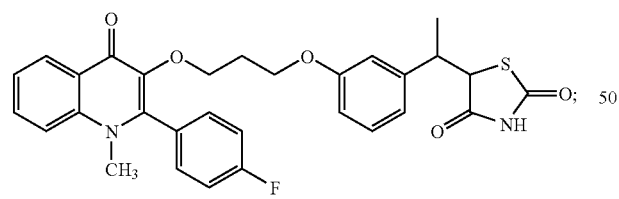
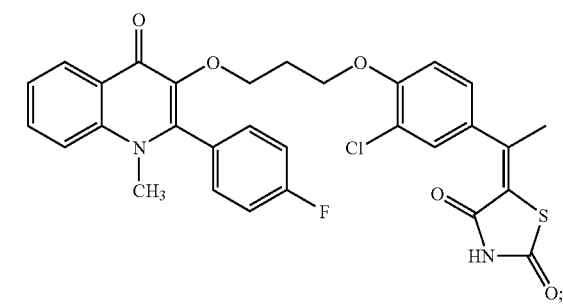
274
-continued
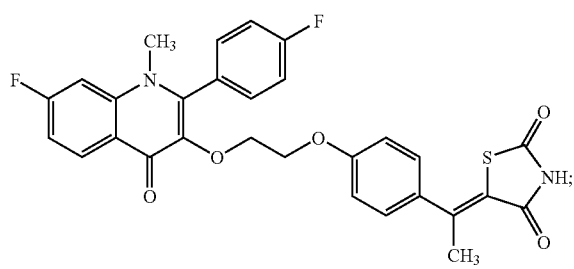
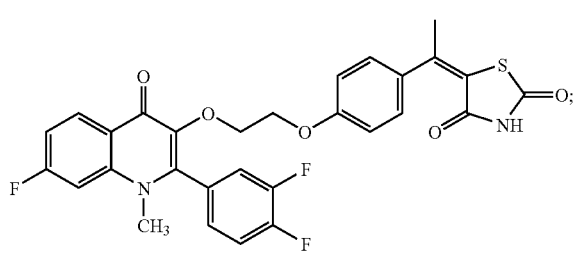
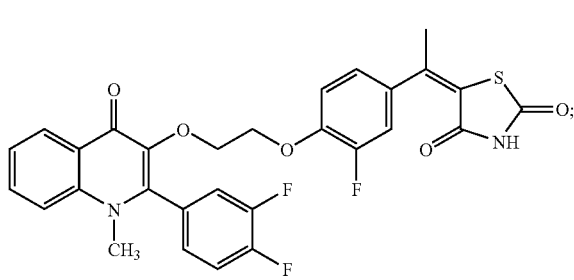
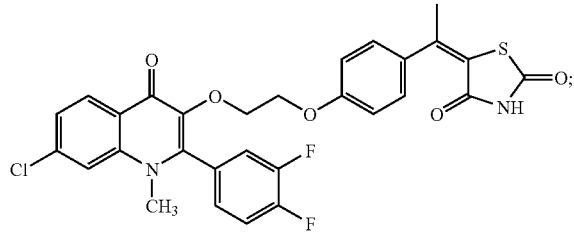
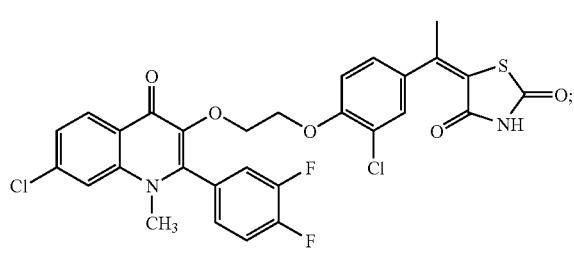
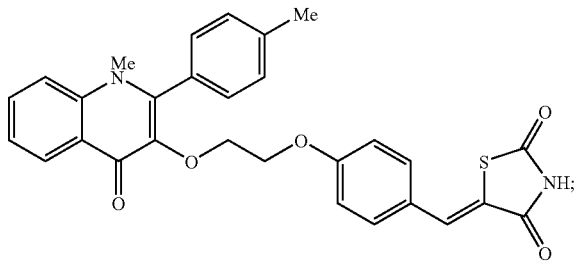

-continued
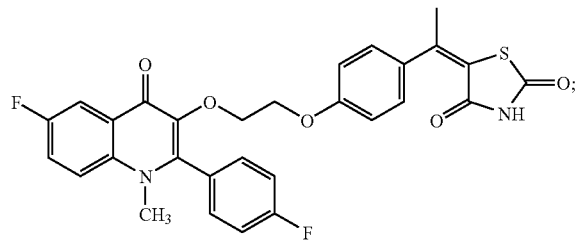
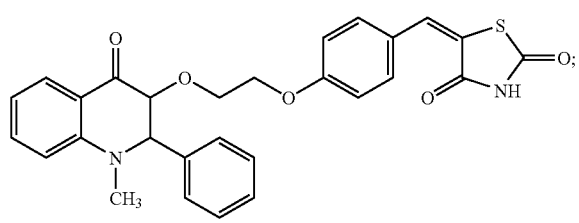
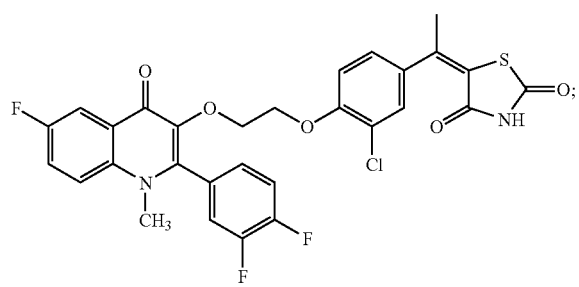
-continued
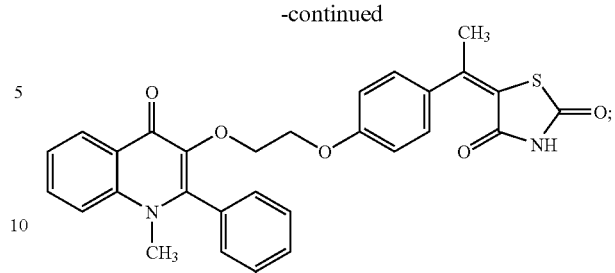
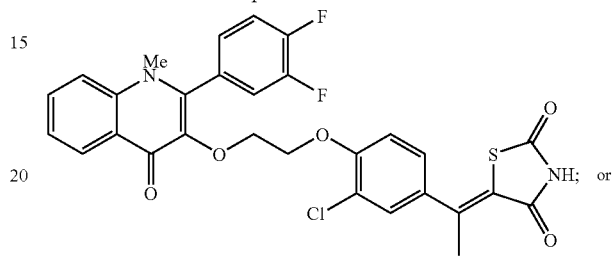
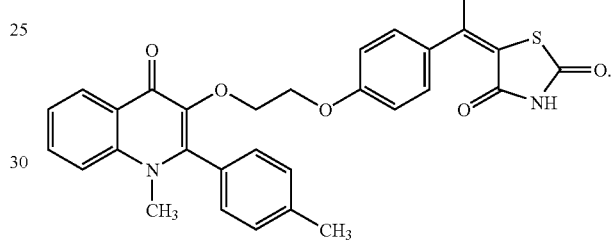
* * * * *